United States Patent
Horan et al.

(10) Patent No.: US 11,542,278 B1
(45) Date of Patent: Jan. 3, 2023

(54) HETEROAROMATIC MACROCYCLIC ETHER CHEMOTHERAPEUTIC AGENTS

(71) Applicant: Nuvalent, Inc., Cambridge, MA (US)

(72) Inventors: Joshua Courtney Horan, Somerville, MA (US); Xinxing Tang, Pudong (CN); Scot Richard Mente, Arlington, MA (US); Henry Efrem Pelish, Newton, MA (US); Matthew D. Shair, Lexington, MA (US); Anupong Tangpeerachaikul, Quincy, MA (US)

(73) Assignee: Nuvalent, Inc., Cambridge, MA (US)

( * ) Notice: Subject to any disclaimer, the term of this patent is extended or adjusted under 35 U.S.C. 154(b) by 0 days.

(21) Appl. No.: 17/514,877

(22) Filed: Oct. 29, 2021

Related U.S. Application Data

(63) Continuation of application No. PCT/US2021/030842, filed on May 5, 2021.

(60) Provisional application No. 63/125,733, filed on Dec. 15, 2020.

(30) Foreign Application Priority Data

May 5, 2020 (CN) .................. PCT/CN20/88590

(51) Int. Cl.
| | |
|---|---|
| *A61K 31/4427* | (2006.01) |
| *C07D 471/22* | (2006.01) |
| *C07D 498/22* | (2006.01) |
| *A61P 35/00* | (2006.01) |
| *C07D 513/22* | (2006.01) |

(52) U.S. Cl.
CPC ............ *C07D 498/22* (2013.01); *A61P 35/00* (2018.01); *C07D 513/22* (2013.01)

(58) Field of Classification Search
CPC .................... A61K 31/4427; C07D 471/22
USPC .......................................... 514/280; 546/48
See application file for complete search history.

(56) References Cited

U.S. PATENT DOCUMENTS

| | | |
|---|---|---|
| 5,569,655 A | 10/1996 | Dority, Jr. et al. |
| 5,849,735 A | 12/1998 | Albright et al. |
| 6,660,867 B2 | 12/2003 | Shimizu et al. |
| 7,312,225 B2 | 12/2007 | Luecking et al. |
| 7,338,973 B2 | 3/2008 | Sui et al. |
| 7,445,211 B1 | 11/2008 | Walton |
| 7,514,466 B2 | 4/2009 | Wilk et al. |
| 7,641,703 B2 | 1/2010 | Guerin et al. |
| 7,696,239 B2 | 4/2010 | Sui et al. |
| 7,915,414 B2 | 3/2011 | Chi et al. |
| 8,012,603 B2 | 9/2011 | Doi et al. |
| 8,129,523 B2 | 3/2012 | Wilk et al. |
| 8,178,520 B2 | 5/2012 | Di Francesco et al. |
| 8,308,996 B2 | 11/2012 | Takahashi et al. |
| 8,309,594 B2 | 11/2012 | Wilk et al. |
| 8,580,840 B2 | 11/2013 | Sui et al. |
| 8,609,712 B2 | 12/2013 | Wilk et al. |
| 8,680,111 B2 | 3/2014 | Bailey et al. |
| 9,133,168 B2 | 9/2015 | Brollo et al. |
| 9,133,215 B2 | 9/2015 | Bailey et al. |
| 9,181,265 B2 | 11/2015 | Feron et al. |
| 9,221,818 B2 | 12/2015 | Pinto et al. |
| 9,318,714 B2 | 4/2016 | Ise |
| 9,446,995 B2 | 9/2016 | Chong |
| 9,502,667 B2 | 11/2016 | Saito et al. |
| 9,518,217 B2 | 12/2016 | Cheng et al. |
| 9,611,274 B2 | 4/2017 | Pinto et al. |
| 9,666,809 B2 | 5/2017 | Lee |
| 9,768,393 B2 | 9/2017 | Shin et al. |
| 9,887,372 B2 | 2/2018 | Jun et al. |
| 9,902,742 B2 | 2/2018 | Pinto et al. |
| 9,929,358 B2 | 3/2018 | Hwang et al. |
| 10,147,887 B2 | 12/2018 | Lee |
| 10,189,803 B2 | 1/2019 | Chong |
| 10,208,068 B2 | 2/2019 | Pinto et al. |
| 10,243,153 B2 | 3/2019 | Ise |

(Continued)

FOREIGN PATENT DOCUMENTS

| | | |
|---|---|---|
| CA | 2160092 A1 | 4/1996 |
| CN | 106243096 A | 12/2016 |

(Continued)

OTHER PUBLICATIONS

Ahn et al., "Entrectinib in patients with locally advanced or metastatic ROS1 fusion-positive non-small cell lung cancer (NSCLC)," IASLC 18th World Conference on Lung Cancer: 16 pages Abstract 8564 (Oct. 15-18, 2017).

Alecensa FDA Approval Media Release., "FDA approves Roche's Alecensa (alectinib) as first-line treatment for people with specific type of lung cancer," Hoffmann-La Roche Ltd.: 6 pages (Nov. 7, 2017).

(Continued)

*Primary Examiner* — Douglas M Willis
(74) *Attorney, Agent, or Firm* — Jones Day

(57) ABSTRACT

Disclosed are heterocyclic heteroaromatic macrocyclic ether compounds of Formula (I):

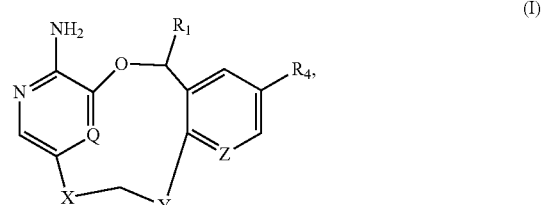

pharmaceutically acceptable salts of the compounds and pharmaceutical compositions thereof. The disclosure further relates to methods of treating or preventing cancer using the heterocyclic heteroaromatic macrocyclic ether compounds, pharmaceutically acceptable salts of the compounds and pharmaceutical compositions thereof.

30 Claims, No Drawings

(56) References Cited

U.S. PATENT DOCUMENTS

| | | |
|---|---|---|
| 10,335,392 B2 | 7/2019 | Xiao et al. |
| 10,593,889 B1 | 3/2020 | Takahashi et al. |
| 11,008,323 B2 | 5/2021 | Schann et al. |
| 2003/0187272 A1 | 10/2003 | Shimizu et al. |
| 2005/0250766 A1 | 11/2005 | Wilk et al. |
| 2005/0272702 A1 | 12/2005 | Wilk et al. |
| 2006/0116415 A1 | 6/2006 | Sui et al. |
| 2007/0116984 A1 | 5/2007 | Park et al. |
| 2007/0213526 A1 | 9/2007 | Levent et al. |
| 2008/0125591 A1 | 5/2008 | Chi et al. |
| 2008/0138651 A1 | 6/2008 | Doi et al. |
| 2008/0244838 A1 | 10/2008 | Guerin et al. |
| 2009/0022694 A1 | 1/2009 | Distefano |
| 2009/0054663 A1 | 2/2009 | Wilk et al. |
| 2009/0143577 A1 | 6/2009 | Wilk et al. |
| 2010/0210658 A1 | 8/2010 | Sui et al. |
| 2010/0216988 A1 | 8/2010 | Alonso et al. |
| 2010/0261719 A1 | 10/2010 | Basarab et al. |
| 2011/0049497 A1 | 3/2011 | Ise |
| 2011/0071136 A1 | 3/2011 | Haddach et al. |
| 2011/0178311 A1 | 7/2011 | Levent et al. |
| 2012/0008068 A1 | 1/2012 | Doi et al. |
| 2012/0121934 A1 | 5/2012 | Takahashi et al. |
| 2012/0157448 A1 | 6/2012 | Cook et al. |
| 2013/0012702 A1 | 1/2013 | Wilk et al. |
| 2013/0056716 A1 | 3/2013 | Cheng et al. |
| 2013/0196952 A1 | 8/2013 | Bunnage et al. |
| 2013/0252961 A1 | 9/2013 | Bailey et al. |
| 2013/0274253 A1 | 10/2013 | Brollo et al. |
| 2013/0289030 A1 | 10/2013 | Feron et al. |
| 2013/0310555 A1 | 11/2013 | Chong |
| 2014/0066479 A1 | 3/2014 | Sui et al. |
| 2014/0135339 A1 | 5/2014 | Bailey et al. |
| 2014/0221338 A1 | 8/2014 | Pinto et al. |
| 2015/0060791 A1 | 3/2015 | Shin et al. |
| 2015/0155497 A1 | 6/2015 | Lee |
| 2015/0207084 A1 | 7/2015 | Hwang et al. |
| 2015/0218441 A1 | 8/2015 | Cho et al. |
| 2015/0255731 A1 | 9/2015 | Lee |
| 2016/0068544 A1 | 3/2016 | Pinto et al. |
| 2016/0163998 A1 | 6/2016 | Saito et al. |
| 2016/0214996 A1 | 7/2016 | Song et al. |
| 2016/0254462 A1 | 9/2016 | Ise |
| 2016/0365521 A1 | 12/2016 | Jun et al. |
| 2017/0008863 A1 | 1/2017 | Chong |
| 2017/0054094 A1 | 2/2017 | Cheng et al. |
| 2017/0158712 A1 | 6/2017 | Pinto et al. |
| 2018/0148461 A1 | 5/2018 | Pinto et al. |
| 2018/0221344 A1 | 8/2018 | Xiao et al. |
| 2018/0346468 A1 | 12/2018 | Schann et al. |
| 2020/0098994 A1 | 3/2020 | Takahashi et al. |
| 2020/0303663 A1 | 9/2020 | Jeon et al. |
| 2020/0317646 A1 | 10/2020 | He et al. |
| 2020/0385396 A1 | 12/2020 | Zhou et al. |
| 2021/0012274 A1 | 1/2021 | Forgatch et al. |
| 2021/0309682 A1 | 10/2021 | Arefyev et al. |
| 2021/0395233 A1 | 12/2021 | Takahashi et al. |
| 2022/0098212 A1 | 3/2022 | Horan et al. |

FOREIGN PATENT DOCUMENTS

| | | |
|---|---|---|
| CN | 108912175 A | 11/2018 |
| CN | 109912433 A | 6/2019 |
| CN | 110357905 A | 10/2019 |
| CN | 111362967 A | 7/2020 |
| CN | 111808147 A | 10/2020 |
| CN | 112321604 A | 2/2021 |
| CN | 112812128 A | 5/2021 |
| CN | 113105440 A | 7/2021 |
| CN | 113121607 A | 7/2021 |
| FR | 2969611 A1 | 6/2012 |
| JP | 2009/234928 A | 10/2009 |
| JP | 2009/266927 A | 11/2009 |
| JP | 2010/0278114 A | 12/2010 |
| JP | 2018/062496 A | 4/2018 |
| KR | 2016/0038813 A | 4/2016 |
| KR | 2019/0103769 A | 9/2019 |
| WO | WO-1996/022282 A1 | 7/1996 |
| WO | WO-2002/050190 A1 | 6/2002 |
| WO | WO-2004/039859 A1 | 5/2004 |
| WO | WO-2005/105817 A2 | 11/2005 |
| WO | WO-2006/034090 A1 | 3/2006 |
| WO | WO-2007/047604 A2 | 4/2007 |
| WO | WO-2009/000412 A1 | 12/2008 |
| WO | WO-2009/004382 A2 | 1/2009 |
| WO | WO-2011/016582 A1 | 2/2011 |
| WO | WO-2011/035019 A1 | 3/2011 |
| WO | WO-2012/016147 A2 | 2/2012 |
| WO | WO-2012/071458 A1 | 5/2012 |
| WO | WO-2012/085222 A1 | 6/2012 |
| WO | WO-2012/089633 A9 | 8/2012 |
| WO | WO-2012/102409 A1 | 8/2012 |
| WO | WO-2013/022818 A1 | 2/2013 |
| WO | WO-2013/132376 A1 | 9/2013 |
| WO | WO-2014/038867 A1 | 3/2014 |
| WO | WO-2014/138912 A1 | 9/2014 |
| WO | WO-2014/207606 A1 | 12/2014 |
| WO | WO-2015/050989 A2 | 4/2015 |
| WO | WO-2015/104711 A1 | 7/2015 |
| WO | WO-2017/023902 A1 | 2/2017 |
| WO | WO-2017/081483 A1 | 5/2017 |
| WO | WO-2017/148325 A1 | 9/2017 |
| WO | WO-2019/057175 A1 | 3/2019 |
| WO | WO-2019/113071 A1 | 6/2019 |
| WO | WO-2019/120263 A1 | 6/2019 |
| WO | WO-2019/164301 A1 | 8/2019 |
| WO | WO-2020/021113 A1 | 1/2020 |
| WO | WO-2020/067290 A1 | 4/2020 |
| WO | WO-2020/069106 A1 | 4/2020 |
| WO | WO-2020/228747 A1 | 11/2020 |
| WO | WO-2021/025371 A1 | 2/2021 |
| WO | WO-2021/058969 A1 | 4/2021 |
| WO | WO-2021/122868 A1 | 6/2021 |
| WO | WO-2021/125791 A1 | 6/2021 |
| WO | WO-2021/226208 A2 | 11/2021 |
| WO | WO-2021/226269 A1 | 11/2021 |
| WO | WO-2022/017408 A1 | 1/2022 |

OTHER PUBLICATIONS

Alectinib Prescribing Information., "Alecensa® (alectinib) capsules, for oral use Initial U.S. Approval: 2015," U.S. Food and Drug Administration: 21 pages (Nov. 2017).

Bauer et al., "Clinical Management of Adverse Events Associated with Lorlatinib," The Oncologist, 24: 1103-1110 (Aug. 24, 2019).

Bestvina et al., "ALK and ROS1 rearrangement in NSCLC: rapidly evolving standards," Oncology, 18: 1555-1556 (Nov. 29, 2017).

Camidge et al., "Clinical trial design for systemic agents in patients with brain metastases from solid tumours: a guideline by the Response Assessment in Neuro-Oncology Brain Metastases working group," The Lancet Oncology, 19(1): e20-e32 (Jan. 2018).

Camidge et al., "Exploratory Analysis of Brigatinib Activity in Patients With Anaplastic Lymphoma Kinase-Positive Non-Small-Cell Lung Cancer and Brain Metastases in Two Clinical Trials," Journal of Clinical Oncology, 36(26): 2693-2701 (May 16, 2018).

Cho et al., "Phase 1/2 Trident-1 Study of Repotrectinib in Patients with ROS1+ or NTRK+ Advanced Solid Tumors," 2020 World Conference on Lung Cancer Singapore: 7 pages Abstract #3255 (Jan. 28-31, 2021).

Cho et al., "Safety and Preliminary Clinical Activity of Repotrectinib in Patients with Advanced ROS1 Fusion-Position Non-Small Cell Lung Cancer (TRIDENT-1 Study)," 2019 ASCO Annual Meeting: 13 pages (May 2019).

Chong et al., "Identification of Existing Drugs That Effectively Target NTRK1 and ROS1 Rearrangements in Lung Cancer," Clinical Cancer Research, 23(1): 204-213 (Jan. 1, 2017).

Cocco et al., "NTRK fusion-positive cancers and TRK inhibitor therapy," Nature Reviews Clinical Oncology, 15: 731-747 (Oct. 17, 2018).

Coleman et al., "Lorlatinib Salvages Central Nervous System Only Relapse on Entrectinib in ROS1-Positive NSCLC," Journal of Thoracic Oncology, 15(8): e142-e144 (Aug. 1, 2020).

(56) References Cited

OTHER PUBLICATIONS

Conde et al., "Assessment of a New ROS1 Immunohistrochemistry Clone (SP384) for the Identification of ROS1," Journal of Thoracic Oncology, 14(12): 2120-2132 (Dec. 1, 2019).
Cortinovis et al., "Challenges in ALK inhibition of ALK-positive non-small-cell lung cancer: from ALK positivity detection to treatment strategies after relapse," Future Oncology, 14(22): 2303-2317 (Aug. 8, 2018).
Cui et al., "Abstract 5226: TPX-0131: A next generation macrocyclic ALK inhibitor that overcomes ALK resistant mutations refractory to current approved ALK inhibitors," American Association for Cancer Research: Poster Abstract#5226 (Aug. 2020).
Dagogo-Jack et al., "MET Alterations Are a Recurring and Actionable Resistance Mechanism in ALK-Positive Lung Cancer," Clinical Cancer Research, 26(11): 2535-2545 (Jun. 1, 2020).
Dagogo-Jack et al., "Tracking the Evolution of Resistance to ALK Tyrosine Kinase Inhibitors Through Longitudinal Analysis of Circulating Tumor DNA," JCO Precision Oncology, 2: pp. 1-14 (Jan. 23, 2018).
Dagogo-Jack et al., "Tracking the Evolution of Resistance to ALK Tyrosine Kinase Inhibitors Through Longitudinal Analysis of Circulating Tumor DNA," JCO Precision Oncology, 2: Supplementary Information pp. 1-9 (Jan. 23, 2018).
Dagogo-Jack et al., "Treatment with Next-Generation ALK Inhibitors Fuels Plasma ALK Mutation Diversity," Clinical Cancer Research, 25(22): 6662-6670 (Nov. 15, 2019).
Davies et al., "Molecular Pathways: ROS1 Fusion Proteins in Cancer," Clinical Cancer Research, 19(15): 4040-4045 (Aug. 1, 2013).
Dearden et al., "Mutation incidence and coincidence in non small-cell lung cancer: meta-analyses by ethnicity and histology (mutMap)," Annals of Oncology, 24: 2371-2376 (Sep. 1, 2013).
Doebele et al., "TRIDENT-1: A Global, Multicenter, Open-label Phase 2 Study Investigating the Activity of Repotrectinib in Advanced Solid Tumors Harboring ROS1 or NTRK1-3 Rearrangements," Turning Point Therapeutics: Poster Abstract #TPS9637 (May 29-Jun. 2, 2020).
Drilon et al., "A Phase 1 Study of the Next-Generaiton ALK/ROS1/TRK Inhibitor Ropotrectinib (TPX-0005) in Patients with Advanced ALK/ROS1/NTRK+ Cancers (TRIDENT-1)," American Society of Clinical Oncology (ASCO) Annual Meeting: Poster Abstract #2513 (Jun. 1-5, 2018).
Drilon et al., "Entrectinib in ROS1 fusion-positive non-small-cell lung cancer: integrated analysis of three phase 1-2 trials," Lancet Oncology, 21: 261-270 (Dec. 11, 2019).
Drilon et al., "Repotrectinib (TPX-0005) Is a Next-Generation ROS1/TRK/ALK Inhibitor That Potently Inhibits ROS1/TRK/ALK Solvent-Front Mutations," Cancer Discovery, 8: 1227-1236 (Aug. 9, 2018).
Drilon et al., "ROS1-dependent cancers—biology, diagnostics and therapeutics," Nature Reviews Clinical Oncology, 18: 35-55 (Jan. 1, 2021).
Drilon et al., "ROS1-dependent cancers—biology, diagnostics and therapeutics," Nature Reviews Clinical Oncology, 18: Supplementary Information, pp. 1-7 (Jan. 1, 2021).
Drilon et al., "Safety and Antitumor Activity of the Multitargeted Pan-TRK, ROS1, and ALK Inhibitor Entrectinib: Combined Results from Two-Phase I Trials (ALKA-372-001 and STARTRK-1)," Cancer Discovery, 7(4): 400-409 (Feb. 9, 2017).
Drilon et al., "Safety and Antitumor Activity of the Multitargeted Pan-TRK, ROS1, and ALK Inhibitor Entrectinib: Combined Results from Two-Phase I Trials (ALKA-372-001 and STARTRK-1)," Cancer Discovery, 7(4): Supplementary Information 1 of 2, pp. 1-2 (Feb. 9, 2017).
Drilon et al., "Safety and Antitumor Activity of the Multitargeted Pan-TRK, ROS1, and ALK Inhibitor Entrectinib: Combined Results from Two-Phase I Trials (ALKA-372-001 and STARTRK-1)," Cancer Discovery, 7(4): Supplementary Information 2 of 2, pp. 1-6 (Feb. 9, 2017).
Drilon et al., "Safety and Preliminary Clinical Activity of Repotrectinib in Patients with Advanced ROS1/TRK Fusion-Positive Solid Tumors (TRIDENT-1 Study)," European Society for Medical Oncology (ESMO): Poster Abstract #4536 (Sep. 27-Oct. 1, 2019).
Elleraas et al., "Conformational Studies and Atropisomerism Kinetics of the ALK Clinical Candidate Lorlatinib (PF-06463922) and Desmethyl Congeners," Angewandte Chemie, 128(11): 3654-3659 (Feb. 15, 2016).
Entrectinib Multi-Discipline Review., "NDA/BLA Multi-disciplinary Reviewand Evaluation NDA 212725," Center for Drug Evaluation and Research: 632 pages (Feb. 1, 2016).
Felip Font et al., "Efficacy and safety of lorlatinib in patients (pts) with ALK+ non-small cell lung cancer (NSCLC) previously treated with 2nd-generation ALK TKIs," Annals of Oncology, 28(5): 478-479 (Sep. 1, 2017).
Fujiwara et al., "Safety and pharmacokinetics of DS-6051b in Japanese patients with non-small cell lung cancer harboring ROS1 fusions: a phase I study," Oncotarget, 9(34): 23729-23737 (May 4, 2018).
Gadgeel et al., "Cumulative incidence rates for CNS and non-CNS progression in two phase II studies of alectinib in ALK-positive NSCLC," BJC, 118: 38-42 (2018).
Gadgeel et al., "Safety and activity of alectinib against systemic disease and brain metastases in patients with crizotinib-resistant ALK-rearranged non-small-cell lung cancer (AF 002JG): results from the dose-fi nding portion of a phase 1/2 study," The Lancet Oncology, 15(1): 1119-1128 (Sep. 2014).
Gainor et al., "Molecular Mechanisms of Resistance to First- and Second-Generation ALK Inhibitors in ALK-Rearranged Lung Cancer," Cancer Discovery, 6(10): 1119-1133 (Oct. 2016).
Gobbini et al., "Real-world outcomes according to treatment strategies in ALK-rearranged non-small-cell lung cancer (NSCLC) patients: an Italian retrospective study," Clinical and Translational Oncology, 22: 294-301 (Mar. 3, 2020).
Guo et al., "Dual potent ALK and ROS1 inhibitors combating drug-resistant mutants: Synthesis and biological evaluation of aminopyridinecontaining diarylaminopyrimidine derivatives," European Journal of Medicinal Chemistry, 158: 322-333 (Sep. 6, 2018).
Hong et al., "Will the clinical development of 4th-generation "double mutant active" ALK TKIs (TPX-0131 and NVL-655) change the future treatment paradigm of ALK+ NSCLC?," Translational Oncology, 14(11): Article 101191 pp. 1-9 (Aug. 5, 2021).
Horn et al., "Monitoring Therapeutic Response and Resistance: Analysis of Circulating Tumor DNA in Patients With ALK+ Lung Cancer," Journal of Thoracic Oncology, 14(11): 1901-1911 (Nov. 2019).
Huang et al., "Discovery of Brigatinib (AP26113), a Phosphine Oxide-Containing, Potent, Orally Active Inhibitor of Anaplastic Lymphoma Kinase," Journal of Medicinal Chemistry, 59: 4948-4964 (May 4, 2016).
International Search Report and Written Opinion for International Application No. PCT/CN2020/088589 dated Feb. 10, 2021.
International Search Report and Written Opinion for International Application No. PCT/CN2020/088590 dated Feb. 3, 2021.
International Search Report and Written Opinion for International Application No. PCT/US2021/030940 dated Sep. 17, 2021.
Johnson et al., "Discovery of (10R)-7-Amino-12-fluoro-2,10,16-trimethyl-15-oxo-10,15,16,17-tetrahydro-2H-8,4-(metheno)pyrazolo[4,3-h][2,5,11]-benzoxadiazacyclotetradecine-3-carbonitrile (PF-06463922), a Macrocyclic Inhibitor of Anaplastic Lymphoma Kinase (ALK) and c-ros Oncogene 1 (ROS1) with Preclinical Brain Exposure and Broad-Spectrum Potency against ALK-Resistant Mutations," Journal of Medicinal Chemistry, 57(11): 4720-4744 (May 13, 2014).
Johnson et al., "Discovery of PF-06463922, a macrocyclic inhibitor of ALK/ROS1 with pre-clinical brain exposure and broad spectrum potency against ALK-resistant mutations," Journal of Medicinal Chemistry, 57(11): Supporting Information S1-S57 (May 13, 2014).
Katayama et al., "The new-generation selective ROS1/NTRK inhibitor DS-6051b overcomes crizotinib resistant ROS1-G2032R mutation in preclinical models," Nature Communications, 10: Article No. 3604 pp. 1-12 (Aug. 9, 2019).

(56) References Cited

OTHER PUBLICATIONS

Katayama et al., "Two Novel ALK Mutations Mediate Acquired Resistance to the Next-Generation ALK Inhibitor Alectinib," Clinical Cancer Research, 20(22): 5686-5696 (Nov. 15, 2014).
Kong et al., "Drug Discovery Targeting Anaplastic Lymphoma Kinase (ALK)," Journal of Medicinal Chemistry: 28 pages (2019).
Ku et al., "Entrectinib resistance mechanisms in ROS1-rearranged non-small cell lung cancer," Investigational New Drugs, 38: 360-368 (Apr. 2020).
Leonetti et al., "COVID-19 in lung cancer patients receiving ALK/ROS1 inhibitor," European Journal of Cancer, 132: 122-124 (Jun. 2020).
Lin et al., "ALK and ROS1 Inhibitors: New Agents Not Yet Approved," 2021 Targeted Therapies of Lung Cancer Meeting: 17 pages (Feb. 17-21, 2021).
Lin et al., "Efficacy of Platinum/Pemetrexed Combination Chemotherapy in ALK-Positive NSCLC Refractory to Second-Generation ALK Inhibitors," Journal of Thoracic Oncology, 15(2): 258-265 (Feb. 2020).
Lin et al., "Impact of EML4-ALK Variant on Resistance Mechanisms and Clinical Outcomes in ALK-Positive Lung Cancer," Journal of Clinical Oncology, 36(12): 1199-1206 (Apr. 20, 2018).
Lin et al., "Recent Advances in Targeting ROS1 in Lung Cancer," Journal of Thoracic Oncology, 12(11): 1611-1625 (Nov. 2017).
Lin et al., "Spectrum of Mechanisms of Resistance to Crizotinib and Lorlatinib in ROS1 Fusion-Positive Lung Cancer," Clinical Cancer Research, 27(10): OF1-OF11 (Mar. 8, 2021).
Liu et al., "Characterization of on-target adverse events caused by TRK inhibitor therapy," Annals of Oncology, 31(9): 1207-1215 (Sep. 2020).
Liu et al., "Design, synthesis and biological evaluations of 2-amino-4-(1-piperidine) pyridine derivatives as novel anti crizotinib-resistant ALK/ROS1 dual inhibitors," European Journal of Medicinal Chemistry, 179: 358-375 (Oct. 1, 2019).
Lorbrena (Lorlatinib) Full Prescribing Information and Label Initial U.S. Approval: Nov. 2018.
Lorlatinib Multi-Discipline Review., "NDA/BLA Multi-disciplinary Review and Evaluation NDA 210868," Center for Drug Evaluation and Research: 302 pages (Feb. 1, 2016).
Lorviqua Public Assessment Report., Published by the European Medicines Agency on Feb. 28, 2019 (148 pages).
Mallinson et al., "Macrocycles in drug discovery," Future Med Chem, 4(11): 1409-1438 (2012).
Noe et al., "ALK Mutation Status Before and After Alectinib Treatment in Locally Advanced or Metastatic ALK-Positive NSCLC: Pooled Analysis of Two Prospective Trials," Journal of Thoracic Oncology, 15(4): 601-608 (Apr. 2020).
Nosaki et al., "P2.06-002 Phase I Study of DS-6051b, a ROS1/NTRK Inhibitor, in Japanese Subjects with Advanced Solid Tumors Harboring Either a ROS1 or NTRK Fusion Gene," Journal of Thoracic Oncology, 12(1): Supplement S1069 (Jan. 1, 2017).
Ou et al., "OA02.03 Clinical Activity of Lorlatinib in Patients with ROS1+ Advanced Non-Small Cell Lung Cancer: Phase 2 Study Cohort EXP-6," Journal of Thoracic Oncology, 13(10): Supplement S322-S323 (Oct. 1, 2018).
Papadopoulos et al., "U.S. Phase I First-in-human Study of Taletrectinib (DS-6051b/AB-106), a ROS1/TRK Inhibitor, in Patients with Advanced Solid Tumors," Clinical Cancer Research, 26(18): 4785-4974 (Sep. 15, 2020).
Peters et al., "Alectinib versus Crizotinib in Untreated ALK-Positive Non-Small-Cell Lung Cancer," The New England Journal of Medicine, 377: 829-838 (Aug. 31, 2017).
Rajan et al., "The mechanism of cancer drug addiction in ALK-positive T-Cell lymphoma," Oncogene, 39: 2103-2117 (Mar. 2020).
Recondo et al., "Diverse Resistance Mechanisms to the Third-Generation ALK Inhibitor Lorlatinib in ALK-Rearranged Lung Cancer," Clinical Cancer Research, 26(1): 242-255 (Oct. 4, 2019).
Sabari et al., "The activity, safety, and evolving role of brigatinib in patients with ALK-rearranged non-small cell lung cancers," OncoTargets and Therapy, 10:1983-1992 (Apr. 6, 2017).
Sakamoto et al., "CH5424802, a Selective ALK Inhibitor Capable of Blocking the Resistant Gatekeeper Mutant," Cancer Cell, 19(5): 679-690 (May 17, 2011).
Sehgal et al., "Cases of ROS1-rearranged lung cancer: when to use crizotinib, entrectinib, lorlatinib, and beyond?" Precis Cancer Med, 3(17): pp. 1-11 (Jun. 15, 2020).
Shaw et al., "ALK Resistance Mutations and Efficacy of Lorlatinib in Advanced Anaplastic Lymphoma Kinase-Positive Non-Small-Cell Lung Cancer," Journal of Clinical Oncology, 37(16): 1370-1379 (Mar. 20, 2019).
Shaw et al., "Crizotinib in ROS1-rearranged advanced non-small-cell lung cancer (NSCLC): updated results, including overall survival, from Profile 1001," Annals of Oncology, 30(7): 1121-1126 (Jul. 2019).
Shaw et al., "First-Line Lorlatinib or Crizotinib in Advanced ALK-Positive Lung Cancer," The New England Journal of Medicine, 383: 2018-2029 (Nov. 19, 2020).
Shaw et al., "First-Line Lorlatinib or Crizotinib in Advanced ALK-Positive Lung Cancer," The New England Journal of Medicine, 383: Supplementary Appendix pp. 1-29 (Nov. 19, 2020).
Shaw et al., "Lorlatinib in non-small-cell lung cancer with ALK or ROS1 rearrangement: an international, multicentre, open-label, single-arm first-in-man phase 1 trial," Lancet Oncology, 18: 1590-1599 (Dec. 2017).
Shaw et al., "Lorlatinib in non-small-cell lung cancer with ALK or ROS1 rearrangement: an international, multicentre, open-label, single-arm first-in-man phase 1 trial," Supplementary Appendix: 1-305 (Dec. 2017).
Soda et al., "Identification of the transforming EML4-ALK fusion gene in non-small-cell lung cancer," Nature, 448: 561-566 (Jul. 11, 2007).
Solomon et al., "Lorlatinib in patients with ALK-positive non-small-cell lung cancer: results from a global phase 2 study," The Lancet Oncology, 19(12): 1654-1667 (Dec. 2018).
Stypinski et al., "Metabolism, Excretion, and Pharmacokinetics of Lorlatinib (PF-06463922) and Evaluation of the Impact of Radiolabel Position and Other Factors on Comparability of Data Across 2 ADME Studies," The Journal of Clinical Pharmacology, 60(9): 1254-1267 (May 22, 2020).
Syed., "Lorlatinib: First Global Approval," Drugs, 79: 93-98 (Jan. 2, 2019).
Syeda-Mahmood et al., "Shape-based Similarity Retreival of Doppler Images for Clinical Decision Support," IEEE Computer Society Conference on Computer Vision and Pattern Recognition: 8 pages (Aug. 5, 2010).
Tangpeerachaikul et al., "Evaluating TRKB Activity of Novel Preclinical Brain-Penetrant ROS1 and ALK Inhibitors," AACR-NCI-EORTC Virutal International Conference on Molecular Targets and Cancer Therapeutics: 10 pages (Oct. 7-10, 2021).
Tangpeerachaikul et al., "NVL-655 Exhibits Antitumor Activity in Lorlatinib-Resistant Subcutaneous and Intracranial Models of ALK-Rearranged NSCLC," AACR-NCI-EORTC Virutal International Conference on Molecular Targets and Cancer Therapeutics: 9 pages (Oct. 7-10, 2021).
Tu et al., "Molecular inhibitory mechanism study on the potent inhibitor brigatinib against four crizotinib-resistant ALK mutations," Journal of Cellular Biochemistry, 120(1): 562-574 (Sep. 6, 2018).
Yamazaki et al., "Mechanistic Understanding of Translational Pharmacokinetic-Pharmacodynamic Relationships in Nonclinical Tumor Models: A Case Study of Orally Available Novel Inhibitors of Anaplastic Lymphoma Kinase," Drug Metabolism and Disposition, 43: 54-62 (Jan. 2015).
Yoda et al., "Sequential ALK Inhibitors Can Select for Lorlatinib-Resistant Compound ALK Mutations in ALK-Positive Lung Cancer," Cancer Discovery, 8(6): 715-729 (Apr. 12, 2018).
Yoda et al., "Sequential ALK Inhibitors Can Select for Lorlatinib-Resistant Compound ALK Mutations in ALK-Positive Lung Cancer," Cancer Discovery, 8(6): Author Manuscript pp. 1-36 (2018).
Yoda et al., "Sequential ALK Inhibitors Can Select for Lorlatinib-Resistant Compound ALK Mutations in ALK-Positive Lung Cancer," Cancer Discovery, 8(6): Supplementary Figures pp. 1-11 (Apr. 12, 2018).

(56) References Cited

OTHER PUBLICATIONS

Yoda et al., "Sequential ALK Inhibitors Can Select for Lorlatinib-Resistant Compound ALK Mutations in ALK-Positive Lung Cancer," Cancer Discovery, 8(6): Supplementry Methods pp. 1-2 (Apr. 12, 2018).

Yun et al., "Repotrectinib Exhibits Potent Antitumor Activity in Treatment-Naïve and Solvent-Front-Mutant ROS1-Rearranged Non-Small Cell Lung Cancer," Clinical Cancer Research, 26(13): OF1-OF9 (Jul. 2020).

Zhang et al., "Determination of the mean pressure gradient in aortic stenosis by Doppler echocardiography," European Heart Journal, 6: 999-1005 (Dec. 1, 1985).

Zhang et al., "The Potent ALK Inhibitor Brigatinib (AP26113) Overcomes Mechanisms of Resistance to First- and Second-Generation ALK Inhibitors in Preclinical Models," Clinical Cancer Research, 22(22): 5527-5538 (Nov. 2016).

Zheng et al., "Investigation on the prognostic impact of concurrent genomic alterations in crizotinib-treated EML4-ALK-rearranged advanced non-small cell lung cancer patients," Lung Cancer, 146: 209-216 (Aug. 2020).

Zhu et al., "A Novel Sequentially Evolved EML4-ALK Variant 3 G1202R/S1206Y Double Mutation In Cis Confers Resistance to Lorlatinib: A Brief Report and Literature Review," JTO Clinical and Research Reports, 2(1): 27 pages (Oct. 25, 2020).

Zhu et al., "An International Real-World Analysis of the Efficacy and Safety of Lorlatinib Through Early or Expanded Access Programs in Patients With Tyrosine Kinase Inhibitor-Refractory ALK-Positive or ROS1-Positive NSCLC," Journal of Thoracic Oncology, 15(9): 1484-1496 (Sep. 2020).

Zou et al., "PF-06463922 is a potent and selective next-generation ROS1/ALK inhibitor capable of blocking crizotinib-resistant ROS1 mutations," PNAS, 112(11): 3493-3498 (Mar. 17, 2015).

Zou et al., "PF-06463922 is a potent and selective next-generation ROS1/ALK inhibitor capable of blocking crizotinib-resistant ROS1 mutations," PNAS, Supporting Information: 1-8 (Mar. 17, 2015).

Zou et al., "The ALK/ROS1 Inhibitor PF-06463922 Has Potency across Resistant ALK Mutants," Cancer Discovery, 5: 902 (Jul. 2, 2015).

Hua et al., "Real-world circulating tumor DNA analysis depicts resistance mechanism and clonal evolution in ALK inhibitor-treated lung adenocarcinoma patients," ESMO Open Cancer Horizons, 7(1): 8 pages (2022).

Tangpeerachalkul et al., "NVL-66: a selective, potent 4G ALK TKI; NVL-655: dose-dependent in vivo anti-tumor activity against double mutant ALK; NVL-655: preclinical CNS penetrance and activity," 2022 Targeted Therapies of Lung Cancer Meeting: 3 pages (Feb. 22-26, 2022).

Zhao et al., "A Bayesian network meta-analysis regarding the comparative efficacy of therapeutics for ALK-positive, brain metastatic non-small cell lung cancer," Pharmacological Research, 174: 105931 (12 pages)(2021).

International Search Report and Written Opinion for International Application No. PCT/US2021/030842 dated Nov. 5, 2021.

Pubchem SID 327469789: 7 pages (2017).

Antonescu et al., "Molecular Characterization of Inflammatory Myofibroblastic Tumors with Frequent ALK and ROS1 Fusions and Rare Novel RET Gene Rearrangement," Am. J. Surg. Pathol., 39(7): Author Manuscript pp. 1-19 (2015).

Arai et al., "Mouse Model for ROS1-Rearranged Lung Cancer," Plos One, 8(2): e56010 pp. 1-7 (2013).

Bayliss et al., "Molecular mechanisms that underpin EML4-ALK driven cancers and their response to targeted drugs," Cellular and Molecular Life Sciences, 73: 1209-1224 (2016).

Besse et al., "Clinical Evaluation of NVL-520, a Highly Selective ROS1 Inhibitor, in Patients with Advanced ROS1-Positive Solid Tumors: The Phase 1/2 ARROS-1 Study," European Lung Cancer Congress: Nuvalent Poster Abstract #78TiP (Mar. 30, 2022).

Birch et al., "Chromosome 3 Anomalies Investigated by Genome Wide SNP Analysis of Benign, Low Malignant Potential and Low Grade Ovarian Serous Tumours," Plos One, 6(12): e28250 pp. 1-20 (2011).

Bresler et al., "ALK mutations confer differential oncogenic activation and sensitivity to ALK inhibition therapy in neuroblastoma," Cancer Cell., 26(5): Author Manuscript pp. 1-29 (2014).

Charest et al., "Fusion of FIG to the Receptor Tyrosine Kinase ROS in a Glioblastoma with an Interstitial del(6)(q21q21)," Genes, Chromosomes & Cancer, 37: 58-71 (2003).

Chia et al., "Prevalence and natural history of ALK positive non-small-cell lung cancer and the clinical impact of targeted therapy with ALK inhibitors," Clinical Epidemiology, 6: 423-432 (2014).

Cocco et al., "NTRK fusion-positive cancers and TRK inhibitor therapy," Nat. Rev. Clin. Oncol., 15(12): Author Manuscript pp. 1-34 (2018).

Davare et al., "Rare but recurrent ROS1 fusions resulting from chromosome 6q22 microdeletions are targetable oncogenes in glioma," Clin. Canc. Res., 24(24): Author Manuscript pp. 1-27 (2018).

Demicco et al., "New Therapeutic Targets in Soft Tissue Sarcoma," Adv. Anat. Pathol., 19(3): Author Manuscript pp. 1-21 (2012).

Deshpande et al., "Abstract P249: Preclinical antitumor activity of NVL-520 in patient-derived models harboring ROS1 fusions, including G2032R solvent front mutation," Mol. Canc. Ther., 20(Supplement 12): P249 (2021).

Doebele et al., "Genomic landscape of entrectinib resistance from ctDNA analysis in STARTRK-2," Annals of Oncology, 30(Supplement 5): v865 (2019).

Drilon et al., "Entrectinib in ROS1 fusion-positive non-small-cell lung cancer: integrated analysis of three phase 1-2 trials," Lancet Oncol., 21(2): Author Manuscript pp. 1-23 (2020).

Drilon et al., "ROS1-dependent cancers—biology, diagnostics and therapeutics," Nat. Rev. Clin. Oncol., 18(1): Author Manuscript pp. 1-45 (2021).

Eid et al., "KinMap: a web-based tool for interactive navigation through human kinome data," BMC Bioinformatics, 18(16): pp. 1-6 (2017).

Entrectinib Prescribing Information Label., "Rozlytrek (entrectinib) capsules, for oral use Initial U.S. Approval: 2019," U.S. Food and Drug Administration: 25 pages (Aug. 2019).

Fleuren et al., "Phosphoproteomic Profiling Reveals ALK and MET as Novel Actionable Targets across Synovial Sarcoma Subtypes," Cancer Research, 77(16): 4279-4292 (2017).

Gainor et al., "Patterns of Metastatic Spread and Mechanisms of Resistance to Crizotinib in ROS1-Positive Non-Small-Cell Lung Cancer," JCO Precision Oncology, 1: pp. 1-13 (2017).

George et al., "Activating mutations in ALK provide a therapeutic target in neuroblastoma," Nature, 455(7215): Author Manuscript pp. 1-11 (2008).

Giacomini et al., "Breakpoint Analysis of Transcriptional and Genomic Profiles Uncovers Novel Gene Fusions Spanning Multiple Human Cancer Types," Plos Genetics, 9(4): e1003464 pp. 1-19 (2013).

Golding et al., "The function and therapeutic targeting of anaplastic lymphoma kinase (ALK) in non-small cell lung cancer (NSCLC)," Molecular Cancer, 17(52): pp. 1-15 (2018).

Gu et al., "Survey of Tyrosine Kinase Signaling Reveals ROS Kinase Fusions in Human Cholangiocarcinoma," Plos One, 6(1): e15640 pp. 1-9 (2011).

Hallberg et al., "The role of the ALK receptor in cancer biology," Annals of Oncology, 27(Supplement 3): ii4-ii15 (2016).

Holla et al., "ALK: a tyrosine kinase target for cancer therapy," Cold Spring Harbor Molecular Case Studies, 3:a001115 pp. 1-20 (2017).

Jordan et al., "Prospective comprehensive molecular characterization of lung adenocarcinomas for efficient patient matching to approved and emerging therapies," Cancer Discov., 7(6): Author Manuscript pp. 1-21 (2017).

Keddy et al., "Resistance Profile and Structural Modeling of Next-Generation ROS1 Tyrosine Kinase Inhibitors," Molecular Cancer Therapeutics, 21(2): 336-346 (2022).

(56) References Cited

OTHER PUBLICATIONS

Li et al., "Efficacy of Crizotinib among Different Types of ROS1 Fusion Partners in Patients with ROS1-Rearranged Non-Small Cell Lung Cancer," Journal of Thoracic Oncology, 13(7): 987-995 (2018).
Lin et al., "Small cell transformation of ROS1 fusion-positive lung cancer resistant to ROS1 inhibition," NPJ Precision Oncology, 4: Article No. 21 pp. 1-8 (2020).
Lin et al., "Spectrum of Mechanisms of Resistance to Crizotinib and Lorlatinib in ROS1 Fusion-Positive Lung Cancer," Clin. Canc. Res., 27(10): Author Manuscript pp. 1-24 (2021).
Liu et al., "Characterization of On-Target Adverse Events Caused by TRK Inhibitor Therapy," Ann. Oncol., 31(9): Author Manuscript pp. 1-17 (2020).
Lorbrena (lorlatinib) Prescribing Information Label; Food and Drug Administation: 31 pages (2021).
Marks et al., "ROS1-GOPC/FIG: a novel gene fusion in hepatic angiosarcoma," Oncotarget, 10(2): 245-251 (2019).
Moog-Lutz et al., "Activation and Inhibition of Anaplastic Lymphoma Kinase Receptor Tyrosine Kinase by Monoclonal Antibodies and Absence of Agonist Activity of Pleiotrophin," The Journal of Biological Chemistry, 280(28): 26039-26048 (2005).
Murray et al., "TPX-0131, a Potent CNS-penetrant, Next-generation Inhibitor of Wild-type ALK and ALK-resistant Mutations," Molecular Cancer Therapeutics, 20(9): 1499-1507 (2021).
Murugan et al., "Anaplastic Thyroid Cancers Harbor Novel Oncogenic Mutations of the ALK Gene," Cancer Research, 71(13): Author Manuscript pp. 1-14 (2011).
Neel et al., "Differential subcellular localization regulates oncogenic signaling by ROS1 kinase fusion proteins," Cancer Research, 79(3): Author Manuscript pp. 1-19 (2019).
Okubo et al., "Aberrant activation of ALK kinase by a novel truncated form ALK protein in neuroblastoma," Oncogene, 31: 4667-4676 (2012).
Ou et al., "A Catalog of 5' Fusion Partners in ROS1-Positive NSCLC Circa 2020," JTO Clinical and Research Reports, 1(3): pp. 1-5 (2020).
Ou et al., "CNS metastasis in ROS1+ NSCLC: An urgent call to action, to understand, and to overcome," Lung Cancer, 130: 201-207 (Apr. 2019).
Patil et al., "The incidence of brain metastases in stage IV ROS1-rearranged non-small cell lung cancer and rate of central nervous system progression on crizotinib," J. Thorac. Oncol., 13(11): Author Manuscript pp. 1-17 (2018).
Pelish et al., "Abstract 1465: NUV-520 (NVL-520) is a brain-penetrant and highly selective ROS1 inhibitor with antitumor activity against the G2032R solvent front mutation," Cancer Res., 81(Supplement 13): Abstract 1465 (2021).
Pelish et al., "NUV-520 is a brain-penetrant and highly selective ROS1 inhibitor with antitumor activity against the G2032R solvent front mutation," American Association for Cancer Research (AACR): Nuvalent Poster Abstract #1465 (Apr. 2021).
Pelish et al., "NUV-655 is a selective, brain-penetrant ALK inhibitor with antitumor activity against the lorlatinib-resistant G1202R/L1196M compound mutation," American Association for Cancer Research (AACR): Nuvalent Poster Abstract #1468 (Apr. 2021).
Perkins et al., "Childhood anaplastic large cell lymphoma has a high incidence of ALK gene rearrangement as determined by immunohistochemical staining and fluorescent in situ hybridisation: a genetic and pathological correlation," British Journal of Haematology, 131(5): 624-627 (2005).
Rikova et al., "Global Survey of Phosphotyrosine Signaling Identifies Oncogenic Kinases in Lung Cancer," Cell, 131(6): 1190-1203 (2007).
Rimkunas et al., "Analysis of Receptor Tyrosine Kinase ROS1-Positive Tumors in Non-Small Cell Lung Cancer: Identification of a FIG-ROS1 Fusion," Clincal Cancer Research, 18(16): 4449-4457 (2012).
Rizvi et al., "Cholangiocarcinoma—evolving concepts and therapeutic strategies," Nat. Rev. Clin. Oncol., 15(2): Author Manuscript pp. 1-37 (2018).
Rozlytrek (entrectinib) Prescribing Information Label; Food and Drug Administation: 25 pages (2019).
Shaw et al., "ALK in Lung Cancer: Past, Present, and Future," Journal of Clinical Oncology, 31(8): 1105-1111 (2013).
Shaw et al., "Lorlatinib in ALK- or ROS 1-rearranged non-small cell lung cancer: an international, multicenter, open-label phase 1 trial," Lancet Oncology, 18(12): Author Manuscript pp. 1-20 (2017).
Shults et al., "Versatile Fluorescence Probes of Protein Kinase Activity," Journal of the American Chemical Society, 125(47): 14248-14249 (2003).
Takeuchi et al., "RET, ROS1 and ALK fusions in lung cancer," Nature Medicine, 18(3): 378-381 (2012).
Tangpeerachaikul et al., "Abstract P247: Evaluating TRKB activity of novel preclinical brain-penetrant ROS1 and ALK inhibitors," Mol. Canc. Ther., 20(Supplement 12): P247 (2021).
Tangpeerachaikul et al., "Preclinical activity of NVL-520 in ROS1-driven cancer models with diverse fusion partners and kinase-domain mutations," American Association for Cancer Research: Nuvalent Poster Abstract #3336 (Apr. 8, 2022).
Tangpeerachaikul et al., "Preclinical activity of NVL-655 in ALK-driven cancer models beyond non-small cell lung cancer," American Association for Cancer Research: Nuvalent Poster Abstract #3337 (Apr. 8, 2022).
Trigg et al., "ALK in Neuroblastoma: Biological and Therapeutic Implications," Cancers, 10(113): pp. 1-26 (2018).
Umapathy et al., "Targeting anaplastic lymphoma kinase in neuroblastoma," APMIS Journal of Pathology, Microbiology and Immunology, 127(5): 288-302 (2019).
Valery et al., "Cholangiocarcinoma with STRN-ALK translocation treated with ALK inhibitors," Digestive and Liver Disease: Article in Press pp. 1-2 (2021).
Weisner et al., "Alternative transcription initiation leads to expression of a novel ALK isoform in cancer," Nature, 56(7573): Author Manuscript pp. 1-35 (2015).
Yamazaki et al., "Translational Pharmacokinetic-Pharmacodynamic Modeling for an Orally Available Novel Inhibitor of Anaplastic Lymphoma Kinase and c-Ros Oncogene 1," The Journal of Pharmacology and Experimental Therapeutics, 351: 67-76 (Oct. 2014).

HETEROAROMATIC MACROCYCLIC ETHER CHEMOTHERAPEUTIC AGENTS

RELATED APPLICATIONS

This application is a continuation of International Patent Application No. PCT/US2021/030842, filed May 5, 2021; which claims the benefit of priority to International Patent Application No. PCT/CN2020/088590, filed May 5, 2020; and U.S. Provisional Patent Application No. 63/125,733, filed Dec. 15, 2020.

BACKGROUND

Receptor tyrosine kinases (RTKs) are cell surface enzymes that receive outside signals, such as whether to grow and divide, and transmit those signals in the cell through kinase activity. Many RTKs are proto-oncogenes; aberrant RTK activity can drive cell survival, growth and proliferation leading to cancer and related disorders. This aberrant kinase activity can be caused by mutations such as activating mutations in the kinase domain, gene rearrangements that result in fusion proteins containing the intact kinase domain, amplification and other means. RTK proto-oncogenes include ROS1, anaplastic lymphoma kinase (ALK), NTRK1 (encodes TRKA), NTRK2 (encodes TRKB), and NTRK3 (encodes TRKC).

ROS1 is an RTK proto-oncogene, with ROS1 rearrangements detected in non-small cell lung cancer (NSCLC), glioblastoma, inflammatory myofibroblastic tumor (IMT), cholangiocarcinoma, ovarian cancer, gastric cancer, colorectal cancer, angiosarcoma, and spitzoid melanoma. Oncogenic ROS1 gene fusions contain the kinase domain of ROS1 (3' region) fused to the 5' region of a variety of partner genes. Examples of ROS1 fusion partner genes observed in NSCLC include SLC34A2, CD74, TPM3, SDC4, EZR, LRIG3, KDELR2, CEP72, CLTL, CTNND2, GOPC, GPRC6A, LIMA1, LRIG3, MSN, MYO5C, OPRM1, SLC6A17 (putative), SLMAP, SRSF6, TFG, TMEM106B, TPD52L1, ZCCHC8 and CCDC6. Other fusion partners include CAPRIN1, CEP85L, CHCHD3, CLIP1 (putative), EEF1G, KIF21A (putative), KLC1, SART3, ST13 (putative), TRIM24 (putative), ERCI, FIPIL1, HLAA, KIAA1598, MYO5A, PPFIBP1, PWWP2A, FN1, YWHAE, CCDC30, NCOR2, NFKB2, APOB, PLG, RBP4, and GOLGB1.

ALK is an RTK proto-oncogene, with ALK rearrangements detected in many cancers, including NSCLC, anaplastic large cell lymphoma (ALCL), IMT, diffuse large B-cell lymphoma (DLBCL), esophageal squamous cell carcinoma (ESCC), renal medullary carcinoma, renal cell carcinoma, breast cancer, colon cancer, serous ovarian cancer, papillary thyroid cancer, and spitzoid tumors, and ALK activating mutations detected in neuroblastoma. Oncogenic ALK gene fusions contain the kinase domain of ALK (3' region) fused to the 5' region of more than 20 different partner genes, the most common being EML4 in NSCLC and NPM in ALCL. Other partner genes include TMP1, WDCP, GTF2IRD1, TPM3, TPM4, CLTC, LMNA, PRKAR1A, RANBP2, TFG, FN1, KLC1, VCL, STRN, HIP1, DCTN1, SQSTM1, TPR, CRIM1, PTPN3, FBXO36, ATIC and KIF5B.

NTRK1, NTRK2 and NTRK3 are RTK proto-oncogenes that encode TRK-family kinases, with NTRK1, NTRK2 and NTRK3 chromosomal rearrangements detected at low frequency in many cancers. For treatment of ROS1-positive or ALK-positive patients, however, TRK inhibition, particularly in the central nervous system (CNS), has been associated with adverse reactions, including dizziness/ataxia/gait disturbance, paraesthesia, weight gain and cognitive changes.

Agents in the prior art used to treat oncogenic ROS1 and ALK have substantial deficiencies. These deficiencies may represent one or more of the following: associated TRK inhibition, limited CNS activity, and inadequate activity against resistance mutations. Treatment of ROS1-positive or ALK-positive patients accompanied by TRK inhibition is associated with adverse reactions, particularly in the CNS, including dizziness/ataxia/gait disturbance, paraesthesia, weight gain and cognitive changes. Additionally, there is a need for CNS-penetrant and TRK-sparing inhibitors of the wild type ROS1 kinase domain and ROS1 with acquired resistance mutations occurring either individually or in combination, including G2032R, D2033N, S1986F, S1986Y, L2026M, L1951R, E1935G, L1947R, G1971E, E1974K, L1982F, F2004C, F2004V, E2020K, C2060G, F2075V, V2089M, V2098I, G2101A, D2113N, D2113G, L2155S, L2032K, and L2086F. Likewise, there is a need for CNS-penetrant and TRK-sparing inhibitors of ALK with acquired resistance mutations. A variety of ALK drug resistance mutations, occurring either individually or in combination, have been reported, including G1202R, L1196M, G1269A, C1156Y, I1171T, I1171N, I1171S, F1174L, V1180L, S1206Y, E1210K, 1151Tins, F1174C, G1202del, D1203N, S1206Y, S1206C, L1152R, L1196Q, L1198P, L1198F, R1275Q, L1152P, C1156T, and F1245V.

SUMMARY

An aspect disclosed herein are compounds of Formula (I) or a pharmaceutically acceptable salt thereof:

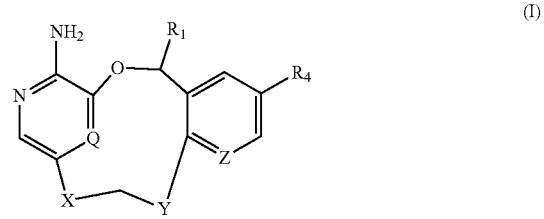

(I)

wherein
Q is CH or N;
Z is $CR_5$ or N;
X is a 5-membered heteroarylene, comprising 1 to 3 heteroatoms selected from the group consisting of nitrogen, oxygen and sulfur; wherein the 5-membered heteroarylene is substituted with 0, 1, or 2 occurrences of $R_2$;
Y is a heteroarylene selected from the group consisting of 1,2*-substituted-imidazolylene, 4*,5-substituted-imidazolylene, 4*,5-substituted-1,2,3-oxadiazolylene, 3*,4-substituted-1,2,5-oxadiazolylene, 3*,4-substituted-1,2-oxazolylene, 4*,5-substituted-1,3-oxazolylene, 2*,3-substituted-pyrazinylene, 1*,5-substituted-pyrazolylene, 3*,4-substituted-pyrazolylene, 3*,4-substituted-pyridazinylene, 2*,3-substituted-pyridinylene, 4*,5-substituted-pyrimidinylene, 2*,3-substituted-pyrrolylene, 5*,6-substituted-1,2,3,4-tetrazinylene, 1*,5-substituted-1,2,3,4-tetrazolylene, 1,5*-substituted-1,2,3,4-tetrazolylene, 4*,5-substituted-1,2,3-thiadiazolylene, 3*,4-substituted-1,2,5-thiadiazolylene, 3*,4-substituted-1,2-thiazolylene, 4*,5-substituted-1,3-thiazolylene, 4*,5-substituted-1,2,3- triazinylene, 5*,6-substituted-1,2,4-triazinylene, 5,6*-substituted-1,2,4-triazinylene, 1*,5-substituted-1,2,3-triazolylene, 4*,5-substituted-1,2,3-triazolylene, 1*,5-substituted-1,2,4-triazolylene, 1,5*-substituted-1,2,4-triazolylene, and 3*,4-substituted-1,2,4-triazolylene; wherein the heteroarylene is substituted with 0, 1, or 2 occurrences of $R_3$;

* indicates the point of attachment of X or Y to the methylene group bonded to X and Y;

in Y the heteroarylene ring atom alpha to the point of attachment to the methylene group and beta to the point of attachment to the aromatic ring comprising Z is nitrogen;

$R_1$ is selected from the group consisting of H, methyl, and hydroxymethyl;

each $R_2$ is independently selected from the group consisting of H, halo, CN, $C_{1-4}$ alkoxy, $C_{1-4}$ alkyl, halo-$C_{1-4}$ alkyl, $C_{3-4}$ cycloalkylmethyl, $C_{3-6}$ cycloalkyl, and $C_{3-6}$ heterocycloalkyl;

$R_3$ is selected from the group consisting of H, halo, CN, $C_{1-4}$ alkoxy, halo-$C_{1-4}$ alkyl, and $C_{1-4}$ alkyl; and each of $R_4$ and $R_5$ is independently H or F.

In certain embodiments, the present disclosure provides a pharmaceutical composition suitable for use in a subject in the treatment or prevention of cancer comprising an effective amount of any of the compounds described herein (e.g., a compound of the disclosure, such as a compound of Formula (I), or a pharmaceutically acceptable salt thereof, and one or more pharmaceutically acceptable excipients. In certain embodiments, the pharmaceutical preparations may be for use in treating or preventing a condition or disease as described herein.

An aspect of the disclosure is methods of treating cancer that is characterized by one or more mutations in the ROS1 or ALK genes, comprising administering to a subject in need thereof an effective amount of a compound as disclosed herein (e.g., a compound of Formula (I) or any of the embodiments thereof disclosed herein). In certain embodiments the compound is an inhibitor of ROS1, other embodiments the compound is an inhibitor of ALK, in additional embodiments the compound is an inhibitor of ROS1 and ALK. In certain aspects, the human subject is in need of such treatment.

These cancers include, but are not limited to, non-small cell lung cancer, inflammatory myofibroblastic tumor, ovarian cancer, spitzoid melanoma, glioblastoma, cholangiocarcinoma, gastric cancer, colorectal cancer, angiosarcoma, anaplastic large cell lymphoma, diffuse large B-cell lymphoma, esophageal squamous cell carcinoma, renal medullary carcinoma, renal cell carcinoma, breast cancer, papillary thyroid cancer, and neuroblastoma.

In some embodiments, the method of treating or preventing cancer may comprise administering a compound of Formula (I) conjointly with one or more other chemotherapeutic agent(s).

DETAILED DESCRIPTION

Definitions

Unless defined otherwise, all technical and scientific terms used herein have the meaning commonly understood by a person skilled in the art of the present disclosure. The following references provide one of skill with a general definition of many of the terms used in this disclosure: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

In some embodiments, chemical structures are disclosed with a corresponding chemical name. In case of conflict, the chemical structure controls the meaning, rather than the name.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited are not substantially changed by the presence of more than that which is recited, but excludes prior art embodiments.

Unless specifically stated or obvious from context, as used herein, the term "or" is understood to be inclusive. Unless specifically stated or obvious from context otherwise, as used herein, the terms "a", "an", and "the" are understood to be singular or plural.

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group, preferably a lower alkyl group, having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include methyl, ethyl, n-propyl, iso-propyl, n-butyl, sec-butyl, tert-butyl, pentyl, hexyl, pentyl and octyl. A $C_1$-$C_6$ straight chained or branched alkyl group is also referred to as a "lower alkyl" group.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents, if not otherwise specified, can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxy, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "$C_{x-y}$" when used in conjunction with a chemical moiety, such as, acyl, acyloxy, alkyl, alkenyl, alkynyl, or alkoxy is meant to include groups that contain from x to y carbons in the chain. For example, the term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-tirfluoroethyl, etc. $C_0$ alkyl indicates a hydrogen where the group is in a terminal position, a bond if internal. The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond respectively.

The term "alkylamino", as used herein, refers to an amino group substituted with at least one alkyl group.

The term "alkylthio", as used herein, refers to a thiol group substituted with an alkyl group and may be represented by the general formula alkylS—.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "amide", as used herein, refers to a group

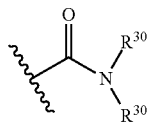

wherein each $R^{30}$ independently represents a hydrogen or hydrocarbyl group, or two $R^{30}$ are taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

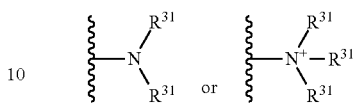

wherein each $R^{31}$ independently represents a hydrogen or a hydrocarbyl group, or two $R^{31}$ are taken together with the N atom to which they are attached complete a heterocycle having from 4 to 8 atoms in the ring structure. The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably, the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

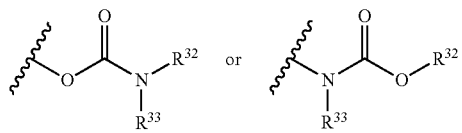

wherein $R^{32}$ and $R^{33}$ independently represent hydrogen or a hydrocarbyl group, such as an alkyl group, or $R^{32}$ and $R^{33}$ taken together with the intervening atom(s) complete a heterocycle having from 4 to 8 atoms in the ring structure.

The terms "carbocycle", and "carbocyclic", as used herein, refers to a saturated or unsaturated ring in which each atom of the ring is carbon. The term carbocycle includes both aromatic carbocycles and non-aromatic carbocycles. Non-aromatic carbocycles include both cycloalkane rings, in which all carbon atoms are saturated, and cycloalkene rings, which contain at least one double bond.

The term "carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

A "cycloalkyl" group is a cyclic hydrocarbon which is completely saturated. "Cycloalkyl" includes monocyclic and bicyclic rings. Typically, a monocyclic cycloalkyl group has from 3 to about 10 carbon atoms, more typically 3 to 8 carbon atoms unless otherwise defined. The second ring of a bicyclic cycloalkyl may be selected from saturated, unsaturated and aromatic rings. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings. A "cycloalkenyl" group is a cyclic hydrocarbon containing one or more double bonds.

The term "carbocyclylalkyl", as used herein, refers to an alkyl group substituted with a carbocycle group.

The term "$C_{3-4}$ cycloalkylmethyl", as used herein, refers to a methyl group substituted with a carbocycle group containing 3 to 4 carbon atoms.

The term "carbonate" is art-recognized and refers to a group —$OCO_2$—$R^{34}$, wherein $R^{34}$ represents a hydrocarbyl group.

The term "carboxy", as used herein, refers to a group represented by the formula —$CO_2H$.

The term "ester", as used herein, refers to a group —$C(O)OR^{35}$ wherein $R^{35}$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The term "heteroalkyl", as used herein, refers to a saturated or unsaturated chain of carbon atoms and at least one heteroatom, wherein no two heteroatoms are adjacent.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The asterisk (*) notation on a heteroarylene ring moiety corresponding to X or Y in the compound of Formula (I) identifies the ring atom of the moiety bonded to the methylene group between X and Y, as exemplified below:

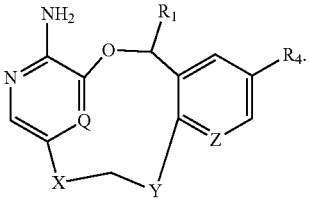

For example, "1*,5-substituted-imidazolylene" for Y means substituted:

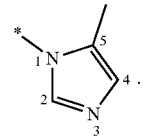

IUPAC numbering rules for heteroarylene rings are used throughout the specification to designate ring atom positions, as shown above. In this example, the 1-position of the imidazolylene is bonded to the methylene group, so it is indicated with the asterisk. The asterisk notation is used in both the names and structures of heteroarylenes for X and Y. Here, for Y the ring atom at the 5-position is not marked because it's bound to the phenyl group bearing variable $R_4$.

For X, an exemplary ring would be "1,5*-substituted-imidazolylene" as shown below.

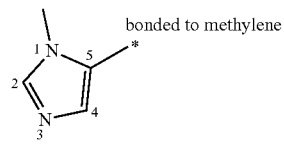

The ring atom bound to the methylene group (the 5-position in this example) is indicated with the asterisk in both the names and structures of ring X heteroarylenes. The ring atom bonded to the aromatic ring bearing Q is not marked.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "heterocyclylalkyl", as used herein, refers to an alkyl group substituted with a heterocycle group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocyclyl, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "silyl" refers to a silicon moiety with three hydrocarbyl moieties attached thereto.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this disclosure, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxy, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group —OSO$_3$H, or a pharmaceutically acceptable salt thereof.

The term "sulfonamide" is art-recognized and refers to the group represented by the general formulae

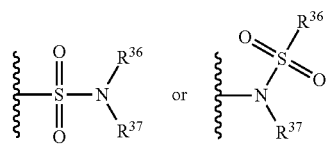

wherein $R^{36}$ and $R^{37}$ independently represent hydrogen or hydrocarbyl, such as alkyl, or $R^{36}$ and $R^{37}$ taken together with the intervening atom(s) complete a heterocycle having from 4 to 8 atoms in the ring structure.

The term "sulfoxide" is art-recognized and refers to the group —S(O)—$R^{38}$, wherein $R^{38}$ represents a hydrocarbyl.

The term "sulfonate" is art-recognized and refers to the group SO$_3$H, or a pharmaceutically acceptable salt thereof.

The term "sulfone" is art-recognized and refers to the group —S(O)$_2$—$R^{39}$, wherein $R^{39}$ represents a hydrocarbyl.

The term "thioalkyl", as used herein, refers to an alkyl group substituted with a thiol group.

The term "thioester", as used herein, refers to a group —C(O)S$R^{40}$ or —SC(O)$R^{40}$ wherein $R^{10}$ represents a hydrocarbyl.

The term "thioether", as used herein, is equivalent to an ether, wherein the oxygen is replaced with a sulfur.

The term "urea" is art-recognized and may be represented by the general formula

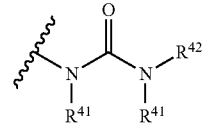

wherein $R^{41}$ and $R^{42}$ independently represent hydrogen or a hydrocarbyl, such as alkyl, or either occurrence of $R^{41}$ taken together with $R^{42}$ and the intervening atom(s) complete a heterocycle having from 4 to 8 atoms in the ring structure.

The term "protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, 3$^{rd}$ Ed., 1999, John Wiley & Sons, NY and Harrison et al., *Compendium of Synthetic Organic Methods*, Vols. 1-8, 1971-1996, John Wiley & Sons, NY. Representative nitrogen protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxyl protecting groups include, but are not limited to, those where the hydroxyl group is either acylated (esterified) or alkylated such as benzyl and trityl ethers, as well as alkyl ethers, tetrahydropyranyl ethers, trialkylsilyl ethers (e.g., TMS or TIPS groups), glycol ethers, such as ethylene glycol and propylene glycol derivatives and allyl ethers.

In certain embodiments, compounds of the disclosure may be racemic. In certain embodiments, compounds of the disclosure may be enriched in one enantiomer. For example, a compound of the disclosure may have greater than about 30% ee, about 40% ee, about 50% ee, about 60% ee, about 70% ee, about 80% ee, about 90% ee, or even about 95% or greater ee. In certain embodiments, compounds of the disclosure may have more than one stereocenter. In certain such embodiments, compounds of the disclosure may be enriched in one or more diastereomer. For example, a compound of the disclosure may have greater than about 30% de, about 40% de, about 50% de, about 60% de, about 70% de, about 80% de, about 90% de, or even about 95% or greater de.

In certain embodiments, the therapeutic preparation may be enriched to provide predominantly one enantiomer of a compound (e.g., of Formula (I)). An enantiomerically enriched mixture may comprise, for example, at least about 60 mol percent of one enantiomer, or more preferably at least about 75, about 90, about 95, or even about 99 mol percent. In certain embodiments, the compound enriched in one enantiomer is substantially free of the other enantiomer, wherein substantially free means that the substance in question makes up less than about 10%, or less than about 5%, or less than about 4%, or less than about 3%, or less than about 2%, or less than about 1% as compared to the amount of the other enantiomer, e.g., in the composition or compound mixture. For example, if a composition or compound mixture contains about 98 grams of a first enantiomer and about 2 grams of a second enantiomer, it would be said to contain about 98 mol percent of the first enantiomer and only about 2% of the second enantiomer.

In certain embodiments, the therapeutic preparation may be enriched to provide predominantly one diastereomer of a compound (e.g., of Formula (I)). A diastereomerically enriched mixture may comprise, for example, at least about 60 mol percent of one diastereomer, or more preferably at least about 75, about 90, about 95, or even about 99 mol percent.

In some embodiments, a moiety in a compound exists as a mixture of tautomers. A "tautomer" is a structural isomer of a moiety or a compound that readily interconverts with another structural isomer. For example, a pyrazole ring has two tautomers:

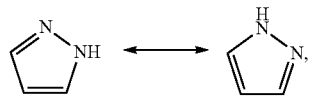 [SMILES: c1cn[nH]c1 ; c1cn[nH]c1]

which differ in the positions of the pi-bonds and a hydrogen atom. Unless explicitly stated otherwise, a drawing of one tautomer of a moiety or a compound encompasses all of the possible tautomers.

The term "subject" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or other primates (e.g., cynomolgus monkeys, rhesus monkeys); mammals, including commercially relevant mammals such as cattle, pigs, horses, sheep, goats, cats, and/or dogs; and/or birds, including commercially relevant birds such as chickens, ducks, geese, quail, and/or turkeys. Preferred subjects are humans.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample. These effects are also called "prophylactic" effects. Thus, as used herein and unless otherwise specified, the terms "prevention" and "preventing" refer to an approach for obtaining beneficial or desired results including, but not limited, to prophylactic benefit. For prophylactic benefit, a therapeutic can be administered to a patient at risk of developing a particular disease, or to a patient reporting one or more of the physiological symptoms of a disease, even though a diagnosis of this disease may not have been made. In one embodiment, a therapeutic is administered prior to clinical manifestation of the unwanted condition (e.g., disease or other unwanted state of the subject) for prophylactic benefit (e.g., it protects the subject against developing the unwanted condition).

As used herein and unless otherwise specified, the terms "treatment" and "treating" refer to therapeutic or palliative measures. Beneficial or desired clinical results include, but are not limited to, alleviation, in whole or in part, of symptoms associated with a disease or disorder or condition, diminishment of the extent of disease, stabilized (i.e., not worsening) state of disease, delay or slowing of disease progression, amelioration or palliation of the disease state (e.g., one or more symptoms of the disease), and remission (whether partial or total), whether detectable or undetectable. "Treatment" can also mean prolonging survival as compared to expected survival if not receiving treatment. In one embodiment, "treatment" comprises administration of a therapeutic after manifestation of the unwanted condition (i.e., it is intended to diminish, ameliorate, or stabilize the existing unwanted condition or side effects thereof).

The term "prodrug" is intended to encompass compounds which, under physiologic conditions, are converted into the therapeutically active agents of the present disclosure (e.g., a compound of Formula (I)). A common method for making a prodrug is to include one or more selected moieties which are hydrolyzed under physiologic conditions to reveal the desired molecule. In other embodiments, the prodrug is converted by an enzymatic activity of the subject. For example, esters or carbonates (e.g., esters or carbonates of alcohols or carboxylic acids) are preferred prodrugs of the present disclosure. In certain embodiments, some or all of the compounds of Formula (I) in a formulation represented above can be replaced with the corresponding suitable prodrug, e.g., wherein a hydroxyl in the parent compound is presented as an ester or a carbonate or carboxylic acid.

An "effective amount", as used herein, refers to an amount that is sufficient to achieve a desired biological effect. A "therapeutically effective amount", as used herein, refers to an amount that is sufficient to achieve a desired therapeutic effect. For example, a therapeutically effective amount can refer to an amount that is sufficient to improve at least one sign or symptom of cancer.

A "response" to a method of treatment can include a decrease in or amelioration of negative symptoms, a decrease in the progression of a disease or symptoms thereof, an increase in beneficial symptoms or clinical outcomes, a lessening of side effects, stabilization of disease, partial or complete remedy of disease, among others.

As used herein and unless otherwise indicated, the term "relapsed" refers to a disorder, disease, or condition that responded to prior treatment (e.g., achieved a complete response) then had progression. The prior treatment can include one or more lines of therapy.

As used herein and unless otherwise indicated, the term "refractory" refers to a disorder, disease, or condition that has not responded to prior treatment that can include one or more lines of therapy.

Compounds

In one aspect, provided herein is a compound of Formula (I), or an enantiomer, a mixture of enantiomers, or a tautomer thereof, or a pharmaceutically acceptable salt thereof:

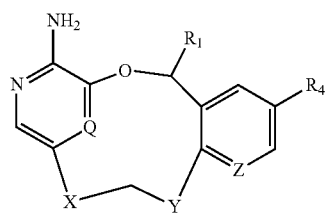

(I)

wherein

Q is CH or N;

Z is $CR_5$ or N;

X is a 5-membered heteroarylene, comprising 1 to 3 heteroatoms selected from the group consisting of nitrogen, oxygen and sulfur; wherein the 5-membered heteroarylene is substituted with 0, 1, or 2 occurrences of $R_2$;

Y is a 5- or 6-membered heteroarylene, comprising 1 to 3 heteroatoms selected from the group consisting of nitrogen, oxygen and sulfur; wherein the 5- or 6-membered heteroarylene is substituted with 0, 1, or 2 occurrences of $R_3$;

in Y, the point of attachment to the methylene group bonded to X and Y and the point of attachment to the aromatic ring comprising Z are on adjacent atoms, and the 5- to 6-membered heteroarylene ring atom alpha to the point of attachment to the methylene group and beta to the point of attachment to the aromatic ring comprising Z is nitrogen;

$R_1$ is selected from the group consisting of H, methyl, and hydroxymethyl; each $R_2$ is independently selected from the group consisting of H, halo, CN, $C_{1-4}$ alkoxy, $C_{1-4}$ alkyl, halo-$C_{1-4}$ alkyl, $C_{3-4}$ cycloalkylmethyl, $C_{3-6}$ cycloalkyl, and $C_{3-6}$ heterocycloalkyl;

each $R_3$ is independently selected from the group consisting of H, halo, CN, $C_{1-4}$ alkoxy, halo-$C_{1-4}$ alkyl, and $C_{1-4}$ alkyl; and each of $R_4$ and $R_5$ is independently H or F;

provided that X is not 3*,4-substituted-pyrazolylene, where * indicates the point of attachment of X or Y to the methylene group bonded to X and Y.

In one aspect, disclosed is a compound of Formula (I) or a pharmaceutically acceptable salt thereof:

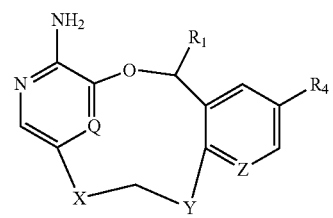

(I)

wherein

Q is CH or N;

Z is $CR_5$ or N;

X is a 5-membered heteroarylene, comprising 1 to 3 heteroatoms selected from the group consisting of nitrogen, oxygen and sulfur; wherein the 5-membered heteroarylene is substituted with 0, 1, or 2 occurrences of $R_2$;

Y is a heteroarylene selected from the group consisting of 1,2*-substituted-imidazolylene, 4*,5-substituted-imidazolylene, 4*,5-substituted-1,2,3-oxadiazolylene, 3*,4-substituted-1,2,5-oxadiazolylene, 3*,4-substituted-1,2-oxazolylene, 4*,5-substituted-1,3-oxazolylene, 2*,3-substituted-pyrazinylene, 1*,5-substituted-pyrazolylene, 3*,4-substituted-pyrazolylene, 3*,4-substituted-pyridazinylene, 2*,3-substituted-pyridinylene, 4*,5-substituted-pyrimidinylene, 2*,3-substituted-pyrrolylene, 5*,6-substituted-1,2,3,4-tetrazinylene, 1*,5-substituted-1,2,3,4-tetrazolylene, 1,5*-substituted-1,2,3,4-tetrazolylene, 4*,5-substituted-1,2,3-thiadiazolylene, 3*,4-substituted-1,2,5-thiadiazolylene, 3*,4-substituted-1,2-thiazolylene, 4*,5-substituted-1,3-thiazolylene, 4*,5-substituted-1,2,3-triazinylene, 5*,6-substituted-1,2,4-triazinylene, 5,6*-substituted-1,2,4-triazinylene, 1*,5-substituted-1,2,3-triazolylene, 4*,5-substituted-1,2,3-triazolylene, 1*,5-substituted-1,2,4-triazolylene, 1,5*-substituted-1,2,4-triazolylene, and 3*,4-substituted-1,2,4-triazolylene; wherein the heteroarylene is substituted with 0, 1, or 2 occurrences of $R_3$;

* indicates the point of attachment of X or Y to the methylene group bonded to X and Y;

in Y the heteroarylene ring atom alpha to the point of attachment to the methylene group and beta to the point of attachment to the aromatic ring comprising Z is nitrogen;

$R_1$ is selected from the group consisting of H, methyl, and hydroxymethyl;

each $R_2$ is independently selected from the group consisting of H, halo, CN, $C_{1-4}$ alkoxy, $C_{1-4}$ alkyl, halo-$C_{1-4}$ alkyl, $C_{3-4}$ cycloalkylmethyl, $C_{3-6}$ cycloalkyl, and $C_{3-6}$ heterocycloalkyl;

each $R_3$ is independently selected from the group consisting of H, halo, CN, $C_{1-4}$ alkoxy, halo-$C_{1-4}$ alkyl, and $C_{1-4}$ alkyl; and each of $R_4$ and $R_5$ is independently H or F.

In one aspect, disclosed is a compound of Formula (I) or a pharmaceutically acceptable salt thereof:

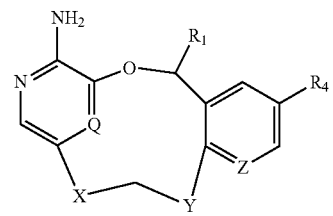

(I)

wherein
Q is CH or N;
Z is $CR_5$ or N;
X is a 5-membered heteroarylene, comprising 1 to 3 heteroatoms selected from the group consisting of nitrogen, oxygen and sulfur; wherein the 5-membered heteroarylene is substituted with 0, 1, or 2 occurrences of $R_2$;
Y is a heteroarylene selected from the group consisting of 1,2*-substituted-imidazolylene, 4*,5-substituted-imidazolylene, 4,5*-substituted-imidazolylene, 4*,5-substituted-1,2,3-oxadiazolylene, 3*,4-substituted-1,2,5-oxadiazolylene, 3*,4-substituted-1,2-oxazolylene, 4*,5-substituted-1,3-oxazolylene, 2*,3-substituted-pyrazinylene, 1*,5-substituted-pyrazolylene, 3*,4-substituted-pyrazolylene, 3*,4-substituted-pyridazinylene, 2*,3-substituted-pyridinylene, 4*,5-substituted-pyrimidinylene, 2*,3-substituted-pyrrolylene, 5*,6-substituted-1,2,3,4-tetrazinylene, 1*,5-substituted-1,2,3,4-tetrazolylene, 1,5*-substituted-1,2,3,4-tetrazolylene, 4*,5-substituted-1,2,3-thiadiazolylene, 3*,4-substituted-1,2,5-thiadiazolylene, 3*,4-substituted-1,2-thiazolylene, 4*,5-substituted-1,3-thiazolylene, 4*,5-substituted-1,2,3-triazinylene, 5*,6-substituted-1,2,4-triazinylene, 5,6*-substituted-1,2,4-triazinylene, 1*,5-substituted-1,2,3-triazolylene, 4*,5-substituted-1,2,3-triazolylene, 1*,5-substituted-1,2,4-triazolylene, 1,5*-substituted-1,2,4-triazolylene, and 3*,4-substituted-1,2,4-triazolylene; wherein the heteroarylene is substituted with 0, 1, or 2 occurrences of $R_3$;
* indicates the point of attachment of X or Y to the methylene group bonded to X and Y;
in Y the heteroarylene ring atom alpha to the point of attachment to the methylene group and beta to the point of attachment to the aromatic ring comprising Z is nitrogen;
$R_1$ is selected from the group consisting of H, methyl, and hydroxymethyl;
each $R_2$ is independently selected from the group consisting of H, halo, CN, $C_{1-4}$ alkoxy, $C_{1-4}$ alkyl, halo-$C_{1-4}$ alkyl, $C_{3-4}$ cycloalkylmethyl, $C_{3-6}$ cycloalkyl, and $C_{3-6}$ heterocycloalkyl;
each $R_3$ is independently selected from the group consisting of H, halo, CN, $C_{1-4}$ alkoxy, halo-$C_{1-4}$ alkyl, and $C_{1-4}$ alkyl; and
each of $R_4$ and $R_5$ is independently H or F.

In some embodiments, X is a 5-membered heteroarylene selected from the group consisting of pyrazolylene, isoxazolylene, isothiazolylene, imidazolylene, and triazolylene. In some embodiments, X is a 5-membered heteroarylene selected from the group consisting of pyrazolylene and triazolylene. In certain embodiments, X is a 5-membered heteroarylene selected from the group consisting of 4*,5-substituted-pyrazolylene, 4,5*-substituted-pyrazolylene, 1*,5-substituted-pyrazolylene, 4*,5-substituted-isoxazolylene, 3*,4-substituted-isoxazolylene, 3*,4-substituted-isothiazolylene, 4*,5-substituted-isothiazolylene, 4*,5-substituted-imidazolylene, 1*,5-substituted-imidazolylene, 1*,5-substituted-triazolylene, and 4*,5-substituted-triazolylene.

In some embodiments, X is a 5-membered heteroarylene selected from the group consisting of pyrazolylene, isoxazolylene, isothiazolylene, imidazolylene, and triazolylene. In some embodiments, X is a 5-membered heteroarylene selected from the group consisting of pyrazolylene and triazolylene. In certain embodiments, X is a 5-membered heteroarylene selected from the group consisting of 4*,5-substituted-pyrazolylene, 4,5*-substituted-pyrazolylene, 1*,5-substituted-pyrazolylene, 4*,5-substituted-isoxazolylene, 4,5*-substituted-isoxazolylene, 3*,4-substituted-isoxazolylene, 3*,4-substituted-isothiazolylene, 4*,5-substituted-isothiazolylene, 4,5*-substituted-isothiazolylene, 4*,5-substituted-imidazolylene, 1*,5-substituted-imidazolylene, 1*,5-substituted-triazolylene, and 4*,5-substituted-triazolylene.

In certain embodiments, X is a 5-membered heteroarylene selected from the group consisting of:

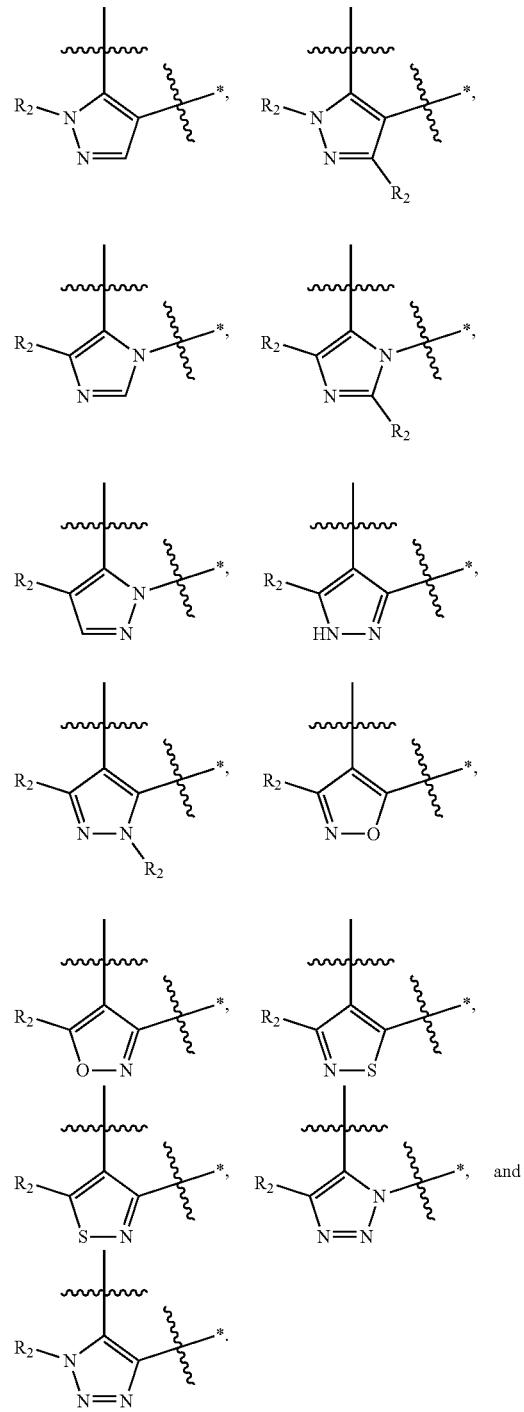

In one embodiment, X is a pyrazolylene. In one embodiment, X is not 3*,4-substituted-pyrazolylene. In one embodiment, X is not

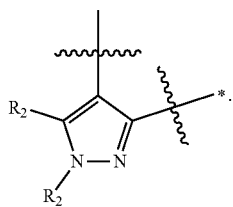

In one embodiment, X is not

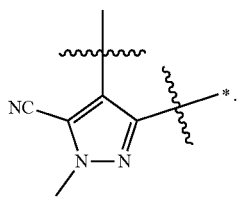 [SMILES: *c1nn(C)c(C#N)c1*]

In another embodiment, X is 3*,4-substituted-pyrazolylene. In another embodiment, X is 4*,5-substituted-pyrazolylene. In another embodiment, X is 4,5*-substituted-pyrazolylene. In another embodiment, X is 1*,5-substituted-pyrazolylene. In one embodiment, X is

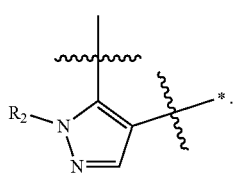

In one embodiment, X is

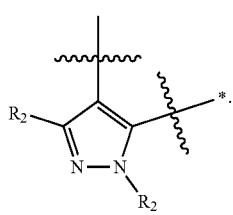

In one embodiment, X is

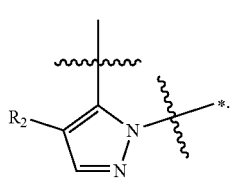

In one embodiment, X is isoxazolylene. In one embodiment, X is 4*,5-substituted-isoxazolylene. In one embodiment, X is 4,5*-substituted-isoxazolylene. In one embodiment, X is 3*,4-substituted-isoxazolylene. In one embodiment, X is

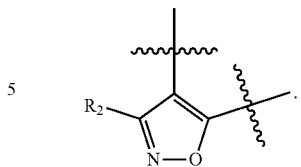

In one embodiment, X is

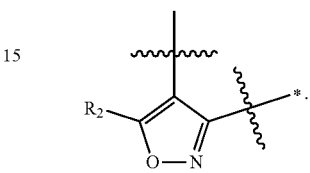

In one embodiment, X is isothiazolylene. In one embodiment, X is 3*,4-substituted-isothiazolylene. In one embodiment, X is 4*,5-substituted-isothiazolylene. In one embodiment, X is 4,5*-substituted-isothiazolylene. In one embodiment, X is

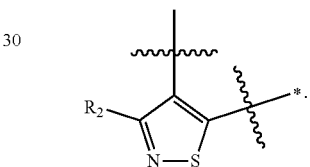

In one embodiment, X is

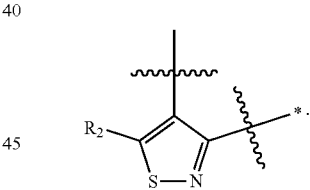

In one embodiment, X is imidazolylene. In one embodiment, X is 4*,5-substituted-imidazolylene. In one embodiment, X is 1*,5-substituted-imidazolylene. In one embodiment, X is

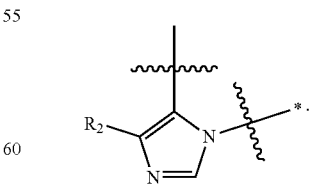

In one embodiment, X is triazolylene. In one embodiment, X is 1*,5-substituted-triazolylene. In one embodiment, X is 4*,5-substituted-triazolylene. In one embodiment, X is In one embodiment, X is


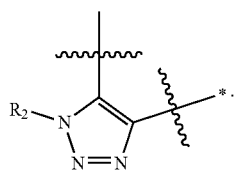

In one embodiment, X is substituted with 0 occurrence of $R_2$ (i.e., all open positions on X are H). In one embodiment, X is substituted with 1 occurrence of $R_2$ that is not H. In one embodiment, X is substituted with 2 occurrences of $R_2$ that are not H.

$R_2$ is independently selected from the group consisting of H, halo, CN, $C_{1-4}$ alkoxy, $C_{1-4}$ alkyl, halo-$C_{1-4}$ alkyl, $C_{3-4}$ cycloalkylmethyl, $C_{3-6}$ cycloalkyl, and $C_{3-6}$ heterocycloalkyl. In one embodiment, $R_2$ is not H. In one embodiment, $R_2$ is $C_{1-4}$ alkyl. In one embodiment, $R_2$ is methyl. In one embodiment, $R_2$ is ethyl. In one embodiment, $R_2$ is isopropyl. In one embodiment, $R_2$ is cyclopropyl. In one embodiment, $R_2$ is cyclobutyl. In one embodiment, $R_2$ is cyclopropylmethyl. In one embodiment, $R_2$ is —$CHF_2$. In one embodiment, $R_2$ is —$CH_2CHF_2$. In one embodiment, $R_2$ is halo. In one embodiment, $R_2$ is fluoro. In one embodiment, $R_2$ is chloro. In one embodiment, $R_2$ is CN. In one embodiment, $R_2$ is methoxy.

In certain embodiments, X is a 5-membered heteroarylene selected from the group consisting of:

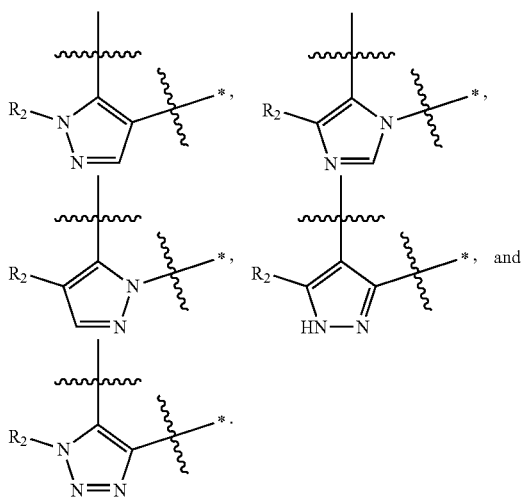

In some embodiments, Y is a heteroarylene selected from the group consisting of 1*,5-substituted-pyrazolylene, 3*,4-substituted-pyrazolylene, 1,2*-substituted-imidazolylene, 4*,5-substituted-imidazolylene, 1*,5-substituted-1,2,3-triazolylene, 4*,5-substituted-1,2,3-triazolylene, 1*,5-substituted-1,2,4-triazolylene, 1,5*-substituted-1,2,4-triazolylene, 4*,5-substituted-1,3-thiazolylene, 2*,3-substituted-pyridinylene, 4*,5-substituted-pyrimidinylene, and 2*,3-substituted-pyrazinylene.

In some embodiments, Y is a heteroarylene selected from the group consisting of 1*,5-substituted-pyrazolylene, 3*,4-substituted-pyrazolylene, 1,2*-substituted-imidazolylene, 4*,5-substituted-imidazolylene, 4,5*-substituted-imidazolylene, 1*,5-substituted-1,2,3-triazolylene, 4*,5-substituted-1,2,3-triazolylene, 1*,5-substituted-1,2,4-triazolylene, 1,5*-substituted-1,2,4-triazolylene, 4*,5-substituted-1,3-thiazolylene, 2*,3-substituted-pyridinylene, 4*,5-substituted-pyrimidinylene, and 2*,3-substituted-pyrazinylene.

In certain embodiments, Y is a heteroarylene selected from the group consisting of:

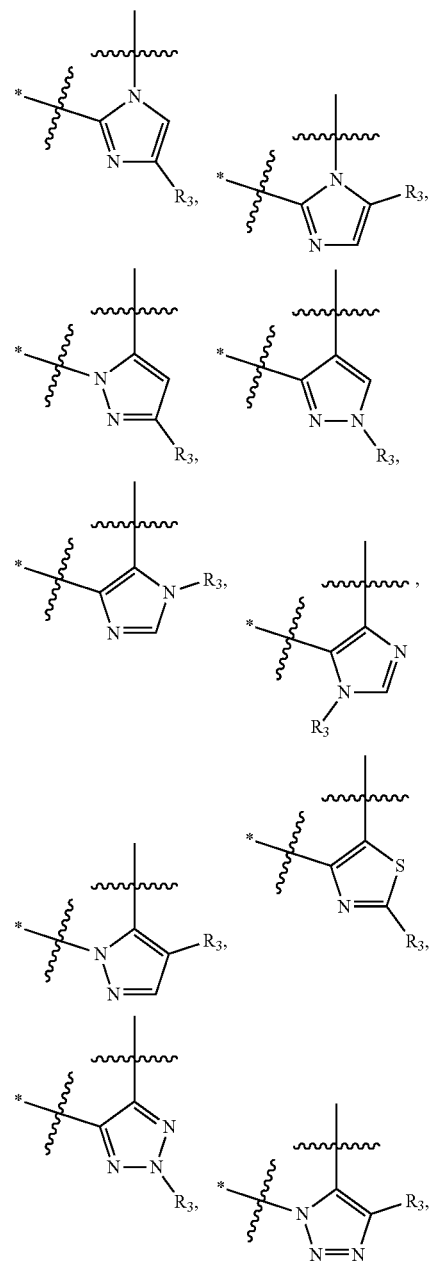

-continued

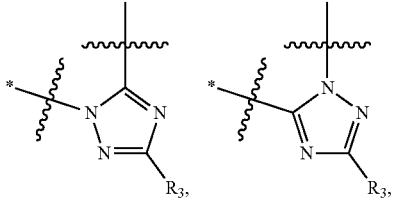

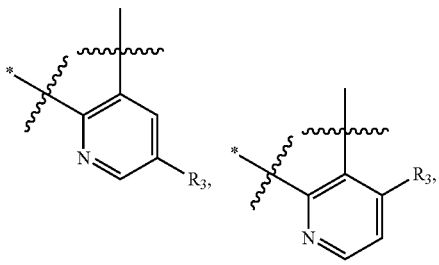

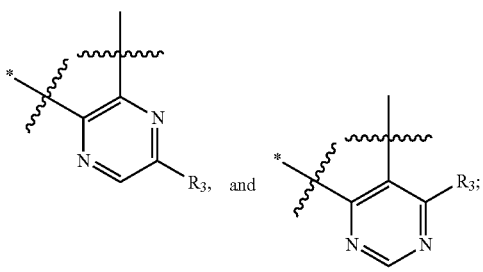

* indicates the point of attachment of Y to the methylene group bonded to X and Y; and $R_3$ is selected from the group consisting of H, halo, CN, $C_{1-4}$ alkoxy, halo-$C_{1-4}$ alkyl, and $C_{1-4}$ alkyl.

In one embodiment, Y is a 5-membered heteroarylene. In one embodiment, Y is pyrazolylene. In one embodiment, Y is 1*,5-substituted-pyrazolylene. In one embodiment, Y is 3*,4-substituted-pyrazolylene. In one embodiment, Y is

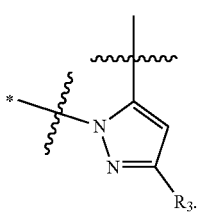

In one embodiment, Y is

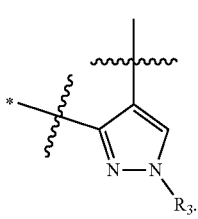

In one embodiment, Y is

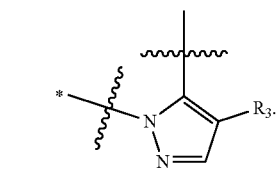

In one embodiment, Y is imidazolylene. In one embodiment, Y is 1,2*-substituted-imidazolylene. In one embodiment, Y is 4*,5-substituted-imidazolylene. In one embodiment, Y is 4,5*-substituted-imidazolylene. In one embodiment, Y is

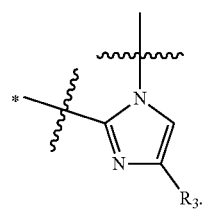

In one embodiment, Y is

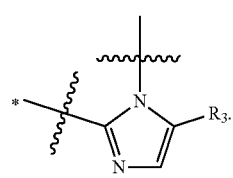

In one embodiment, Y is

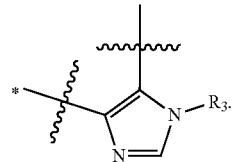

In one embodiment, Y is

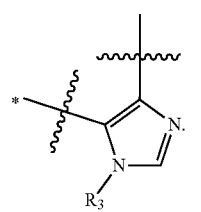

In one embodiment, Y is triazolylene. In one embodiment, Y is 1*,5-substituted-1,2,3-triazolylene. In one embodiment, Y is 4*,5-substituted-1,2,3-triazolylene. In one embodiment, Y is 1*,5-substituted-1,2,4-triazolylene. In one embodiment, Y is 1,5*-substituted-1,2,4-triazolylene. In one embodiment, Y is

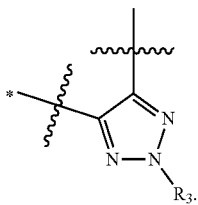

In one embodiment, Y is

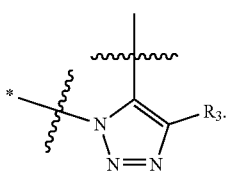

In one embodiment, Y is

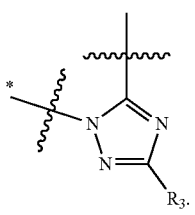

In one embodiment, Y is

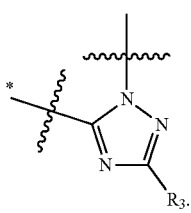

In one embodiment, Y is thiazolylene. In one embodiment, Y is 4*,5-substituted-1,3-thiazolylene. In one embodiment, Y is

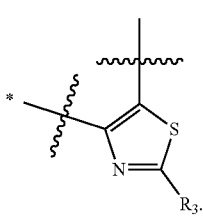

In one embodiment, Y is a 6-membered heteroarylene. In one embodiment, Y is pyridinylene. In one embodiment, Y is 2*,3-substituted-pyridinylene. In one embodiment, Y is

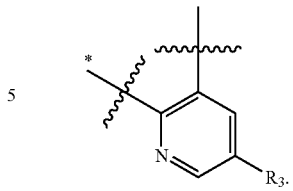

In one embodiment, Y is

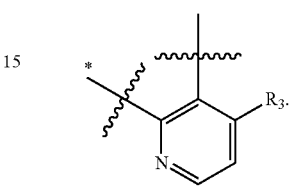

In one embodiment, Y is pyrimidinylene. In one embodiment, Y is 4*,5-substituted-pyrimidinylene. In one embodiment, Y is

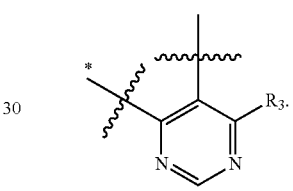

In one embodiment, Y is pyrazinylene. In one embodiment, Y is 2*,3-substituted-pyrazinylene. In one embodiment, Y is

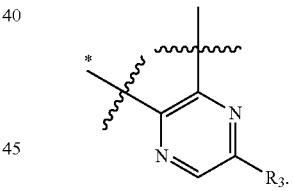

In one embodiment, Y is substituted with 0 occurrence of $R_3$ (i.e., all open positions on Y are H). In one embodiment, Y is substituted with 1 occurrence of $R_3$ that is not H. In one embodiment, Y is substituted with 2 occurrences of $R_3$ that are not H.

In one embodiment, $R_3$ is selected from the group consisting of H, halo, CN, $C_{1-4}$ alkoxy, halo-$C_{1-4}$ alkyl, and Cia alkyl. In one embodiment, $R_3$ is not H. In one embodiment, $R_3$ is $C_{1-4}$ alkyl. In one embodiment, $R_3$ is methyl. In one embodiment, $R_3$ is ethyl. In one embodiment, $R_3$ is halo. In one embodiment, $R_3$ is flouro. In one embodiment, $R_3$ is chloro. In one embodiment, $R_3$ is CN.

In one embodiment, X is a pyrazolylene provided herein (e.g., a 4*,5-substituted-pyrazolylene provided herein), and Y is a pyrazolylene provided herein. In another embodiment, Y is an imidazolylene provided herein. In another embodiment, Y is a triazolylene provided herein. In another embodiment, Y is a thiazolylene provided herein. In another embodiment, Y is a pyridinylene provided herein. In another embodiment, Y is a pyrimidinylene provided herein. In another embodiment, Y is a pyrazinylene provided herein.

In one embodiment, X is an isoxazolylene provided herein, and Y is a pyrazolylene provided herein. In another embodiment, Y is an imidazolylene provided herein. In another embodiment, Y is a triazolylene provided herein. In another embodiment, Y is a thiazolylene provided herein. In another embodiment, Y is a pyridinylene provided herein. In another embodiment, Y is a pyrimidinylene provided herein. In another embodiment, Y is a pyrazinylene provided herein.

In one embodiment, X is an isothiazolylene provided herein, and Y is a pyrazolylene provided herein. In another embodiment, Y is an imidazolylene provided herein. In another embodiment, Y is a triazolylene provided herein. In another embodiment, Y is a thiazolylene provided herein. In another embodiment, Y is a pyridinylene provided herein. In another embodiment, Y is a pyrimidinylene provided herein. In another embodiment, Y is a pyrazinylene provided herein.

In one embodiment, X is an imidazolylene provided herein, and Y is a pyrazolylene provided herein. In another embodiment, Y is an imidazolylene provided herein. In another embodiment, Y is a triazolylene provided herein. In another embodiment, Y is a thiazolylene provided herein. In another embodiment, Y is a pyridinylene provided herein. In another embodiment, Y is a pyrimidinylene provided herein. In another embodiment, Y is a pyrazinylene provided herein.

In one embodiment, X is a triazolylene provided herein, and Y is a pyrazolylene provided herein. In another embodiment, Y is an imidazolylene provided herein. In another embodiment, Y is a triazolylene provided herein. In another embodiment, Y is a thiazolylene provided herein. In another embodiment, Y is a pyridinylene provided herein. In another embodiment, Y is a pyrimidinylene provided herein. In another embodiment, Y is a pyrazinylene provided herein.

In some embodiments, Q is CH. In other embodiments, Q is N.

In some embodiments, Z is $CR_5$. In particular embodiments, $R_5$ is H. In particular embodiments, $R_5$ is F. In other embodiments, Z is N.

In some embodiments, $R_4$ is H. In other embodiments, $R_4$ is F.

In some embodiments, the compound of Formula (I) has the structure (I-A):

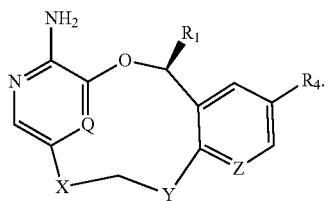

(I-A)

In other embodiments, the compound of Formula (I) has the structure (I-B):

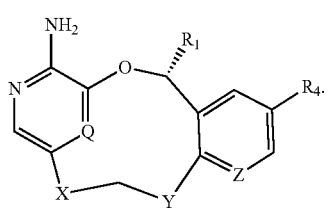

(I-B)

In one embodiment, the compound is a compound of any one of the following formulas, or an enantiomer, a mixture of enantiomers, or a tautomer thereof, or a pharmaceutically acceptable salt thereof:

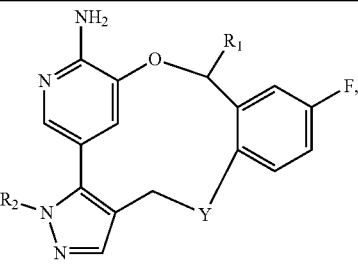

(II)

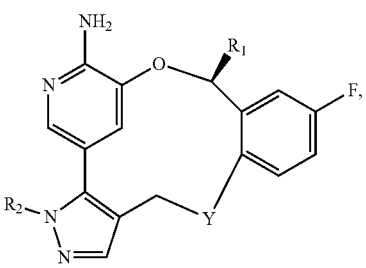

(II-A)

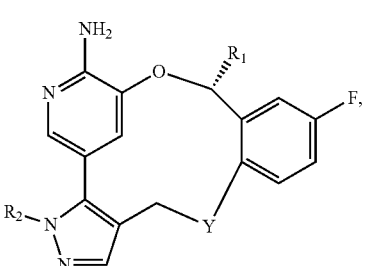

(II-B)

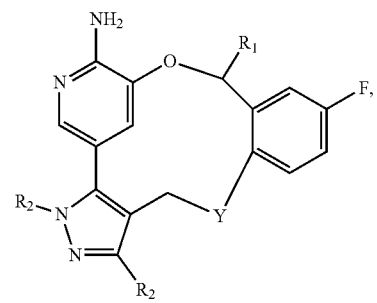

(III)

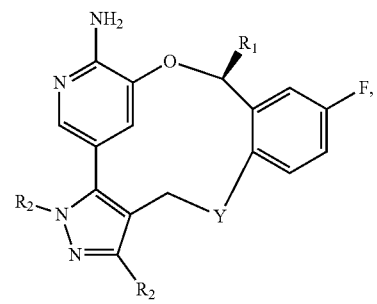

(III-A)

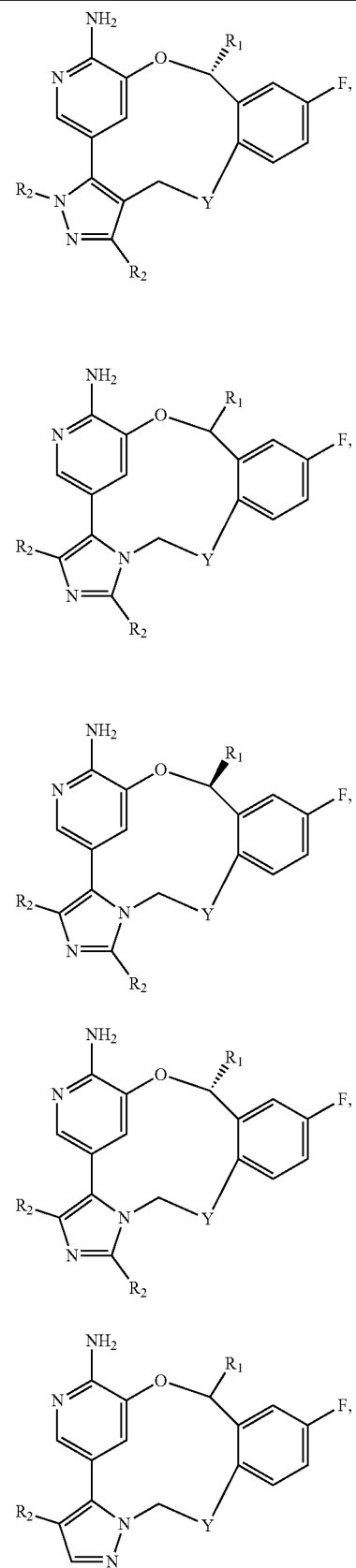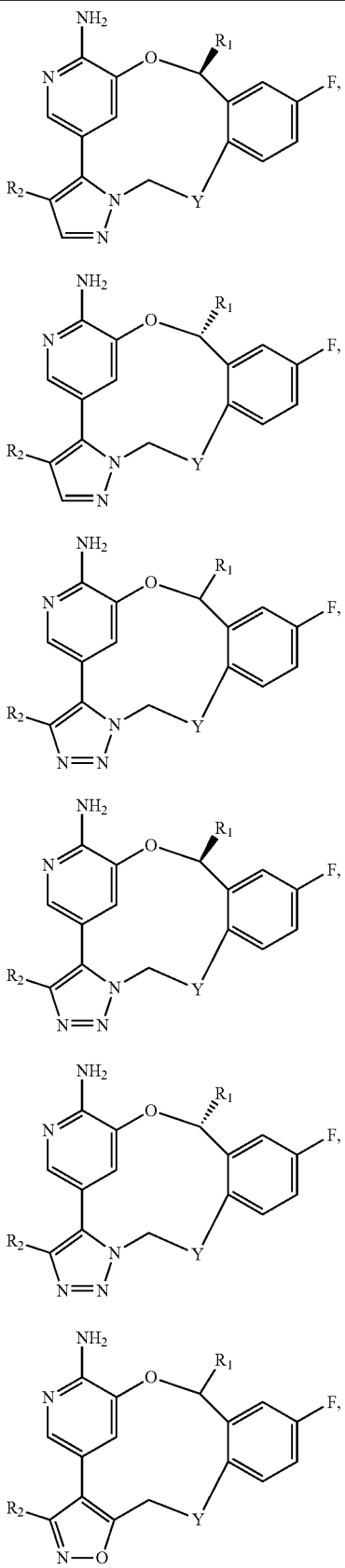

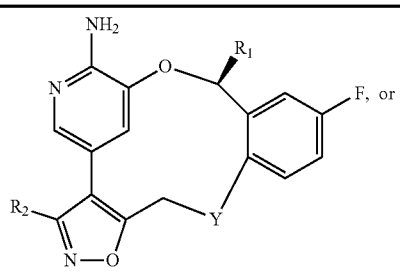
(VII-A)

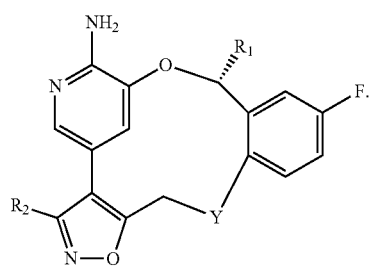
(VII-B)

In some embodiments, R₂ is each independently selected from the group consisting of H, CN, methyl, ethyl, isobutyl, methoxy, chloro, trifluoromethyl, cyclopropyl, cyclopropylmethyl, 2-fluoroethyl, difluoromethyl, 2,2-difluoroethyl, cyclobutyl, and oxetanyl.

In some embodiments, R₃ is selected from the group consisting of H, fluoro, chloro, CN, methyl, and ethyl.

In certain embodiments, the compound is selected from the group consisting of:

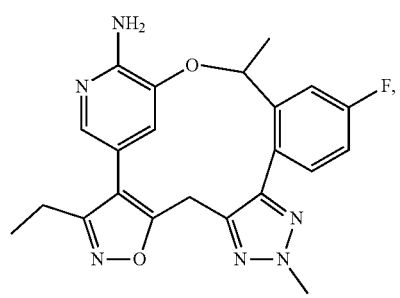

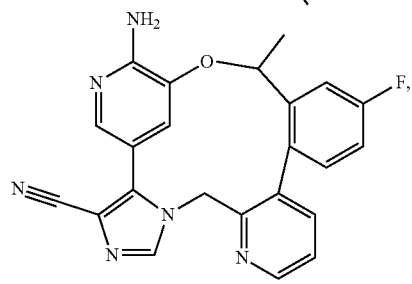

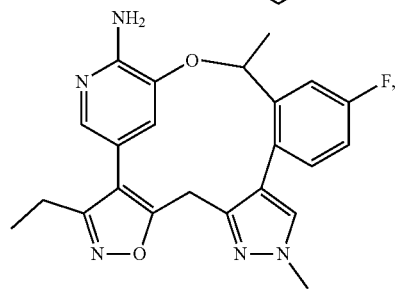

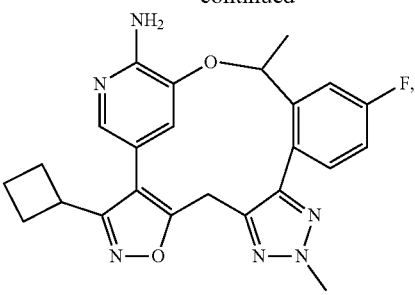

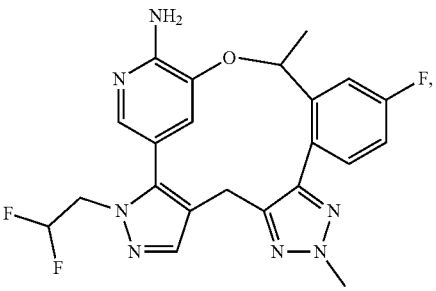

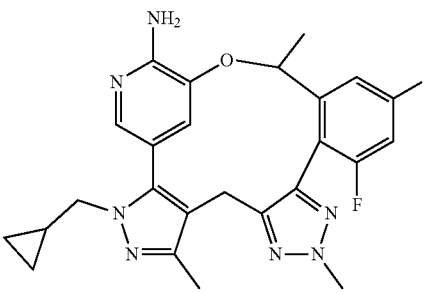

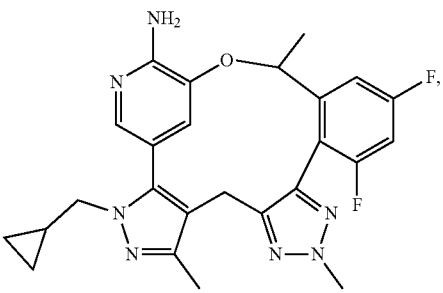

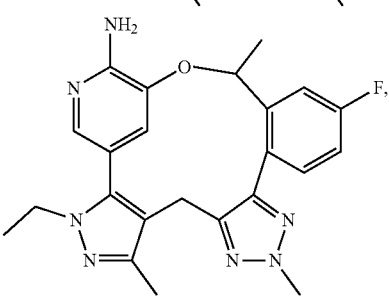

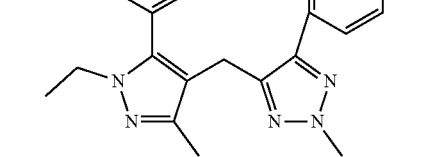

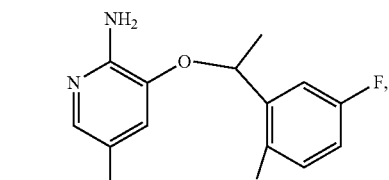

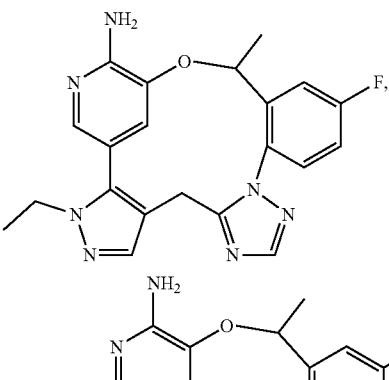

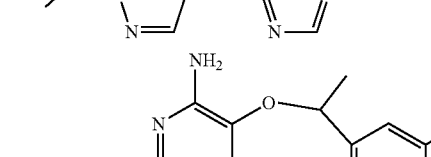

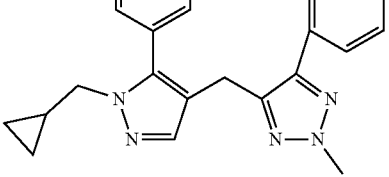, and

31
-continued
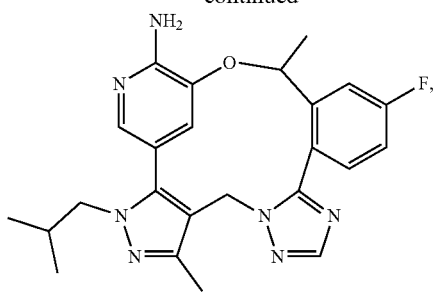
or an enantiomer, a mixture of enantiomers, or a tautomer thereof, or a pharmaceutically acceptable salt thereof.
In certain embodiments, the compound is selected from the group consisting of:
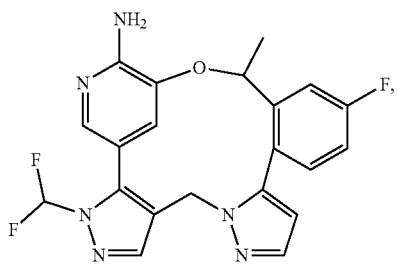
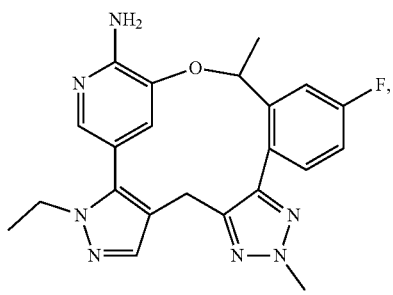
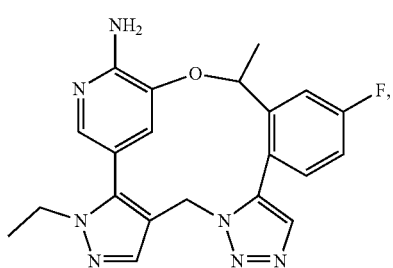
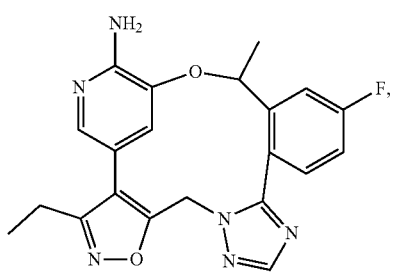
32
-continued
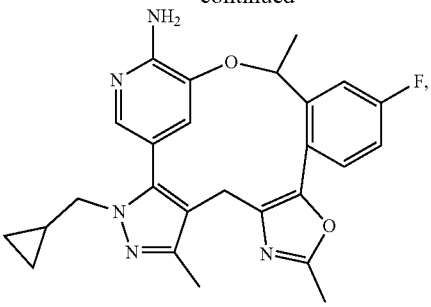
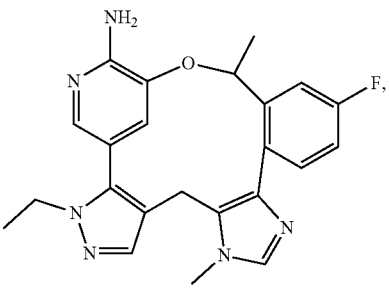
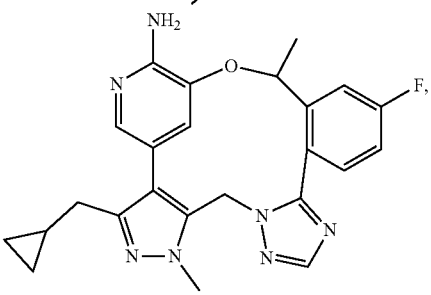
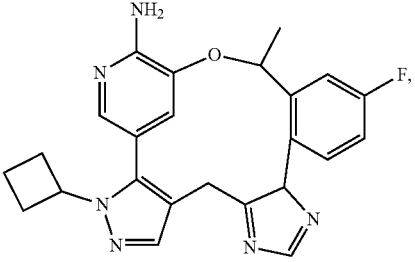
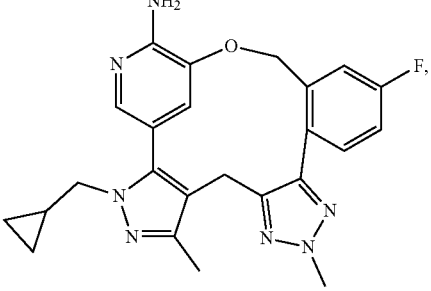
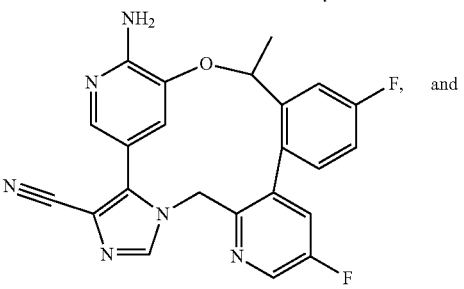

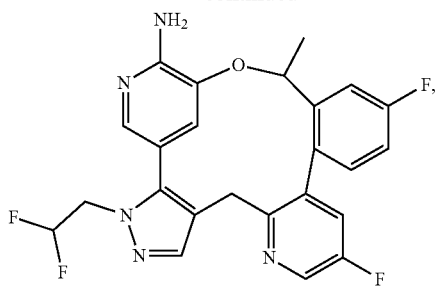 [SMILES: CC1Oc2cc(cnc2N)-c2c(cnn2CC(F)F)Cc2ncc(F)cc2-c2ccc(F)cc21]
or an enantiomer, a mixture of enantiomers, or a tautomer thereof, or a pharmaceutically acceptable salt thereof.
In certain embodiments, the compound is selected from the group consisting of:
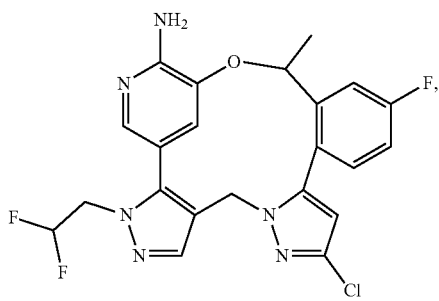
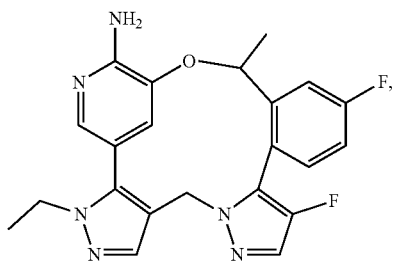
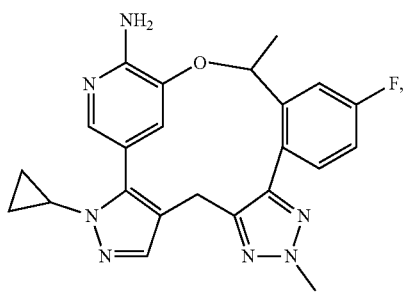
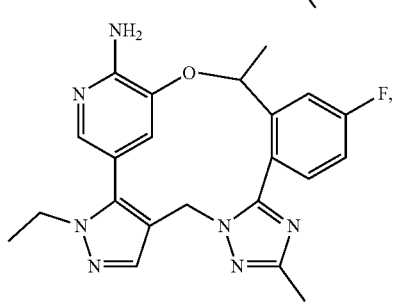
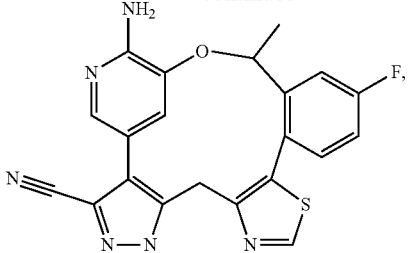
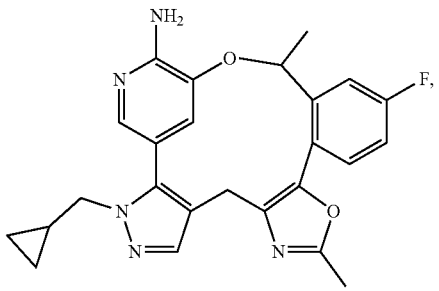
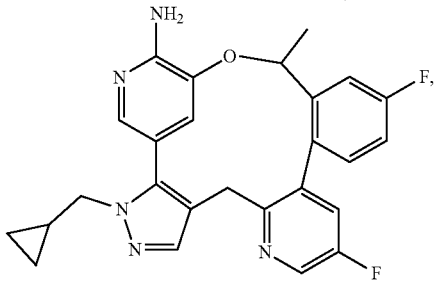
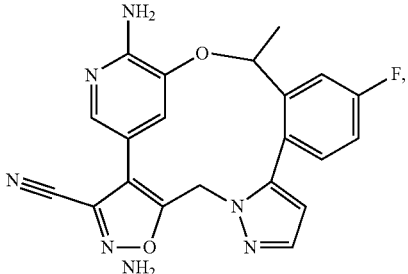
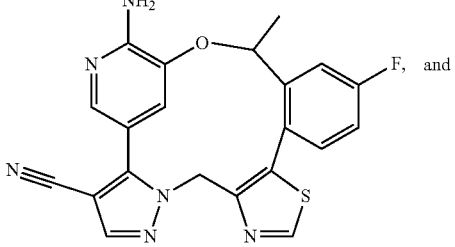, and
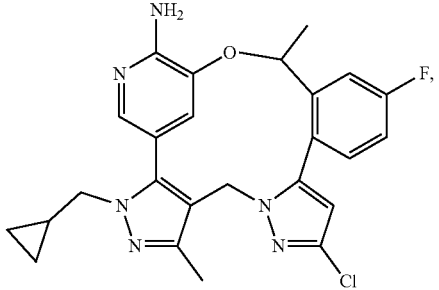
or an enantiomer, a mixture of enantiomers, or a tautomer thereof, or a pharmaceutically acceptable salt thereof.

In certain embodiments, the compound is selected from the group consisting of:
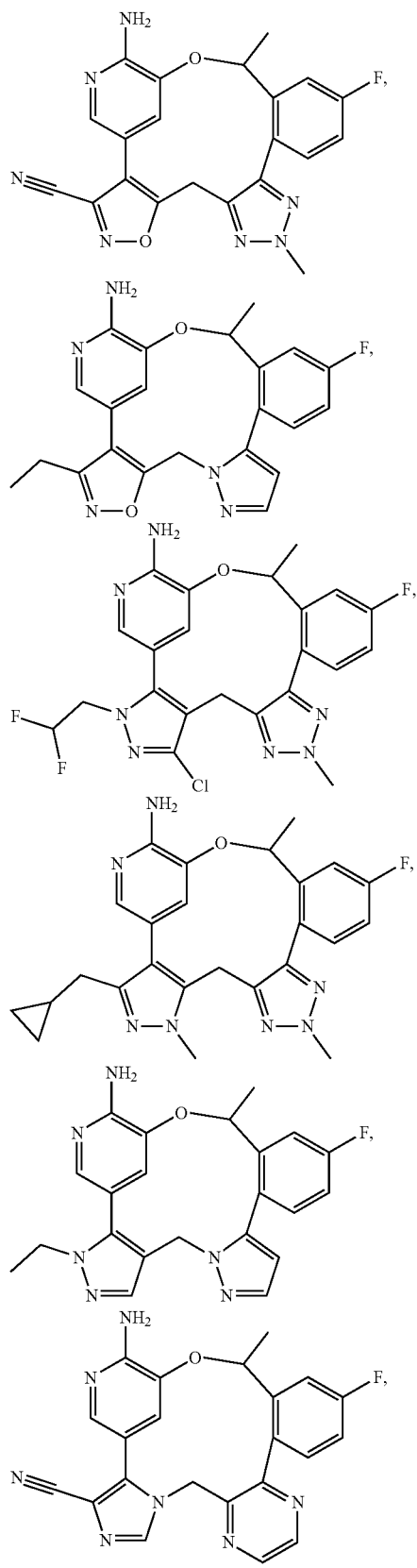
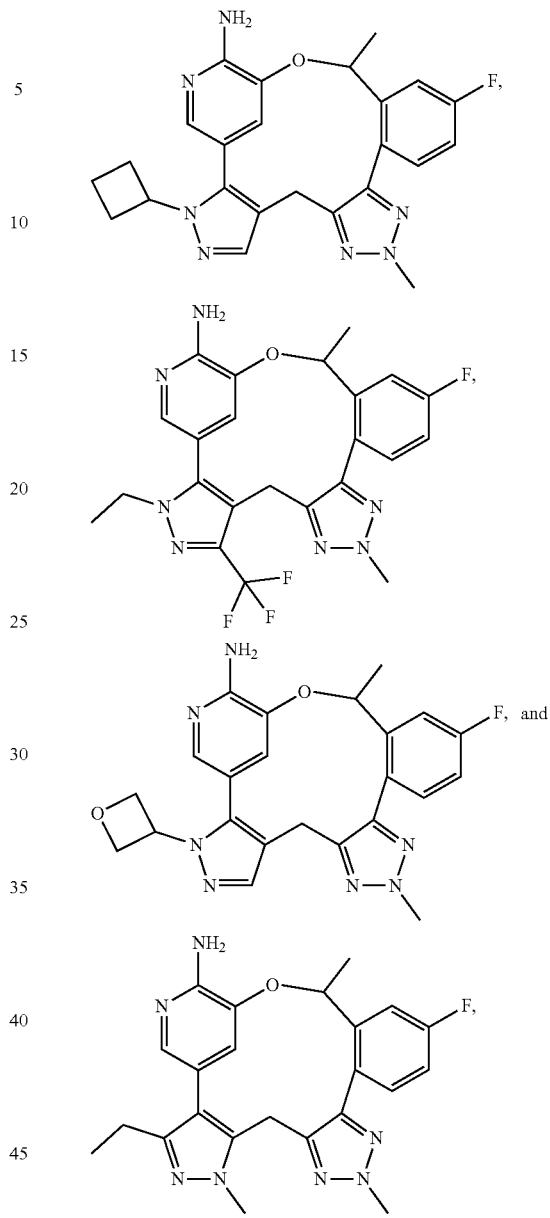
or an enantiomer, a mixture of enantiomers, or a tautomer thereof, or a pharmaceutically acceptable salt thereof.
In certain embodiments, the compound is selected from the group consisting of:
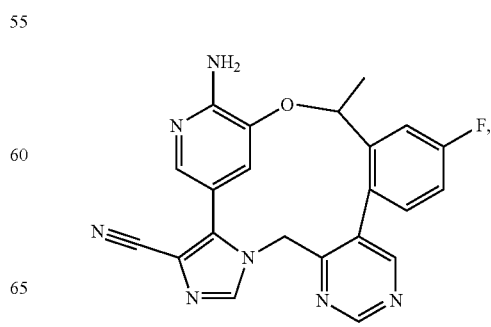

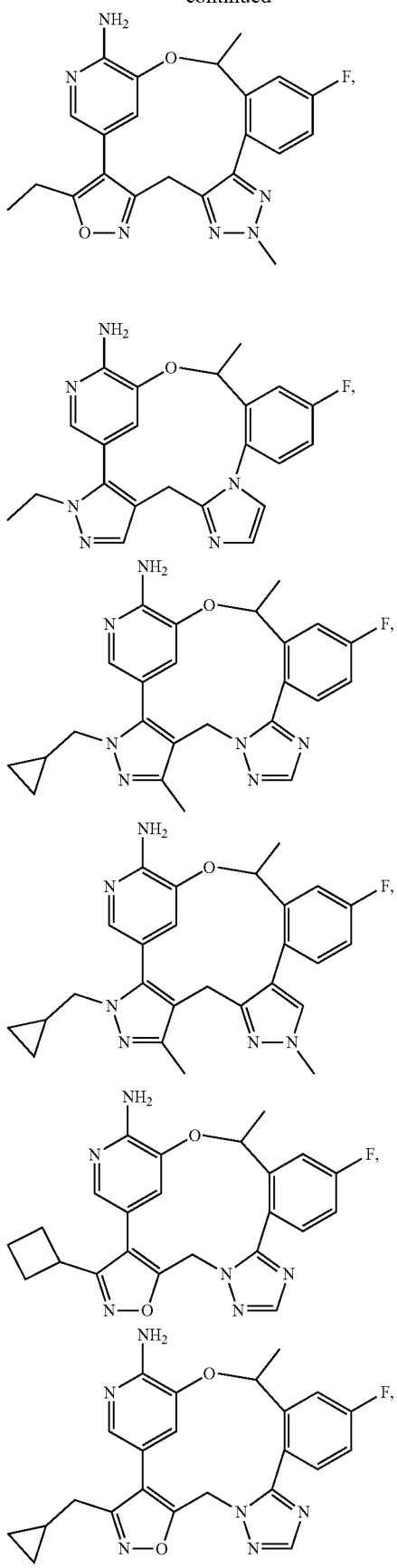
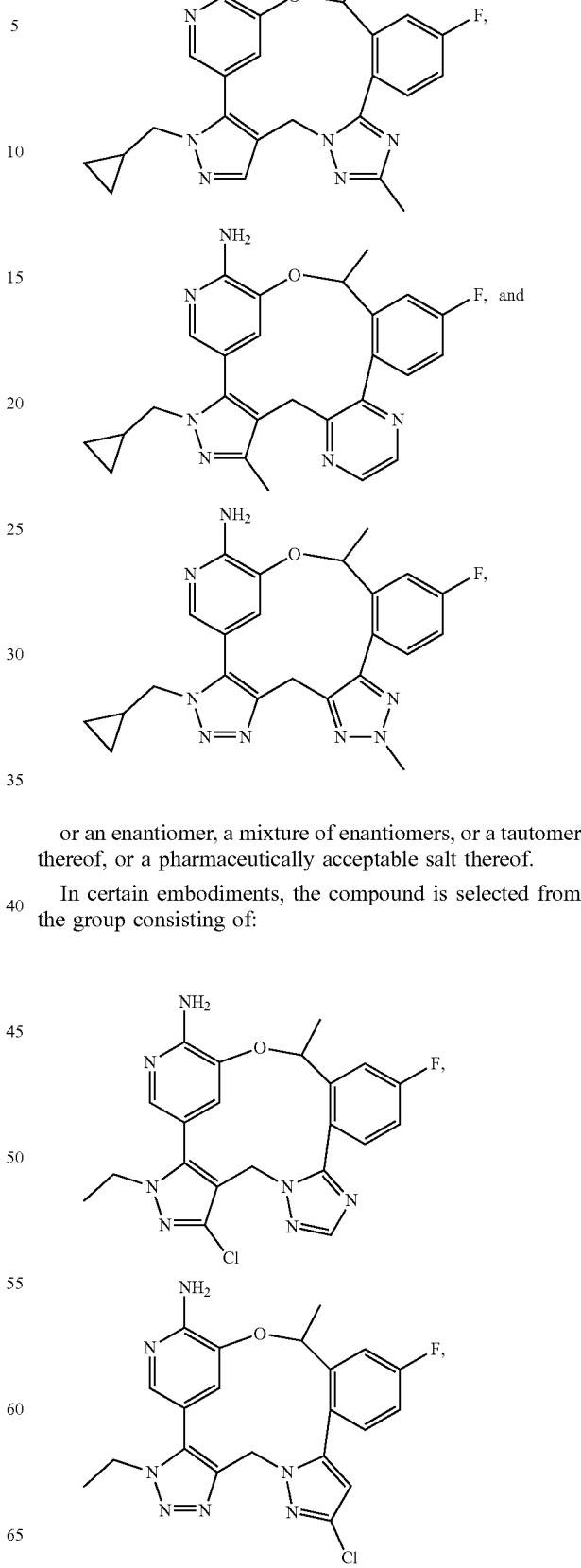
or an enantiomer, a mixture of enantiomers, or a tautomer thereof, or a pharmaceutically acceptable salt thereof.
In certain embodiments, the compound is selected from the group consisting of:

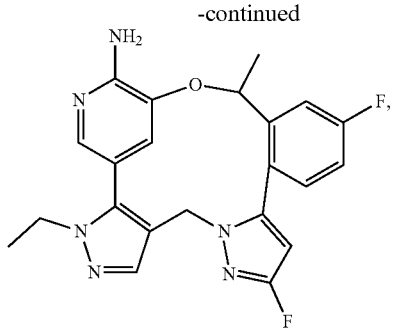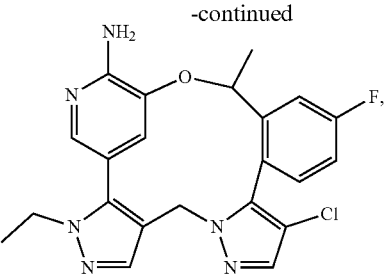
or an enantiomer, a mixture of enantiomers, or a tautomer thereof, or a pharmaceutically acceptable salt thereof.

In certain embodiments, the compound is selected from the group consisting of:
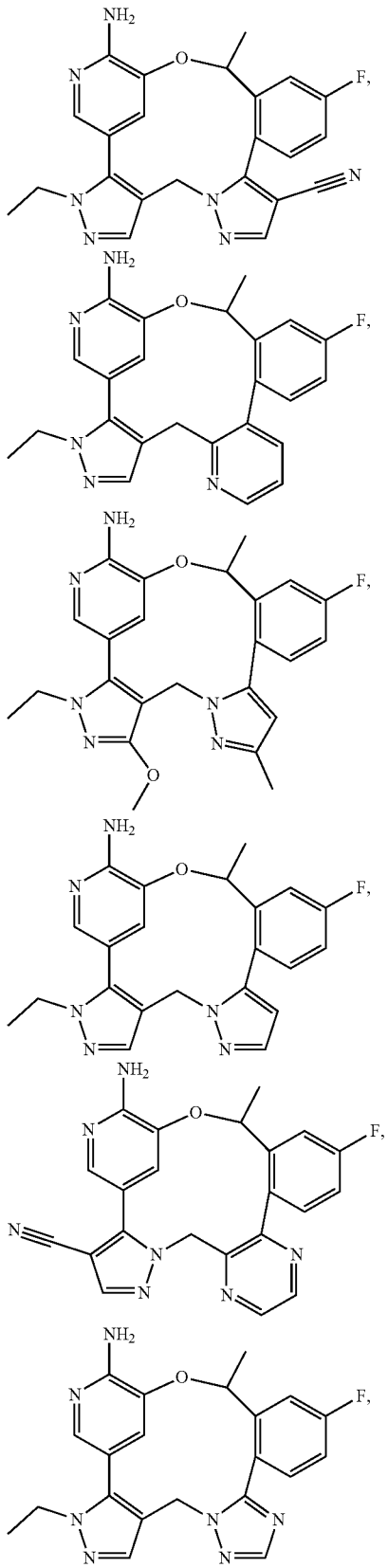
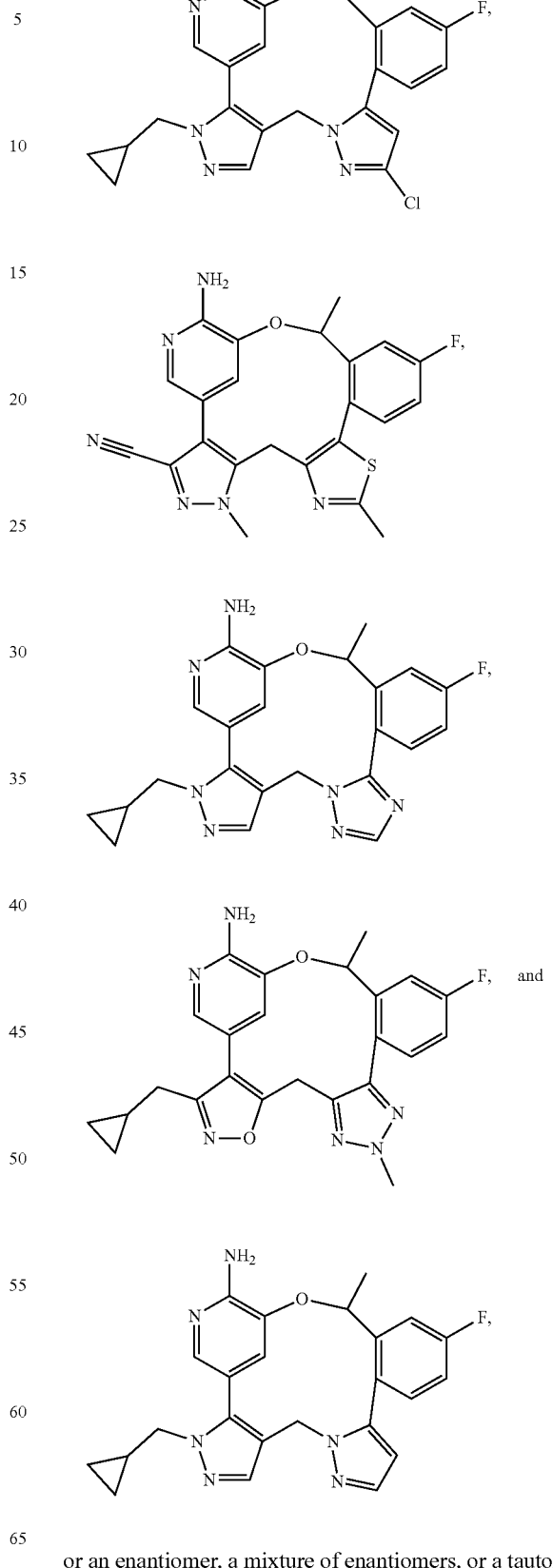
or an enantiomer, a mixture of enantiomers, or a tautomer thereof, or a pharmaceutically acceptable salt thereof.

In certain embodiments, the compound is selected from the group consisting of:
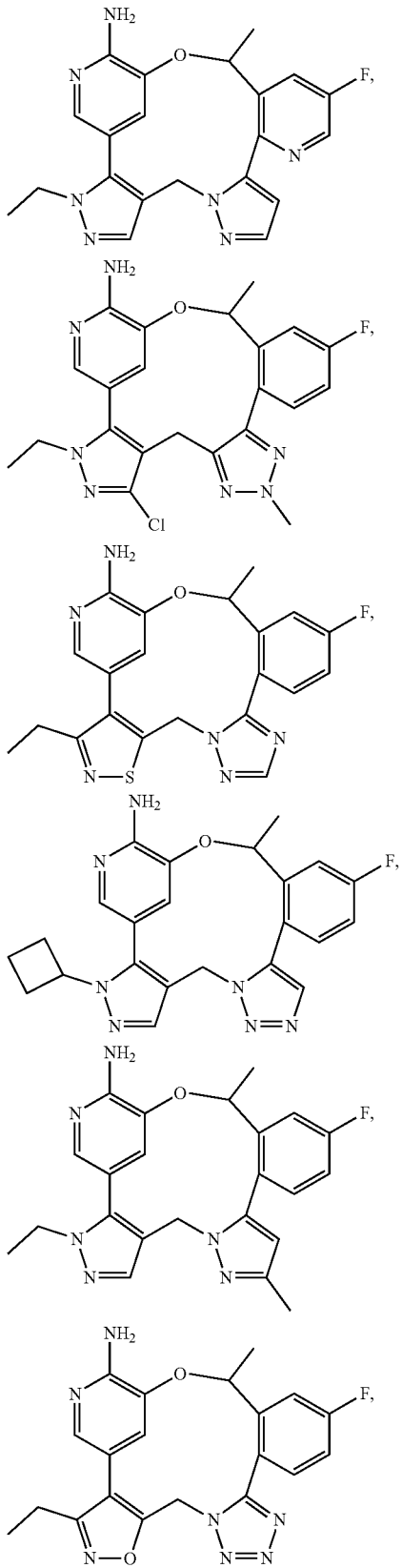
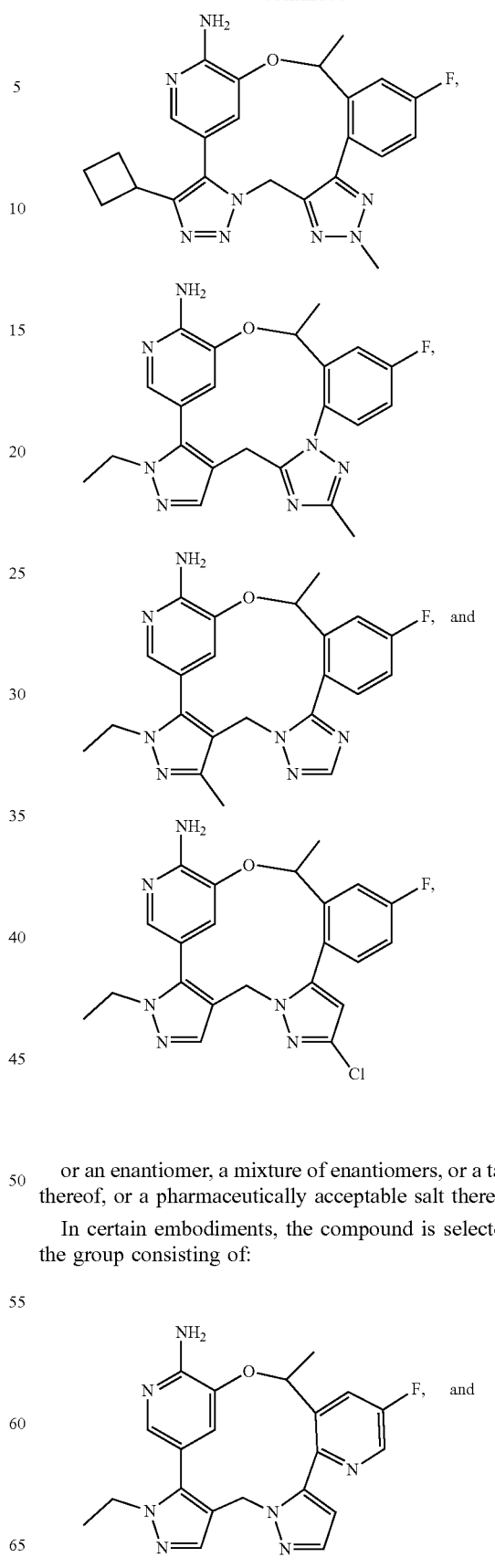
or an enantiomer, a mixture of enantiomers, or a tautomer thereof, or a pharmaceutically acceptable salt thereof.
In certain embodiments, the compound is selected from the group consisting of:
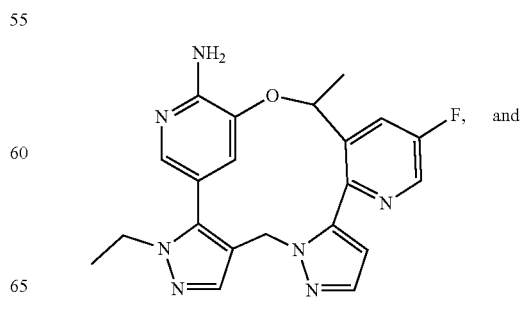

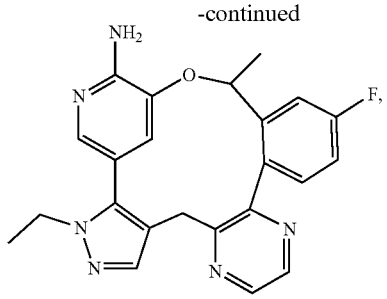
or an enantiomer, a mixture of enantiomers, or a tautomer thereof, or a pharmaceutically acceptable salt thereof.
In certain embodiments, the compound is selected from the group consisting of:
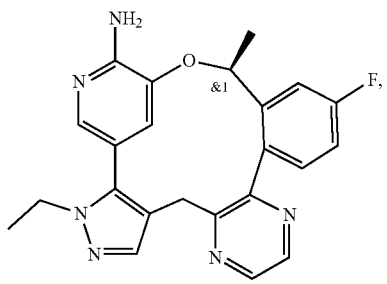
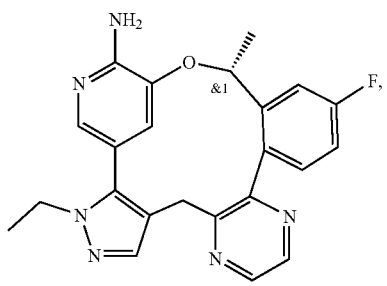
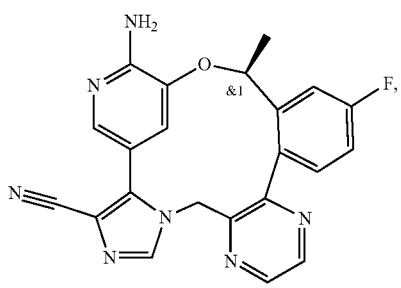
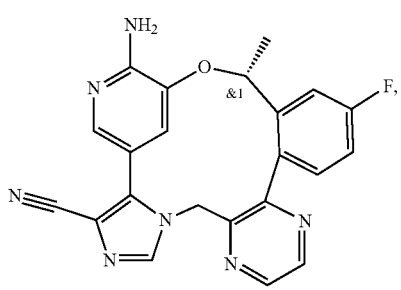
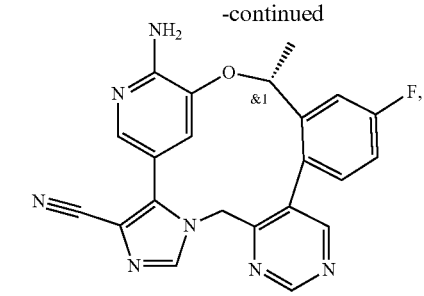
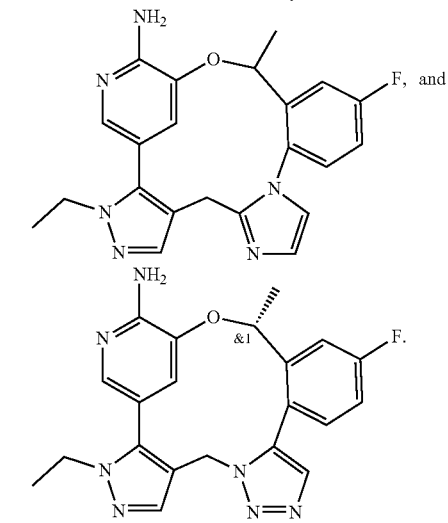
In certain embodiments, the compound is selected from the group consisting of:
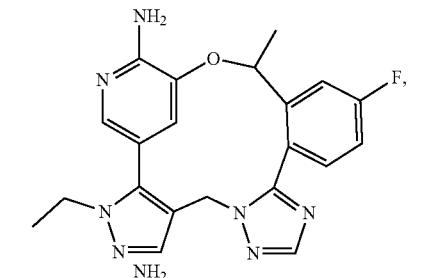
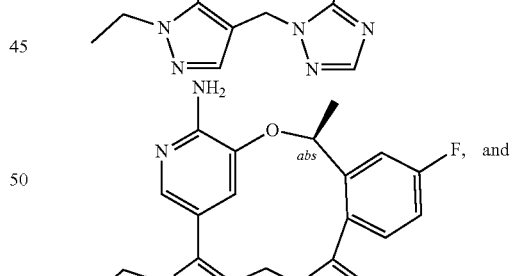
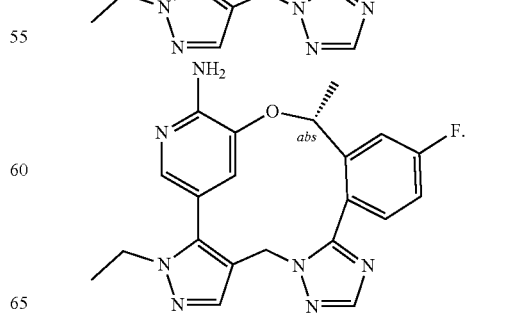

In certain embodiments, the compound is:
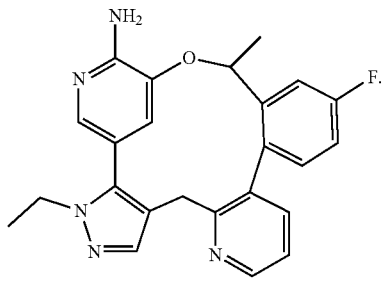 [SMILES: CCn1ncc2c1-c1cnc(N)c(c1)OC(C)c1cc(F)ccc1-c1cccnc1C2]
In certain embodiments, the compound is:
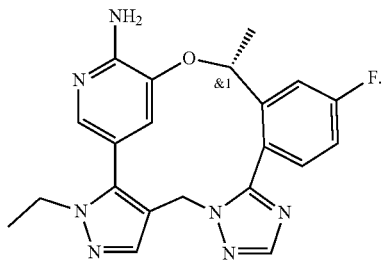 [SMILES: CCn1ncc2c1-c1cnc(N)c(c1)O[C@H](C)c1cc(F)ccc1-c1ncnn1C2]
In certain embodiments, the compound is selected from the group consisting of:
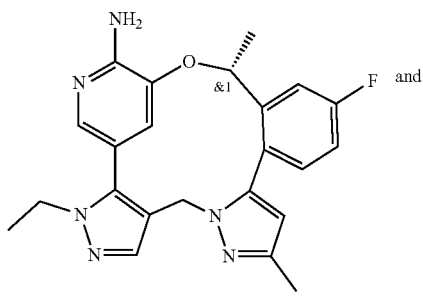
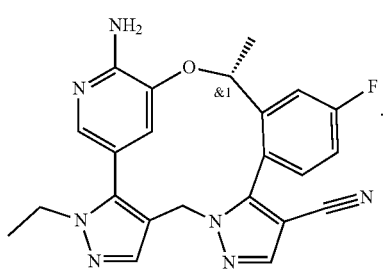
In certain embodiments, the compound is selected from the group consisting of:
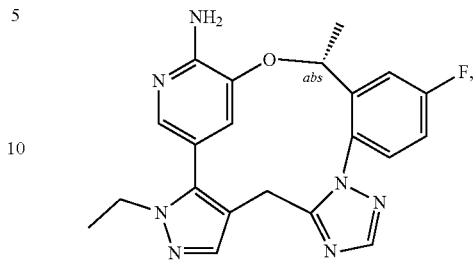
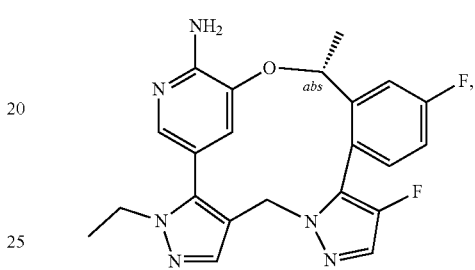
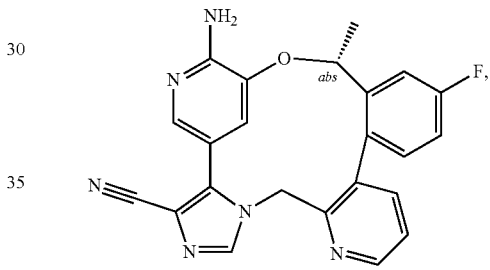
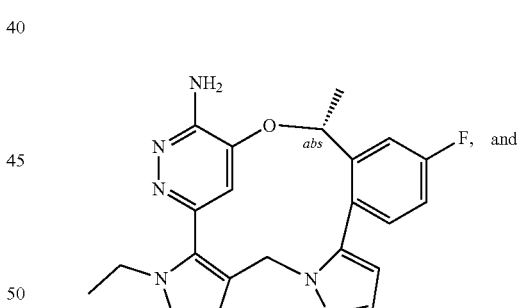
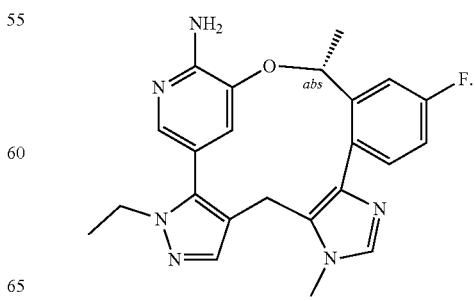

In certain embodiments, the compound is selected from the group consisting of:
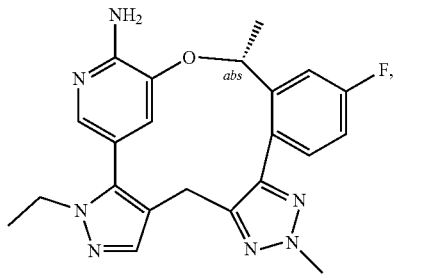
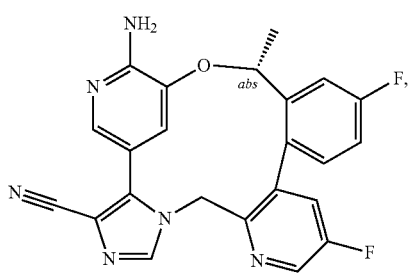
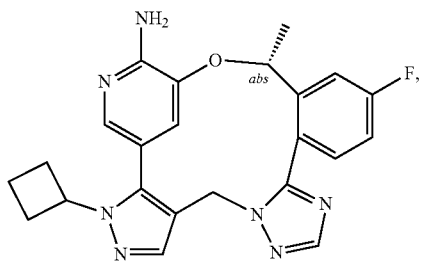
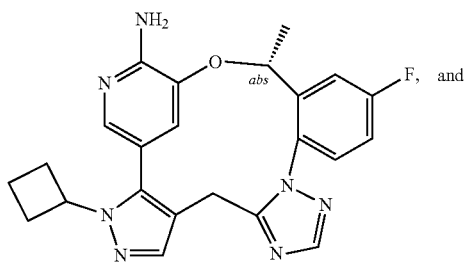, and
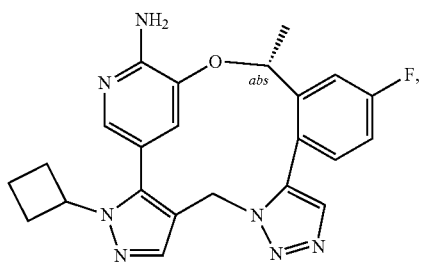
In certain embodiments, the compound is selected from the group consisting of:
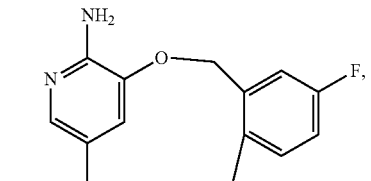
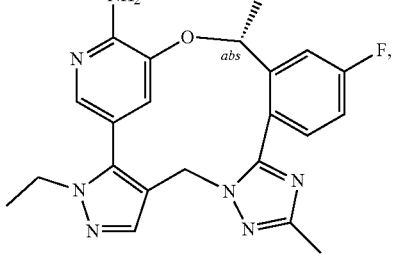
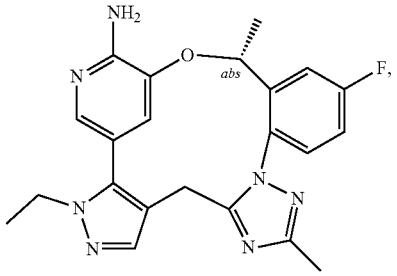
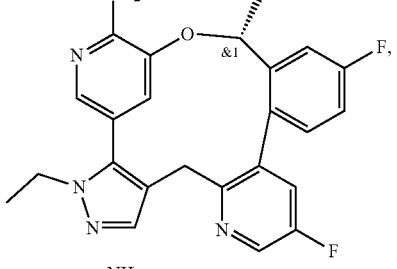
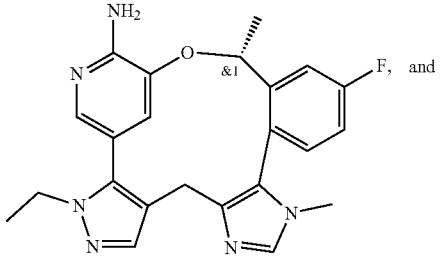, and
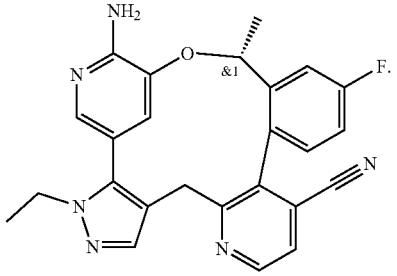 [SMILES: CCn1ncc2c1-c1cnc(N)c(c1)O[C@H](C)c1cc(F)ccc1-c1c(C#N)ccnc1C2]

In certain embodiments, the compound is selected from the group consisting of:
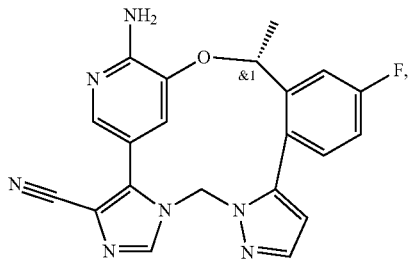
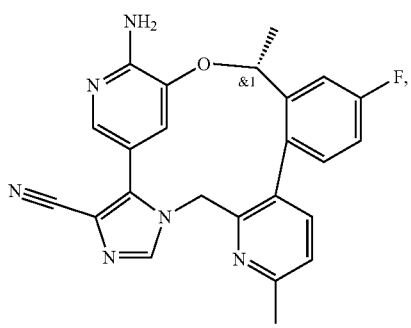
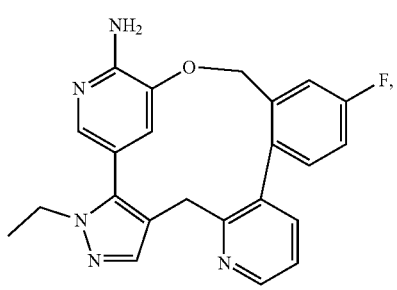
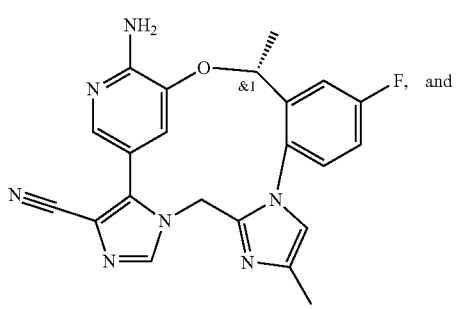
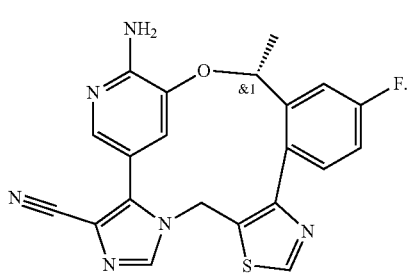
In certain embodiments, the compound is selected from the group consisting of:
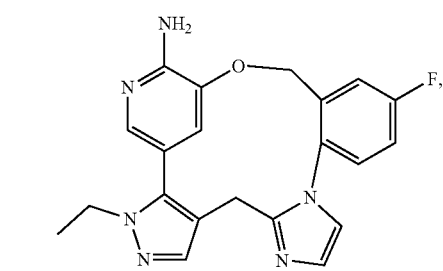
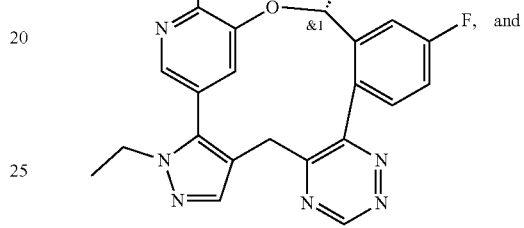
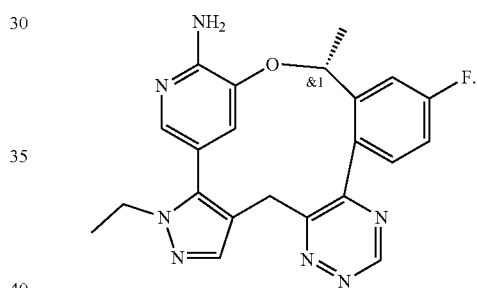
In certain embodiments, the compound is selected from the group consisting of:
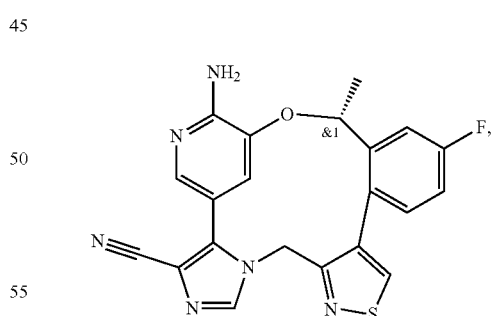
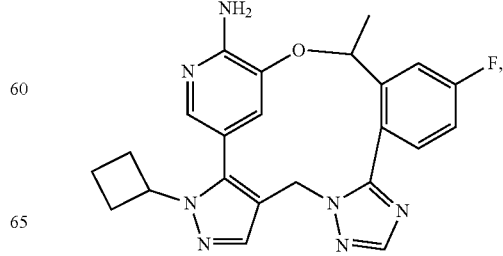

-continued
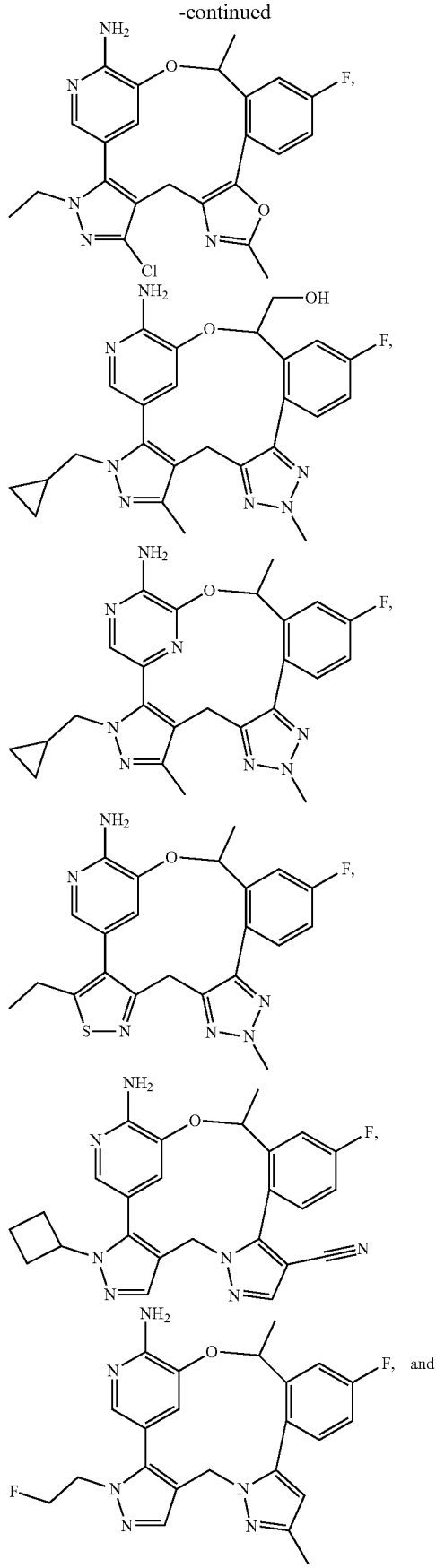
In certain embodiments, the compound is selected from the group consisting of:
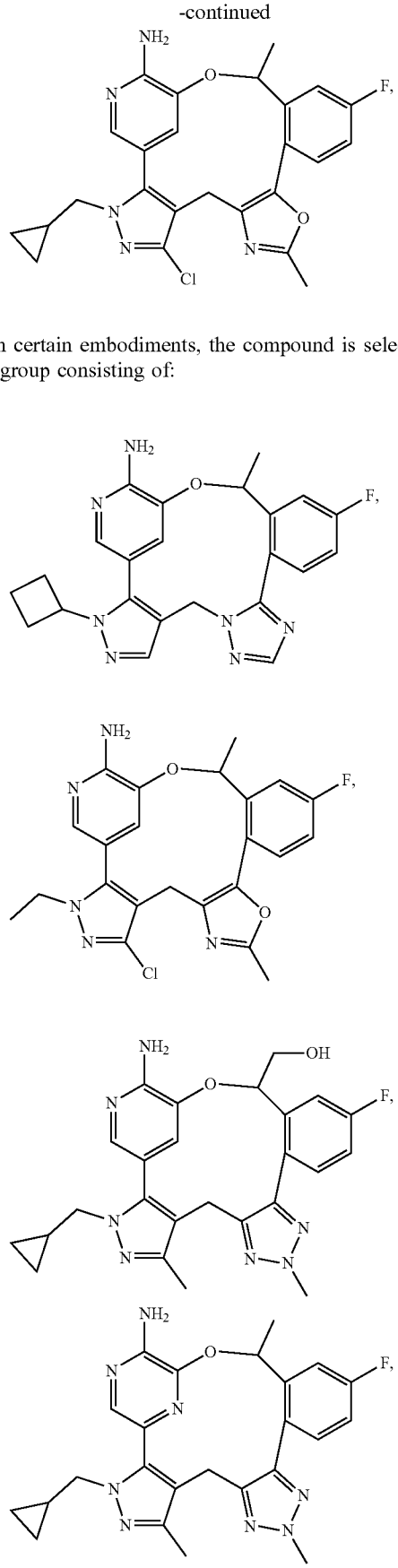

-continued
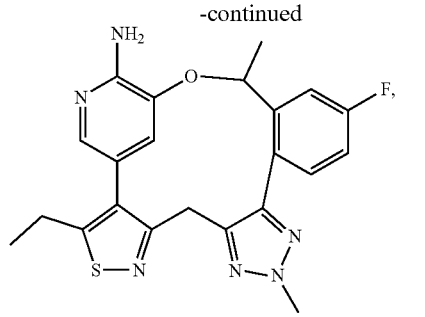
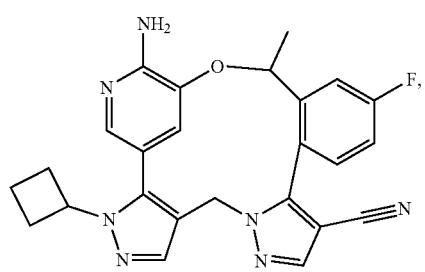
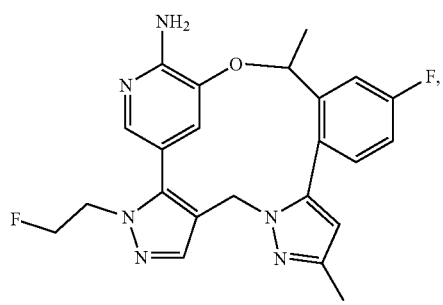
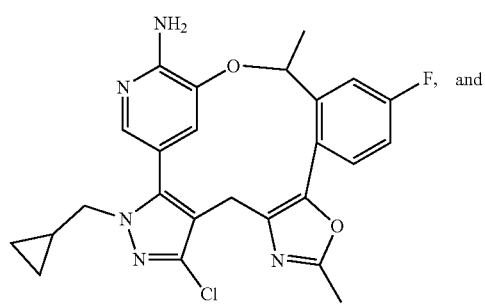
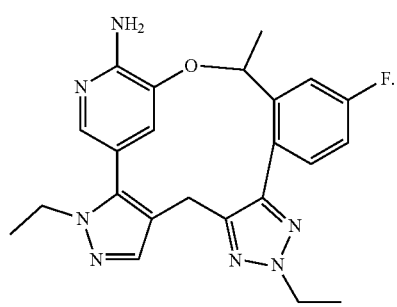
or an enantiomer, a mixture of enantiomers, or a tautomer thereof, or a pharmaceutically acceptable salt thereof.
In certain embodiments, the compound is selected from the group consisting of:
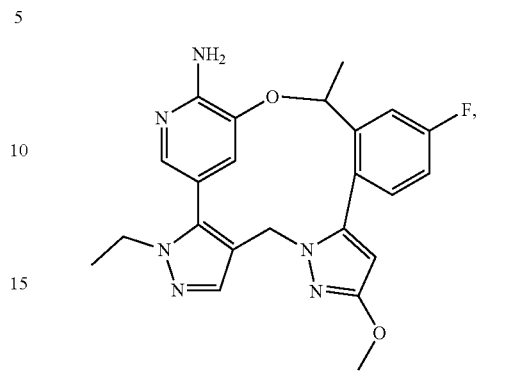
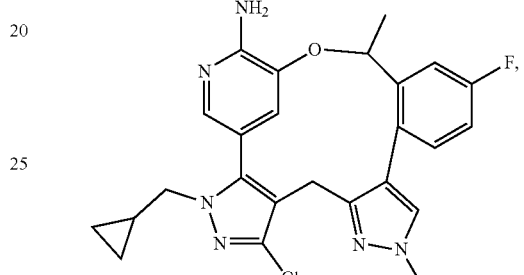
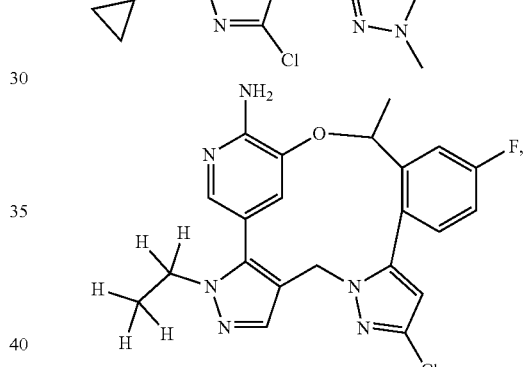
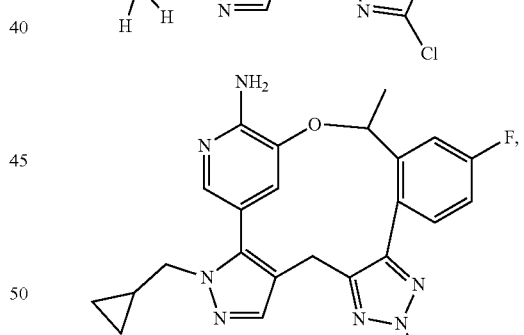
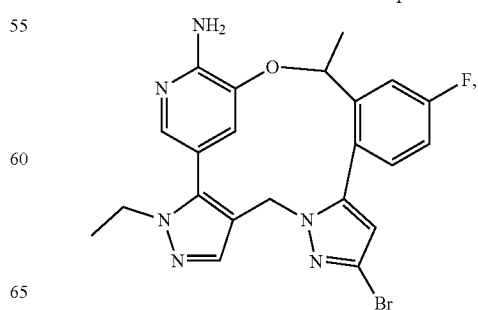
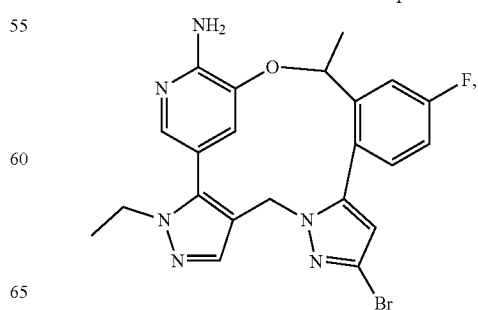

-continued
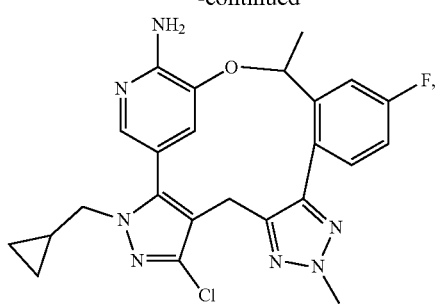
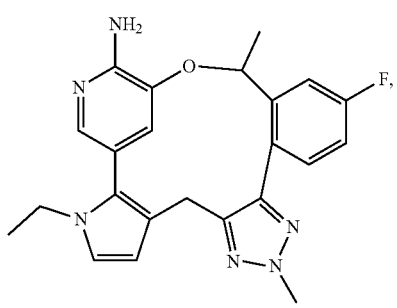
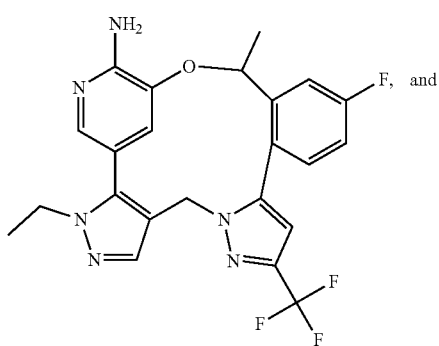, and
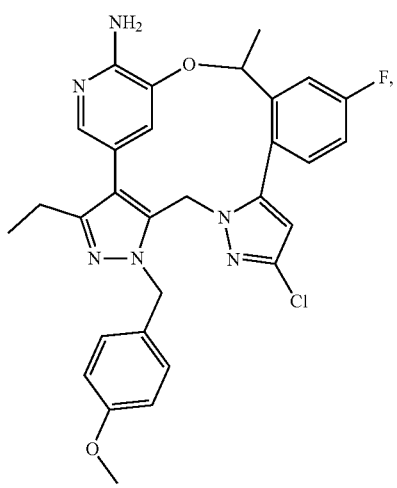
or an enantiomer, a mixture of enantiomers, or a tautomer thereof, or a pharmaceutically acceptable salt thereof.
In certain embodiments, the compound is selected from the group consisting of:
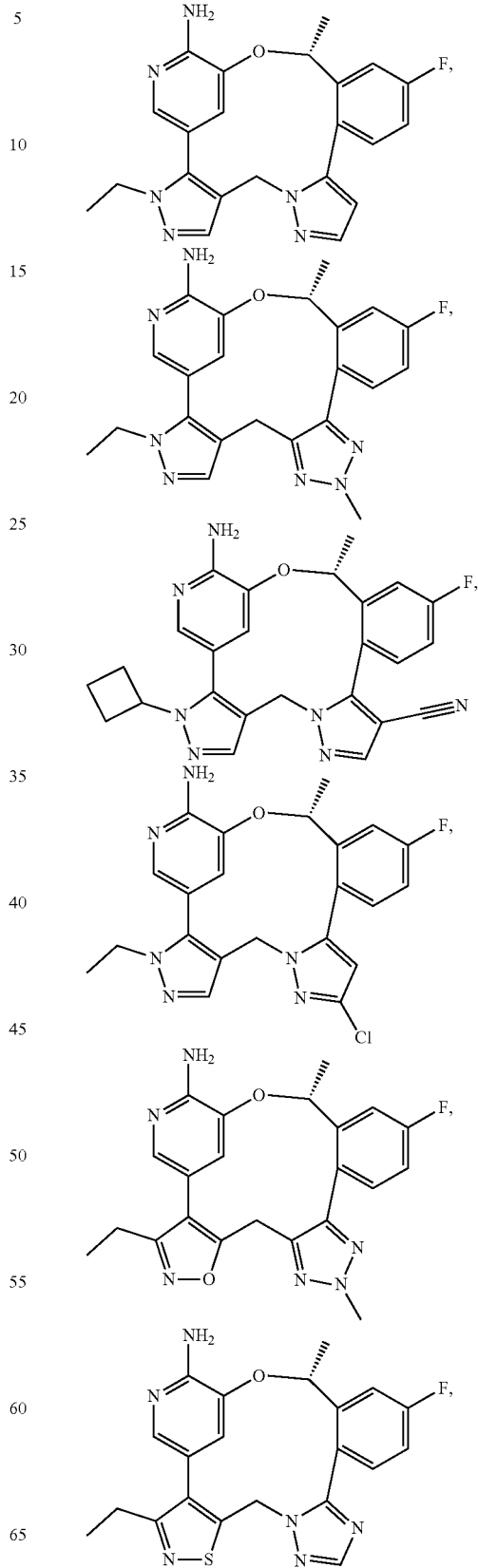

-continued
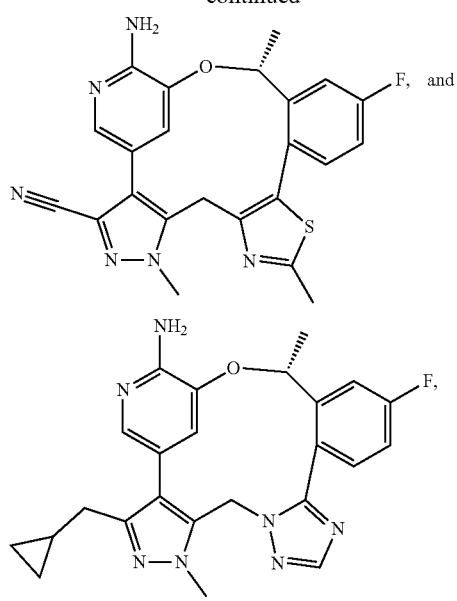
or a pharmaceutically acceptable salt thereof.
In one embodiment, provided herein is a compound in Table 1:
TABLE 1
| | |
|---|---|
| 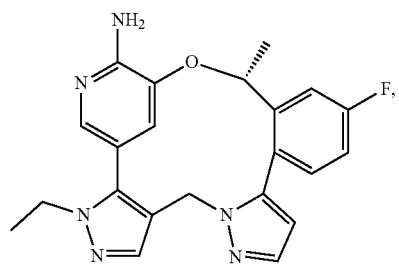 [SMILES: CCn1ncc2c1-c1cnc(N)c(c1)O[C@H](C)c1cc(F)ccc1-c1ccnn1C2] | 1 |
| 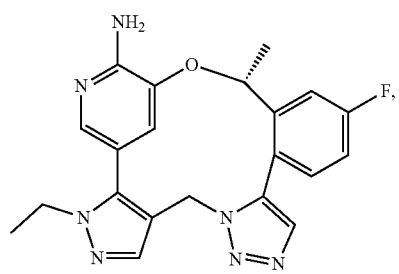 [SMILES: CCn1ncc2c1-c1cnc(N)c(c1)O[C@H](C)c1cc(F)ccc1-c1cnnn1C2] | 2 |
| 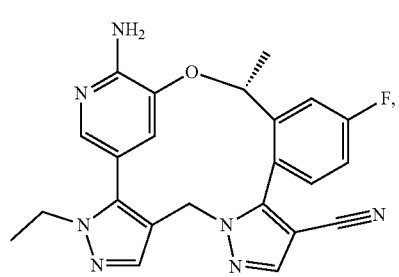 [SMILES: CCn1ncc2c1-c1cnc(N)c(c1)O[C@H](C)c1cc(F)ccc1-c1c(C#N)cnn1C2] | 3 |
TABLE 1-continued
| | |
|---|---|
| 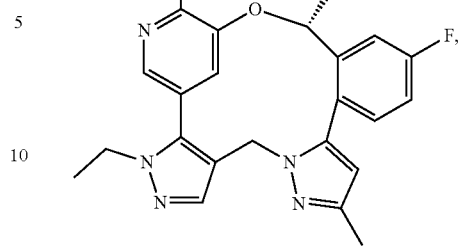 | 4 |
| 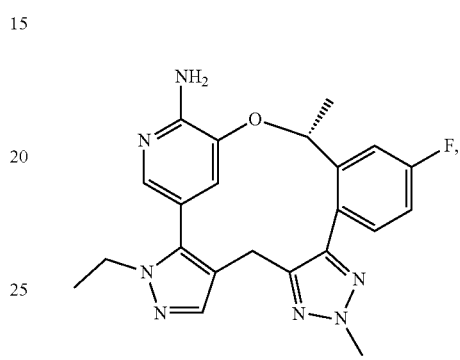 | 5 |
| 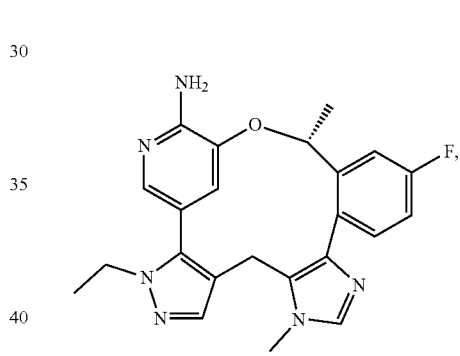 | 6 |
| 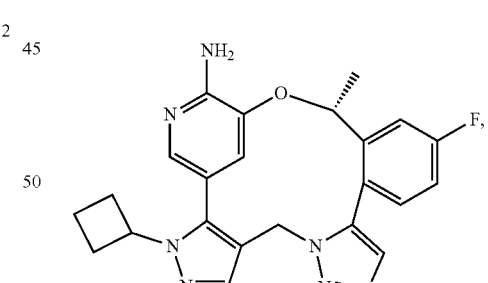 | 7 |
| 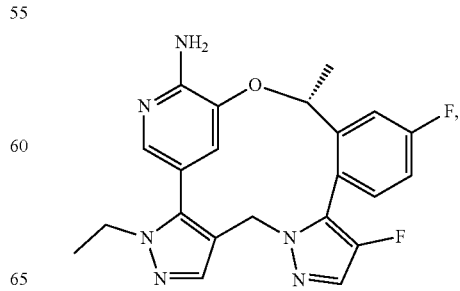 | 8 |

TABLE 1-continued
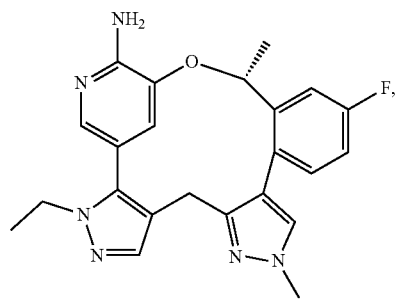 [SMILES: CCn1ncc2c1-c1cnc(N)c(c1)O[C@H](C)c1cc(F)ccc1-c1cn(C)nc1C2]
9
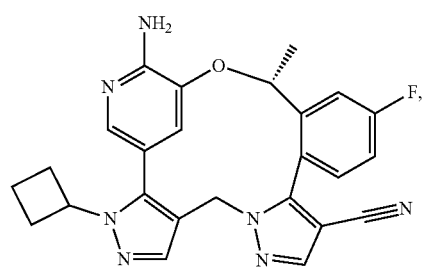 [SMILES: C[C@H]1Oc2cc(cnc2N)-c2c(cnn2C2CCC2)Cn2ncc(C#N)c2-c2ccc(F)cc21]
10
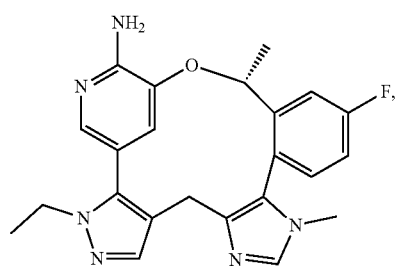 [SMILES: CCn1ncc2c1-c1cnc(N)c(c1)O[C@H](C)c1cc(F)ccc1-c1c(ncn1C)C2]
11
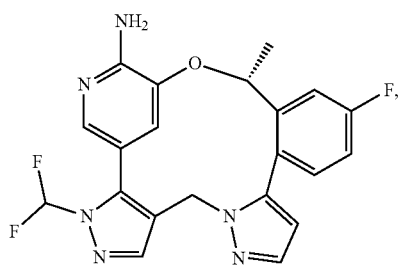 [SMILES: C[C@H]1Oc2cc(cnc2N)-c2c(cnn2C(F)F)Cn2nccc2-c2ccc(F)cc21]
12
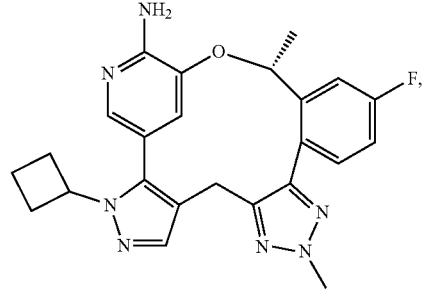 [SMILES: C[C@H]1Oc2cc(cnc2N)-c2c(cnn2C2CCC2)Cc2nn(C)nc2-c2ccc(F)cc21]
13
TABLE 1-continued
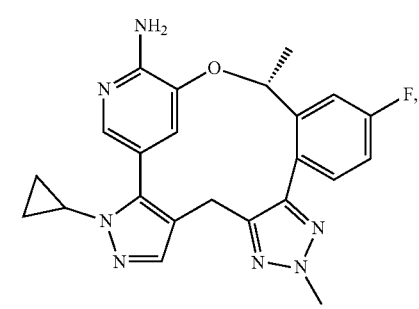 [SMILES: C[C@H]1Oc2cc(cnc2N)-c2c(cnn2C2CC2)Cc2nn(C)nc2-c2ccc(F)cc21]
14
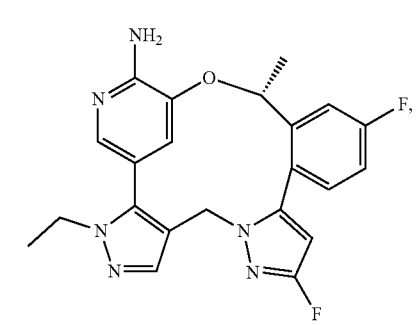 [SMILES: CCn1ncc2c1-c1cnc(N)c(c1)O[C@H](C)c1cc(F)ccc1-c1cc(F)nn1C2]
15
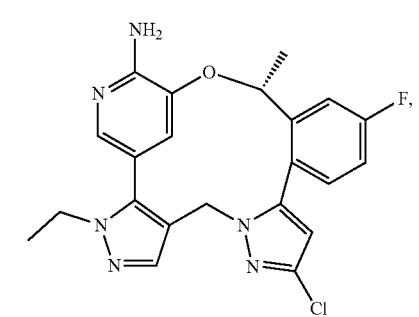 [SMILES: CCn1ncc2c1-c1cnc(N)c(c1)O[C@H](C)c1cc(F)ccc1-c1cc(Cl)nn1C2]
16
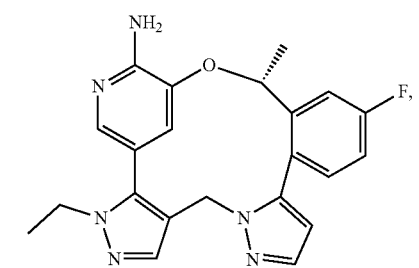 [SMILES: CCn1ncc2c1-c1cnc(N)c(c1)O[C@H](C)c1cc(F)ccc1-c1ccnn1C2]
17
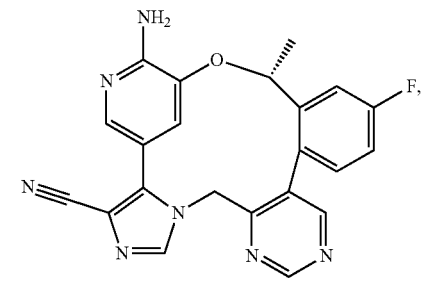 [SMILES: C[C@H]1Oc2cc(cnc2N)-c2c(C#N)ncn2Cc2ncncc2-c2ccc(F)cc21]
18

TABLE 1-continued
| | |
|---|---|
| 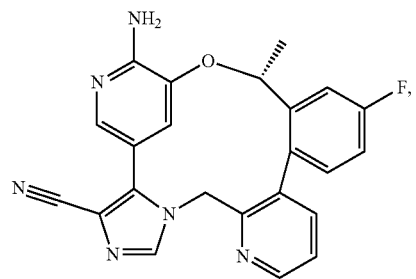 | 19 |
| 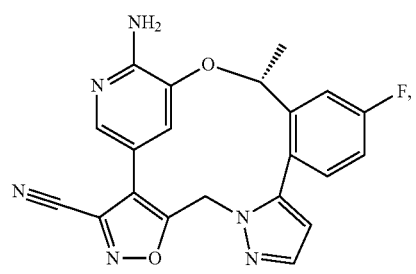 [SMILES: C[C@H]1Oc2cc(cnc2N)-c2c(C#N)noc2Cn2nccc2-c2ccc(F)cc21] | 20 |
| 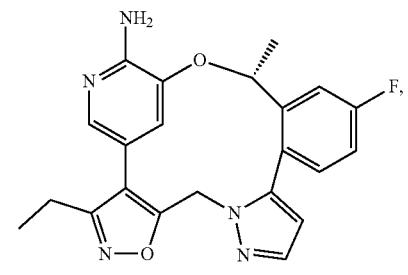 [SMILES: CCc1noc2c1-c1cnc(N)c(c1)O[C@H](C)c1cc(F)ccc1-c1ccnn1C2] | 21 |
| 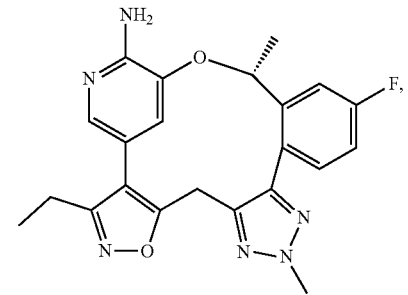 [SMILES: CCc1noc2c1-c1cnc(N)c(c1)O[C@H](C)c1cc(F)ccc1-c1nn(C)nc1C2] | 22 |
| 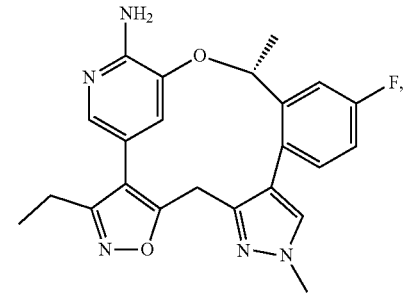 [SMILES: CCc1noc2c1-c1cnc(N)c(c1)O[C@H](C)c1cc(F)ccc1-c1cn(C)nc1C2] | 23 |
TABLE 1-continued
| | |
|---|---|
| 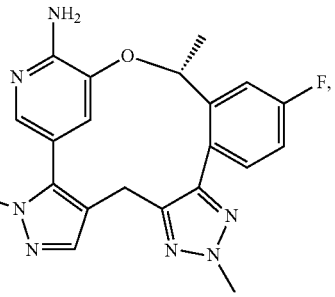 | 24 |
| 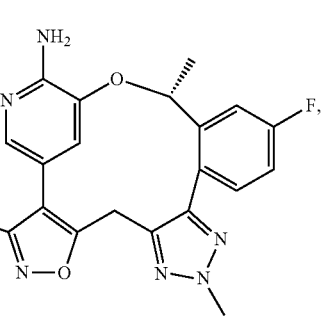 | 25 |
| 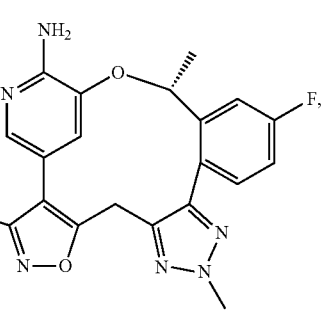 | 26 |
| 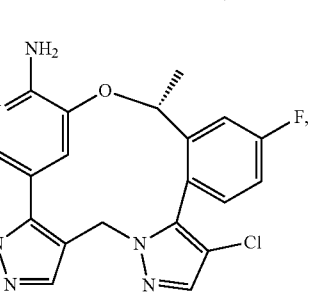 | 27 |
| 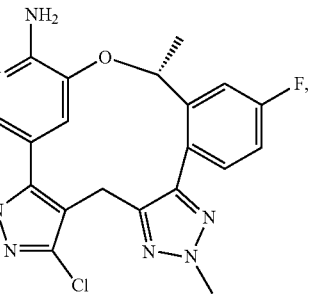 | 28 |

TABLE 1-continued
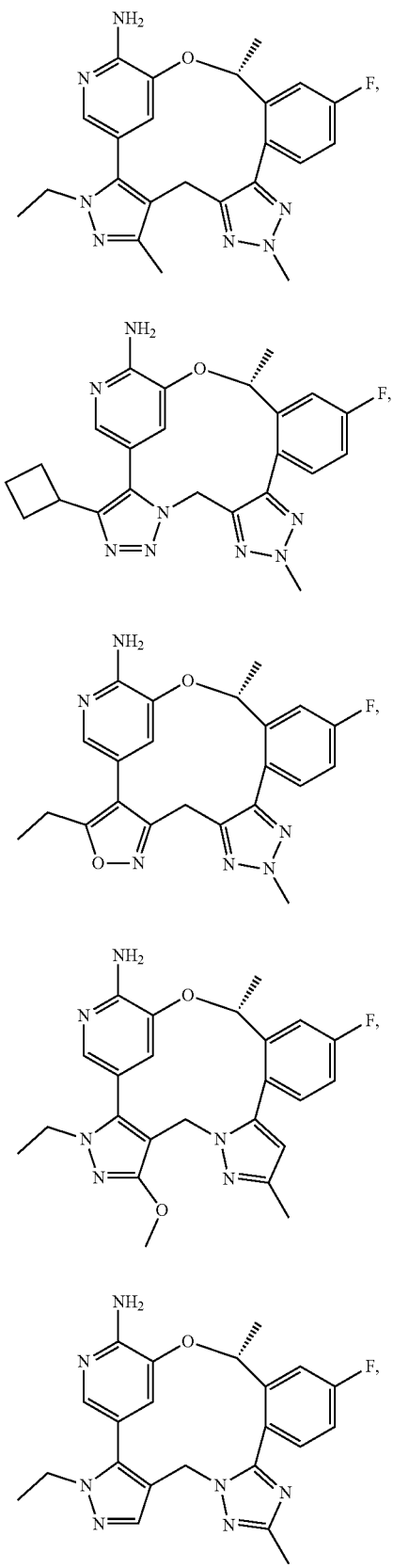
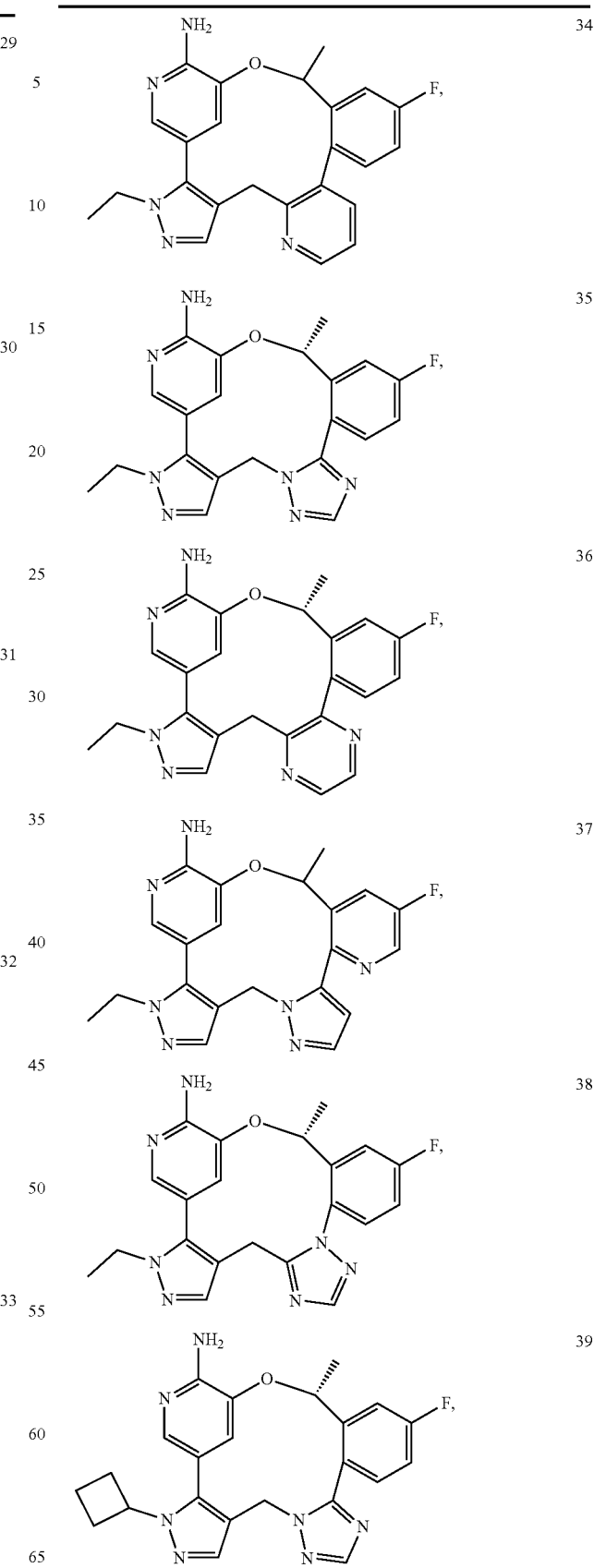

TABLE 1-continued
40
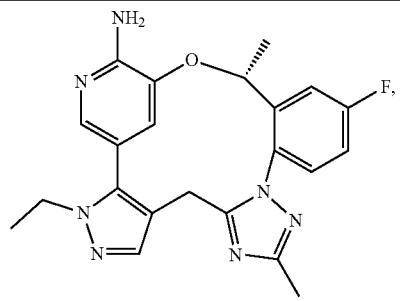
41
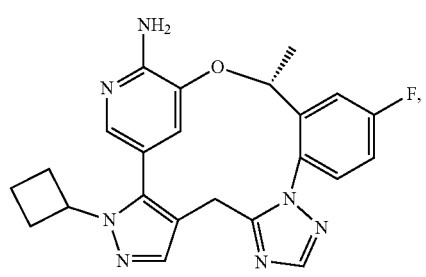 [SMILES: C[C@H]1Oc2cc(cnc2N)-c2c(cnn2C2CCC2)Cc2ncnn2-c2ccc(F)cc21]
42
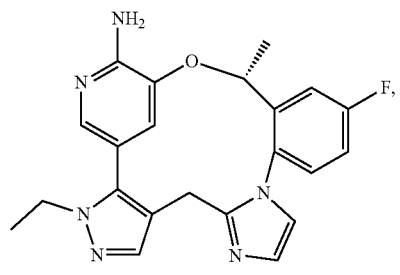 [SMILES: CCn1ncc2c1-c1cnc(N)c(c1)O[C@H](C)c1cc(F)ccc1-n1ccnc1C2]
43
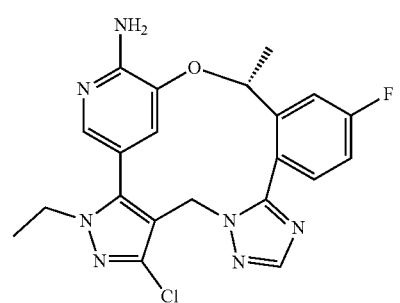 [SMILES: CCn1nc(Cl)c2c1-c1cnc(N)c(c1)O[C@H](C)c1cc(F)ccc1-c1ncnn1C2]
44
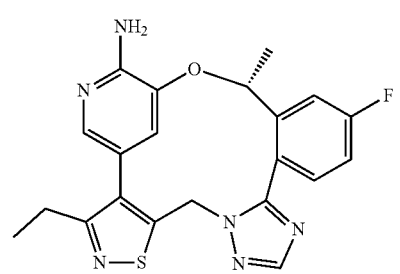 [SMILES: CCc1nsc2c1-c1cnc(N)c(c1)O[C@H](C)c1cc(F)ccc1-c1ncnn1C2]
TABLE 1-continued
45
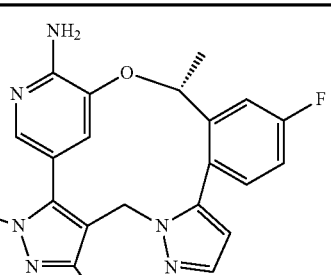
46
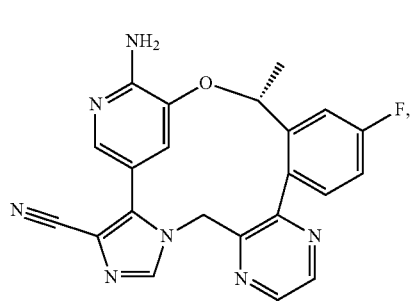 [SMILES: C[C@H]1Oc2cc(cnc2N)-c2c(C#N)ncn2Cc2nccnc2-c2ccc(F)cc21]
47
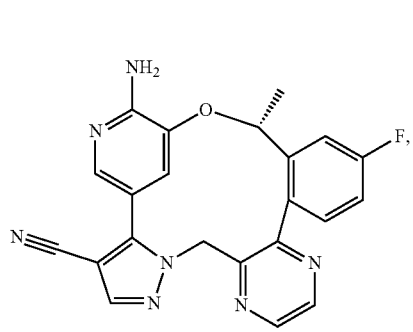 [SMILES: C[C@H]1Oc2cc(cnc2N)-c2c(C#N)cnn2Cc2nccnc2-c2ccc(F)cc21]
48
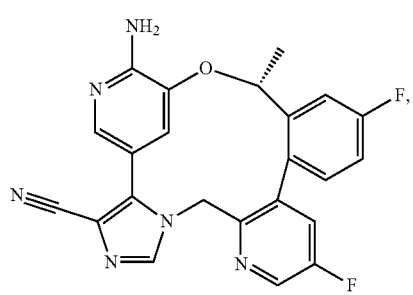 [SMILES: C[C@H]1Oc2cc(cnc2N)-c2c(C#N)ncn2Cc2ncc(F)cc2-c2ccc(F)cc21]
49
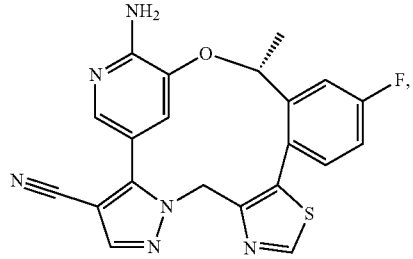 [SMILES: C[C@H]1Oc2cc(cnc2N)-c2c(C#N)cnn2Cc2ncsc2-c2ccc(F)cc21]

TABLE 1-continued
50 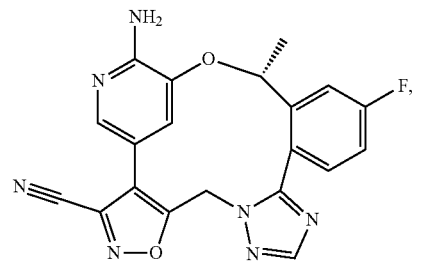 [SMILES: C[C@H]1Oc2cc(cnc2N)-c2c(C#N)noc2Cn2ncnc2-c2ccc(F)cc21]
51 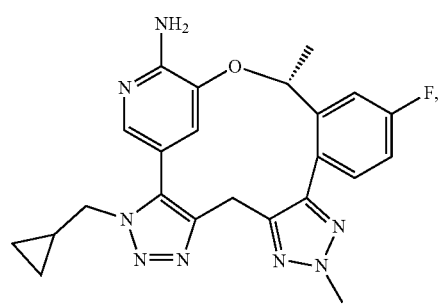 [SMILES: C[C@H]1Oc2cc(cnc2N)-c2c(nnn2CC2CC2)Cc2nn(C)nc2-c2ccc(F)cc21]
52 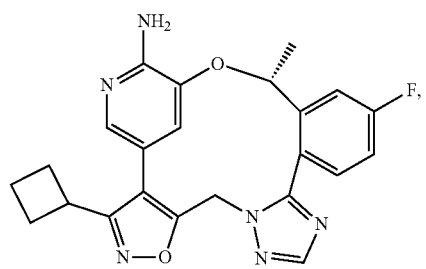 [SMILES: C[C@H]1Oc2cc(cnc2N)-c2c(C3CCC3)noc2Cn2ncnc2-c2ccc(F)cc21]
53 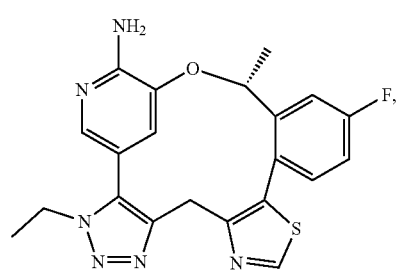 [SMILES: CCn1nnc2c1-c1cnc(N)c(c1)O[C@H](C)c1cc(F)ccc1-c1scnc1C2]
54 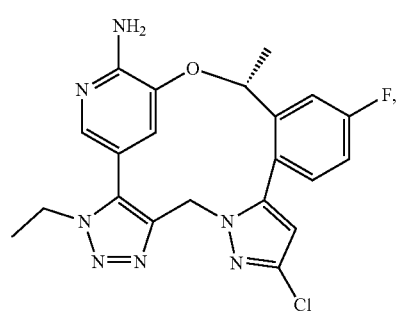 [SMILES: CCn1nnc2c1-c1cnc(N)c(c1)O[C@H](C)c1cc(F)ccc1-c1cc(Cl)nn1C2]
TABLE 1-continued
55 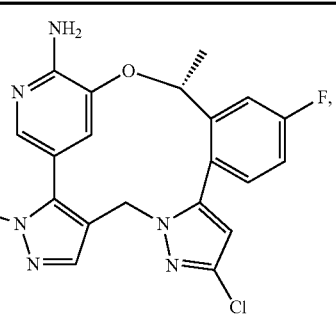
56 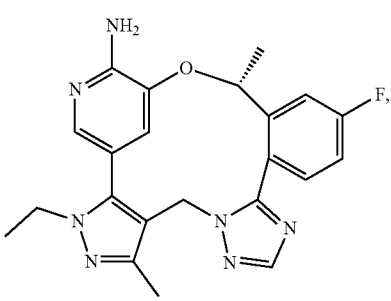 [SMILES: CCn1nc(C)c2c1-c1cnc(N)c(c1)O[C@H](C)c1cc(F)ccc1-c1ncnn1C2]
57 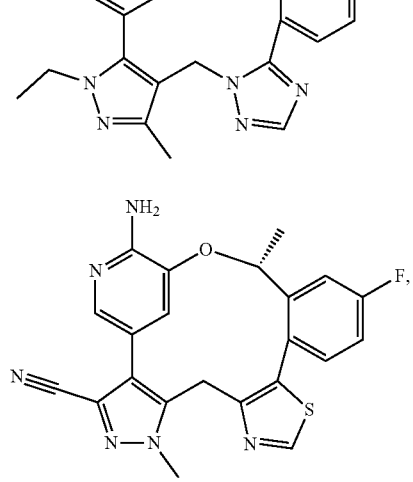
58 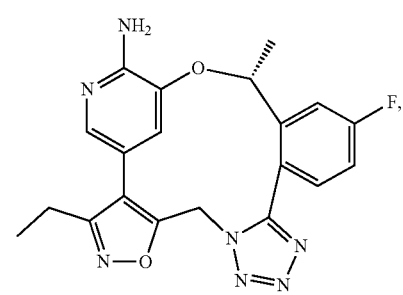 [SMILES: CCc1noc2c1-c1cnc(N)c(c1)O[C@H](C)c1cc(F)ccc1-c1nnnn1C2]
59 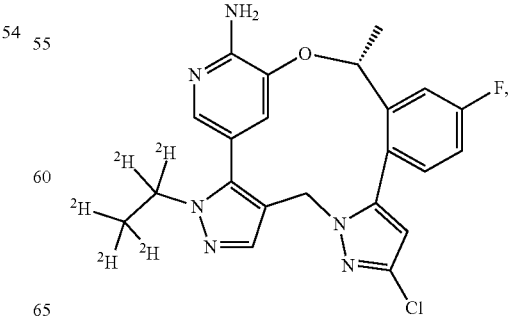

TABLE 1-continued
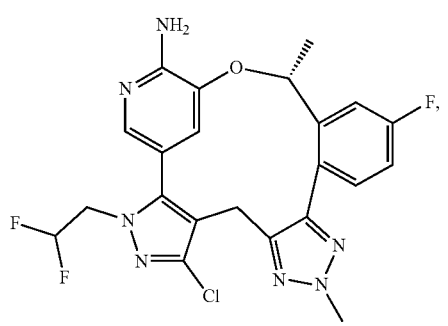 [SMILES: C[C@H]1Oc2cc(cnc2N)-c2c(c(Cl)nn2CC(F)F)Cc2nn(C)nc2-c2ccc(F)cc21] 60
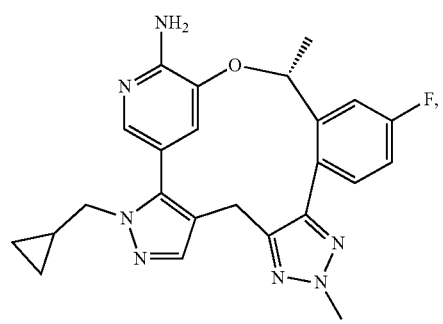 [SMILES: C[C@H]1Oc2cc(cnc2N)-c2c(cnn2CC2CC2)Cc2nn(C)nc2-c2ccc(F)cc21] 61
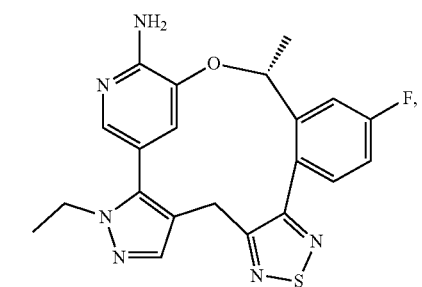 [SMILES: CCn1ncc2c1-c1cnc(N)c(c1)O[C@H](C)c1cc(F)ccc1-c1nsnc1C2] 62
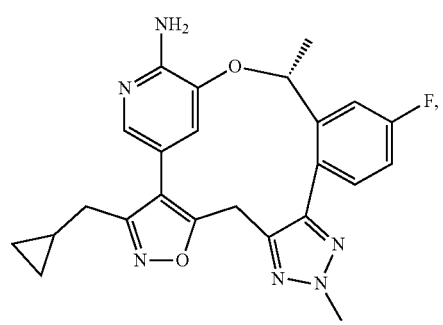 [SMILES: C[C@H]1Oc2cc(cnc2N)-c2c(CC3CC3)noc2Cc2nn(C)nc2-c2ccc(F)cc21] 63
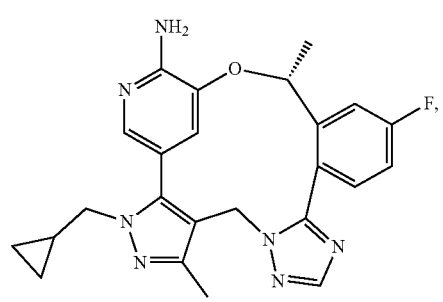 [SMILES: Cc1nn(CC2CC2)c2c1Cn1ncnc1-c1ccc(F)cc1[C@@H](C)Oc1cc-2cnc1N] 64
TABLE 1-continued
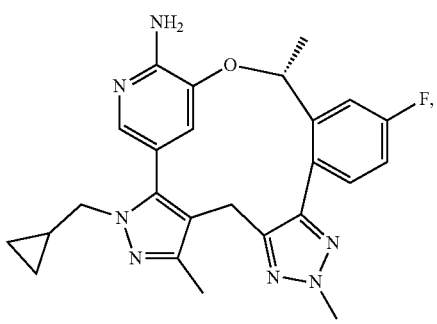 [SMILES: Cc1nn(CC2CC2)c2c1Cc1nn(C)nc1-c1ccc(F)cc1[C@@H](C)Oc1cc-2cnc1N] 65
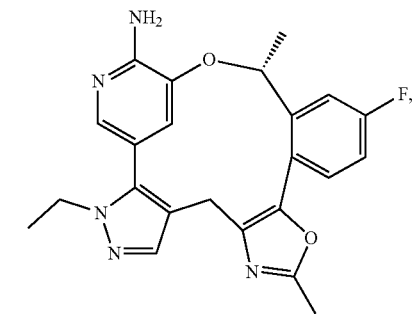 [SMILES: CCn1ncc2c1-c1cnc(N)c(c1)O[C@H](C)c1cc(F)ccc1-c1oc(C)nc1C2] 66
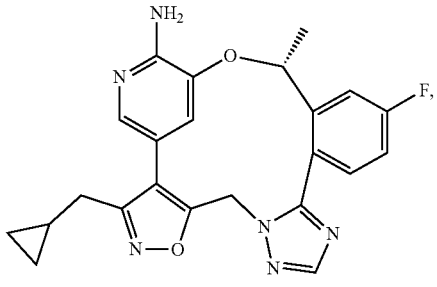 [SMILES: C[C@H]1Oc2cc(cnc2N)-c2c(CC3CC3)noc2Cn2ncnc2-c2ccc(F)cc21] 67
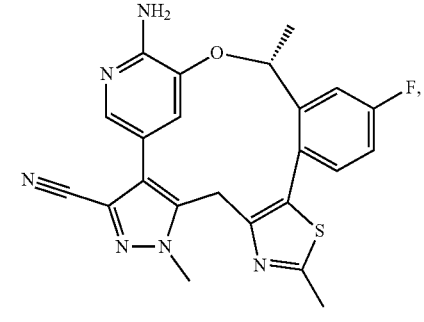 [SMILES: Cc1nc2c(s1)-c1ccc(F)cc1[C@@H](C)Oc1cc(cnc1N)-c1c(C#N)nn(C)c1C2] 68
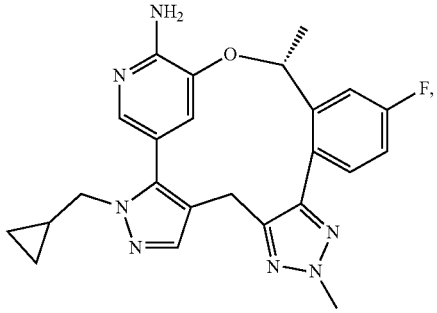 [SMILES: C[C@H]1Oc2cc(cnc2N)-c2c(cnn2CC2CC2)Cc2nn(C)nc2-c2ccc(F)cc21] 69

TABLE 1-continued
| | |
|---|---|
| 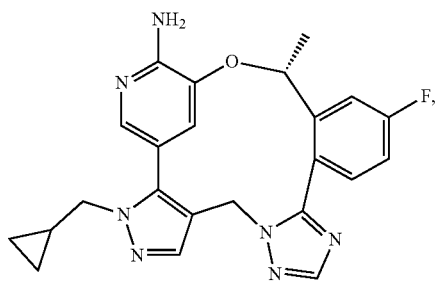 [SMILES: C[C@H]1Oc2cc(cnc2N)-c2c(cnn2CC2CC2)Cn2ncnc2-c2ccc(F)cc21] 70 | 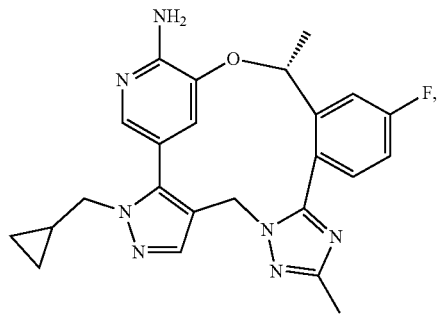 75 |
| 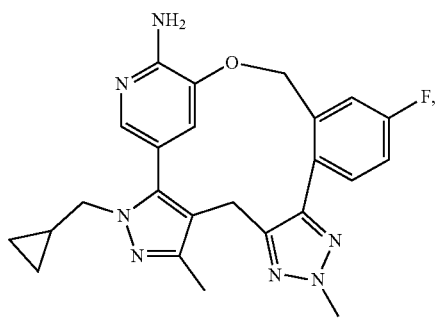 [SMILES: Cc1nn(CC2CC2)c2c1Cc1nn(C)nc1-c1ccc(F)cc1COc1cc-2cnc1N] 71 | 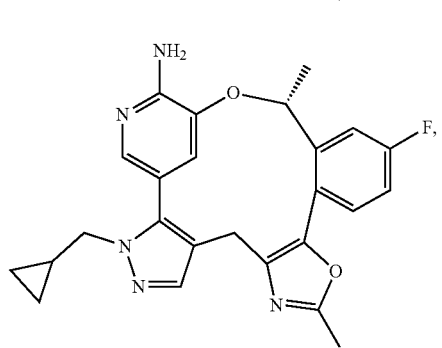 76 |
| 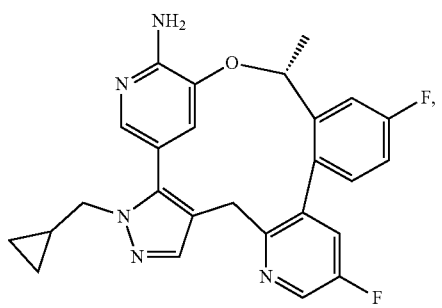 [SMILES: C[C@H]1Oc2cc(cnc2N)-c2c(cnn2CC2CC2)Cc2ncc(F)cc2-c2ccc(F)cc21] 72 | 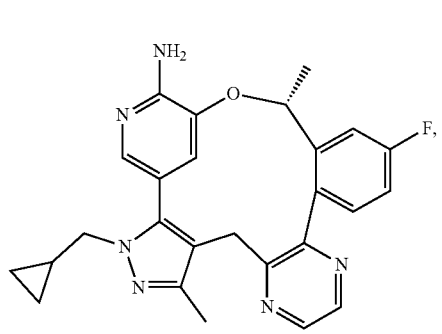 77 |
| 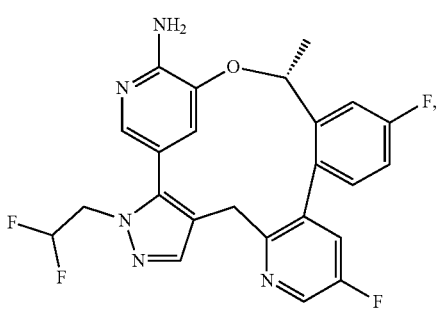 [SMILES: C[C@H]1Oc2cc(cnc2N)-c2c(cnn2CC(F)F)Cc2ncc(F)cc2-c2ccc(F)cc21] 73 | 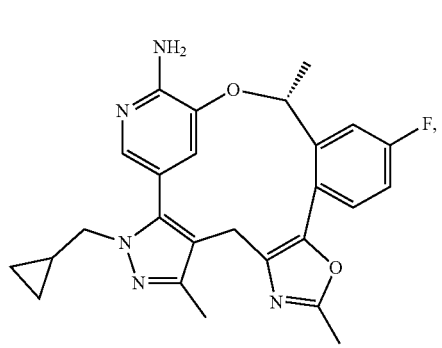 78 |
| 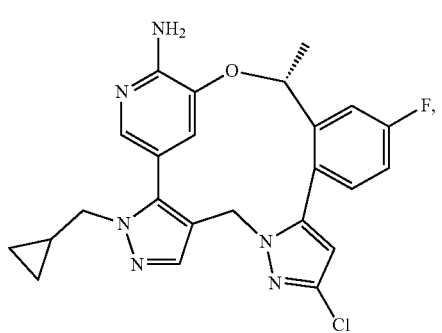 [SMILES: C[C@H]1Oc2cc(cnc2N)-c2c(cnn2CC2CC2)Cn2nc(Cl)cc2-c2ccc(F)cc21] 74 | 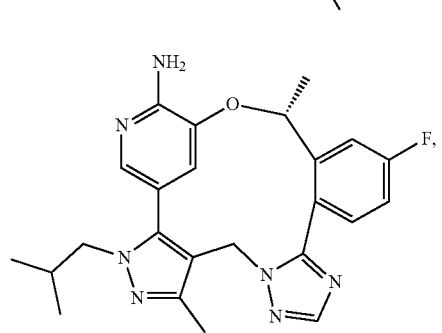 79 |

TABLE 1-continued
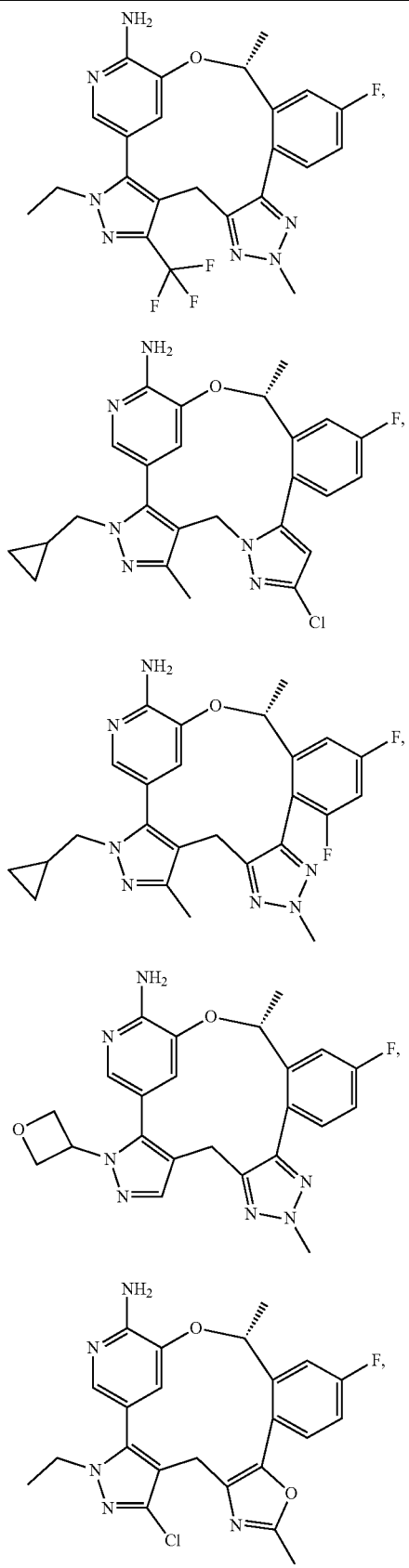
TABLE 1-continued
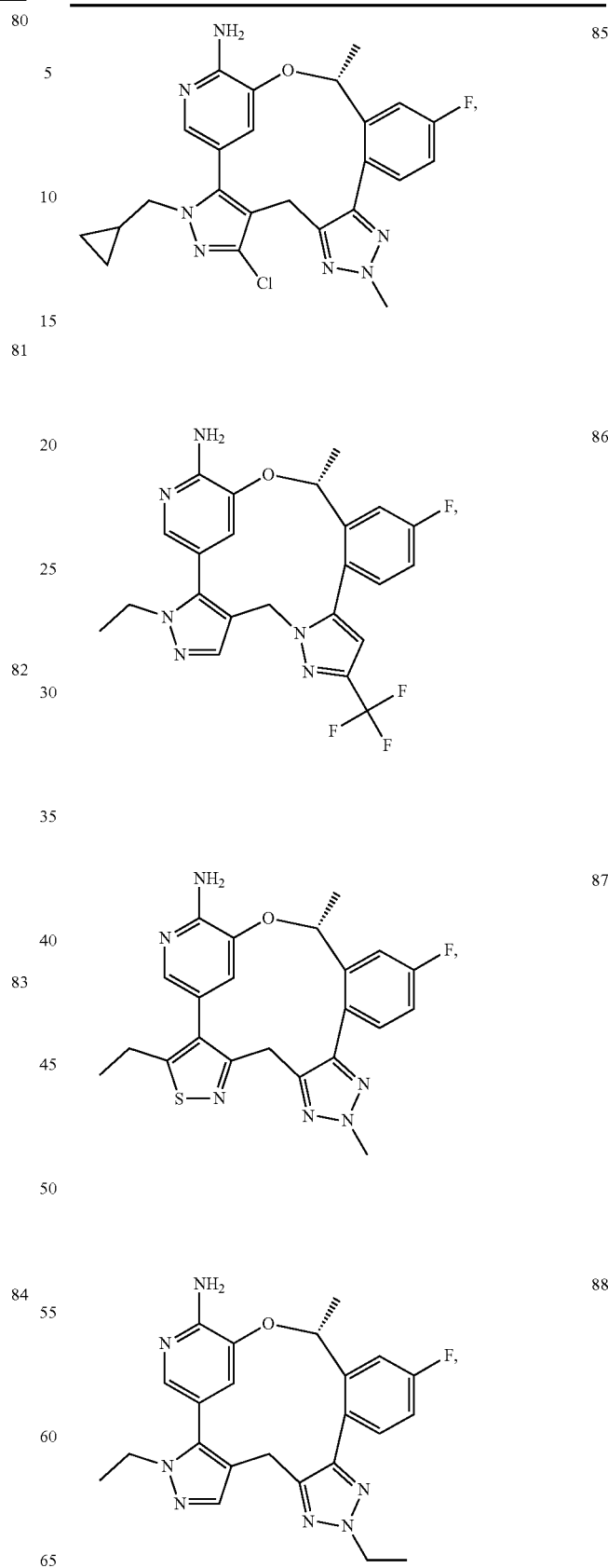

TABLE 1-continued
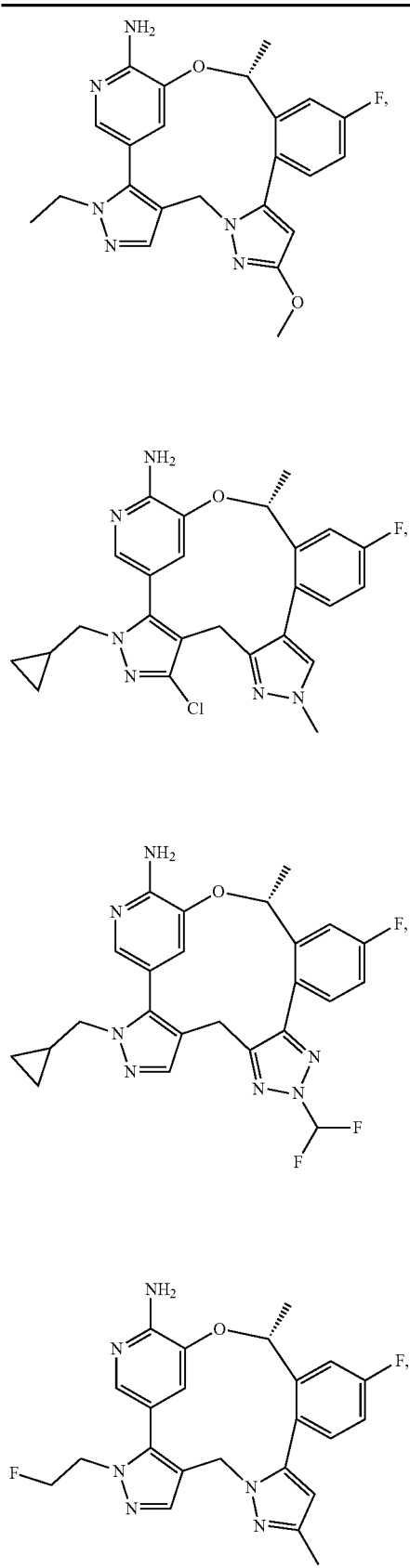
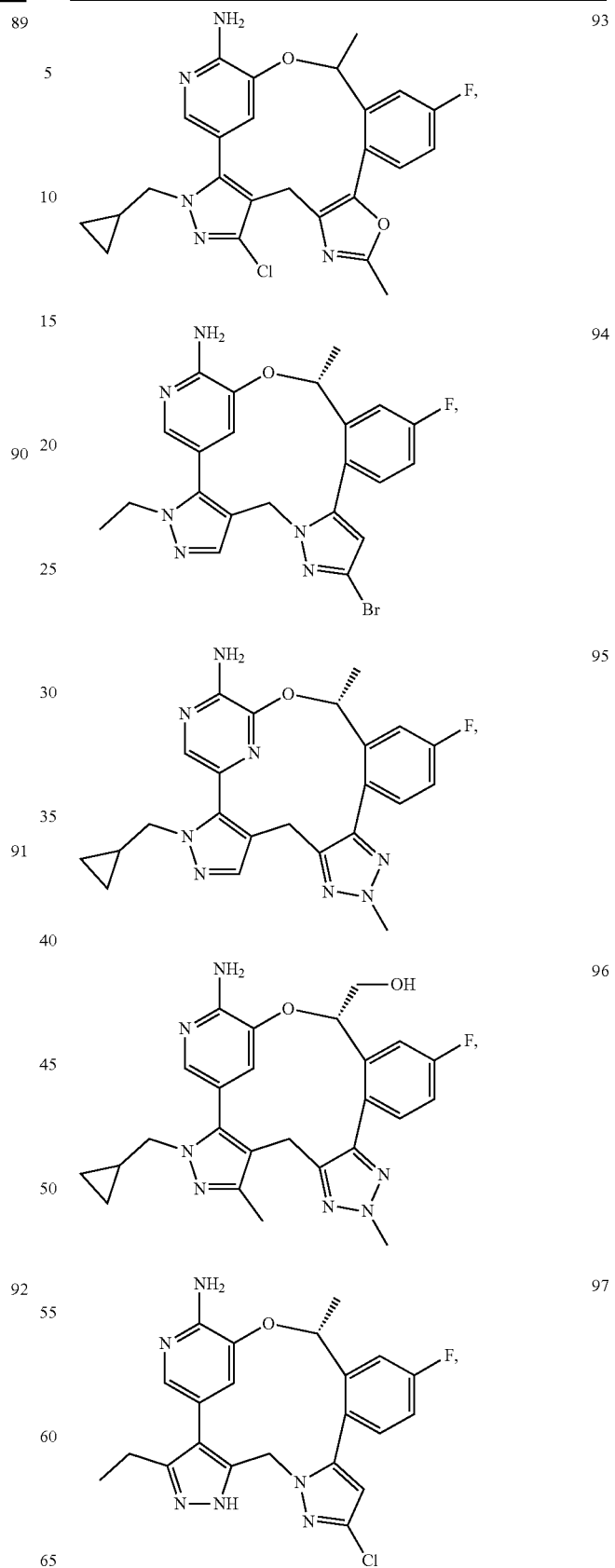

TABLE 1-continued

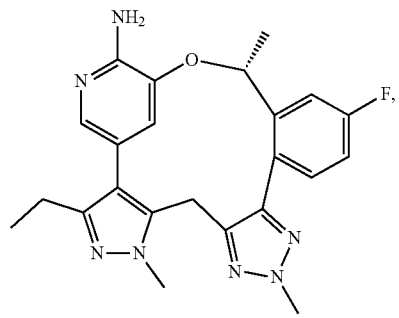 [SMILES: CCc1nn(C)c2c1-c1cnc(N)c(c1)O[C@H](C)c1cc(F)ccc1-c1nn(C)nc1C2]
98

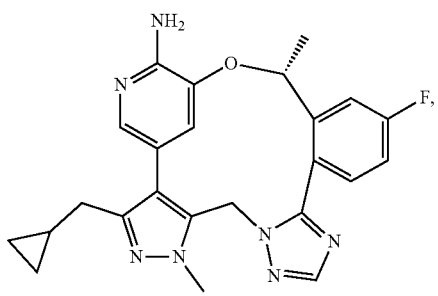 [SMILES: C[C@H]1Oc2cc(cnc2N)-c2c(CC3CC3)nn(C)c2Cn2ncnc2-c2ccc(F)cc21]
99

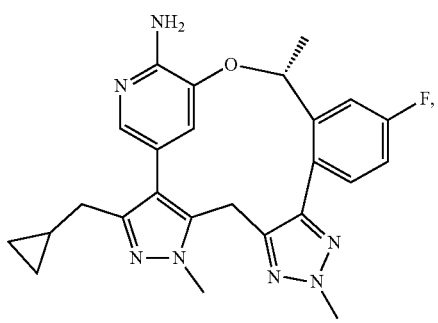 [SMILES: C[C@H]1Oc2cc(cnc2N)-c2c(CC3CC3)nn(C)c2Cc2nn(C)nc2-c2ccc(F)cc21]
100

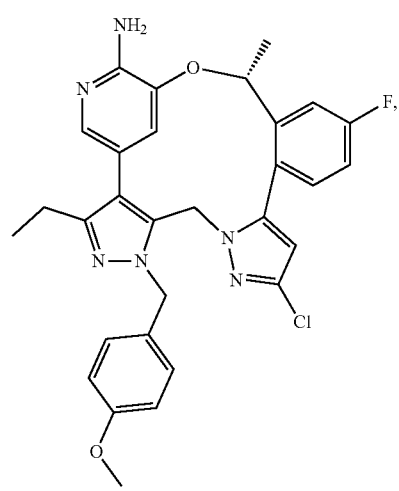 [SMILES: CCc1nn(Cc2ccc(OC)cc2)c2c1-c1cnc(N)c(c1)O[C@H](C)c1cc(F)ccc1-c1cc(Cl)nn1C2]
101

TABLE 1-continued

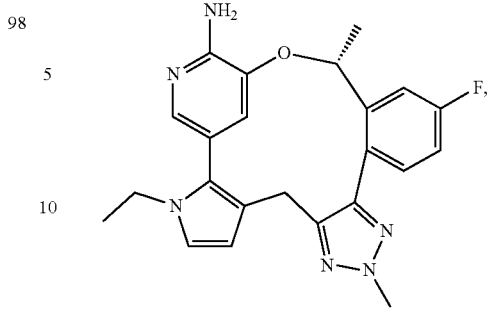
102 or a pharmaceutically acceptable salt thereof.

For any compound in Table 1 that has a chiral center due to the presence of non-hydrogen $R_1$, the R-enantiomer, the S-enantiomer, and the racemic compound of such compound are all specifically provided herein, even if not specifically shown in Table 1.

In one embodiment, provided herein is a pharmaceutically acceptable salt of a compound of Formula (I). In one embodiment, provided herein is a pharmaceutically acceptable salt of any compound in Table 1.

In certain embodiments, the pharmaceutically acceptable salt of the compound is selected from the group consisting of alkyl ammonium salts, dialkyl ammonium salts, trialkyl ammonium salts, tetra-alkyl ammonium salts, L-arginine salts, benenthamine salts, benzathine salts, betaine salts, calcium hydroxide salts, choline salts, deanol salts, diethanolamine salts, diethylamine salts, 2-(diethylamino)ethanol salts, ethanolamine salts, ethylenediamine salts, N-methylglucamine salts, hydrabamine salts, 1H-imidazole salts, lithium salts, L-lysine salts, magnesium salts, 4-(2-hydroxyethyl)morpholine salts, piperazine salts, potassium salts, 1-(2-hydroxyethyl)pyrrolidine salts, sodium salts, triethanolamine salts, tromethamine salts, Na salts, Ca salts, K salts, Mg salts, and Zn salts.

In specific embodiments, the pharmaceutically acceptable salt is a solvate selected from the group consisting of water, methanol, ethanol, and dimethylformamide.

In certain embodiments the compound is a pharmaceutical composition including a pharmaceutically acceptable carrier or excipient.

In specific embodiments, the composition is in a form selected from the group consisting of a tablet, a capsule, a granule, a lyophile for reconstitution, a powder, a solution, a syrup, a suppository, an injection, a transdermal delivery system, and a solution suitable for topical administration.

Methods of Use

Provided herein are methods of treating cancer comprising administering a compound of the disclosure, such as a compound of Formula (I), or an enantiomer, a mixture of enantiomers, or a tautomer thereof, or a pharmaceutically acceptable salt thereof.

Cancer is a disease of uncontrolled cell proliferation that results from alterations in certain genes. Some of these alterations occur in genes that encode receptor tyrosine kinases (RTKs), a family of membrane-bound proteins that transmit signals from outside the cell to promote cell survival, growth, and proliferation. Aberrant RTK activation can lead to excessive cell growth and hence cancer. Generally, RTKs contain an N-terminal domain that binds extracellular ligands, a transmembrane domain, and a C-terminal kinase domain that catalyzes intracellular signal transduction.

In some embodiments, the compound of Formula (I) is an inhibitor of human ROS1. ROS1 is an RTK encoded by the ROS1 gene. The ligands and biological functions of human ROS1 are unknown, but its homologs in some other species have been shown to bind extracellular ligands and stimulate cell differentiation. For example, mouse ROS1 is essential for male gamete maturation and reproduction. In humans, ROS1 chromosomal rearrangements are a well-documented cause of cancer, representing 1-2% of non-small cell lung cancer (NSCLC) and a subset of many other cancers. These rearrangements result in the fusion of the C-terminus of ROS1 with the N-terminus of various partner proteins, the most common of which is CD74. ROS1 fusions have constitutive kinase activity that drives tumor growth through MAPK, PI3K, and JAK/STAT signaling pathways. Small-molecule tyrosine kinase inhibitors (TKIs) have been used to target ROS1 fusions in cancer, including crizotinib and entrectinib. Crizotinib was the first FDA-approved TKI for the treatment of ROS1-positive NSCLC, with an overall response rate of 60-80% and median progression-free survival of 9-19 months. Despite an initial response, most patients acquire resistance to crizotinib and relapse. The predominant mechanism of resistance is the G2032R mutation in the solvent front, which dramatically reduces crizotinib affinity. No inhibitors with activity against ROS1-G2032R fusions have been FDA-approved, indicating a need in the art.

In some embodiments, the compound of Formula (I) is an inhibitor of human anaplastic lymphoma kinase (ALK). ALK, also known as cluster of differentiation 246 (CD246), is an RTK encoded by the ALK gene. ALK and ROS1 are evolutionarily related; both belong to the insulin receptor superfamily, and their kinase domains share around 80% sequence similarity. A few ALK ligands in humans have been identified, including pleiotrophin and midkine growth factors. While the roles of ALK in humans remain inconclusive, much evidence from mouse studies suggests that it is important for the development of the nervous system. Like ROS1, ALK chromosomal rearrangements also lead to constitutively active fusion proteins that promote oncogenic transformation through MAPK, JAK/STAT, or other signaling pathways. ALK rearrangements represent 3-5% of NSCLC, roughly half of anaplastic large-cell lymphoma (ALCL), and a subset of many other cancers, with the predominant fusions being EML4-ALK for NSCLC and NPM1-ALK for ALCL. Oncogenic point mutations and amplification of ALK have also been observed, albeit at a much lower frequency than translocations. Crizotinib, ceritinib, alectinib, brigatinib, and lorlatinib are FDA-approved TKIs for the treatment of ALK-positive NSCLC and other cancers, either in front-line or after prior therapy. Crizotinib, for example, shows an overall response rate of 60-80% and median progression-free survival of 8-11 months, which is comparable to its activity in ROS1-positive NSCLC. Despite an initial response, many resistance mutations have emerged to the aforementioned FDA-approved TKIs. Some of these mutations, such as the combined L1196M gatekeeper and G1202R solvent front mutation, are resistant to all of the approved drugs. New treatments of ALK-positive cancer harboring resistance mutations are a need in the art.

In further embodiments, the compound of Formula (I) is an inhibitor of human tropomyosin receptor kinases (TRKs). The TRK family comprises receptor tyrosine kinases TRKA, TRKB, and TRKC, which are encoded by the NTRK1, NTRK2, and NTRK3 genes, respectively. Each TRK is activated by a different but overlapping set of neurotrophin ligands such as NGF, BDNF, and NT-3. All TRKs modulate similar downstream signaling pathways, consistent with sequence divergence in the ligand-binding domain but convergence in the kinase domain (90% similarity). TRKs play crucial roles in the nervous system of developing and adult mammals by regulating processes such as memory, movement, pain, and proprioception. Like ROS1 and ALK, NTRK rearrangements lead to constitutively active TRK fusions that drive oncogenic transformation through MAPK, PI3K, and other pathways. TRK fusions are found in many cancers and represent over 80% of the cases in secretory breast carcinoma, mammary analogue secretory carcinomas, infantile fibrosarcoma, and congenital mesoblastic nephroma. Thus, inhibition of TRKs is advantageous for treating cancers expressing TRK fusions.

Many ROS1 and ALK inhibitors in the prior art also exhibit potent inhibition of native non-oncogenic TRKs. This is a substantial drawback because native TRKs play important functions in the nervous system, and inadvertent inhibition of native TRKs is associated with adverse reactions including dizziness, ataxia, gait disturbance, paraesthesia, weight gain, and cognitive changes. New therapies that spare TRKs while selectively targeting ROS1 and/or ALK, in their non-mutant and/or mutant forms, are a need in the art.

In one embodiment, provided herein is a method of decreasing a level of ROS1 or ALK in a cell, comprising contacting the cell with a compound or a pharmaceutical composition or a pharmaceutical combination provided herein. In an embodiment, such contact occurs in a cell in a mammal such as a human. In an embodiment, such contact occurs in a cell in human patient having a cancer provided herein.

In one embodiment, a compound provided herein selectively inhibits ROS1. In one embodiment, the compound selectively inhibits ROS1 over ALK. By way of non-limiting example, the ratio of selectivity can be greater than a factor of about 1.5, greater than a factor of about 2, greater than a factor of about 3, greater than a factor of about 4, greater than a factor of about 5, greater than a factor of about 10, greater than a factor of about 20, greater than a factor of about 30, greater than a factor of about 50, or greater than a factor of about 100, where selectivity can be measured by ratio of $IC_{50}$ values, among other means. In one embodiment, the selectivity of ROS1 over ALK is measured by the ratio of the $IC_{50}$ value against ALK to the $IC_{50}$ value against ROS1.

In one embodiment, the compound selectively inhibits ROS1 over TRK (e.g., TRKA, TRKB, and/or TRBC). By way of non-limiting example, the ratio of selectivity can be greater than a factor of about 5, greater than a factor of about 10, greater than a factor of about 50, greater than a factor of about 100, greater than a factor of about 200, greater than a factor of about 400, greater than a factor of about 600, greater than a factor of about 800, greater than a factor of about 1000, greater than a factor of about 1500, greater than a factor of about 2000, greater than a factor of about 5000, greater than a factor of about 10,000, or greater than a factor of about 20,000, where selectivity can be measured by ratio of $IC_{50}$ values, among other means. In one embodiment, the selectivity of ROS1 over TRK is measured by the ratio of the $IC_{50}$ value against TRK to the $IC_{50}$ value against ROS1.

In one embodiment, a compound provided herein selectively inhibits ALK. In one embodiment, the compound selectively inhibits ALK over ROS1. By way of non-limiting example, the ratio of selectivity can be greater than a factor of about 1.5, greater than a factor of about 2, greater than a factor of about 3, greater than a factor of about 4, greater than a factor of about 5, or greater than a factor of about 10, where selectivity can be measured by ratio of $IC_{50}$ values, among other means. In one embodiment, the selectivity of ALK over ROS1 is measured by the ratio of the $IC_{50}$ value against ROS1 to the $IC_{50}$ value against ALK.

In one embodiment, the compound selectively inhibits ALK over TRK (e.g., TRKA, TRKB, and/or TRBC). By way of non-limiting example, the ratio of selectivity can be greater than a factor of about 5, greater than a factor of about 10, greater than a factor of about 50, greater than a factor of about 100, greater than a factor of about 200, greater than a factor of about 400, greater than a factor of about 600, greater than a factor of about 800, greater than a factor of about 1000, greater than a factor of about 1500, greater than a factor of about 2000, greater than a factor of about 5000, or greater than a factor of about 10,000, where selectivity can be measured by ratio of $IC_{50}$ values, among other means. In one embodiment, the selectivity of ALK over TRK is measured by the ratio of the $IC_{50}$ value against TRK to the $IC_{50}$ value against ALK.

In one embodiment, the compound selectively inhibits ROS1 and ALK over TRK (e.g., TRKA, TRKB, and/or TRBC). By way of non-limiting example, the ratio of selectivity can be greater than a factor of about 5, greater than a factor of about 10, greater than a factor of about 50, greater than a factor of about 100, greater than a factor of about 200, greater than a factor of about 400, greater than a factor of about 600, greater than a factor of about 800, greater than a factor of about 1000, greater than a factor of about 1500, greater than a factor of about 2000, greater than a factor of about 5000, greater than a factor of about 10,000, or greater than a factor of about 20,000, where selectivity can be measured by ratio of $IC_{50}$ values, among other means. In one embodiment, the selectivity of ROS1 and ALK over TRK is measured by the ratio of the $IC_{50}$ value against TRK to the $IC_{50}$ value against ROS1 and ALK.

In one embodiment, provided herein is a method for selectively inhibiting ROS1 over ALK wherein the inhibition takes place in a cell. In one embodiment, provided herein is a method for selectively inhibiting ROS1 over TRK (e.g., TRKA, TRKB, and/or TRBC) wherein the inhibition takes place in a cell. In one embodiment, the method comprises contacting ROS1 with an effective amount of a compound provided herein. In an embodiment, such contact occurs in a cell. In an embodiment, such contact occurs in a cell in a mammal such as a human. In an embodiment, such contact occurs in a cell in human patient having a cancer provided herein.

In one embodiment, provided herein is a method for selectively inhibiting ROS1 over ALK wherein the inhibition takes place in a subject suffering from cancer, said method comprising administering an effective amount of a compound or a pharmaceutical composition provided herein to said subject. In certain embodiments, provided herein is a method of treating a subject suffering from a cancer associated with ROS1, said method comprising selectively inhibiting ROS1 over ALK by administering an amount of a compound or a pharmaceutical composition provided herein to said subject, wherein said amount is sufficient for selective inhibiting ROS1 over ALK.

In one embodiment, provided herein is a method for selectively inhibiting ROS1 over TRK (e.g., TRKA, TRKB, and/or TRBC) wherein the inhibition takes place in a subject suffering from cancer, said method comprising administering an effective amount of a compound or a pharmaceutical composition provided herein to said subject. In certain embodiments, provided herein is a method of treating a subject suffering from a cancer associated with ROS1, said method comprising selectively inhibiting ROS1 over TRK (e.g., TRKA, TRKB, and/or TRBC) by administering an amount of a compound or a pharmaceutical composition provided herein to said subject, wherein said amount is sufficient for selective inhibiting ROS1 over TRK (e.g., TRKA, TRKB, and/or TRBC).

In one embodiment, provided herein is a method for selectively inhibiting ALK over ROS1 wherein the inhibition takes place in a cell. In one embodiment, provided herein is a method for selectively inhibiting ALK over TRK (e.g., TRKA, TRKB, and/or TRBC) wherein the inhibition takes place in a cell. In one embodiment, the method comprises contacting ALK with an effective amount of a compound provided herein. In an embodiment, such contact occurs in a cell. In an embodiment, such contact occurs in a cell in a mammal such as a human. In an embodiment, such contact occurs in a cell in human patient having a cancer provided herein.

In one embodiment, provided herein is a method for selectively inhibiting ALK over ROS1 wherein the inhibition takes place in a subject suffering from cancer, said method comprising administering an effective amount of a compound or a pharmaceutical composition provided herein to said subject. In certain embodiments, provided herein is a method of treating a subject suffering from a cancer associated with ALK, said method comprising selectively inhibiting ALK over ROS1 by administering an amount of a compound or a pharmaceutical composition provided herein to said subject, wherein said amount is sufficient for selective inhibiting ALK over ROS1.

In one embodiment, provided herein is a method for selectively inhibiting ALK over TRK (e.g., TRKA, TRKB, and/or TRBC) wherein the inhibition takes place in a subject suffering from cancer, said method comprising administering an effective amount of a compound or a pharmaceutical composition provided herein to said subject. In certain embodiments, provided herein is a method of treating a subject suffering from a cancer associated with ALK, said method comprising selectively inhibiting ALK over TRK (e.g., TRKA, TRKB, and/or TRBC) by administering an amount of a compound or a pharmaceutical composition provided herein to said subject, wherein said amount is sufficient for selective inhibiting ALK over TRK (e.g., TRKA, TRKB, and/or TRBC).

As used herein and unless otherwise specified, inhibition of ROS1 includes inhibition of wild type ROS1, or a mutation thereof; inhibition of ALK includes inhibition of wild type ALK, or a mutation thereof; and inhibition of TRK includes inhibition of wild type TRK, or a mutation thereof.

Cancers treated by methods of the present disclosure include, but are not limited to, lung cancer, e.g., non-small cell lung cancer, inflammatory myofibroblastic tumor, ovarian cancer, e.g., serous ovarian carcinoma, melanoma, e.g., spitzoid melanoma, glioblastoma, bile duct cancer, e.g., cholangiocarcinoma, gastric cancer, colorectal cancer, angiosarcoma, anaplastic large cell lymphoma, diffuse large B-cell lymphoma, large B-cell lymphoma, esophageal cancer, e.g., esophageal squamous cell carcinoma, kidney cancer, e.g., renal medullary carcinoma or renal cell carcinoma, breast cancer, e.g., triple negative breast cancer, thyroid cancer, e.g., papillary thyroid cancer, neuroblastoma, epithelioid hemangioendothelioma, colon cancer, and spitzoid tumor.

Cancers treated by methods of the present disclosure include cancers originating from one or more oncogenic proteins selected from ROS1, ALK, TRKA, TRKB, and TRKC. In certain embodiments, cancers treated by methods of the present disclosure include cancers that are drug resistant to treatments directed at one or more oncogenic proteins selected from ROS1, ALK, TRKA, TRKB, and TRKC.

In one embodiment, the cancer in a method provided herein is anaplastic lymphoma kinase positive (ALK+). As used herein and unless otherwise specified, an "ALK positive" (ALK+) cancer, disease, or disorder refers to a cancer, disease, or disorder characterized by inappropriately high expression of an ALK gene and/or the presence of a mutation in an ALK gene. In one embodiment, the mutation alters the biological activity of an ALK nucleic acid molecule or polypeptide. As used herein and unless otherwise specified, a "mutation" or "mutant" of ALK comprises one or more deletions, substitutions, insertions, inversions, duplications, translocations, or amplifications in the amino acid or nucleotide sequences of ALK, or fragments thereof. As used herein and unless otherwise specified, an ALK "rearrangement" refers to genetic translocations involving the ALK gene that may result in ALK fusion genes and/or ALK fusion proteins. The ALK fusion can also include one or more deletions, substitutions, insertions, inversions, duplications, translocations, or amplifications or a fragment thereof, as long as the mutant retains kinase phosphorylation activity.

In one embodiment, the ALK mutation comprises one or more ALK point mutations. In some embodiments, cancers treated by methods of the present disclosure include one or more mutations in ALK kinase. In one embodiment, the one or more ALK point mutations are selected from point mutations at L1152, C1156, I1171, F1174, V1180, L1196, L1198, G1202, D1203, S1206, E1210, F1245, G1269, and R1275. In one embodiment, the one or more ALK point mutations are selected from G1202R, G1202K, L1196M, G1269A, C1156Y, I1171T, I1171N, I1171S, F1174L, V1180L, S1206Y, E1210K, 1151Tins, F1174C, G1202del, D1203N, S1206Y, S1206C, L1152R, L1196Q, L1198P, L1198F, R1275Q, L1152P, C1156T, and F1245V. In one embodiment, the ALK mutation is G1202R. In one embodiment, the ALK mutation is L1196M. In one embodiment, the ALK mutation is G1269A. In one embodiment, the ALK mutation is L1198F. In one embodiment, the ALK mutation is co-mutation of G1202R and one or more mutations selected from L1196M, G1269A, and L1198F. In one embodiment, the ALK mutation is G1202R/L1196M dual mutation. In one embodiment, the ALK mutation is G1202R/G1269A dual mutation. In one embodiment, the ALK mutation is G1202R/L1198F dual mutation.

In one embodiment, the ALK mutation comprises one or more ALK rearrangements (in one embodiment, one rearrangement). In one embodiment, the ALK mutation comprises one or more ALK fusions (in one embodiment, one fusion). In some embodiments, cancers treated by methods of the present disclosure include ALK fusions. In one embodiment, the ALK fusion is with one of the fusion partners selected from EML4, TMP1, WDCP, GTF2IRD1, TPM3, TPM4, CLTC, LMNA, PRKAR1A, RANBP2, TFG, FN1, KLC1, VCL, STRN, HIP1, NPM1, DCTN1, SQSTM1, TPR, CRIM1, PTPN3, FBXO36, ATIC and KIF5B. In one embodiment, the ALK mutation is EML4-ALK, a fusion between the echinoderm microtubule-associated protein-like 4 (EML4) gene and the ALK tyrosine kinase domain. There are many variants of EML4-ALK that differ by breakpoint junctions, with variant 1 (v1) and variant 3 (v3) being the most prevalent clinically.

In one embodiment, the ALK mutation comprises one ALK rearrangement and one or more ALK point mutations. In one embodiment, the ALK mutation is EML4-ALK wt (variant 1). In one embodiment, the ALK mutation is EML4-ALK G1202R (variant 1). In one embodiment, the ALK mutation is EML4-ALK L1196M/G1202R (variant 1). In one embodiment, the ALK mutation is EML4-ALK G1202R/G1269A (variant 1). In one embodiment, the ALK mutation is EML4-ALK G1202R/L1198F (variant 1).

In one embodiment, the ALK+ cancer is determined by an FDA-approved test or other tests known in the art. The tests that can be used include, e.g., FoundationOne CDx™ (F1CDx) (a sequencing based in vitro diagnostic device for detection of substitutions, insertion and deletion alterations (indels), and copy number alterations (CNAs) in 324 genes and select gene rearrangements, as well as genomic signatures including microsatellite instability (MSI) and tumor mutational burden (TMB) using DNA isolated from formalin-fixed paraffin embedded (FFPE) tumor tissue specimens); VENTANA ALK (D5F3) CDx Assay (qualitative detection of the anaplastic lymphoma kinase (ALK) protein in formalin-fixed, paraffin-embedded (FFPE) non-small cell lung carcinoma (NSCLC) tissue stained with the BenchMark XT or BenchMark ULTRA automated staining instrument); and Vysis ALK Break Apart FISH Probe Kit test (a qualitative test to detect rearrangements involving the ALK gene via fluorescence in situ hybridization (FISH) in formalin-fixed, paraffin-embedded (FFPE) non-small cell lung cancer (NSCLC) tissue specimens). In one embodiment, the test is a fluorescence in situ hybridization (FISH) test, e.g., Vysis ALK Break Apart FISH Probe Kit test. Additional information for FDA-approved tests can be found at, e.g., https://www.fda.gov/MedicalDevices/ProductsandMedicalProcedures/InVitroDiagnostics/ucm303030.htm; and additional information for Vysis ALK Break Apart FISH Probe Kit can be found at, e.g., https://www.molecular.abbott/us/en/products/oncology/vysis-alk-break-apart-fish-probe-kit; the entirety of which are incorporated herein by reference.

Also provided are methods of treating a subject having a cancer (e.g., a ALK positive cancer) that include: determining whether a cancer cell in a sample obtained from a subject having a cancer and previously administered a first ALK inhibitor, has one or more ALK inhibitor resistance mutations; and administering a compound of Formula (I) or a pharmaceutically acceptable salt or solvate thereof as a monotherapy or in combination with another anticancer agent to the subject if the subject has a cancer cell that has one or more ALK inhibitor resistance mutations. In some embodiments, the one or more ALK inhibitor resistance mutations confer increased resistance to a cancer cell or tumor to treatment with the first ALK inhibitor. In some embodiments, the one or more ALK inhibitor resistance mutations include one or more ALK inhibitor resistance mutations. For example, the one or more ALK inhibitor resistance mutations can include a substitution at one or more of amino acid positions 1202, 1196, 1269, 1156, 1171, 1174, 1180, 1206, 1210, 1151, 1174, 1203, 1206, 1152, 1196, 1198, 1275, 1152, 1156, and 1245, e.g., G1202R, L1196M, G1269A, C1156Y, I1171T, I1171N, I1171S, F1174L, V1180L, S1206Y, E1210K, 1151Tins, F1174C, G1202del, D1203N, S1206Y, S1206C, L1152R, L1196Q, L1198P, L1198F, R1275Q, L1152P, C1156T, and F1245V. In some embodiments, another anticancer agent is any anticancer agent known in the art. For example, another anticancer agent can be another ALK inhibitor (e.g., a second ALK inhibitor).

In one embodiment, the cancer in a method provided herein is ROS1 positive (ROS1+). As used herein and unless otherwise specified, a "ROS1 positive" (ROS1+) cancer, disease, or disorder refers to a cancer, disease, or disorder characterized by inappropriately high expression of a ROS1 gene and/or the presence of a mutation in a ROS1 gene. In one embodiment, the mutation alters the biological activity of a ROS1 nucleic acid molecule or polypeptide. As used herein and unless otherwise specified, a "mutation" or "mutant" of ROS1 comprises one or more deletions, substitutions, insertions, inversions, duplications, translocations, or amplifications in the amino acid or nucleotide sequences of ROS1, or fragments thereof. As used herein and unless otherwise specified, a ROS1 "rearrangement" refers to genetic translocations involving the ROS1 gene that may result in ROS1 fusion genes and/or ROS1 fusion proteins. The ROS1 fusion can also include one or more deletions, substitutions, insertions, inversions, duplications, translocations, or amplifications or a fragment thereof, as long as the mutant retains kinase phosphorylation activity.

In one embodiment, the ROS1 mutation comprises one or more ROS1 point mutations. In some embodiments, cancers treated by methods of the present disclosure include one or more mutations in ROS1 kinase. In one embodiment, the one or more ROS1 point mutations are selected from point mutations at E1935, L1947, L1951, G1971, E1974, L1982, S1986, F2004, E2020, L2026, G2032, D2033, C2060, F2075, L2086, V2089, V2098, G2101, D2113, and L2155. In one embodiment, the one or more ROS1 point mutations are selected from G2032R, G2032K, D2033N, S1986F, S1986Y, L2026M, L1951R, E1935G, L1947R, G1971E, E1974K, L1982F, F2004C, F2004V, E2020K, C2060G, F2075V, V2089M, V2098I, G2101A, D2113N, D2113G, L2155S, and L2086F. In one embodiment, the ROS1 mutation is G2032R. In one embodiment, the ROS1 mutation is S1986F. In one embodiment, the ROS1 mutation is S1986Y. In one embodiment, the ROS1 mutation is L2026M. In one embodiment, the ROS1 mutation is D2033N. In one embodiment, the ROS1 mutation is L2086F. In one embodiment, the ROS1 mutation is F2004C. In one embodiment, the ROS1 mutation is F2004V. In one embodiment, the ROS1 mutation is G2101A. In one embodiment, the ROS1 mutation is L1982F. In one embodiment, the ROS1 mutation is co-mutation of G2032R and one or more of S1986F, S1986Y, F2004C, F2004V, L2026M, or D2033N.

In one embodiment, the ROS1 mutation comprises one or more ROS1 rearrangements (in one embodiment, one rearrangement). In one embodiment, the ROS1 mutation comprises one or more ROS1 fusions (in one embodiment, one fusion). In some embodiments, cancers treated by methods of the present disclosure include ROS1 fusions. In one embodiment, the ROS1 fusion is with one of the fusion partners selected from SLC34A2, CD74, TPM3, SDC4, EZR, LRIG3, KDELR2, CEP72, CLTL, CTNND2, GOPC (e.g., GOPC-S, GOPC-L), GPRC6A, LIMA1, LRIG3, MSN, MYO5C, OPRM1, SLC6A17 SLMAP, SRSF6, TFG, TMEM106B, TPD52L1, ZCCHC8, CCDC6, CAPRIN1, CEP85L, CHCHD3, CLIP1, EEF1G, KIF21A, KLC1, SART3, ST13, TRIM24, ERCI, FIPIL1, HLAA, KIAA1598, MYO5A, PPFIBP1, PWWP2A, FN1, YWHAE, CCDC130, NCOR2, NFKB2, APOB, PLG, RBP4, and GOLGB1. In one embodiment, the ROS1 fusion is CD74-ROS1 fusion. In one embodiment, the ROS1 fusion is SDC4-ROS1 fusion. In one embodiment, the ROS1 fusion is EZR-ROS1 fusion. In one embodiment, the ROS1 fusion is SLC34A2-ROS1 fusion. In one embodiment, the ROS1 fusion is GOPC-ROS1 fusion (e.g., GOPC-ROS1-S, GOPC-ROS1-L). In one embodiment, the ROS1 fusion is CEP85L-ROS1 fusion.

In one embodiment, the ROS1 mutation comprises one ROS1 rearrangement and one or more ROS1 point mutations. In one embodiment, the ROS1 mutation comprises one or more ROS1 rearrangements from CD74-ROS1, EZR-ROS1, SLC34A2-ROS1, GOPC-ROS1 (e.g., GOPC-ROS1-S, GOPC-ROS1-L), and CEP85L-ROS1, and one or more ROS1 point mutations selected from F2004C, F2004V, and G2032R. In one embodiment, the ROS1 mutation comprises one or more ROS1 rearrangements from CD74-ROS1, EZR-ROS1, and SLC34A2-ROS1, and ROS1 point mutation of G2101A.

In one embodiment, the ROS1 mutation is CD74-ROS1 F2004C. In one embodiment, the ROS1 mutation is CD74-ROS1 F2004V. In one embodiment, the ROS1 mutation is CD74-ROS1 G2101A. In one embodiment, the ROS1 mutation is CD74-ROS1 G2032R. In one embodiment, the ROS1 mutation is CD74-ROS1 S1986F. In one embodiment, the ROS1 mutation is CD74-ROS1 L2026M. In one embodiment, the ROS1 mutation is CD74-ROS1 D2033N. In one embodiment, the ROS1 mutation is EZR-ROS1 F2004C. In one embodiment, the ROS1 mutation is EZR-ROS1 F2004V. In one embodiment, the ROS1 mutation is EZR-ROS1 G2101A. In one embodiment, the ROS1 mutation is EZR-ROS1 G2032R. In one embodiment, the ROS1 mutation is SLC34A2-ROS1 F2004C. In one embodiment, the ROS1 mutation is SLC34A2-ROS1 F2004V. In one embodiment, the ROS1 mutation is SLC34A2-ROS1 G2101A. In one embodiment, the ROS1 mutation is SLC34A2-ROS1 G2032R. In one embodiment, the ROS1 mutation is GOPC-ROS1 F2004C (e.g., GOPC-ROS1-S F2004C, GOPC-ROS1-L F2004C). In one embodiment, the ROS1 mutation is GOPC-ROS1 F2004V (e.g., GOPC-ROS1-S F2004V, GOPC-ROS1-L F2004V). In one embodiment, the ROS1 mutation is GOPC-ROS1 G2032R (e.g., GOPC-ROS1-S G2032R, GOPC-ROS1-L G2032R). In one embodiment, the ROS1 mutation is CEP85L-ROS1 F2004C. In one embodiment, the ROS1 mutation is CEP85L-ROS1 F2004V. In one embodiment, the ROS1 mutation is CEP85L-ROS1 G2032R. In one embodiment, the ROS1 mutation is GOPC-ROS1 L1982F (e.g., GOPC-ROS1-S L1982F, GOPC-ROS1-L L1982F). In one embodiment, the ROS1 mutation is CD74-ROS1 L1982F.

In one embodiment, the ROS1+ cancer is determined by an FDA-approved test or other tests known in the art. The tests that can be used include, e.g., Oncomine™ Dx Target Test by Thermo Fisher Scientific. (a qualitative in vitro diagnostic test that uses targeted high-throughput, parallel-sequencing technology to detect sequence variations in 23 genes in DNA and RNA isolated from formalin-fixed, paraffin-embedded tumor (FFPE) tissue samples from patients with non-small cell lung cancer (NSCLC) using the Ion PGM Dx System); Vysis ROS1 Break Apart FISH Probe Kit (a qualitative test to detect rearrangements involving ROS1 gene rearrangements at 6q22 via fluorescence in situ hybridization (FISH) in formalin-fixed, paraffin-embedded (FFPE) non-small cell lung cancer (NSCLC) tissue specimens) or RTReal Time-Polymerase Chain Reaction (RT-PCR) or NGSNext Generation Sequencing via a local diagnostic test.

Also provided are methods of treating a subject having a cancer (e.g., a ROS1 positive cancer) that include: determining whether a cancer cell in a sample obtained from a subject having a cancer and previously administered a first ROS1 inhibitor, has one or more ROS1 inhibitor resistance mutations; and administering a compound of Formula (I) or a pharmaceutically acceptable salt or solvate thereof as a monotherapy or in conjunction with another anticancer agent to the subject if the subject has a cancer cell that has one or more ROS1 inhibitor resistance mutations. In some embodiments, the one or more ROS1 inhibitor resistance mutations confer increased resistance to a cancer cell or tumor to treatment with the first ROS1 inhibitor. In some embodiments, the one or more ROS1 inhibitor resistance mutations include one or more ROS1 inhibitor resistance mutations. For example, the one or more ROS1 inhibitor resistance mutations can include a substitution at one or more of amino acid positions 2032, 2033, 1986, 2026, 1951, 1935, 1947, 1971, 1974, 1982, 2004, 2020, 2060, 2075, 2089, 2098, 2101, 2113, 2155, 2032, and 2086, e.g., G2032R, D2033N, S1986F, S1986Y, L2026M, L1951R, E1935G, L1947R, G1971E, E1974K, L1982F, F2004C, F2004V, E2020K, C2060G, F2075V, V2089M, V2098I, G2101A, D2113N, D2113G, L2155S, L2032K, and L2086F. In some embodiments, another anticancer agent is any anticancer agent known in the art. For example, another anticancer agent can be another ROS1 inhibitor (e.g., a second ROS1 inhibitor).

In one embodiment, a compound provided herein is a CNS-penetrating compound. In one embodiment, after the administration of an effective amount of a compound provided herein (e.g., orally or intravenously), the compound is able to penetrate CNS (e.g., blood-brain barrier) and achieve a concentration in CNS (e.g., brain) that is still sufficient to inhibit (e.g., selectively inhibit) ROS1 or ALK or both.

In one embodiment, provided herein is a method for treating CNS metastases of a cancer, comprising administering to a subject in need thereof an effective amount of a compound provided herein, e.g., a compound of Formula (I), or an enantiomer, a mixture of enantiomers, or a tautomer thereof, or a pharmaceutically acceptable salt thereof. In one embodiment, the CNS metastases is brain metastases. In one embodiment, the cancer is a ROS1+ cancer. In one embodiment, the cancer is an ALK+ cancer.

In some embodiments, the compound is an inhibitor of human tropomyosin receptor kinase A, B, or C. In certain embodiments, the $IC_{50}$ of the compound for inhibition of mutant or non-mutant ROS1 or ALK is no more than one-fifth of the $IC_{50}$ of the compound for inhibition of wild-type tropomyosin receptor kinase A, B, or C. TRK inhibition, particularly in the central nervous system (CNS), has been associated with adverse reactions, including dizziness/ataxia/gait disturbance, paraesthesia, weight gain and cognitive changes.

In some embodiments, provided is a method of minimizing adverse events in a subject in need of treatment for cancer (e.g., a ROS1 positive cancer or an ALK positive cancer), the method comprising administering to the subject a therapeutically effective amount of a compound provided herein, e.g., a compound of Formula (I), an enantiomer, a mixture of enantiomers, or a tautomer thereof, or a pharmaceutically acceptable salt thereof, and wherein the method minimizes adverse events associated with TRK inhibitors. In some embodiments, the cancer is a ROS1-associated cancer or an ALK-associated (or ALK+) cancer. In some embodiments, the adverse events are TRK-related CNS adverse events.

As used herein "minimizing" adverse events refers to a reduction in the incidence of adverse events in a subject or patient population compared to the paradigmatic incidence of adverse events in a subject or patient population treated with TRK inhibitors (e.g., entrectinib, repotrectinib, or lorlatinib). In some embodiments, the incidence of an adverse event refers to the frequency or percentage of a specific adverse event over a subject or patient population. In some embodiments, the incidence of an adverse event refers to the total number of adverse events experienced by an individual subject. In some embodiments, minimizing adverse events refers to minimizing TRK-related CNS adverse events. In some embodiments, minimizing TRK-related CNS adverse events means less than 40% of the patient population has a TRK-related CNS adverse event. In some embodiments, minimizing TRK-related CNS adverse events means less than 35%, less than 30%, less than 25%, less than 20%, less than 15%, less than 10% or less than 5% of the patient population has a TRK-related CNS adverse event. In some embodiments, minimizing TRK-related CNS adverse events means less than 12% of the patient population have more than one TRK-related CNS adverse event. In some embodiments, minimizing TRK-related CNS adverse events means less than 11%, less than 10%, less than 9%, less than 8%, less than 7%, less than 6%, less than 5%, less than 4%, or less than 3% of the patient population have more than one TRK-related CNS adverse event.

In some embodiments, TRK-related CNS adverse events refers to one or more of the following: dizziness, ataxia, gait disturbance, paraesthesia, weight gain, hyperphagia, paresthesias, abnormal movement, cognitive changes, speech effects (e.g, dysarthria, slow speech, or speech disorder), mood disorder (e.g., irritability, anxiety, depression, affect lability, personality change, mood swings, affective disorder, aggression, agitation, mood altered, depressed mood, euphoric mood, or mania), and cognitive disorder (e.g., memory impairment, cognitive disorder, amnesia, confusion, disturbance in attention, delirium, mental impairment, attention deficit/hyperactivity disorder, dementia, or reading disorder).

In one embodiment, provided herein is a method for preventing or limiting TRK-related CNS side effect or adverse event in a cancer treatment, comprising administering to a subject in need thereof an effective amount of a compound provided herein, e.g., a compound of Formula (I), or an enantiomer, a mixture of enantiomers, or a tautomer thereof, or a pharmaceutically acceptable salt thereof. In one embodiment, the method prevents the occurrence of the TRK-related CNS adverse event. In one embodiment, the method limits the frequency of occurrence of the TRK-related CNS adverse event. In one embodiment, the method limits the severity of the TRK-related side effect. In one embodiment, provided herein is a method for treating CNS metastases of a cancer with reduced TRK-related side effect, comprising administering to a subject in need thereof an effective amount of a compound provided herein, e.g., a compound of Formula (I), or an enantiomer, a mixture of enantiomers, or a tautomer thereof, or a pharmaceutically acceptable salt thereof. In one embodiment, the reduction/limiting/prevention in CNS side effect or adverse event is determined in a statistical sample, as compared to a standard of care treatment, e.g., an approved ROS1 and/or ALK inhibitor (e.g., crizotinib, entrectinib, lorlatinib, or repotrectinib) for ROS1+ and/or ALK+ cancer. In one embodiment, the TRK-related side effect is a TRKB-related CNS side effect. In one embodiment, the TRK-related CNS side effect or adverse event is dizziness, ataxia, gait disturbance, paraesthesia, weight gain, cognitive impairment, a mood disorder, or sleep disturbance.

In one embodiment, provided herein is a method for treating cancer, comprising administering to a subject in need thereof a therapeutically effective amount of a compound provided herein, e.g., a compound of Formula (I), or an enantiomer, a mixture of enantiomers, or a tautomer thereof, or a pharmaceutically acceptable salt thereof. In one embodiment, the cancer is a ROS1-associated cancer. In one embodiment, the cancer is a ROS1+ cancer. In one embodiment, the cancer is an ALK-associated cancer. In one embodiment, the cancer is an ALK+ cancer. In one embodiment, the cancer is identified to be ROS1+. In one embodiment, the cancer is identified to be ALK+.

In one embodiment, provided herein is a method for treating a ROS1+ cancer, comprising administering to a subject in need thereof a therapeutically effective amount of a compound provided herein, e.g., a compound of Formula (I), or an enantiomer, a mixture of enantiomers, or a tautomer thereof, or a pharmaceutically acceptable salt thereof.

In one embodiment, provided herein is a method for treating an ALK+ cancer, comprising administering to a subject in need thereof a therapeutically effective amount of a compound provided herein, e.g., a compound of Formula (I), or an enantiomer, a mixture of enantiomers, or a tautomer thereof, or a pharmaceutically acceptable salt thereof.

In one embodiment, provided herein is a method for treating cancer in a subject, comprising: (i) identifying the cancer in the subject to be ROS1+, and (ii) administering to the subject a therapeutically effective amount of a compound provided herein, e.g., a compound of Formula (I), or an enantiomer, a mixture of enantiomers, or a tautomer thereof, or a pharmaceutically acceptable salt thereof.

In one embodiment, provided herein is a method for treating cancer in a subject, comprising: (i) identifying the cancer in the subject to be ALK+, and (ii) administering to the subject a therapeutically effective amount of a compound provided herein, e.g., a compound of Formula (I), or an enantiomer, a mixture of enantiomers, or a tautomer thereof, or a pharmaceutically acceptable salt thereof.

In one embodiment, the cancer (or ROS1+ cancer, or ALK+ cancer) is a solid tumor. In one embodiment, the cancer (or ROS1+ cancer, or ALK+ cancer) is lung cancer, e.g., non-small cell lung cancer (NSCLC), glioblastoma, inflammatory myofibroblastic tumor (IMT), bile duct cancer, e.g., cholangiocarcinoma, ovarian cancer, e.g., serous ovarian carcinoma, gastric cancer, colorectal cancer, angiosarcoma, melanoma, e.g., spitzoid melanoma, epithelioid hemangioendothelioma, esophageal cancer, e.g., esophageal squamous cell carcinoma (ESCC), kidney cancer, e.g., renal medullary carcinoma or renal cell carcinoma, breast cancer, e.g., triple negative breast cancer, colon cancer, thyroid cancer, e.g., papillary thyroid cancer, spitzoid tumor, or neuroblastoma.

In one embodiment, the cancer is lung cancer. In one embodiment, the cancer is non-small cell lung cancer. In one embodiment, the cancer is ROS1+ non-small cell lung cancer. In one embodiment, the cancer is ALK+ non-small cell lung cancer. In one embodiment, the cancer is relapsed or refractory non-small cell lung cancer. In one embodiment, the cancer is relapsed or refractory ROS1+ non-small cell lung cancer. In one embodiment, the cancer is relapsed or refractory ALK+ non-small cell lung cancer. In one embodiment, the cancer is newly diagnosed non-small cell lung cancer. In one embodiment, the cancer is newly diagnosed ROS1+ non-small cell lung cancer. In one embodiment, the cancer is newly diagnosed ALK+ non-small cell lung cancer.

In one embodiment, the cancer is glioblastoma. In one embodiment, the cancer is ROS1+ glioblastoma. In one embodiment, the cancer is ALK+ glioblastoma. In one embodiment, the cancer is relapsed or refractory glioblastoma. In one embodiment, the cancer is relapsed or refractory ROS1+ glioblastoma. In one embodiment, the cancer is relapsed or refractory ALK+ glioblastoma. In one embodiment, the cancer is newly diagnosed glioblastoma. In one embodiment, the cancer is newly diagnosed ROS1+ glioblastoma. In one embodiment, the cancer is newly diagnosed ALK+ glioblastoma.

In one embodiment, the cancer is IMT. In one embodiment, the cancer is ROS1+ IMT. In one embodiment, the cancer is ALK+ IMT. In one embodiment, the cancer is relapsed or refractory IMT. In one embodiment, the cancer is relapsed or refractory ROS1+ IMT. In one embodiment, the cancer is relapsed or refractory ALK+ IMT. In one embodiment, the cancer is newly diagnosed IMT. In one embodiment, the cancer is newly diagnosed ROS1+ IMT. In one embodiment, the cancer is newly diagnosed ALK+ IMT.

In one embodiment, the cancer is bile duct cancer. In one embodiment, the cancer is cholangiocarcinoma. In one embodiment, the cancer is ROS1+ cholangiocarcinoma. In one embodiment, the cancer is ALK+ cholangiocarcinoma. In one embodiment, the cancer is relapsed or refractory cholangiocarcinoma. In one embodiment, the cancer is relapsed or refractory ROS1+ cholangiocarcinoma. In one embodiment, the cancer is relapsed or refractory ALK+ cholangiocarcinoma. In one embodiment, the cancer is newly diagnosed cholangiocarcinoma. In one embodiment, the cancer is newly diagnosed ROS1+ cholangiocarcinoma. In one embodiment, the cancer is newly diagnosed ALK+ cholangiocarcinoma.

In one embodiment, the cancer is ovarian cancer. In one embodiment, the cancer is ROS1+ ovarian cancer. In one embodiment, the cancer is ALK+ ovarian cancer. In one embodiment, the cancer is relapsed or refractory ovarian cancer. In one embodiment, the cancer is relapsed or refractory ROS1+ ovarian cancer. In one embodiment, the cancer is relapsed or refractory ALK+ ovarian cancer. In one embodiment, the cancer is newly diagnosed ovarian cancer. In one embodiment, the cancer is newly diagnosed ROS1+ ovarian cancer. In one embodiment, the cancer is newly diagnosed ALK+ ovarian cancer. In one embodiment, the ovarian cancer is serous ovarian carcinoma. In one embodiment, the ovarian cancer is high grade serous ovarian carcinoma.

In one embodiment, the cancer is gastric cancer. In one embodiment, the cancer is ROS1+ gastric cancer. In one embodiment, the cancer is ALK+ gastric cancer. In one embodiment, the cancer is relapsed or refractory gastric cancer. In one embodiment, the cancer is relapsed or refractory ROS1+ gastric cancer. In one embodiment, the cancer is relapsed or refractory ALK+ gastric cancer. In one embodiment, the cancer is newly diagnosed gastric cancer. In one embodiment, the cancer is newly diagnosed ROS1+ gastric cancer. In one embodiment, the cancer is newly diagnosed ALK+ gastric cancer.

In one embodiment, the cancer is colorectal cancer. In one embodiment, the cancer is ROS1+ colorectal cancer. In one embodiment, the cancer is ALK+ colorectal cancer. In one embodiment, the cancer is relapsed or refractory colorectal cancer. In one embodiment, the cancer is relapsed or refractory ROS1+ colorectal cancer. In one embodiment, the cancer is relapsed or refractory ALK+ colorectal cancer. In one embodiment, the cancer is newly diagnosed colorectal cancer. In one embodiment, the cancer is newly diagnosed ROS1+ colorectal cancer. In one embodiment, the cancer is newly diagnosed ALK+ colorectal cancer.

In one embodiment, the cancer is angiosarcoma. In one embodiment, the cancer is ROS1+ angiosarcoma. In one embodiment, the cancer is ALK+ angiosarcoma. In one embodiment, the cancer is relapsed or refractory angiosarcoma. In one embodiment, the cancer is relapsed or refractory ROS1+ angiosarcoma. In one embodiment, the cancer is relapsed or refractory ALK+ angiosarcoma. In one embodiment, the cancer is newly diagnosed angiosarcoma. In one embodiment, the cancer is newly diagnosed ROS1+ angiosarcoma. In one embodiment, the cancer is newly diagnosed ALK+ angiosarcoma.

In one embodiment, the cancer is melanoma. In one embodiment, the cancer is spitzoid tumor. In one embodiment, the cancer is spitzoid melanoma. In one embodiment, the cancer is ROS1+ spitzoid melanoma. In one embodiment, the cancer is ALK+ spitzoid melanoma. In one embodiment, the cancer is relapsed or refractory spitzoid melanoma. In one embodiment, the cancer is relapsed or refractory ROS1+ spitzoid melanoma. In one embodiment, the cancer is relapsed or refractory ALK+ spitzoid melanoma. In one embodiment, the cancer is newly diagnosed spitzoid melanoma. In one embodiment, the cancer is newly diagnosed ROS1+ spitzoid melanoma. In one embodiment, the cancer is newly diagnosed ALK+ spitzoid melanoma.

In one embodiment, the cancer is epithelioid hemangioendothelioma. In one embodiment, the cancer is ROS1+ epithelioid hemangioendothelioma. In one embodiment, the cancer is ALK+ epithelioid hemangioendothelioma. In one embodiment, the cancer is relapsed or refractory epithelioid hemangioendothelioma. In one embodiment, the cancer is relapsed or refractory ROS1+ epithelioid hemangioendothelioma. In one embodiment, the cancer is relapsed or refractory ALK+ epithelioid hemangioendothelioma. In one embodiment, the cancer is newly diagnosed epithelioid hemangioendothelioma. In one embodiment, the cancer is newly diagnosed ROS1+ epithelioid hemangioendothelioma. In one embodiment, the cancer is newly diagnosed ALK+ epithelioid hemangioendothelioma.

In one embodiment, the cancer is esophageal cancer. In one embodiment, the cancer is ESCC. In one embodiment, the cancer is ROS1+ ESCC. In one embodiment, the cancer is ALK+ ESCC. In one embodiment, the cancer is relapsed or refractory ESCC. In one embodiment, the cancer is relapsed or refractory ROS1+ ESCC. In one embodiment, the cancer is relapsed or refractory ALK+ ESCC. In one embodiment, the cancer is newly diagnosed ESCC. In one embodiment, the cancer is newly diagnosed ROS1+ ESCC. In one embodiment, the cancer is newly diagnosed ALK+ ESCC.

In one embodiment, the cancer is kidney cancer. In one embodiment, the cancer is renal medullary carcinoma. In one embodiment, the cancer is ROS1+ renal medullary carcinoma. In one embodiment, the cancer is ALK+ renal medullary carcinoma. In one embodiment, the cancer is relapsed or refractory renal medullary carcinoma. In one embodiment, the cancer is relapsed or refractory ROS1+ renal medullary carcinoma. In one embodiment, the cancer is relapsed or refractory ALK+ renal medullary carcinoma. In one embodiment, the cancer is newly diagnosed renal medullary carcinoma. In one embodiment, the cancer is newly diagnosed ROS1+ renal medullary carcinoma. In one embodiment, the cancer is newly diagnosed ALK+ renal medullary carcinoma. In one embodiment, the cancer is renal cell carcinoma. In one embodiment, the cancer is ROS1+ renal cell carcinoma. In one embodiment, the cancer is ALK+ renal cell carcinoma. In one embodiment, the cancer is relapsed or refractory renal cell carcinoma. In one embodiment, the cancer is relapsed or refractory ROS1+ renal cell carcinoma. In one embodiment, the cancer is relapsed or refractory ALK+ renal cell carcinoma. In one embodiment, the cancer is newly diagnosed renal cell carcinoma. In one embodiment, the cancer is newly diagnosed ROS1+ renal cell carcinoma. In one embodiment, the cancer is newly diagnosed ALK+ renal cell carcinoma.

In one embodiment, the cancer is breast cancer. In one embodiment, the cancer is ROS1+ breast cancer. In one embodiment, the cancer is ALK+ breast cancer. In one embodiment, the cancer is relapsed or refractory breast cancer. In one embodiment, the cancer is relapsed or refractory ROS1+ breast cancer. In one embodiment, the cancer is relapsed or refractory ALK+ breast cancer. In one embodiment, the cancer is newly diagnosed breast cancer. In one embodiment, the cancer is newly diagnosed ROS1+ breast cancer. In one embodiment, the cancer is newly diagnosed ALK+ breast cancer. In one embodiment, the breast cancer is triple negative breast cancer.

In one embodiment, the cancer is colon cancer. In one embodiment, the cancer is ROS1+ colon cancer. In one embodiment, the cancer is ALK+ colon cancer. In one embodiment, the cancer is relapsed or refractory colon cancer. In one embodiment, the cancer is relapsed or refractory ROS1+ colon cancer. In one embodiment, the cancer is relapsed or refractory ALK+ colon cancer. In one embodiment, the cancer is newly diagnosed colon cancer. In one embodiment, the cancer is newly diagnosed ROS1+ colon cancer. In one embodiment, the cancer is newly diagnosed ALK+ colon cancer.

In one embodiment, the cancer is thyroid cancer. In one embodiment, the cancer is papillary thyroid cancer. In one embodiment, the cancer is ROS1+ papillary thyroid cancer. In one embodiment, the cancer is ALK+ papillary thyroid cancer. In one embodiment, the cancer is relapsed or refractory papillary thyroid cancer. In one embodiment, the cancer is relapsed or refractory ROS1+ papillary thyroid cancer. In one embodiment, the cancer is relapsed or refractory ALK+ papillary thyroid cancer. In one embodiment, the cancer is newly diagnosed papillary thyroid cancer. In one embodiment, the cancer is newly diagnosed ROS1+ papillary thyroid cancer. In one embodiment, the cancer is newly diagnosed ALK+ papillary thyroid cancer.

In one embodiment, the cancer is neuroblastoma. In one embodiment, the cancer is ROS1+ neuroblastoma. In one embodiment, the cancer is ALK+ neuroblastoma. In one embodiment, the cancer is relapsed or refractory neuroblastoma. In one embodiment, the cancer is relapsed or refractory ROS1+ neuroblastoma. In one embodiment, the cancer is relapsed or refractory ALK+ neuroblastoma. In one embodiment, the cancer is newly diagnosed neuroblastoma. In one embodiment, the cancer is newly diagnosed ROS1+ neuroblastoma. In one embodiment, the cancer is newly diagnosed ALK+ neuroblastoma.

In one embodiment, the cancer (or ROS1+ cancer, or ALK+ cancer) is a hematological cancer. In one embodiment, the cancer (or ROS1+ cancer, or ALK+ cancer) is lymphoma. In one embodiment, the lymphoma is non-Hodgkin lymphoma. In one embodiment, the lymphoma is anaplastic large cell lymphoma (ALCL), diffuse large B-cell lymphoma (DLBCL), or large B-cell lymphoma. In addition to hematological cancer, methods for treating other blood disorder or hematologic malignancy that is ROS1+ or ALK+ are also provided herein.

In one embodiment, the cancer is ALCL. In one embodiment, the cancer is ROS1+ ALCL. In one embodiment, the cancer is ALK+ ALCL. In one embodiment, the cancer is relapsed or refractory ALCL. In one embodiment, the cancer is relapsed or refractory ROS1+ ALCL. In one embodiment, the cancer is relapsed or refractory ALK+ ALCL. In one embodiment, the cancer is newly diagnosed ALCL. In one embodiment, the cancer is newly diagnosed ROS1+ ALCL. In one embodiment, the cancer is newly diagnosed ALK+ ALCL.

In one embodiment, the cancer is DLBCL. In one embodiment, the cancer is ROS1+ DLBCL. In one embodiment, the cancer is ALK+ DLBCL. In one embodiment, the cancer is relapsed or refractory DLBCL. In one embodiment, the cancer is relapsed or refractory ROS1+ DLBCL. In one embodiment, the cancer is relapsed or refractory ALK+ DLBCL. In one embodiment, the cancer is newly diagnosed DLBCL. In one embodiment, the cancer is newly diagnosed ROS1+ DLBCL. In one embodiment, the cancer is newly diagnosed ALK+ DLBCL.

In one embodiment, the cancer is large B-cell lymphoma. In one embodiment, the cancer is ROS1+ large B-cell lymphoma. In one embodiment, the cancer is ALK+ large B-cell lymphoma. In one embodiment, the cancer is relapsed or refractory large B-cell lymphoma. In one embodiment, the cancer is relapsed or refractory ROS1+ large B-cell lymphoma. In one embodiment, the cancer is relapsed or refractory ALK+ large B-cell lymphoma. In one embodiment, the cancer is newly diagnosed large B-cell lymphoma. In one embodiment, the cancer is newly diagnosed ROS1+ large B-cell lymphoma. In one embodiment, the cancer is newly diagnosed ALK+ large B-cell lymphoma.

In one embodiment, the cancer (or ROS1+ cancer, or ALK+ cancer) is new diagnosed. In one embodiment, the cancer (or ROS1+ cancer, or ALK+ cancer) is previously untreated.

In one embodiment, the cancer (or ROS1+ cancer, or ALK+ cancer) is relapsed or refractory. In one embodiment, the cancer is relapsed. In one embodiment, the cancer (or ROS1+ cancer, or ALK+ cancer) is refractory.

In one embodiment, the subject is previously untreated. In one embodiment, the subject is treatment naïve to tyrosine kinase inhibitor (TKI) therapy. In one embodiment, the subject has received one or more prior lines of therapy. In one embodiment, the subject has received two or more prior lines of therapy. In one embodiment, the subject has developed resistance to one or more of the prior line of therapy. In one embodiment, the prior therapy comprises a tyrosine kinase inhibitor (TKI). In one embodiment, the prior therapy comprises one or more of crizotinib, ceritinib, alectinib, brigatinib, lorlatinib, entrectinib, repotrectinib, cabozantinib, foretinib, taletrectinib, merestinib, masitinib, and ensartinib. In one embodiment, the prior therapy comprises one or more chemotherapies. In one embodiment, the one or more chemotherapies are in addition to the TKI therapy.

In one embodiment, the cancer (or ROS1+ cancer, or ALK+ cancer) is resistant to a tyrosine kinase inhibitor (TKI).

In one embodiment, the cancer is resistant lung cancer. In one embodiment, the cancer is resistant non-small cell lung cancer. In one embodiment, the cancer is non-small cell lung cancer resistant to a TKI. In one embodiment, the cancer is ROS1+ non-small cell lung cancer resistant to a TKI. In one embodiment, the cancer is ALK+ non-small cell lung cancer resistant to a TKI.

In one embodiment, the cancer is lung cancer (e.g., NSCLC), and the cancer is relapsed after, or refractory to, prior treatment by a TKI.

In one embodiment, a compound provided herein is administered as first-line treatment. In one embodiment, a compound provided herein is administered as second-line treatment. In one embodiment, a compound provided herein is administered as third or fourth-line treatment.

In one embodiment, the cancer (or ROS1+ cancer, or ALK+ cancer) is metastatic. In one embodiment, the cancer has CNS metastases. In one embodiment, the cancer has brain metastases. In one embodiment, the cancer is metastatic non-small cell lung cancer (NSCLC). In one embodiment, the cancer is metastatic ROS1+ NSCLC. In one embodiment, the cancer is metastatic ALK+ NSCLC.

In one embodiment, provided herein is a method for treating a patient with metastatic ALK+ non-small cell lung cancer (NSCLC), comprising administering to the patient a therapeutically effective amount of a compound provided herein, e.g., a compound of Formula (I), or an enantiomer, a mixture of enantiomers, or a tautomer thereof, or a pharmaceutically acceptable salt thereof.

In one embodiment, provided herein is a method for treating a patient with metastatic ROS1+ non-small cell lung cancer (NSCLC), comprising administering to the patient a therapeutically effective amount of a compound provided herein, e.g., a compound of Formula (I), or an enantiomer, a mixture of enantiomers, or a tautomer thereof, or a pharmaceutically acceptable salt thereof.

In one embodiment, the patient is an adult patient. In one embodiment, the patient is a pediatric patient.

In one embodiment, provided herein is a method for treating an adult patient with metastatic ROS1+ NSCLC, comprising administering to the patient a therapeutically effective amount of a compound provided herein, e.g., a compound of Formula (I), or an enantiomer, a mixture of enantiomers, or a tautomer thereof, or a pharmaceutically acceptable salt thereof.

In one embodiment, provided herein is a method for treating an adult patient with metastatic ROS1+ NSCLC, comprising administering to the patient a therapeutically effective amount of a compound provided herein, e.g., a compound of Formula (I), or an enantiomer, a mixture of enantiomers, or a tautomer thereof, or a pharmaceutically acceptable salt thereof, wherein the patient has progressed on or is intolerant of at least 1 prior TKI therapy.

In one embodiment, provided herein is a method for treating an adult patient with metastatic NSCLC that is ROS1+ with solvent front mutation G2032R, comprising administering to the patient a therapeutically effective amount of a compound provided herein, e.g., a compound of Formula (I), or an enantiomer, a mixture of enantiomers, or a tautomer thereof, or a pharmaceutically acceptable salt thereof, wherein the patient has progressed on or is intolerant of at least 1 prior TKI therapy.

In one embodiment, provided herein is a method for treating a ROS1-associated (or ROS1+) cancer in a subject in need thereof, wherein the cancer has developed resistance to a tyrosine kinase inhibitor (TKI), the method comprising administering to the subject a therapeutically effective amount of a compound provided herein, e.g., a compound of Formula (I), or an enantiomer, a mixture of enantiomers, or a tautomer thereof, or a pharmaceutically acceptable salt thereof.

In one embodiment, provided herein is a method for treating a ROS1-associated (or ROS1+) cancer in a subject in need thereof, wherein the cancer has developed resistance to a tyrosine kinase inhibitor (TKI), and wherein the cancer has been identified as having one or more ROS1 inhibitor resistance mutations, the method comprising administering to the subject a therapeutically effective amount of a compound provided herein, e.g., a compound of Formula (I), or an enantiomer, a mixture of enantiomers, or a tautomer thereof, or a pharmaceutically acceptable salt thereof. In one embodiment, the one or more ROS1 inhibitor resistance mutations comprise one or more amino acid substitutions at an amino acid position selected from 1986, 2004, 2026, 2032, and 2033. In one embodiment, the one or more ROS1 inhibitor resistance mutations comprise one or more amino acid substitutions selected from S1986F, S1986Y, F2004C, F2004V, L2026M, G2032R, D2033N, L2086F, and G2101A. In one embodiment, the one or more ROS1 inhibitor resistance mutations is G2032R. In one embodiment, the one or more ROS1 inhibitor resistance mutations comprise G2032R and one or more of S1986F, S1986Y, F2004C, F2004V, L2026M, D2033N, or G2101A. In one embodiment, the ROS1 inhibitor resistance mutation is L2086F.

In one embodiment, provided herein is a method for treating a ALK-associated (or ALK+) cancer in a subject in need thereof, wherein the cancer has developed resistance to a tyrosine kinase inhibitor (TKI), the method comprising administering to the subject a therapeutically effective amount of a compound provided herein, e.g., a compound of Formula (I), or an enantiomer, a mixture of enantiomers, or a tautomer thereof, or a pharmaceutically acceptable salt thereof.

In one embodiment, provided herein is a method for treating a ALK-associated (or ALK+) cancer in a subject in need thereof, wherein the cancer has developed resistance to a tyrosine kinase inhibitor (TKI), and wherein the cancer has been identified as having one or more ALK inhibitor resistance mutations, the method comprising administering o the subject a therapeutically effective amount of a compound provided herein, e.g., a compound of Formula (I), or an enantiomer, a mixture of enantiomers, or a tautomer thereof, or a pharmaceutically acceptable salt thereof. In one embodiment, the one or more ALK inhibitor resistance mutations comprise one or more amino acid substitutions at an amino acid position selected from 1196, 1198, 1202, and 1269. In one embodiment, the one or more ALK inhibitor resistance mutations comprise one or more amino acid substitutions selected from L1196M, L1198F, G1202R, and G1269A. In one embodiment, the one or more ALK inhibitor resistance mutations is G1202R. In one embodiment, the one or more ALK inhibitor resistance mutations comprise G1202R and one or more of L1196M, L1198F, and G1269A.

In one embodiment, provided herein is a method for treating an adult patient with metastatic NSCLC that is ALK+ with mutation G1202R, comprising administering to the patient a therapeutically effective amount of a compound provided herein, e.g., a compound of Formula (I), or an enantiomer, a mixture of enantiomers, or a tautomer thereof, or a pharmaceutically acceptable salt thereof, wherein the patient has progressed on or is intolerant of at least 1 prior TKI therapy.

In one embodiment, provided herein is a method for treating a ALK-associated (or ALK+) cancer in a subject in need thereof, wherein the cancer has developed resistance to a tyrosine kinase inhibitor (TKI), the method comprising administering to the subject a therapeutically effective amount of a compound provided herein, e.g., a compound of Formula (I), or an enantiomer, a mixture of enantiomers, or a tautomer thereof, or a pharmaceutically acceptable salt thereof.

In one embodiment, the TKI is a ROS1 inhibitor. In one embodiment, the TKI is an ALK inhibitor. In one embodiment, the TKI is crizotinib, ceritinib, alectinib, brigatinib, lorlatinib, entrectinib, repotrectinib, cabozantinib, foretinib, merestinib, taletrectinib, masitinib, or ensartinib. In one embodiment, the TKI is crizotinib. In one embodiment, the TKI is entrectinib.

In certain embodiments, the subject has relapsed after first-line treatment of the cancer. In other embodiments, the subject has relapsed after second-line treatment of the cancer.

In one embodiment, the cancer or disease is in a pediatric patient (including an infantile patient). In one embodiment, the cancer is systemic anaplastic large cell lymphoma (ALCL) that is ALK+ in pediatric patients 1 year of age or older, and young adults. In another embodiment, the cancer is relapsed or refractory systemic anaplastic large cell lymphoma (ALCL) that is ALK+ in pediatric patients 1 year of age or older, and young adults. In one embodiment, the cancer is systemic anaplastic large cell lymphoma (ALCL) that is ROS1+ in pediatric patients 1 year of age or older, and young adults. In another embodiment, the cancer is relapsed or refractory systemic anaplastic large cell lymphoma (ALCL) that is ROS1+ in pediatric patients 1 year of age or older, and young adults.

In certain embodiments, the methods for treating or preventing cancer can be demonstrated by one or more responses such as increased apoptosis, inhibition of tumor growth, reduction of tumor metastasis, inhibition of tumor metastasis, reduction of microvessel density, decreased neovascularization, inhibition of tumor migration, tumor regression, and increased survival of the subject.

Combination Treatments

In some embodiments, the method of treating or preventing cancer may comprise administering a compound of Formula (I) conjointly with one or more other chemotherapeutic agent(s).

As used herein and unless otherwise specified, by "conjointly" or "in combination with", it is not intended to imply that the other agent and the compound of Formula (I) must be administered at the same time and/or formulated for delivery together, although these methods of delivery are within the scope of this disclosure. The compound provided herein can be administered concurrently with, prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, 12 weeks, or 16 weeks before), or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, 12 weeks, or 16 weeks after), one or more other agents (e.g., one or more other additional agents). In general, each therapeutic agent is administered at a dose and/or on a time schedule determined for that particular agent. The other therapeutic agent can be administered with the compound provided herein in a single composition or separately in a different composition. Triple therapy is also contemplated herein.

Chemotherapeutic agents that may be conjointly administered with compounds of the disclosure include: 1-amino-4-phenylamino-9,10-dioxo-9,10-dihydroanthracene-2-sulfonate (acid blue 25), 1-amino-4-[4-hydroxyphenylamino]-9,10-dioxo-9,10-dihydroanthracene-2-sulfonate, 1-amino-4-[4-aminophenylamino]-9,10-dioxo-9,10-dihydroanthracene-2-sulfonate, 1-amino-4-[1-naphthylamino]-9,10-dioxo-9,10-dihydroanthracene-2-sulfonate, 1-amino-4-[4-fluoro-2-carboxyphenylamino]-9,10-dioxo-9,10-dihydroanthracene-2-sulfonate, 1-amino-4-[2-anthracenylamino]-9,10-dioxo-9,10-dihydroanthracene-2-sulfonate, ABT-263, afatinib dimaleate, axitinib, aminoglutethimide, amsacrine, anastrozole, APCP, asparaginase, AZD5363, Bacillus Calmette-Guérin vaccine (bcg), bicalutamide, bleomycin, bortezomib, β-methylene-ADP (AOPCP), buserelin, busulfan, cabazitaxel, cabozantinib, campothecin, capecitabine, carboplatin, carfilzomib, carmustine, ceritinib, chlorambucil, chloroquine, cisplatin, cladribine, clodronate, cobimetinib, colchicine, crizotinib, cyclophosphamide, cyproterone, cytarabine, dacarbazine, dactinomycin, daunorubicin, demethoxyviridin, dexamethasone, dichloroacetate, dienestrol, diethylstilbestrol, docetaxel, doxorubicin, epirubicin, eribulin, erlotinib, estradiol, estramustine, etoposide, everolimus, exemestane, filgrastim, fludarabine, fludrocortisone, fluorouracil, fluoxymesterone, flutamide, gefitinib, gemcitabine, genistein, goserelin, GSK1120212, hydroxyurea, idarubicin, ifosfamide, imatinib, interferon, irinotecan, ixabepilone, lenalidomide, letrozole, leucovorin, leuprolide, levamisole, lomustine, lonidamine, mechlorethamine, medroxyprogesterone, megestrol, melphalan, mercaptopurine, mesna, metformin, methotrexate, miltefosine, mitomycin, mitotane, mitoxantrone, MK-2206, mutamycin, N-(4-sulfamoylphenylcarbamothioyl) pivalamide, NF279, NF449, nilutamide, nocodazole, octreotide, olaparib, oxaliplatin, paclitaxel, pamidronate, pazopanib, pemexetred, pentostatin, perifosine, PF-04691502, plicamycin, pomalidomide, porfimer, PPADS, procarbazine, quercetin, raltitrexed, ramucirumab, reactive blue 2, rituximab, rolofylline, romidepsin, rucaparib, selumetinib, sirolimus, sodium 2,4-dinitrobenzenesulfonate, sorafenib, streptozocin, sunitinib, suramin, talazoparib, tamoxifen, temozolomide, temsirolimus, teniposide, testosterone, thalidomide, thioguanine, thiotepa, titanocene dichloride, tonapofylline, topotecan, trametinib, trastuzumab, tretinoin, veliparib, vinblastine, vincristine, vindesine, vinorelbine, and vorinostat (SAHA). In other embodiments, chemotherapeutic agents that may be conjointly administered with compounds of the disclosure include: ABT-263, dexamethasone, 5-fluorouracil, PF-04691502, romidepsin, and vorinostat (SAHA). In other embodiments, chemotherapeutic agents that may be conjointly administered with compounds of the disclosure include: 1-amino-4-phenylamino-9,10-dioxo-9,10-dihydroanthracene-2-sulfonate (acid blue 25), 1-amino-4-[4-hydroxyphenyl-amino]-9,10-dioxo-9,10-dihydroanthracene-2-sulfonate, 1-amino-4-[4-aminophenylamino]-9,10-dioxo-9, 10-dihydroanthracene-2-sulfonate, 1-amino-4-[1-naphthylamino]-9,10-dioxo-9,10-dihydroanthracene-2-sulfonate, 1-amino-4-[4-fluoro-2-carboxyphenylamino]-9, 10-dioxo-9,10-dihydroanthracene-2-sulfonate, 1-amino-4-[2-anthracenylamino]-9,10-dioxo-9,10-dihydroanthracene-2-sulfonate, APCP, O-methylene-ADP (AOPCP), capecitabine, cladribine, cytarabine, fludarabine, doxorubicin, gemcitabine, N-(4-sulfamoylphenylcarbamothioyl) pivalamide, NF279, NF449, PPADS, quercetin, reactive blue 2, rolofylline sodium 2,4-dinitrobenzenesulfonate, sumarin, and tonapofylline.

Many combination therapies have been developed for the treatment of cancer. In certain embodiments, compounds of the disclosure (e.g., compounds of Formula (I)) may be conjointly administered with one or more combination therapies. Examples of combination therapies with which compounds of the disclosure may be conjointly administered are included in Table 2.

TABLE 2

Exemplary combinatorial therapies for the treatment of cancer

| Name | Therapeutic agents |
| --- | --- |
| ABV | Doxorubicin, Bleomycin, Vinblastine |
| ABVD | Doxorubicin, Bleomycin, Vinblastine, Dacarbazine |
| AC (Breast) | Doxorubicin, Cyclophosphamide |
| AC (Sarcoma) | Doxorubicin, Cisplatin |

TABLE 2-continued

Exemplary combinatorial therapies for the treatment of cancer

| Name | Therapeutic agents |
| --- | --- |
| AC (Neuroblastoma) | Cyclophosphamide, Doxorubicin |
| ACE | Cyclophosphamide, Doxorubicin, Etoposide |
| ACe | Cyclophosphamide, Doxorubicin |
| AD | Doxorubicin, Dacarbazine |
| AP | Doxorubicin, Cisplatin |
| ARAC-DNR | Cytarabine, Daunorubicin |
| B-CAVe | Bleomycin, Lomustine, Doxorubicin, Vinblastine |
| BCVPP | Carmustine, Cyclophosphamide, Vinblastine, Procarbazine, Prednisone |
| BEACOPP | Bleomycin, Etoposide, Doxorubicin, Cyclophosphamide, Vincristine, Procarbazine, Prednisone, Filgrastim |
| BEP | Bleomycin, Etoposide, Cisplatin |
| BIP | Bleomycin, Cisplatin, Ifosfamide, Mesna |
| BOMP | Bleomycin, Vincristine, Cisplatin, Mitomycin |
| CA | Cytarabine, Asparaginase |
| CABO | Cisplatin, Methotrexate, Bleomycin, Vincristine |
| CAF | Cyclophosphamide, Doxorubicin, Fluorouracil |
| CAL-G | Cyclophosphamide, Daunorubicin, Vincristine, Prednisone, Asparaginase |
| CAMP | Cyclophosphamide, Doxorubicin, Methotrexate, Procarbazine |
| CAP | Cyclophosphamide, Doxorubicin, Cisplatin |
| CAV | Cyclophosphamide, Doxorubicin, Vincristine |
| CAVE ADD | CAV and Etoposide |
| CA-VP16 | Cyclophosphamide, Doxorubicin, Etoposide |
| CC | Cyclophosphamide, Carboplatin |
| CDDP/VP-16 | Cisplatin, Etoposide |
| CEF | Cyclophosphamide, Epirubicin, Fluorouracil |
| CEPP(B) | Cyclophosphamide, Etoposide, Prednisone, with or without/Bleomycin |
| CEV | Cyclophosphamide, Etoposide, Vincristine |
| CF | Cisplatin, Fluorouracil or Carboplatin Fluorouracil |
| CHAP | Cyclophosphamide or Cyclophosphamide, Altretamine, Doxorubicin, Cisplatin |
| ChlVPP | Chlorambucil, Vinblastine, Procarbazine, Prednisone |
| CHOP | Cyclophosphamide, Doxorubicin, Vincristine, Prednisone |
| CHOP-BLEO | Add Bleomycin to CHOP |
| CISCA | Cyclophosphamide, Doxorubicin, Cisplatin |
| CLD-BOMP | Bleomycin, Cisplatin, Vincristine, Mitomycin |
| CMF | Methotrexate, Fluorouracil, Cyclophosphamide |
| CMFP | Cyclophosphamide, Methotrexate, Fluorouracil, Prednisone |
| CMFVP | Cyclophosphamide, Methotrexate, Fluorouracil, Vincristine, Prednisone |
| CMV | Cisplatin, Methotrexate, Vinblastine |
| CNF | Cyclophosphamide, Mitoxantrone, Fluorouracil |
| CNOP | Cyclophosphamide, Mitoxantrone, Vincristine, Prednisone |
| COB | Cisplatin, Vincristine, Bleomycin |
| CODE | Cisplatin, Vincristine, Doxorubicin, Etoposide |
| COMLA | Cyclophosphamide, Vincristine, Methotrexate, Leucovorin, Cytarabine |
| COMP | Cyclophosphamide, Vincristine, Methotrexate, Prednisone |
| Cooper Regimen | Cyclophosphamide, Methotrexate, Fluorouracil, Vincristine, Prednisone |
| COP | Cyclophosphamide, Vincristine, Prednisone |
| COPE | Cyclophosphamide, Vincristine, Cisplatin, Etoposide |
| COPP | Cyclophosphamide, Vincristine, Procarbazine, Prednisone |
| CP(Chronic lymphocytic leukemia) | Chlorambucil, Prednisone |
| CP (Ovarian Cancer) | Cyclophosphamide, Cisplatin |
| CVD | Cisplatin, Vinblastine, Dacarbazine |
| CVI | Carboplatin, Etoposide, Ifosfamide, Mesna |
| CVP | Cyclophosphamide, Vincristine, Prednisome |
| CVPP | Lomustine, Procarbazine, Prednisone |
| CYVADIC | Cyclophosphamide, Vincristine, Doxorubicin, |

TABLE 2-continued

Exemplary combinatorial therapies for the treatment of cancer

| Name | Therapeutic agents |
|---|---|
| | Dacarbazine |
| DA | Daunorubicin, Cytarabine |
| DAT | Daunorubicin, Cytarabine, Thioguanine |
| DAV | Daunorubicin, Cytarabine, Etoposide |
| DCT | Daunorubicin, Cytarabine, Thioguanine |
| DHAP | Cisplatin, Cytarabine, Dexamethasone |
| DI | Doxorubicin, Ifosfamide |
| DTIC/Tamoxifen | Dacarbazine, Tamoxifen |
| DVP | Daunorubicin, Vincristine, Prednisone |
| EAP | Etoposide, Doxorubicin, Cisplatin |
| EC | Etoposide, Carboplatin |
| EFP | Etoposie, Fluorouracil, Cisplatin |
| ELF | Etoposide, Leucovorin, Fluorouracil |
| EMA 86 | Mitoxantrone, Etoposide, Cytarabine |
| EP | Etoposide, Cisplatin |
| EVA | Etoposide, Vinblastine |
| FAC | Fluorouracil, Doxorubicin, Cyclophosphamide |
| FAM | Fluorouracil, Doxorubicin, Mitomycin |
| FAMTX | Methotrexate, Leucovorin, Doxorubicin |
| FAP | Fluorouracil, Doxorubicin, Cisplatin |
| F-CL | Fluorouracil, Leucovorin |
| FEC | Fluorouracil, Cyclophosphamide, Epirubicin |
| FED | Fluorouracil, Etoposide, Cisplatin |
| FL | Flutamide, Leuprolide |
| FZ | Flutamide, Goserelin acetate implant |
| HDMTX | Methotrexate, Leucovorin |
| Hexa-CAF | Altretamine, Cyclophosphamide, Methotrexate, Fluorouracil |
| IDMTX/6-MP | Methotrexate, Mercaptopurine, Leucovorin |
| IE | Ifosfamide, Etoposie, Mesna |
| IfoVP | Ifosfamide, Etoposide, Mesna |
| IPA | Ifosfamide, Cisplatin, Doxorubicin |
| M-2 | Vincristine, Carmustine, Cyclophosphamide, Prednisone, Melphalan |
| MAC-III | Methotrexate, Leucovorin, Dactinomycin, Cyclophosphamide |
| MACC | Methotrexate, Doxorubicin, Cyclophosphamide, Lomustine |
| MACOP-B | Methotrexate, Leucovorin, Doxorubicin, Cyclophosphamide, Vincristine, Bleomycin, Prednisone |
| MAID | Mesna, Doxorubicin, Ifosfamide, Dacarbazine |
| m-BACOD | Bleomycin, Doxorubicin, Cyclophosphamide, Vincristine, Dexamethasone, Methotrexate, Leucovorin |
| MBC | Methotrexate, Bleomycin, Cisplatin |
| MC | Mitoxantrone, Cytarabine |
| MF | Methotrexate, Fluorouracil, Leucovorin |
| MICE | Ifosfamide, Carboplatin, Etoposide, Mesna |
| MINE | Mesna, Ifosfamide, Mitoxantrone, Etoposide |
| mini-BEAM | Carmustine, Etoposide, Cytarabine, Melphalan |
| MOBP | Bleomycin, Vincristine, Cisplatin, Mitomycin |
| MOP | Mechlorethamine, Vincristine, Procarbazine |
| MOPP | Mechlorethamine, Vincristine, Procarbazine, Prednisone |
| MOPP/ABV | Mechlorethamine, Vincristine, Procarbazine, Prednisone, Doxorubicin, Bleomycin, Vinblastine |
| MP (multiple myeloma) | Melphalan, Prednisone |
| MP (prostate cancer) | Mitoxantrone, Prednisone |
| MTX/6-MO | Methotrexate, Mercaptopurine |
| MTX/6-MP/VP | Methotrexate, Mercaptopurine, Vincristine, Prednisone |
| MTX-CDDPAdr | Methotrexate, Leucovorin, Cisplatin, Doxorubicin |
| MV (breast cancer) | Mitomycin, Vinblastine |
| MV (acute myelocytic leukemia) | Mitoxantrone, Etoposide |
| M-VAC Methotrexate | Vinblastine, Doxorubicin, Cisplatin |
| MVP Mitomycin | Vinblastine, Cisplatin |
| MVPP | Mechlorethamine, Vinblastine, Procarbazine, Prednisone |
| NFL | Mitoxantrone, Fluorouracil, Leucovorin |
| NOVP | Mitoxantrone, Vinblastine, Vincristine |
| OPA | Vincristine, Prednisone, Doxorubicin |
| OPPA | Add Procarbazine to OPA. |
| PAC | Cisplatin, Doxorubicin |
| PAC-I | Cisplatin, Doxorubicin, Cyclophosphamide |
| PA-CI | Cisplatin, Doxorubicin |
| PCV | Lomustine, Procarbazine, Vincristine |
| PFL | Cisplatin, Fluorouracil, Leucovorin |
| POC | Prednisone, Vincristine, Lomustine |
| ProMACE | Prednisone, Methotrexate, Leucovorin, Doxorubicin, Cyclophosphamide, Etoposide |
| ProMACE/cytaBOM | Prednisone, Doxorubicin, Cyclophosphamide, Etoposide, Cytarabine, Bleomycin, Vincristine, Methotrexate, Leucovorin, Cotrimoxazole |
| PRoMACE/MOPP | Prednisone, Doxorubicin, Cyclophosphamide, Etoposide, Mechlorethamine, Vincristine, Procarbazine, Methotrexate, Leucovorin |
| Pt/VM | Cisplatin, Teniposide |
| PVA | Prednisone, Vincristine, Asparaginase |
| PVB | Cisplatin, Vinblastine, Bleomycin |
| PVDA | Prednisone, Vincristine, Daunorubicin, Asparaginase |
| SMF | Streptozocin, Mitomycin, Fluorouracil |
| TAD | Mechlorethamine, Doxorubicin, Vinblastine, Vincristine, Bleomycin, Etoposide, Prednisone |
| TTT | Methotrexate, Cytarabine, Hydrocortisone |
| Topo/CTX | Cyclophosphamide, Topotecan, Mesna |
| VAB-6 | Cyclophosphamide, Dactinomycin, Vinblastine, Cisplatin, Bleomycin |
| VAC | Vincristine, Dactinomycin, Cyclophosphamide |
| VACAdr | Vincristine, Cyclophosphamide, Doxorubicin, Dactinomycin, Vincristine |
| VAD | Vincristine, Doxorubicin, Dexamethasone |
| VATH | Vinblastine, Doxorubicin, Thiotepa, Flouxymesterone |
| VBAP | Vincristine, Carmustine, Doxorubicin, Prednisone |
| VBCMP | Vincristine, Carmustine, Melphalan, Cyclophosphamide, Prednisone |
| VC | Vinorelbine, Cisplatin |
| VCAP | Vincristine, Cyclophosphamide, Doxorubicin, Prednisone |
| VD | Vinorelbine, Doxorubicin |
| VelP | Vinblastine, Cisplatin, Ifosfamide, Mesna |
| VIP | Etoposide, Cisplatin, Ifosfamide, Mesna |
| VM | Mitomycin, Vinblastine |
| VMCP | Vincristine, Melphalan, Cyclophosphamide, Prednisone |
| VP | Etoposide, Cisplatin |
| V-TAD | Etoposide, Thioguanine, Daunorubicin, Cytarabine |
| 5 + 2 | Cytarabine, Daunorubicin, Mitoxantrone |
| 7 + 3 | Cytarabine with/, Daunorubicin or Idarubicin or Mitoxantrone |
| "8 in 1" | Methylprednisolone, Vincristine, Lomustine, Procarbazine, Hydroxyurea, Cisplatin, Cytarabine, Dacarbazine |

In certain embodiments, the conjoint therapies of the disclosure comprise conjoint administration with other types of chemotherapeutic agents, such as immuno-oncology agents. Cancer cells often have specific cell surface antigens that can be recognized by the immune system. Thus, immuno-oncology agents, such as monoclonal antibodies, can selectively bind to cancer cell antigens and effect cell death. Other immuno-oncology agents can suppress tumor-mediated inhibition of the native immune response or otherwise activate the immune response and thus facilitate recognition of the tumor by the immune system. Exemplary antibody immuno-oncology agents, include, but are not limited to, abagovomab, adecatumumab, afutuzumab, alemtuzumab, anatumomab mafenatox, apolizumab, blinatumomab, BMS-936559, catumaxomab, durvalumab, epacadostat, epratuzumab, indoximod, inotuzumab ozogamicin, intelumumab, ipilimumab, isatuximab, lambrolizumab, MED14736, MPDL3280A, nivolumab, obinutuzumab, ocaratuzumab, ofatumumab, olatatumab, pembrolizumab, pidilizumab, rituximab, ticilimumab, samalizumab, and tremelimumab. In some embodiments, the antibody immuno-oncology agents are selected from anti-CD73 monoclonal antibody (mAb), anti-CD39 mAb, anti-PD-1 mAb, and anti-CTLA4 mAb. Thus, in some embodiments, the methods of the disclosure comprise conjoint administration of one or more immuno-oncology agents, such as the agents mentioned above.

In some embodiments, the combination therapy comprises conjoint administration of a compound of the disclosure, such as a compound of Formula (I), with SH2 inhibitors, such as CGP78850, CPG85793, C90, C126, G7-18NATE, G7-B1, and NSC642056.

In some embodiments, the combination therapy comprises conjoint administration of a compound of the disclosure, such as a compound of Formula (I), with MEK inhibitors, such as trametinib, cobimetinib, binimetinib, selumetinib, PD-325901, CI-1040, and TAK-733.

In some embodiments, the combination therapy comprises conjoint administration of a compound of the disclosure, such as a compound of Formula (I), with a MET inhibitor selected from JNJ-38877605, PF-04217903, foretinib, AMG 458, tivantinib, cabozantinib, crizotinib, capmatinib hydrochloride, tepotinib hydrochloride, and savolitinib.

In some embodiments, the combination therapy comprises conjoint administration of a compound of the disclosure, such as Formula (I), with a SHP2 inhibitor selected from TNO-155, RMC-4630, JAB-3068, or RLY-1971.

In some embodiments, the combination therapy comprises conjoint administration of a compound of the disclosure, such as a compound of Formula (I), with a RAS inhibitor selected from aliskiren, captopril, losartan, irbesartan, olmesartan, candesartan, valsartan, fimasartan, azilsartan, telmisartan, eprosartan, benazepril, enalapril, lisinopril, perindopril, quinapril, ramipril, and trandolapril.

In some embodiment, the combination therapy comprises administration of a compound provided herein, e.g., a compound of Formula (I), in combination with a TKI. In one embodiment, the TKI is a ROS1 inhibitor. In one embodiment, the TKI is an ALK inhibitor. In one embodiment, the TKI is crizotinib, ceritinib, alectinib, brigatinib, lorlatinib, entrectinib, repotrectinib, cabozantinib, foretinib, merestinib, taletrectinib, masitinib, or ensartinib. In one embodiment, the TKI is crizotinib. In one embodiment, the TKI is entrectinib. In one embodiment, the TKI is alectinib. In one embodiment, the TKI is brigatinib.

In some embodiments, the combination therapy comprises conjoint administration of a compound of the disclosure, such as a compound of Formula (I), with anti-PD-1 therapy. In certain embodiments, the combination therapy comprises conjoint administration of a compound of the disclosure, such as a compound of Formula (I), with oxaliplatin. In other embodiments, the combination therapy comprises conjoint administration of a compound of the disclosure, such as a compound of Formula (I), with doxorubicin.

In certain embodiments, a compound of the disclosure may be conjointly administered with non-chemical methods of cancer treatment. In certain embodiments, a compound of the disclosure may be conjointly administered with radiation therapy. In certain embodiments, a compound of the disclosure may be conjointly administered with surgery, with thermoablation, with focused ultrasound therapy, with cryotherapy, or with any combination of these.

In certain embodiments, compounds of the disclosure may be conjointly administered with one or more other compounds of the disclosure. Moreover, such combinations may be conjointly administered with other therapeutic agents, such as other agents suitable for the treatment of cancer, immunological or neurological diseases, such as the agents identified above. In certain embodiments, conjointly administering one or more additional chemotherapeutic agents with a compound of the disclosure provides a synergistic effect. In certain embodiments, conjointly administering one or more additional chemotherapeutic agents provides an additive effect.

Pharmaceutical Compositions

In certain embodiments, the present disclosure provides a pharmaceutical preparation suitable for use in a human patient, comprising any of the compounds shown above (e.g., a compound of the disclosure, such as a compound of Formula (I), and one or more pharmaceutically acceptable excipients. In certain embodiments, the pharmaceutical preparations may be for use in treating or preventing a condition or disease as described herein. Any of the disclosed compounds may be used in the manufacture of medicaments for the treatment of any diseases or conditions disclosed herein.

The compositions and methods of the present disclosure may be utilized to treat a subject in need thereof. In certain embodiments, the subject is a mammal such as a human, or a non-human mammal. When administered to subject, such as a human, the composition or the compound is preferably administered as a pharmaceutical composition comprising, for example, a compound of the disclosure and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In a preferred embodiment, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as an eye drop.

A pharmaceutically acceptable carrier can contain physiologically acceptable agents that act, for example, to stabilize, increase solubility or to increase the absorption of a compound such as a compound of the disclosure. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a self-emulsifying drug delivery system or a self-microemulsifying drug delivery system. The pharmaceutical composition (preparation) also can be a liposome or other polymer matrix, which can have incorporated therein, for example, a compound of the disclosure. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of a subject without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the subject. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other nontoxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin, or as an eye drop). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the subject being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the disclosure, with the carrier and, optionally, one or more accessory ingredients. In general, the formulations are prepared by uniformly and intimately bringing into association a compound of the present disclosure with liquid carriers, or finely divided solid carriers, or both, and then, if necessary, shaping the product.

Formulations of the disclosure suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present disclosure as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in microencapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions for rectal, vaginal, or urethral administration may be presented as a suppository, which may be prepared by mixing one or more active compounds with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the pharmaceutical compositions for administration to the mouth may be presented as a mouthwash, or an oral spray, or an oral ointment.

Alternatively or additionally, compositions can be formulated for delivery via a catheter, stent, wire, or other intraluminal device. Delivery via such devices may be especially useful for delivery to the bladder, urethra, ureter, rectum, or intestine.

Formulations which are suitable for vaginal administration also include pessaries, tampons, creams, gels, pastes, foams or spray formulations containing such carriers as are known in the art to be appropriate.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present disclosure to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this disclosure. Exemplary ophthalmic formulations are described in U.S. Publication Nos. 2005/0080056, 2005/0059744, 2005/0031697 and 2005/004074 and U.S. Pat. No. 6,583,124, the contents of which are incorporated herein by reference. If desired, liquid ophthalmic formulations have properties similar to that of lacrimal fluids, aqueous humor or vitreous humor or are compatible with such fluids. A preferred route of administration is local administration (e.g., topical administration, such as eye drops, or administration via an implant).

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this disclosure, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the subject being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the subject's condition, the disorder being treated, the stability of the compound, and, if desired, another type of therapeutic agent being administered with the compound of the disclosure. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the disclosure will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present disclosure, the active compound may be administered two or three times daily. In preferred embodiments, the active compound will be administered once daily.

In certain embodiments, compounds of the disclosure may be used alone or conjointly administered with another type of therapeutic agent. As used herein, the phrase "conjoint administration" refers to any form of administration of two or more different therapeutic compounds such that the second compound is administered while the previously administered therapeutic compound is still effective in the body (e.g., the two compounds are simultaneously effective in the subject, which may include synergistic effects of the two compounds). For example, the different therapeutic compounds can be administered either in the same formulation or in a separate formulation, either concomitantly or sequentially. In certain embodiments, the different therapeutic compounds can be administered within one hour, 12 hours, 24 hours, 36 hours, 48 hours, 72 hours, or a week of one another. Thus, a subject who receives such treatment can benefit from a combined effect of different therapeutic compounds.

In certain embodiments, conjoint administration of compounds of the disclosure with one or more additional therapeutic agent(s) (e.g., one or more additional chemotherapeutic agent(s)) provides improved efficacy relative to each individual administration of the compound of the disclosure (e.g., compound of Formula I or Ia) or the one or more additional therapeutic agent(s). In certain such embodiments, the conjoint administration provides an additive effect, wherein an additive effect refers to the sum of each of the effects of individual administration of the compound of the disclosure and the one or more additional therapeutic agent(s).

This disclosure includes the use of pharmaceutically acceptable salts of compounds of the disclosure in the compositions and methods of the present disclosure. In certain embodiments, contemplated salts of the disclosure include, but are not limited to, alkyl, dialkyl, trialkyl or tetra-alkyl ammonium salts. In certain embodiments, contemplated salts of the disclosure include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the disclosure include, but are not limited to, Na, Ca, K, Mg, Zn or other metal salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Pharmaceutically acceptable anionic salts include acetate, aspartate, benzenesulfonate, benzoate, besylate, bicarbonate, bitartrate, bromide, camsylate, carbonate, chloride, citrate, decanoate, edetate, esylate, fumarate, glucetate, gluconate, glutamate, glycolate, hexanoate, hydroxynaphthoate, iodide, isethionate, lactate, lactobionate, malate, maleate, mandelate, mesylate, methylsulfate, mucate, napsylate, nitrate, octanoate, oleate, pamoate, pantothenate, phosphate, polygalacturonate, propionate, salicylate, stearate, acetate, succinate, sulfate, tartrate, teoclate, and tosylate.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

The disclosure now being generally described, it will be more readily understood by reference to the following examples which are included merely for purposes of illustration of certain aspects and embodiments of the present disclosure, and are not intended to limit the disclosure.

General Synthetic Procedures

The starting materials and reagents used in preparing these compounds are either available from commercial supplier such as Aldrich Chemical Co., Bachem, etc., or can be made by methods well known in the art. The schemes are merely illustrative of some methods by which the compounds disclosed herein can be synthesized and various modifications to these schemes can be made and will be suggested to one of skill in the art having referred to this disclosure. The starting materials and the intermediates and the final products of the reaction may be isolated and purified if desired using conventional techniques, including but not limited to filtration, distillation, crystallization, chromatography, and the like and may be characterized using conventional means, including physical constants and spectral data. In some instances, reactions may produce more than one regioisomeric product. In these cases, chromatography may be used to separate the isomers and NOE or NOESY NMR spectroscopy may be used to aid structural assignment.

Unless specified otherwise, the reactions described herein take place at atmospheric pressure over a temperature range from about −78° C. to about 150° C.

| Abbreviations | Definition |
|---|---|
| Solvents | |
| EA, EtOAc | ethyl acetate |
| PE, pet. ether | petroleum ether |
| THF | tetrahydrofuran |
| DCM | dichloromethane |
| DMF | N,N-dimethylformamide |
| DMA | N,N-dimethylacetamide |
| NMP | N-methyl-2-pyrrolidone |
| DMSO | dimethyl sulfoxide |
| IPA | isopropyl alcohol |
| DME | dimethoxyethane |
| MeCN, ACN | acetonitrile |
| DCE | dichloroethane |
| Reagents | |
| DAST | diethylaminosulfur trifluoride |
| DIAD | diisopropyl azodicarboxylate |
| DEAD | diethyl azodicarboxylate |
| DBAD | di-tert-butyl azodicarboxylate |
| DIPEA, DIEA | N,N-diisopropylethylamine |
| TEA | triethylamine |
| ATP | adenosine triphosphate |
| TFA | trifluoroacetic acid |
| FA | formic acid |
| DIBAL, DIBAL-H, DIBALH | diisobutylaluminium hydride |
| AcOH, HOAc | acetic acid |
| TES | triethylsilane |
| n-BuLi, BuLi | n-butyllithium |
| LDA | lithium diisopropylamide |
| NBS | N-bromosuccinimide |
| NIS | N-iodosuccinimide |
| NCS | N-chlorosuccinimide |
| DMP | Dess-Martin periodinane |
| DEA | diethylamine |
| DMF-DMA | 1,1-dimethoxy-N,N-dimethylmethanamine |
| TMP | 2,2,6,6-tetramethylpiperidine |
| NMO | N-methylmorpholine N-oxide |
| TBSCl | tert-butyldimethylsilyl chloride |
| KOAc, AcOK | potassium acetate |
| NaOAc, AcONa | sodium acetate |
| SEMCl | 2-(trimethylsilyl)ethoxymethyl chloride |
| tBuLi, t-BuLi | tert-butyllithium |
| NFSI | N-fluorobenzenesulfonimide |
| AIBN | azobisisobutyronitrile |
| EDCI | 1-ethyl-3-(3-dimethylaminopropyl)carbodiimide |
| HOBT | hydroxybenzotriazole |
| TBAF | tetra-n-butylammonium fluoride |
| HATU | 1-[bis(dimethylamino)methylene]-1H-1,2,3-triazolo-[4,5-b]pyridinium 3-oxide hexafluorophosphate |
| XPhos | 2-dicyclohexylphosphino-2',4',6'-triisopropylbiphenyl |
| cataCXium A | di(1-adamantyl)-n-butylphosphine |
| DPPP | 1,3-bis(diphenylphosphino)propane |
| DPPF | 1,1'-bis(diphenylphosphino)ferrocene |
| TfOH | triflic acid |
| HMTA | 1,3,5,7-tetraazaadamantane |
| PMBCl | p-methoxybenzyl chloride |
| HEPES | 4-(2-hydroxyethyl)-1-piperazineethanesulfonic acid |
| EGTA | ethylene glycol-bis(2-aminoethylether)-N,N,N',N'-tetraacetic acid |
| Other | |
| HPLC | high-pressure liquid chromatography |
| Prep | preparative |
| wt | wild-type |
| rt, r.t., RT | room-temperature |
| SFC | supercritical fluid chromatography |
| V/V | volume/volume |
| LC/MS, LC-MS, LCMS | liquid chromatography-mass spectrometry |
| MS | mass spectrometry |
| ESI, ES+, ES− | electrospray ionization |
| NMR | nuclear magnetic resonance |

-continued

| Abbreviations | Definition |
|---|---|
| Ppm | parts per million |
| sat | saturated |
| aq | aqueous |
| TLC | thin layer chromatography |
| tR | retention time |

The compounds of the invention can be prepared by a variety of synthetic methods, as further described and illustrated herein. It will be understood by those with skill in the art that the following general synthetic methods are representative and not intended to be limiting. Racemic compounds can be enantiomerically enriched via chiral, preparative, SFC or HPLC separation. Variable A denotes a carbon, nitrogen or sulfur atom that can be the same or different as another instance of variable A. Variable X denotes a chloride, bromide or iodide atom that can be the same or different as another instance of variable X. Variable Z denotes a nitrogen atom, or C—H or C—F group that can be the same or different as another instance of variable Z.

Method A

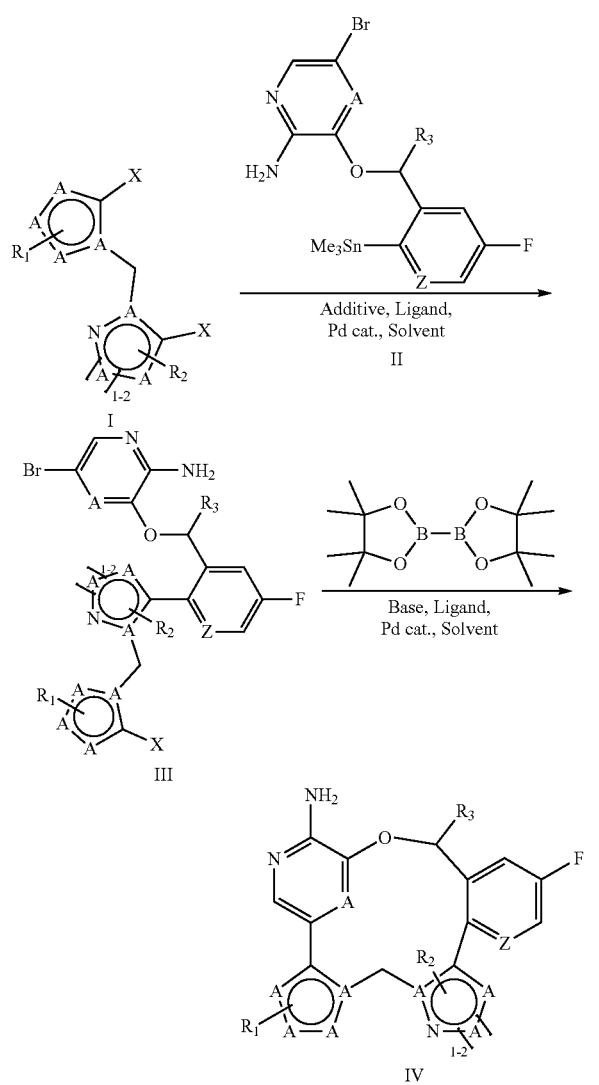

Poly-halide I may be coupled with stannane II using Stille coupling conditions to provide compounds of type III. Various additives including (but not limited to) LiCl or CuI may be optionally employed to facilitate this reaction. Intramolecular ring closure of poly-halide III may be effected using two-step, one-pot borylation/Suzuki cross-coupling conditions to afford compounds of type IV.

Method B

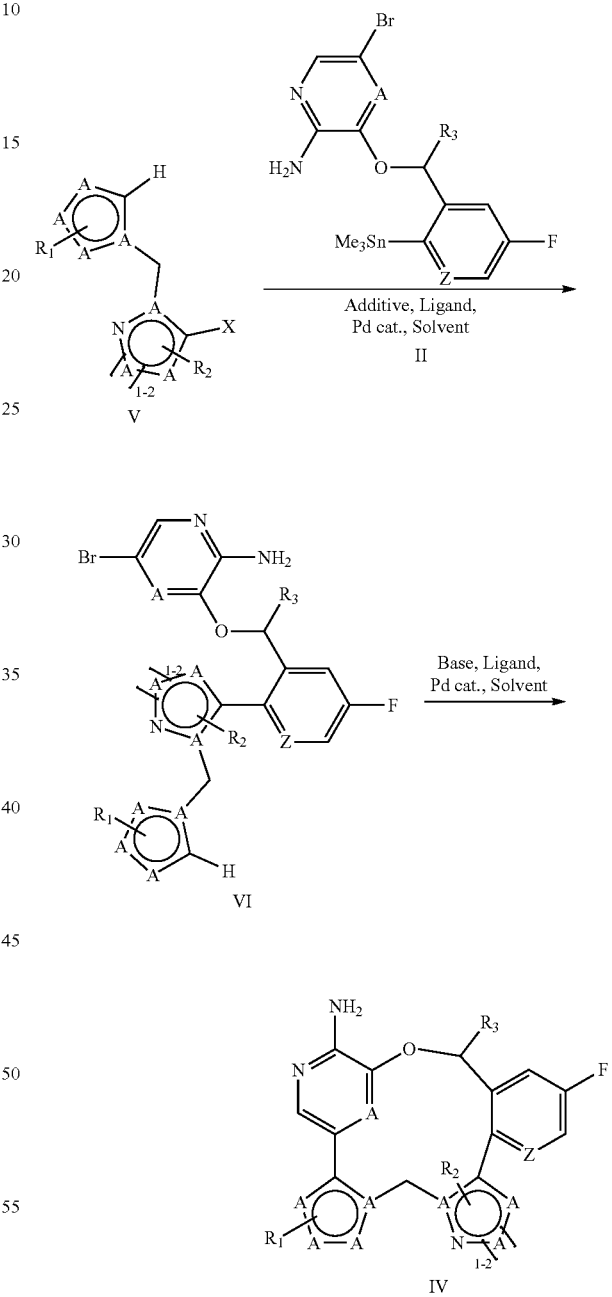

Halide V may be coupled with stannane II using Stille coupling conditions to provide compounds of type VI. Various additives including (but not limited to) LiCl or CuI may be optionally employed to facilitate this reaction. Intramolecular ring closure of halide VI may be effected using C—H insertion cross-coupling conditions to afford compounds of type IV. Potassium acetate or potassium pivalate are effective bases for the macrocyclization step.

Method C

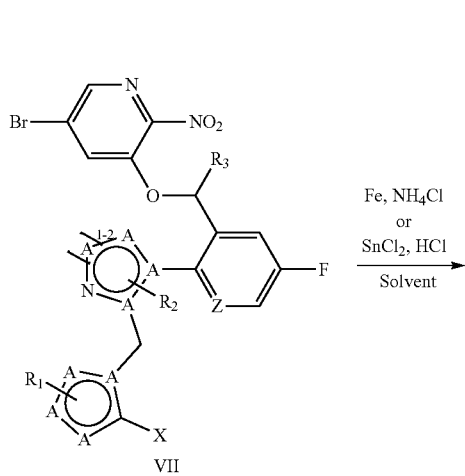

VII

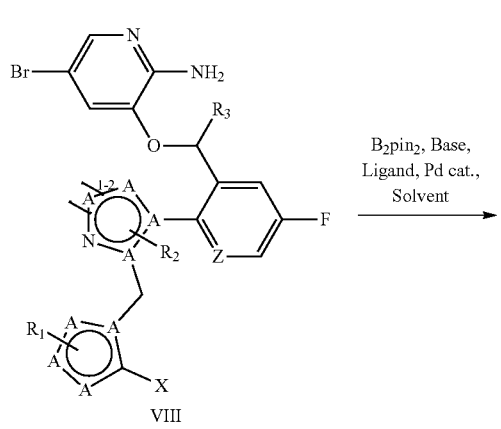

VIII

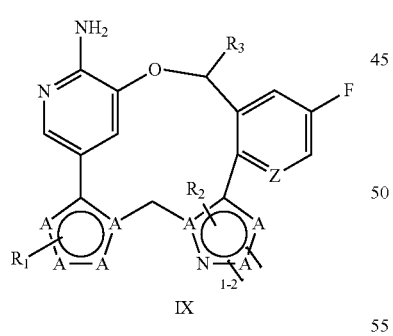

IX

Method D

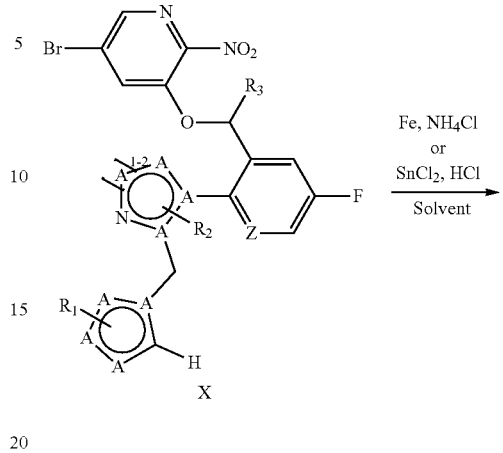

X

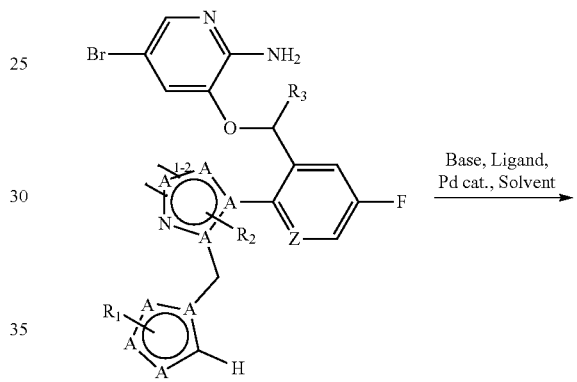

XI

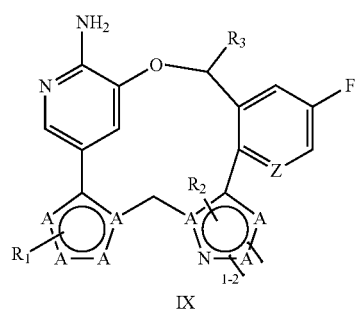

IX

Nitropyridine VII may be reduced using Fe metal conditions to provide aminopyridines of type VIII. In cases where the substrate contains an isoxazole moiety, yields can be improved by using SnCl₂ conditions instead. Intramolecular ring closure of VIII may be effected using two-step, one-pot borylation/Suzuki cross-coupling conditions to afford compounds of type IX.

Nitropyridine X may be reduced using Fe metal conditions to provide aminopyridines of type XI. In cases where the substrate contains an isoxazole moiety, yields can be improved by using SnCl₂ conditions instead. Intramolecular ring closure of XI may be effected using C—H insertion cross-coupling conditions to afford compounds of type IX. Potassium acetate or potassium pivalate are effective bases for the macrocyclization step.

Method E

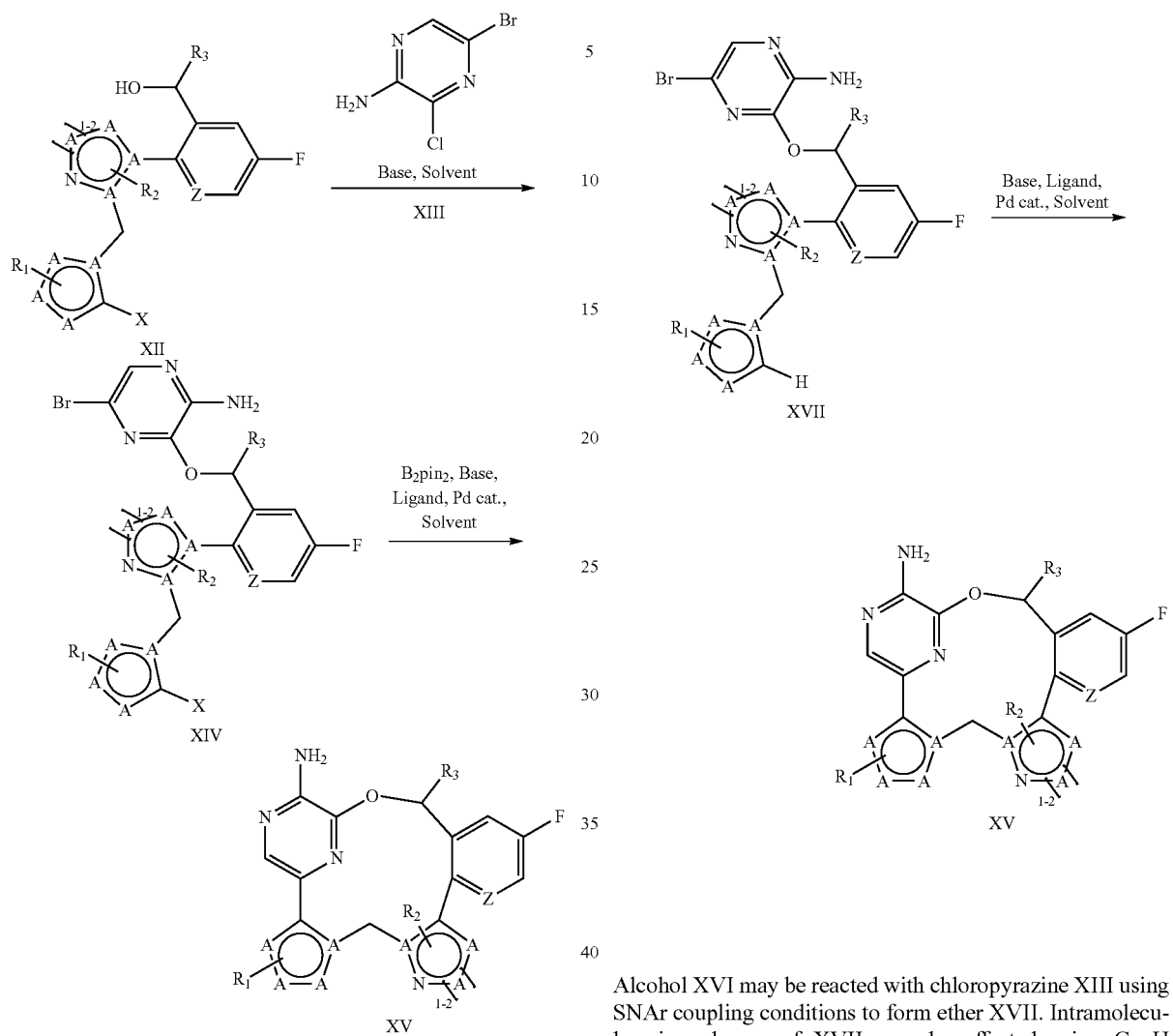

Alcohol XII may be reacted with chloropyrazine XIII using SNAr coupling conditions to form ether XIV. Intramolecular ring closure of XIV may be effected using two-step, one-pot borylation/Suzuki cross-coupling conditions to afford compounds of type XV.

Method F

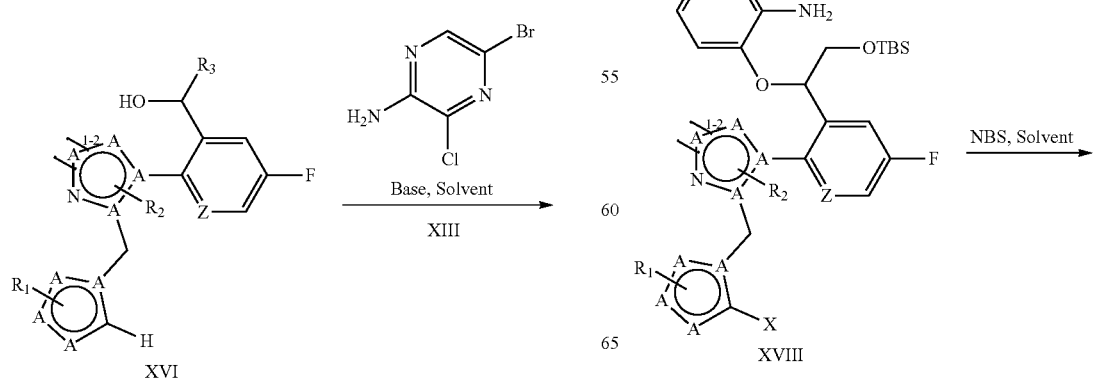

Alcohol XVI may be reacted with chloropyrazine XIII using SNAr coupling conditions to form ether XVII. Intramolecular ring closure of XVII may be effected using C—H insertion cross-coupling conditions to afford compounds of type XV. Potassium acetate or potassium pivalate are effective bases for the macrocyclization step.

Method G

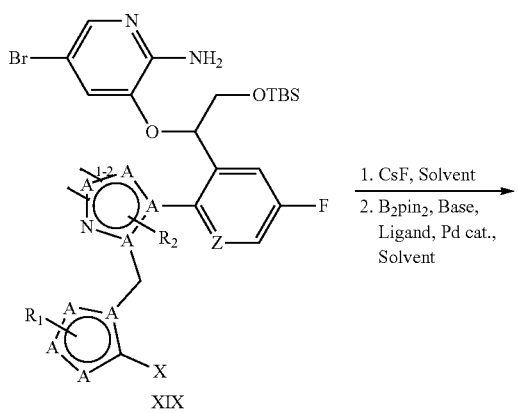

XIX

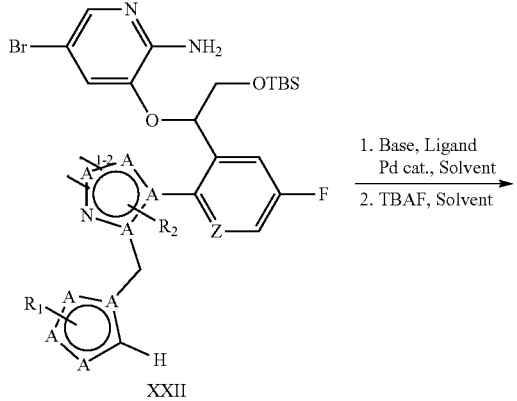

XXII

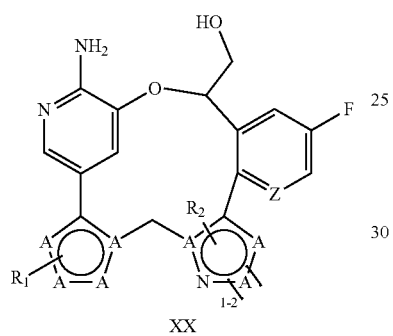

XX

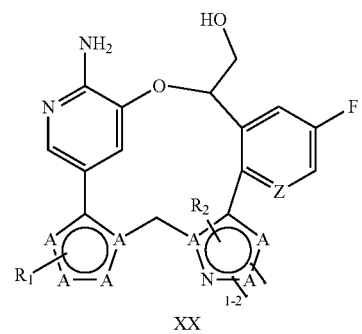

XX

Aminopyridine XVIII may be brominated with a suitable brominating reagent to provide bromide XIX. Desilylation of XIX using a suitable fluoride ion source, followed by intramolecular ring closure using two-step, one-pot borylation/Suzuki cross-coupling conditions may afford compounds of type XX.

Method H

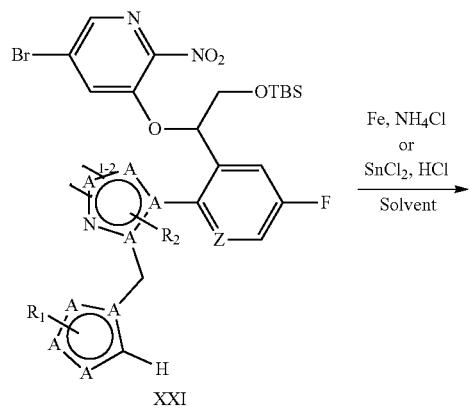

XXI

Nitropyridine XXI may be reduced using Fe metal conditions to provide aminopyridines of type XXII. In cases where the substrate contains an isoxazole moiety, yields can be improved by using SnCl$_2$ conditions instead. Intramolecular ring closure of XXII using C—H insertion cross-coupling conditions, followed by TBAF desilylation affords compounds of type XX. Potassium acetate or potassium pivalate are effective bases for the macrocyclization step.

Method I

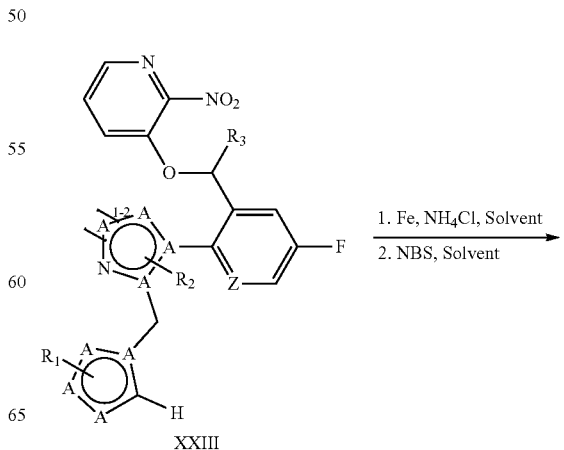

XXIII

-continued

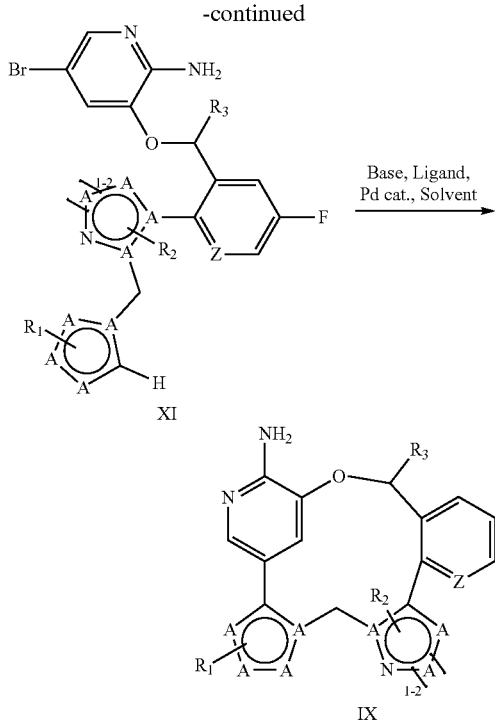

XI

IX

Nitropyridine XXIII may be converted to compound XI by reduction using Fe metal conditions followed by bromination with a suitable brominating reagent. Intramolecular ring closure of XI may be effected using C—H insertion cross-coupling conditions to afford compounds of type IX. Potassium acetate or potassium pivalate are effective bases for the macrocyclization step.

Method J

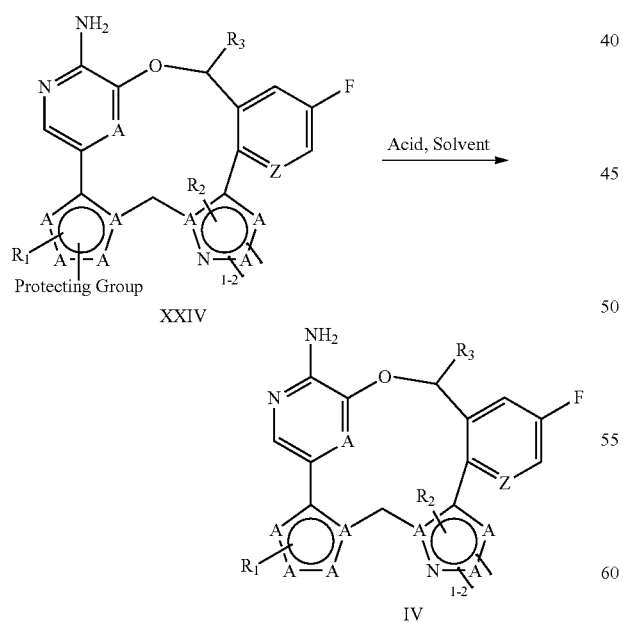

XXIV

IV

Compounds of type XXIV may be deprotected to provide compounds of type IV by treatment with a suitable acid in solution (e.g. TFA or HCl). Protecting groups amenable to this method include, but are not limited to, the methoxymethyl, 2-(trimethylsilyl)ethoxymethyl, tetrahydropyranyl, and p-methoxybenzyl groups.

Method K

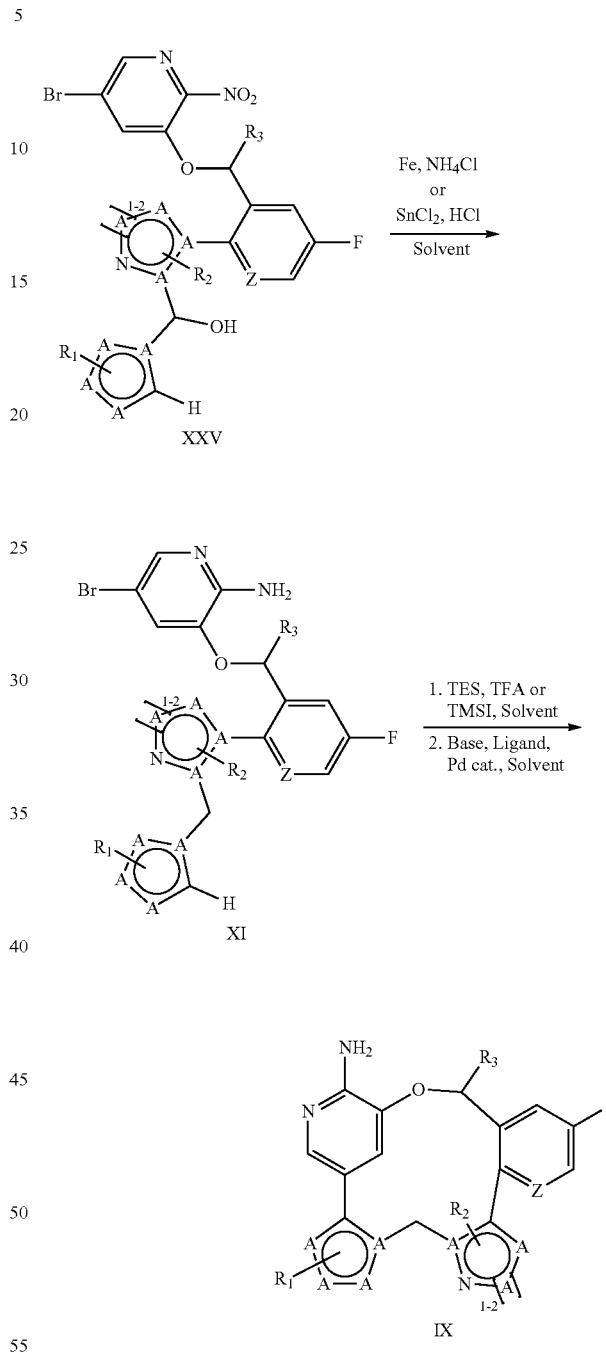

XXV

XI

IX

Nitropyridine XXV may be reduced using Fe metal conditions to provide aminopyridines of type XI. In cases where the substrate contains an isoxazole moiety, yields can be improved by using SnCl$_2$ conditions instead. Intramolecular ring closure of XI may be effected using C—H insertion cross-coupling conditions to afford compounds of type IX. Potassium acetate or potassium pivalate are effective bases for the macrocyclization step.

Method L

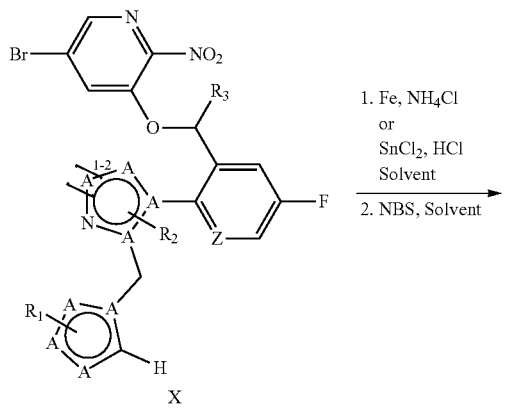

X

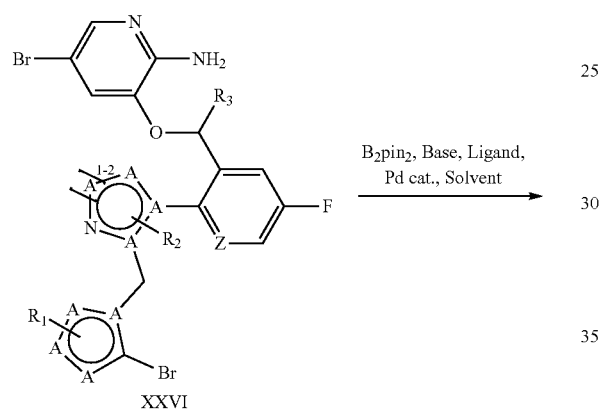

XXVI

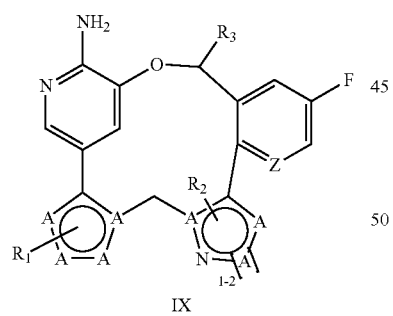

IX

Nitropyridine X may be reduced using iron metal, and then brominated with NBS to provide aminopyridines of type XXVI. In cases where the substrate contains an isoxazole moiety, yields can be improved by using SnCl₂ reducing conditions instead of iron. Intramolecular ring closure of XXVI may be effected using two-step, one-pot borylation/ Suzuki cross-coupling conditions to afford compounds of type IX.

Method M

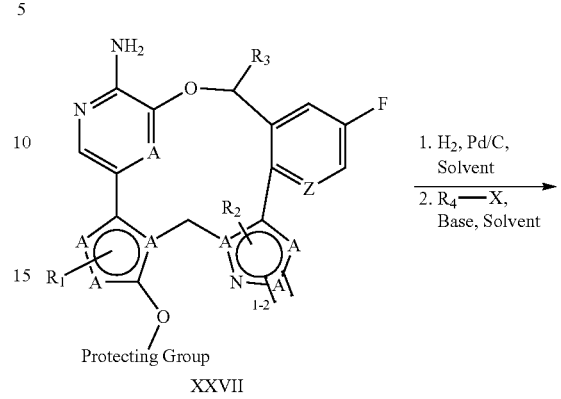

XXVII

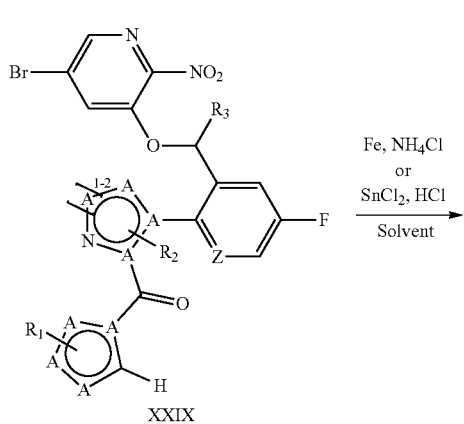

XXVIII

Compounds of type XXVII may be first deprotected by hydrogenolysis using palladium on carbon under a hydrogen atmosphere, followed by alkylation of the resulting hydroxyl group with an alkyl halide (e.g. methyl iodide) to provide compounds of type XXVIII. Protecting groups amenable to this method include, but are not limited to, the benzyl and p-methoxybenzyl groups.

Method N

XXIX

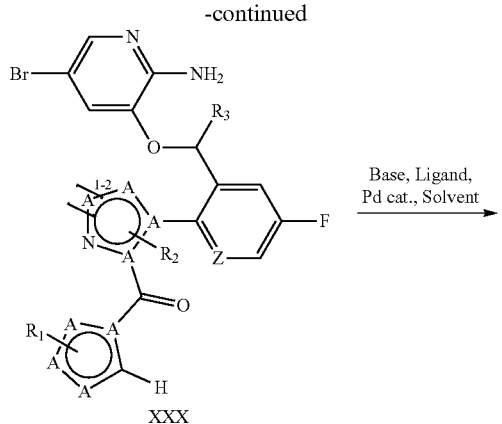

XXX

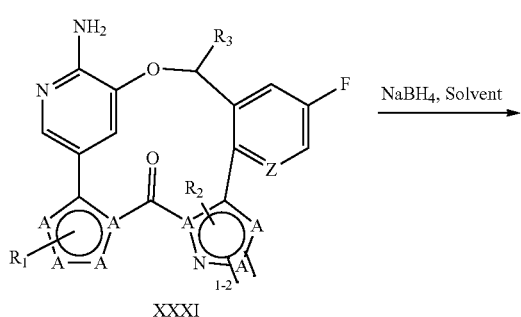

XXXI

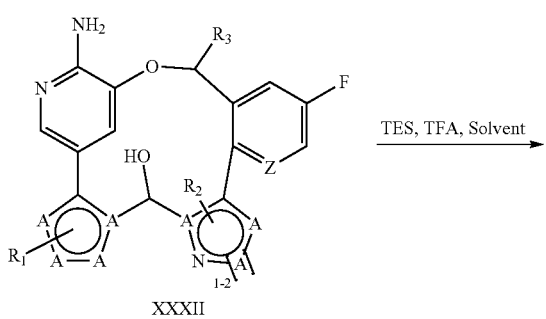

XXXII

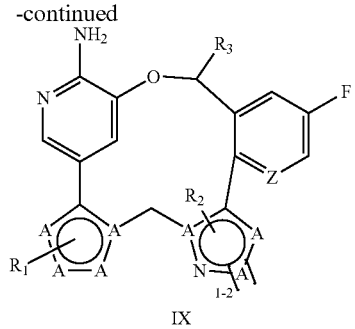

IX

Nitropyridine XXIX may be reduced using Fe metal conditions to provide aminopyridines of type XXX. In cases where the substrate contains an isoxazole moiety, yields can be improved by using $SnCl_2$ conditions instead. Intramolecular ring closure of XXX may be effected using C—H insertion cross-coupling conditions to afford ketones of type XXXI. Potassium acetate or potassium pivalate are effective bases for the macrocyclization step. Reduction of the ketone XXXI to the alcohols of type XXXII can be effected using sodium borohydride. Finally, deoxygenation may be performed using triethylsilane and trifluoroacetic acid to afford compounds of type IX.

Those having skill in the art will recognize that the starting materials and reaction conditions may be varied, the sequence of the reactions altered, and additional steps employed to produce compounds encompassed by the present disclosure, as demonstrated by the following examples. In some cases, protection of certain reactive functionalities may be necessary to achieve some of the above transformations. In general, the need for such protecting groups as well as the conditions necessary to attach and remove such groups will be apparent to experienced organic chemists. The disclosures of all articles and references mentioned in this application, including patents, are incorporated herein by reference.

The preparation of the compounds of the present disclosure is illustrated further by the following examples, which are not to be construed as limiting the disclosure in scope or spirit to the specific procedures and compounds described in them.

Analytical Methods

LCMS data was collected using one of the following methods:

| LCMS Method | Method Details |
|---|---|
| A | Instrument: Agilent1260-6125B |
| | Column: YMC Triart C18, 50 × 4.6 mm, 5 μm |
| | Mobile phase: A is $H_2O$ (+0.05% FA) and B is $CH_3CN$ (+0.05% FA) |
| | Run Time: 20% B (0.1 mm); 20-95% B (1.4 mm); 95% B (0.7 min); 20% B (0.5 min) |
| | Flow rate: 2.5 mL/min |
| | Column temperature: 35° C. |
| | Wavelength: 220 nm/254 nm |
| B | Instrument: SHIMADZU 2020 |
| | Column: Inertsustain C18, 50 × 4 6 mm, μm |
| | Mobile phase: A is $H_2O$ (+0.1% FA) and B is $CH_3CN$ |
| | Run Time: 15% B (0.6 mm); 15-95% B (3.2 mm); 95% B (0.5 min); 15% B (0.7 min) |
| | Flow rate: 2.5 mL/min |
| | Column temperature: 35° C. |
| | Wavelength: 220 nm/254 nm |
| C | Instrument: SHIMADZU 2020 |
| | Column: YMC-Triart C18, 50 × 4.6 mm, μm |
| | Mobile phase: A is $H_2O$ (+0.1% FA) and B is $CH_3CN$ |

-continued

| LCMS Method | Method Details |
|---|---|
| | Run Time: 20% B (0.1 mm); 20-95% B (1.7 mm); 95% B (0.7 min); 20% B (0.4 min)<br>Flow rate: 2.5 mL/min<br>Column temperature: 35° C.<br>Wavelength: 220 nm/254 nm |
| D | Instrument: SHIMADZU 2020<br>Column: YMC-Triart C18, 50 × 4.6 mm, μm<br>Mobile phase: A is $H_2O$ (+0.1% FA) and B is $CH_3CN$<br>Run Time: 0% B (0.6 min); 0-50% B (3.2 mm); 50% B (0.5 mm); 0% B (0.4 mm)<br>Flow rate: 2.5 mL/min<br>Column temperature: 35° C.<br>Wavelength: 220 nm/254 nm |
| E | Instrument: SHIMADZU 2020<br>Column: Inertsustain C18, 50 × 4 6 mm, 5 μm<br>Mobile phase: A is $H_2O$ (+0.1% FA) and B is $CH_3CN$<br>Run Time: 0% B (0.1 min); 0-50% B (1.7 mm); 50% B (0.7 mm); 0% B (0.4 mm)<br>Flow rate: 2.5 mL/min<br>Column temperature: 35° C.<br>Wavelength: 220 nm/254 nm |
| F | Instrument: SHIMADZU 2020<br>Column: Shim-pack GIST C18, 50 × 4.6 mm, 5 μm<br>Mobile phase: A is $H_2O$ (+0.1% FA) and B is $CH_3CN$<br>Run Time: 20% B (0.1 mm); 20-95% B (1.7 mm); 95% B (0.7 min); 20% B (0.4 min)<br>Flow rate: 2.5 mL /min<br>Column temperature: 35° C.<br>Wavelength: 220 nm/254 nm |
| G | Instrument: SHIMADZU 2020<br>Column: Shim-pack GIST C18, 50 × 4.6 mm, 5 μm<br>Mobile phase: A is $H_2O$ (+0.1% FA) and B is $CH_3CN$<br>Run Time: 0% B (0.6 min); 0-50% B (3.2 min); 50% B (0.5 min); 0% B (0.4 min)<br>Flow rate: 2.5 mL /min<br>Column temperature: 35° C.<br>Wavelength: 220 nm/254 nm |
| H | Instrument: SHIMADZU 2020<br>Column: Inertsil ODS-3 C18, 50 × 4.6 mm, 5 μm<br>Mobile phase: A is $H_2O$ (+0.04% aq. $NH_3$) and B is $CH_3CN$<br>Run Time: 20% B (0.1 min); 20-95% B (1.7 min); 95% B (0.7 min); 20% B (0.4 min)<br>Flow rate: 2.5 mL /min<br>Column temperature: 35° C.<br>Wavelength: 220 nm/254 nm |
| I | Instrument: SHIMADZU 2010<br>Column: Shim-pack GIST C18,50 × 4 6 mm, 5 μm<br>Mobile phase: A is 10% $CH_3CN$ in $H_2O$ +0.05% FA and B is $CH_3CN$<br>Run Time: 20-95% B (1.8 min); 95% B (0.9 min)<br>Flow rate: 2.3 mL /min<br>Column temperature: 40° C.<br>Wavelength: 220 nm/254 nm |
| J | Instrument: SHIMADZU 2020<br>Column: Inertsil ODS-3 C18, 50 × 4.6 mm, 5 μm<br>Mobile phase: A is $H_2O$ (+0.04% aq. $NH_3$) and B is $CH_3CN$<br>Run Time: 15% B (0.6 min); 15-95% B (3.2 min); 95% B (0.5 min); 15% B (0.4 min)<br>Flow rate: 2.5 mL /min<br>Column temperature: 35° C.<br>Wavelength: 220 nm/254 nm |
| K | Instrument: SHIMADZU 2020<br>Column: Kromasil EternityXT C18, 50 × 4.6 mm, 5 μm<br>Mobile phase: A is $H_2O$ (+0.1% FA) and B is $CH_3CN$<br>Run Time: 20% B (0.1 mm); 20-95% B (1.7 mm); 95% B (0.7 min); 20% B (0.4 min)<br>Flow rate: 2.5 mL /min<br>Column temperature: 35° C.<br>Wavelength: 220 nm/254 nm |
| L | Instrument: SHIMADZU 2020<br>Column: YMC Triart C18, 50 × 4.6 mm, 5 ittm<br>Mobile phase: A is $H_2O$ (+0.1% FA) and B is $CH_3CN$<br>Run Time: 15% B (0.6 mm); 15-95% B (3.2 mm); 95% B (0.5 mm); 15% B (0.4 min)<br>Flow rate: 2.5 mL /min<br>Column temperature: 35° C.<br>Wavelength: 220 nm/254 nm |
| M | Instrument: SHIMADZU 2020<br>Column: Shim-pack GIST C18,50 × 4 6 mm, 5 μm<br>Mobile phase: A is $H_2O$ (+0.05% FA) and B is $CH_3CN$ |

| LCMS Method | Method Details |
|---|---|
| | Run Time: 0% B (0.6 min); 0-70% B (3.2 mm); 70% B (0.5 mm); 0% B (0.4 mm)<br>Flow rate: 2.5 mL /min<br>Column temperature: 35° C.<br>Wavelength: 220 nm/254 nm |

SYNTHETIC EXAMPLES

Synthesis of 3-chloro-5-iodo-1H-pyrazole

Intermediates

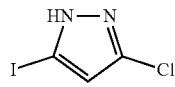

Under a nitrogen atmosphere, to a solution of 3-chloro-N,N-dimethyl-1H-pyrazole-1-sulfonamide (1.90 g, 9.06 mmol) in THF (40 mL) was added n-butyllithium (4.35 mL, 10.9 mmol) dropwise at −78° C. A thick precipitate formed, and the solution was allowed to stir for 30 min after the addition. To the stirred suspension, a solution of 1-iodopyrrolidine-2,5-dione (2.24 g, 9.97 mmol) in THF (10 mL) was added dropwise at −78° C. After 1 h, the resulting clear solution was warmed to room temperature. The reaction was quenched by sat. NH$_4$Cl at 0° C. and extracted with DCM (3×50 mL). The organic layer was separated, washed with brine, dried over anhydrous Na$_2$SO$_4$ and concentrated. The residue was purified by column chromatography on silica gel (30% EtOAc in PE) to give 3-chloro-5-iodo-N,N-dimethyl-1H-pyrazole-1-sulfonamide (3.0 g, yield: 89%) as a white solid. LC/MS (ESI): m/z=336 [M+H]$^+$.

In a round bottom flask with magnetic stirrer, 3-chloro-5-iodo-N,N-dimethyl-1H-pyrazole-1-sulfonamide (3.00 g, 8.94 mmol) in DCM (8 mL) was cooled to 0° C. and treated with TFA (8.0 mL, 108 mmol). The mixture was stirred for 1.5 h. The reaction was quenched with sat. NaHCO$_3$ and extracted with EA (2×50 mL). The extracts were dried over with anhydrous Na$_2$SO$_4$ and concentrated under reduced pressure to give crude 3-chloro-5-iodo-1H-pyrazole (2.1 g, yield: 100%) as a yellow solid. LC/MS (ESI): m/z=229 [M+H]$^+$.

Synthesis of (nitromethyl)cyclobutane

To a solution of (nitromethylidene)cyclobutane (9.8 g, 86.63 mmol) in MeOH (50 mL), was added NaBH$_4$ (4.94 g, 130 mmol) at 0° C., and stirred at 0° C. for 60 min. The reaction was quenched by adding cold water and filtered. The filtrate was dissolved in EtOAc, washed once with water, once with brine, dried over anhydrous Na$_2$SO$_4$, and filtered. The filtrate was concentrated to give a residue, which was purified by flash chromatography (0→5% MeOH in DCM) to give (nitromethyl)cyclobutane (4.4 g, 44% yield) as a colorless oil. LC/MS ESI (m/z): 116 [M+H]$^+$.

Synthesis of (5-bromo-1,3-thiazol-4-yl)methanol

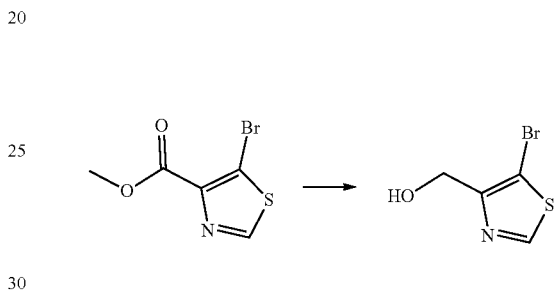

To a solution of methyl 5-bromo-1,3-thiazole-4-carboxylate (5.00 g, 22.5 mmol) in THF (100 mL) at 0° C. was added LiBH$_4$ (2.94 g, 135 mmol). Then MeOH (10 mL) was added dropwise to the above solution. The mixture was stirred at r.t. for 16 h. The reaction was quenched with water and extracted with EA (50 mL×3). The organic phase was washed with brine, dried over Na$_2$SO$_4$, and concentrated under vacuum to yield crude (5-bromo-1,3-thiazol-4-yl)methanol as a light-yellow solid (1.00 g, 23% yield). LC/MS ESI (m/z): 194 [M+H]$^+$.

Synthesis of 5-chloro-3-iodo-1-methyl-1H-pyrazole

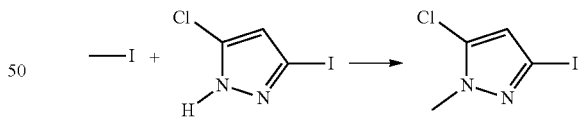

To a mixture of 5-chloro-3-iodo-1H-pyrazole (100 mg, 0.440 mmol) and K$_2$CO$_3$ (121 mg, 0.880 mmol) in DMF (8 mL) was added methyl iodide (0.03 mL, 0.5 mmol) at 25° C. The mixture was then stirred at r.t. for 30 min. The reaction mixture was quenched with ice water, extracted twice into EA, washed with brine, dried over anhydrous Na$_2$SO$_4$, filtered and concentrated to give crude 5-chloro-3-iodo-1-methyl-1H-pyrazole (100 mg, 94% yield) as a yellow liquid. The material can be used as-is, or further purified by flash-, high-pressure-, or supercritical fluid-chromatography to separate possible regioisomers. LC/MS (ESI) m/z: 243 [M+H]$^+$.

The following intermediates were synthesized using a similar experimental protocol:
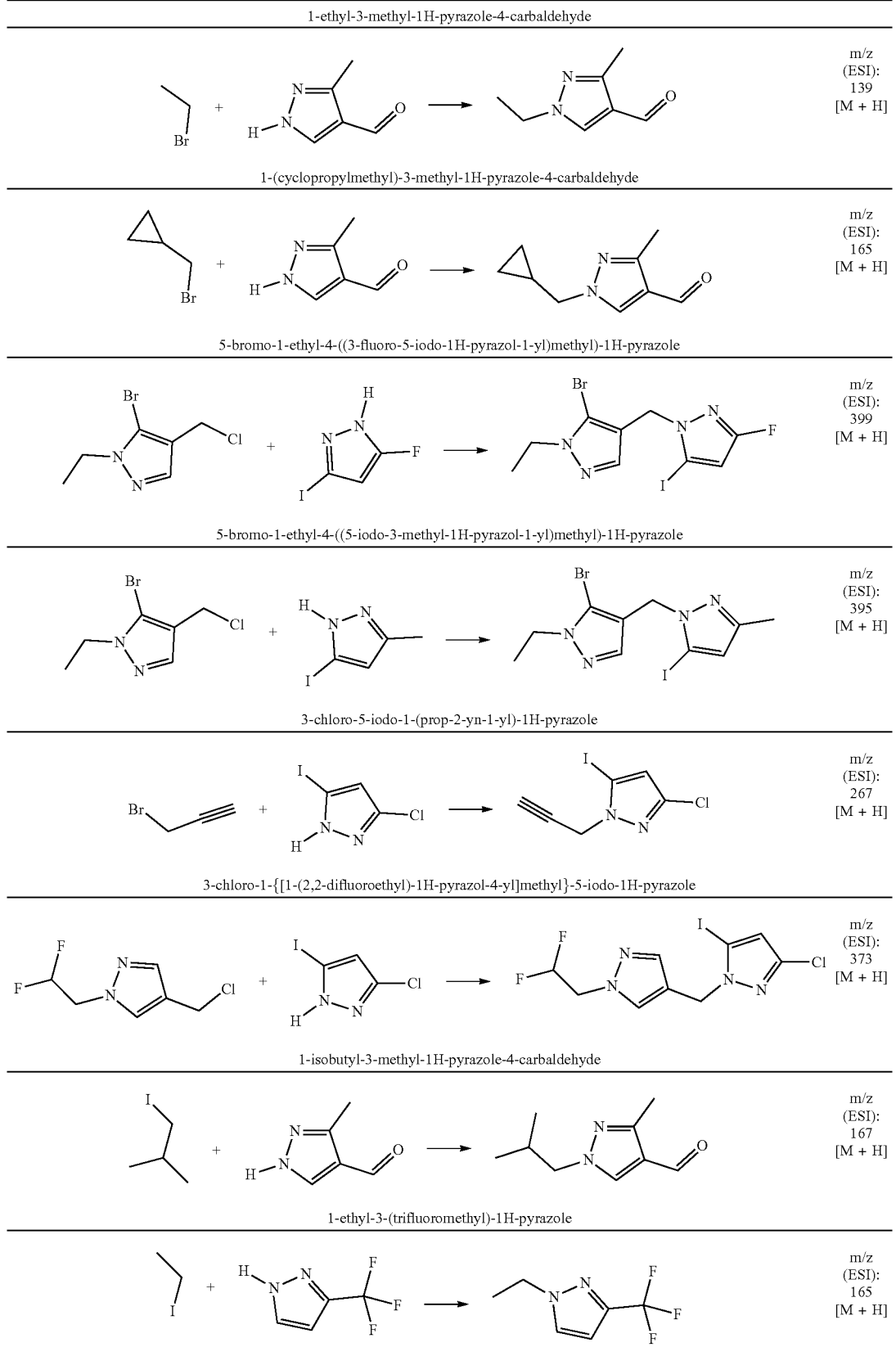

| 5-bromo-1-((1-ethyl-1H-pyrazol-4-yl)methyl)-3-methoxy-1H-pyrazole | |
|---|---|
| 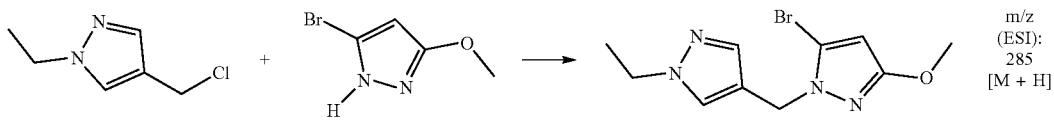 | m/z (ESI): 285 [M + H] |

| methyl 3-ethyl-1-methyl-1H-pyrazole-5-carboxylate | |
|---|---|
| 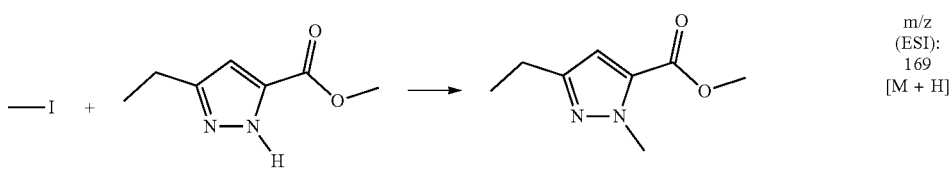 | m/z (ESI): 169 [M + H] |

Synthesis of 1-ethyl-1H-pyrrole-3-carbaldehyde

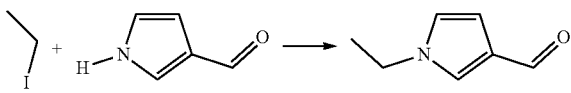

To a solution of 1H-pyrrole-3-carbaldehyde (5.00 g, 52.6 mmol) in DMF (30 mL) was added $K_2CO_3$ (12.4 g, 89.4 mmol) and iodoethane (5.0 mL, 63 mmol) at 0° C. The mixture was stirred at r.t. for 16 h, filtered, and the filtrate was diluted with ethyl acetate (30 mL). The solution was washed with brine (50 mL), dried over anhydrous $Na_2SO_4$ and concentrated. The residue was purified by flash chromatography (0%→35% EA in PE) to give 1-ethyl-1H-pyrrole-3-carbaldehyde (4.0 g, 62% yield) as a yellow oil. LC/MS (ESI) m/z: 124.1 [M+H]$^+$.

The following intermediates were synthesized using a similar experimental protocol:

| 1-(2,2-difluoroethyl)-1H-pyrazole-4-carbaldehyde | |
|---|---|
| 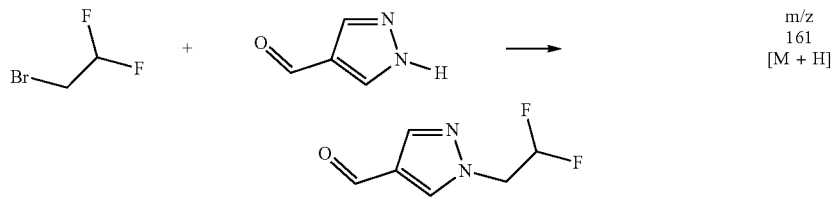 | m/z 161 [M + H] |

| 4-chloro-1-((1-ethyl-1H-pyrazol-4-yl)methyl)-1H-pyrazole | |
|---|---|
| 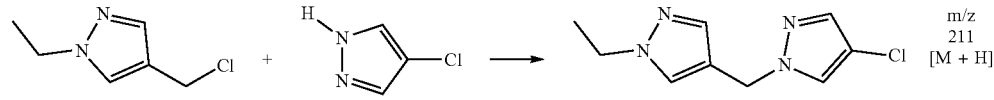 | m/z 211 [M + H] |

| 1-((5-bromopyrimidin-4-yl)methyl)-1H-imidazole-4-carbonitrile | |
|---|---|
| 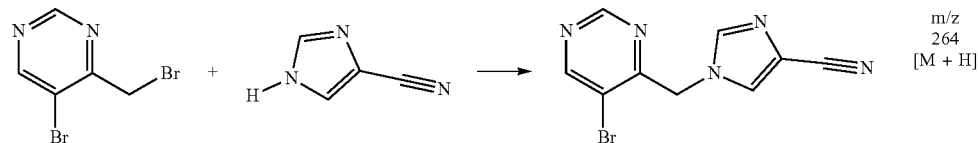 | m/z 264 [M + H] |

| 1-(ethyl-d5)-1H-pyrazole-4-carbaldehyde | |
|---|---|
| 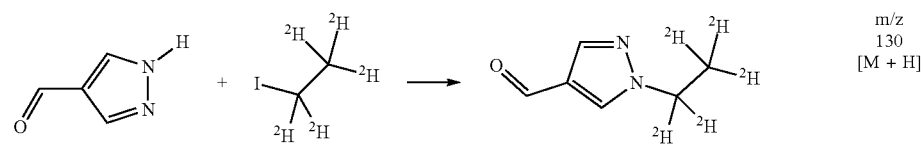 | m/z 130 [M + H] |

-continued

| 4-iodo-1-(oxetan-3-yl)-1H-pyrazole | |
|---|---|
| 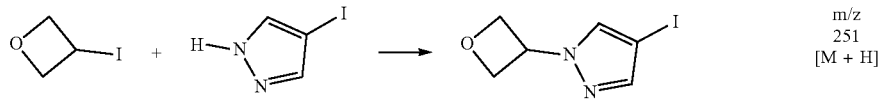 | m/z 251 [M + H] |
| 1-(cyclopropylmethyl)-1H-pyrazole-4-carbaldehyde | |
| 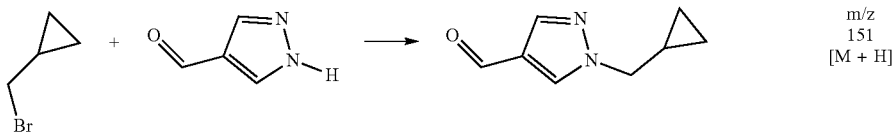 | m/z 151 [M + H] |

Synthesis of 3-ethylisoxazole-5-carbaldehyde

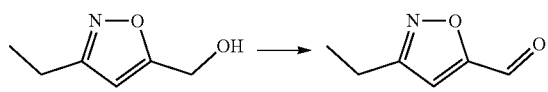

To a solution of (3-ethylisoxazol-5-yl)methanol (4.00 g, 31.5 mmol) in DCM (100 mL) was added DMP (16.01 g, 37.75 mmol) at 0° C. and the mixture was stirred at r.t. for 1 h (additional equivalents of oxidizing agent may be added to ensure complete oxidation of substrates containing multiple alcohol groups). The mixture was washed with sat. $Na_2S_2O_3$ (100 mL) and sat. $NaHCO_3$ (100 ML), dried over anhydrous $Na_2SO_4$ and concentrated to dryness. The residue was purified by flash chromatography on silica gel (20% EtOAc in PE) to give 3-ethylisoxazole-5-carbaldehyde (3.37 g, yield: 86%) as a yellow oil. LC/MS (ESI): m/z=126 [M+H]$^+$.

Synthesis of (1-ethyl-1H-pyrazol-4-yl)methanol

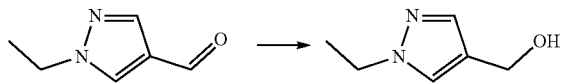

To a solution of 1-ethyl-1H-pyrazole-4-carbaldehyde (2.10 g, 16.9 mmol) in THF (10 mL) was added diisobutylaluminium hydride (13.5 mL, 20.3 mmol) at −78° C. (this protocol can be modified to enable full reduction of esters to alcohols by increasing the number of equivalents of reducing agent). The mixture was stirred −78° C. for 0.5 h, then warmed to 25° C. for 1 h. The reaction was quenched by sat. aq. $NH_4Cl$ (5 mL), then extracted with EtOAc (15 mL×3). The combined organic layers were washed with brine (15 mL) and dried over anhydrous $Na_2SO_4$, then concentrated. The residue was purified by flash chromatography (50→100% EtOAc in PE) to give (1-ethyl-1H-pyrazol-4-yl)methanol (480 mg, yield: 23%) as a light-yellow oil. LCMS (ESI) m/z: 127 [M+H]$^+$.

Synthesis of 4-(chloromethyl)-1-ethyl-1H-pyrazole

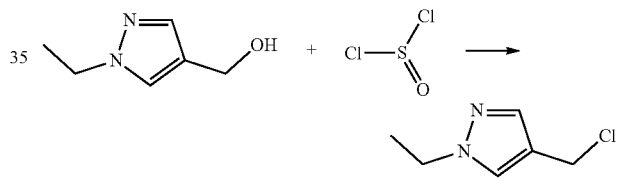

To a solution of (1-ethyl-1H-pyrazol-4-yl)methanol (1.40 g, 11.1 mmol) in DCM (15 mL) at 0° C. was added $SOCl_2$ (3.96 g, 33.3 mmol) dropwise under an $N_2$ atmosphere. After the addition, the mixture was stirred at 0° C. for 2 h. The mixture was concentrated to dryness to give crude 4-(chloromethyl)-1-ethyl-1H-pyrazole (1.60 g, 100% yield) as a yellow oil. LC/MS (ESI) m/z: 145 [M+H]$^+$.

The following intermediates were synthesized using a similar experimental protocol:

| 5-bromo-4-(chloromethyl)-1-ethyl-1H-pyrazole | |
|---|---|
| 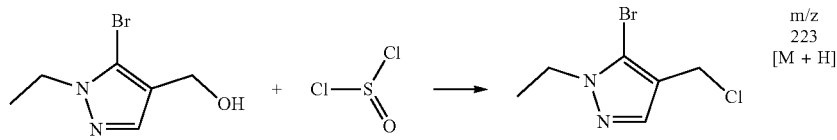 | m/z 223 [M + H] |
| 5-bromo-4-(chloromethyl)-1-(difluoromethyl)-1H-pyrazole | |
| 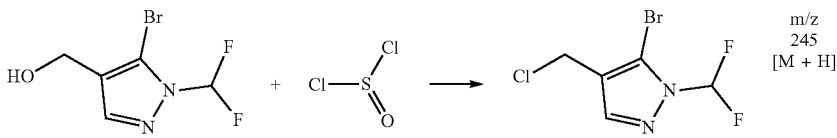 | m/z 245 [M + H] |

Synthesis of 5-(chloromethyl)-3-ethylisoxazole

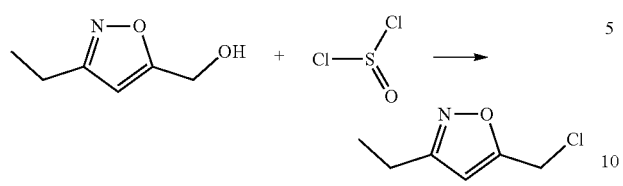

To a stirred solution of (3-ethyl-1,2-oxazol-5-yl)methanol (4.10 g, 32.3 mmol) in dry DCM (10 mL) was added triethylamine (5.8 mL, 42 mmol), followed by the addition of thionyl chloride (2.8 mL, 39 mmol) at 0° C. over a period of 10 min. After the addition, the reaction mixture was stirred at r.t. for 5.0 h under $N_2$. The reaction mixture was cooled to 0° C. and quenched with 10% aq. NaCl. The mixture was then extracted with DCM twice, and the combined extracts were washed with sat. aq. $NaHCO_3$, dried over anhydrous $Na_2SO_4$ and concentrated in vacuo. The residue was purified by column chromatography on silica gel (10→30% EA in PE) to give 5-(chloromethyl)-3-ethyl-1,2-oxazole (4.20 g, yield: 90%) as a yellow oil. LC/MS ESI (m/z): 146 $[M+H]^+$.

The following intermediates were synthesized using a similar experimental protocol:

| 5-(chloromethyl)-3-cyclobutylisoxazole |
|---|
| 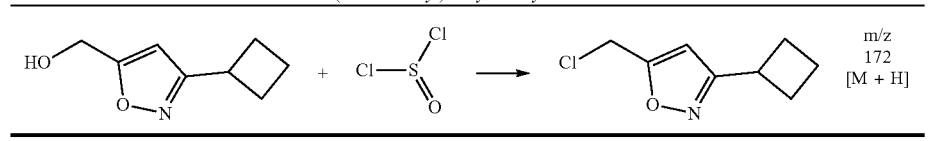 |

Synthesis of 5-bromo-2-methylthiazole-4-carbaldehyde

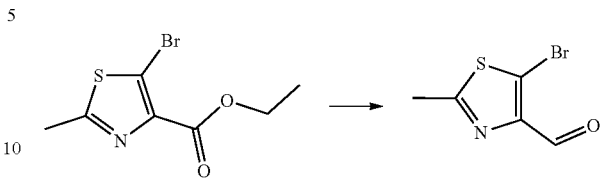

To a solution of ethyl 5-bromo-2-methylthiazole-4-carboxylate (4.13 g, 16.5 mmol) in THF (120 mL) was added diisobutylaluminium hydride (16.5 mL, 24.8 mmol, 1.5 M in THF) dropwise at −78° C. The mixture was stirred at −78° C. for 3 h. After 3 h, the reaction mixture was sequentially diluted with EA (50 mL), water (1.0 mL), aq. NaOH solution (15%, 1.0 mL), and then water (10 mL) at 0° C. After warming to r.t., the mixture was stirred for 15 min. Anhydrous $MgSO_4$ was added, stirring was continued for 15 min, and then the mixture was filtered to remove solids. The filtrate was concentrated in vacuo to give crude 5-bromo-2-methylthiazole-4-carbaldehyde (2.59 g, 76%) as a yellow solid. LC/MS ESI (m/z): 206 $[M+H]^+$.

Synthesis of 5-(bromomethyl)isoxazole-3-carbonitrile

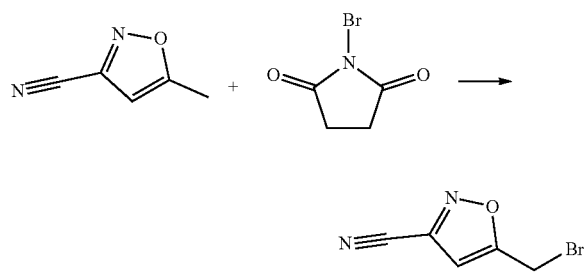

To a solution of 5-methylisoxazole-3-carbonitrile (3.0 g, 28 mmol) and NBS (3.2 g, 56 mmol) in DCE (120 mL) was added AIBN (230 mg, 1.40 mmol) under $N_2$ at 25° C. Then the resulting solution was heated to 80° C. and stirred for 16 h. After cooling to r.t., the reaction mixture was diluted with DCM, washed with sat. $NaHCO_3$ solution and brine, dried over anhydrous $Na_2SO_4$, filtered and concentrated. The residue was purified by column chromatography on silica gel (10% EtOAc in PE) to give 5-(bromomethyl)isoxazole-3-carbonitrile as a yellow oil (2.2 g, yield: 42%). LC/MS ESI (m/z): 187 $[M+H]^+$.

Synthesis of 5-bromo-3-chloro-1-ethyl-1H-pyrazole

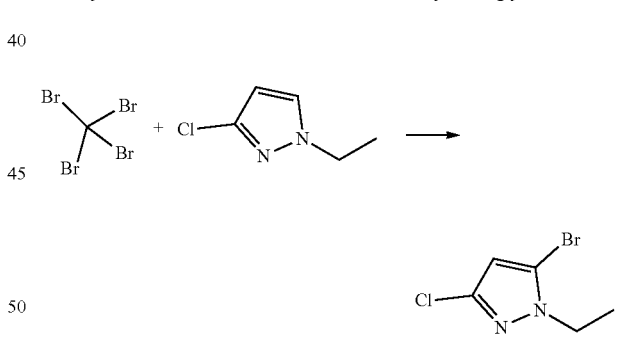

To a solution of 3-chloro-1-ethyl-1H-pyrazole (3.00 g, 23.0 mmol) in THF (20 mL) was added n-BuLi (2.5 M in hexanes, 10.1 mL, 25.3 mmol) at −78° C. The mixture was stirred at −78° C. for 1 h. Then a solution of $CBr_4$ (7.6 g, 23 mmol) in THF (15 mL) was added dropwise. The mixture was stirred at −78° C. for 1 h, then quenched with water (10 mL). The mixture was extracted with EA (20 mL) for three times. The organic layer was combined, dried over $Na_2SO_4$, concentrated under reduced pressure. The residue was purified by flash chromatography eluting with EA in PE (0→10%) to give 5-bromo-3-chloro-1-ethyl-1H-pyrazole (3.5 g, 73%) as a pale-yellow oil. LC/MS (ESI): m/z=209 $[M+H]^+$.

The following intermediates were synthesized using a similar experimental protocol:

| 5-bromo-1-(cyclopropylmethyl)-3-methyl-1H-pyrazole |
|---|
| 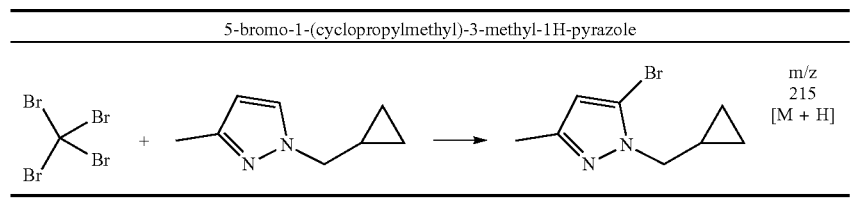 m/z 215 [M + H] |

Synthesis of 5-iodo-2-methyl-2H-1,2,3-triazole-4-carbaldehyde

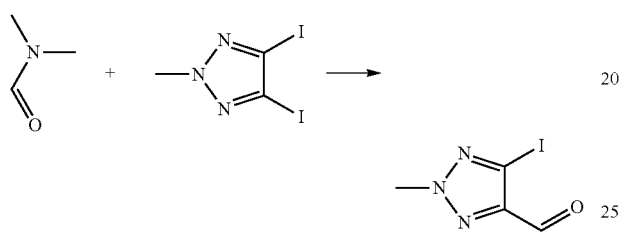

To a solution of 4,5-diiodo-2-methyl-2H-1,2,3-triazole (2.5 g, 7.4 mmol) in THF (30 mL) was added n-butyllithium (2.5 M in hexane, 3.2 mL, 8.2 mmol) and stirred at −78° C. for 1 h. Then DMF (0.57 mL, 7.4 mmol) was added to the mixture and stirred at −78° C. for 1 h. The mixture was quenched with sat. aq. NH₄Cl (30 mL) at 0° C. and extracted with EA (100 mL×3). The combined organic layers were combined, dried over anhydrous Na₂SO₄, filtered, and concentrated in vacuo. The residue was purified by column chromatography on silica gel (PE:EA=3:1, V/V) to give 5-iodo-2-methyl-2H-1,2,3-triazole-4-carbaldehyde (1.15 g, 65%) as a light-yellow solid. LC/MS (ESI) m/z: 238 [M+H]⁺.

Synthesis of (5-iodo-1-methyl-1H-pyrazol-4-yl)methanol

To a mixture of 5-iodo-1-methyl-1H-pyrazole-4-carbaldehyde (2.00 g, 8.47 mmol) in MeOH (30 mL) was added NaBH₄ (84 mg, 2.5 mmol) at −10° C. The mixture was stirred at 20° C. for 1 h. The mixture was quenched with sat. NH₄Cl (10 mL) and extracted with EA (60 mL×3). The combined organic layers were dried over anhydrous Na₂SO₄, filtered and concentrated. The residue was purified by column chromatography on silica gel (5% MeOH in DCM) to afford (5-iodo-1-methyl-1H-pyrazol-4-yl)methanol as a light-yellow solid (840 mg, yield: 41%). LC/MS ESI (m/z): 239 [M+H]⁺.

The following intermediates were synthesized using a similar experimental protocol:

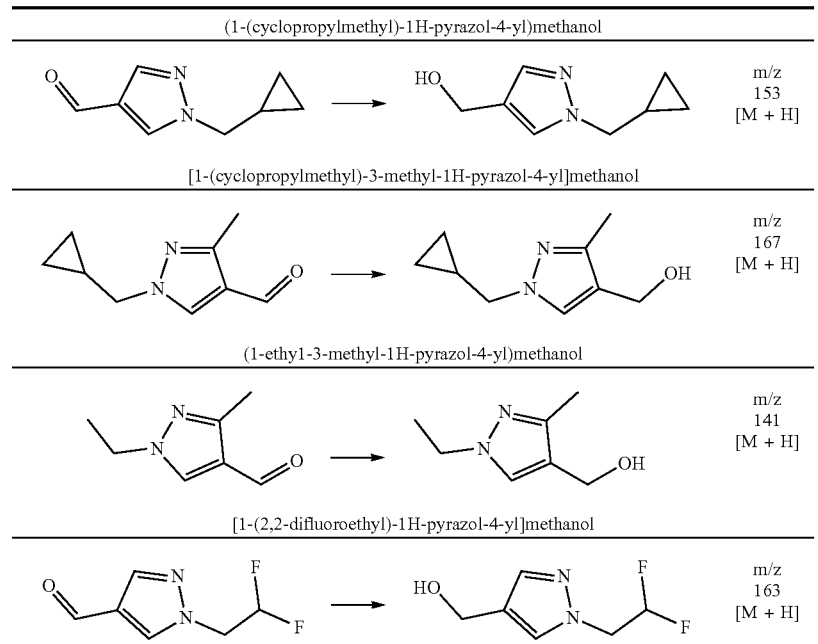

| (1-(ethyl-d5)-1H-pyrazol-4-yl)methanol |
|---|
| 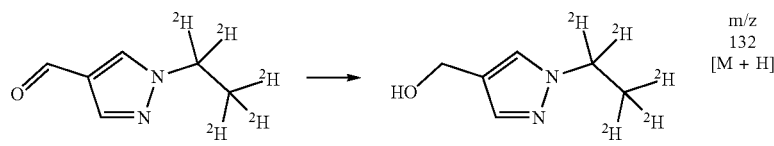 m/z 132 [M + H] |

Synthesis of (3-iodo-1-methyl-1H-pyrazol-4-yl)methanol

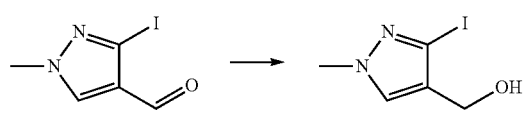

To a solution of 3-iodo-1-methyl-1H-pyrazole-4-carbaldehyde (2.00 g, 8.47 mmol) in dry THF (20 mL) was added DIBAL-H (1.0 M in toluene, 12 mL, 12 mmol) dropwise at −70° C. (additional equivalents of reducing agent may be utilized in cases where more than one hydride transfer is required). The mixture was stirred at −70° C. for 2 h before quenching with sat. aq. NH$_4$Cl. The resulting mixture was filtered, and the filter cake was washed with THF. The combined filtrates were concentrated under reduced pressure; the residue was diluted with DCM, washed with water and brine, dried over anhydrous Na$_2$SO$_4$ and concentrated. The residue was purified by column chromatography on silica gel (0→20% of EA in PE) to give (3-iodo-1-methyl-1H-pyrazol-4-yl)methanol (1.6 g, 79% yield) as a yellow oil. LC/MS ESI (m/z): 239 [M+H]$^+$.

The following intermediates were synthesized using a similar experimental protocol:

| (1-ethyl-3-methoxy-1H-pyrazol-4-yl)methanol |
|---|
| 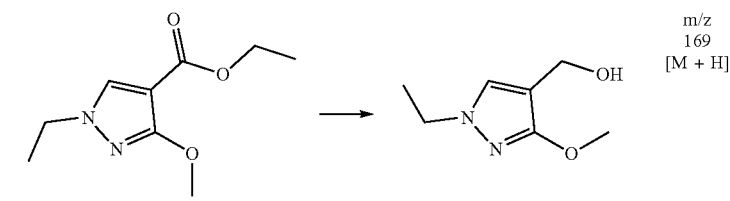 m/z 169 [M + H] |

Synthesis of (5-iodo-2-methyl-2H-1,2,3-triazol-4-yl)methanol

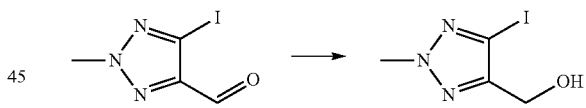

A mixture of 5-iodo-2-methyl-2H-1,2,3-triazole-4-carbaldehyde (1.05 g, 4.40 mmol) in MeOH (5 mL) was added NaBH$_4$ (0.15 g, 4.4 mmol) and stirred at 0° C. for 1 h. The mixture was quenched with sat. aq. NH$_4$Cl solution (30 mL) at 0° C. and extracted with EA (50 mL×3). The combined organic layers were dried over anhydrous Na$_2$SO$_4$, filtered, and concentrated in vacuo. The residue was purified by flash chromatography (PE:EA=1:1, V/V) to give (5-iodo-2-methyl-2H-1,2,3-triazol-4-yl)methanol (960 mg, 91%) as a light-yellow solid. LC/MS (ESI) m/z: 240 [M+H]$^+$.

The following intermediates were synthesized using a similar experimental protocol:

| (1-isobutyl-3-methyl-1H-pyrazol-4-yl)methanol |
|---|
| 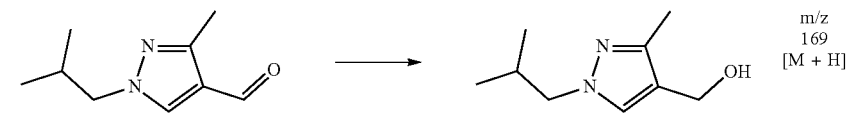 m/z 169 [M + H] |

Synthesis of 4-(chloromethyl)-3-iodo-1-methyl-1H-pyrazole

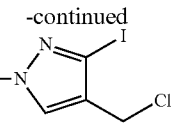

To a solution of (3-iodo-1-methyl-1H-pyrazol-4-yl)methanol (1.00 g, 4.20 mmol) in DCM (20 mL) was added thionyl chloride (0.90 mL, 13 mmol) at 0° C. After addition, the mixture was stirred at r.t. for 3 h, and then concentrated to give crude 4-(chloromethyl)-3-iodo-1-methyl-H-pyrazole (1.0 g, 93%) as a yellow oil. LCMS (ESI): m/z=257 [M+H]z.

The following intermediates were synthesized using a similar experimental protocol:

4-(chloromethyl)-1-(cyclopropylmethyl)-1H-pyrazole

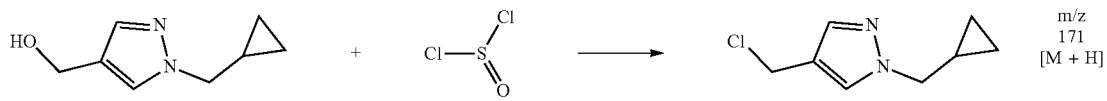

m/z 171 [M + H]

4-(chloromethyl)-1-(cyclopropylmethyl)-3-methyl-1H-pyrazole

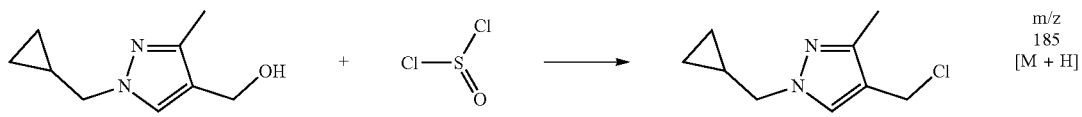

m/z 185 [M + H]

4-(chloromethyl)-1-ethyl-3-methoxy-1H-pyrazole

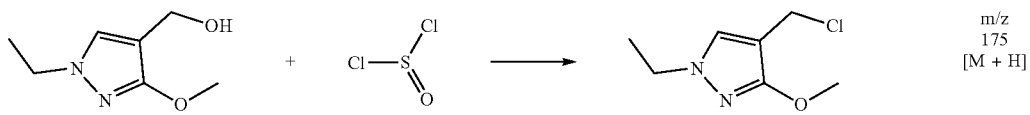

m/z 175 [M + H]

5-bromo-4-(chloromethyl)-1-cyclobutyl-1H-pyrazole

m/z 249 [M + H]

4-(chloromethyl)-1-ethyl-3-methyl-1H-pyrazole

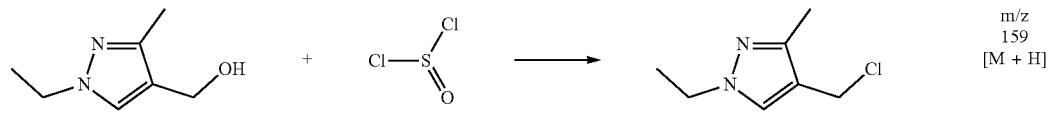

m/z 159 [M + H]

4-(chloromethyl)-1-(2,2-difluoroethyl)-1H-pyrazole

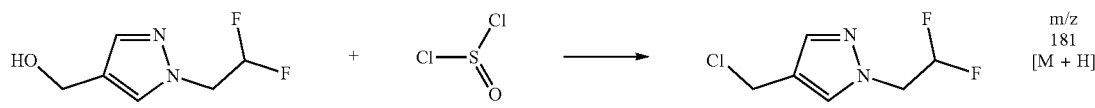

m/z 181 [M + H]

5-(chloromethyl)-3-(cyclopropylmethyl)isoxazole

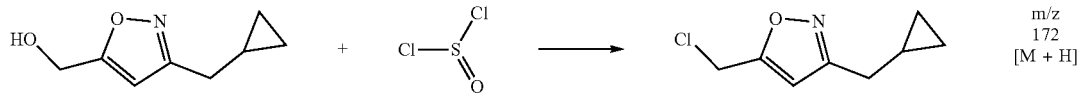

m/z 172 [M + H]

4-(chloromethyl)-1-(2-fluoroethyl)-1H-pyrazole

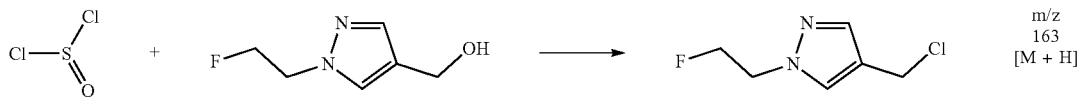

m/z 163 [M + H]

Synthesis of 5-bromo-1-ethyl-4-iodo-1H-pyrazole

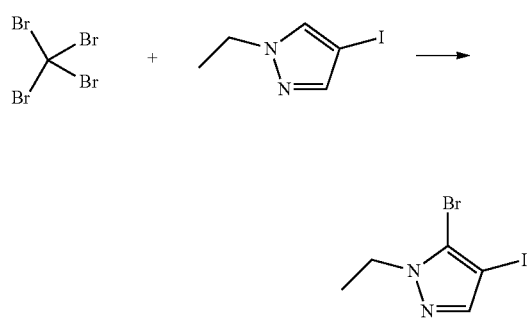

To a solution of 1-ethyl-4-iodo-1H-pyrazole (105.0 g, 425.6 mmol) in THF (900 mL) at −78° C. was added LDA (2.0 M in heptane/THF/ethylbenzene, 212.8 mL, 425.6 mmol) dropwise under a N₂ atmosphere over 1 h. After the addition, the mixture was stirred at −78° C. for 0.5 h, and then a solution of tetrabromomethane (148.0 g, 445.0 mmol) in THF (50 mL) was added dropwise over 0.5 h. The resulting mixture was stirred at −78° C. for an additional 1 h. The reaction flask was transferred to an ice bath, and the mixture was quenched with sat. NH₄Cl aq. solution (200 mL). The aq. phase was extracted with DCM twice (250 mL×2). The combined organic layers were washed with brine, dried over anhydrous Na₂SO₄, filtered and concentrated. The residue was purified by column chromatography on silica gel (2% EtOAc in PE) to give the target product as a brown solid (90 g, yield: 70%). LC/MS ESI (m/z): 301 [M+H]⁺.

The following intermediates were synthesized using a similar experimental protocol:

5-bromo-1-cyclobutyl-4-iodo-1H-pyrazole

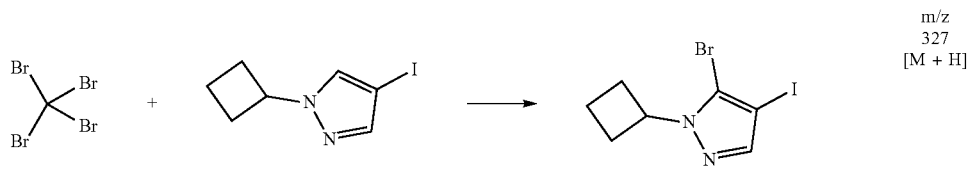

m/z 327 [M + H]

5-bromo-1-cyclopropyl-4-iodo-1H-pyrazole

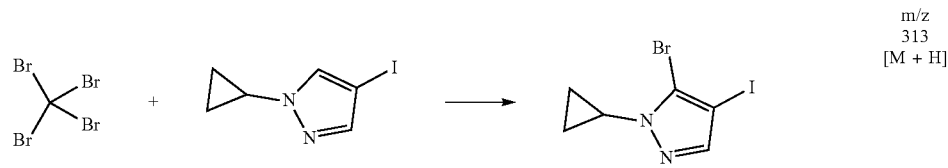

m/z 313 [M + H]

4-chloro-1-((1-ethyl-1H-pyrazol-4-yl)methyl)-5-iodo-1H-pyrazole

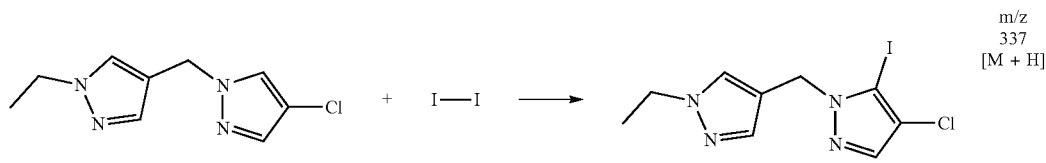

m/z 337 [M + H]

Synthesis of 2-ethyl-4,5-diiodo-2H-1,2,3-triazole

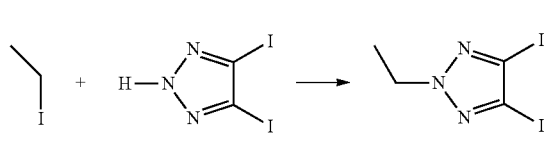

To a solution of 4,5-diiodo-2H-1,2,3-triazole (50 mg, 0.18 mmol) in THF (5 mL) was added NaH (14 mg, 0.36 mmol, 60% in mineral oil) at 0° C. Then iodoethane (2.94 g, 0.890 mmol) was added and the mixture was stirred at 25° C. for 16 h. The reaction was quenched by H$_2$O (5 mL) at 0° C., then extracted with EtOAc (15 mL×3). The combined organic layers were washed with brine (15 mL), dried over anhydrous Na$_2$SO$_4$, then concentrated. The residue was purified by flash chromatography (silica gel, 0→25% EtOAc in PE) to give 2-ethyl-4,5-diiodo-2H-1,2,3-triazole (1.47 g, yield: 68%) as a white solid. LC/MS (ESI) m/z: 350 [M+H]$^+$.

Synthesis of 1-(cyclopropylmethyl)-3-methyl-1H-pyrazole

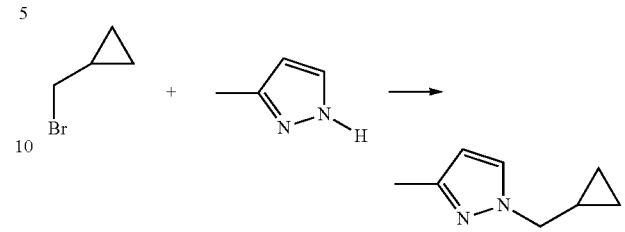

A mixture of 3-methyl-1H-pyrazole (5.90 mL, 73.1 mmol), (bromomethyl)cyclopropane (7.90 mL, 80.4 mmol) and K$_2$CO$_3$ (20.20 g, 146.2 mmol) in DMF (100 mL) was stirred at 80° C. for 16 h. The reaction mixture was added water and extracted with EtOAc. The organic layer was washed with brine, dried over anhydrous Na$_2$SO$_4$ and concentrated in vacuo. The residue was purified by flash column chromatography to afford 1-(cyclopropylmethyl)-3-methyl-1H-pyrazole (6.00 g, 60%) as a yellow solid. LC/MS (ESI) m/z: 137 [M+H]$^+$.

The following intermediates were synthesized using a similar experimental protocol:

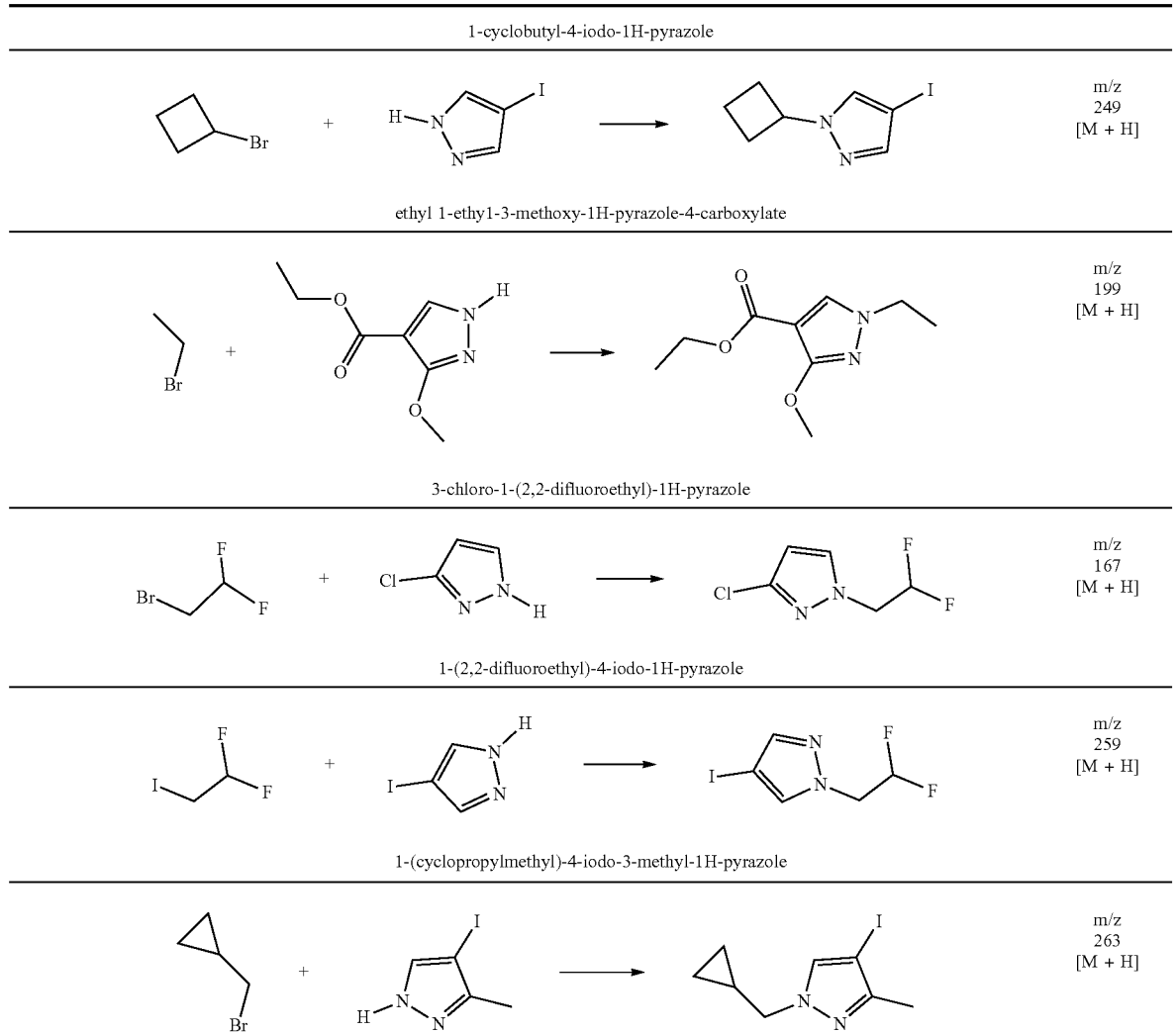

| methyl 1-(2-fluoroethyl)-1H-pyrazole-4-carboxylate |
|---|
| 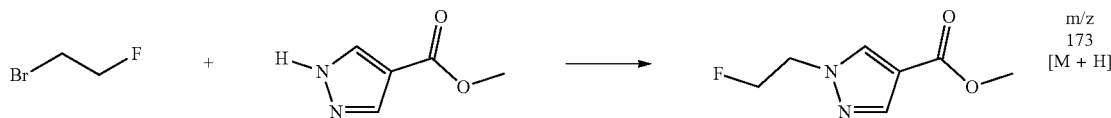 m/z 173 [M + H] |

| 1-((3-chloropyrazin-2-yl)methyl)-1H-pyrazole-4-carbonitrile |
|---|
| 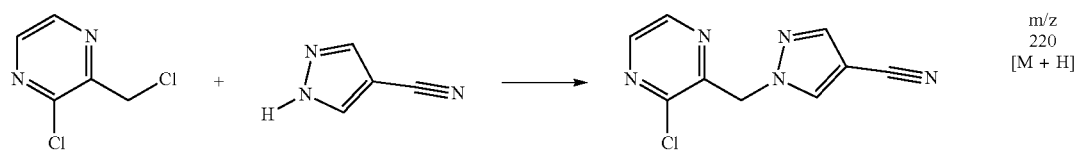 m/z 220 [M + H] |

Synthesis of 5-bromo-1-ethyl-1H-pyrazole-4-carbaldehyde

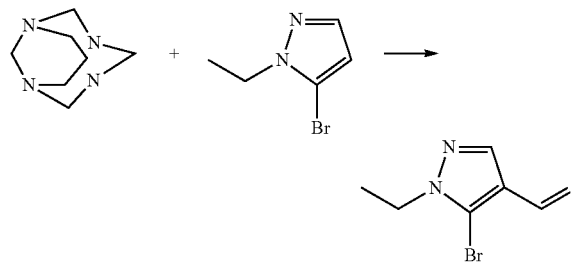

To a solution of 5-bromo-1-ethyl-11H-pyrazole (100 g, 571 mmol) in TFA (700 mL) at 0° C. was added 1,3,5,7-tetraazaadamantane (120 g, 857 mmol). The resulting mixture was stirred at 90° C. for 16 h. After cooling to r.t., the mixture was concentrated under reduced pressure to remove most of the TFA. The residue was diluted with DCM (600 mL), washed with sat. $NaHCO_3$ and brine, dried over anhydrous $Na_2SO_4$, filtered and concentrated. The residue was purified by column chromatography on silica gel (10% EtOAc in PE) to give 5-bromo-1-ethyl-1H-pyrazole-4-carbaldehyde as a white solid (60 g, yield: 52%). LC/MS ESI (m/z): 203 [M+H]$^+$.

The following intermediates were synthesized using a similar experimental protocol:

| 5-chloro-3-iodo-(1-methyl-1H-pyrazole-4-carbaldehyde) |
|---|
| 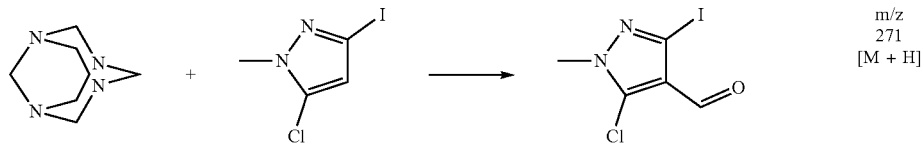 m/z 271 [M + H] |

| 5-bromo-1-(cyclopropylmethyl)-3-methyl-1H-pyrazole-4-carbaldehyde |
|---|
| 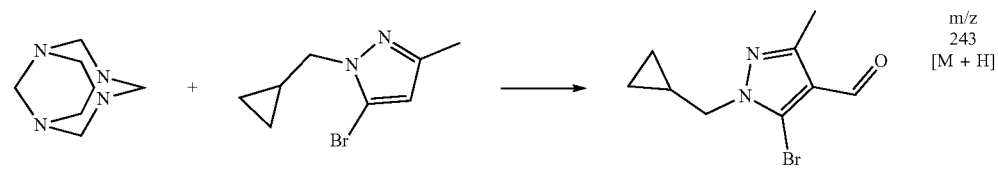 m/z 243 [M + H] |

| 5-bromo-3-chloro-1-ethyl-1H-pyrazole-4-carbaldehyde |
|---|
| 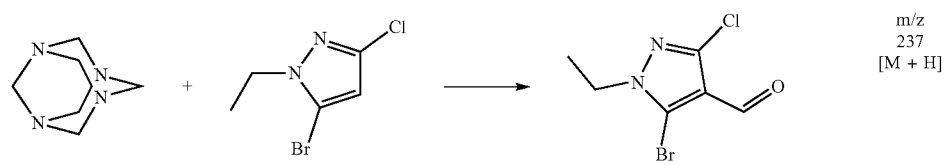 m/z 237 [M + H] |

-continued

| 3-chloro-1-(2,2-difluoroethyl)-1H-pyrazole-4-carbaldehyde |
|---|

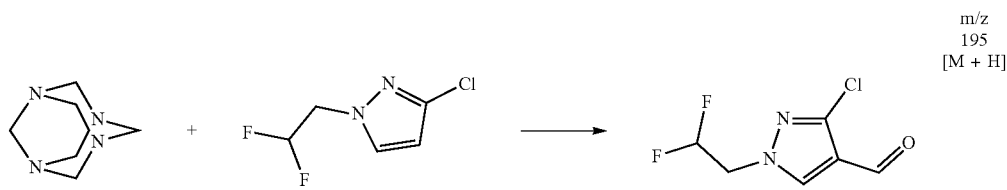

m/z 195 [M + H]

| 1-ethyl-3-(trifluoromethyl)-1H-pyrazole-4-carbaldehyde |
|---|

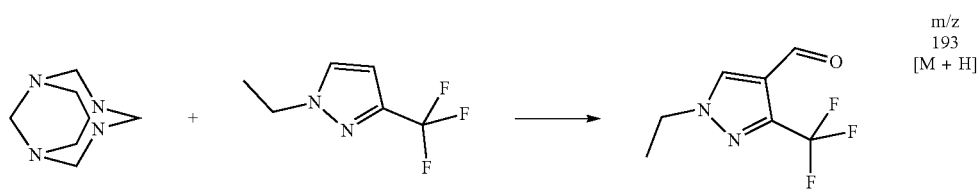

m/z 193 [M + H]

Synthesis of 1-(5-bromo-1,3-thiazol-4-yl)prop-2-yn-1-ol

To a solution of 5-bromo-1,3-thiazole-4-carbaldehyde (1.80 g, 9.37 mmol) in THF (20 mL) was added ethynylmagnesium bromide (28.1 mL, 14.1 mmol). The mixture was stirred at r.t. overnight and then quenched with water. The mixture was twice extracted with EA (100 mL). The combined organic layers were concentrated under reduced pressure. The residue was purified by flash column chromatography on silica gel eluting with EA in PE (0→30%) to give 1-(5-bromo-1,3-thiazol-4-yl)prop-2-yn-1-ol (1.50 g, 73%) as a colorless oil. LC/MS (ESI): m/z=218 [M+H]⁺.

The following intermediates were synthesized using a similar experimental protocol:

| 1-(2-bromo-4-fluorophenyl)prop-2-yn-1-ol |
|---|

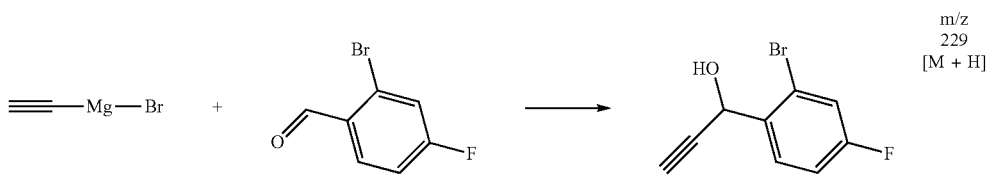

m/z 229 [M + H]

| 1-(5-iodo-2-methyl-2H-1,2,3-triazol-4-yl)prop-2-yn-1-ol |
|---|

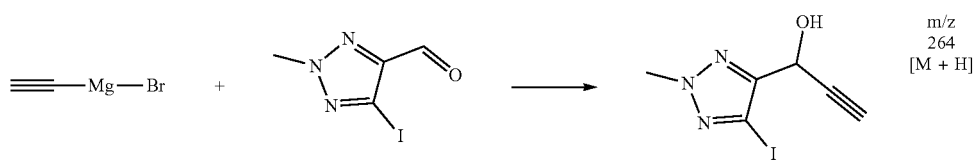

m/z 264 [M + H]

Synthesis of (4-bromo-3-ethylisothiazol-5-yl)methanol

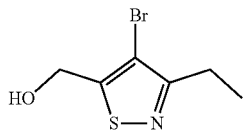

To a stirred mixture of 5-((tetrahydro-2H-pyran-2-yl)oxy)pent-3-yn-2-one (5.00 g, 25.5 mmol) and (aminooxy)sulfonic acid (3.20 g, 25.1 mmol) in H$_2$O (100 mL) at 0° C. The resulting mixture was stirred at ambient temperature for 4 h. And then was added NaHCO$_3$ (2.40 g, 28.1 mmol) and sodium hydrosulfide (2.20 g, 38.3 mmol). The resulting mixture was stirred at 80° C. for 16 h. The filtrate was extracted with ethyl acetate and washed with brine, dried over Na$_2$SO$_4$ and concentrated under vacuum. The residue was purified by flash chromatography on silica gel (0→20% ethyl acetate in petroleum ether) to afford (3-ethylisothiazol-5-yl)methanol (1.46 g, 40% yield) as a yellow oil.

A mixture of (3-ethylisothiazol-5-yl)methanol (1.80 g, 12.6 mmol), dibromine (7.00 g, 44.1 mmol) and potassium acetate (1.96 g, 20.0 mmol) in AcOH (40 mL) was stirred at ambient temperature for 16 h. The resulting mixture was quenched with Na$_2$S$_2$O$_3$. The solution was basified with NaHCO$_3$ and extracted with DCM, dried over Na$_2$SO$_4$ and concentrated under vacuum. The residue was purified by flash phase chromatography on silica gel (0→15% ethyl acetate in petroleum ether) to afford (4-bromo-3-ethylisothiazol-5-yl)methanol (2.04 g, 73% yield) as a yellow oil. LC-MS (ESI) m/z: 222 [M+H]$^+$.

Synthesis of 4-fluoro-2-iodobenzonitrile

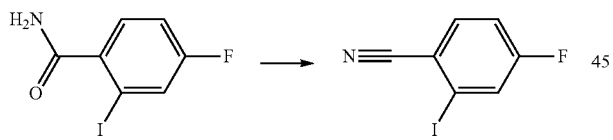

A mixture of 4-fluoro-2-iodobenzamide (4.00 g, 15.1 mmol) in thionyl chloride (30 mL) was stirred at 90° C. for 16 h. The mixture was concentrated to give crude 4-fluoro-2-iodobenzonitrile (2.40 g, 64% yield) as a yellow oil. LC/MS (ESI) m/z: 248 [M+H]$^+$.

The following intermediates were synthesized using a similar experimental protocol:

Synthesis of (4-fluoro-2-iodophenyl)hydrazine

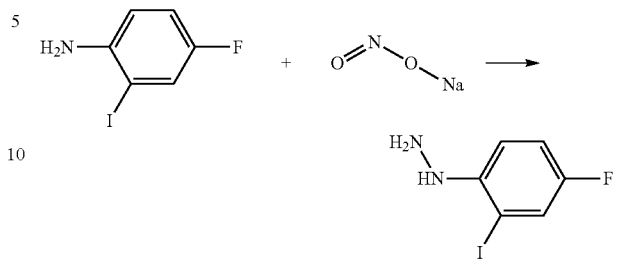

To a mechanically stirred solution of 4-fluoro-2-iodoaniline (5.0 g, 21 mmol) in AcOH (10 mL) was slowly added conc. HCl (40 mL). The solution quickly became a thick suspension. The reaction was then cooled to 0° C. in an ice bath and treated slowly dropwise with a solution of sodium nitrite (1.63 g, 23.6 mmol) in water (8 mL). The reaction was stirred for 1 h, then a solution of SnCl$_2$ (8.46 g, 44.5 mmol) in conc. HCl (8 mL) was added slowly. The reaction was allowed to warm to r.t. over 2 h. The suspension was filtered, washed with water and dried under vacuum to give crude (4-fluoro-2-iodophenyl)hydrazine hydrochloride (4.1 g, yield: 77%) as a gray solid. LC/MS (ESI) m/z: 253 [M+H]$^+$.

Synthesis of 5-bromo-4-(bromomethyl)-1-ethyl-1H-pyrazole

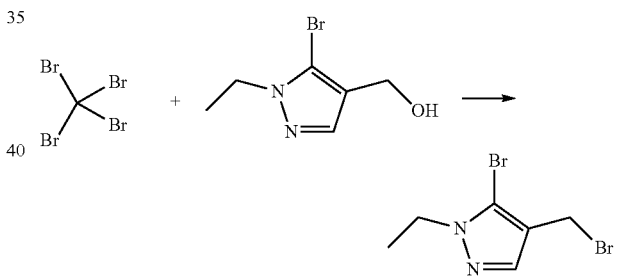

To a stirred solution of (5-bromo-1-ethyl-1H-pyrazol-4-yl)methanol (4.00 g, 19.5 mmol) and triphenylphosphine (6.14 g, 23.4 mmol) in dry DCM (50 mL) was added a solution of tetrabromomethane (7.76 g, 23.4 mmol) in DCM dropwise at 0° C. After the addition, the reaction mixture was stirred at r.t. for 24 h. The reaction mixture was concentrated in vacuo and the residue was purified by silica gel column chromatography (eluent: PE/EtOAc 50/1 to 10/1) to give 5-bromo-4-(bromomethyl)-1-ethyl-1H-pyrazole (3.0 g, 57% yield) as a white solid. LC/MS ESI (m/z): 267 [M+H]$^+$.

| 5-((5-iodo-2-methyl-2H-1,2,3-triazol-4-yl)methyl)isoxazole-3-carbonitrile | |
|---|---|
| 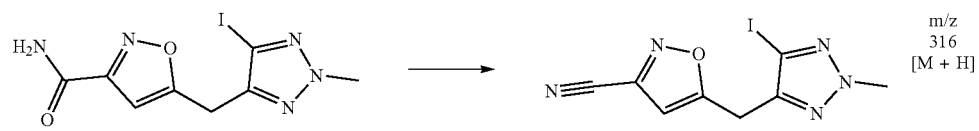 | m/z 316 [M + H] |

Synthesis of (3-cyano-1-methyl-1H-pyrazol-5-yl)boronic Acid

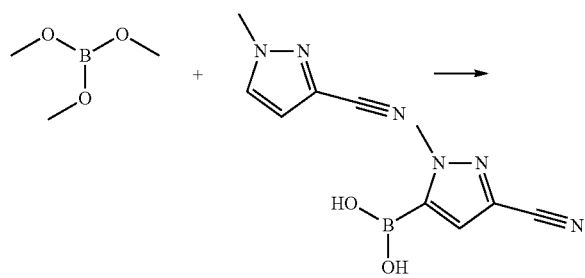

To a solution of 1-methyl-1H-pyrazole-3-carbonitrile (1.0 g, 9.3 mmol) in THF (15 mL) was added LDA (2 M in THF, 4.7 mL, 9.3 mmol) dropwise under the atmosphere of N₂ at −78° C. After stirring for 0.5 h at −78° C., trimethyl borate (1.9 g, 19 mmol) in THF (2 mL) was added dropwise. After stirring at −78° C. for 1 h, the reaction was quenched with sat. aq. ammonium chloride. The reaction was diluted with EtOAc and washed first with H₂O and then brine. The organic layer was dried over anhydrous Na₂SO₄, filtered, and concentrated under vacuum. The residue was purified by silica gel column chromatography (0→80% EtOAc in PE) to give (3-cyano-1-methyl-1H-pyrazol-5-yl)boronic acid (800 mg, 57% yield) as a yellow oil. LC/MS ESI (m/z): 152 [M+H]⁺.

Synthesis of 3-cyclobutyl-1,2-oxazole-5-carbaldehyde

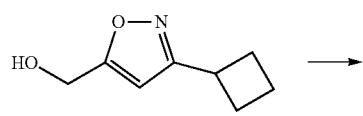

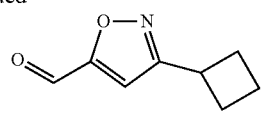

To a solution of (3-cyclobutyl-1,2-oxazol-5-yl)methanol (500 mg, 3.26 mmol) in DCM (100 mL) was added MnO₂ (2.80 g, 32.64 mmol). The mixture was stirred at r.t. overnight and then filtered. The filtrate was concentrated under reduced pressure and purified by flash column chromatography (silica gel eluting with 0→15% EA in PE) to give 3-cyclobutyl-1,2-oxazole-5-carbaldehyde (260 mg, 53%) as a colorless oil. LC/MS (ESI): m/z=152 [M+H]⁺.

The following intermediates were synthesized using a similar experimental protocol:

| 5-ethylisothiazole-3-carbaldehyde | |
|---|---|
| 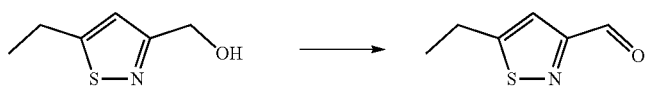 | m/z 142 [M + H] |

| 3-ethyl-1-methyl-1H-pyrazole-5-carbaldehyde | |
|---|---|
| 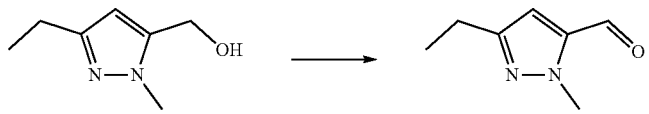 | m/z 139 [M + H] |

Synthesis of 3-(cyclopropylmethyl)isoxazole-5-carbaldehyde

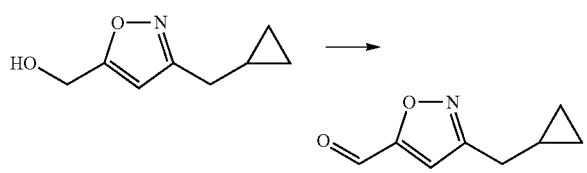

To a solution of [3-(cyclopropylmethyl)-1,2-oxazol-5-yl]methanol (1.10 g, 7.18 mmol) in DCM (10 mL) was added Dess-Martin periodinane (3.65 g, 8.62 mmol) at 0° C. After stirring at 0° C. for 2 h, the reaction mixture was diluted with sat. aq. Na₂CO₃ solution (20 mL) and DCM (10 mL). The organic layer was separated, washed with brine (10 mL), dried over anhydrous Na₂SO₄, filtered and concentrated in vacuo to give a residue, which was purified by column chromatography on silica gel (0→25% of EA in PE, V/V) to give 3-(cyclopropylmethyl)-1,2-oxazole-5-carbaldehyde (0.90 g, 83%) as a yellow oil. LC/MS ESI (m/z): 152 [M+H]+.

Synthesis of 2-(5-bromo-1-ethyl-1H-pyrazol-4-yl)acetonitrile

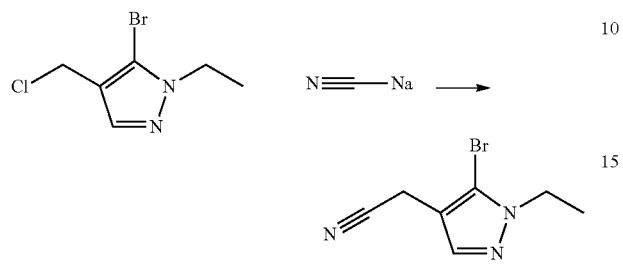

To a solution of 5-bromo-4-(chloromethyl)-1-ethyl-1H-pyrazole (5.00 g, 22.4 mmol) in DMSO (50 mL) was added NaCN (2.20 g, 44.7 mmol) at 25° C. After stirring at 25° C. for 2 h, the mixture was treated with EtOAc and H₂O. The organic layer was separated, washed with brine, dried over anhydrous Na₂SO₄, filtered, and concentrated. The residue was purified by column chromatography on silica gel (20% EtOAc in PE) to give 2-(5-bromo-1-ethyl-1H-pyrazol-4-yl)acetonitrile (4.5 g, yield: 94%) as a light-yellow oil. LC/MS ESI (m/z): 214 [M+H]+.

The following intermediates were synthesized using a similar experimental protocol:

2-(5-bromo-1-cyclobutyl-1H-pyrazol-4-yl)acetonitrile

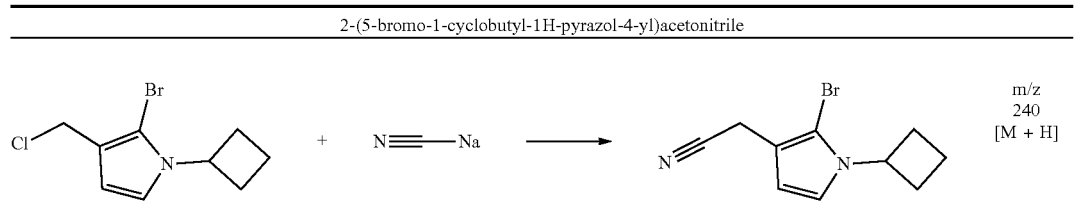

Synthesis of 1-(3-bromo-5-fluoropyridin-2-yl)ethan-1-one

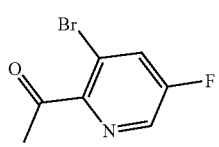

To a solution of 3-bromo-5-fluoropicolinic acid (4.80 g, 21.8 mmol) in DMF (20 mL) were added N,O-dimethylhydroxylamine hydrochloride (3.19 g, 32.7 mmol), HOBT (5.90 g, 43.6 mmol), EDCI (8.45 g, 43.6 mmol) and DIPEA (14.1 g, 109 mmol) at 0° C. The mixture was stirred for 12 h at room temperature. The mixture was filtered through celite to remove solids. The filtrate was concentrated under reduced pressure and the residue was purified by flash chromatography on silica gel (0→10% of EtOAc in PE) to give 3-bromo-5-fluoro-N-methoxy-N-methylpicolinamide (4.5 g, 78% yield) as a pale-yellow solid. LC/MS ESI (m/z): 263 [M+H]+.

To a solution of 3-bromo-5-fluoro-N-methoxy-N-methylpicolinamide (3.50 g, 13.3 mmol) in THF (5 mL) cooled to −20° C. was added methylmagnesium bromide (4.43 mL, 13.3 mmol, 3 M in THF). The mixture was stirred at −20° C. for 2 h and then quenched with ice water. The resulting mixture was extracted with EtOAc twice and the combined extracts were washed with brine, dried over anhydrous Na₂SO₄, filtered and concentrated. The residue was purified by flash chromatography on silica gel (0→30% of EtOAc in PE) to give 1-(3-bromo-5-fluoropyridin-2-yl)ethan-1-one (2.6 g, 90% yield) as a white solid. LC/MS ESI (m/z): 218 [M+H]+.

Synthesis of 5-(cyclopropylmethyl)-3-iodo-1-methyl-1H-pyrazole

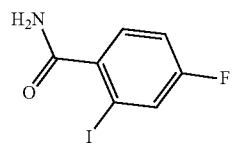 [SMILES: NC(=O)c1ccc(F)cc1I]

To a stirred solution of 3-iodo-1-methyl-1H-pyrazole-5-carbaldehyde (2.3 g, 9.7 mmol) in THF (40 mL) was added cyclopropylmagnesium bromide (0.5 M in hexane, 20.5 mL, 10.3 mmol) at 0° C. under N₂. The reaction was stirred at 0° C. for 1.5 h, then quenched with sat. NH₄Cl (5 mL) and concentrated to dryness. The residue was purified by flash chromatography (0→50% of EtOAc in PE) to get cyclopropyl(3-iodo-1-methyl-1H-pyrazol-5-yl)methanol (1.6 g, 19% yield) as a yellow solid. LC/MS (ESI) (m/z): 279 [M+H]+.

To a stirred solution of cyclopropyl(3-iodo-1-methyl-1H-pyrazol-5-yl)methanol (1.0 g, 3.6 mmol) in DCM (18 mL) was added TES (4.20 g, 36.0 mmol) and TFA (2.7 mL, 36 mmol) at 0° C. The reaction was stirred at r.t. overnight. The reaction was concentrated to dryness. The residue was purified by flash chromatography (0→10% EtOAc in PE) to give 5-(cyclopropylmethyl)-3-iodo-1-methyl-1H-pyrazole (0.60 g, 51% yield) as a yellow solid. LC/MS (ESI) (m/z): 263 [M+H]+.

Synthesis of 4-fluoro-2-iodobenzamide

To a solution of 4-fluoro-2-iodobenzoic acid (5.00 g, 18.8 mmol) in DCM (100 mL) was added oxalyl chloride (5.00 g, 39.4 mmol), followed by the addition of DMF (0.07 mL, 0.9 mmol) at 0° C. After the addition, the resulting mixture was stirred at 25° C. for 2 h. The mixture was concentrated in vacuo to dryness to give crude 4-fluoro-2-iodobenzoyl chloride as a yellow oil.

To a solution of 4-fluoro-2-iodobenzoyl chloride in dry DCM (50 mL) cooled to 0° C., was added a pre-cooled solution of aq. NH$_3$ (14 mL, 370 mmol, 28% in H$_2$O) dropwise over 10 min. The internal temperature was maintained below 5° C. during the addition. The resulting mixture was stirred at r.t. for 4 h and then concentrated to dryness. The residual white solids were triturated with water and PE, and then dried in a vacuum oven to give target product 4-fluoro-2-iodobenzamide (11 g, 92% yield over 2 steps) as a white solid. LC/MS (ESI): m/z=266 [M+H]$^+$.

Synthesis of 5-bromo-1-cyclopropyl-1H-pyrazole-4-carbaldehyde

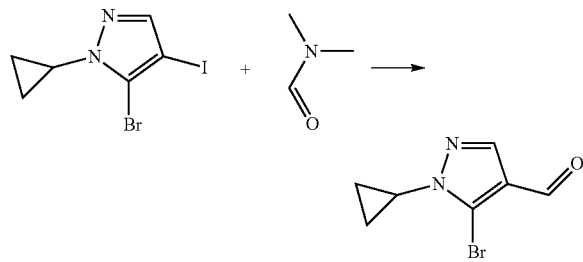

To a solution of 5-bromo-1-cyclopropyl-4-iodo-1H-pyrazole (2.5 g, 7.98 mmol) in THF (30 mL) at −78° C. was added i-PrMgCl (1.3 M in THF, 7.37 mL, 9.58 mmol) dropwise under N$_2$ atmosphere. After the addition, the mixture was stirred at 0° C. for 60 min, cooled back to −78° C., and then anhydrous DMF (0.80 mL, 10 mmol) was added. The resulting mixture was stirred at −78° C. for an additional 2 h. The mixture was quenched with sat. NH$_4$Cl solution, then extracted with DCM (200 mL×2). The organic layer was separated, washed with brine, dried over anhydrous Na$_2$SO$_4$, filtered and concentrated. The residue was purified by column chromatography on silica gel (PE:EA=2:1-1:1, V/V) to give the target product as a yellow oil (932 mg, yield: 54%). LC/MS ESI (m/z): 215 [M+H]$^+$.

Synthesis of Ethyl 5-ethylisothiazole-3-carboxylate

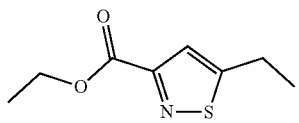

To a mixture of butan-2-one (10.0 g, 139 mmol) and diethyl oxalate (20.3 g, 139 mmol), was added sodium ethoxide (3.0 M in EtOH, 57.6 mL, 166 mmol) at 0° C., and the resulting mixture was stirred at r.t. overnight. Then the reaction mixture was quenched by adding sat. aq. NH$_4$Cl solution (50 mL), acidified by 1.0 M HCl to pH 3 and concentrated in vacuo to remove EtOH. The residue was extracted with EtOAc (3×20 mL). Then the combined organic layers were washed with sat. aq. NH$_4$Cl solution (20 mL) and brine (20 mL), dried over anhydrous Na$_2$SO$_4$, filtered and concentrated in vacuo. The residue was purified by flash chromatography with EtOAc in PE (0→75%, V/V) to give ethyl 2,4-dioxohexanoate (19.0 g, 80%) as an orange oil. LC/MS (ESI) (m/z): 173 [M+H]$^+$.

To a solution of ethyl 2,4-dioxohexanoate (3.00 g, 17.4 mmol) in toluene (30 mL) and acetic acid (3 mL) was added ammonium acetate (3.36 g, 43.6 mmol) at 0° C. Then the resulting mixture was stirred at 80° C. overnight. Then the reaction mixture was concentrated in vacuo to dryness. The residue was basified by adding sat. aq. NaHCO$_3$ solution to pH 7 and extracted with EtOAc (3×20 mL). Then the combined organic phases were washed with sat. aq. NaHCO$_3$ solution (20 mL) and brine (20 mL), dried over anhydrous Na$_2$SO$_4$, filtered and concentrated in vacuo. The residue was purified by flash column chromatography on silica gel with EtOAc in PE (0→30%, V/V) to give ethyl 4-amino-2-oxohex-3-enoate (19.0 g, 80%) as a yellow solid. The product was a mixture of (Z)- and (E)-olefins. LC/MS (ESI) (m/z): 172 [M+H]$^+$.

To a solution of ethyl 4-amino-2-oxohex-3-enoate (1.30 g, 7.59 mmol) in THF (15 mL), was added phosphorus pentasulfide (0.84 g, 7.6 mmol) at r.t. and the resulting mixture was stirred at r.t. overnight. After overnight, the reaction mixture was concentrated in vacuo to dryness. The residue was dissolved in EtOAc (50 mL), then aq. 30% H$_2$O$_2$ (6 mL) was added at 0° C. and stirred at 0° C. for 10 min. After 10 min, the reaction mixture was extracted with EtOAc (3×20 mL). Then the combined organic phases were washed with sat. aq. NH$_4$Cl solution (20 mL) and brine (20 mL), dried over anhydrous Na$_2$SO$_4$, filtered and concentrated in vacuo. The residue was purified by flash column chromatography on silica with EtOAc in PE (0→30%, V/V) to give ethyl 5-ethylisothiazole-3-carboxylate (0.72 g, 51%) as a yellow oil. LC/MS (ESI) (m/z): 186 [M+H]$^+$.

Synthesis of 5-bromo-1-cyclobutyl-1H-pyrazole-4-carbaldehyde

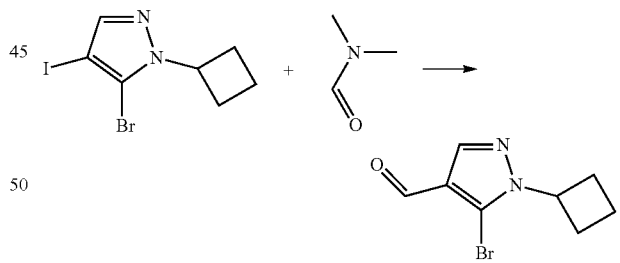

To a solution of 5-bromo-1-cyclobutyl-4-iodo-1H-pyrazole (11.0 g, 33.6 mmol) in THF (60 mL) was added i-PrMgCl.LiCl (1.3 M in THF, 31.0 mL, 40.4 mmol) at −5° C. to −10° C. After stirring at −10° C. for 15 min, anhydrous DMF (3.38 mL, 43.7 mmol) was added. The solution was stirred at −10° C. for 30 min, then slowly poured into stirred ice-water. The mixture was extracted with ethyl acetate (100 mL×2), then washed with brine (50 mL×2), dried over anhydrous Na$_2$SO$_4$ and concentrated. The residue was purified by flash chromatography (silica gel, 0-10% ethyl acetate in petroleum ether) to afford 5-bromo-1-cyclobutyl-1H-pyrazole-4-carbaldehyde (6.0 g, 78%) as a yellow solid. LC/MS ESI (m/z): 229 [M+H]$^+$.

Synthesis of 4-(azidomethyl)-5-bromo-1-ethyl-1H-pyrazole

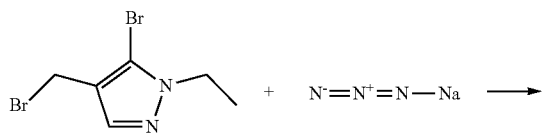

for 14 h. Then, the reaction mixture was added dropwise to ice-water (150 mL) and basified to pH 8 with chilled aq. 1 N NaOH solution. The resulting solution was concentrated in vacuo to dryness by oil pump. The residue was suspended in DCM (188 mL) and MeOH (12 mL) and the solids were removed by filtration. The filtrate was concentrated in vacuo to give 2-(5-bromo-1-ethyl-1H-pyrazol-4-yl)acetamide (4.1 g, 95%) as a white solid. LC/MS (ESI): m/z=232 [M+H]$^+$ The following intermediates were synthesized using a similar experimental protocol:

2-(5-bromo-1-cyclobutyl-1H-pyrazol-4-yl)acetamide

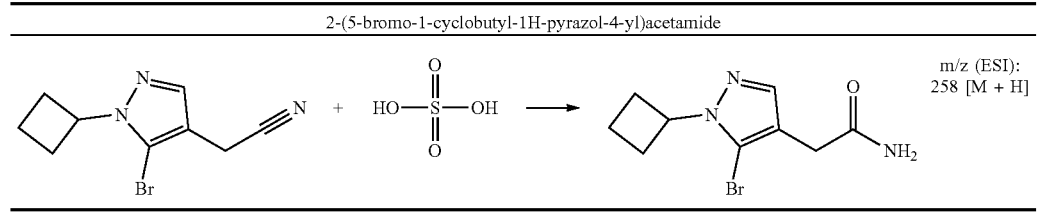

m/z (ESI): 258 [M + H]

-continued

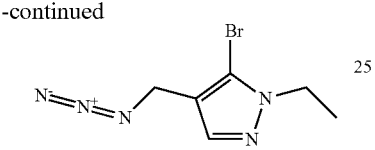

To a solution of 5-bromo-4-(bromomethyl)-1-ethyl-1H-pyrazole (1.0 g, 3.7 mmol) in DMF (50 mL) was added NaN$_3$ (728 mg, 89.5 mmol) at 0° C. The mixture was stirred at 0° C. for 0.5 h. The reaction mixture was diluted with EtOAc and washed with brine twice. The final organic layer was dried over anhydrous Na$_2$SO$_4$, filtered and concentrated. The residue was purified by column chromatography on silica gel (20% EtOAc in PE) to give 4-(azidomethyl)-5-bromo-1-ethyl-1H-pyrazole as a yellow oil (750 mg, yield: 87%). LC/MS (ESI) m/z: 230 [M+H]$^+$

Synthesis of 2-(5-bromo-1-ethyl-1H-pyrazol-4-yl)acetamide

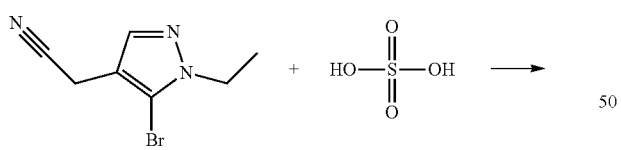

2-(5-bromo-1-ethyl-1H-pyrazol-4-yl)acetonitrile (4.00 g, 18.7 mmol) was added to conc. H$_2$SO$_4$ (12 mL) at 0° C. After the addition, the mixture was warmed to r.t. and stirred

Synthesis of methyl 3-bromo-5-fluoropicolinate

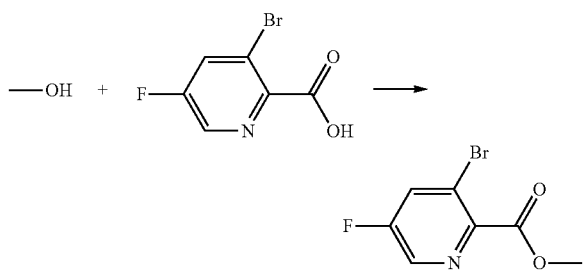

To a solution of 3-bromo-5-fluoropyridine-2-carboxylic acid (1.0 g, 4.5 mmol) and MeOH (30 mL) at 0° C. was added SOCl$_2$ (1.7 mL, 23 mmol) dropwise under N$_2$ atmosphere. After the addition, the mixture was stirred at 0° C. for 2 h. The mixture was quenched with ice-water, then extracted with DCM (40 mL×2). The combined organic layers were washed with brine, dried over anhydrous Na$_2$SO$_4$, filtered and concentrated. The residue was purified by column chromatography on silica gel (PE:EA=5:1) to give methyl 3-bromo-5-fluoropicolinate as a pale-yellow solid (1.0 g, yield: 94%). LC/MS ESI (m/z): 234 [M+H]$^+$.

Synthesis of 3-bromo-5-fluoro-2-(trimethylstannyl)pyridine

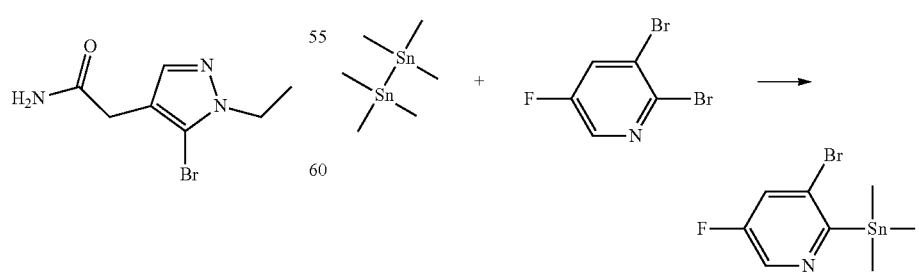

A mixture of 2,3-dibromo-5-fluoropyridine (1.0 g, 3.9 mmol), hexamethyldistannane (1.35 g, 4.12 mmol) and Pd(PPh$_3$)$_4$ (0.23 g, 0.20 mmol) in toluene (50 mL) was heated to 110° C. under N$_2$ for 16 h. The mixture was concentrated, diluted with EtOAc (50 mL), washed with brine (30 mL), dried over anhydrous Na$_2$SO$_4$ and concentrated. The residue was purified by neutral Al$_2$O$_3$ chromatography (100% petroleum ether) to afford 3-bromo-5-fluoro-2-(trimethylstannyl)pyridine (1.2 g, 90% yield) as a colorless oil. LC/MS (ESI) m/z: 340 [M+H]$^+$.

Synthesis of
(3-ethyl-1-methyl-1H-pyrazol-5-yl)methanol

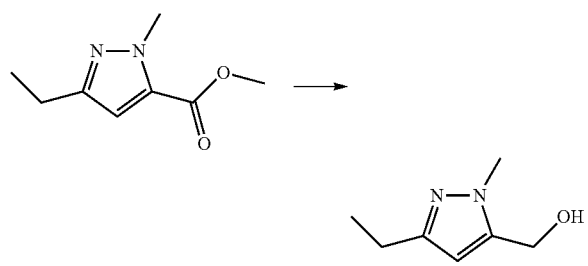

To a solution of methyl 3-ethyl-1-methyl-1H-pyrazole-5-carboxylate (3.10 g, 18.4 mmol) in THF (60 mL) was added DIBAL-H (46.1 mL, 46.1 mmol, 1.0 M in toluene) at −78° C. over 30 min. During the addition, the internal temperature was monitored to stay below −60° C. The reaction was stirred for 1 h in a dry ice/acetone bath and then 1 h in an ice bath. The mixture was cooled back to −78° C., and excess EtOAc was slowly added. A separate three-neck flask equipped with a mechanical stirrer was charged with a sat. aq. solution of HCl (1M). The organic solution was slowly poured with stirring into the HCl solution, and the mixture was stirred at r.t. for 1 h. The layers of the biphasic mixture were separated, and the aq. layer was washed with EtOAc. The combined organics were washed with brine, dried over MgSO$_4$, filtered, and concentrated in vacuo. The resulting material was purified by silica gel column chromatography (50% EtOAc in PE) to give (3-ethyl-1-methyl-1H-pyrazol-5-yl)methanol (2.2 g, 85%) as a colorless oil. LC/MS ESI (m/z): 141 [M+H]$^+$.

Synthesis of
(1-(2-fluoroethyl)-1H-pyrazol-4-yl)methanol

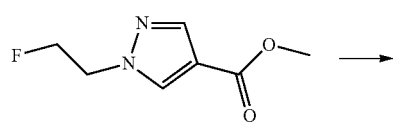

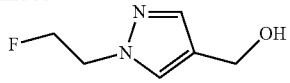

To a solution of methyl 1-(2-fluoroethyl)-1H-pyrazole-4-carboxylate (530 mg, 3.08 mmol) in THF (10 mL) was added DIBAL-H (2.5 M in MePh, 5.13 mL, 12.8 mmol) at −78° C. Then the mixture was stirred at r.t. for 16 h, then water (0.3 mL), aq. NaOH (1 M, 0.3 mL), and additional water (0.8 mL) were added sequentially with stirring. The mixture was partitioned between EA and water and then the water layer was further extracted with EA (3×10 mL). The combined organic solution was washed with sat aq. NH$_4$Cl (10 mL) and brine (10 mL), dried over anhydrous Na$_2$SO$_4$, and concentrated in vacuo to give a residue. The residue was purified by flash chromatography (0→50% EA in PE) to give [1-(2-fluoroethyl)-1H-pyrazol-4-yl]methanol (380 mg, yield: 86%) as a colorless liquid. LC/MS ESI (m/z): 145 [M+H]$^+$.

The following intermediates were synthesized using a similar experimental protocol:

| (5-ethylisothiazol-3-yl)methanol | | |
|---|---|---|
| 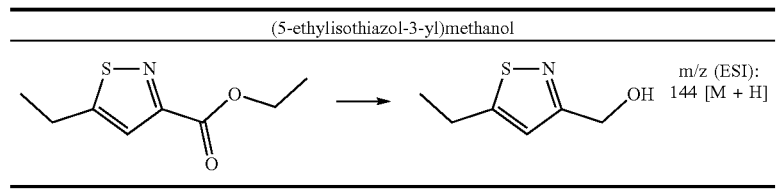 | | m/z (ESI): 144 [M + H] |

Synthesis of
(5-bromo-1-cyclobutyl-1H-pyrazol-4-yl)methanol

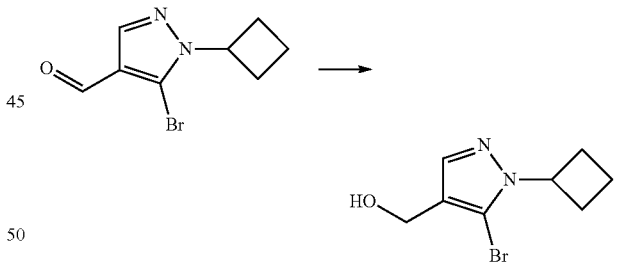

To a solution of 5-bromo-1-cyclobutyl-1H-pyrazole-4-carbaldehyde (6.00 g, 26.2 mmol) in THF (50 mL) was added diisobutylaluminium hydride (1.0 M in toluene, 39.28 mL, 39.28 mmol) at −78° C. over 30 min (This protocol can be modified to enable full reduction of esters to alcohols by increasing the number of equivalents of reducing agent). During the addition, the internal temperature was monitored to stay below −60° C. The reaction was stirred for 1 h at −78° C., then the mixture was poured into aq. HCl (1M) and extracted with ethyl acetate (100 mL×2), then washed with brine (50 mL×2), dried over anhydrous Na$_2$SO$_4$ and concentrated. The residue was purified by silica gel chromatography (30% ethyl acetate in petroleum ether) to give (5-bromo-1-cyclobutyl-1H-pyrazol-4-yl)methanol (4.4 g, 73%) as a colorless oil. LC/MS ESI (m/z): 231 [M+H]$^+$.

The following intermediates were synthesized using a similar experimental protocol:

| (5-bromo-1-(difluoromethyl)-1H-pyrazol-4-yl)methanol |
|---|
| 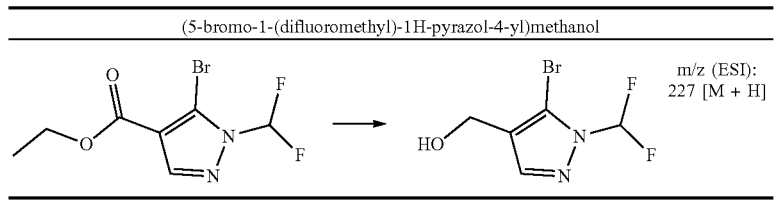 m/z (ESI): 227 [M + H] |

Synthesis of (3-bromo-5-fluoropyridin-2-yl)methanol

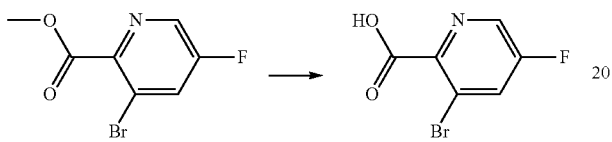

To a solution of methyl 3-bromo-5-fluoropyridine-2-carboxylate (1.00 g, 4.27 mmol) in THF (15 mL) at −78° C. was added DIBAL-H (1.21 mL, 8.54 mmol) dropwise under $N_2$ atmosphere. The mixture was stirred at 0° C. for 2 h., then quenched with ice-water, and extracted with DCM (40 mL×2). The combined organic layers were washed with brine, dried over anhydrous $Na_2SO_4$, filtered and concentrated. The residue was purified by column chromatography on silica gel (DCM:MeOH=20:1) to give (3-bromo-5-fluoropyridin-2-yl)methanol as a pale-yellow solid (600 mg, yield: 68%). LC/MS ESI (m/z): 206 [M+H]$^+$.

The following intermediates were synthesized using a similar experimental protocol:

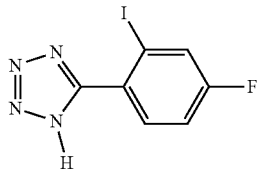

A mixture of 4-fluoro-2-iodobenzonitrile (2.5 g, 10 mmol), trimethylsilylazide (2.92 g, 25.3 mmol) and dibutylstannanone (0.50 g, 2.0 mmol) in toluene (20 mL) was stirred at 120° C. for 18 h. After cooling to r.t., the mixture was filtered, the filtrate was concentrated under reduced pressure. The residue was diluted with DCM (50 mL), then washed with water and brine, dried over anhydrous $Na_2SO_4$, filtered and concentrated. The residue was purified by flash chromatography (silica gel, 0→50% EA in PE) to give 5-(4-fluoro-2-iodophenyl)-1H-tetrazole (2.4 g, 82% yield) as a yellow oil. LC/MS (ESI) m/z: 291 [M+H]$^+$.

| (3-ethyl-1-(4-methoxybenzyl)-1H-pyrazol-5-yl)methanol |
|---|
| 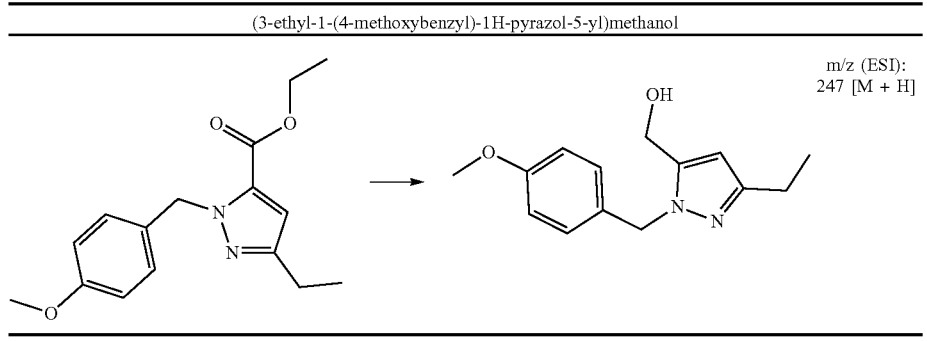 m/z (ESI): 247 [M + H] |

Synthesis of 5-(4-fluoro-2-iodophenyl)-1H-tetrazole

Synthesis of 4-(azidomethyl)-5-bromo-1-cyclobutyl-1H-pyrazole

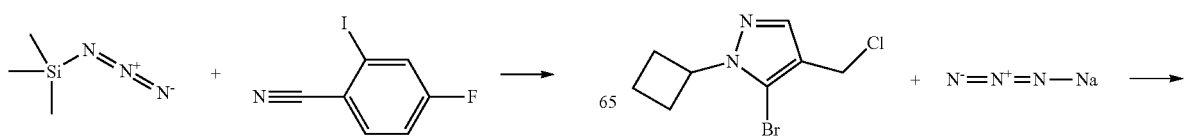

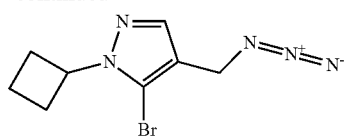

To a solution of 5-bromo-4-(chloromethyl)-1-cyclobutyl-1H-pyrazole (3.00 g, 12.0 mmol) in DMF (60 mL) was added NaN₃ (1.17 g, 18.0 mmol) portion-wise at 0° C. After the addition, the resulting mixture was stirred at 60° C. for 2.5 h. After cooling to 0° C., the reaction was diluted with water (200 mL) and extracted with EA (2×100 mL). The combined extracts were washed with brine, concentrated in vacuo and purified by flash chromatography (10% of EtOAc in PE) to give 4-(azidomethyl)-5-bromo-1-cyclobutyl-1H-pyrazole (2.91 g, yield: 95%) as a colorless oil. LC/MS ESI (m/z): 256 [M+H]⁺.

Synthesis of 5-((5-bromo-1H-1,2,4-triazol-1-yl)methyl)-3-ethylisoxazole

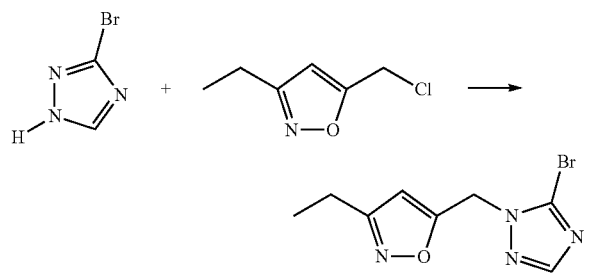

A mixture of 5-(chloromethyl)-3-ethyl-1,2-oxazole (2.00 g, 13.7 mmol), 3-bromo-1H-1,2,4-triazole (2.03 g, 13.7 mmol), ethylbis(propan-2-yl)amine (4.54 mL, 27.47 mmol), potassium iodide (1.14 g, 6.87 mmol) in anhydrous MeCN (20 mL) was stirred at 80° C. for 2 h. The reaction mixture was filtered to remove solid, and the filtrate was partitioned between EA and water, and the layers separated. The water layer was further extracted with EA and the combined organic layers were dried over anhydrous Na₂SO₄ and concentrated. The residue was purified by flash chromatography (0→3% MeOH in DCM) to provide a 5:1 mixture of regioisomers (3.0 g, yield: 85.7%) as a colorless oil. The isomers were separated by prep-SFC (ChiralPak IG, 250× 21.2 mm I.D., 5 m, 40% MeOH+0.1% aq. NH₃ in CO₂, 50 mL/min) to give 5-((5-bromo-1H-1,2,4-triazol-1-yl)methyl)-3-ethylisoxazole (peak 1, minor isomer, 650 mg, assigned with NOESY analysis) as a colorless oil. LC/MS ESI (m/z): 257 [M+H]⁺.

Synthesis of ethyl 5-bromo-1-(difluoromethyl)-1H-pyrazole-4-carboxylate

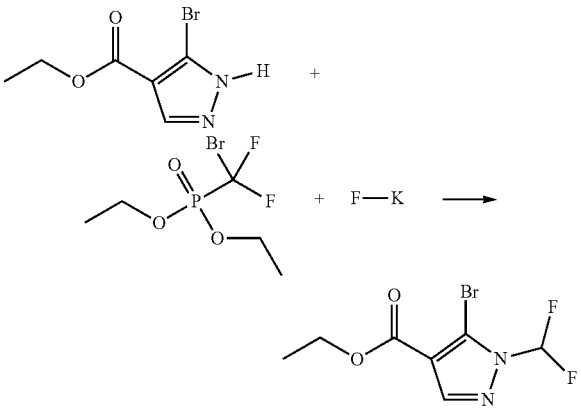

To a solution of ethyl 5-bromo-1H-pyrazole-4-carboxylate (14.0 g, 63.9 mmol) and KF (7.96 g, 63.9 mmol) in MeCN (60 mL) was added diethyl (bromodifluoromethyl)phosphonate (27.43 g, 102.7 mmol) at 0° C. The resulting mixture was stirred at r.t. overnight. The mixture was slowly poured into ice-water and extracted with EA twice. The combined extracts were washed with brine, dried over anhydrous Na₂SO₄ and concentrated. The residue was purified by flash chromatography (silica gel, 0→5% of EtOAc in petroleum ether) to afford ethyl 5-bromo-1-(difluoromethyl)-1H-pyrazole-4-carboxylate (4.0 g, 23% yield) as a white solid. LC/MS ESI (m/z): 269 [M+H]⁺.

The following intermediates were synthesized using a similar experimental protocol:

| 4-((1-(cyclopropylmethyl)-1H-pyrazol-4-yl)methyl)-2-(difluoromethyl)-5-iodo-2H-1,2,3-triazole |
|---|
| 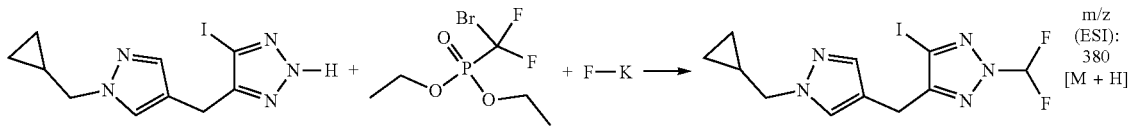 m/z (ESI): 380 [M + H] |

Synthesis of 1-[(5-bromo-1,3-thiazol-4-yl)methyl]pyrazole-4-carbonitrile

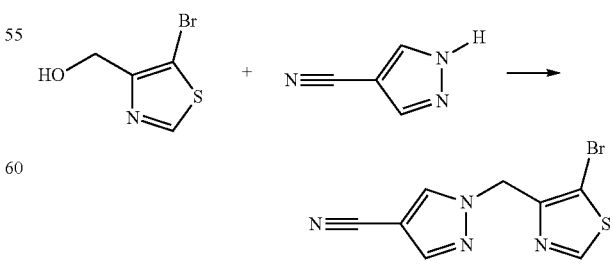

To a solution of (5-bromo-1,3-thiazol-4-yl)methanol (400 mg, 2.06 mmol), 4-cyanopyrazole (288 mg, 3.09 mmol) and PPh₃ (649 mg, 2.47 mmol) in THF (6 mL) was added DIAD (500 mg, 2.47 mmol) at 0° C. dropwise. The mixture was then stirred at r.t. for 16 h. The solvent was removed under vacuum, and the residue was purified via silica gel (PE/EA=1:1) to yield 1-[(5-bromo-1,3-thiazol-4-yl)methyl]pyrazole-4-carbonitrile (460 mg, 83%) as a white solid. LC/MS ESI (m/z): 269 [M+H]⁺.

The following intermediates were synthesized using a similar experimental protocol:

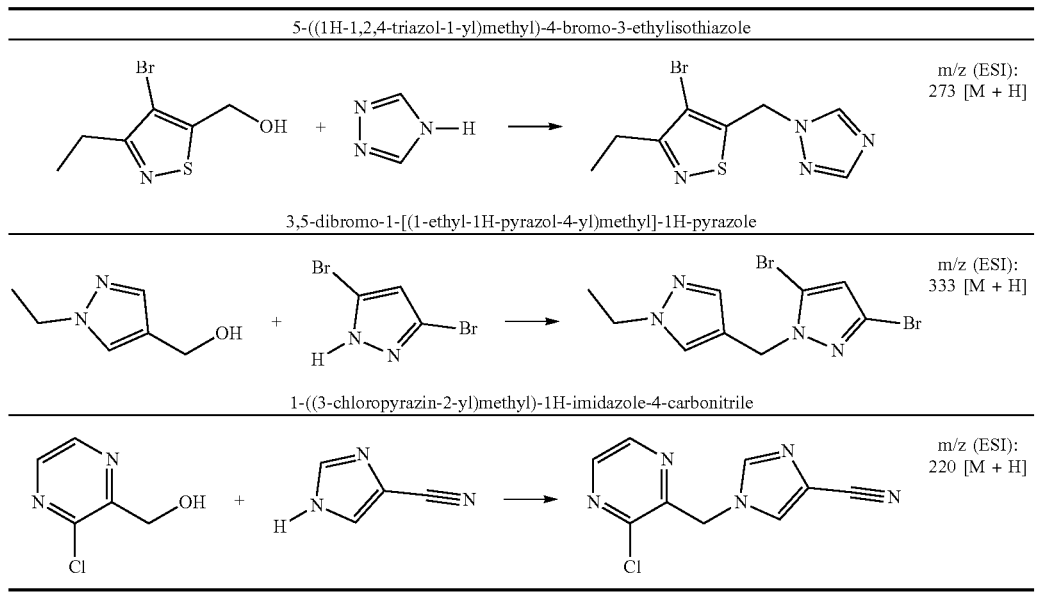

Synthesis of 5-((5-iodo-1H-pyrazol-1-yl)methyl)isoxazole-3-carbonitrile

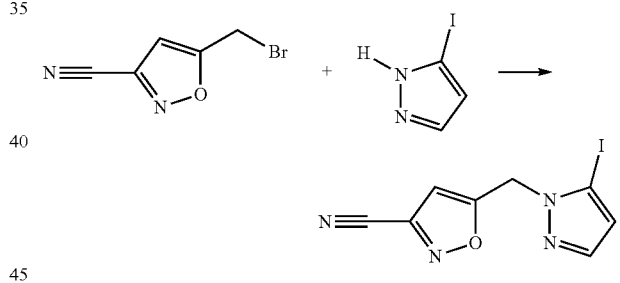

To a solution of 5-(bromomethyl)isoxazole-3-carbonitrile (2.20 g, 11.7 mmol) in DMF (100 mL) were added 5-iodo-H-pyrazole (2.50 g, 12.9 mmol) and K₂Ct₃ (4.90 g, 35.3 mmol) at 25° C. After stirring at 25° C. for 2 h, the reaction mixture was diluted with EtOAc and then washed with H₂O and brine. The organic layer was dried over anhydrous Na₂SO₄. After filtration, the filtrate was concentrated under vacuum. The residue was processed by SFC (ChiralPak AD, 40% MeOH+0.1% NH₃.H₂O) to purify and separate regioisomers to give 5-((5-iodo-1H-pyrazol-1-yl)methyl)isoxazole-3-carbonitrile as a light-yellow oil (350 mg, yield: 10%, minor regioisomer). LC/MS ESI (m/z): 301 [M+H]⁺.

The following intermediates were synthesized using a similar experimental protocol:

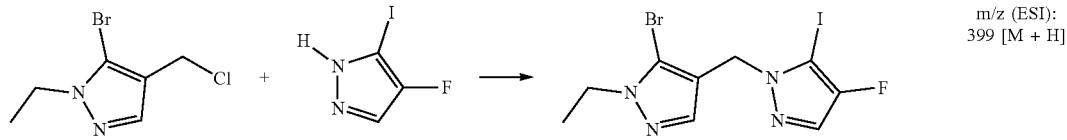

-continued 5-bromo-1-ethyl-4-((5-iodo-1H-pyrazol-1-yl)methyl)-1H-pyrazole

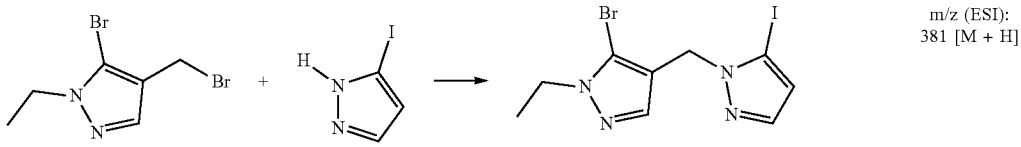

m/z (ESI): 381 [M + H]

1-((5-bromo-1-ethyl-1H-pyrazol-4-yl)methyl)-5-iodo-1H-pyrazole-4-carbonitrile

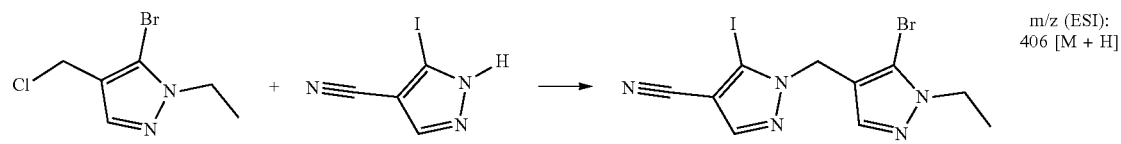

m/z (ESI): 406 [M + H]

5-bromo-1-(difluoromethyl)-3-((5-iodo-1H-pyrazol-1-yl)methyl)-1H-pyrazole

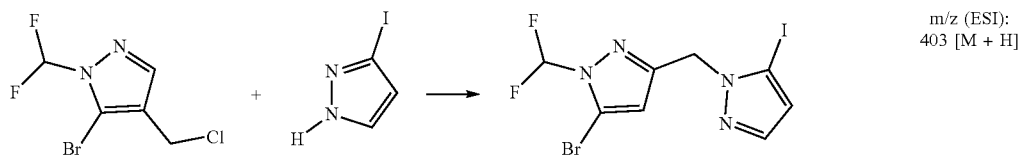

m/z (ESI): 403 [M + H]

3-ethyl-5-((5-iodo-1H-pyrazol-1-yl)methyl)isoxazole

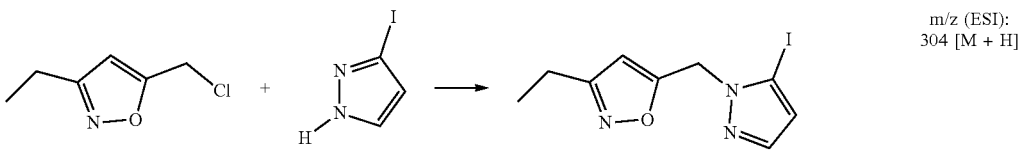

m/z (ESI): 304 [M + H]

5-bromo-1-[(1-ethyl-3-methyl-1H-pyrazol-4-yl)methyl]-1H-1,2,4-triazole

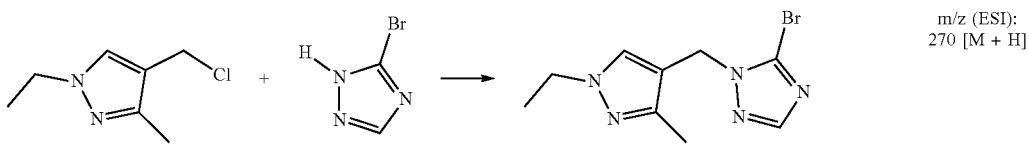

m/z (ESI): 270 [M + H]

5-((5-bromo-1H-1,2,4-triazol-1-yl)methyl)-3-cyclobutylisoxazole

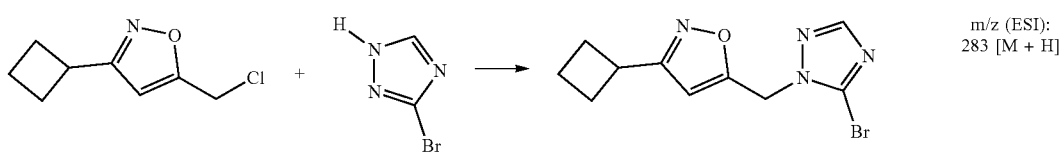

m/z (ESI): 283 [M + H]

5-bromo-1-{[1-(cyclopropylmethyl)-3-methyl-1H-pyrazol-4-yl]methyl}-1H-1,2,4-triazole

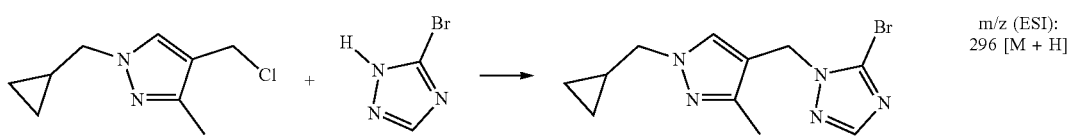

m/z (ESI): 296 [M + H]

Synthesis of 3-ethyl-5-(((tetrahydro-2H-pyran-2-yl)oxy)methyl)isoxazole

Synthesis of (2-(3-chloro-1H-pyrazol-1-yl)-5-fluorophenyl)methanol

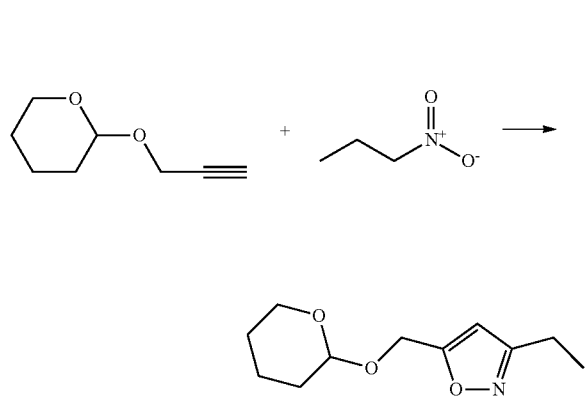

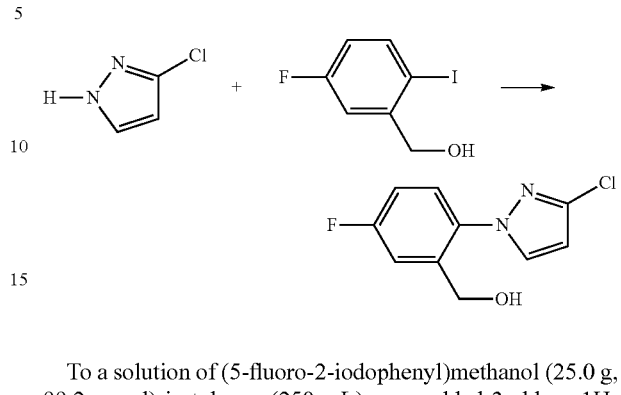

To a stirred solution of 2-(prop-2-yn-1-yloxy)tetrahydro-2H-pyran (5.00 g, 36.7 mmol) and 1-nitropropane (7.00 g, 78.6 mmol) in toluene (40 mL) was added phenyl isocyanate (17.0 mL, 119 mmol), followed by the addition of triethylamine (2.94 mL, 21.2 mmol). The reaction mixture was heated to 120° C. and stirred for 24 h. After cooling to r.t., the reaction mixture was quenched with 1 mL of water, and the mixture was stirred at r.t. for 1 h. The precipitates were removed by filtration, and the filtrate was concentrated. The residue was purified by column chromatography on silica gel (0→20% EtOAc in PE) to give 3-ethyl-5-(((tetrahydro-2H-pyran-2-yl)oxy)methyl)isoxazole (10.0 g, 61% yield) as a yellow syrup. LC/MS ESI (m/z): 212 [M+H]$^+$.

The following intermediates were synthesized using a similar experimental protocol:

To a solution of (5-fluoro-2-iodophenyl)methanol (25.0 g, 99.2 mmol) in toluene (250 mL) were added 3-chloro-1H-pyrazole (11.2 g, 109 mmol), K$_2$CO$_3$ (27.4 g, 198.4 mmol) and CuI (1.9 g, 9.9 mmol). The reaction was stirred at 120° C. under N$_2$ for 12 h. The reaction was filtered and concentrated. The residue was purified by flash chromatography (5→25% EtOAc in PE) to give (2-(3-chloro-1H-pyrazol-1-yl)-5-fluorophenyl)methanol (21.1 g, 85% yield) as a white solid. LC/MS (ESI) (m/z): 227 [M+H]$^+$.

Synthesis of 3-methoxy-1-((2-(trimethylsilyl)ethoxy)methyl)-1H-pyrazole

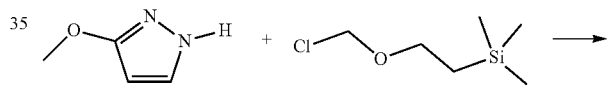

---

3-(cyclopropylmethyl)-5-(((tetrahydro-2H-pyran-2-yl)oxy)methyl)isoxazole m/z (ESI): 238 [M + H]

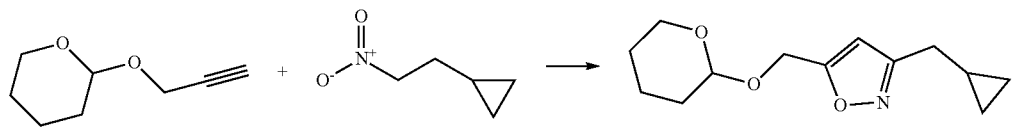

---

3-cyclobutyl-5-(((tetrahydro-2H-pyran-2-yl)oxy)methyl)isoxazole m/z (ESI): 238 [M + H]

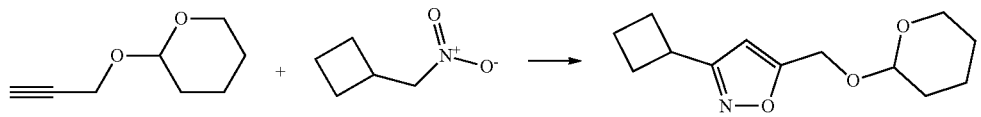

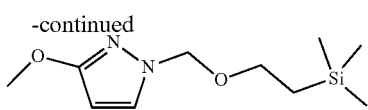

To a stirred solution of 3-methoxy-1H-pyrazole (1.00 g, 10.2 mmol) in THF (15 mL) was added NaH (0.46 g, 12 mmol, 60% in mineral oil) at 0° C. under $N_2$. After stirring at 0° C. for 1 h, a solution of [2-(chloromethoxy)ethyl] trimethylsilane (2.5 mL, 14 mmol) in THF (3 mL) was added dropwise. The reaction was stirred at 0° C. for 1 h, quenched with sat. $NH_4Cl$ (10 mL) and extracted with EtOAc (100 mL). The organic phase was separated, dried over anhydrous $Na_2SO_4$ and concentrated to dryness to give 3-methoxy-1-((2-(trimethylsilyl)ethoxy)methyl)-1H-pyrazole (2.20 g, 91% yield) as a yellow oil. LC/MS (ESI) (m/z): 229.1 $[M+H]^+$.

The following intermediates were synthesized using a similar experimental protocol:

4,5-diiodo-2-((2-(trimethylsilyl)ethoxy)methyl)-2H-1,2,3-triazole

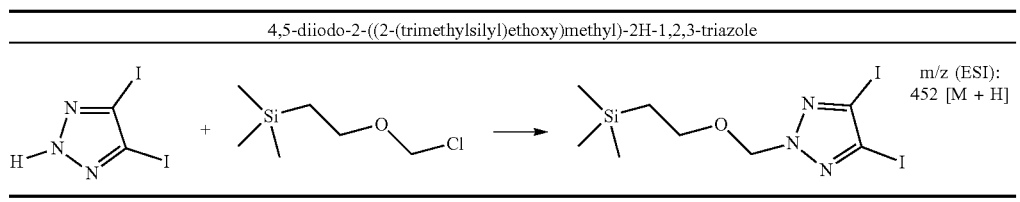

m/z (ESI): 452 [M + H]

Synthesis of (E)-1-(3-bromo-5-fluoropyridin-2-yl)-3-(dimethylamino)prop-2-en-1-one

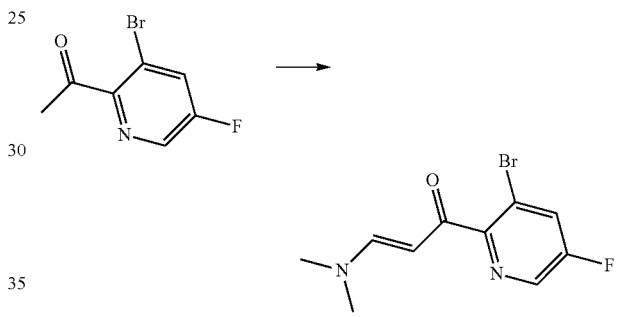

A solution of 1-(3-bromo-5-fluoropyridin-2-yl)ethan-1-one (2.60 g, 11.9 mmol) in (dimethoxymethyl)dimethylamine (10 mL) was stirred at 120° C. for 12 h. After cooling to r.t., the mixture was concentrated by oil pump and the residue was purified by flash chromatography on silica gel (0→40% EtOAc in PE) to give (E)-1-(3-bromo-5-fluoropyridin-2-yl)-3-(dimethylamino)prop-2-en-1-one (3.0 g, 92% yield) as a yellow solid. LC/MS ESI (m/z): 273 $[M+H]^+$.

The following intermediates were synthesized using a similar experimental protocol:

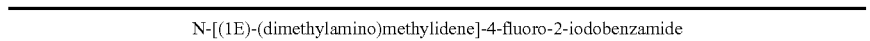

N-[(1E)-(dimethylamino)methylidene]-4-fluoro-2-iodobenzamide

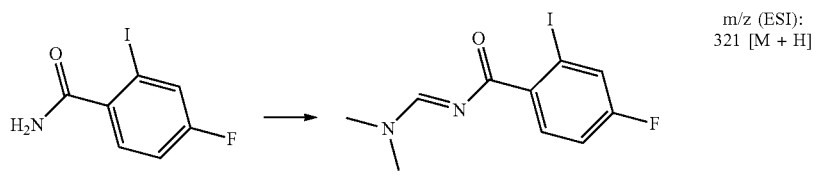

m/z (ESI): 321 [M + H]

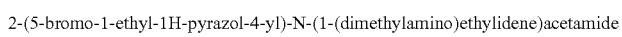

2-(5-bromo-1-ethyl-1H-pyrazol-4-yl)-N-(1-(dimethylamino)ethylidene)acetamide

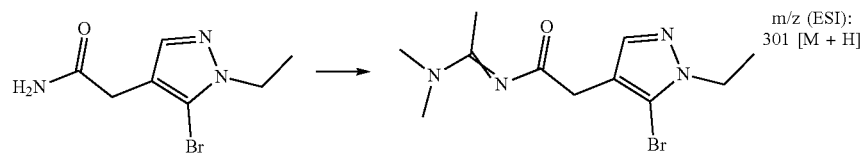

m/z (ESI): 301 [M + H]

Synthesis of (5-bromo-1,3-thiazol-4-yl)(1-ethyl-1H-1,2,3-triazol-4-yl)methanol

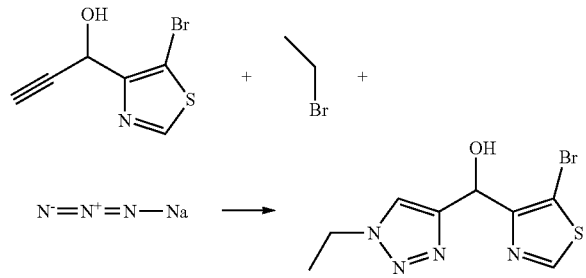

In a sealed tube a solution of bromoethane (1.68 g, 15.1 mmol), sodium azide (0.98 g, 15.1 mmol) in THF (5 mL) and H$_2$O (5 mL) was stirred at 80° C. for 4 h. The resulting mixture was cooled to r.t., and then 1-(5-bromo-1,3-thiazol-4-yl)prop-2-yn-1-ol (1.10 g, 5.04 mmol), Na ascorbate (0.20 g, 1.01 mmol), CuSO$_4$ (0.16 g, 1.01 mmol), t-BuOH (10 mL) were added successively. The mixture was stirred at 50° C. for 18 h and then filtered. The filtrate was concentrated under reduced pressure. The residue was purified by flash column chromatography on silica gel (0→10% MeOH in DCM) to give (5-bromothiazol-4-yl)(1-ethyl-1H-1,2,3-triazol-4-yl)methanol (0.7 g, 48%) as a colorless oil. MS (ESI): m/z=289 [M+H]$^+$.

Synthesis of 1-[(3-iodopyridin-2-yl)methyl]-1H-imidazole-4-carbonitrile

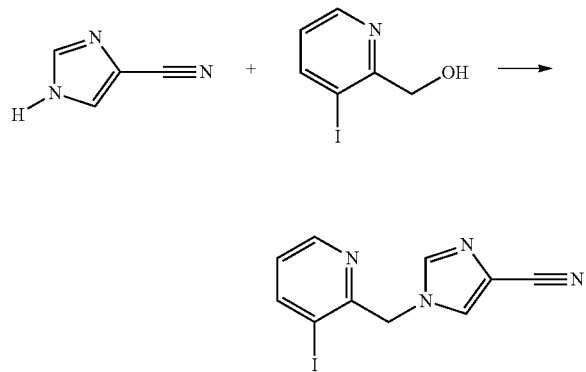

The solution of triphenylphosphane (712 mg, 2.72 mmol) in THF (7 mL) was cooled to 0° C. under N$_2$. Then DIAD (549 mg, 2.71 mmol) in THF (7 mL) was added. And then the mixture was stirred at 0° C. until a white solid is precipitated. Then to the mixture was added 1H-imidazole-4-carbonitrile (152 mg, 1.63 mmol) in THF (4 mL) at 0° C. And then to the mixture was added (3-iodopyridin-2-yl)methanol (319 mg, 1.36 mmol) in THF (6 mL). The mixture was stirred at r.t. for 2 h. The reaction mixture was concentrated and diluted by DCM. The solution was washed with sat. aq. NaCl and dried over anhydrous Na$_2$SO$_4$, filtered, and concentrated. The residue was purified by flash chromatography (silica gel, 0→100% EA in PE) to give 1-[(3-iodopyridin-2-yl)methyl]-1H-imidazole-4-carbonitrile (309 mg, yield: 73%) as a yellow oil. LC/MS (ESI) m/z: 311 [M+H]$^+$.

The following intermediates were synthesized using a similar experimental protocol:

| 1-((3-bromo-5-fluoropyridin-2-yl)methyl)-1H-imidazole-4-carbonitrile |
|---|
| 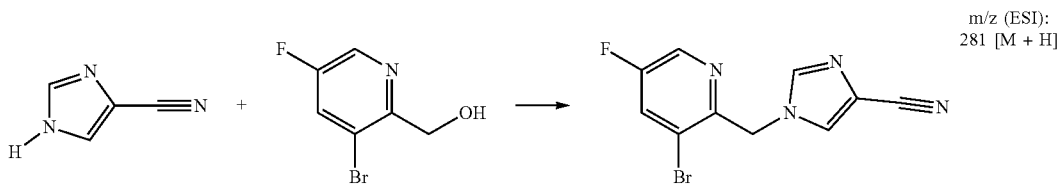 m/z (ESI): 281 [M + H] |

Synthesis of 4-[(3-chloro-5-iodo-1H-pyrazol-1-yl)methyl]-1-ethyl-1H-1,2,3-triazole

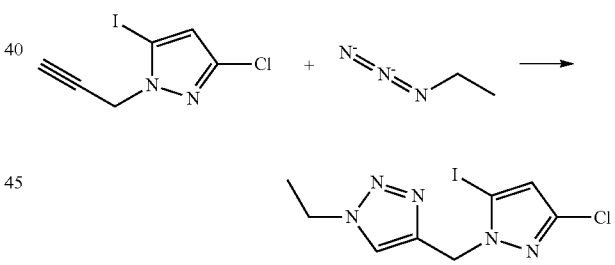

To a solution of 3-chloro-5-iodo-1-(prop-2-yn-1-yl)-1H-pyrazole (0.550 g, 2.06 mmol) in tert-butyl alcohol (15 mL) were added water (15 mL), CuSO$_4$ (20 mg, 0.14 mmol) and sodium ascorbate (20 mg, 0.10 mmol), followed by the addition of ethylazide (10 mL, 5.0 mmol, 0.5 N in THF) at 25° C. After addition, the resulting mixture was stirred at 50° C. in a sealed tube for 16 h. The mixture was then concentrated in vacuo to remove most of tert-butyl alcohol. The residue was treated with DCM (20 mL) and H$_2$O (10 mL). The organic layer was separated, dried over anhydrous Na$_2$SO$_4$, filtered and concentrated under vacuum. The residue was purified by flash chromatography (0→50% EtOAc in PE) and SFC (ChiralPak AD, 250×4.6 mm 5 um, 30% EtOH+0.1% aq. NH$_3$ in CO$_2$) to afford 4-[(3-chloro-5-iodo-1H-pyrazol-1-yl)methyl]-1-ethyl-1H-1,2,3-triazole (210 mg, 30% yield) as a white solid. LC/MS (ESI): m/z=338 [M+H]$^+$.

The following intermediates were synthesized using a similar experimental protocol:

| (1-(cyclopropylmethyl)-1H-1,2,3-triazol-4-yl)(5-iodo-2-methyl-2H-1,2,3-triazol-4-yl)methanol |
|---|
| 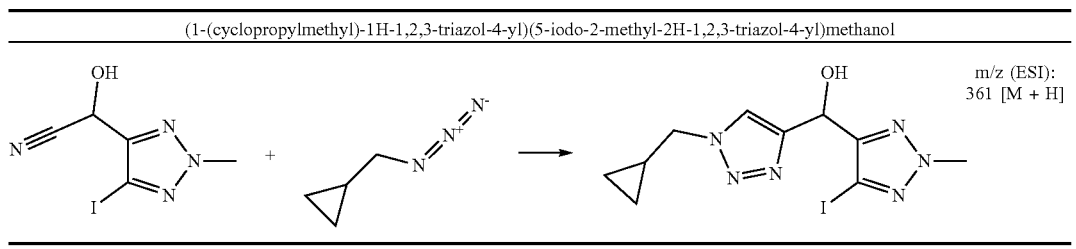 m/z (ESI): 361 [M + H] |

Synthesis of 3-chloro-1-((1-(ethyl-d5)-1H-pyrazol-4-yl)methyl)-5-iodo-1H-pyrazole

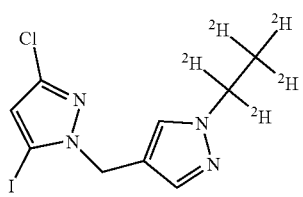 [SMILES: [2H]C([2H])([2H])C([2H])([2H])n1cc(Cn2nc(Cl)cc2I)cn1]

To a stirred solution of (1-(ethyl-d5)-1H-pyrazol-4-yl)methanol (1.07 g, 8.16 mmol) in DCM (20 mL) was added $SOCl_2$ (1.80 mL, 24.5 mmol) at 0° C. The reaction was stirred at 25° C. for 16 h. The reaction mixture was concentrated to give crude 4-(chloromethyl)-1-(ethyl-d5)-1H-pyrazole (1.22 g, 99% yield) as a yellow oil.

To a mixture of 3-chloro-5-iodo-1H-pyrazole (1.83 g, 8.02 mmol) and $Cs_2CO_3$ (7.84 g, 24.06 mmol) in DMF (30 mL) was added a solution of 4-(chloromethyl)-1-(ethyl-d5)-1H-pyrazole (1.20 g, 8.02 mmol) in DMF (3 mL) at 0° C. under $N_2$. The reaction was stirred at 80° C. for 1 h. The reaction mixture was poured into water (60 mL) and extracted with EtOAc (30 mL×2). The combined organic layers were washed with brine (30 mL), dried over anhydrous $Na_2SO_4$ and concentrated to dryness. The residue was purified by column chromatography on silica gel (PE:EA=3:1), then recrystallized from DCM and PE to afford 3-chloro-1-((1-(ethyl-d5)-1H-pyrazol-4-yl)methyl)-5-iodo-1H-pyrazole (700 mg, 26% yield) as a white solid. LC/MS (ESI) (m/z): 342 [M+H]$^+$.

Synthesis of 4-bromo-3-ethyl-5-((5-iodo-1H-1,2,4-triazol-1-yl)methyl)isothiazole

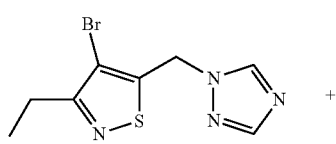 +

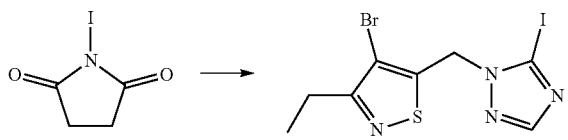

To a stirred solution of 5-((1H-1,2,4-triazol-1-yl)methyl)-4-bromo-3-ethylisothiazole (1.90 g, 6.99 mmol) in AcOH (60 mL) at ambient temperature was added NIS (3.60 g, 21.0 mmol). The resulting mixture was stirred at 80° C. for 16 h. The filtrate was extracted with EtOAc. The combined organic layers were washed with brine, dried over $Na_2SO_4$ and concentrated under vacuum. The residue was purified by flash phase chromatography on silica gel (0→30% EtOAc in petroleum ether) to afford 4-bromo-3-ethyl-5-((5-iodo-1H-1,2,4-triazol-1-yl)methyl)isothiazole (2.0 g) as an off-white solid. LC-MS (ESI) m/z: 399 [M+H]$^+$.

Synthesis of (3-ethylisoxazol-5-yl)methanol

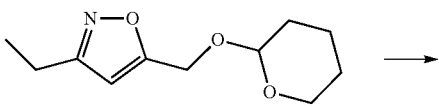

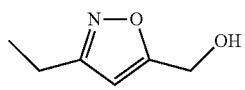

To a solution of 3-ethyl-5-[(oxan-2-yloxy)methyl]-1,2-oxazole (17.4 g, 82.4 mmol) in MeOH (10 mL) was added Amberlyst 15 (26 mg, 83 mmol). The mixture was stirred vigorously at 45° C. for 6 h. Filtration and removal of solvent in vacuum gave a red residue, which was purified by column chromatography on silica gel (15→30% EtOAc in PE) to give (3-ethyl-1,2-oxazol-5-yl)methanol (8.05 g, yield: 77%) as a pale-yellow oil. LC/MS ESI (m/z): 128 [M+H]$^+$.

The following intermediates were synthesized using a similar experimental protocol:

| (3-(cyclopropylmethyl)isoxazol-5-yl)methanol |
|---|
| 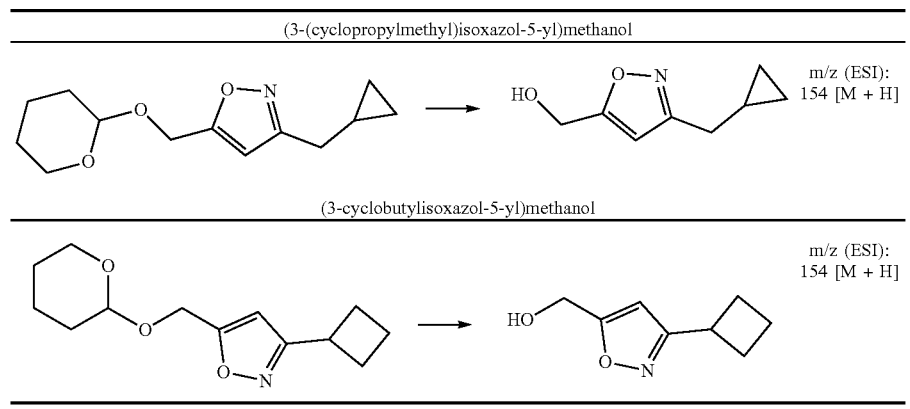 m/z (ESI): 154 [M + H] |
| (3-cyclobutylisoxazol-5-yl)methanol |
| m/z (ESI): 154 [M + H] |

Synthesis of 5-bromo-3-methoxy-1H-pyrazole

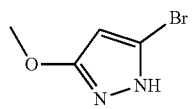

To a stirred solution of 3-methoxy-1-((2-(trimethylsilyl)ethoxy)methyl)-1H-pyrazole (2.20 g, 9.63 mmol) in THF (30 mL) was added n-BuLi (4.0 mL, 10 mmol, 2.5 M in THF) at −78° C. under N$_2$. After stirring at −78° C. for 1 h, a solution of CBr$_4$ (2.20 g, 6.63 mmol) in THF (10 mL) was added dropwise. The reaction was stirred at 0° C. for 1 h, quenched with sat. NH$_4$Cl (10 mL), and extracted with EtOAc (150 mL). The organic phase was separated, dried over anhydrous Na$_2$SO$_4$ and concentrated. The residue was purified by column chromatography on silica gel (PE:EtOAc=4:1, V/V) to give 5-bromo-3-methoxy-1-((2-(trimethylsilyl)ethoxy)methyl)-1H-pyrazole (1.8 g, 58% yield) as a yellow oil. LC/MS (ESI) (m/z): 307.0 [M+H]$^+$.

A solution of 5-bromo-3-methoxy-1-((2-(trimethylsilyl)ethoxy)methyl)-1H-pyrazole (1.80 g, 5.86 mmol) and TFA (3.00 mL, 40.4 mmol) in DCM (15 mL) was stirred at 25° C. for 4 h. The reaction mixture was concentrated under reduced pressure. The residue was diluted with acetonitrile (15 mL) and aq. NH$_4$OH (3.0 mL, 22 mmol). The mixture was stirred at 25° C. for 3 h. The reaction was concentrated under reduced pressure to give 5-bromo-3-methoxy-1H-pyrazole (1.5 g, 87% yield) as a yellow oil. LC/MS ESI (m/z): 177.0 [M+H]$^+$.

Synthesis of 5-bromo-1-((1-(cyclopropylmethyl)-1H-pyrazol-4-yl)methyl)-1H-1,2,4-triazole

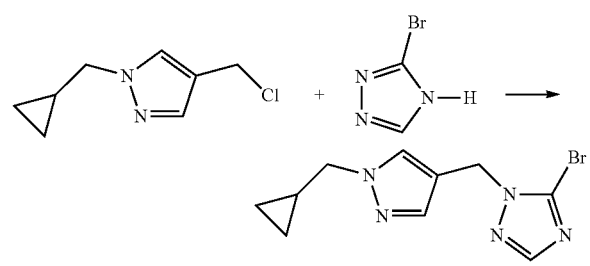

To a mixture of 4-(chloromethyl)-1-(cyclopropylmethyl)-1H-pyrazole (950 mg, 5.56 mmol) and K$_2$CO$_3$ (1.50 g, 11.1 mmol) in DMF (15 mL) was added 3-bromo-4H-1,2,4-triazole (906 mg, 6.10 mmol). And then the mixture was stirred at 50° C. for 2 h. The reaction mixture was concentrated by oil pump and diluted with EtOAc. The solution was washed with brine, dried over anhydrous Na$_2$SO$_4$, filtered and concentrated. The residue was purified by prep-HPLC (Column: YMC TA C18 250*20 mm 5 um, MeCN in H$_2$O+0.1% FA) to give 5-bromo-1-((1-(cyclopropylmethyl)-1H-pyrazol-4-yl)methyl)-1H-1,2,4-triazole (100 mg, 6% yield over two steps) as a white solid. LC/MS ESI (m/z): 282 [M+H]$^+$.

The following intermediates were synthesized using a similar experimental protocol:

| 1-((5-bromo-1-cyclobutyl-1H-pyrazol-4-yl)methyl)-5-iodo-1H-pyrazole-4-carbonitrile |
|---|
| 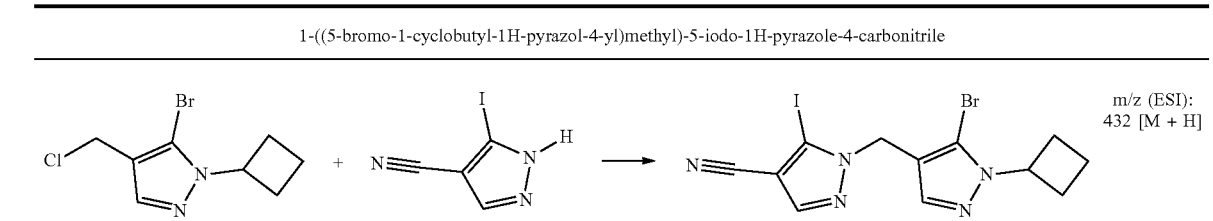 m/z (ESI): 432 [M + H] |

-continued 5-bromo-4-((3-chloro-5-iodo-1H-pyrazol-1-yl)methyl)-1-ethyl-1H-pyrazole

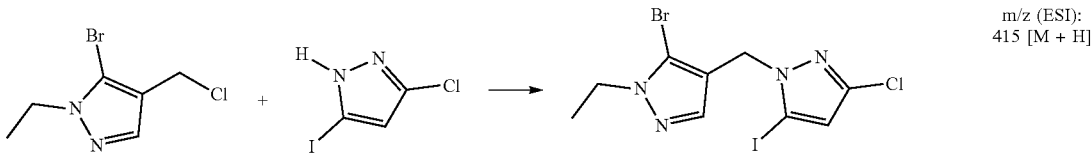

m/z (ESI): 415 [M + H]

1-ethyl-4-[(5-iodo-3-methyl-1H-pyrazol-1-yl)methyl]-3-methoxy-1H-pyrazole

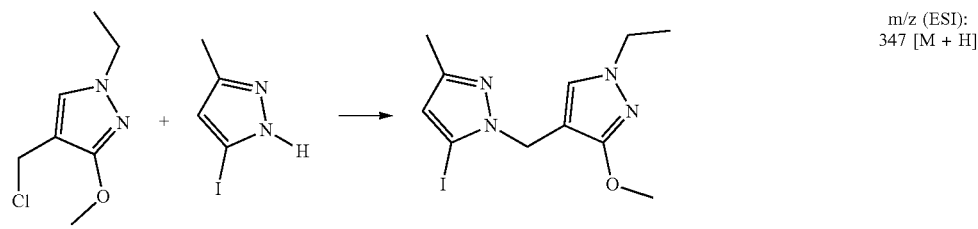

m/z (ESI): 347 [M + H]

5-((5-bromo-1H-1,2,4-triazol-1-yl)methyl)-3-(cyclopropylmethyl)isoxazole

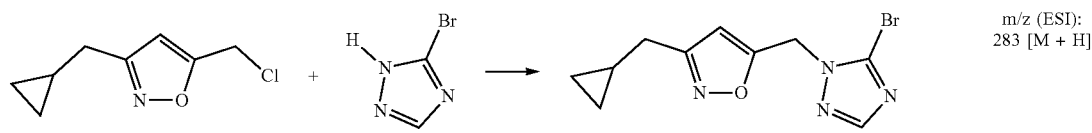

m/z (ESI): 283 [M + H]

3-chloro-1-((1-(cyclopropylmethyl)-1H-pyrazol-4-yl)methyl)-5-iodo-1H-pyrazole

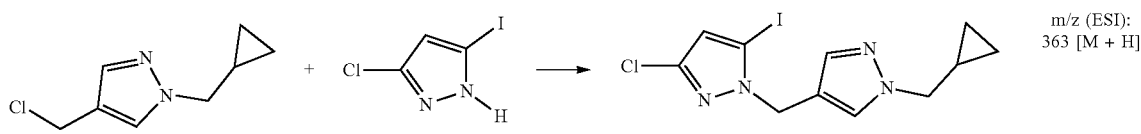

m/z (ESI): 363 [M + H]

3-chloro-1-((1-(cyclopropylmethyl)-3-methyl-1H-pyrazol-4-yl)methyl)-5-iodo-1H-pyrazole

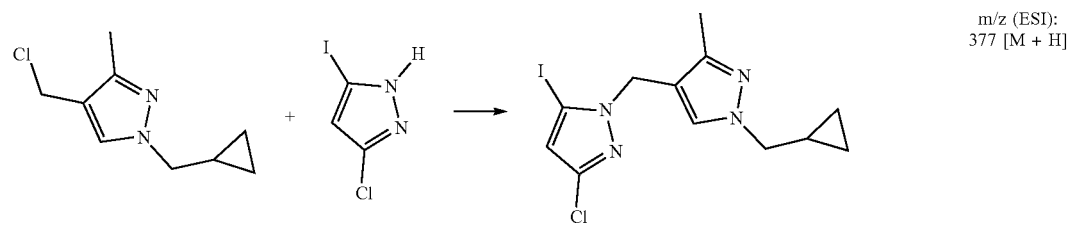

m/z (ESI): 377 [M + H]

5-bromo-1-[(1-ethyl-1H-pyrazol-4-yl)methyl]-3-(trifluoromethyl)-1H-pyrazole

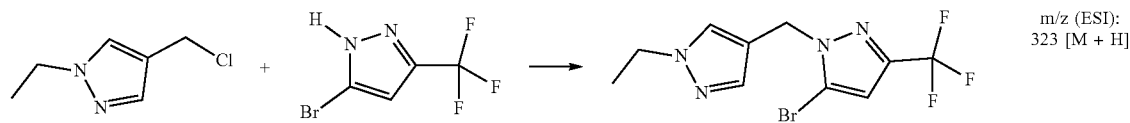

m/z (ESI): 323 [M + H]

5-bromo-1-((1-(2-fluoroethyl)-1H-pyrazol-4-yl)methyl)-3-methyl-1H-pyrazole

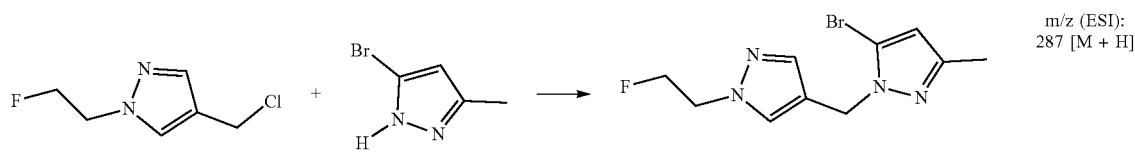

m/z (ESI): 287 [M + H]

| 3-ethyl-5-((5-(4-fluoro-2-iodophenyl)-1H-tetrazol-1-yl)methyl)isoxazole | |
|---|---|
| 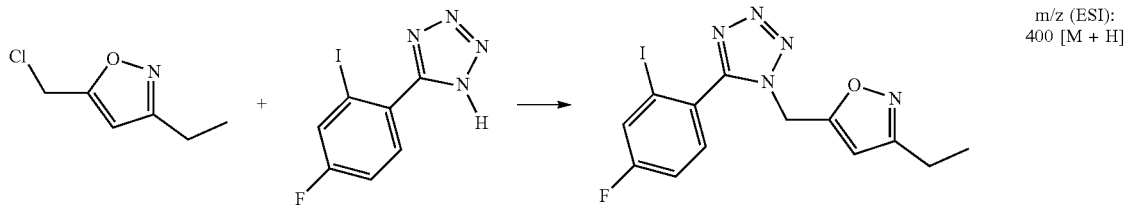 | m/z (ESI): 400 [M + H] |

Synthesis of 4-[(5-bromo-1,3-thiazol-4-yl)methyl]-1-ethyl-1H-1,2,3-triazole

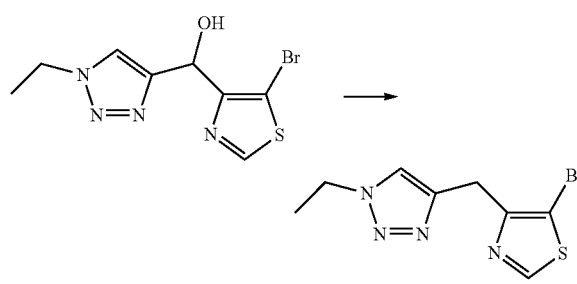

To a solution of (5-bromo-1,3-thiazol-4-yl)(1-ethyl-1H-1,2,3-triazol-4-yl)methanol (700 mg, 2.42 mmol) in TFA (20 mL) was added triethylsilane (7.8 mL, 48 mmol). The vessel was sealed, and the resulting mixture was stirred at 50° C. for 16 h. The reaction mixture was concentrated under reduced pressure. The residue was purified by flash column chromatography on silica gel eluting with EA in PE (0-*100%) to give 4-[(5-bromo-1,3-thiazol-4-yl)methyl]-1-ethyl-1H-1,2,3-triazole (0.6 g, 91%) as a pale-yellow solid. LC/MS (ESI): m/z=273 [M+H]⁺.

The following intermediates were synthesized using a similar experimental protocol:

| 5-bromo-1-ethyl-4-((5-iodo-1-methyl-1H-imidazol-4-yl)methyl)-1H-pyrazole | |
|---|---|
| 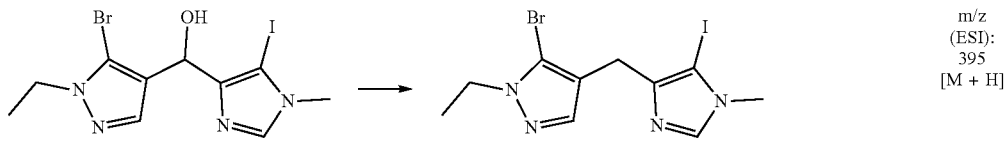 | m/z (ESI): 395 [M + H] |
| 5-bromo-1-ethyl-4-((4-iodo-1-methyl-1H-imidazol-5-yl)methyl)-1H-pyrazole | |
| 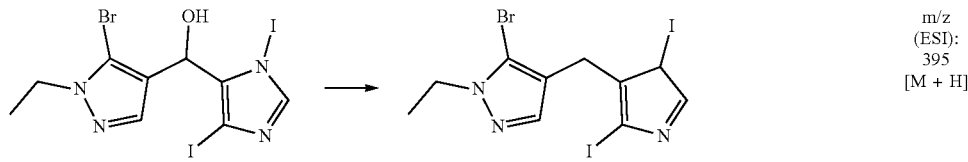 | m/z (ESI): 395 [M + H] |
| 4-((5-bromo-1-cyclopropyl-1H-pyrazol-4-yl)methyl)-5-iodo-2-methyl-2H-1,2,3-triazole | |
| 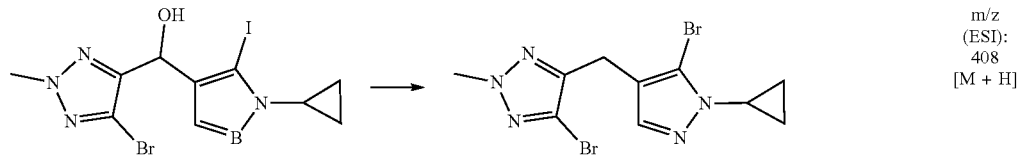 | m/z (ESI): 408 [M + H] |
| ethyl 5-((5-iodo-2-methyl-2H-1,2,3-triazol-4-yl)methyl)isoxazole-3-carboxylate | |
| 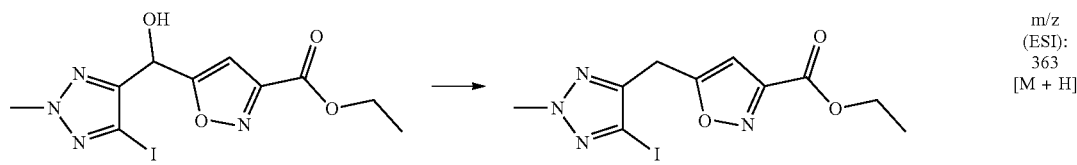 | m/z (ESI): 363 [M + H] |

-continued 4-((1-(2,2-difluoroethyl)-1H-pyrazol-4-yl)methyl)-5-iodo-2-methyl-2H-1,2,3-triazole

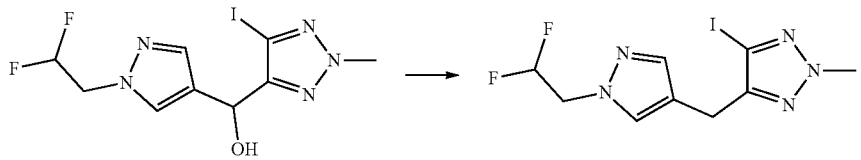 [SMILES: Cn1nc(I)c(C(O)c2cnn(CC(F)F)c2)n1 ; Cn1nc(I)c(Cc2cnn(CC(F)F)c2)n1]

m/z (ESI): 354 [M + H]

4-[(3-cyclobutyl-1,2-oxazol-5-yl)methyl]-5-iodo-2-methyl-2H-1,2,3-triazole

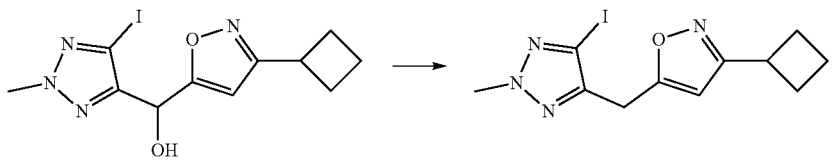 [SMILES: Cn1nc(I)c(C(O)c2cc(C3CCC3)no2)n1 ; Cn1nc(I)c(Cc2cc(C3CCC3)no2)n1]

m/z (ESI): 345 [M + H]

4-[(5-ethyl-1,2-oxazol-3-yl)methyl]-5-iodo-2-methyl-2H-1,2,3-triazole

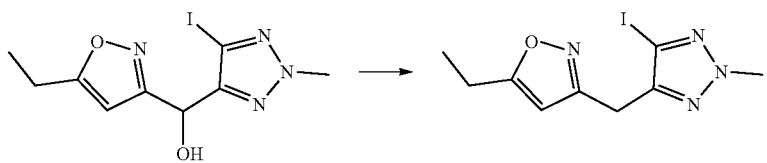 [SMILES: CCc1cc(C(O)c2nn(C)nc2I)no1 ; CCc1cc(Cc2nn(C)nc2I)no1]

m/z (ESI): 319 [M + H]

3-ethyl-5-((5-iodo-2-methyl-2H-1,2,3-triazol-4-yl)methyl)isoxazole

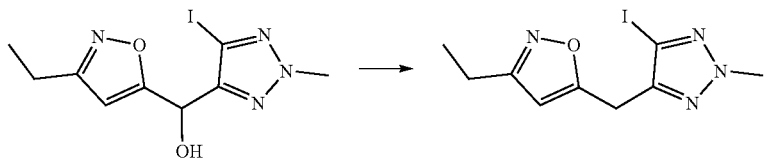 [SMILES: CCc1cc(C(O)c2nn(C)nc2I)on1 ; CCc1cc(Cc2nn(C)nc2I)on1]

m/z (ESI): 319 [M + H]

4-((1H-imidazol-2-yl)methyl)-5-bromo-1-ethyl-1H-pyrazole

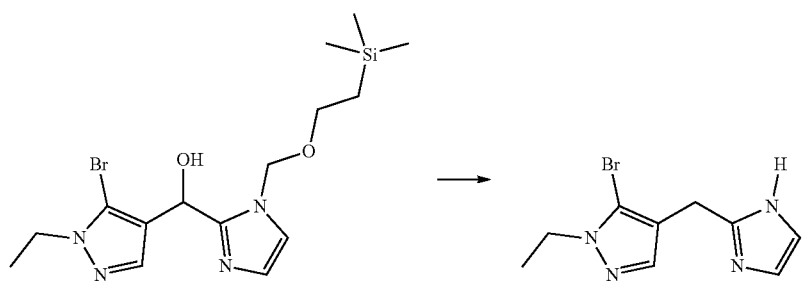 [SMILES: CCn1ncc(C(O)c2nccn2COCC[Si](C)(C)C)c1Br ; CCn1ncc(Cc2ncc[nH]2)c1Br]

m/z (ESI): 255 [M + H]

2-((5-bromo-1-ethyl-1H-pyrazol-4-yl)methyl)-3-chloropyrazine

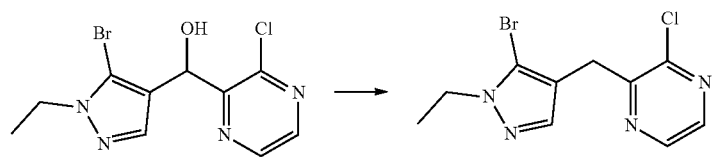 [SMILES: CCn1ncc(C(O)c2nccnc2Cl)c1Br ; CCn1ncc(Cc2nccnc2Cl)c1Br]

m/z (ESI): 301 [M + H]

3-bromo-2-((5-bromo-1-ethyl-1H-pyrazol-4-yl)methyl)pyridine

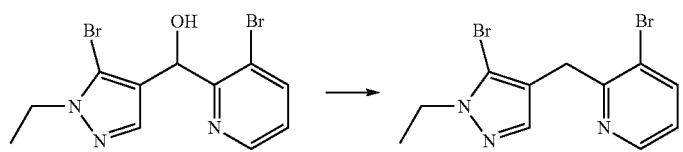 [SMILES: CCn1ncc(C(O)c2ncccc2Br)c1Br ; CCn1ncc(Cc2ncccc2Br)c1Br]

m/z (ESI): 344 [M + H]

-continued 5-((5-bromothiazol-4-yl)methyl)-1-methyl-1H-pyrazole-3-carbonitrile

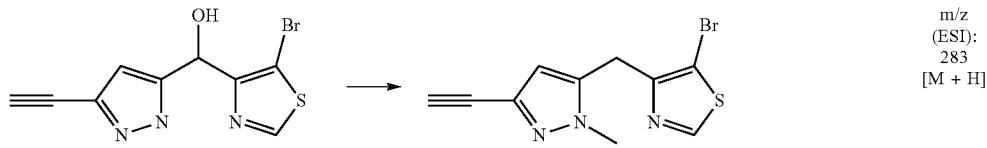

m/z (ESI): 283 [M + H]

1-(cyclopropylmethyl)-4-((5-iodo-2-methyl-2H-1,2,3-triazol-4-yl)methyl)-1H-1,2,3-triazole

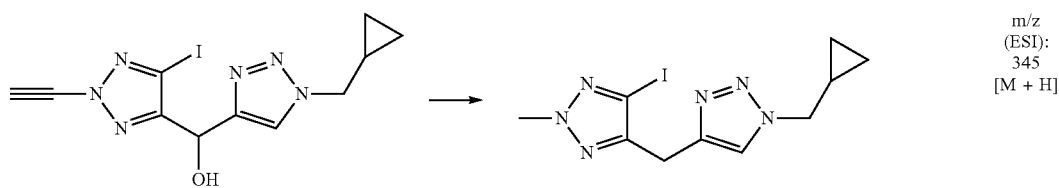

m/z (ESI): 345 [M + H]

3-(cyclopropylmethyl)-5-((5-iodo-2-methyl-2H-1,2,3-triazol-4-yl)methyl)isoxazole

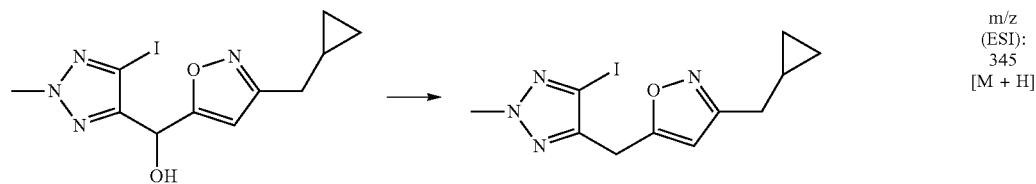

m/z (ESI): 345 [M + H]

4-((3-chloro-1-(2,2-difluoroethyl)-1H-pyrazol-4-yl)methyl)-5-iodo-2-methyl-2H-1,2,3-triazole

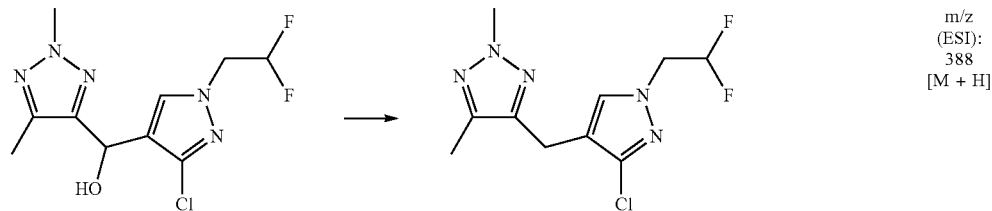

m/z (ESI): 388 [M + H]

5-((5-bromo-2-methylthiazol-4-yl)methyl)-1-methyl-1H-pyrazole-3-carbonitrile

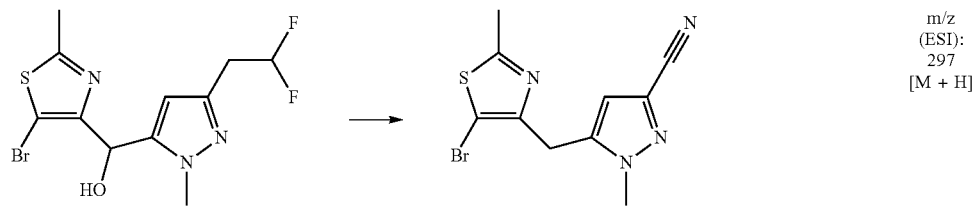

m/z (ESI): 297 [M + H]

3-bromo-2-((1-(cyclopropylmethyl)-1H-pyrazol-4-yl)methyl)-5-fluoropyridine

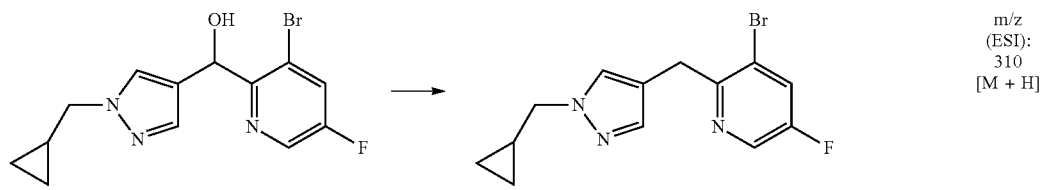

m/z (ESI): 310 [M + H]

-continued 3-bromo-2-((1-(2,2-difluoroethyl)-1H-pyrazol-4-yl)methyl)-5-fluoropyridine

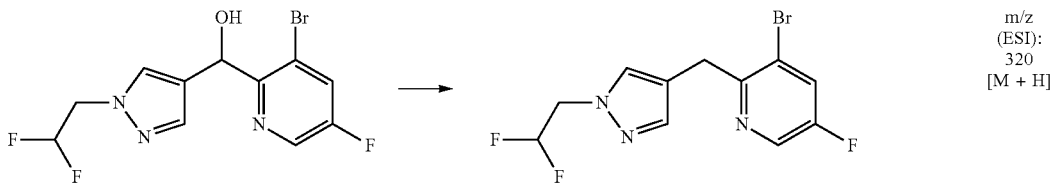

m/z (ESI): 320 [M + H]

2-chloro-3-((1-(cyclopropylmethyl)-3-methyl-1H-pyrazol-4-yl)methyl)pyrazine

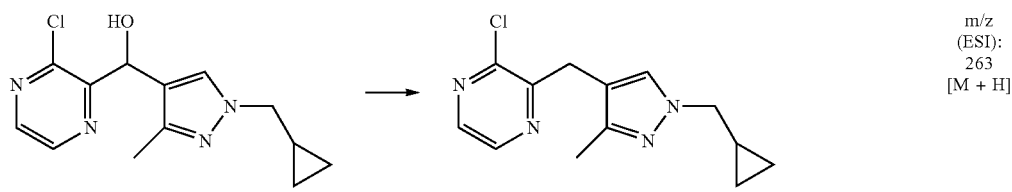

m/z (ESI): 263 [M + H]

5-ethyl-3-((5-iodo-2-methyl-2H-1,2,3-triazol-4-yl)methyl)isothiazole

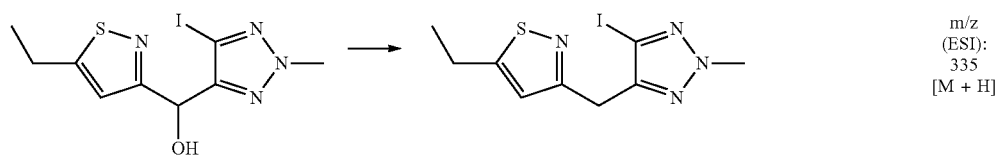

m/z (ESI): 335 [M + H]

4-{[3-chloro-1-(cyclopropylmethyl)-1H-pyrazol-4-yl]methyl}-5-iodo-2-methyl-2H-1,2,3-triazole

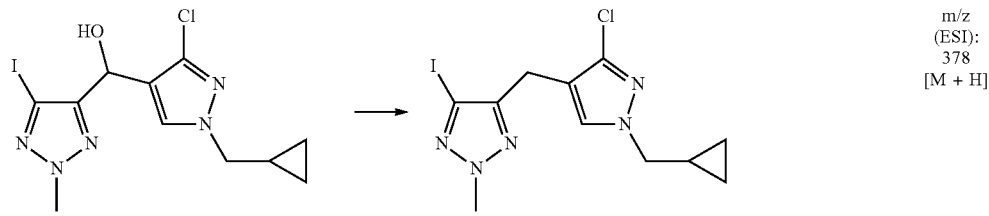

m/z (ESI): 378 [M + H]

3-{[3-chloro-1-(cyclopropylmethyl)-1H-pyrazol-4-yl]methyl}-4-iodo-1-methyl-1H-pyrazole

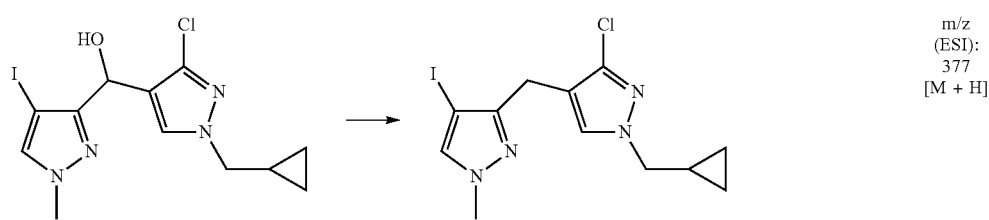

m/z (ESI): 377 [M + H]

(R)-3-(2-(1-((5-bromo-2-nitropyridin-3-yl)oxy)ethyl)-4-fluorophenyl)-4-((1-ethyl-1H-pyrazol-4-yl)methyl)-1,2,5-thiadiazole

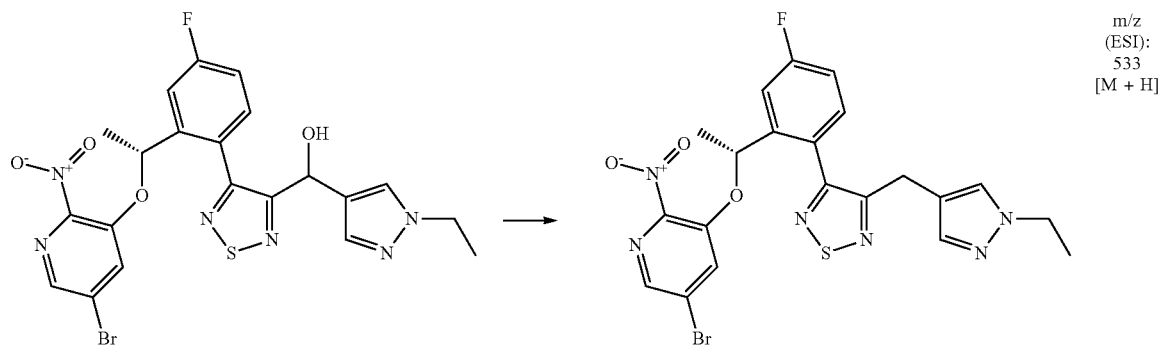

m/z (ESI): 533 [M + H]

-continued

| 4-((3-ethyl-1-methyl-1H-pyrazol-5-yl)methyl)-5-iodo-2-methyl-2H-1,2,3-triazole | |
|---|---|
| 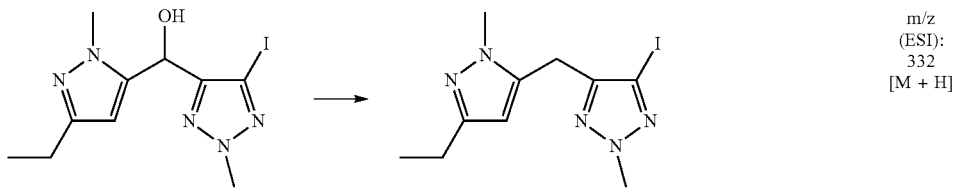 | m/z (ESI): 332 [M + H] |
| 4-{[3-(cyclopropylmethyl)-1-methyl-1H-pyrazol-5-yl]methyl}-5-iodo-2-methyl-2H-1,2,3-triazole | |
| 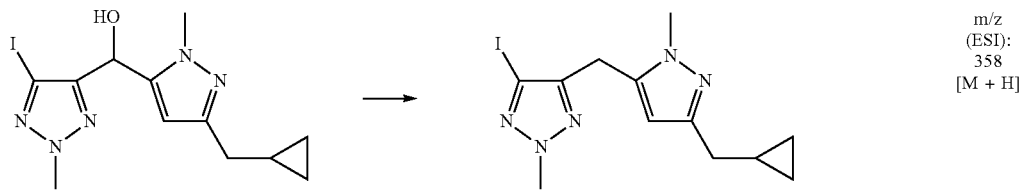 | m/z (ESI): 358 [M + H] |

Synthesis of 5-((5-bromothiazol-4-yl)(hydroxy)methyl)-1-methyl-1H-pyrazole-3-carbonitrile

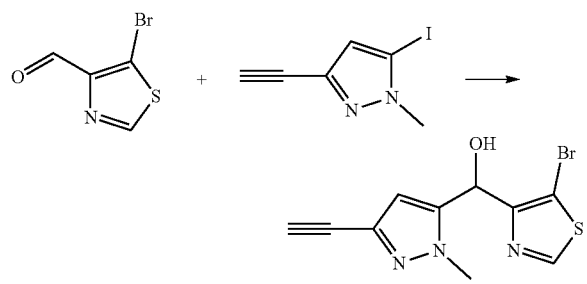

To a stirred solution of 5-iodo-1-methyl-1H-pyrazole-3-carbonitrile (650 mg, 2.79 mmol) in THF (20 mL) was added isopropylmagnesium bromide (3.1 mL, 1 M in THF, 3.1 mmol) at 0° C. After stirring at 0° C. for 30 min, a solution of 5-bromo-1,3-thiazole-4-carbaldehyde (643 mg, 3.35 mmol) in THF (2 mL) was added dropwise. The reaction was stirred at 0° C. for another 30 min, quenched with sat. NH₄Cl (10 mL), extracted with EtOAc (20 mL×2). The combined organic phase was washed with brine (20 mL), dried over Na₂SO₄ and concentrated. The residue was purified by column chromatography on silica gel (50% EtOAc in PE) to give 5-((5-bromothiazol-4-yl)(hydroxy)methyl)-1-methyl-1H-pyrazole-3-carbonitrile (450 mg, 54% yield) as a yellow oil. LC/MS (ESI) (m/z): 299 [M+H]⁺.

The following intermediates were synthesized using a similar experimental protocol:

| (5-bromo-1-ethyl-1H-pyrazol-4-yl)(5-iodo-2-methyl-2H-1,2,3-triazol-4-yl)methanol | |
|---|---|
| 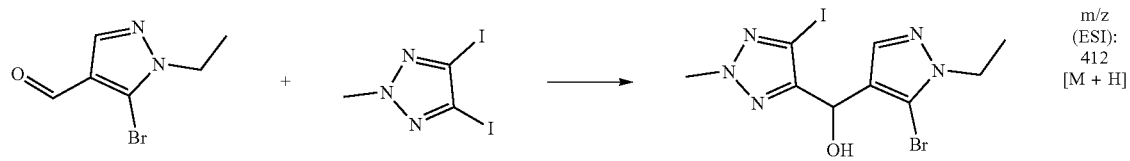 | m/z (ESI): 412 [M + H] |
| (5-bromo-1-ethyl-1H-pyrazol-4-yl)(4-iodo-1-methyl-1H-pyrazol-3-yl)methanol | |
| 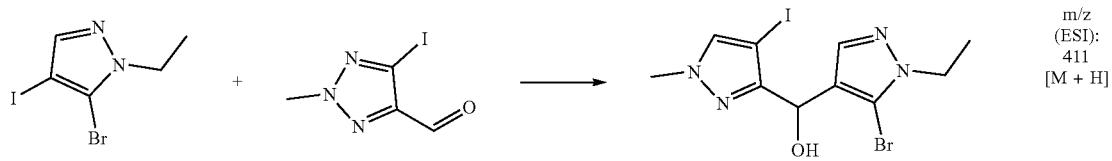 | m/z (ESI): 411 [M + H] |
| (5-bromo-1-cyclobutyl-1H-pyrazol-4-yl)(5-iodo-2-methyl-2H-1,2,3-triazol-4-yl)methanol | |
| 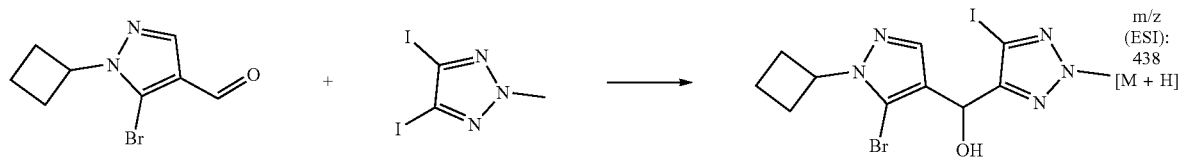 | m/z (ESI): 438 [M + H] |

-continued (5-bromo-1-cyclopropyl-1H-pyrazol-4-yl)(5-iodo-2-methyl-2H-1,2,3-triazol-4-yl)methanol

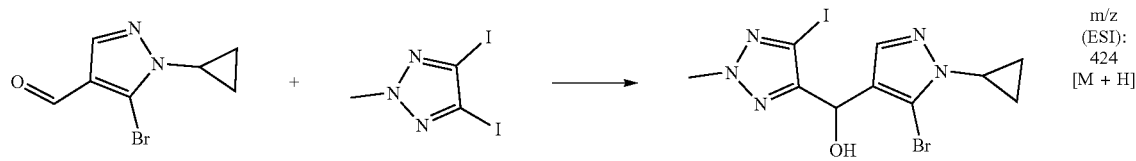

m/z (ESI): 424 [M + H]

ethyl 5-(hydroxy(5-iodo-2-methyl-2H-1,2,3-triazol-4-yl)methyl)isoxazole-3-carboxylate

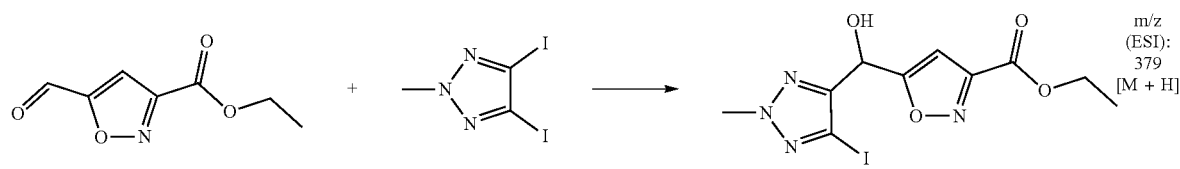

m/z (ESI): 379 [M + H]

(3-ethylisoxazol-5-yl)(5-iodo-2-methyl-2H-1,2,3-triazol-4-yl)methanol

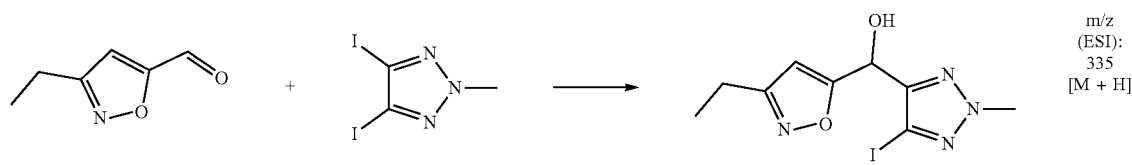

m/z (ESI): 335 [M + H]

(5-bromo-1-ethyl-1H-pyrazol-4-yl)(1-((2-(trimethylsilyl)ethoxy)methyl)-1H-imidazol-2-yl)methanol

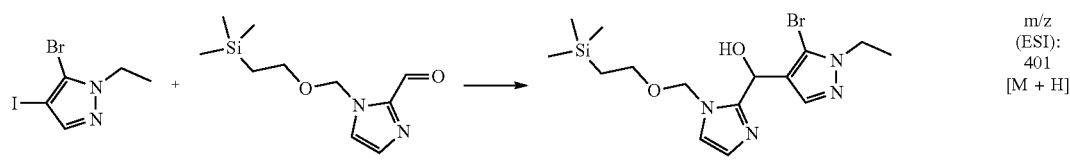

m/z (ESI): 401 [M + H]

(5-bromo-1-ethyl-1H-pyrazol-4-yl)(3-bromopyridin-2-yl)methanol

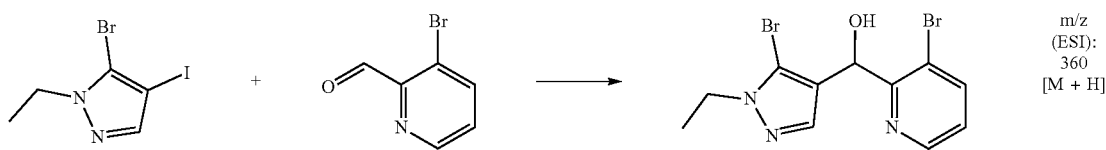

m/z (ESI): 360 [M + H]

(1-(cyclopropylmethyl)-1H-pyrazol-4-yl)(5-iodo-2-methyl-2H-1,2,3-triazol-4-yl)methanol

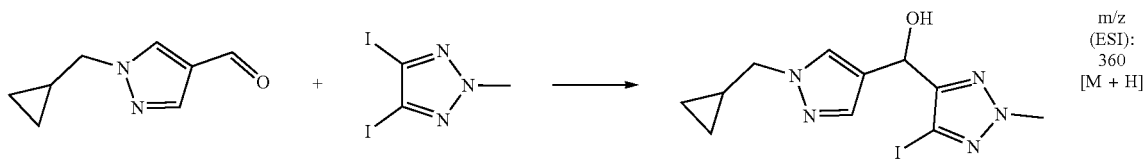

m/z (ESI): 360 [M + H]

(3-(cyclopropylmethyl)isoxazol-5-yl)(5-iodo-2-methyl-2H-1,2,3-triazol-4-yl)methanol

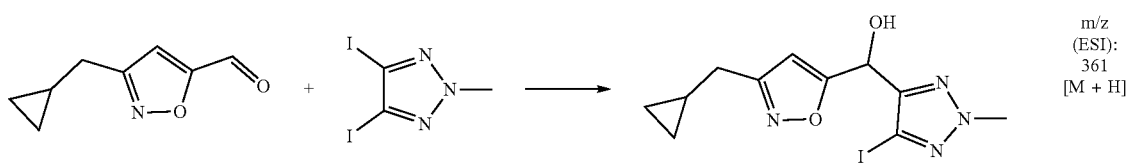

m/z (ESI): 361 [M + H]

-continued (5-iodo-2-methyl-2H-1,2,3-triazol-4-yl)(1-(oxetan-3-yl)-1H-pyrazol-4-yl)methanol

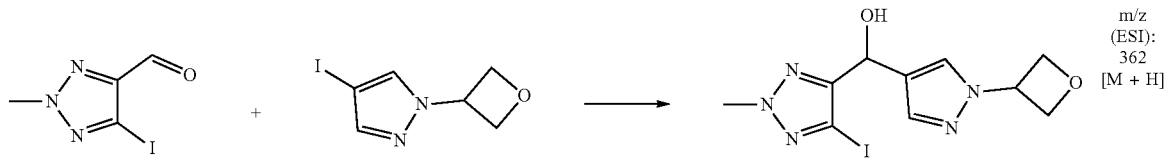

m/z (ESI): 362 [M + H]

(1-ethyl-3-(trifluoromethyl)-1H-pyrazol-4-yl)(5-iodo-2-methyl-2H-1,2,3-triazol-4-yl)methanol

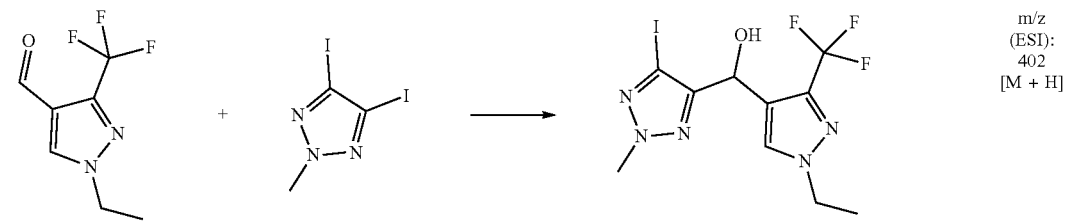

m/z (ESI): 402 [M + H]

(5-ethylisothiazol-3-yl)(5-iodo-2-methyl-2H-1,2,3-triazol-4-yl)methanol

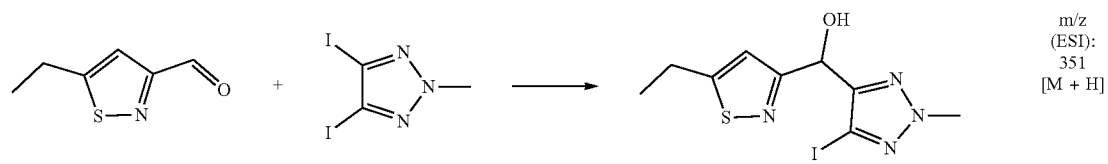

m/z (ESI): 351 [M + H]

(1-ethyl-1H-pyrazol-4-yl)(2-ethyl-5-iodo-2H-1,2,3-triazol-4-yl)methanol

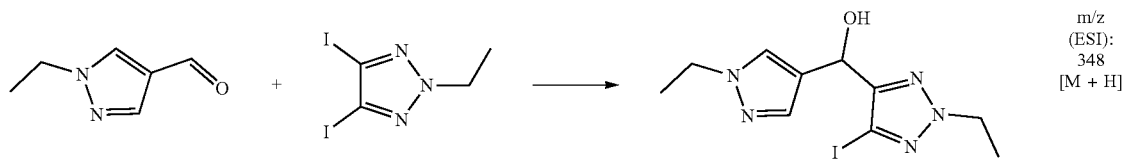

m/z (ESI): 348 [M + H]

(1-(cyclopropylmethyl)-1H-pyrazol-4-yl)(5-iodo-2-62-(trimethylsilyl)ethoxy)methyl)-2H-1,2,3-triazol-4-yl)methanol

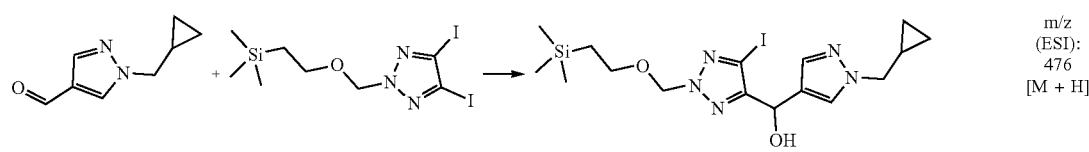

m/z (ESI): 476 [M + H]

(3-ethyl-1-methyl-1H-pyrazol-5-yl)(5-iodo-2-methyl-2H-1,2,3-triazol-4-yl)methanol

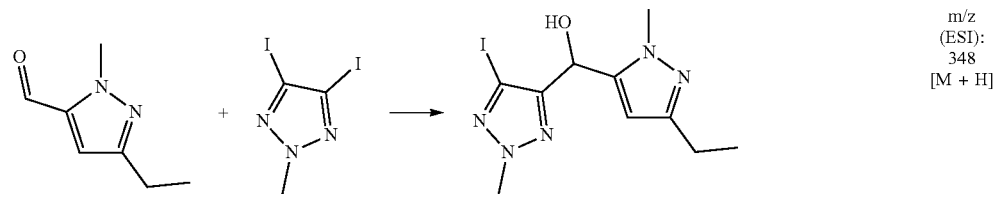

m/z (ESI): 348 [M + H]

(1-ethyl-1H-pyrrol-3-yl)(5-iodo-2-methyl-2H-1,2,3-triazol-4-yl)methanol

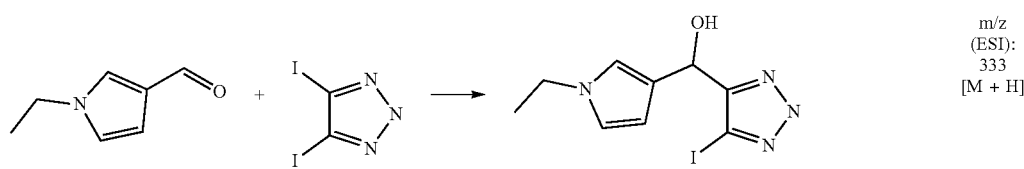

m/z (ESI): 333 [M + H]

Synthesis of [2-(1,3-dioxolan-2-yl)-4-fluorophenyl] trimethylstannane

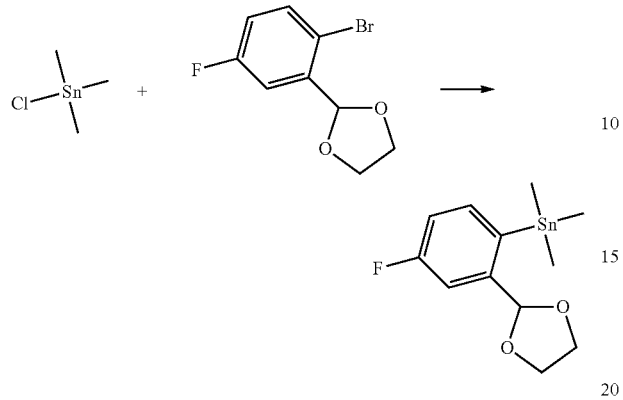

To a mixture of 2-(2-bromo-5-fluorophenyl)-1,3-dioxolane (1.0 g, 4.0 mmol) in THF (20 mL) was added n-BuLi (1.78 mL, 4.45 mmol, 2.5 M) dropwise at −78° C. The mixture was stirred at −78° C. for 1 h. Then, trimethyltin chloride (4.45 mL, 4.45 mmol, 1.0 M in THF) was added dropwise to the mixture. The resulting mixture was stirred at −78° C. for 15 min. The mixture was quenched with sat. NH$_4$Cl (50 mL) at 0° C. and extracted with EtOAc (50 mL×3). The combined extracts were washed with brine (20 mL×2), dried over anhydrous Na$_2$SO$_4$, filtered and concentrated. The residue was purified by flash chromatography on silica gel (10% EtOAc in PE) to give [2-(1,3-dioxolan-2-yl)-4-fluorophenyl]trimethylstannane (600 mg, yield: 44%) as a colorless oil. LC/MS ESI (m/z): 333 [M+H]$^+$.

Synthesis of 4-(5-ethyl-1,2-oxazole-3-carbonyl)-5-iodo-2-methyl-2H-1,2,3-triazole

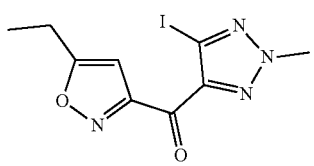 [SMILES: CCc1cc(C(=O)c2nn(C)nc2I)no1]

To a mixture of 5-ethyl-1,2-oxazole-3-carboxylic acid (1.6 g, 11.3 mmol), EDCI (3.36 g, 17.5 mmol), HOBt (2.37 g, 17.5 mmol), N,O-dimethylhydroxylamine hydrochloride (1.25 g, 12.9 mmol) and TEA (2.29 g, 22.7 mmol) in DMF (10 mL) was stirred at 0° C. The mixture was stirred at r.t. for 2 h. The mixture was concentrated in vacuo and extracted with EA (80 mL×3). The organic layer was separated and washed with sat. aq. NaHCO$_3$ solution (40 mL×3) and brine (10 mL), dried over anhydrous Na$_2$SO$_4$, filtered and concentrated. The residue was purified by column chromatography on silica gel (DCM:MeOH=20:1, V/V) to give 5-ethyl-N-methoxy-N-methyl-1,2-oxazole-3-carboxamide (1.5 g, 70%) as a light-yellow solid. LC/MS ESI (m/z): 185 [M+H]$^+$.

To a mixture of 4,5-diiodo-2-methyl-2H-1,2,3-triazole (1.65 g, 4.93 mmol) in THF (20 mL) was degassed with N$_2$ for three times and added isopropylmagnesium bromide (3.79 mL, 4.93 mmol, 1.3 M in 2-methyltetrahydrofuran) at 0° C. for 2 h. 5-ethyl-N-methoxy-N-methyl-1,2-oxazole-3-carboxamide (0.91 g, 4.93 mmol) was added to the mixture and stirred at 0° C. for 2 h. The mixture was quenched with sat. aq. NH$_4$Cl solution (100 mL) and extracted with EA (80 mL×3). The organic layer was separated, dried over anhydrous Na$_2$SO$_4$, filtered and concentrated in vacuo to give a residue, which was purified by column chromatography on silica gel (PE:EA=2:1, V/V) to give 4-(5-ethyl-1,2-oxazole-3-carbonyl)-5-iodo-2-methyl-2H-1,2,3-triazole (310 mg, 19%) as a light-yellow oil. LC/MS ESI (m/z): 333 [M+H]$^+$.

Synthesis of 5-bromo-1-((3-(cyclopropylmethyl)-1-methyl-1H-pyrazol-5-yl)methyl)-1H-1,2,4-triazole

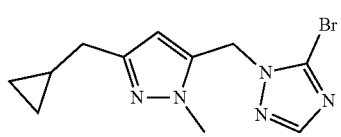 [SMILES: Cn1nc(CC2CC2)cc1Cn1ncnc1Br]

To a stirred solution of (3-(cyclopropylmethyl)-1-methyl-1H-pyrazol-5-yl) methanol (1.05 g, 6.32 mmol) in DCM (20 mL) was added SOCl$_2$ (1.40 mL, 19 mmol) at 0° C. After stirring at r.t. for 2 h, the reaction mixture was concentrated to give crude 5-(chloromethyl)-3-(cyclopropylmethyl)-1-methyl-1H-pyrazole (1.16 g, 99% yield) as a yellow oil.

To a mixture of 5-bromo-1H-1,2,4-triazole (0.88 g, 5.96 mmol) and Cs$_2$CO$_3$ (1.94 g, 5.96 mmol) in DMF (30 mL) was added a solution of 5-(chloromethyl)-3-(cyclopropylmethyl)-1-methyl-1H-pyrazole (1.10 g, 5.96 mmol) in DMF (3 mL) dropwise. The reaction was stirred at 80° C. for 5 h. The reaction mixture was poured into water and extracted with EtOAc twice. The organic layers were washed with brine, dried over anhydrous Na$_2$SO 4 and concentrated in vacuo. The residue was purified by flash column chromatography on silica gel (PE:EA=2:1) and SFC (ChiralPak IA, 250×21.2 mm I.D., 5 μm, 30% MeOH+0.1% aq. NH$_3$ in CO$_2$) to afford 5-bromo-1-((3-(cyclopropylmethyl)-1-methyl-1H-pyrazol-5-yl)methyl)-1H-1,2,4-triazole (300 mg, 18% yield) as a colorless oil. LC/MS (ESI) (m/z): 296 [M+H]$^+$.

Synthesis of 5-bromo-1-((1-isobutyl-3-methyl-1H-pyrazol-4-yl)methyl)-1H-1,2,4-triazole

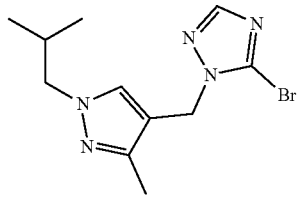 [SMILES: Cc1nn(CC(C)C)cc1Cn1ncnc1Br]

To a solution of (1-isobutyl-3-methyl-1H-pyrazol-4-yl) methanol (800 mg, 4.76 mmol) in anhydrous dichloromethane (30 mL) was added thionyl chloride (3.45 mL, 47.6 mmol). The resulting mixture was stirred at r.t. for 2 h. This reaction solution was concentrated directly to afford crude 4-(chloromethyl)-1-isobutyl-3-methyl-1H-pyrazole (950 mg) as a white solid.

To a solution of crude 4-(chloromethyl)-1-isobutyl-3-methyl-1H-pyrazole (500 mg, 2.68 mmol) in DMF (20 mL) was added 3-bromo-4H-1,2,4-triazole (594 mg, 4.01 mmol)

and K$_2$CO$_3$ (925 mg, 6.70 mmol) under N$_2$ atmosphere. The resulting mixture was stirred at r.t. for 18 h. This solution was diluted with EtOAc. This solution was washed with water (30 mL×3) and brine (30 mL), dried over Na$_2$SO$_4$ and concentrated to dryness. The residue was purified by chromatography on silica gel (50% EtOAc in PE) followed by SFC (ChiralCel OD, 250×21.2 mm, 30% MeOH+0.1% aq. NH$_3$ in CO$_2$) to obtain 5-bromo-1-((1-isobutyl-3-methyl-1H-pyrazol-4-yl)methyl)-1H-1,2,4-triazole (92 mg, yield: 12%) as a colorless liquid. LC/MS (ESI): m/z=298 [M+H]$^+$.

Synthesis of 5-((5-bromo-2-methylthiazol-4-yl)(hydroxy)methyl)-1-methyl-1H-pyrazole-3-carbonitrile

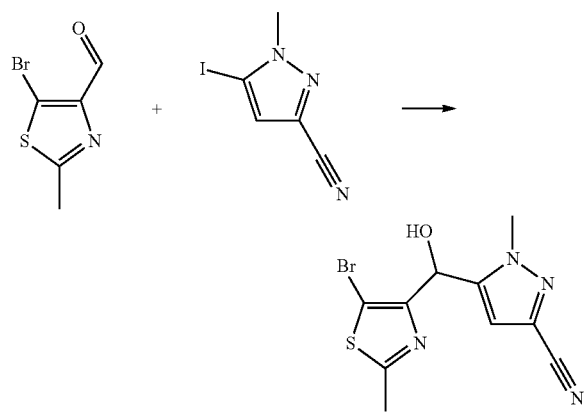

To a solution of 5-iodo-1-methyl-1H-pyrazole-3-carbonitrile (900 mg, 3.86 mmol) in THF (9 mL) was added isopropylmagnesium chloride-lithium chloride complex (3.27 mL, 4.25 mmol, 1.3 M in THF) dropwise at 0° C., and the mixture was stirred at r.t. for 2 h. After 2 h, 5-bromo-2-methylthiazole-4-carbaldehyde (796 mg, 3.86 mmol) was added and the resulting mixture was stirred at r.t. overnight. After overnight, the reaction mixture was quenched by adding sat. aq. NH$_4$Cl solution (10 mL), extracted with EA (3×10 mL), combined all organic phases, washed with sat. aq. NH$_4$Cl solution (10 mL) and brine (10 mL), dried over anhydrous Na$_2$SO$_4$, filtered and concentrated in vacuo. The residue was purified by flash chromatography (0→5% MeOH in DCM) to give 5-((5-bromo-2-methylthiazol-4-yl)(hydroxy)methyl)-1-methyl-1H-pyrazole-3-carbonitrile (553 mg, 46%) as a yellow gum. LC/MS ESI (m/z): 313 [M+H]$^+$.

The following intermediates were synthesized using a similar experimental protocol:

Synthesis of (5-bromo-1-ethyl-1H-pyrazol-4-yl)(3-chloropyrazin-2-yl)methanol

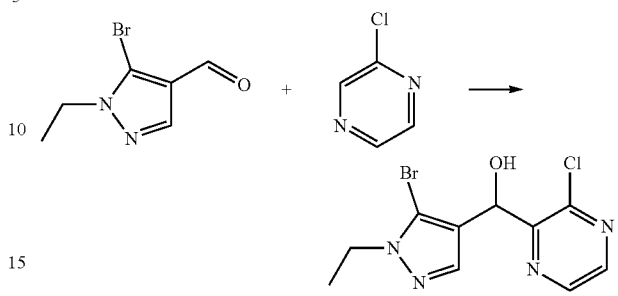

To a solution of 2-chloropyrazine (1.00 g, 8.73 mmol) in THF (35 mL) at −78° C. was added LiTMP (1.0 M in THF, 11.4 mL, 11.4 mmol) dropwise under N$_2$ atmosphere. After the addition, the mixture was stirred at −70° C. for 0.5 h, then a solution of 5-bromo-1-ethyl-1H-pyrazole-4-carbaldehyde (2.13 g, 10.5 mmol) in THF (5 mL) was added. The resulting mixture was stirred at −70° C. for an additional 1.5 h. The mixture was quenched with sat. NH$_4$Cl solution, then extracted with DCM twice (40 mL×2). The combined organic layer was washed with brine, dried over anhydrous Na$_2$SO$_4$, filtered and concentrated. The residue was purified by column chromatography on silica gel (30% EtOAc in PE) to give (5-bromo-1-ethyl-1H-pyrazol-4-yl)(3-chloropyrazin-2-yl)methanol as a yellow oil (1.29 g, 47% yield). LC/MS ESI (n/z): 317 [M+H]$^+$.

Synthesis of (1-ethyl-1H-pyrrol-3-yl)(5-iodo-2-methyl-2H-1,2,3-triazol-4-yl)methanone

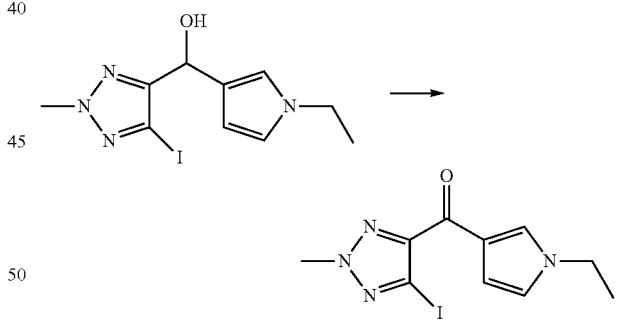

| [1-(cyclopropylmethyl)-3-methyl-1H-pyrazol-4-yl](5-iodo-2-methyl-2H-1,2,3-triazol-4-yl)methanol | |
|---|---|
| 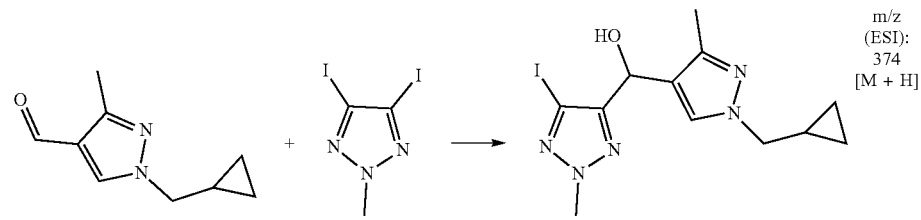 | m/z (ESI): 374 [M + H] |

To a solution of (1-ethyl-1H-pyrrol-3-yl)(5-iodo-2-methyl-2H-1,2,3-triazol-4-yl)methanol (400 mg, 1.20 mmol) in DCM (10 mL) was added manganese(IV) oxide (1.57 g, 18.1 mmol). Then the mixture was stirred at r.t. for 2 h. The reaction was filtered, and the residue was washed by DCM. The filtrate was concentrated and the residue was purified by chromatography on silica gel (0%-50% of PE in EA) to give (1-ethyl-1H-pyrrol-3-yl)(5-iodo-2-methyl-2H-1,2,3-triazol-4-yl)methanone (188 mg, 47% yield) as a yellow solid. LC/MS (ESI) n/z: 331.3 [M+H]$^+$.

Synthesis of 4-[(4-cyclobutyl-1H-1,2,3-triazol-1-yl)methyl]-5-iodo-2-methyl-2H-1,2,3-triazole

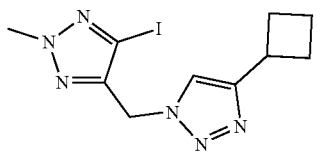 [SMILES: Cn1nc(I)c(Cn2cc(C3CCC3)nn2)n1]

A mixture of (5-iodo-2-methyl-2H-1,2,3-triazol-4-yl)methanol (900 mg, 4.00 mmol) in SOCl$_2$ (5.8 mL, 80 mmol) was stirred at r.t. for 1 h. The mixture was quenched with sat. aq. NaHCO$_3$ solution (20 mL) at 0° C. and extracted with EA (50 mL×3). The organic layer was combined and dried over anhydrous Na$_2$SO$_4$, filtered and concentrated in vacuo to give a residue, which was purified by flash chromatography (50% EtOAc in PE) to give 4-(chloromethyl)-5-iodo-2-methyl-2H-1,2,3-triazole (900 mg, 87%) as a light-yellow oil. LC/MS (ESI) m/z: 258 [M+H]$^+$.

To a mixture of 4-(chloromethyl)-5-iodo-2-methyl-2H-1,2,3-triazole (900 mg, 3.40 mmol) and NaN$_3$ (454 mg, 6.90 mmol) in DMF (10 mL) was stirred at 0° C. The mixture was stirred at r.t. for 2 h. The mixture was extracted with EA (50 mL×3). The organic layer was combined and dried over anhydrous Na$_2$SO$_4$, filtered and concentrated in vacuo to give a residue, which was purified by flash chromatography (50% EtOAc in PE) to give 4-(azidomethyl)-5-iodo-2-methyl-2H-1,2,3-triazole (880 mg, 95%) as a light-yellow oil.

A mixture of 4-(azidomethyl)-5-iodo-2-methyl-2H-1,2,3-triazole (200 mg, 0.75 mmol), ethynylcyclobutane (182 mg, 2.27 mmol), CuSO$_4$ (20 mg, 0.12 mmol), and sodium ascorbate (20 mg, 0.10 mmol) in t-BuOH (10 mL) and H$_2$O (10 mL) was stirred at r.t. for 2 h. The mixture was extracted with EA (40 mL×3). The organic layer was combined, washed with brine (10 mL), dried over anhydrous Na$_2$SO$_4$, filtered and concentrated in vacuo to give a residue, which was purified by flash chromatography (5% MeOH in DCM) to give 4-cyclobutyl-1-[(5-iodo-2-methyl-2H-1,2,3-triazol-4-yl)methyl]-1H-1,2,3-triazole (100 mg, 38%) as a light-yellow oil. LC/MS ESI (m/z): 345 [M+H]$^+$.

Synthesis of (5-bromo-1-ethyl-1H-pyrazol-4-yl)(5-iodo-1-methyl-1H-imidazol-4-yl)methanol

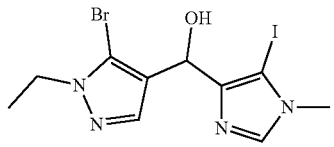 [SMILES: CCn1ncc(C(O)c2ncn(C)c2I)c1Br]

To a suspension of 4,5-diiodo-1H-imidazole (8.0 g, 25.01 mmol) and LiCl (0.13 g, 3.13 mmol) in THF (50 mL) at −10° C. was added methylmagnesium bromide (3 M, 6.59 mL, 6.59 mmol) dropwise under N$_2$ atmosphere. The mixture was stirred at −10° C. for 30 min. Then to the mixture was added isopropylmagnesium bromide (1.3 M, 2.65 mL, 3.44 mmol) dropwise, the resulting mixture was stirred at r.t. for 1.5 h. After this, to the mixture was added 5-bromo-1-ethyl-1H-pyrazole-4-carbaldehyde (6.09 g, 30.0 mmol) at −10° C. and the resulting mixture was stirred at r.t. for additional 2 h. The reaction mixture was quenched with sat. aq. NH$_4$Cl solution (50 mL), extracted with EtOAc (3×50 mL), washed with brine (30 mL), dried over anhydrous Na$_2$SO$_4$, filtered and concentrated. The residue was purified by flash chromatography (silica gel, 0-30% MeOH in DCM) to give (5-bromo-1-ethyl-1H-pyrazol-4-yl)(5-iodo-1H-imidazol-4-yl)methanol as a white solid (3.5 g, yield: 35%). LC/MS (ESI) m/z: 397 [M+H]$^+$.

To a solution of (5-bromo-1-ethyl-1H-pyrazol-4-yl)(5-iodo-1H-imidazol-4-yl)methanol (3.50 g, 8.82 mmol) in DMF (60 mL) at −10° C. was added cesium carbonate (4.31 g, 13.2 mmol). The mixture was stirred at −10° C. for 15 min. After this, to the suspension was added iodomethane (0.60 mL, 9.7 mmol) dropwise and the resulting mixture was stirred at −10° C. for 1.5 h. Then the reaction mixture was filtered, the filtrate was diluted with water (50 mL), extracted with EtOAc (3×50 mL). The combined organic layers were concentrated, washed with sat. aq. NH$_4$Cl solution (3×30 mL) and brine (30 mL), dried over anhydrous Na$_2$SO$_4$, filtered, and concentrated. The residue was purified by flash chromatography (silica gel, 0-10% MeOH in DCM) to give (5-bromo-1-ethyl-1H-pyrazol-4-yl)(5-iodo-1-methyl-1H-imidazol-4-yl)methanol as a white solid (903 mg, yield: 25%). LC/MS (ESI) m/z: 411 [M+H]$^+$.

Synthesis of (5-bromo-1-ethyl-1H-pyrazol-4-yl)(4-iodo-1-methyl-1H-imidazol-5-yl)methanol

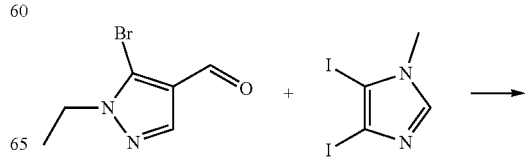

To a solution of 4,5-diiodo-1-methyl-1H-imidazole (2.00 g, 5.99 mmol) in DCM (100 mL) at −70° C. was added ethylmagnesium bromide (1 M, 6.59 mL, 6.59 mmol) drop-

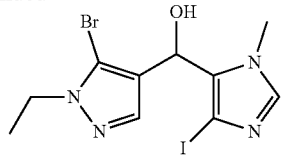

wise under N₂ atmosphere. The mixture was stirred at −70° C. for 30 min. Then to the mixture was added a solution of 5-bromo-1-ethyl-1H-pyrazole-4-carbaldehyde (1.34 g, 6.59 mmol) in DCM (10 mL) and stirred at −70° C. for 2 h. The reaction mixture was quenched with sat. aq. NH₄Cl solution (50 mL), extracted with DCM (3×50 mL), washed with brine, dried over anhydrous Na₂SO₄, filtered and concentrated. The residue was purified by column chromatography on silica gel (30% EtOAc in PE) to give (5-bromo-1-ethyl-1H-pyrazol-4-yl)(4-iodo-1-methyl-1H-imidazol-5-yl)methanol as a yellow oil (1.80 g, yield: 73%). LC/MS (ESI) m/z: 411 [M+H]⁺.

Synthesis of (4-bromo-1-methyl-1H-pyrazol-3-yl) (1-(cyclopropylmethyl)-1H-pyrazol-4-yl)methanol

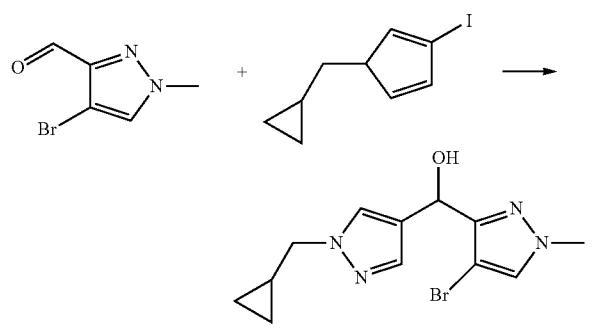

To a stirred solution of 1-(cyclopropylmethyl)-4-iodo-1H-pyrazole (415 mg, 1.67 mmol) in THF (5 mL) was added i-PrMgCl.LiCl (1.3 mL, 1.3 M in THF, 1.7 mmol) dropwise at 0° C. under N₂. After stirring at 0° C. for 1 h, a solution of 4-bromo-1-methyl-1H-pyrazole-3-carbaldehyde (316 mg, 1.67 mmol) in THF (1 mL) was added at 0° C. The reaction was stirred at r.t. for 2 h, quenched with sat. NH₄Cl (10 mL), extracted with EtOAc (10 mL), dried over Na₂SO₄ and concentrated to dryness. The residue was purified by column chromatography on silica gel (PE:EtOAc=1:1) to give (4-bromo-1-methyl-1H-pyrazol-3-yl)(1-(cyclopropylmethyl)-1H-pyrazol-4-yl)methanol (258 mg, 50% yield) as a yellow oil. LC/MS (ESI) (m/z): 311 [M+H]⁺.

The following intermediates were synthesized using a similar experimental protocol:

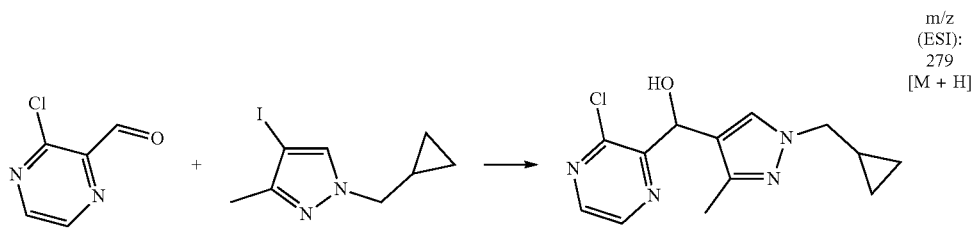

(3-chloropyrazin-2-yl)(1-(cyclopropylmethyl)-3-methyl-1H-pyrazol-4-yl)methanol m/z (ESI): 279 [M + H]

Synthesis of Tert-Butyl (E)-2-((5-bromo-1-ethyl-1H-pyrazol-4-yl)methylene)hydrazine-1-carboxylate

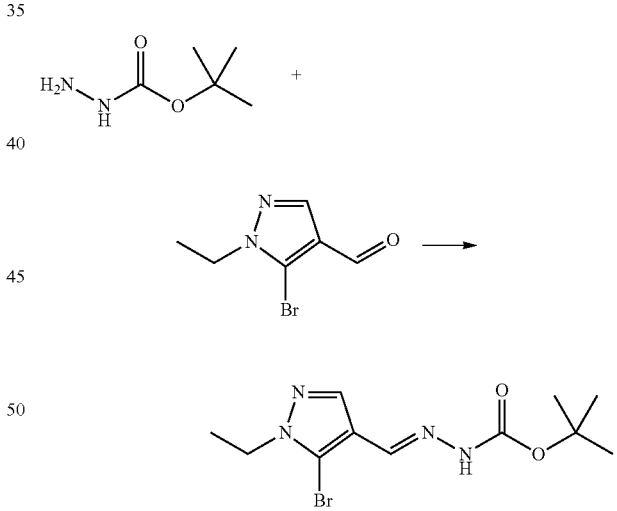

A solution of 5-bromo-1-ethyl-1H-pyrazole-4-carbaldehyde (3 g, 14.8 mmol) and (tert-butoxycarbonyl)hydrazine (1.9 g, 14.8 mmol) in MeOH (30 mL) was stirred at 25° C. for 12 h. The mixture was concentrated under reduced pressure to give crude tert-butyl (E)-2-((5-bromo-1-ethyl-1H-pyrazol-4-yl)methylene)hydrazine-1-carboxylate (4.71 g, 100% yield) as a yellow solid which was used in the next step without further purification. LC/MS (ESI): m/z=317 [M+H]⁺.

The following intermediates were synthesized using a similar experimental protocol:

| (E)-tert-butyl 2-((5-bromo-1-cyclobutyl-1H-pyrazol-4-yl)methylene)hydrazinecarboxylate |
|---|

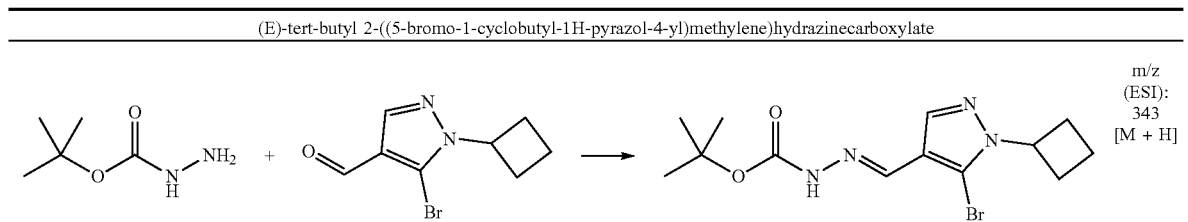

m/z (ESI): 343 [M + H]

| tert-butyl (E)-2-((5-bromo-3-chloro-1-ethyl-1H-pyrazol-4-yl)methylene)hydrazine-1-carboxylate |
|---|

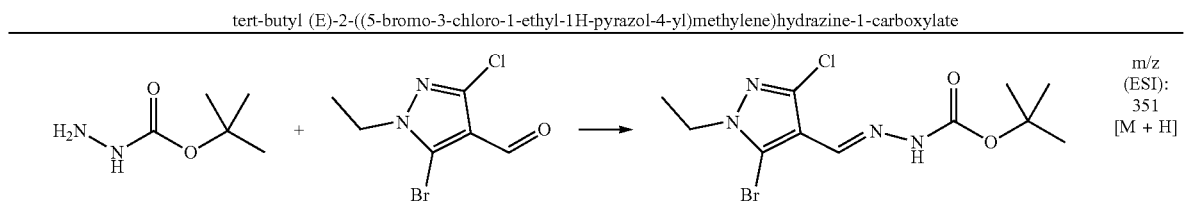

m/z (ESI): 351 [M + H]

| tert-butyl (E)-2-((1-(cyclopropylmethyl)-1H-pyrazol-4-yl)methylene)hydrazine-1-carboxylate |
|---|

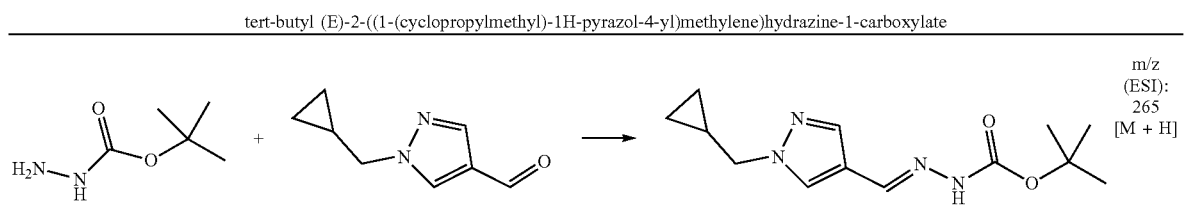

m/z (ESI): 265 [M + H]

Synthesis of (5-ethyl-1,2-oxazol-3-yl)(5-iodo-2-methyl-2H-1,2,3-triazol-4-yl)methanol

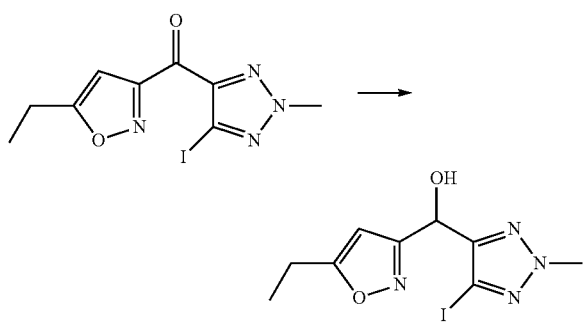

A mixture of 4-(5-ethyl-1,2-oxazole-3-carbonyl)-5-iodo-2-methyl-2H-1,2,3-triazole (310 mg, 0.93 mmol) in MeOH (2 mL) was added NaBH$_4$ (35 mg, 0.93 mmol) stirred at r.t. for 1 h. The mixture was quenched with sat. aq. NH$_4$Cl solution (10 mL) at 0° C. and extracted with EA (20 mL×3). The organic layer was separated, dried over anhydrous Na$_2$SO$_4$, filtered and concentrated to give a residue, which was purified by column chromatography on silica gel (PE:EA=1:1, V/V) to give (5-ethyl-1,2-oxazol-3-yl)(5-iodo-2-methyl-2H-1,2,3-triazol-4-yl)methanol (150 mg, 48.1%) as a light-yellow oil. LC/MS ESI (n/z): 335 [M+H]$^+$.

The following intermediates were synthesized using a similar experimental protocol:

| 1-(2-{1-[(5-bromo-1-ethyl-1H-pyrazol-4-yl)methyl-1H-1,2,4-triazol-5-yl}-5-fluorophenyl)ethan-1-ol |
|---|

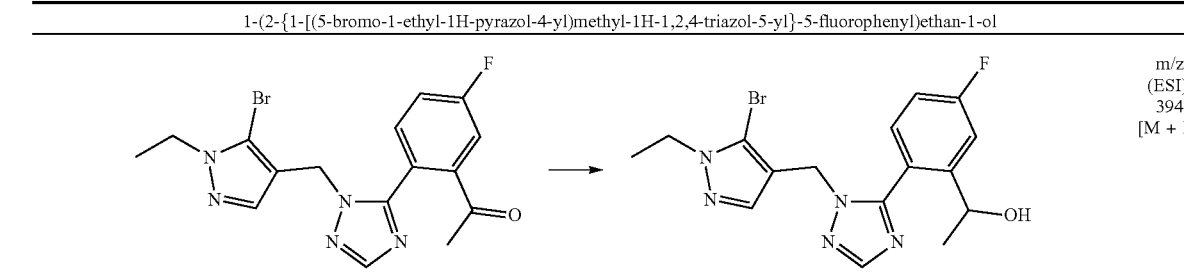

m/z (ESI): 394 [M + H]

1-(2-(1-((5-bromo-1-cyclobutyl-1H-pyrazol-4-yl)methyl)-1H-1,2,4-triazol-5-yl)-5-fluorophenyl)ethanol

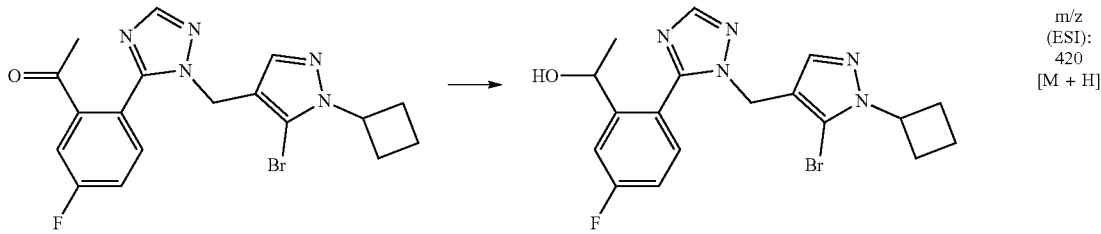

m/z (ESI): 420 [M + H]

1-(2-(1-((5-bromo-1-ethyl-1H-pyrazol-4-yl)methyl)-3-methyl-1H-1,2,4-triazol-5-yl)-5-fluorophenyl)ethanol

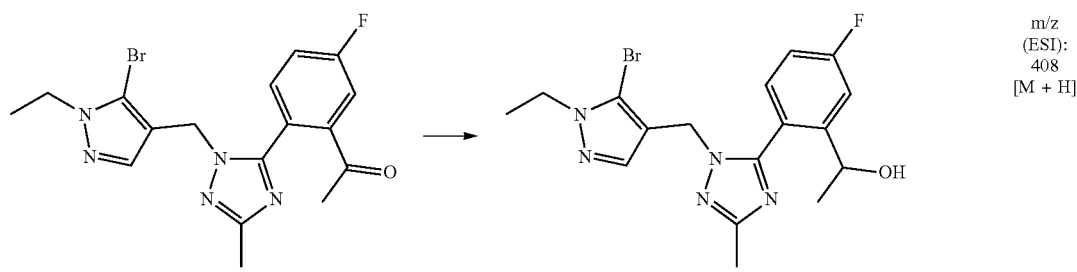

m/z (ESI): 408 [M + H]

1-(2-(5-((5-bromo-1-ethyl-1H-pyrazol-4-yl)methyl)-3-methyl-1H-1,2,4-triazol-1-yl)-5-fluorophenyl)ethan-1-ol

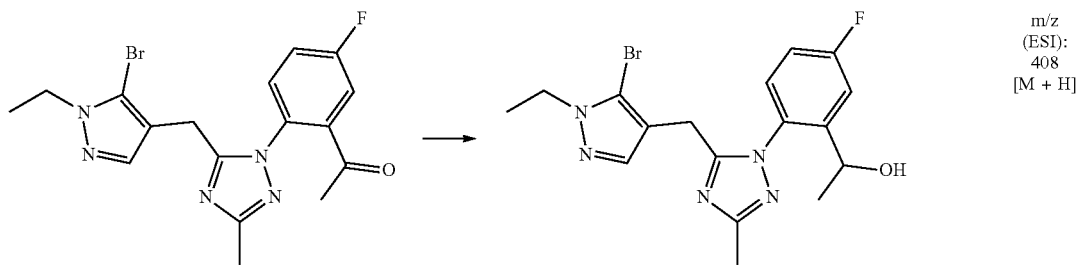

m/z (ESI): 408 [M + H]

1-(2-{1-[(5-bromo-3-chloro-1-ethyl-1H-pyrazol-4-yl)methyl-1H-1,2,4-triazol-5-yl}-5-fluorophenyl)ethan-1-ol

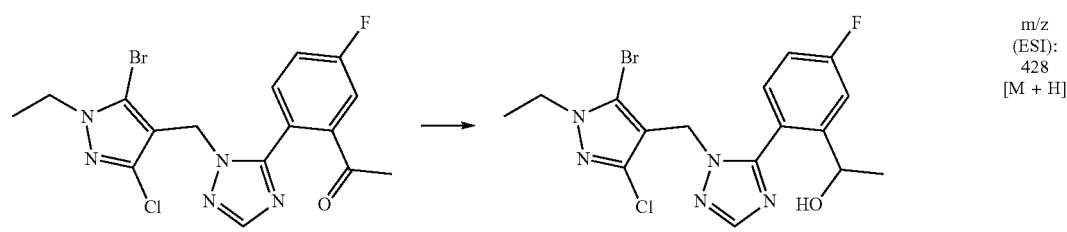

m/z (ESI): 428 [M + H]

1-(2-(1-((5-bromo-1-ethyl-1H-pyrazol-4-yl)methyl)-1H-pyrazol-5-yl)-5-fluoropyridin-3-yl)ethan-1-ol

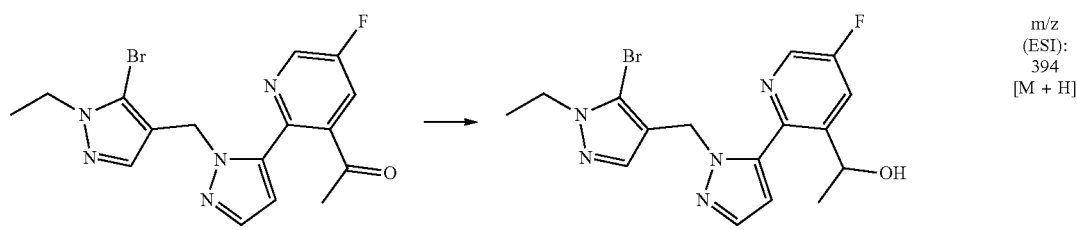

m/z (ESI): 394 [M + H]

1-(2-(4-((3-chloro-1-ethyl-1H-pyrazol-4-yl)methyl)-2-methyloxazol-5-yl)-5-fluorophenyl)ethan-1-ol

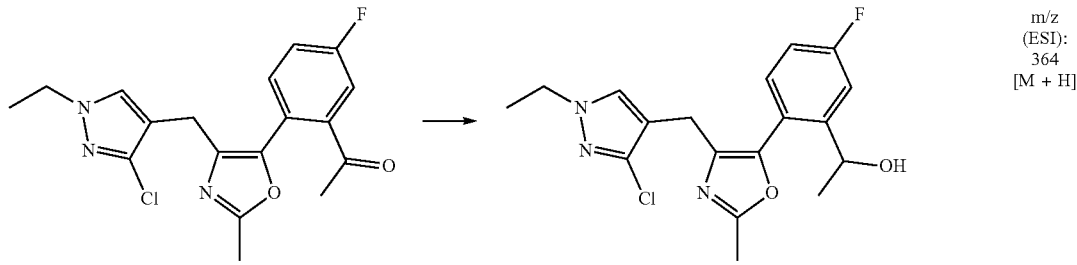

m/z (ESI): 364 [M + H]

(4-(2-((R)-1-((5-bromo-2-nitropyridin-3-yl)oxy)ethyl)-4-fluorophenyl)-1,2,5-thiadiazol-3-yl)(1-ethyl-1H-pyrazol-4-yl)methanol

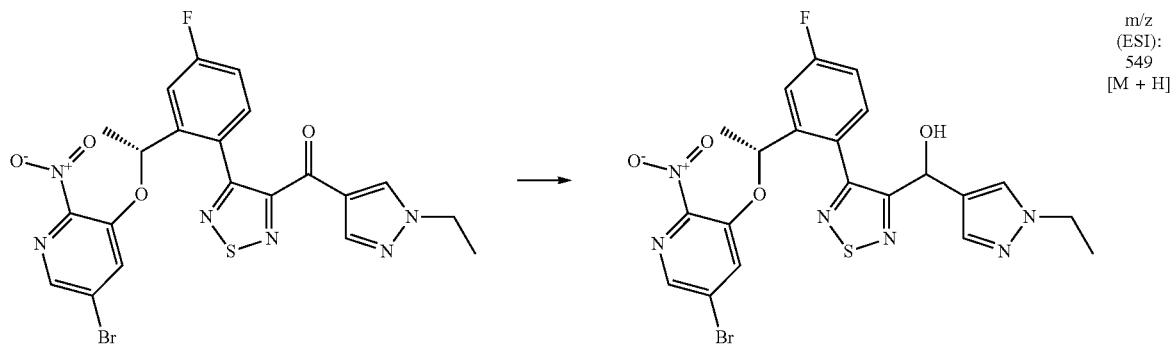

m/z (ESI): 549 [M + H]

1-(2-(1-((3-ethylisoxazol-5-yl)methyl)-1H-tetrazol-5-yl)-5-fluorophenyl)ethan-1-ol

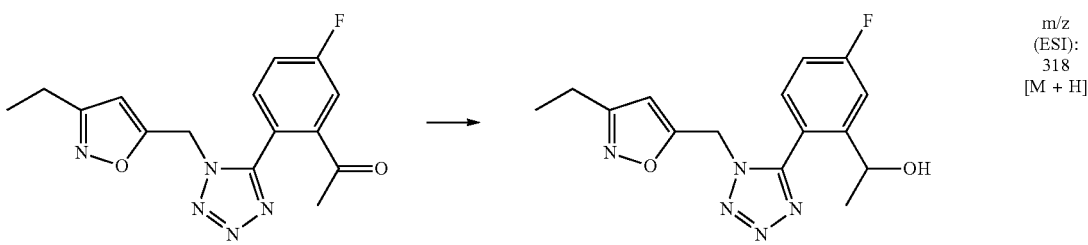

m/z (ESI): 318 [M + H]

1-(2-(4-((1-ethyl-1H-pyrazol-4-yl)methyl)-2-methyloxazol-5-yl)-5-fluorophenyl)ethan-1-ol

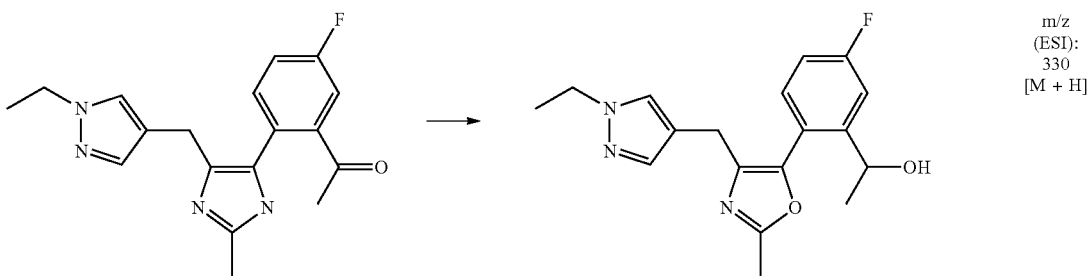

m/z (ESI): 330 [M + H]

1-(2-(1-((1-(cyclopropylmethyl)-1H-pyrazol-4-yl)methyl)-3-methyl-1H-1,2,4-triazol-5-yl)-5-fluorophenyl)ethan-1-ol

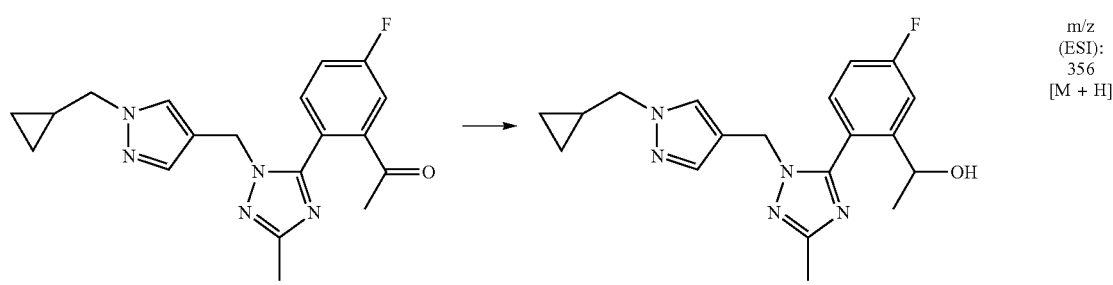

m/z (ESI): 356 [M + H]

[5-(2-bromo-4-fluorophenyl)-2-methyl-1,3-oxazol-4-yl][3-chloro-1-(cyclopropylmethyl)-1H-pyrazol-4-yl]methanol

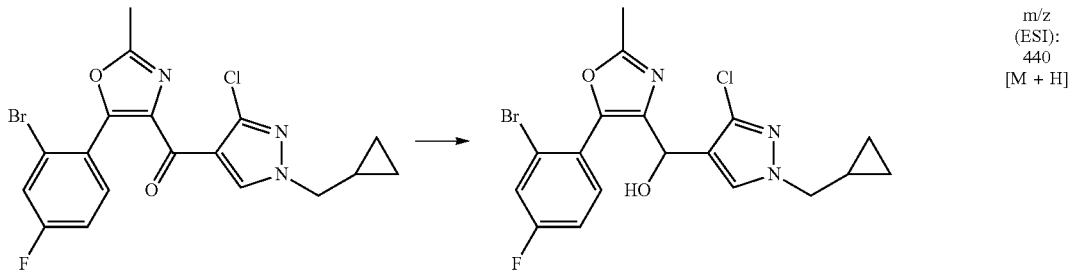

m/z (ESI): 440 [M + H]

1-[2-(4-{[3-chloro-1-(cyclopropylmethyl)-1H-pyrazol-4-yl]methyl}-2-methyl-1,3-oxazol-5-yl)-5-fluorophenyl]ethan-1-ol

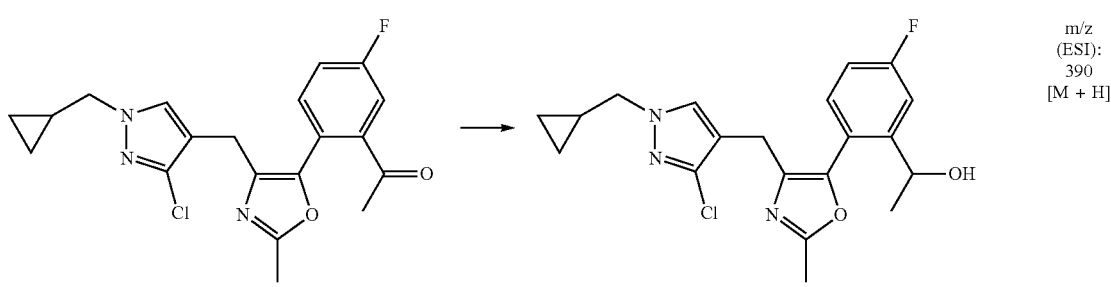

m/z (ESI): 390 [M + H]

Synthesis of 2-ethyl-4-[(1-ethyl-1H-pyrazol-4-yl)methyl]-5-iodo-2H-1,2,3-triazole

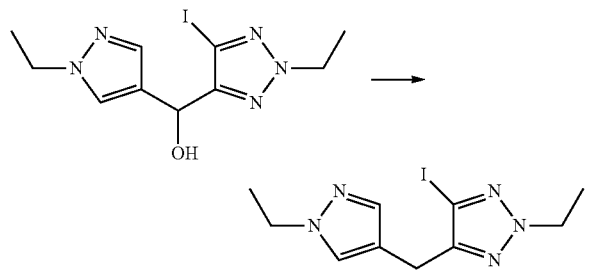

To a solution of (1-ethyl-1H-pyrazol-4-yl)(2-ethyl-5-iodo-2H-1,2,3-triazol-4-yl)methanol (190 mg, 0.547 mmol) in DCM (1 mL), were added Et₃SiH (191 mg, 1.64 mmol) and TFA (250 mg, 2.19 mmol) at 0° C., and then the mixture was stirred at 25° C. for 2 h. The mixture was concentrated, basified with sat. aq. NaHCO₃ to pH 7, then extracted with DCM (15 mL×3). The combined organic layers were washed with brine (15 mL) and dried over Na₂SO₄, then concentrated. The residue purified by flash chromatography (silica gel, 10→50% EtOAc in PE) to give 2-ethyl-4-[(1-ethyl-1H-pyrazol-4-yl)methyl]-5-iodo-2H-1,2,3-triazole (184 mg, yield: 98%) as a light-yellow oil. LC/MS (ESI) m/z: 332.0 [M+H]⁺.

The following intermediates were synthesized using a similar experimental protocol:

4-[(5-bromo-1-cyclobutyl-1H-pyrazol-4-yl)methyl]-5-iodo-2-methyl-2H-1,2,3-triazole

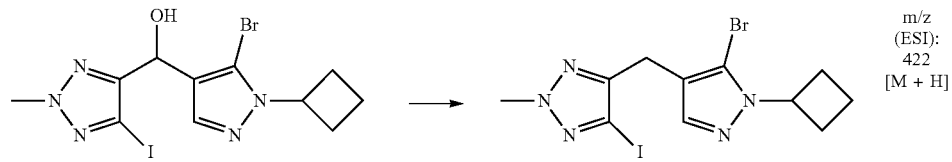

m/z (ESI): 422 [M + H]

4-iodo-2-methyl-5-((1-(oxetan-3-yl)-1H-pyrazol-4-yl)methyl)-2H-1,2,3-triazole

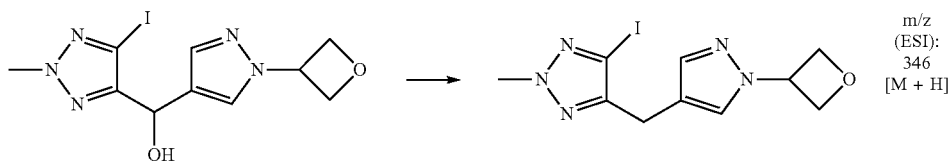

m/z (ESI): 346 [M + H]

| 5-(2-bromo-4-fluorophenyl)-4-{[3-chloro-1-(cyclopropylmethyl)-1H-pyrazol-4-yl]methyl}-2-methyl-1,3-oxazole | |
|---|---|
| 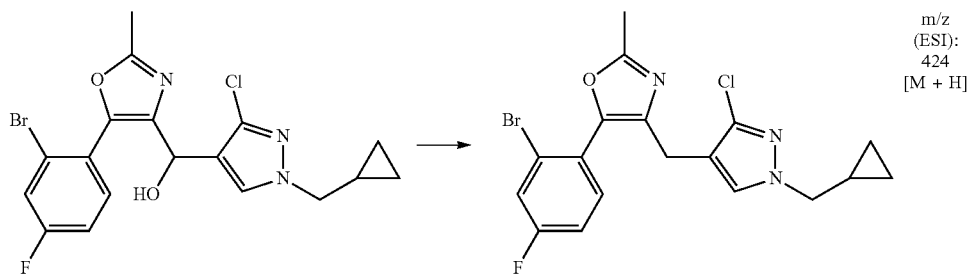 | m/z (ESI): 424 [M + H] |

Synthesis of (3-cyclobutylisoxazol-5-yl)(5-iodo-2-methyl-2H-1,2,3-triazol-4-yl)methanol

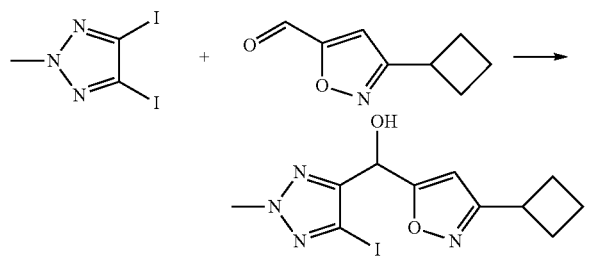

To a solution of 4,5-diiodo-2-methyl-2H-1,2,3-triazole (1.1 g, 3.18 mmol) in THF (20 mL) was added isopropylmagnesium bromide (3.2 mL) at −15° C. After the mixture was stirred for 1 h, a solution of 3-cyclobutyl-1,2-oxazole-5-carbaldehyde (400 mg, 2.65 mmol) in THF (10 mL) was added. The resulting mixture was stirred at r.t. for 1 h. The reaction mixture was quenched with water and extracted with EtOAc (100 mL). The combined EtOAc layers were washed with brine, dried over Na$_2$SO$_4$ and concentrated under reduced pressure. The residue was purified by flash column chromatography on silica gel eluting with MeOH in DCM (0 →5%) to give (3-cyclobutylisoxazol-5-yl)(5-iodo-2-methyl-2H-1,2,3-triazol-4-yl)methanol (420 mg, 44%) as a pale-yellow oil. LC/MS (ESI): m/z=361 [M+H]$^+$.

The following intermediates were synthesized using a similar experimental protocol:

| (1-(2,2-difluoroethyl)-1H-pyrazol-4-yl)(5-iodo-2-methyl-2H-1,2,3-triazol-4-yl)methanol | |
|---|---|
| 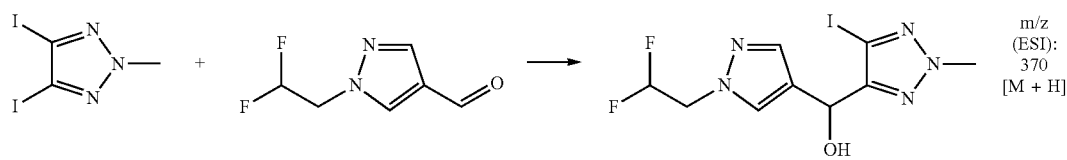 | m/z (ESI): 370 [M + H] |

| (3-chloro-1-(2,2-difluoroethyl)-1H-pyrazol-4-yl)(5-iodo-2-methyl-2H-1,2,3-triazol-4-yl)methanol | |
|---|---|
| 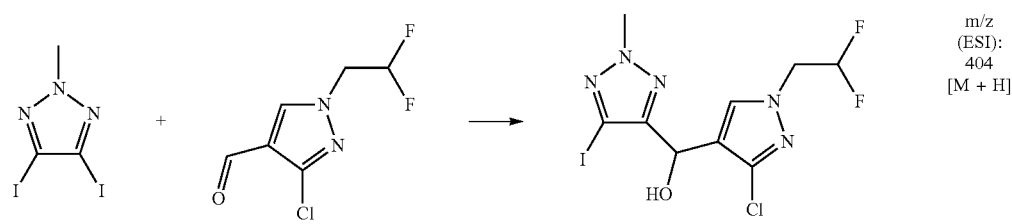 | m/z (ESI): 404 [M + H] |

| (3-bromo-5-fluoropyridin-2-yl)(1-(cyclopropylmethyl)-1H-pyrazol-4-yl)methanol | |
|---|---|
| 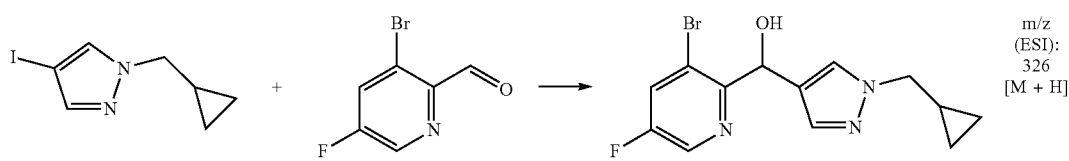 | m/z (ESI): 326 [M + H] |

(3-bromo-5-fluoropyridin-2-yl)(1-(2,2-difluoroethyl)-1H-pyrazol-4-yl)methanol

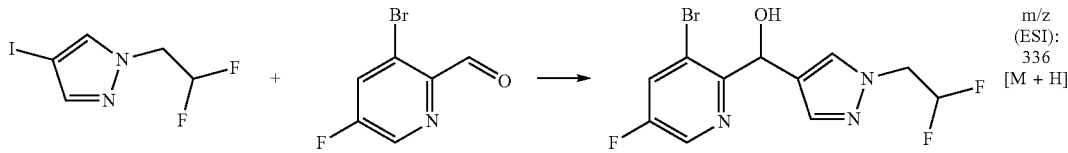

m/z (ESI): 336 [M + H]

[3-chloro-1-(cyclopropylmethyl)-1H-pyrazol-4-yl](5-iodo-2-methyl-2H-1,2,3-triazol-4-yl)methanol

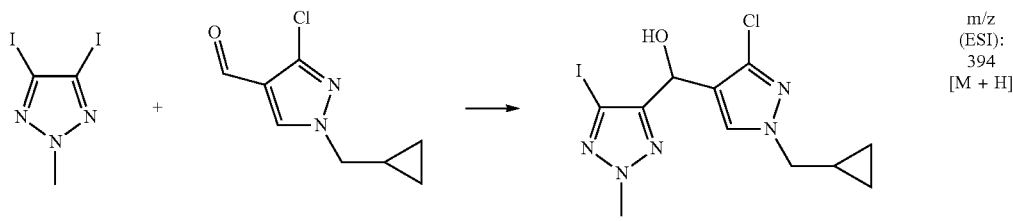

m/z (ESI): 394 [M + H]

[3-chloro-1-(cyclopropylmethyl)-1H-pyrazol-4-yl](4-iodo-1-methyl-1H-pyrazol-3-yl)methanol

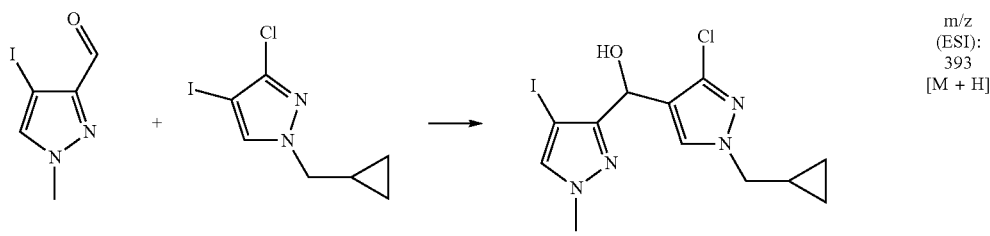

m/z (ESI): 393 [M + H]

[3-(cyclopropylmethyl)-1-methyl-1H-pyrazol-5-yl](5-iodo-2-methyl-2H-1,2,3-triazol-4-yl)methanol

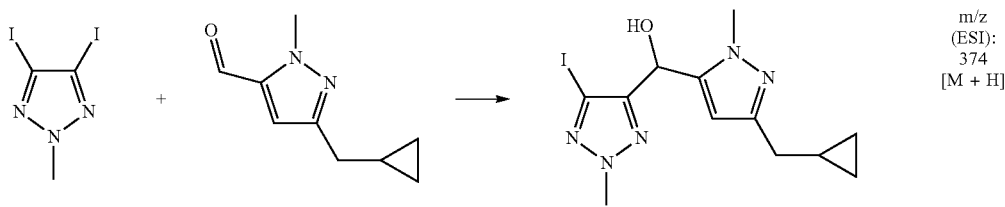

m/z (ESI): 374 [M + H]

Synthesis of 5-bromo-1-ethyl-4-((4-iodo-1-methyl-1H-pyrazol-3-yl)methyl)-1H-pyrazole

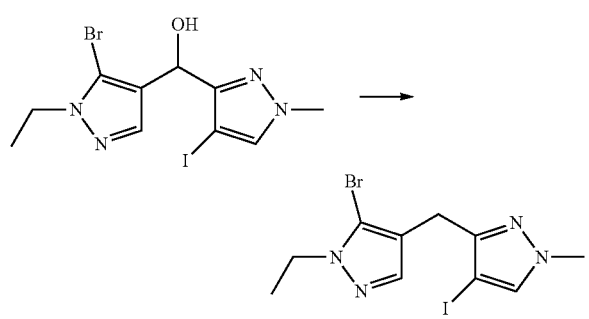

To a solution of (5-bromo-1-ethyl-1H-pyrazol-4-yl)(4-iodo-1-methyl-1H-pyrazol-3-yl)methanol (800 mg, 1.90 mmol) in DCM (5 mL) were added triethylsilane (1.80 g, 15.6 mmol) and TFA (1.45 mL, 19.5 mmol) at 0° C. After stirring at 0° C. for 2 h, the mixture was neutralized to pH 8 with sat. NaHCO₃. The resulting mixture was diluted with EtOAc, washed with brine, dried over anhydrous Na₂SO₄, filtered and concentrated. The residue was purified by column chromatography on silica gel (0→60% EA in PE) to give 5-bromo-1-ethyl-4-((4-iodo-1-methyl-1H-pyrazol-3-yl)methyl)-1H-pyrazole as a yellow oil (700 mg, yield: 91%). LC/MS ESI (m/z): 395 [M+H]⁺.

Synthesis of 4-[(5-bromo-1-ethyl-H-pyrazol-4-yl)methyl]-5-iodo-2-methyl-2H-1,2,3-triazole

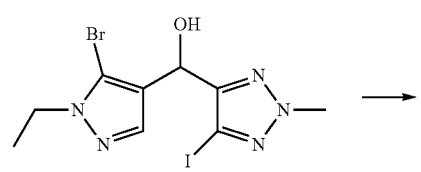

219

-continued

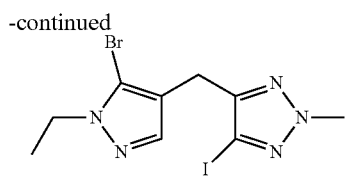

A mixture of (5-bromo-1-ethyl-1H-pyrazol-4-yl)(5-iodo-2-methyl-2H-1,2,3-triazol-4-yl)methanol (800 mg, 1.94 mmol) and TES (2.8 mL, 16 mmol) in TFA (5 mL) was stirred at 30° C. for 0.5 h. The mixture was adjusted to pH 8 with NaHCO$_3$ at 0° C., and then extracted with EA (50 mL×2). The combined organic phases were dried over anhydrous Na$_2$SO$_4$, filtered, and concentrated. The residue was purified by flash chromatography on silica gel (30% EtOAc in PE) to give 4-[(5-bromo-1-ethyl-1H-pyrazol-4-yl)methyl]-5-iodo-2-methyl-2H-1,2,3-triazole (750 mg, yield: 97%) as a light-yellow solid. LC/MS ESI (m/z): 396 [M+H]$^+$.

The following intermediates were synthesized using a similar experimental protocol:

| 4-{[1-(cyclopropylmethyl)-3-methyl-1H-pyrazol-4-yl]methyl}-5-iodo-2-methyl-2H-1,2,3-triazole | |
|---|---|
| 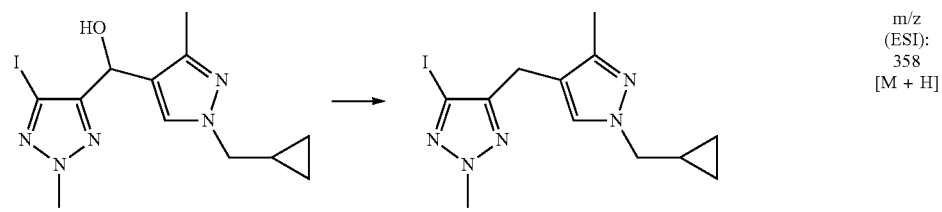 | m/z (ESI): 358 [M + H] |

| 4-((1-(cyclopropylmethyl)-1H-pyrazol-4-yl)methyl)-5-iodo-2-methyl-2H-1,2,3-triazole | |
|---|---|
| 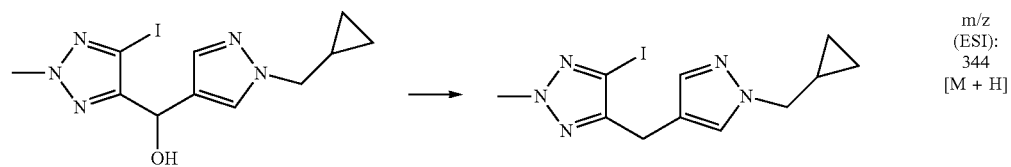 | m/z (ESI): 344 [M + H] |

| 4-bromo-3-((1-(cyclopropylmethyl)-1H-pyrazol-4-yl)methyl)-1-methyl-1H-pyrazole | |
|---|---|
| 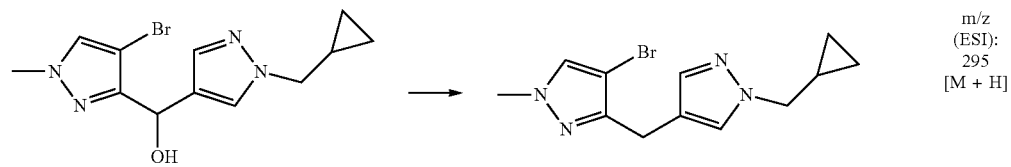 | m/z (ESI): 295 [M + H] |

| 4-((1-ethyl-3-(trifluoromethyl)-1H-pyrazol-4-yl)methyl)-5-iodo-2-methyl-2H-1,2,3-triazole | |
|---|---|
| 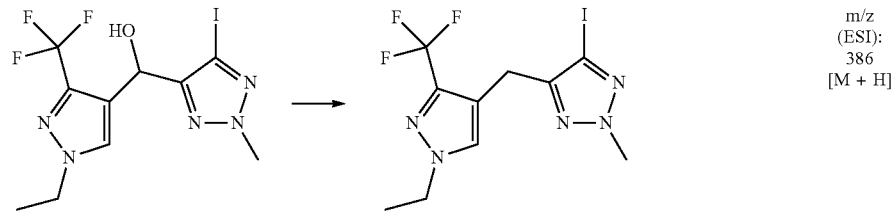 | m/z (ESI): 386 [M + H] |

| 4-((1-(cyclopropylmethyl)-1H-pyrazol-4-yl)methyl)-5-iodo-2H-1,2,3-triazole | |
|---|---|
| 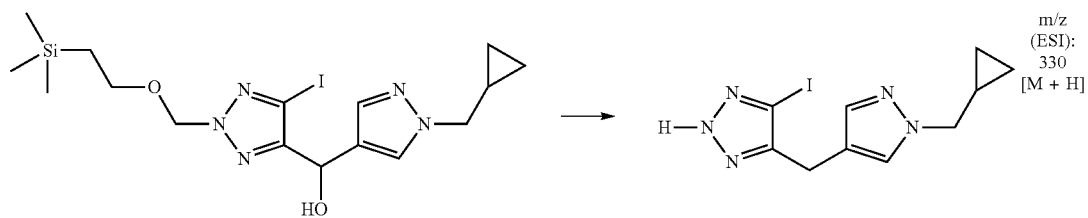 | m/z (ESI): 330 [M + H] |

Synthesis of 5-bromo-1-(cyclopropylmethyl)-4-((5-iodo-1H-pyrazol-1-yl)methyl)-3-methyl-1H-pyrazole

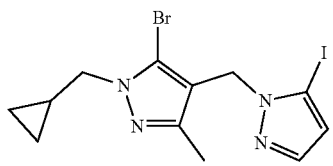 [SMILES: Cc1nn(CC2CC2)c(Br)c1Cn1nccc1I]

To a solution of 5-bromo-1-(cyclopropylmethyl)-3-methyl-1H-pyrazole-4-carbaldehyde (1.00 g, 4.11 mmol) in THF (20 mL) was added dropwise DIBAL-H (5.50 mL, 8.23 mmol) at −78° C. under $N_2$. The reaction mixture was stirred at −78° C. for 2 h under $N_2$. The reaction mixture was allowed to warm to r.t. The reaction mixture was added sat. potassium sodium tartrate tetrahydrate solution and stirred at r.t. for 2 h. The mixture was extracted with EtOAc twice and the combined organic layers were washed with brine, dried over anhydrous $Na_2SO_4$ and concentrated in vacuo. The residue was purified by flash column chromatography to afford (5-bromo-1-(cyclopropylmethyl)-3-methyl-1H-pyrazol-4-yl)methanol (800 mg, 79%) as a white solid. LC/MS (ESI) m/z: 245 [M+H]$^+$.

To a solution of (5-bromo-1-(cyclopropylmethyl)-3-methyl-1H-pyrazol-4-yl)methanol (1.50 g, 6.12 mmol) in DCM (20 mL) was added $SOCl_2$ (1.4 mL, 18 mmol). The mixture was stirred at r.t. for 2 h. The reaction mixture was concentrated to afford crude 5-bromo-4-(chloromethyl)-1-(cyclopropylmethyl)-3-methyl-1H-pyrazole (1.6 g, 99%) as a colorless oil.

To a mixture of 5-iodo-1H-pyrazole (662 mg, 3.42 mmol) and $K_2CO_3$ (1.41 g, 10.2 mmol) in DMF (30 mL) was added a solution of 5-bromo-4-(chloromethyl)-1-(cyclopropylmethyl)-3-methyl-1H-pyrazole (900 mg, 3.45 mmol) in DMF (1 mL) dropwise at 0° C. The mixture was stirred at 80° C. for 8 h under $N_2$. The mixture was cooled to r.t. and diluted with EtOAc. This mixture was washed with brine, dried over anhydrous $Na_2SO_4$, concentrated. The residue was purified by flash column chromatography and further purified by SFC to afford 5-bromo-1-(cyclopropylmethyl)-4-((5-iodo-1H-pyrazol-1-yl)methyl)-3-methyl-1H-pyrazole (170 mg, 12%) as a colorless oil. LC/MS (ESI) m/z: 421 [M+H]$^+$.

Synthesis of tert-butyl 2-((5-bromo-1-ethyl-1H-pyrazol-4-yl)methyl)hydrazine-1-carboxylate

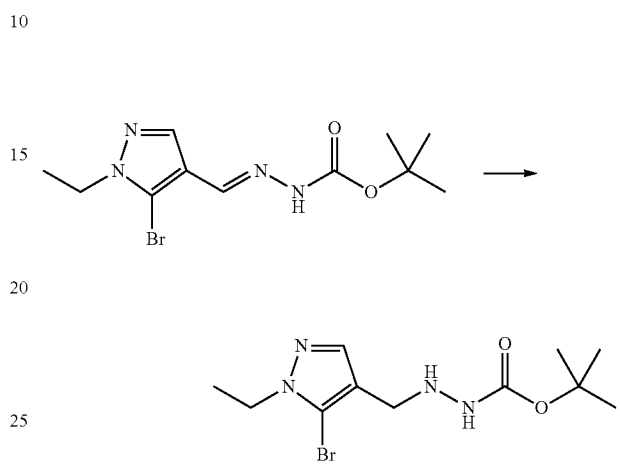

To a solution of tert-butyl (E)-2-((5-bromo-1-ethyl-1H-pyrazol-4-yl)methylene)hydrazine-1-carboxylate (4.71 g, 14.8 mmol) in AcOH (15 mL) and MeOH (10 mL) was added $NaBH_3CN$ (1.20 g, 18.9 mmol) at r.t. The resulting mixture was stirred at 25° C. for 12 h. After concentration under reduced pressure, the residue was dissolved in EtOAc, washed with aq. $Na_2CO_3$ and brine, dried over anhydrous $Na_2SO_4$ and concentrated under reduced pressure. The residue was purified by flash chromatography on silica gel (0→30% EtOAc in PE) to give tert-butyl 2-((5-bromo-1-ethyl-1H-pyrazol-4-yl)methyl)hydrazine-1-carboxylate (3.5 g, 69% yield) as a white solid. LC/MS (ESI): m/z=319 [M+H]$^+$.

The following intermediates were synthesized using a similar experimental protocol:

tert-butyl 2-((5-bromo-3-chloro-1-ethyl-1H-pyrazol-4-yl)methyl)hydrazine-1-carboxylate

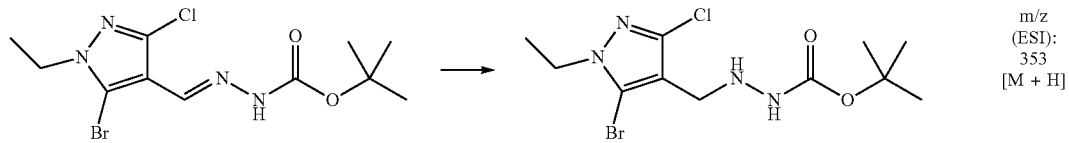

m/z (ESI): 353 [M + H]

tert-butyl2-((1-(cyclopropylmethyl)-1H-pyrazol-4-yl)methyl)hydrazine-1-carboxylate

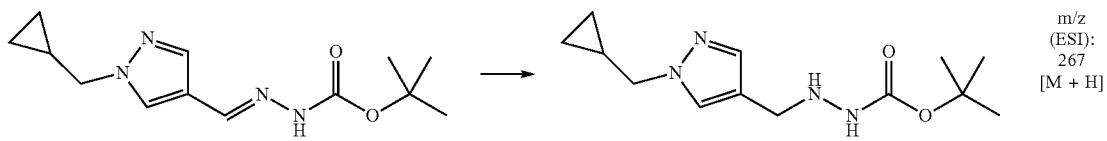

m/z (ESI): 267 [M + H]

Synthesis of (R)-1-(5-fluoro-2-iodophenyl)ethyl benzoate

Synthesis of 1-[(5-bromo-1-ethyl-1H-pyrazol-4-yl)methyl]-5-iodo-4-(trimethylsilyl)-1H-1,2,3-triazole

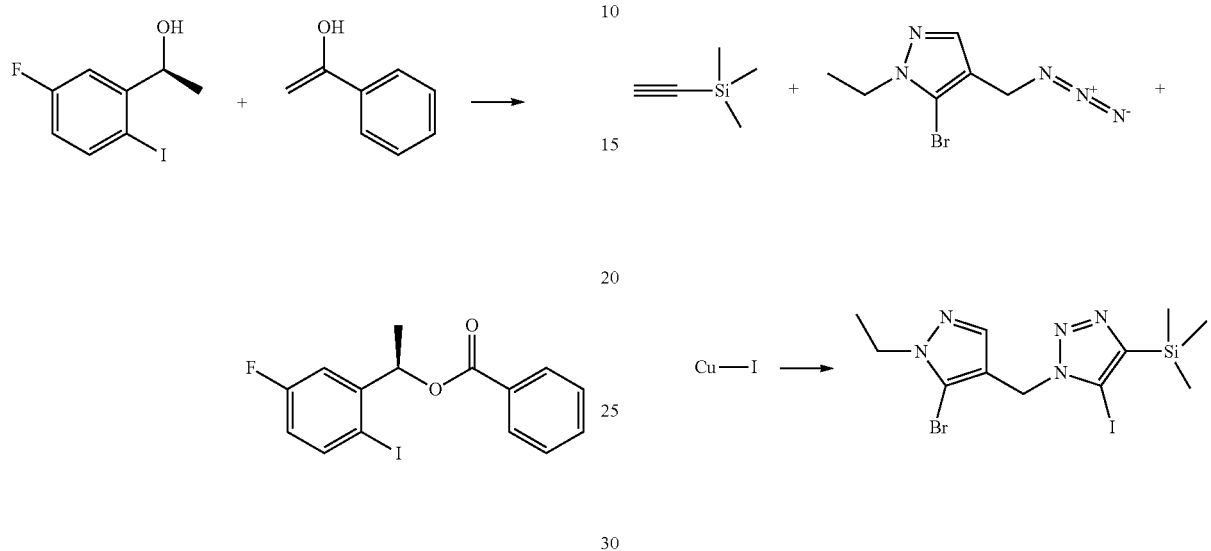

To a mixture of (1S)-1-(5-fluoro-2-iodophenyl)ethan-1-ol (1.00 g, 3.76 mmol), benzoic acid (0.550 g, 4.51 mmol) and triphenylphosphine (1.18 g, 4.51 mmol) in THF (30 mL) was added DIAD (0.89 mL, 4.5 mmol) dropwise at 0° C. under N$_2$. The resulting mixture was stirred at r.t. overnight, poured into water, and then extracted with EtOAc (50 mL×2). The combined organic layers were washed with brine, dried over anhydrous Na$_2$SO$_4$ and concentrated. The residue was purified by column chromatography (silica gel, 1→5% ethyl acetate in petroleum ether) to afford (1R)-1-(5-fluoro-2-iodophenyl)ethyl benzoate (1.2 g, 86%) as a yellow solid. LC/MS (ESI): m/z=371 [M+H]$^+$.

The following intermediates were synthesized using a similar experimental protocol:

To a solution of 4-(azidomethyl)-5-bromo-1-ethyl-1H-pyrazole (1.20 g, 5.21 mmol) in MeCN (15 mL) were added CuI (1.12 g, 5.89 mmol), DIPEA (760 mg, 5.89 mmol), NBS (1.05 g, 5.89 mmol) and ethynyltrimethylsilane (0.83 mL, 5.9 mmol). Then the mixture was degassed with N$_2$ three times and stirred at 25° C. for 16 h. The reaction mixture was concentrated, and the residue was treated with ice water and EtOAc. The organic layer was separated, washed with brine, dried over anhydrous Na$_2$SO$_4$, filtered, and concentrated to dryness. The residue was purified by flash chromatography (silica gel, 0→20% MeOH in DCM) to give 1-[(5-bromo-1-ethyl-1H-pyrazol-4-yl)methyl]-5-iodo-4-(trimethylsilyl)-1H-1,2,3-triazole (320 mg, yield: 14%) as a yellow oil. LC/MS (ESI) m/z: 454[M+H]$^+$.

| (R)-3-(1-(5-fluoro-2-iodophenyl)ethoxy)-2-nitropyridine | m/z (ESI): 389 [M + H] |
|---|---|
| 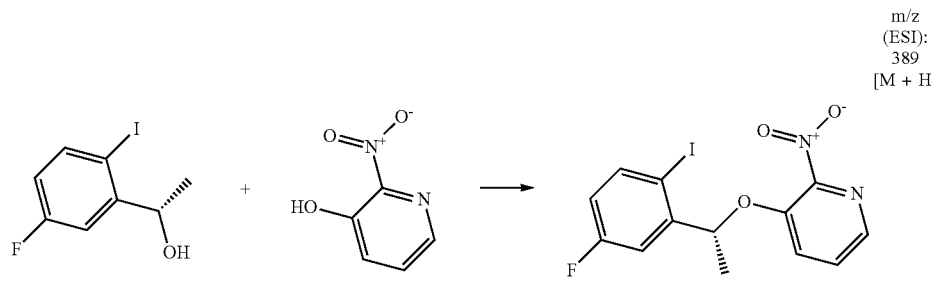 | |

The following intermediates were synthesized using a similar experimental protocol:

1-((5-bromo-1-cyclobutyl-1H-pyrazol-4-yl)methyl)-5-iodo-4-(trimethylsilyl)-1H-1,2,3-triazole

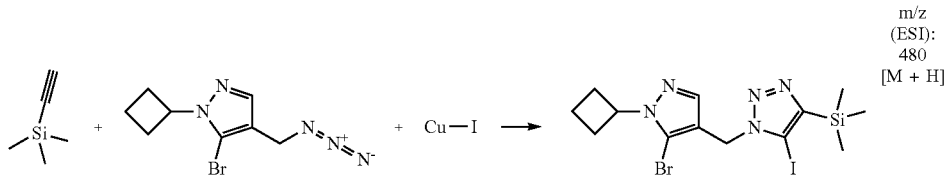

m/z (ESI): 480 [M + H]

Synthesis of 3-(((tert-butyldimethylsilyl)oxy)methyl)-5-fluorobenzo[c][1,2]oxaborol-1 (3H)-ol

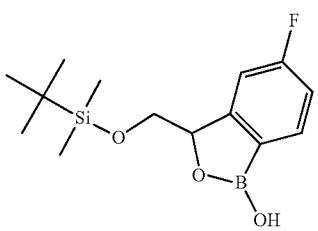 [SMILES: CC(C)(C)[Si](C)(C)OCC1OB(O)c2ccc(F)cc21]

To a solution of (5-fluoro-2-iodophenyl)methanol (10.0 g, 39.7 mmol) in CHCl$_3$ (150 mL) was added manganese dioxide (3.4 g, 39.7 mmol). The resulting mixture was stirred at 66° C. overnight. After cooling to r.t., the reaction mixture was filtered, and the filtrate was concentrated. The residue was purified by column chromatography on silica gel (0→30% EA in PE) to give 5-fluoro-2-iodobenzaldehyde (9.1 g, yield: 92%) as a pale-yellow solid. LC-MS ESI (m/z): 251 [M+H]$^+$ Under a N$_2$ atmosphere, a solution of methyltriphenylphosphonium bromide (14.7 g, 41.1 mmol) in dry THF (100 mL) was cooled to −10° C. and potassium tert-butoxide (4.60 g, 41.1 mmol) was added. After 15 min, 5-fluoro-2-iodobenzaldehyde (8.60 g, 34.2 mmol) was added and the reaction mixture was stirred at ambient temperature for 2 h. Ice-water (150 mL) was added and the mixture was extracted with EA (3×50 mL). The combined organic layers were dried over Na$_2$SO$_4$, filtered, and evaporated in vacuo at 25° C. The residue was purified by flash chromatography (0→20% EA in PE) to give 2-ethenyl-4-fluoro-1-iodobenzene (10 g, yield: 118%) as a colorless oil containing solvents. LC/MS (ESI) m/z: 249 [M+H]$^+$.

To a solution of 2-ethenyl-4-fluoro-1-iodobenzene (8.50 g, 34.3 mmol) in t-BuOH (75 mL) and H$_2$O (25 mL) was added N-methylmorpholine N-oxide (12.0 g, 51.4 mmol, 50% in water) and K$_2$OsO$_4$·2H$_2$O (0.10 g, cat.). The reaction was stirred at r.t. for 48 h. The reaction was quenched by the addition of sat. aq. Na$_2$S2O$_3$ solution. The mixture was stirred at r.t. for another 4 h. The mixture was extracted with EA (50 mL×3), dried over anhydrous Na$_2$SO$_4$, filtered and concentrated. The residue was purified by flash chromatography (0→100% EA in PE) to give 1-(5-fluoro-2-iodophenyl)ethane-1,2-diol (6.1 g, yield: 63%) as a white solid. LC-MS ESI (m/z): 283 [M+H]$^+$ To a solution of 1-(5-fluoro-2-iodophenyl)ethane-1,2-diol (5.30 g, 18.8 mmol) in DMF (50 mL) were added imidazole (2.60 g, 37.6 mmol) and tert-butyldimethylsilyl chloride (3.00 g, 19.7 mmol). The mixture was stirred at r.t. overnight, diluted with water, and then extracted with EA (30 mL×3). The combined organic layers were washed with brine (50 mL), dried over anhydrous Na$_2$SO$_4$, filtered and concentrated. The residue was purified by flash chromatography (0→50% EA in PE) to give 2-[(tert-butyldimethylsilyl)oxy]-1-(5-fluoro-2-iodophenyl)ethan-1-ol (6.4 g, yield: 86%). LC-MS ESI (m/z): 397 [M+H]$^+$ To solution of 2-[(tert-butyldimethylsilyl)oxy]-1-(5-fluoro-2-iodophenyl)ethan-1-ol (3.0 g, 7.6 mmol) in THF (40.0 mL) was added i-PrMgCl (14.6 mL, 18.9 mmol, 1.3 M) dropwise at 0° C. The mixture was stirred at r.t. for 1 h. Trimethyl borate (2.00 g, 18.9 mmol) was added dropwise to the mixture at 0° C. and stirring was continued at r.t. for 2 h. The reaction was quenched by sat. aq. NH$_4$Cl and extracted with EA (3×30 mL). The combined organic layers were washed with brine, dried over anhydrous Na$_2$SO$_4$, filtered, and concentrated. The residue was purified by column chromatography on silica gel (0→100% EA in PE) to give 3-{[(tert-butyldimethylsilyl)oxy]methyl}-5-fluoro-1,3-dihydro-2,1-benzoxaborol-1-ol (1.3 g, yield: 58%) as a colorless oil. LC-MS ESI (m/z): 297 [M+H]$^+$.

Synthesis of 5-bromo-1-ethyl-4-(hydrazinylmethyl)-1H-pyrazole Hydrochloride

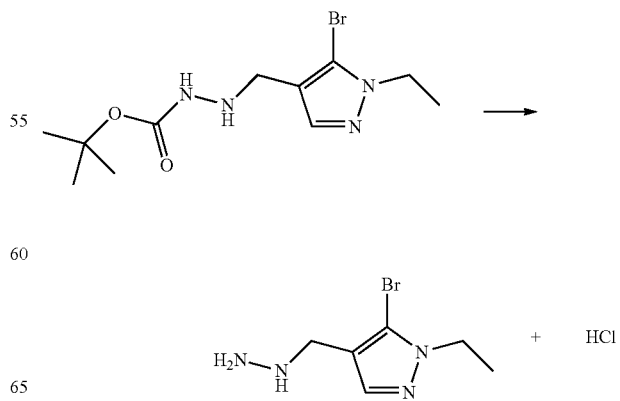

To a solution of tert-butyl 2-((5-bromo-1-ethyl-1H-pyrazol-4-yl)methyl)hydrazine-1-carboxylate (3.5 g, 11 mmol) in MeOH (15 mL) was added a solution of HCl in dioxane (10 mL, 4 N). The reaction mixture was stirred at 25° C. for 12 h. The mixture was concentrated under reduced pressure and the residue was triturated with PE. The resulting solids were collected by filtration, washed with PE and dried in vacuo to give 5-bromo-1-ethyl-4-(hydrazinylmethyl)-1H-pyrazole hydrochloride (2.5 g, 89% yield) as a white solid. LC/MS (ESI): m/z=219 [M+H]$^+$.

The following intermediates were synthesized using a similar experimental protocol:

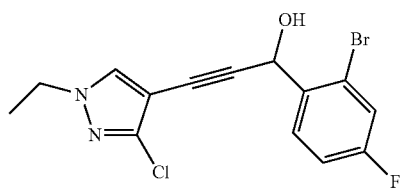

5-bromo-1-cyclobutyl-4-(hydrazinylmethyl)-1H-pyrazole hydrochloride

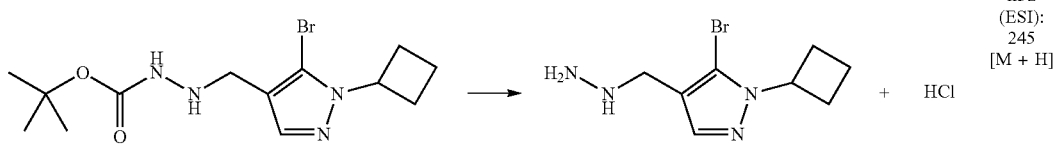

m/z (ESI): 245 [M + H]

5-bromo-3-chloro-1-ethyl-4-(hydrazineylmethyl)-1H-pyrazole hydrochloride

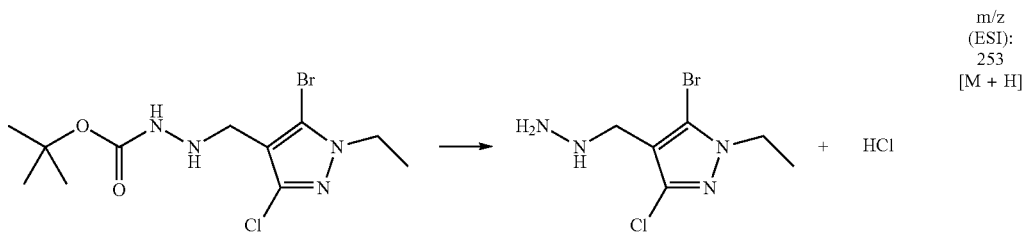

m/z (ESI): 253 [M + H]

1-(cyclopropylmethyl)-4-(hydrazinylmethyl)-1H-pyrazole hydrochloride

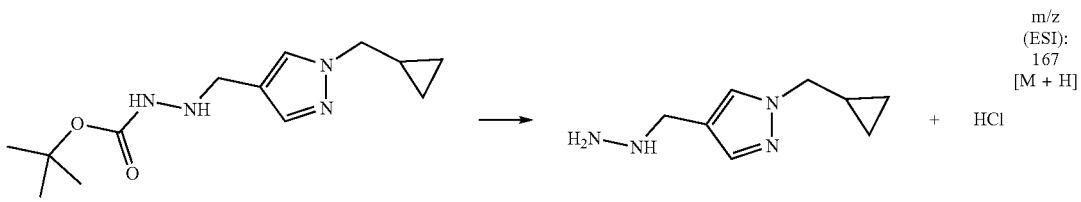

m/z (ESI): 167 [M + H]

Synthesis of 1-(2-bromo-4-fluorophenyl)-3-(3-chloro-1-ethyl-1H-pyrazol-4-yl)prop-2-yn-1-ol

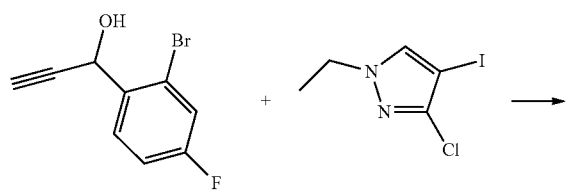

To a mixture of 1-(2-bromo-4-fluorophenyl) prop-2-yn-1-ol (4.00 g, 17.5 mmol) and 3-chloro-1-ethyl-4-iodo-1H-pyrazole (4.90 g, 19.2 mmol) in triethylamine (40 mL) was added Pd(PPh$_3$)$_2$Cl$_2$ (1.2 g, 1.7 mmol) and CuI (0.67 g, 3.5 mmol). The reaction solution was stirred at r.t. for 18 h under N$_2$. The reaction was concentrated in vacuo and the residue was purified by flash chromatography (0→50% of EtOAc in PE) to give 1-(2-bromo-4-fluorophenyl)-3-(3-chloro-1-ethyl-1H-pyrazol-4-yl) prop-2-yn-1-ol (3.3 g, 53% yield) as a yellow oil. LC/MS ESI (m/z): 357 [M+H]$^+$.

The following intermediates were synthesized using a similar experimental protocol:

| 1-(2-bromo-4-fluorophenyl)-3-(1-(cyclopropylmethyl)-3-methyl-1H-pyrazol-4-yl)prop-2-yn-1-ol |
|---|
| 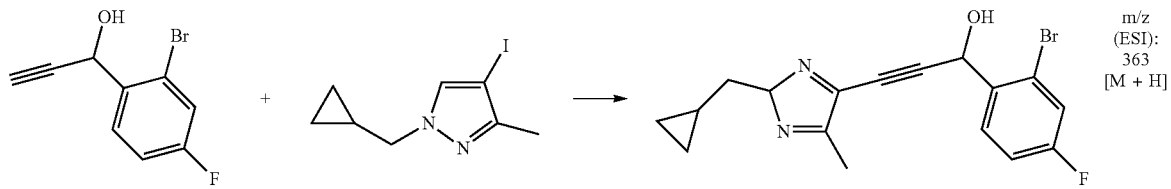 |
| 1-(2-bromo-4-fluorophenyl)-3-[1-(cyclopropylmethyl)-1H-pyrazol-4-yl]prop-2-yn-1-ol |
| 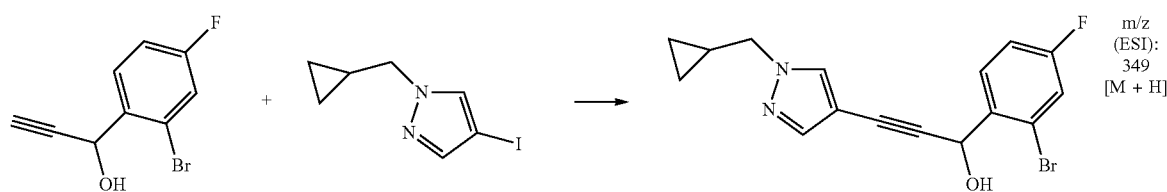 |

Synthesis of (R)-5-fluoro-3-methylbenzo[c][1,2]oxaborol-1 (3H)-ol

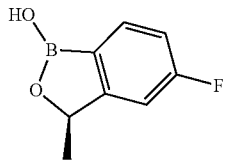

To a solution of (1R)-1-(5-fluoro-2-iodophenyl)ethyl benzoate (300 mg, 0.81 mmol) in methanol (8 mL) was added a solution of NaOH (32 mg, 0.81 mmol) in water (8 mL). The mixture was stirred at r.t. overnight. The reaction mixture was poured into water and then extracted with EtOAc (50 mL×2). The combined organic layers were washed with brine, dried over anhydrous $Na_2SO_4$ and concentrated. The residue was purified by column chromatography (silica gel, 1→5% ethyl acetate in petroleum ether) to afford (1R)-1-(5-fluoro-2-iodophenyl)ethan-1-ol (150 mg, 70%) as a white solid. LC/MS (ESI): m/z=267 [M+H]$^+$.

Isopropylmagnesium chloride-lithium chloride complex, 1.3M solution in THF (72.3 mL, 94.0 mmol) was added to the mixture of (1R)-1-(5-fluoro-2-iodophenyl)ethan-1-ol (10.00 g, 37.59 mmol) in THF (120 mL) at −40° C. under $N_2$ dropwise. The mixture was stirred at −40° C. under $N_2$ for 1 h, then warmed to −10° C. for another 0.5 h before trimethyl borate (10.67 mL, 93.97 mmol) was added dropwise over 10 min at −10° C. After stirring at r.t. overnight under $N_2$, The reaction mixture was poured into sat. $NH_4Cl$ solution (100 mL) and then extracted with EtOAc (50 mL×2). The combined organic layers were washed with brine, dried over anhydrous $Na_2SO_4$ and concentrated. The residue was purified by column chromatography (silica gel, 1→10% EtOAc in PE) to afford (R)-5-fluoro-3-methylbenzo[c] [1,2] oxaborol-1 (3H)-ol (4.0 g, 64%) as a colorless oil. LC/MS (ESI): m/z=167 [M+H]$^+$.

Synthesis of 3-(1-(5-fluoro-2-iodophenyl)ethoxy)-2-nitropyridine

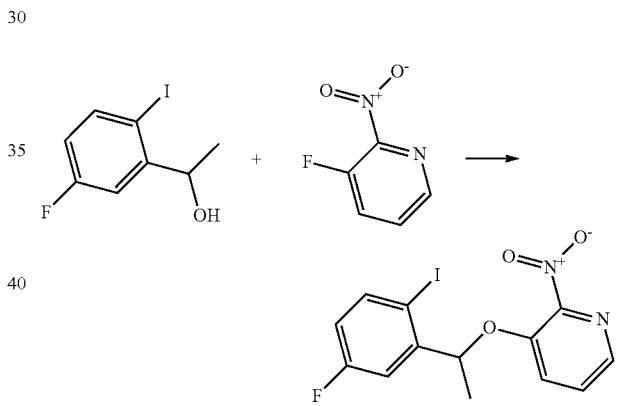

To a solution of 1-(5-fluoro-2-iodophenyl)ethan-1-ol (9.20 g, 34.6 mmol) in THF (180 mL) at 0° C. was added portion-wise NaH (1.38 g, 34.6 mmol, 60% in mineral oil) over 10 min. After the addition, the mixture was stirred at 0° C. for 15 min, and then a solution of 3-fluoro-2-nitropyridine (4.91 g, 34.6 mmol) in THF (20 mL) was added dropwise. The ice bath was removed, and the mixture was stirred at r.t. for 3 h. The reaction mixture was partitioned between DCM (200 mL) and water (200 mL). The organic layer was separated, washed with brine, and concentrated in vacuo. The residue was purified by flash chromatography (0→30% EtOAc in PE) to give 3-(1-(5-fluoro-2-iodophenyl)ethoxy)-2-nitropyridine (5.3 g, yield: 39%) as a white solid. LC/MS ESI (m/z): 389 [M+H]$^+$ The following intermediates were synthesized using a similar experimental protocol:

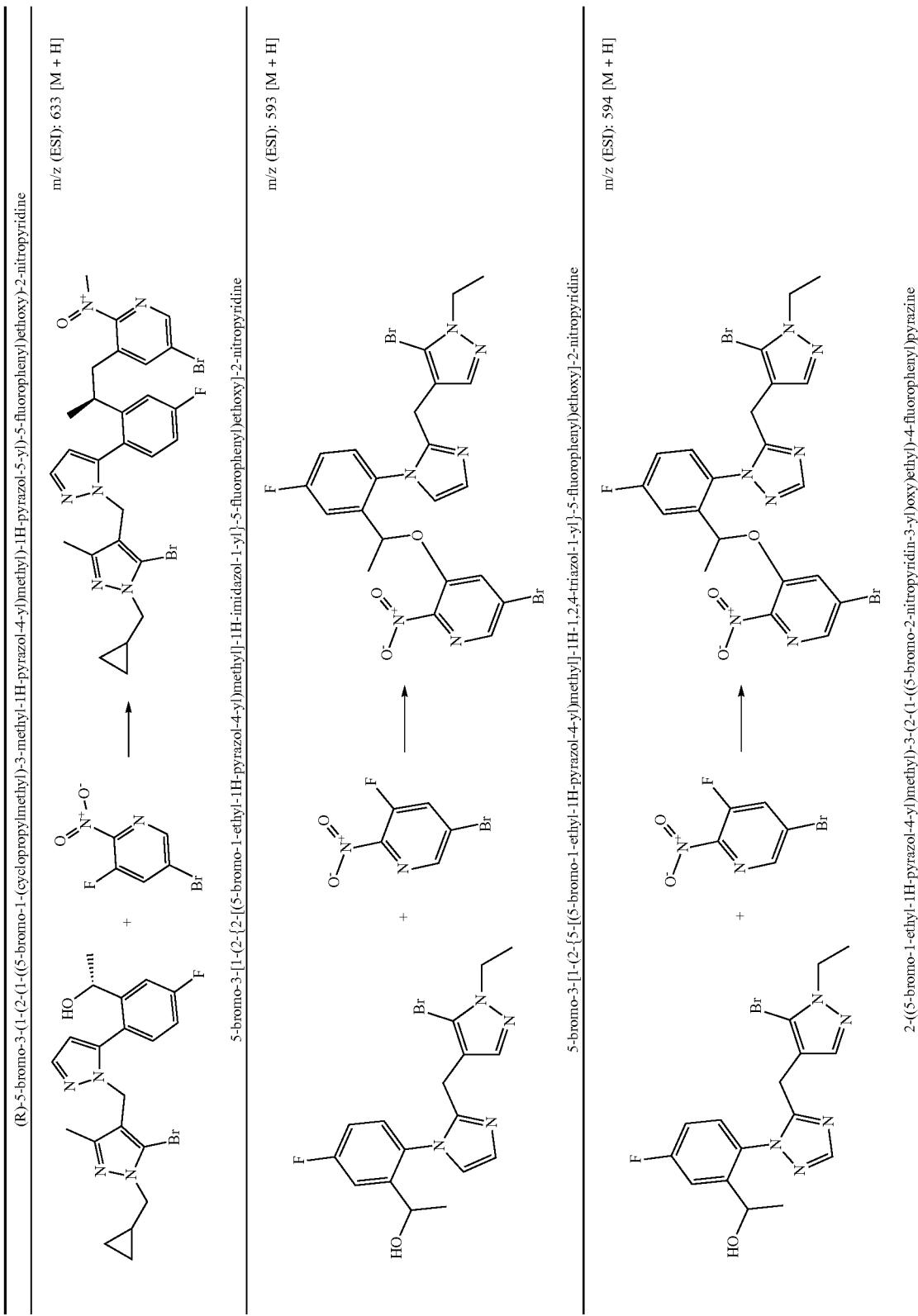

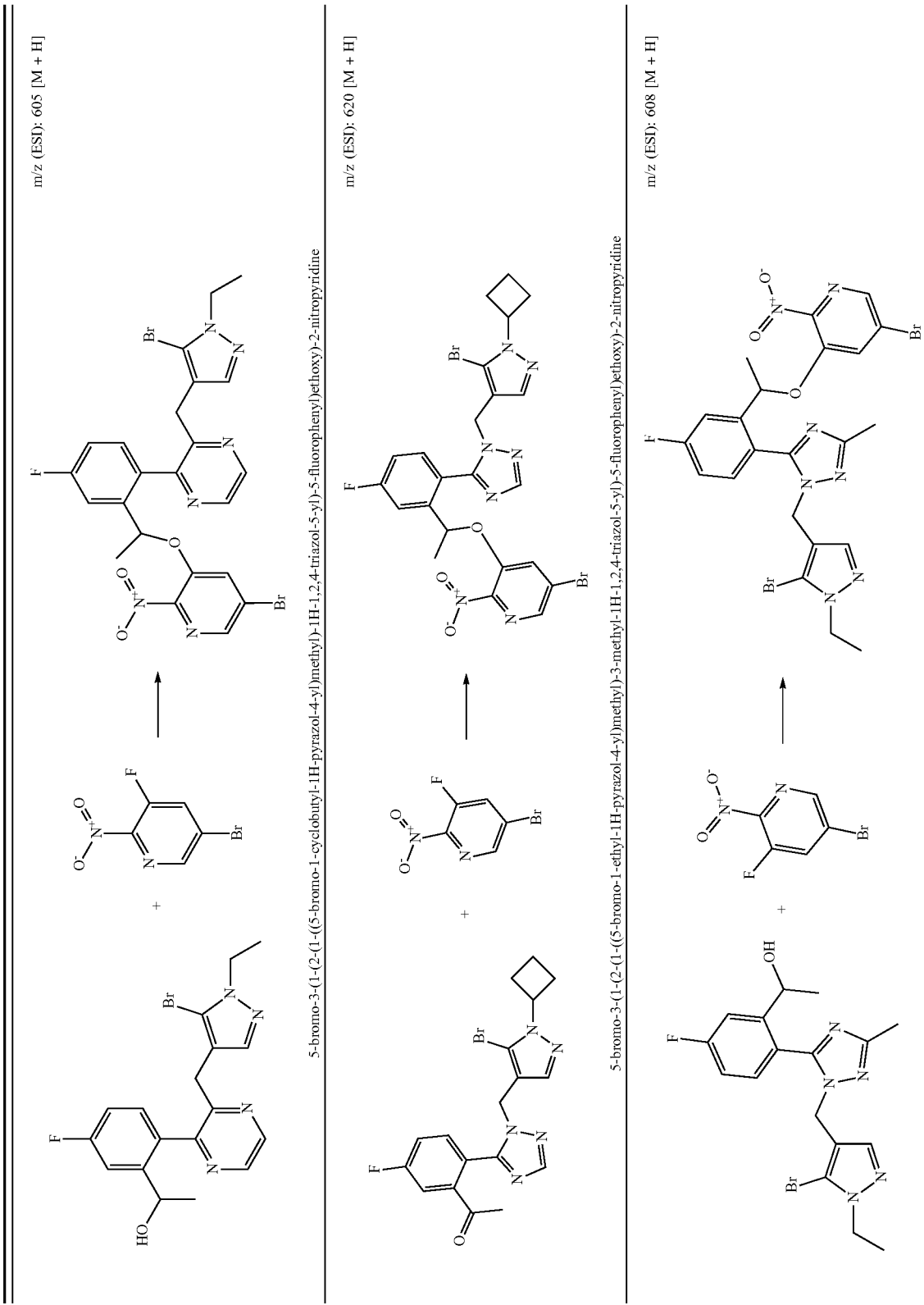

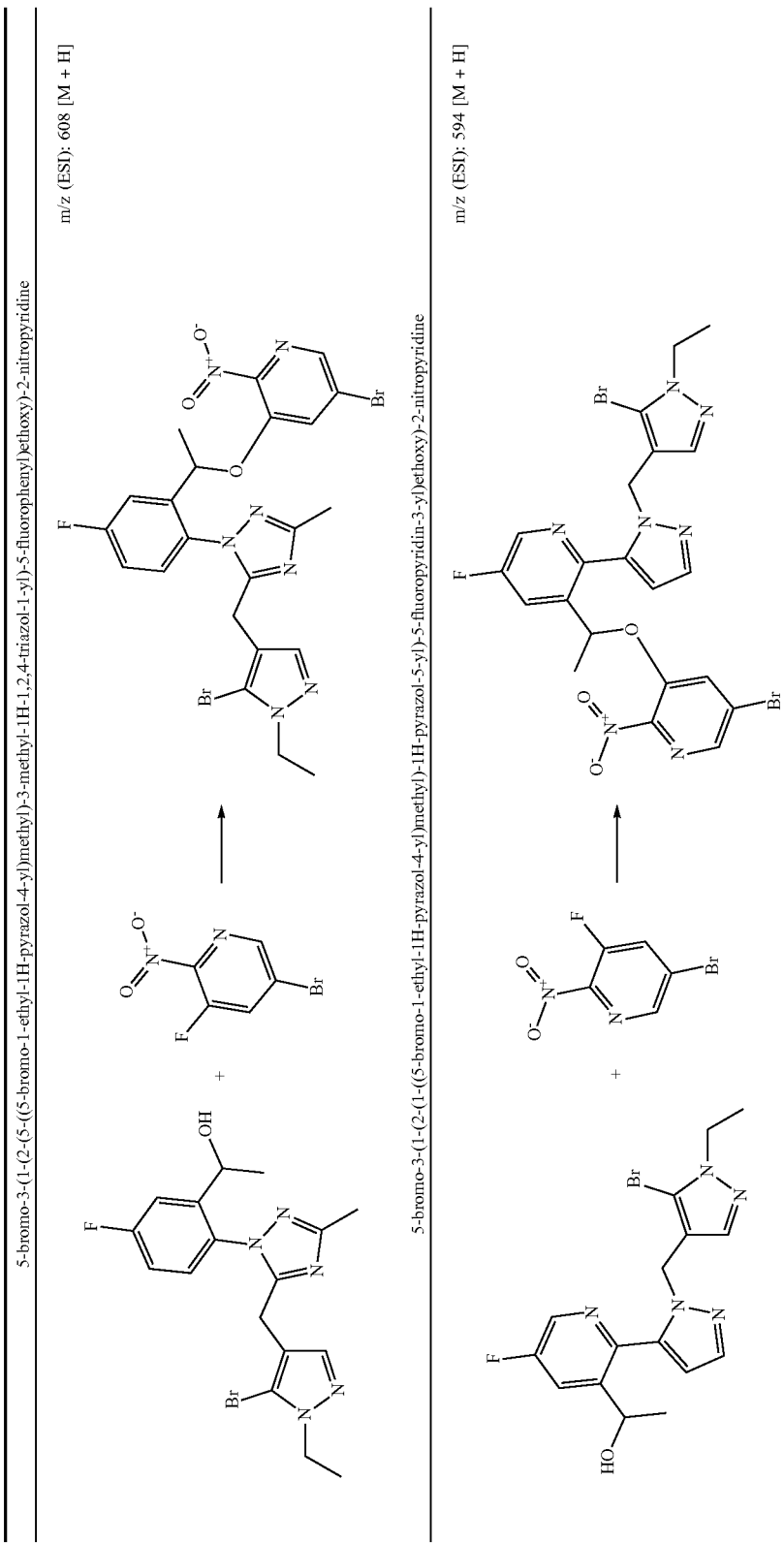

-continued
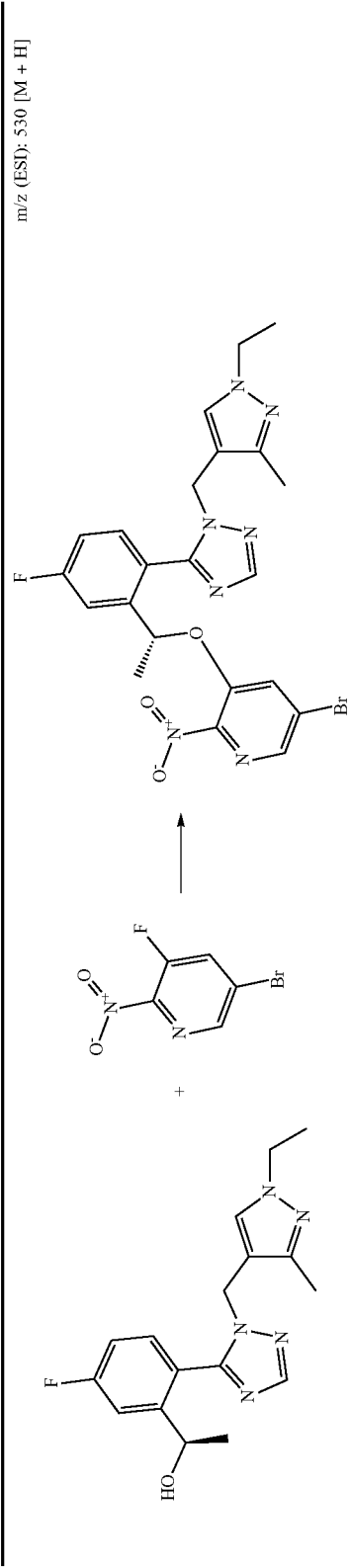
m/z (ESI): 530 [M + H]
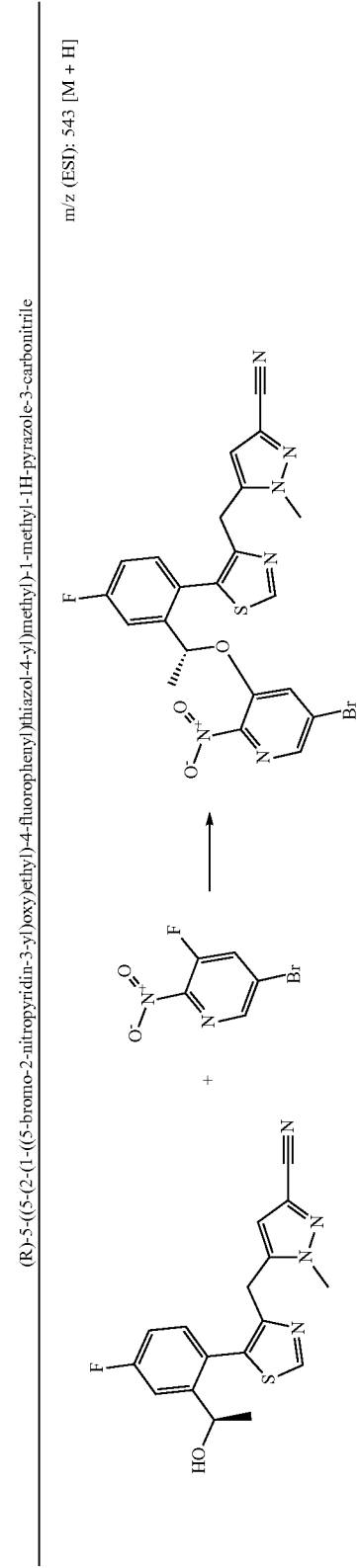
(R)-5-((5-(2-(1-((5-bromo-2-nitropyridin-3-yl)oxy)ethyl)-4-fluorophenyl)thiazol-4-yl)methyl)-1-methyl-1H-pyrazole-3-carbonitrile
m/z (ESI): 543 [M + H]
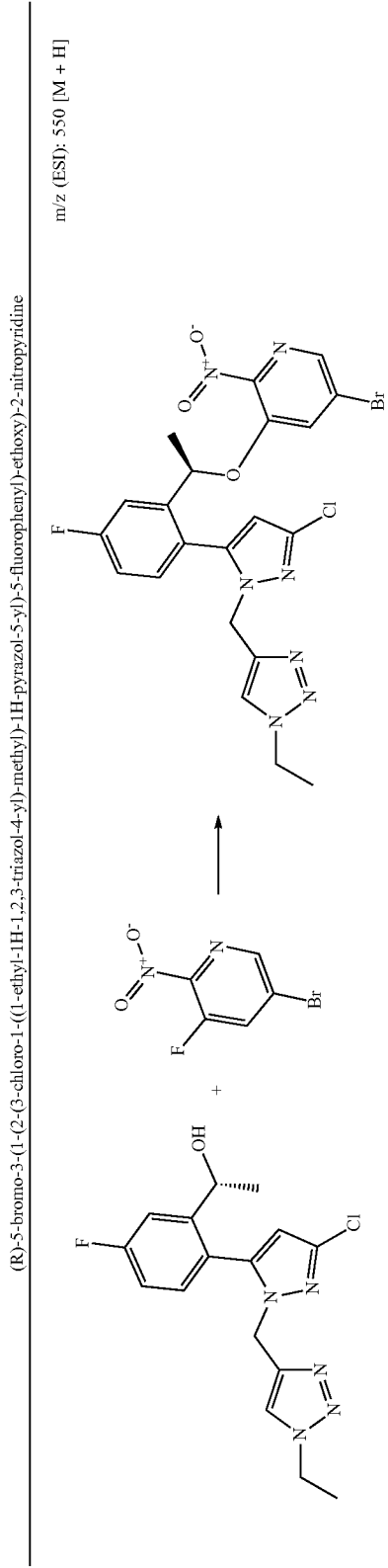
(R)-5-bromo-3-(1-(2-(3-chloro-1-((1-ethyl-1H-1,2,3-triazol-4-yl)methyl)-1H-pyrazol-5-yl)-5-fluorophenyl)ethoxy)-2-nitropyridine
m/z (ESI): 550 [M + H]

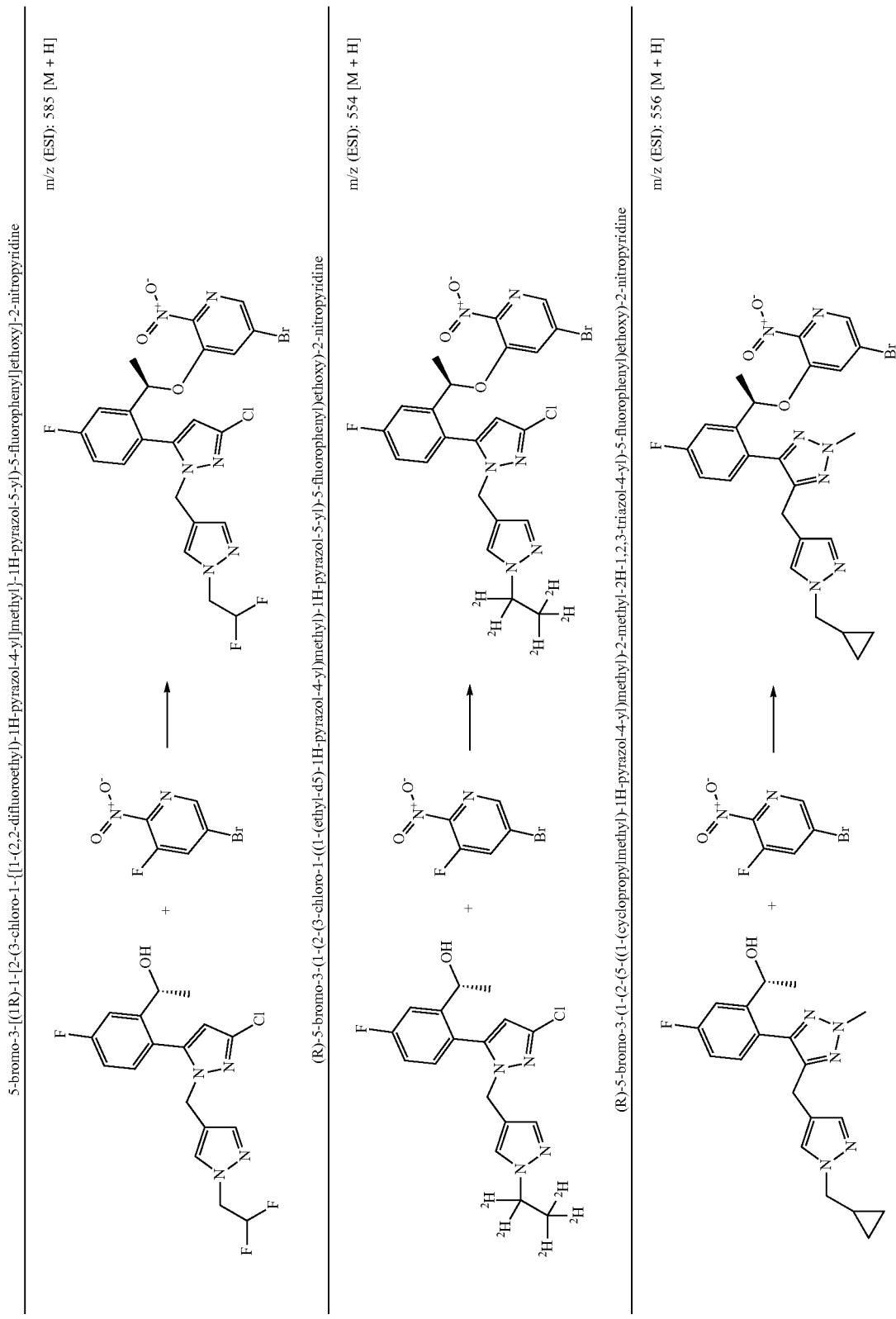

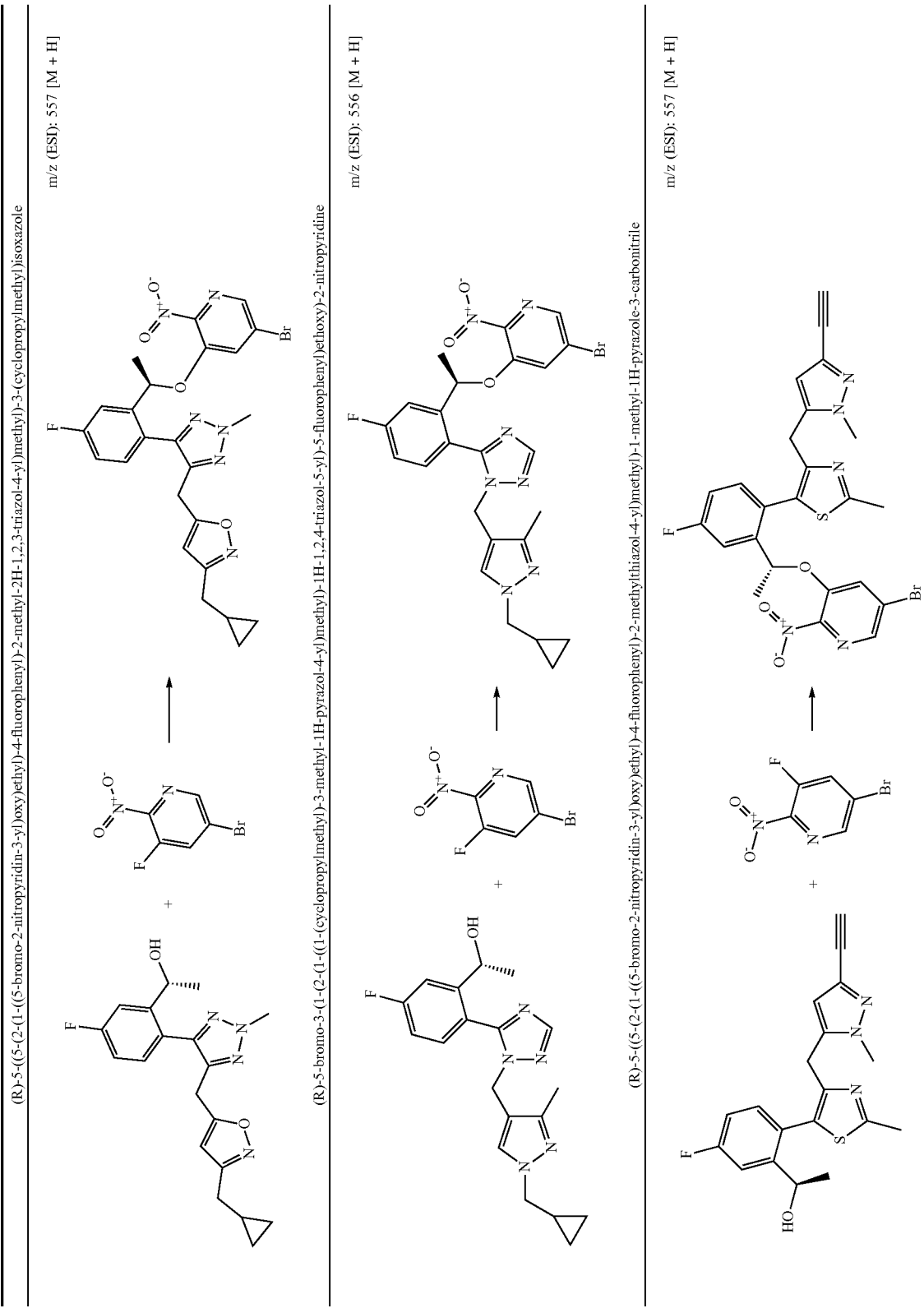

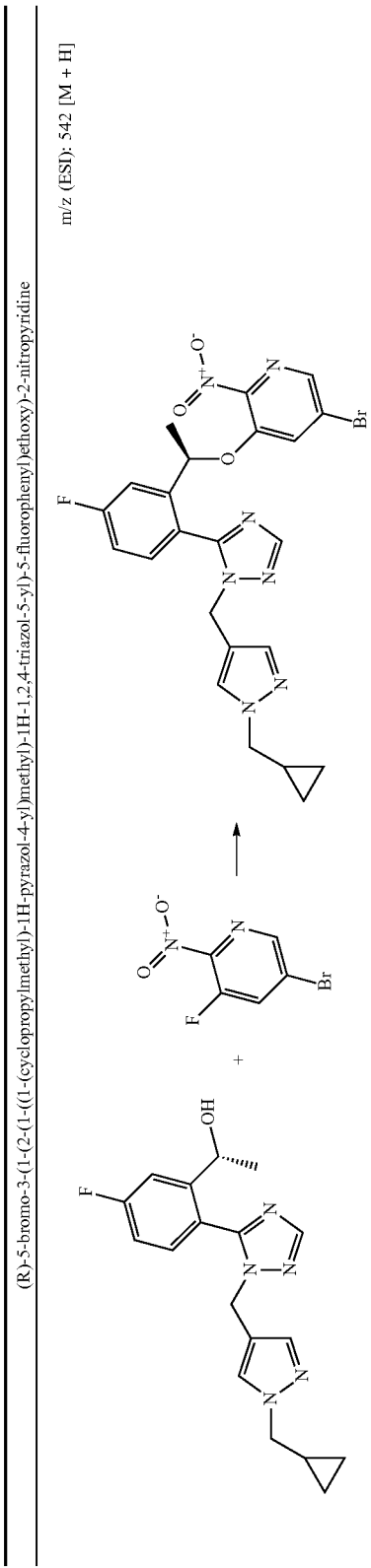
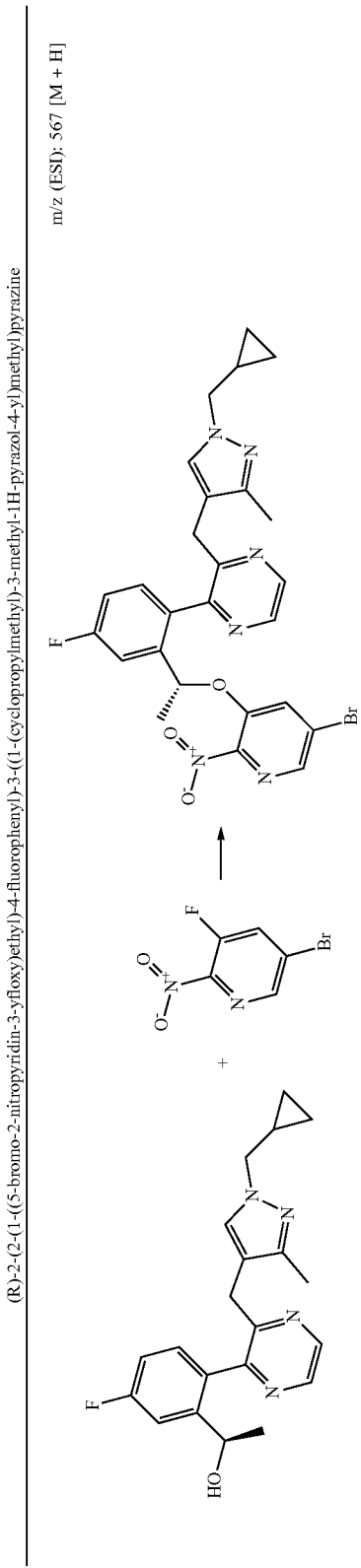
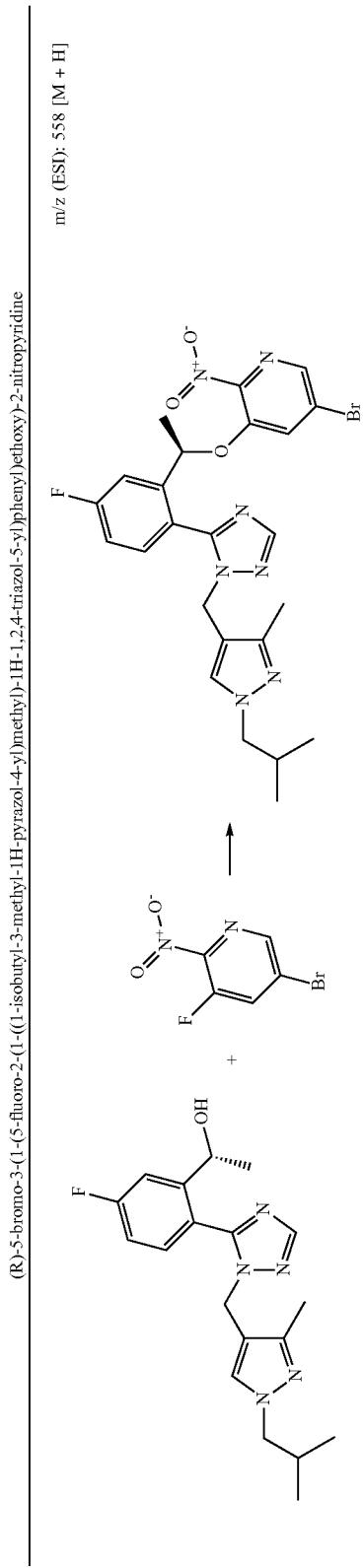

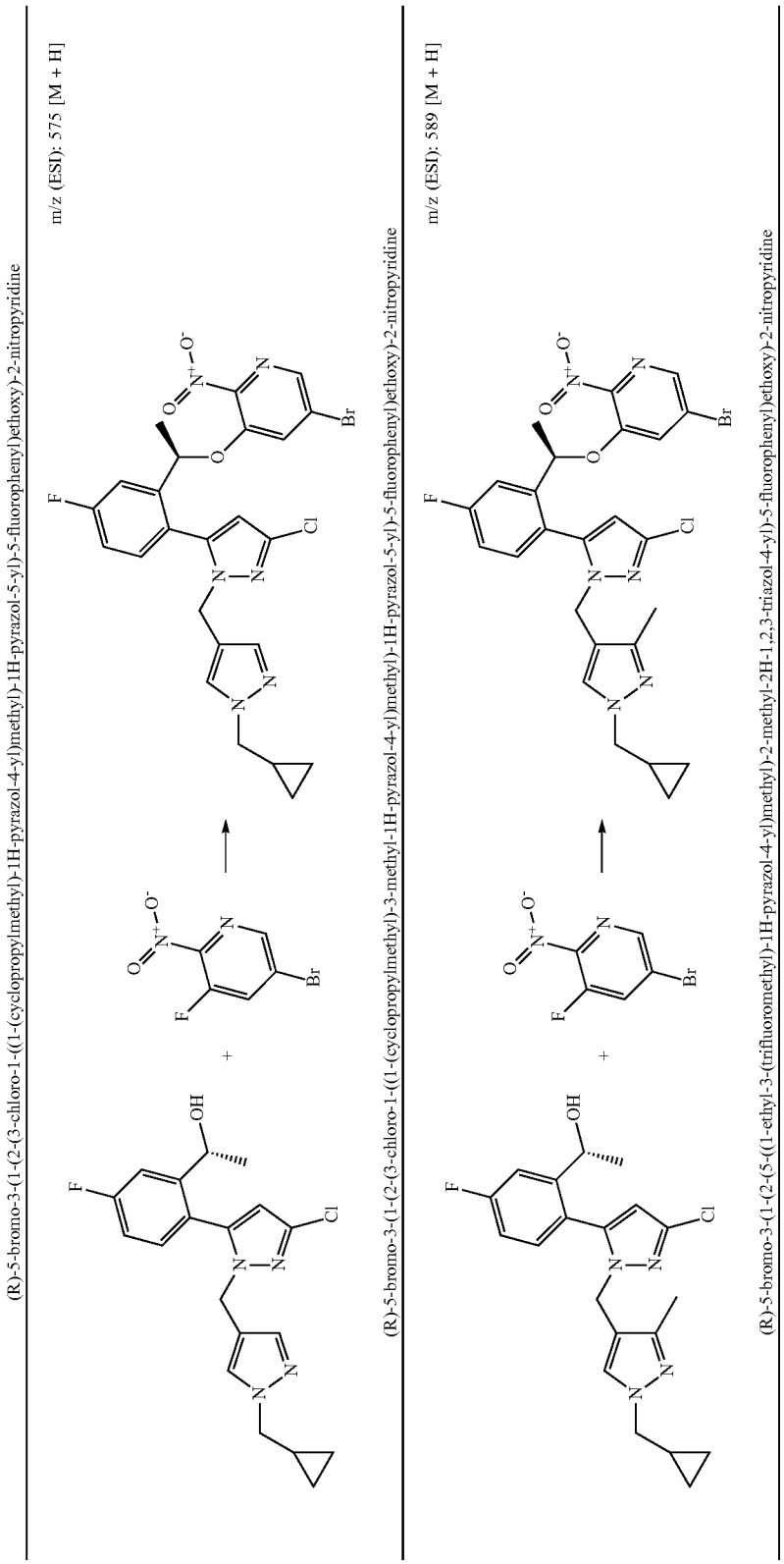

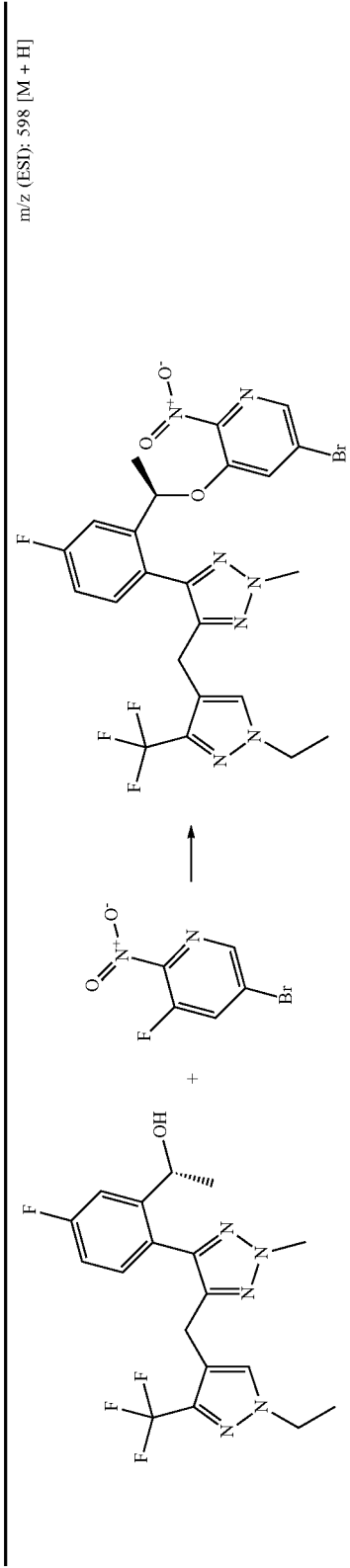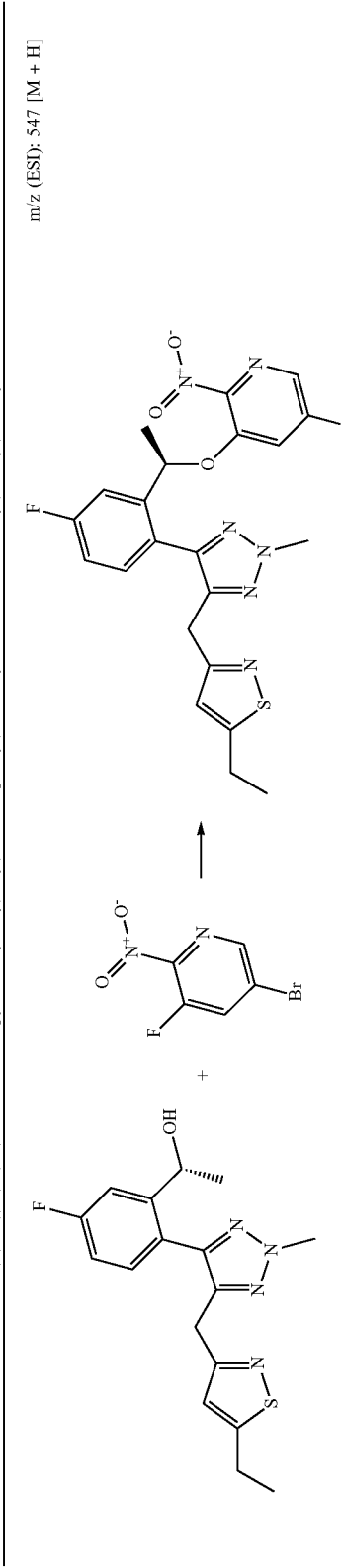

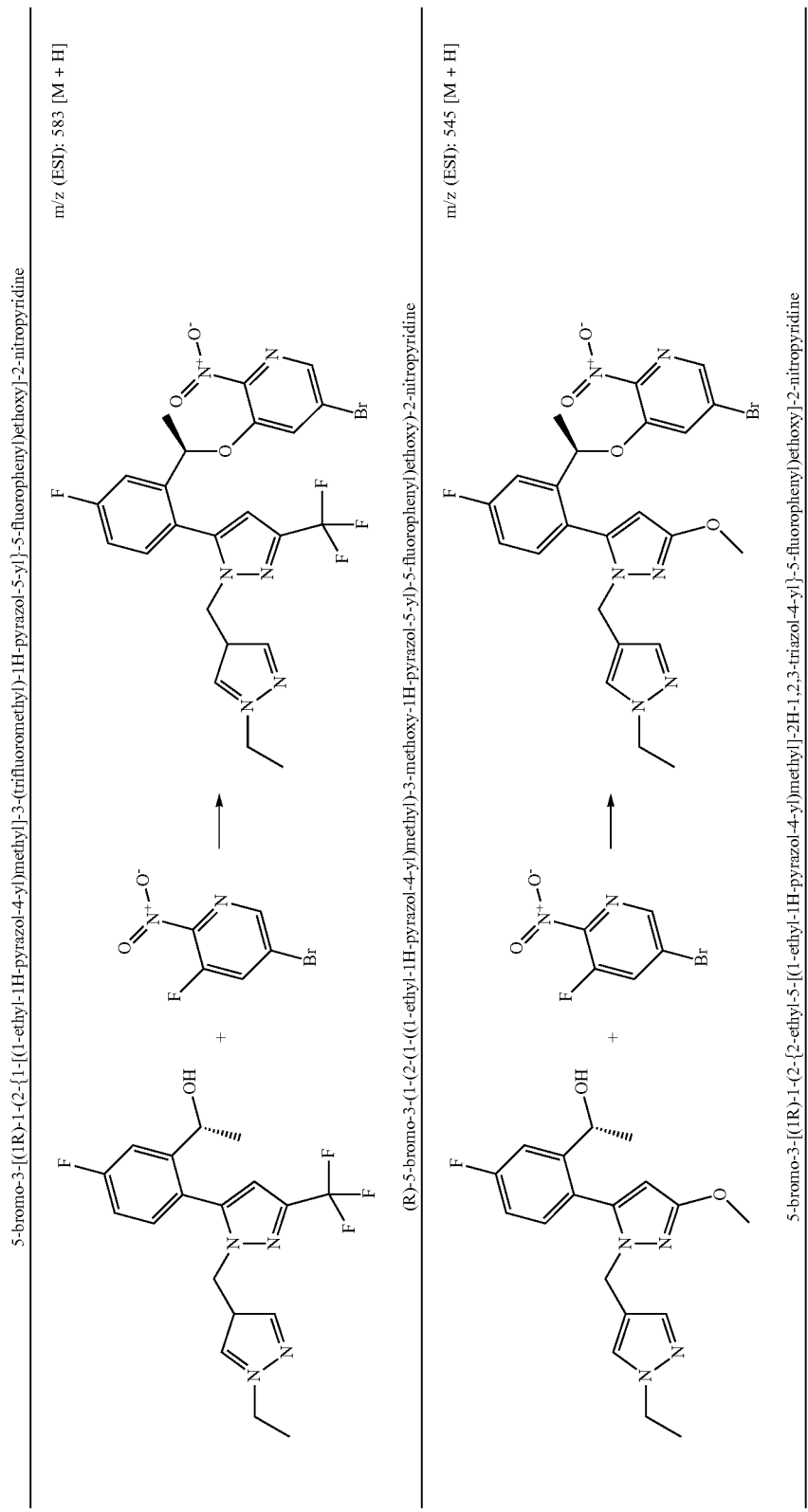

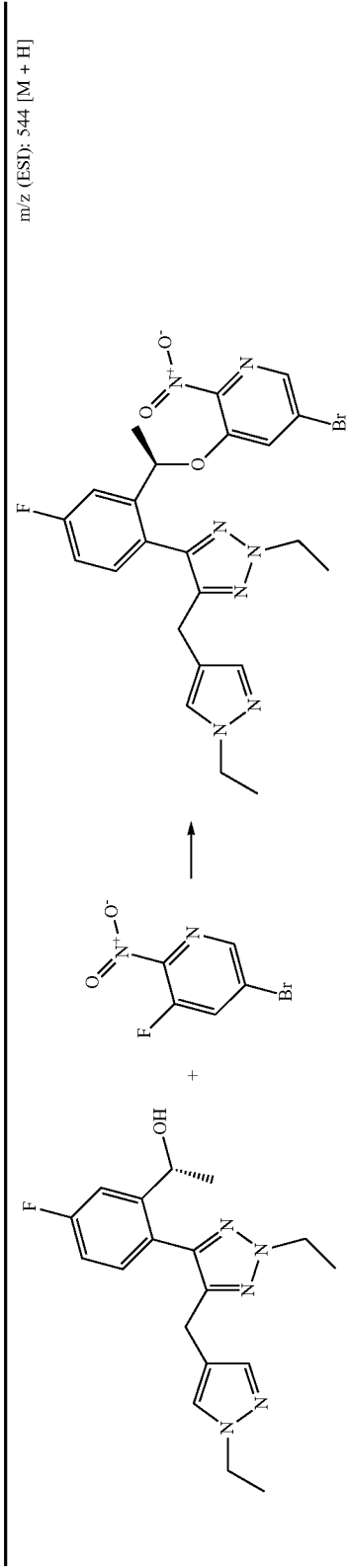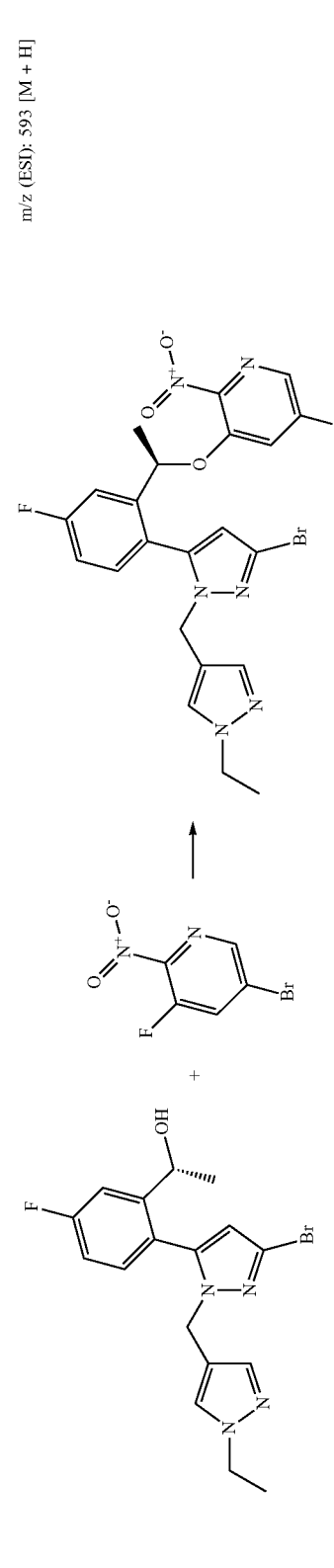

-continued
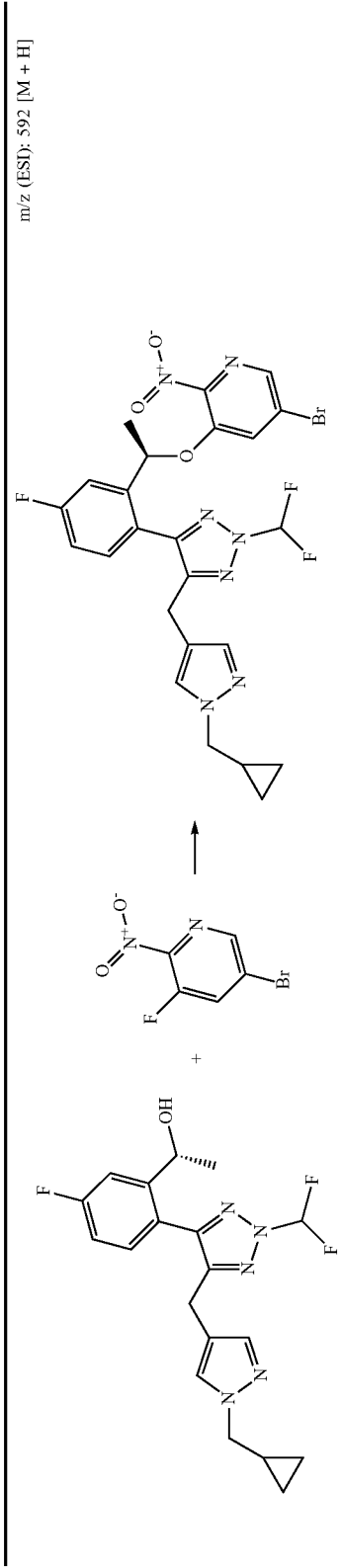
m/z (ESI): 592 [M + H]
(R)-5-(2-(1-((5-bromo-2-nitropyridin-3-yl)oxy)ethyl)-4-((3-chloro-1-ethyl-1H-pyrazol-4-yl)methyl)-4-fluorophenyl)-4-((3-chloro-1-ethyl-1H-pyrazol-4-yl)methyl)-2-methyloxazole
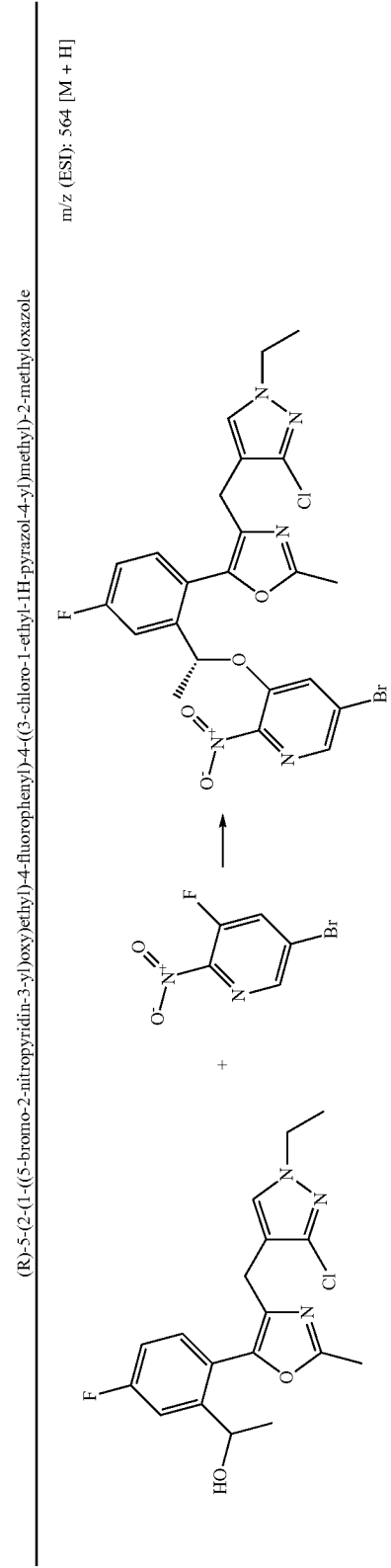
m/z (ESI): 564 [M + H]
(R)-5-bromo-3-(1-(5-fluoro-2-(1-((1-(2-fluoroethyl)-1H-pyrazol-4-yl)methyl)-3-methyl-1H-pyrazol-5-yl)phenyl)ethoxy)-2-nitropyridine
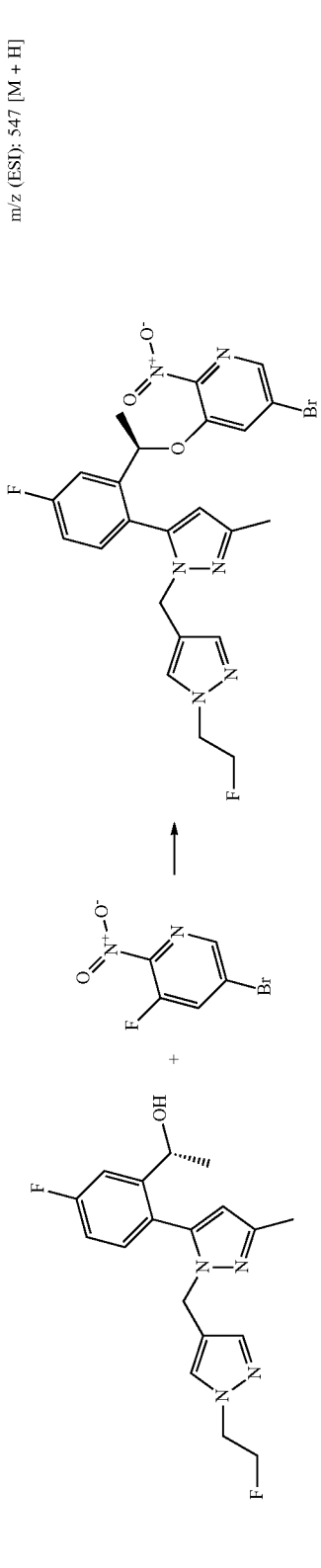
m/z (ESI): 547 [M + H]

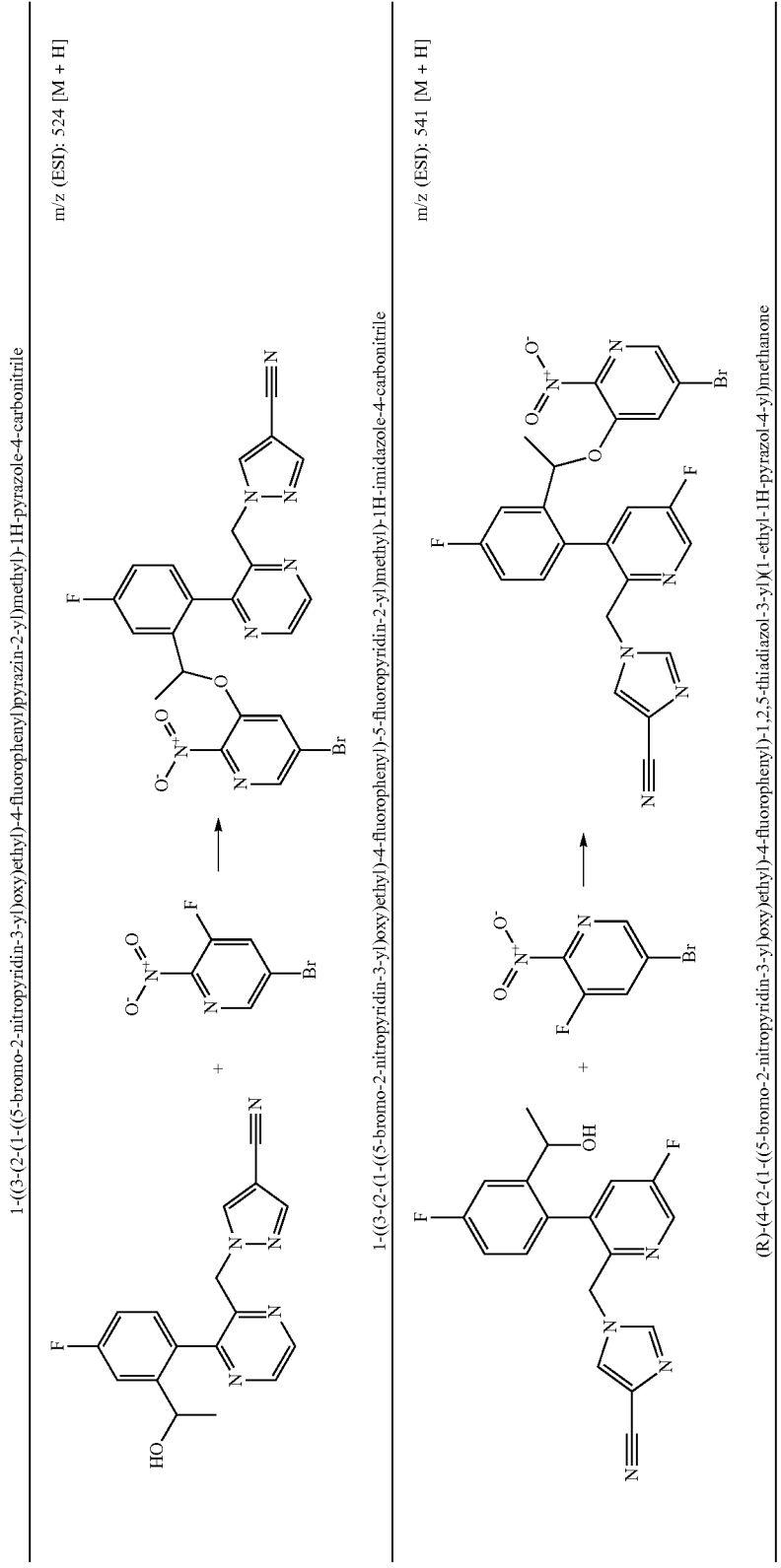

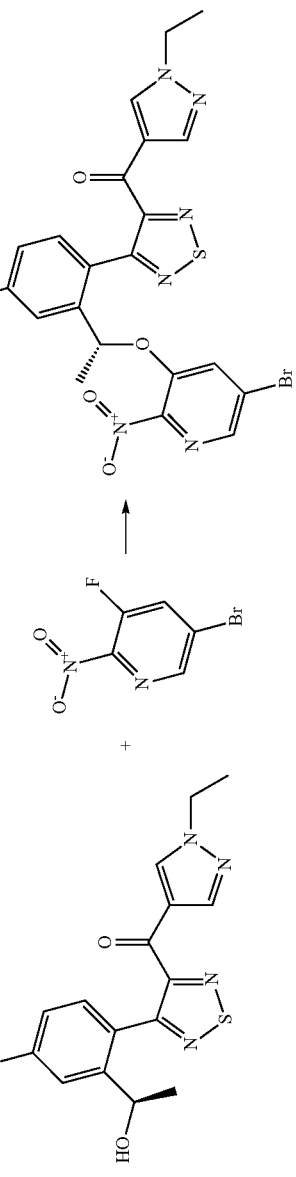
5-((5-(2-(1-((5-bromo-2-nitropyridin-3-yl)oxy)ethyl)-4-fluorophenyl)-1H-tetrazol-1-yl)methyl)-3-ethylisoxazole
m/z (ESI): 547 [M + H]
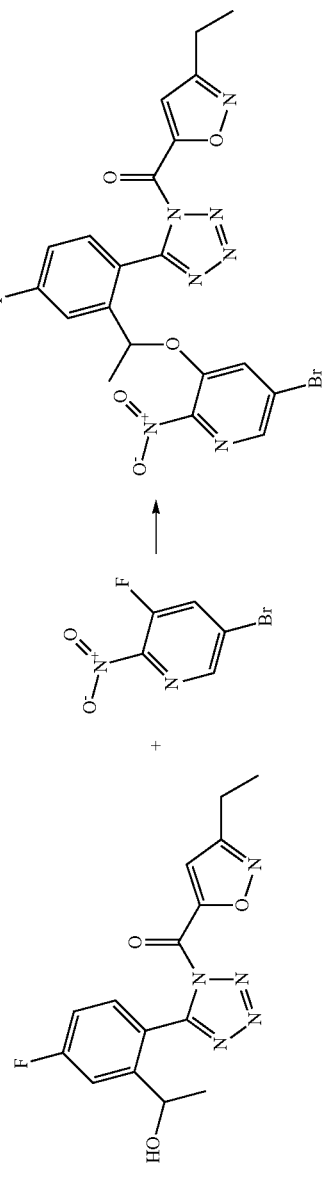
5-bromo-3-(1-(2-(1-((1-(cyclopropylmethyl)-1H-pyrazol-4-yl)methyl)-3-methyl-1H-1,2,4-triazol-5-yl)-5-fluorophenyl)ethoxy)-2-nitropyridine
m/z (ESI): 518 [M + H]

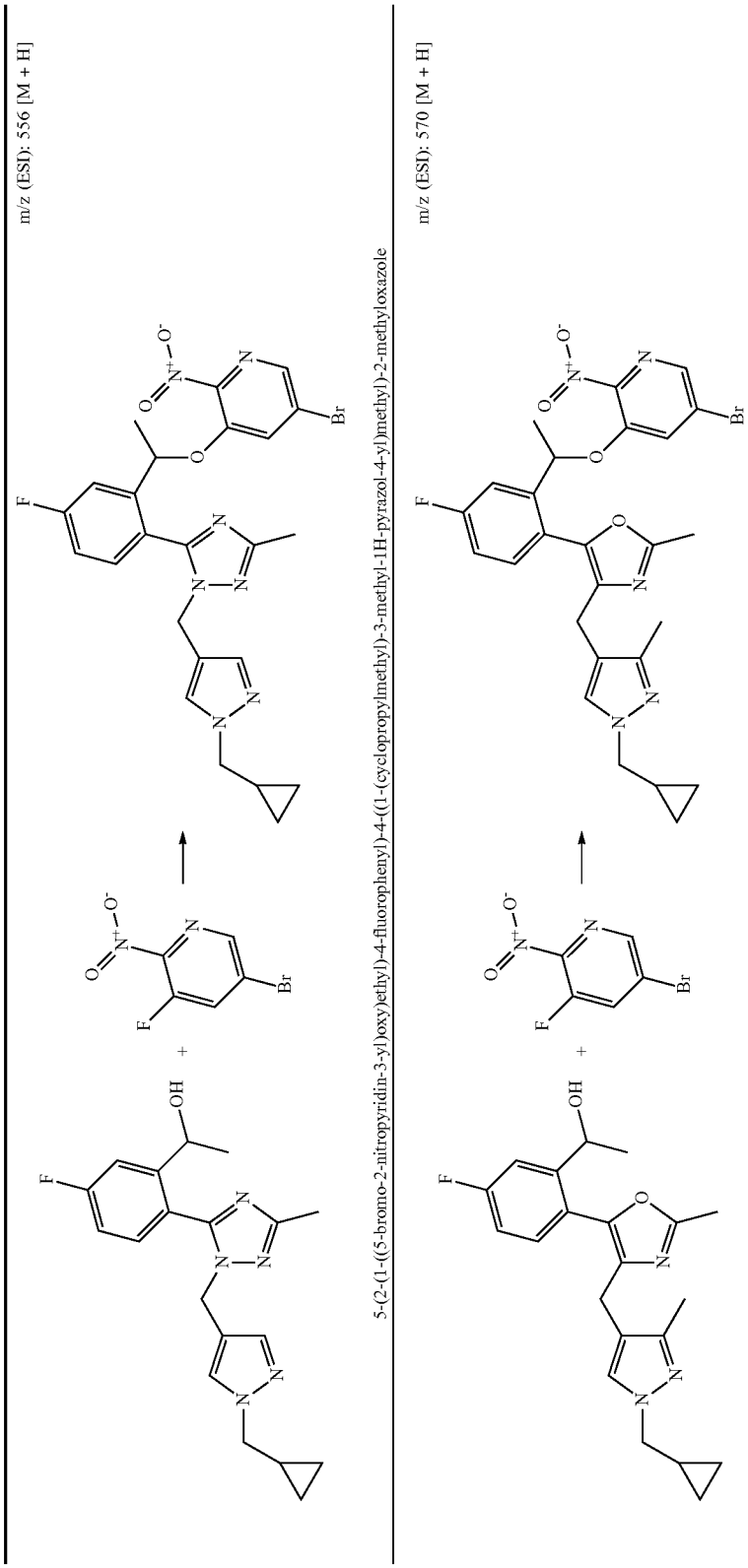

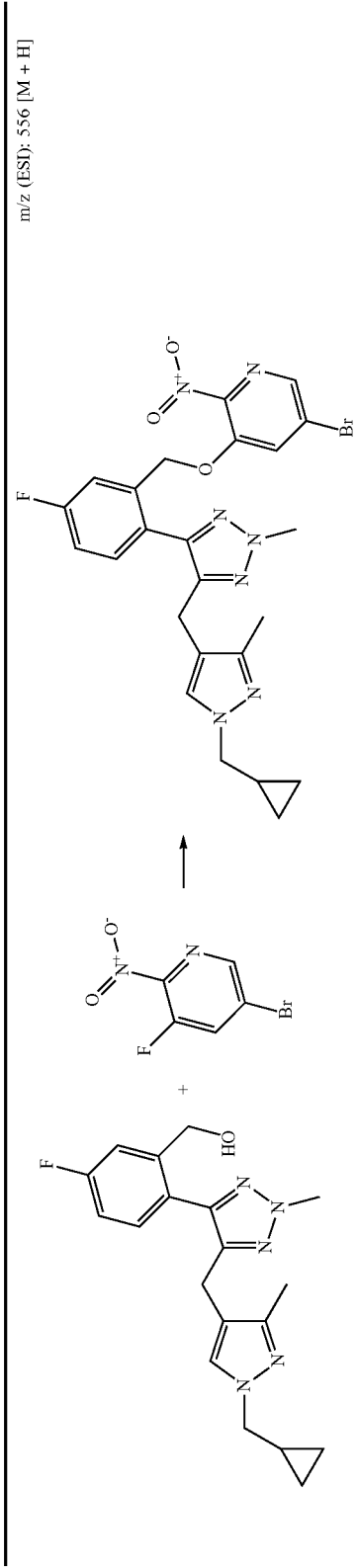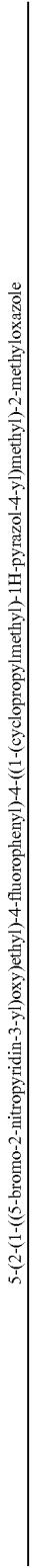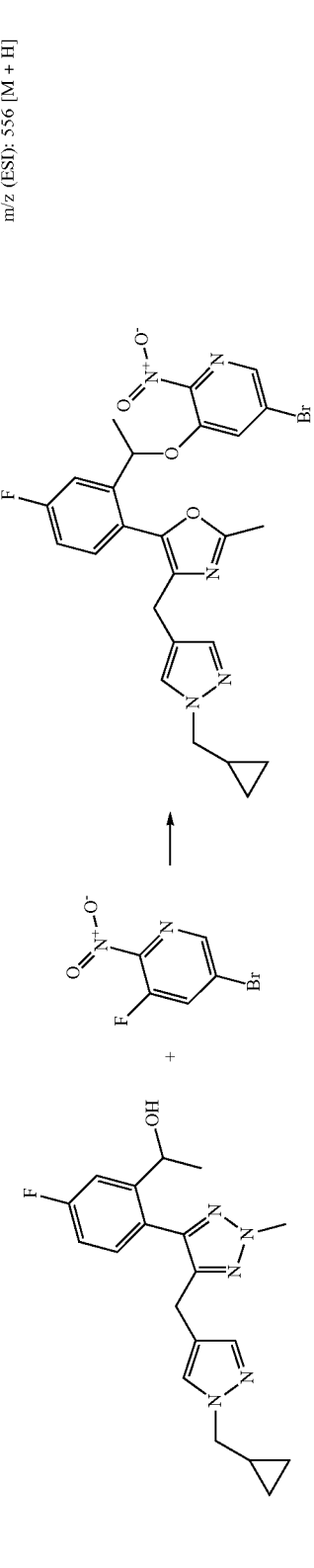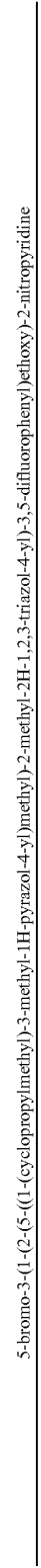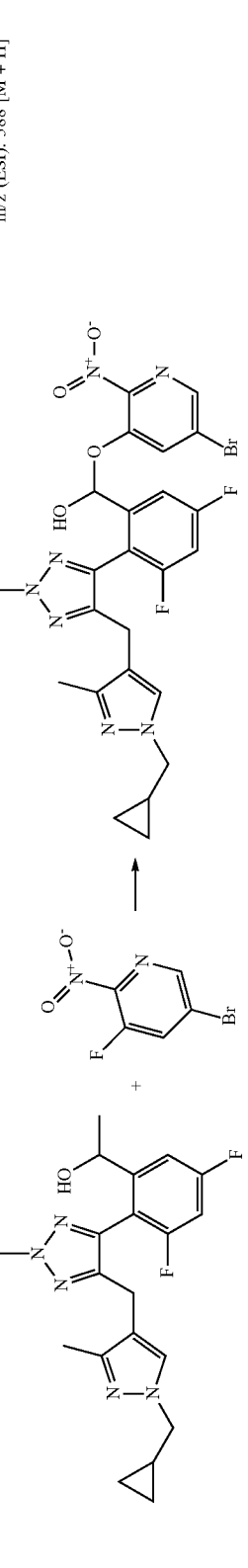

-continued
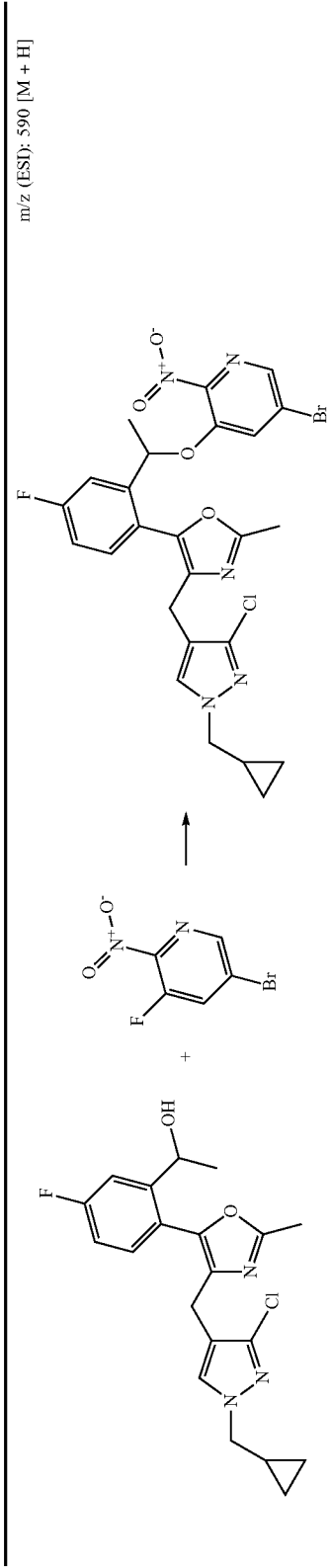
m/z (ESI): 590 [M + H]
(R)-5-bromo-3-(1-(2-(3-chloro-1-((3-ethyl-1-(4-methoxybenzyl)-1H-pyrazol-5-yl)methyl)-1H-pyrazol-5-yl)-5-fluorophenyl)ethoxy)-2-nitropyridine
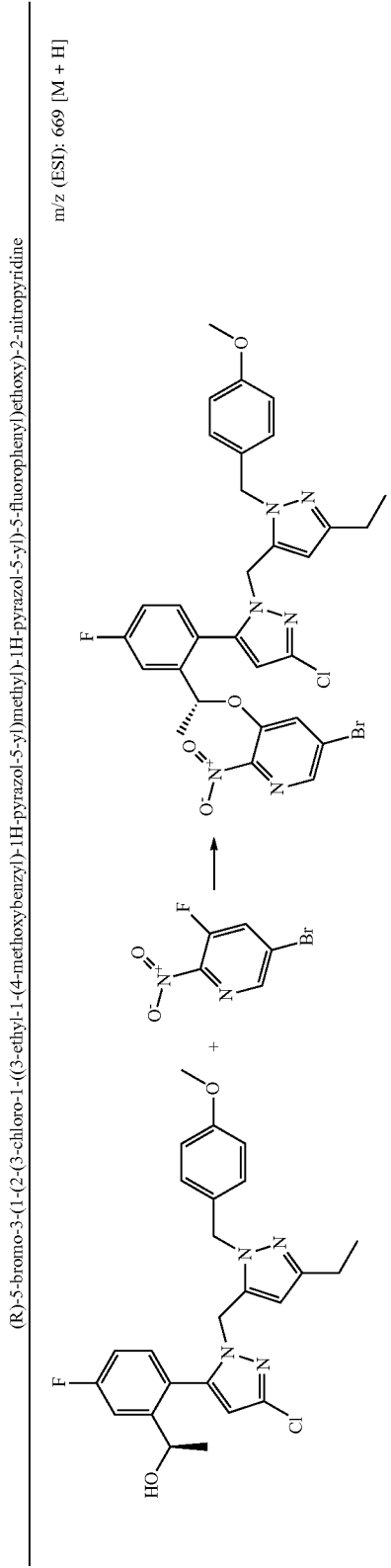
m/z (ESI): 669 [M + H]
(R)-5-bromo-3-(1-(2-(1-((3-(cyclopropylmethyl)-1-methyl-1H-pyrazol-5-yl)methyl)-1H-1,2,4-triazol-5-yl)-5-fluorophenyl)ethoxy)-2-nitropyridine
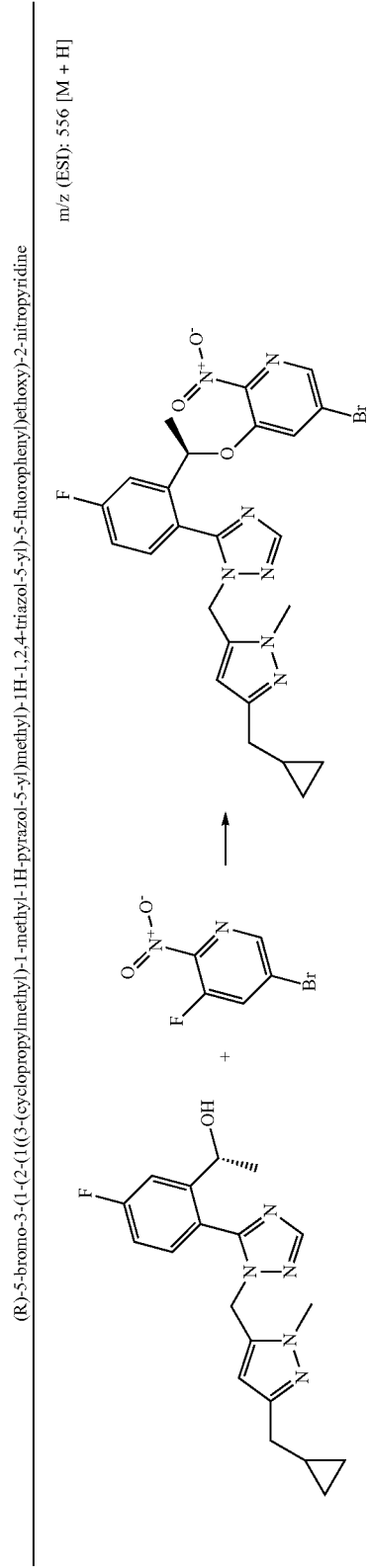
m/z (ESI): 556 [M + H]

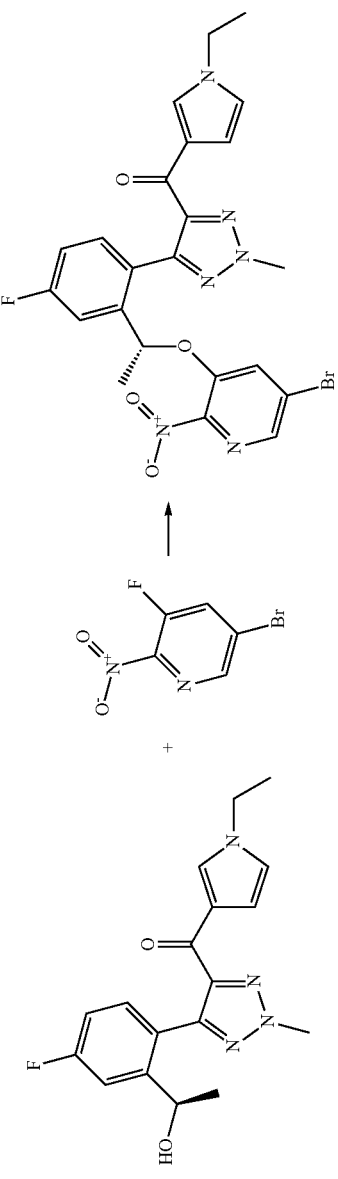
(R)-(5-(2-(1-((5-bromo-2-nitropyridin-3-yl)oxy)ethyl)-4-fluorophenyl)-2-methyl-2H-1,2,3-triazol-4-yl)(1-ethyl-1H-pyrrol-3-yl)methanone
m/z (ESI): 543 [M + H]

Synthesis of 1-[(5-bromo-1-ethyl-1H-pyrazol-4-yl)methyl]-5-iodo-1H-1,2,3-triazole

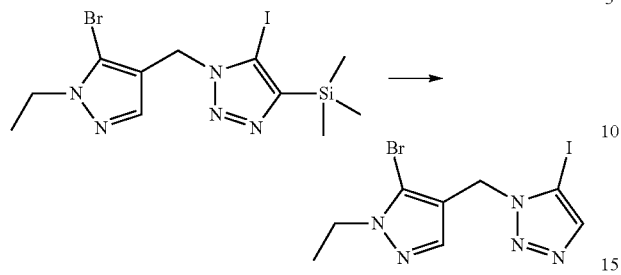

To a solution of 1-[(5-bromo-1-ethyl-1H-pyrazol-4-yl)methyl]-5-iodo-4-(trimethylsilyl)-1H-1,2,3-triazole (400 mg, 0.88 mmol) in MeOH (10 mL) was added K$_2$CO$_3$ (365 mg, 2.64 mmol). The mixture was stirred at 25° C. for 16 h and then concentrated to dryness. The residue was purified by flash chromatography (silica gel, 0→10% MeOH in DCM) to give product 1-[(5-bromo-1-ethyl-1H-pyrazol-4-yl)methyl]-5-iodo-1H-1,2,3-triazole (280 mg, yield: 83%) as a yellow solid. LC/MS (ESI) m/z: 382 [M+H]$^+$.

The following intermediates were synthesized using a similar experimental protocol:

| 1-((5-bromo-1-cyclobutyl-1H-pyrazol-4-yl)methyl)-5-iodo-1H-1,2,3-triazole | | |
|---|---|---|
| 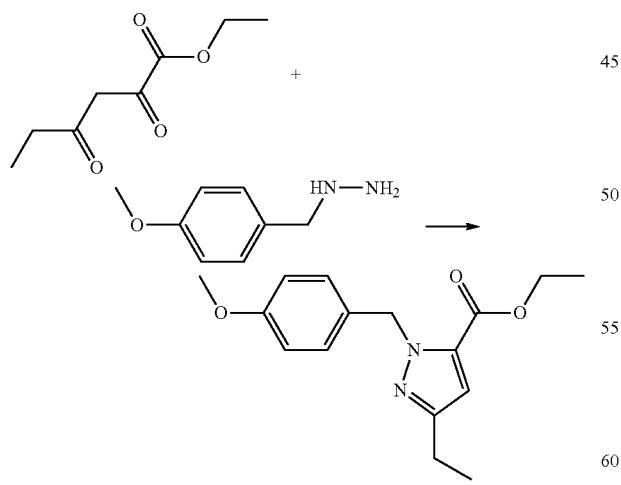 | | m/z (ESI): 408 [M + H] |

Synthesis of ethyl 3-ethyl-1-(4-methoxybenzyl)-1H-pyrazole-5-carboxylate

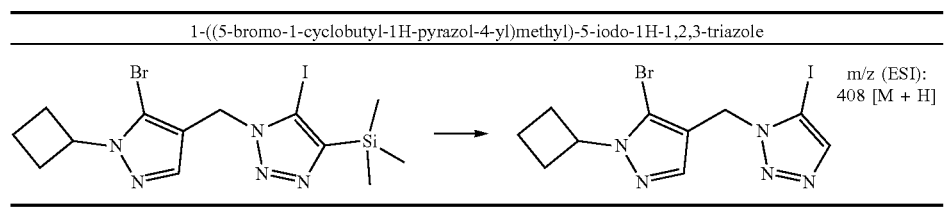

To a stirred solution of ethyl 2,4-dioxohexanoate (4.10 g, 23.8 mmol) in AcOH (33 mL) was added KOAc (5.83 g, 59.5 mmol) and [(4-methoxyphenyl)methyl]hydrazine hydrochloride (4.49 g, 23.8 mmol) at 0° C. The reaction was stirred at 0° C. for 1 h and then the reaction was stirred at r.t. for 12 h. The reaction mixture was concentrated under reduced pressure, the residue was diluted with EtOAc (50 mL), washed with sat. NaHCO$_3$ (50 mL), dried over anhydrous Na$_2$SO$_4$ and evaporated to dryness. The residue was purified by column chromatography on silica gel (10→25% EtOAc in PE) to give ethyl 3-ethyl-1-[(4-methoxyphenyl)methyl]-1H-pyrazole-5-carboxylate (3.8 g, 55%) as a yellow oil. LC/MS (ESI) (m/z): 289 [M+H]$^+$.

Synthesis of tert-butyl 2-((5-bromo-1-cyclobutyl-1H-pyrazol-4-yl)methyl)hydrazinecarboxylate

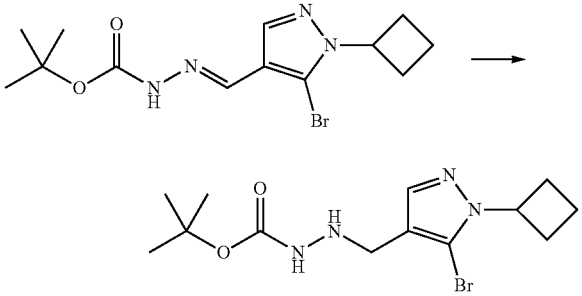

To a solution of (E)-tert-butyl 2-((5-bromo-1-cyclobutyl-1H-pyrazol-4-yl)methylene)hydrazinecarboxylate (3.14 g, 9.15 mmol) in MeOH (20 mL) was added acetic acid (20.0 mL, 349 mmol), followed by the addition of NaBH$_3$CN (1.15 g, 18.3 mmol) at room temperature. The mixture was stirred at r.t. overnight. After concentration, the residue was diluted with DCM, washed with sat. NaHCO$_3$ and brine, dried over anhydrous Na$_2$SO$_4$, filtered and concentrated. The residue was purified by flash chromatography (silica gel, 0→100% EA in PE) to give tert-butyl 2-((5-bromo-1-cyclobutyl-1H-pyrazol-4-yl)methyl)hydrazinecarboxylate (2.65 g, 84%) as a colorless oil. LC/MS ESI (m/z): 345 [M+H]$^+$.

Synthesis of 1-(2-bromo-4-fluorophenyl)-3-(3-chloro-1-ethyl-1H-pyrazol-4-yl)propan-1-ol

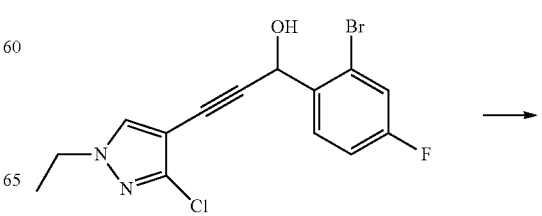

-continued

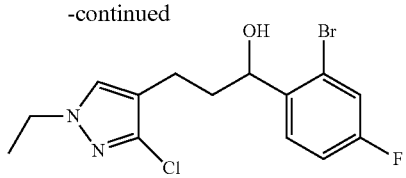

To a stirred solution of 1-(2-bromo-4-fluorophenyl)-3-(3-chloro-1-ethyl-1H-pyrazol-4-yl) prop-2-yn-1-ol (3.3 g, 9.2 mmol) in EtOAc (30 mL) was added PtO$_2$ (0.6 g, 0.4 mmol). The reaction solution was stirred at r.t. for 48 h under H$_2$. The reaction was filtered and concentrated to give 1-(2-bromo-4-fluorophenyl)-3-(3-chloro-1-ethyl-1H-pyrazol-4-yl) propan-1-ol (3.2 g, 97% yield) as a yellow oil. LC/MS ESI (m/z): 361 [M+H]$^+$.

The following intermediates were synthesized using a similar experimental protocol:

| 1-(2-bromo-4-fluorophenyl)-3-(1-(cyclopropylmethyl)-3-methyl-1H-pyrazol-4-yl)propan-1-ol |
|---|

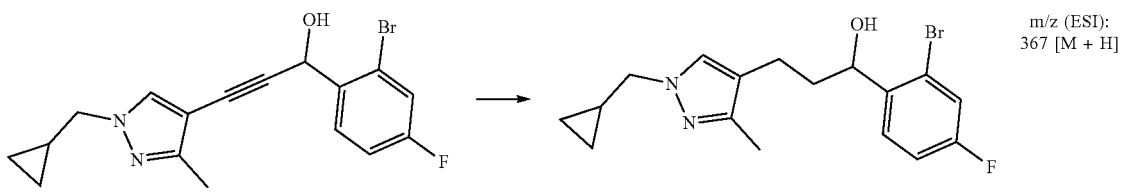

m/z (ESI): 367 [M + H]

| 1-(2-bromo-4-fluorophenyl)-3-[1-(cyclopropylmethyl)-1H-pyrazol-4-yl]propan-1-ol |
|---|

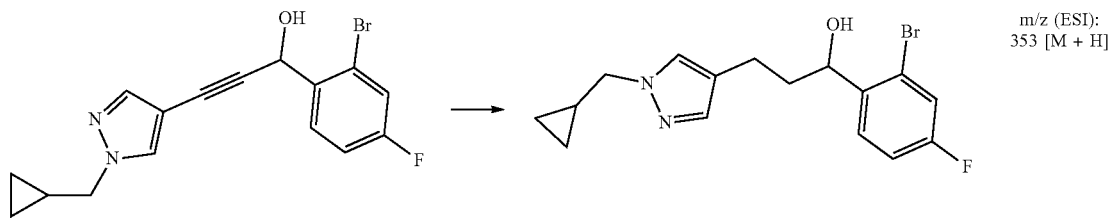

m/z (ESI): 353 [M + H]

Synthesis of 5-((5-iodo-2-methyl-2H-1,2,3-triazol-4-yl)methyl)isoxazole-3-carboxamide

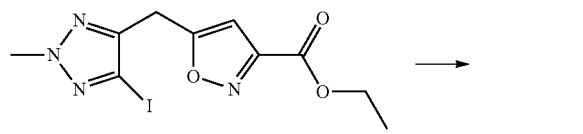

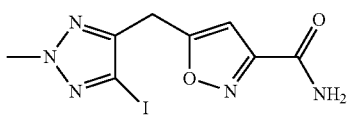

To a solution of ethyl 5-[(5-iodo-2-methyl-2H-1,2,3-triazol-4-yl)methyl]-1,2-oxazole-3-carboxylate (380 mg, 1.05 mmol) in MeOH (0.5 mL) was added NH$_3$ (5 mL, 25 mmol, 5 N in methanol) at 25° C. The resulting mixture was stirred for 3 h at 60° C. The reaction mixture was quenched by ice water and then diluted with EtOAc. The organic layer was separated, washed with sat. aq. NH$_4$Cl solution and brine, dried over anhydrous Na$_2$SO$_4$, filtered and concentrated to dryness. The residue was purified by flash chromatography (silica gel, 0→40% EtOAc in PE) to give 5-((5-iodo-2-methyl-2H-1,2,3-triazol-4-yl)methyl)isoxazole-3-carboxamide (330 mg, 94%) as a yellow solid. LC/MS ESI (m/z): 334 [M+H]$^+$.

Synthesis of 3-[(1R)-1-(5-fluoro-2-iodophenyl)ethoxy]pyridin-2-amine

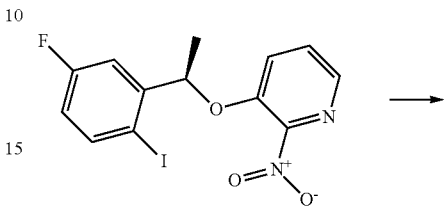

-continued

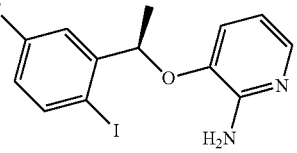

A mixture of (R)-3-(1-(5-fluoro-2-iodophenyl)ethoxy)-2-nitropyridine (15.5 g, 40.0 mmol), iron powder (22.4 g, 400 mmol) and NH$_4$Cl (21.6 g, 400 mmol) in co-solvent of EtOH (550 mL) and H$_2$O (110 mL) was stirred at 80° C. for 1 h. After cooling to r.t., the mixture was filtered, the filtrate was concentrated under reduced pressure. The residue was diluted with DCM (500 mL), then washed with water and brine, dried over anhydrous Na$_2$SO$_4$, filtered and concentrated. The residue was purified by column chromatography on silica gel (50% EtOAc in PE) to give 3-[(1R)-1-(5-fluoro-2-iodophenyl)ethoxy]pyridin-2-amine as a white solid (10.5 g, yield: 73%). LC/MS ESI (m/z): 359 [M+H]$^+$.

The following intermediates were synthesized using a similar experimental protocol:

| 3-(1-(5-fluoro-2-iodophenyl)ethoxy)pyridin-2-amine |
|---|
| 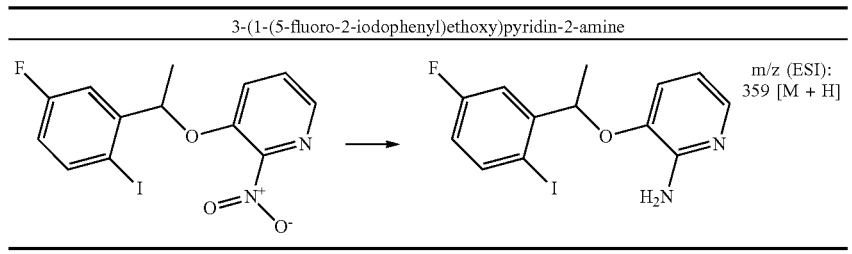 m/z (ESI): 359 [M + H] |

Synthesis of 1-(2-bromo-4-fluorophenyl)-3-(3-chloro-1-ethyl-1H-pyrazol-4-yl)propan-1-one Synthesis of 5-(2-bromo-4-fluorophenyl)-4-((1-ethyl-1H-pyrazol-4-yl)methyl)-2-methyloxazole

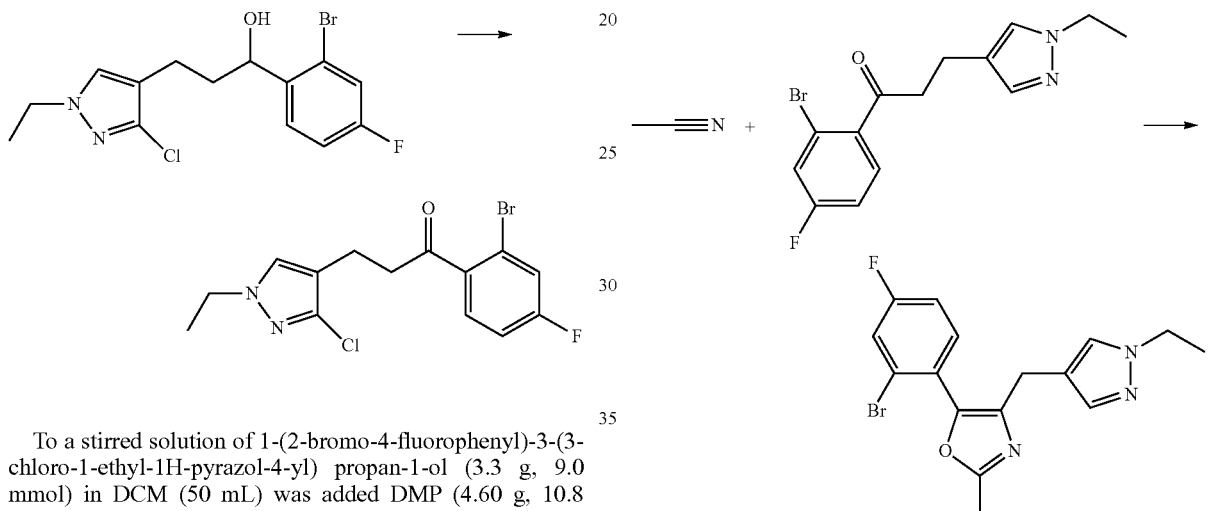

To a stirred solution of 1-(2-bromo-4-fluorophenyl)-3-(3-chloro-1-ethyl-1H-pyrazol-4-yl) propan-1-ol (3.3 g, 9.0 mmol) in DCM (50 mL) was added DMP (4.60 g, 10.8 mmol) at 0° C. The reaction was stirred at r.t. for 2 h. The reaction was filtered, the filtrate was washed with sat. NaHCO$_3$ (50 mL) and brine (20 mL), dried over anhydrous Na$_2$SO$_4$ and concentrated. The residue was purified by flash chromatography (0→50% EtOAc in PE) to give 1-(2-bromo-4-fluorophenyl)-3-(3-chloro-1-ethyl-1H-pyrazol-4-yl)propan-1-one (2.06 g, 64% yield) as a yellow oil. LC/MS ESI (m/z): 359 [M+H]$^+$.

The following intermediates were synthesized using a similar experimental protocol:

To a solution of iodosobenzene (0.680 g, 3.07 mmol) and acetonitrile (15 mL) was added triflic acid (1.15 g, 7.68 mmol) at 0° C. The mixture was stirred at 0° C. for 0.5 h, then 1-(2-bromo-4-fluorophenyl)-3-(1-ethyl-1H-pyrazol-4-yl)propan-1-one (1.00 g, 3.07 mmol) was added. The mixture was stirred at 80° C. for 16 h. The reaction was quenched with sat. aq. ammonium chloride and ice. The reaction mixture was concentrated and diluted with DCM.

| 1-(2-bromo-4-fluorophenyl)-3-(1-(cyclopropylmethyl)-3-methyl-1H-pyrazol-4-yl)propan-1-one |
|---|
| 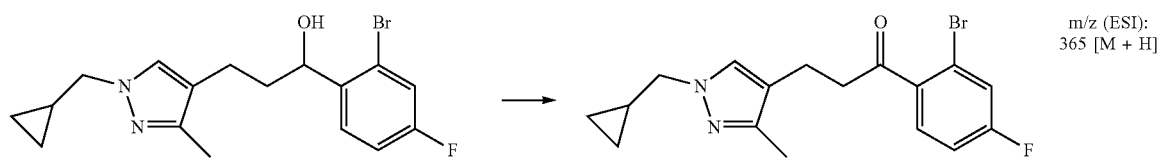 m/z (ESI): 365 [M + H] |

| 1-(2-bromo-4-fluorophenyl)-3-[1-(cyclopropylmethyl)-1H-pyrazol-4-yl]propan-1-one |
|---|
| 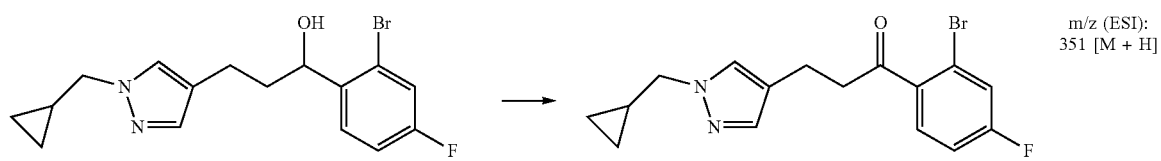 m/z (ESI): 351 [M + H] |

This solution was washed with sat. aq. NaCl, dried over anhydrous Na₂SO₄, filtered, and concentrated. The residue was purified by flash chromatography (silica gel, 0→50% EA in PE) to give 5-(2-bromo-4-fluorophenyl)-4-[(1-ethyl-1H-pyrazol-4-yl)methyl]-2-methyl-1,3-oxazole (450 mg, 40% yield) as a white solid. LC/MS (ESI) m/z: 364 [M+H]⁺.

The following intermediates were synthesized using a similar experimental protocol:

5-(2-bromo-4-methylphenyl)-4-((1-(cyclopropylmethyl)-3-methyl-1H-pyrazol-4-yl)methyl)-2-methyloxazole m/z (ESI): 400 [M + H]

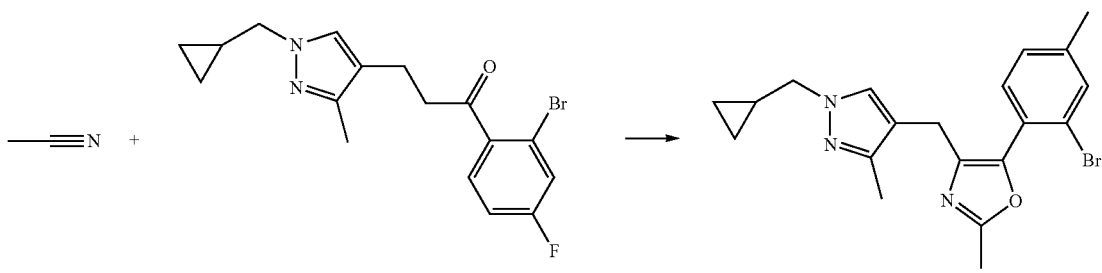

5-(2-bromo-4-fluorophenyl)-4-((1-(cyclopropylmethyl)-1H-pyrazol-4-yl)methyl)-2-methyloxazole m/z (ESI): 390 [M + H]

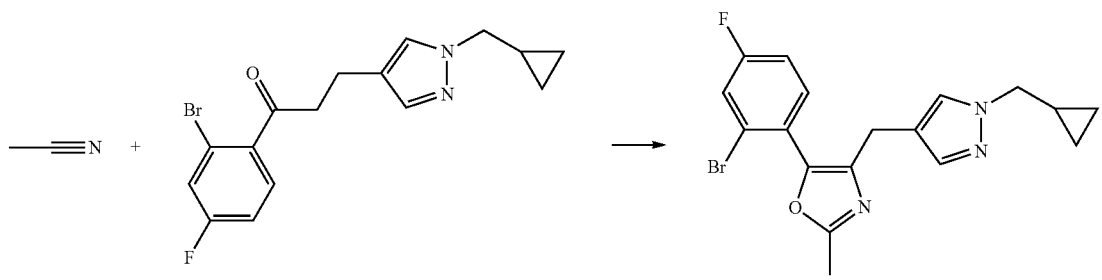

Synthesis of 3-bromo-2-(1-((5-bromo-1-ethyl-1H-pyrazol-4-yl)methyl)-1H-pyrazol-5-yl)-5-fluoropyridine

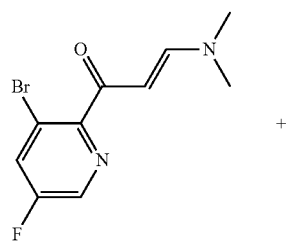

+

To a solution of (E)-1-(3-bromo-5-fluoropyridin-2-yl)-3-(dimethylamino)prop-2-en-1-one (3.00 g, 11.0 mmol) in AcOH (20 mL) were added 5-bromo-1-ethyl-4-(hydrazinylmethyl)-1H-pyrazole hydrochloride (2.81 g, 11.0 mmol) and sodium acetate (4.51 g, 54.9 mmol). The resulting mixture was stirred for 16 h at 80° C. After concentration in vacuo, the residue was dissolved in DCM, then washed with water and brine, dried over anhydrous $Na_2SO_4$, filtered and concentrated. The residue was purified by flash chromatography on silica gel (0→40% EtOAc in PE) to give 3-bromo-2-(1-((5-bromo-1-ethyl-1H-pyrazol-4-yl)methyl)-1H-pyrazol-5-yl)-5-fluoropyridine as a yellow solid. (1.2 g, 25% yield). LC/MS ESI (m/z): 428 [M+H]⁺.

The following intermediates were synthesized using a similar experimental protocol:

1-[(5-bromo-1-ethyl-1H-pyrazol-4-yl)methyl]-5-(4-fluoro-2-iodophenyl)-1H-1,2,4-triazole m/z (ESI): 476 [M + H]

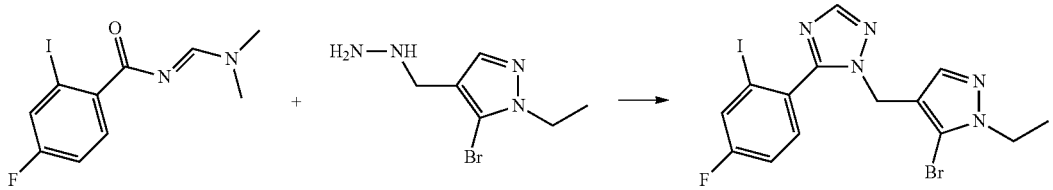 [SMILES: CN(C)/C=N/C(=O)c1ccc(F)cc1I ; CCn1ncc(CNN)c1Br ; CCn1ncc(Cn2ncnc2-c2ccc(F)cc2I)c1Br]

1-((5-bromo-1-cyclobutyl-1H-pyrazol-4-yl)methyl)-5-(4-fluoro-2-iodophenyl)-1H-1,2,4-triazole m/z (ESI): 502 [M + H]

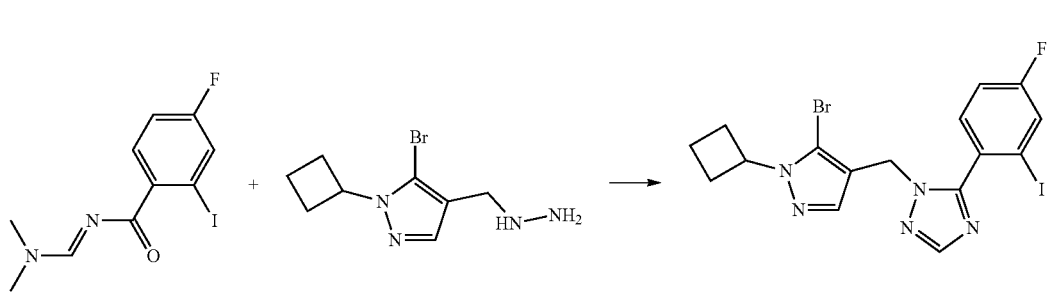 [SMILES: CN(C)/C=N/C(=O)c1ccc(F)cc1I ; NNCc1cnn(C2CCC2)c1Br ; Fc1ccc(-c2ncnn2Cc2cnn(C3CCC3)c2Br)c(I)c1]

-continued

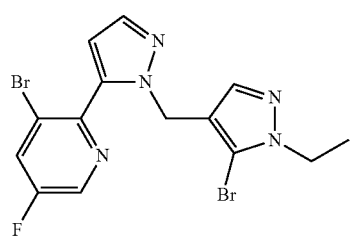

Synthesis of 5-bromo-3-[(1R)-1-(5-fluoro-2-iodophenyl)ethoxy]pyridin-2-amine

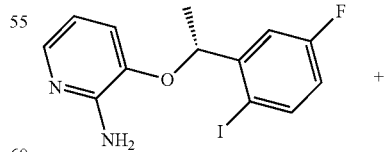

+

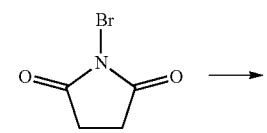

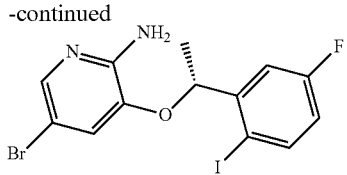

To a solution of 3-[(1R)-1-(5-fluoro-2-iodophenyl)ethoxy]pyridin-2-amine (21.0 g, 58.6 mmol) in HOAc (2000 mL) at 0° C. was added the solution of N-bromosuccinimide (12.52 g, 70.36 mmol) in HOAc (360 mL) dropwise over 30 min. After the addition, the mixture was stirred at r.t. for 16 h. The reaction mixture was directly concentrated in vacuo and the residue was purified by flash chromatography (0→20% EtOAc in PE) to give 5-bromo-3-[(1R)-1-(5-fluoro-2-iodophenyl)ethoxy]pyridin-2-amine (10.5 g, 41% yield) as a white solid. LC/MS ESI (m/z): 437 [M+H]$^+$.

The following intermediates were synthesized using a similar experimental protocol:

2-(5-bromo-1-ethyl-1H-pyrazol-4-yl)acetamide (500 mg, 2.15 mmol) was added to DMF-DMA (3.46 mL, 25.9 mmol) at 25° C. The resulting mixture was stirred at 25° C. for 14 h. Then, the reaction mixture was concentrated by oil pump. The residue was added to a solution of N-(4-fluoro-2-iodophenyl)hydrazine HCl salt (712 mg, 3.02 mmol) in AcOH (10 mL). The mixture was stirred at 70° C. for 2 h. After cooling to r.t., the reaction mixture was concentrated in vacuo and the residue was treated with sat. NaHCO$_3$ (100 mL). The mixture was then extracted with EA (70 mL) twice. The combined extracts were concentrated and purified by flash chromatography (0→80% EA in PE) to give 5-[(5-bromo-1-ethyl-1H-pyrazol-4-yl)methyl]-1-(4-fluoro-2-iodophenyl)-1H-1,2,4-triazole (480 mg, 47%) as a white solid. LC/MS (ESI): m/z=476 [M+H]$^+$ 5-bromo-3-(1-(5-fluoro-2-iodophenyl)ethoxy)pyridin-2-amine m/z (ESI): 437 [M + H]

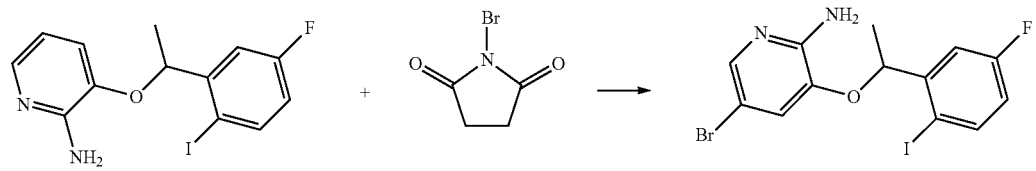 [SMILES: CC(Oc1cccnc1N)c1cc(F)ccc1I ; O=C1CCC(=O)N1Br ; CC(Oc1cc(Br)cnc1N)c1cc(F)ccc1I]

Synthesis of 5-[(5-bromo-1-ethyl-1H-pyrazol-4-yl)methyl]-1-(4-fluoro-2-iodophenyl)-1H-1,2,4-triazole Synthesis of 1-(2-(1-((3-ethylisoxazol-5-yl)methyl)-1H-1,2,4-triazol-5-yl)-5-fluorophenyl)ethan-1-ol

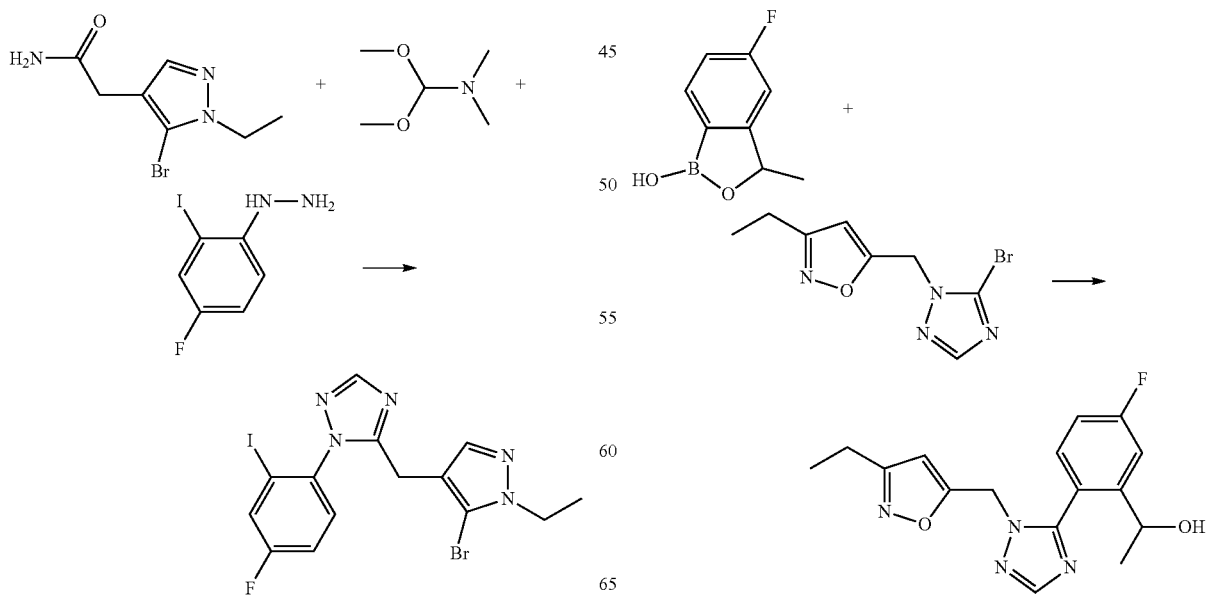

To a solution of 5-bromo-1-[(3-ethyl-1,2-oxazol-5-yl)methyl]-1H-1,2,4-triazole (260 mg, 1.01 mmol) in toluene (10 mL) was added 5-fluoro-3-methyl-1,3-dihydro-2,1-benzoxaborol-1-ol (250 mg, 1.52 mmol), Pd(PPh$_3$)$_4$ (0.12 g, 0.10 mmol), EtOH (5 mL) and aq. Na$_2$CO$_3$ (2.0 mL, 4.0 mmol, 2.0 M). The resulting mixture was charged with N$_2$ twice, then stirred at 95° C. for 12 h. After cooling to r.t., the mixture was filtered, the filtrate was concentrated under reduced pressure. The residue was diluted with dichloromethane (20 mL), then washed with water and brine, dried over anhydrous Na$_2$SO$_4$, filtered and concentrated. The residue was purified by column chromatography on silica gel (0→3% MeOH in DCM) to give 1-(2-{1-[(3-ethyl-1,2-oxazol-5-yl)methyl]-1H-1,2,4-triazol-5-yl}-5-fluorophenyl)ethan-1-ol (200 mg, yield: 63%) as a white solid. LC/MS ESI (m/z): 317 [M+H]$^+$.

The following intermediates were synthesized using a similar experimental protocol:

(1R)-1-[2-(5-{[1-(cyclopropylmethyl)-3-methyl-1H-pyrazol-4-yl]methyl}-2-methyl-2H-1,2,3-triazol-4-yl)-5-fluorophenyl]ethan-1-ol

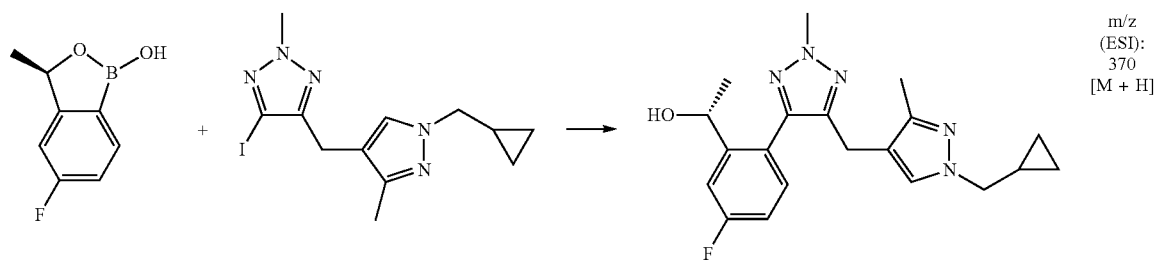

m/z (ESI): 370 [M + H]

(R)-1-(2-(1-((5-bromo-1-(cyclopropylmethyl)-3-methyl-1H-pyrazol-4-yl)methyl)-1H-pyrazol-5-yl)-5-fluorophenyl)ethan-1-ol

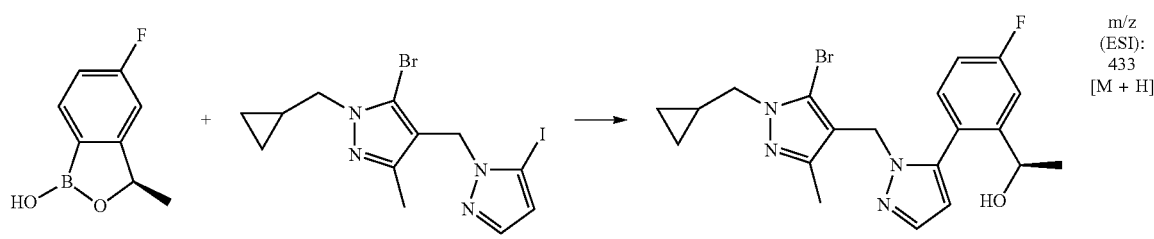

m/z (ESI): 433 [M + H]

1-(2-(3-((5-bromo-1-ethyl-1H-pyrazol-4-yl)methyl)pyrazin-2-yl)-5-fluorophenyl)ethan-1-ol

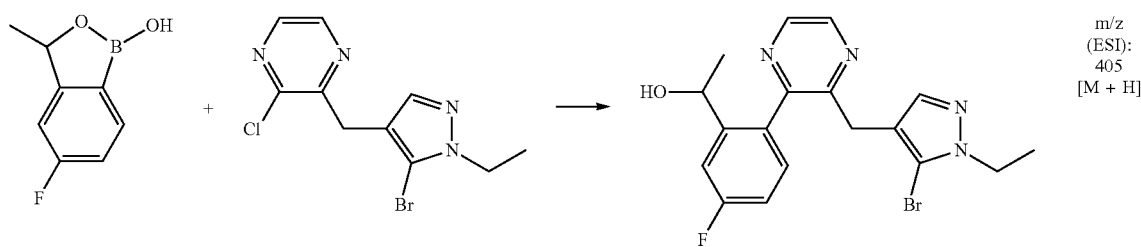

m/z (ESI): 405 [M + H]

1-(2-(1-((4-bromo-3-ethylisothiazol-5-yl)methyl)-1H-1,2,4-triazol-5-yl)-5-fluorophenyl)ethan-1-ol

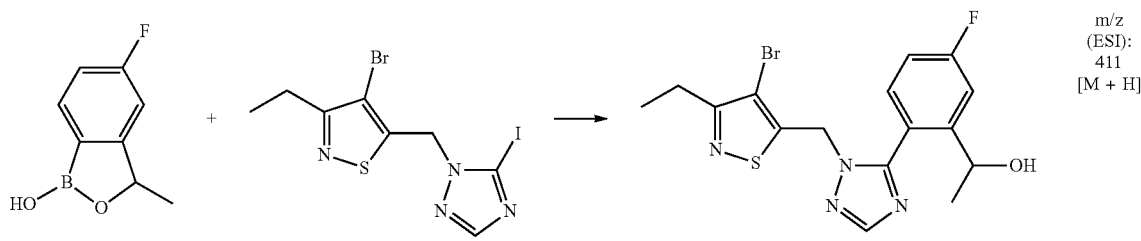

m/z (ESI): 411 [M + H]

-continued 1-(2-(2-((5-bromo-1-ethyl-1H-pyrazol-4-yl)methyl)pyridin-3-yl)-5-fluorophenyl)ethan-1-ol

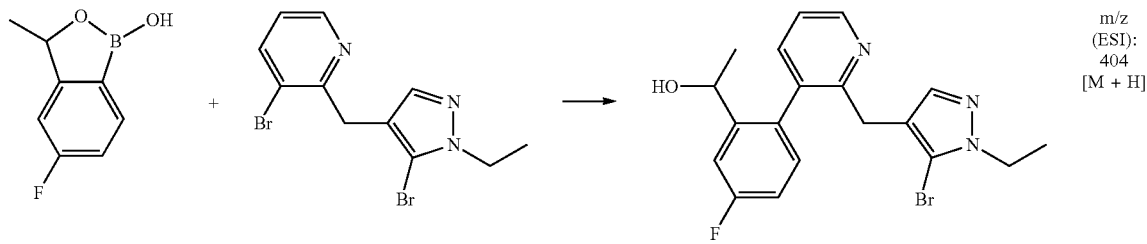

m/z (ESI): 404 [M + H]

(1R)-1-(2-{1-[(1-ethyl-3-methyl-1H-pyrazol-4-yl)methyl]-1H-1,2,4-triazol-5-yl}-5-fluorophenyl)ethan-1-ol

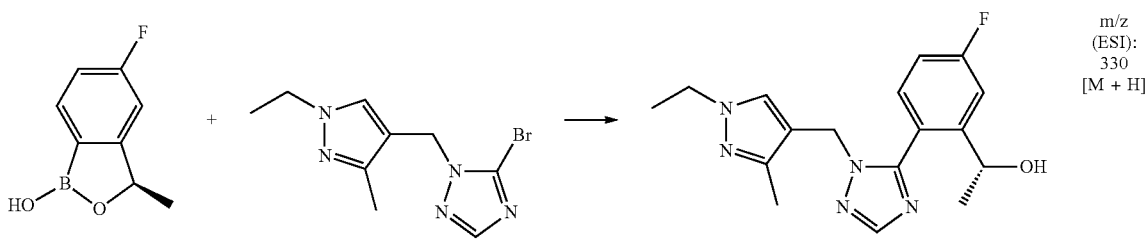

m/z (ESI): 330 [M + H]

(R)-1-(2-(1-((3-cyclobutylisoxazol-5-yl)methyl)-1H-1,2,4-triazol-5-yl)-5-fluorophenyl)ethan-1-ol

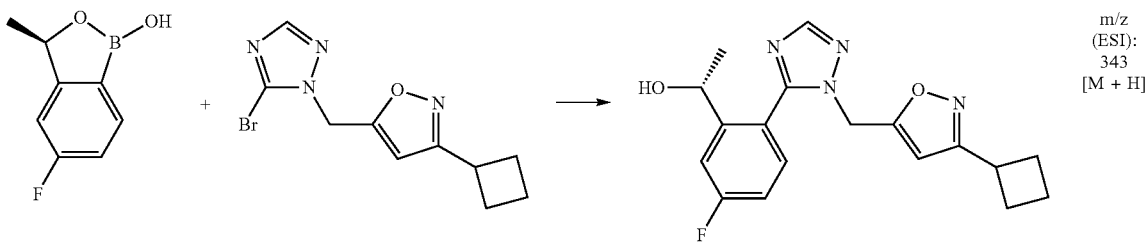

m/z (ESI): 343 [M + H]

(R)-1-(2-(4-((1-ethyl-1H-1,2,3-triazol-4-yl)methyl)thiazol-5-yl)-5-fluorophenyl)ethan-1-ol

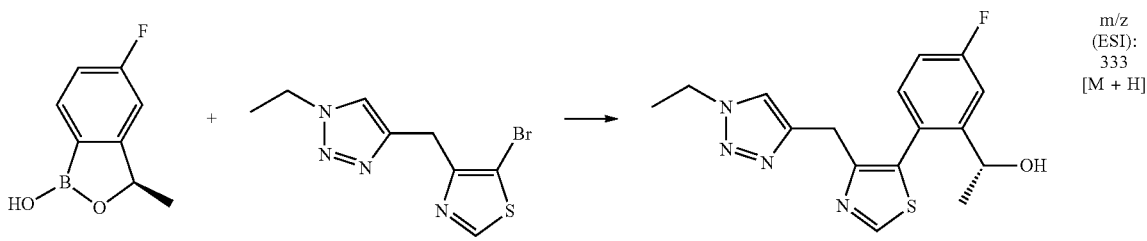

m/z (ESI): 333 [M + H]

(R)-5-((5-(4-fluoro-2-(1-hydroxyethyl)phenyl)thiazol-4-yl)methyl)-1-methyl-1H-pyrazole-3-carbonitrile

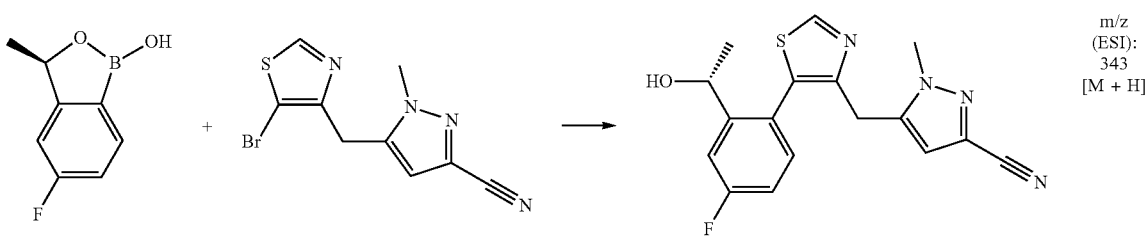

m/z (ESI): 343 [M + H]

(R)-1-(2-(5-((1-(cyclopropylmethyl)-1H-1,2,3-triazol-4-yl)methyl)-2-methyl-2H-1,2,3-triazol-4-yl)-5-fluorophenyl)ethan-1-ol
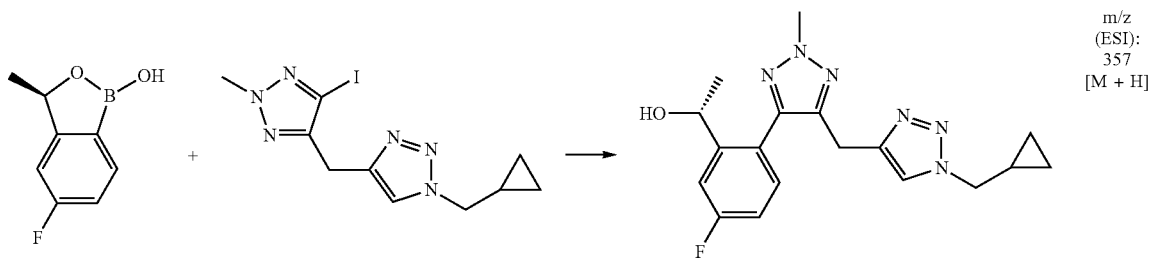
m/z (ESI): 357 [M + H]
(R)-1-(2-(3-chloro-1-((1-ethyl-1H-1,2,3-triazol-4-yl)-methyl)-1H-pyrazol-5-yl)-5-fluorophenyl)-1-ethanol
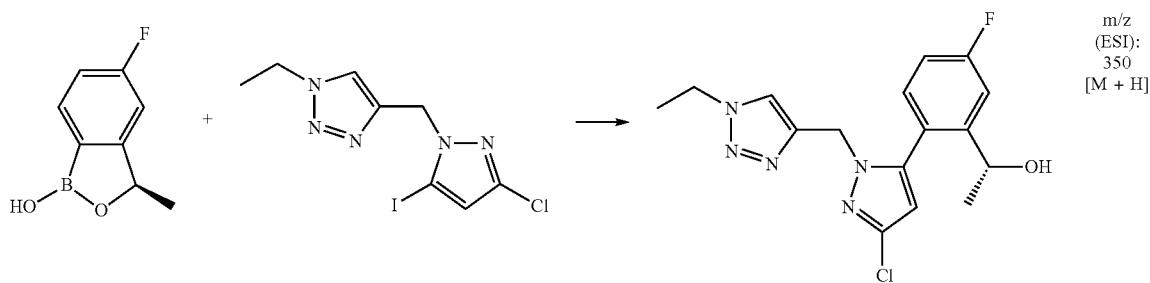
m/z (ESI): 350 [M + H]
(1R)-1-[2-(3-chloro-1-{[1-(2,2-difluoroethyl)-1H-pyrazol-4-yl]methyl}-1H-pyrazol-5-yl)-5-fluorophenyl]ethan-1-ol
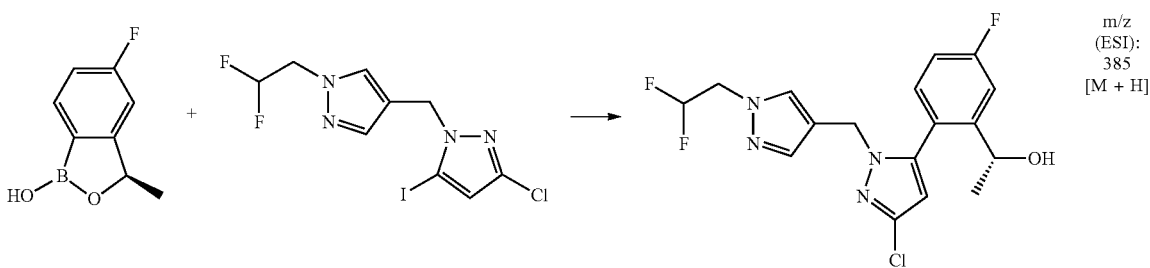
m/z (ESI): 385 [M + H]
(R)-1-(2-(3-chloro-1-((1-(ethyl-d5)-1H-pyrazol-4-yl)methyl)-1H-pyrazol-5-yl)-5-fluorophenyl)ethan-1-ol
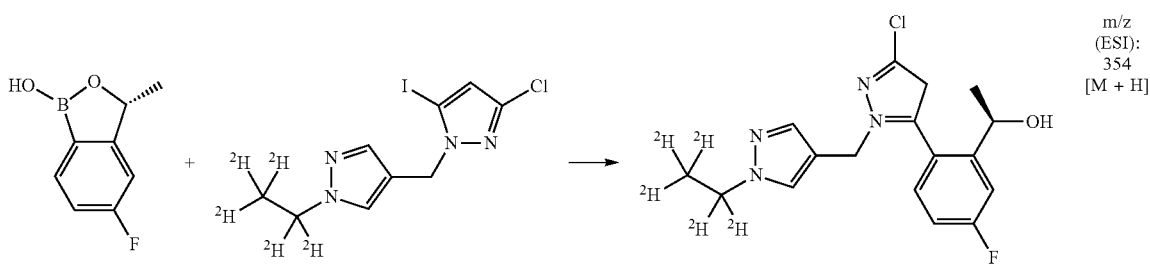
m/z (ESI): 354 [M + H]

-continued (R)-1-(2-(5-((1-(cyclopropylmethyl)-1H-pyrazol-4-yl)methyl)-2-methyl-2H-1,2,3-triazol-4-yl)-5-fluorophenyl)ethan-1-ol

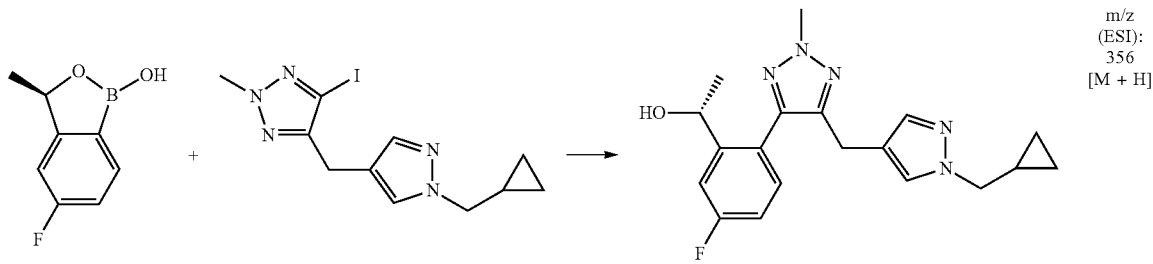

m/z (ESI): 356 [M + H]

(R)-1-(2-(5-((3-(cyclopropylmethyl)isoxazol-5-yl)methyl)-2-methyl-2H-1,2,3-triazol-4-yl)-5-fluorophenyl)ethan-1-ol

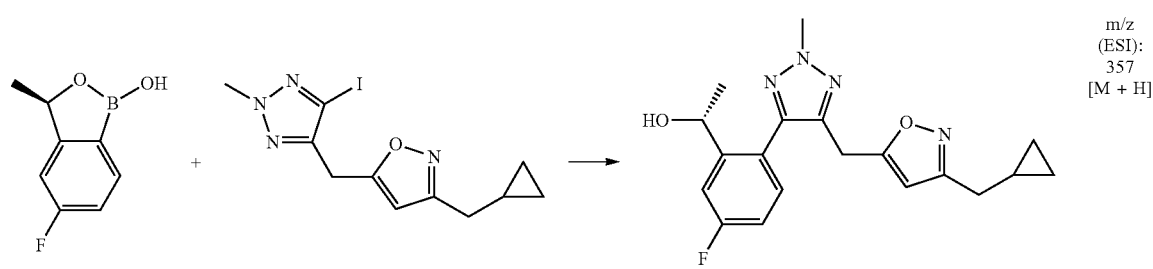

m/z (ESI): 357 [M + H]

(R)-1-(2-(1-((3-(cyclopropylmethyl)isoxazol-5-yl)methyl)-1H-1,2,4-triazol-5-yl)-5-fluorophenyl)ethan-1-ol

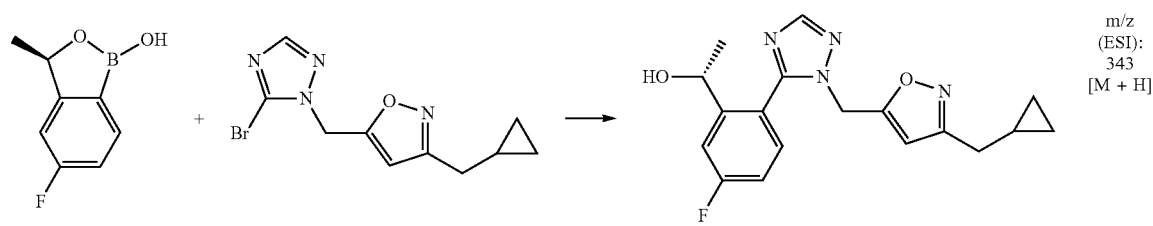

m/z (ESI): 343 [M + H]

(R)-1-(2-(5-((3-chloro-1-(2,2-difluoroethyl)-1H-pyrazol-4-yl)methyl)-2-methyl-2H-1,2,3-triazol-4-yl)-5-fluorophenyl)ethan-1-ol

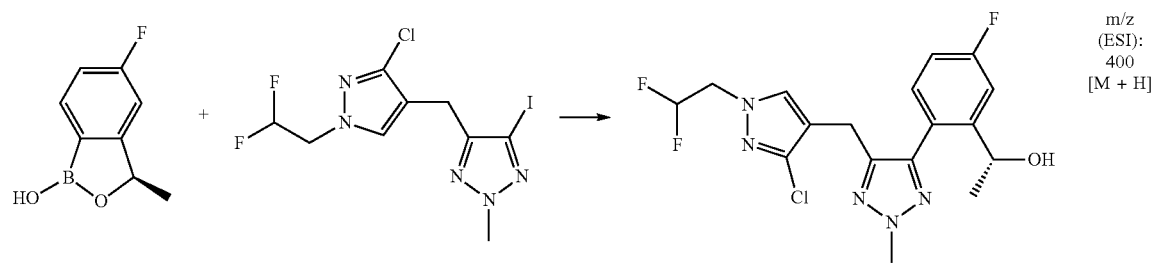

m/z (ESI): 400 [M + H]

(R)-1-(2-(3-((1-(cyclopropylmethyl)-1H-pyrazol-4-yl)methyl)-1-methyl-1H-pyrazol-4-yl)-5-fluorophenyl)ethan-1-ol

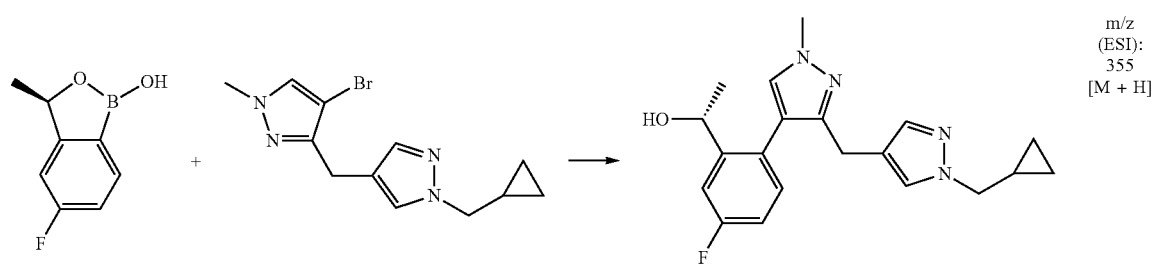

m/z (ESI): 355 [M + H]

-continued (R)-1-(2-(1-(((1-(cyclopropylmethyl)-3-methyl-1H-pyrazol-4-yl)methyl)-1H-1,2,4-triazol-5-yl)-5-fluorophenyl)ethan-1-ol

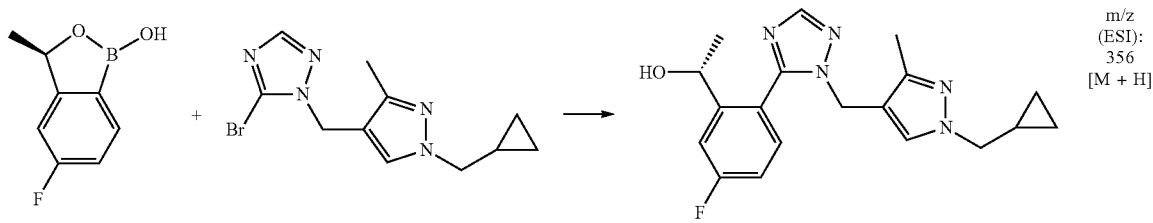

m/z (ESI): 356 [M + H]

(R)-5-(((5-(4-fluoro-2-(1-hydroxyethyl)phenyl)-2-methylthiazol-4-yl)methyl)-1-methyl-1H-pyrazole-3-carbonitrile

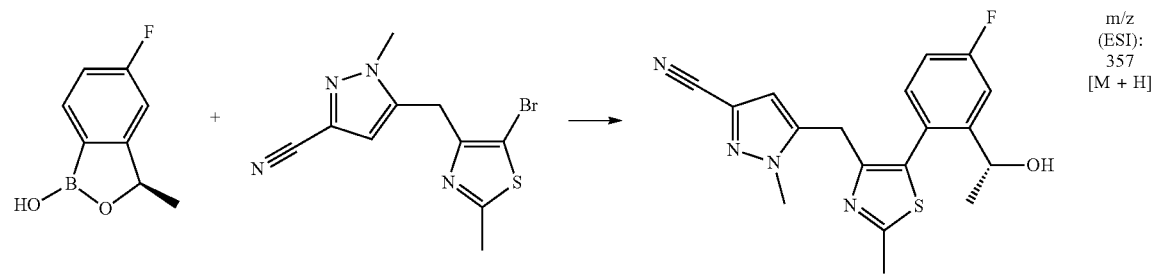

m/z (ESI): 357 [M + H]

(R)-1-(2-(1-(((1-(cyclopropylmethyl)-1H-pyrazol-4-yl)methyl)-1H-1,2,4-triazol-5-yl)-5-fluorophenyl)ethan-1-ol

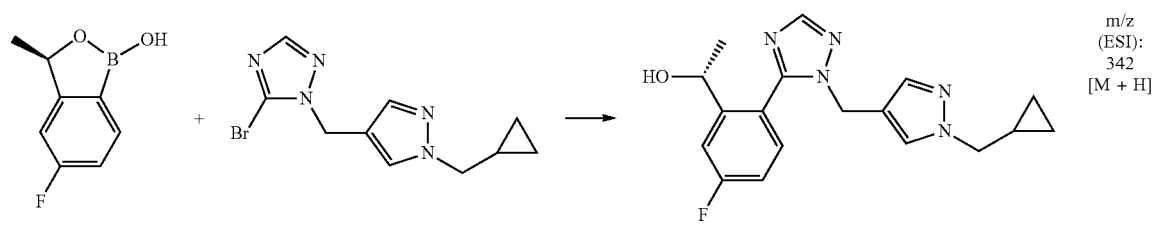

m/z (ESI): 342 [M + H]

(R)-1-(2-(2-(((1-(cyclopropylmethyl)-1H-pyrazol-4-yl)methyl)-5-fluoropyridin-3-yl)-5-fluorophenyl)ethan-1-ol

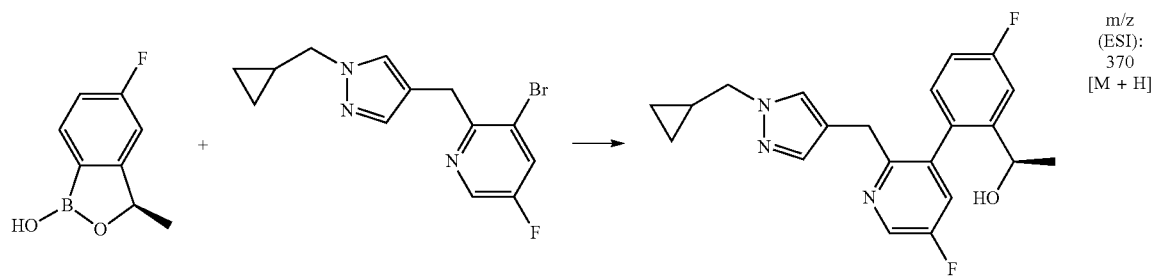

m/z (ESI): 370 [M + H]

(R)-1-(2-(2-(((1-(2,2-difluoroethyl)-1H-pyrazol-4-yl)methyl)-5-fluoropyridin-3-yl)-5-fluorophenyl)ethan-1-ol

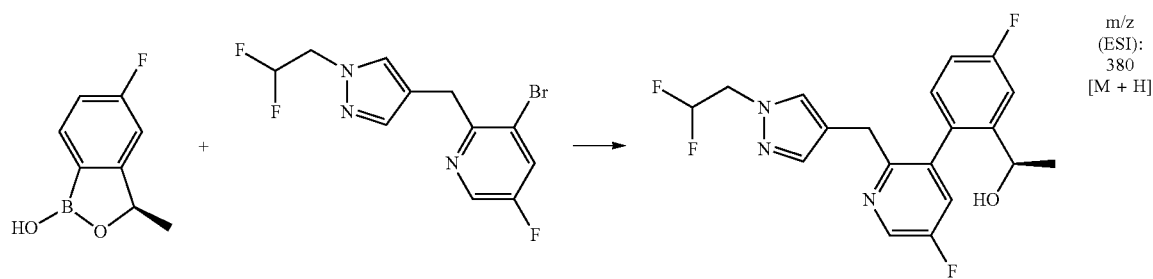

m/z (ESI): 380 [M + H]

(R)-1-(2-(3-((1-(cyclopropylmethyl)-3-methyl-1H-pyrazol-4-yl)methyl)pyrazin-2-yl)-5-fluorophenyl)ethan-1-ol

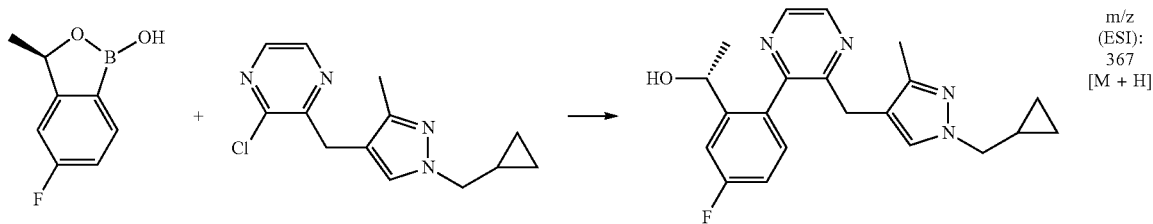

m/z (ESI): 367 [M + H]

(R)-1-(5-fluoro-2-(1-((1-isobutyl-3-methyl-1H-pyrazol-4-yl)methyl)-1H-1,2,4-triazol-5-yl)phenyl)ethan-1-ol

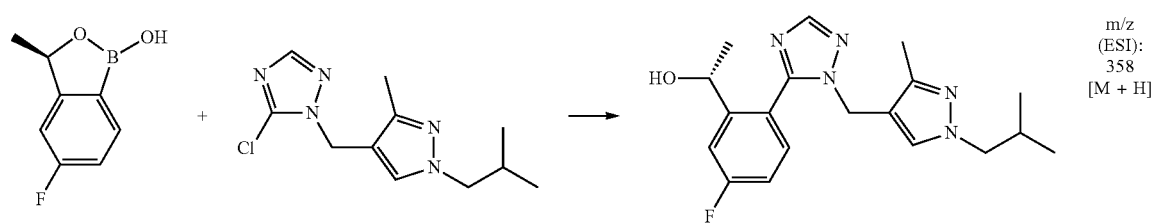

m/z (ESI): 358 [M + H]

(R)-1-(2-(3-chloro-1-((1-(cyclopropylmethyl)-1H-pyrazol-4-yl)methyl)-1H-pyrazol-5-yl)-5-fluorophenyl)ethan-1-ol

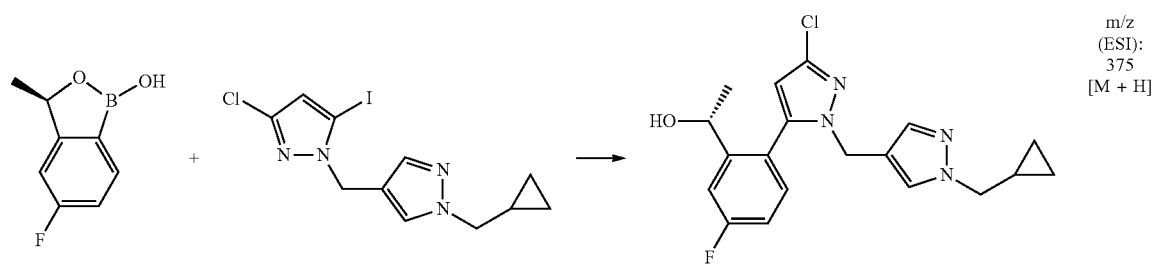

m/z (ESI): 375 [M + H]

(R)-1-(5-fluoro-2-(2-methyl-5-((1-(oxetan-3-yl)-1H-pyrazol-4-yl)methyl)-2H-1,2,3-triazol-4-yl)phenyl)ethan-1-ol

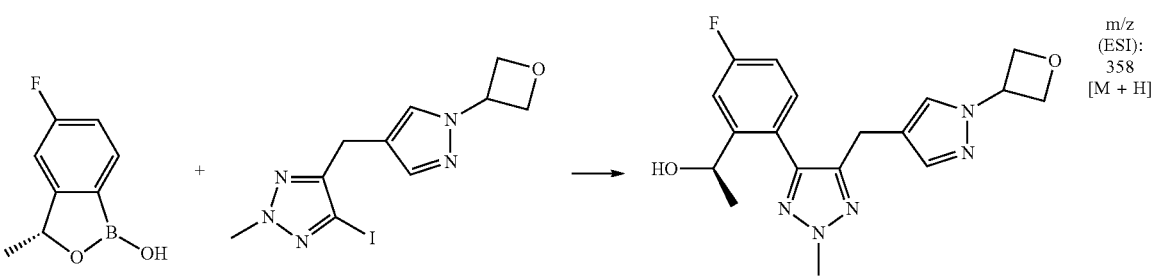

m/z (ESI): 358 [M + H]

(R)-1-(2-(3-chloro-1-((1-(cyclopropylmethyl)-3-methyl-1H-pyrazol-4-yl)methyl)-1H-pyrazol-5-yl)-5-fluorophenyl)ethan-1-ol

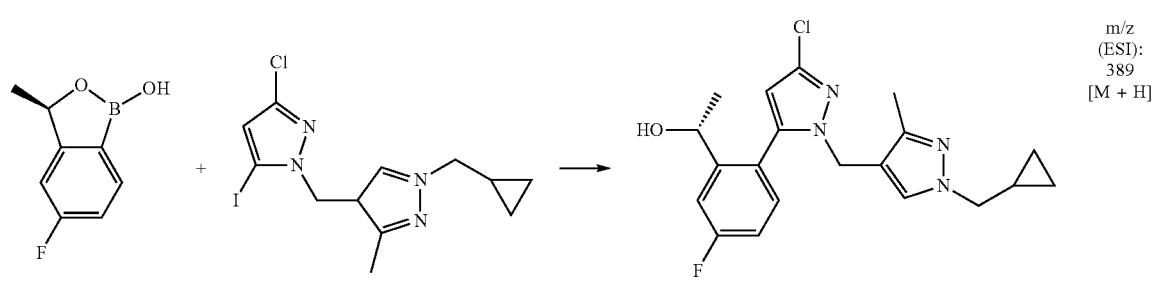

m/z (ESI): 389 [M + H]

(R)-1-(2-(5-((1-ethyl-3-(trifluoromethyl)-1H-pyrazol-4-yl)methyl)-2-methyl-2H-1,2,3-triazol-4-yl)-5-fluorophenyl)ethan-1-ol

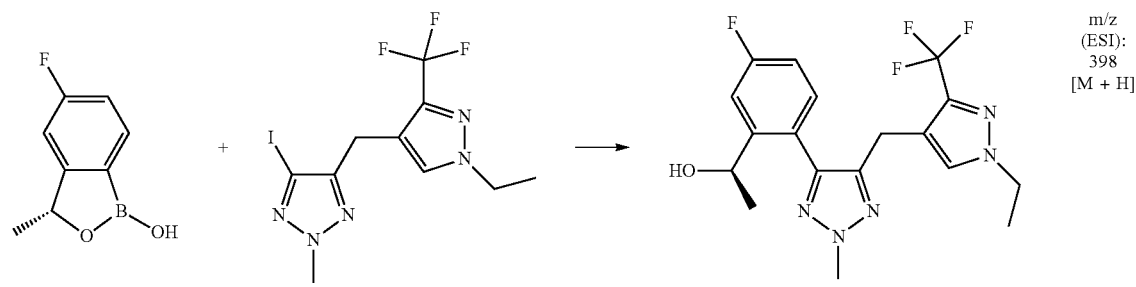

m/z (ESI): 398 [M + H]

(R)-1-(2-(5-((5-ethylisothiazol-3-yl)methyl)-2-methyl-2H-1,2,3-triazol-4-yl)-5-fluorophenyl)ethan-1-ol

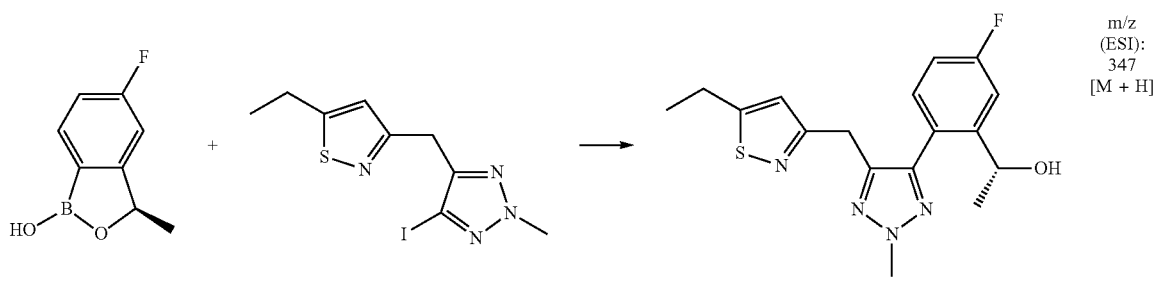

m/z (ESI): 347 [M + H]

(1R)-1-[2-(5-{[3-chloro-1-(cyclopropylmethyl)-1H-pyrazol-4-yl]methyl}-2-methyl-2H-1,2,3-triazol-4-yl)-5-fluorophenyl]ethan-1-ol

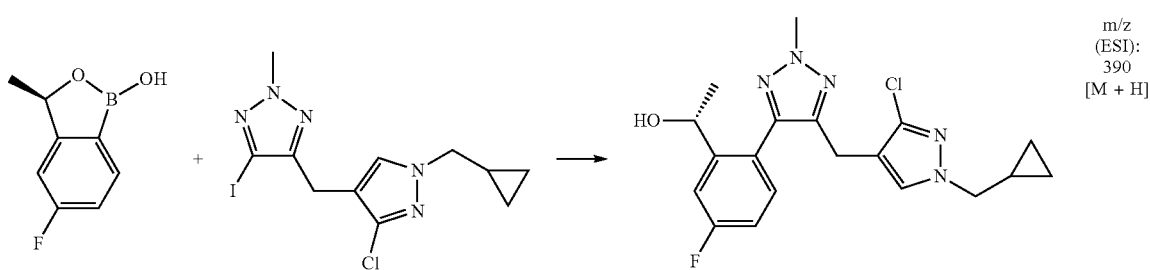

m/z (ESI): 390 [M + H]

(1R)-1-[2-(3-{[3-chloro-1-(cyclopropylmethyl)-1H-pyrazol-4-yl]methyl}-1-methyl-1H-pyrazol-4-yl)-5-fluorophenyl]ethan-1-ol

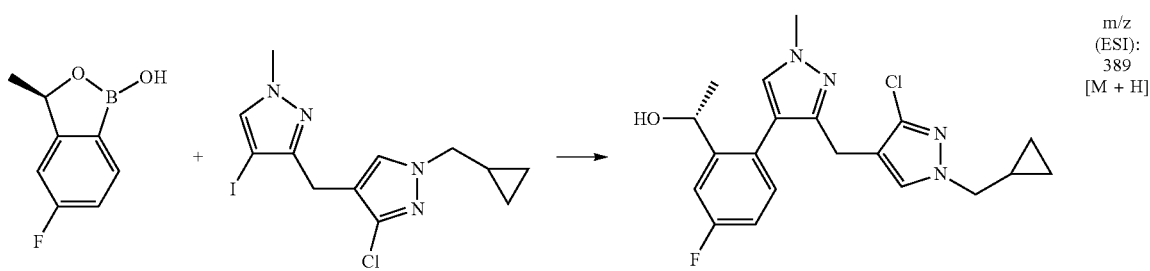

m/z (ESI): 389 [M + H]

(1R)-1-(2-{1-[(1-ethyl-1H-pyrazol-4-yl)methyl]-3-(trifluoromethyl)-1H-pyrazol-5-yl}-5-fluorophenyl)ethan-1-ol
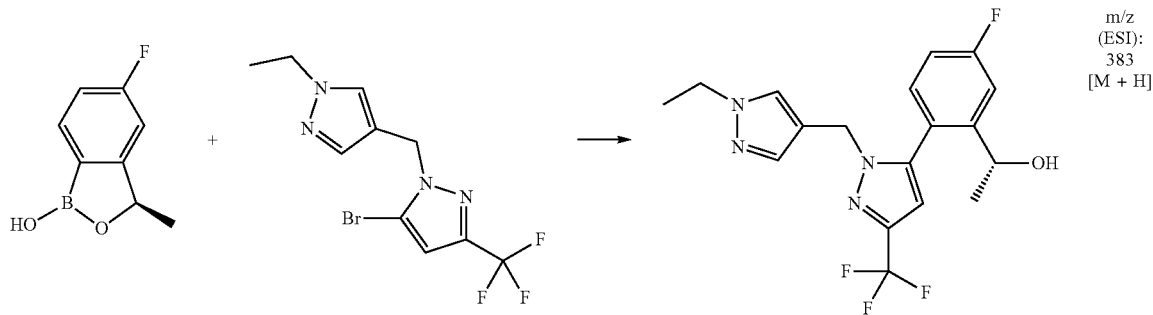
m/z (ESI): 383 [M + H]
(R)-1-(2-(1-((1-ethyl-1H-pyrazol-4-yl)methyl)-3-methoxy-1H-pyrazol-5-yl)-5-fluorophenyl)ethan-1-ol
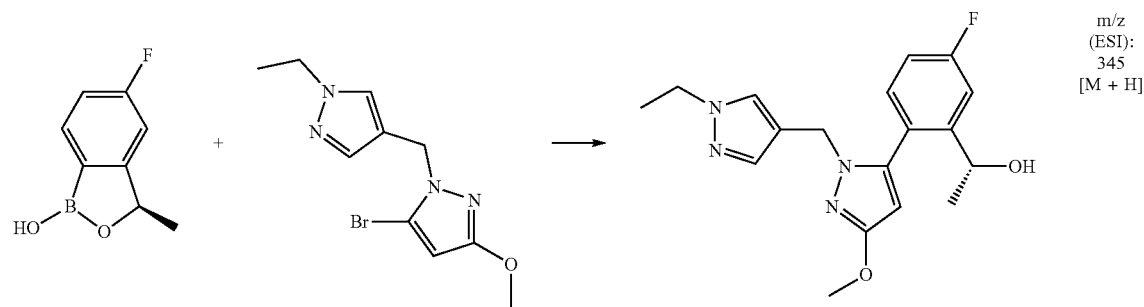
m/z (ESI): 345 [M + H]
(1R)-1-(2-{2-ethyl-5-[(1-ethyl-1H-pyrazol-4-yl)methyl]-2H-1,2,3-triazol-4-yl}-5-fluorophenyl)ethan-1-ol
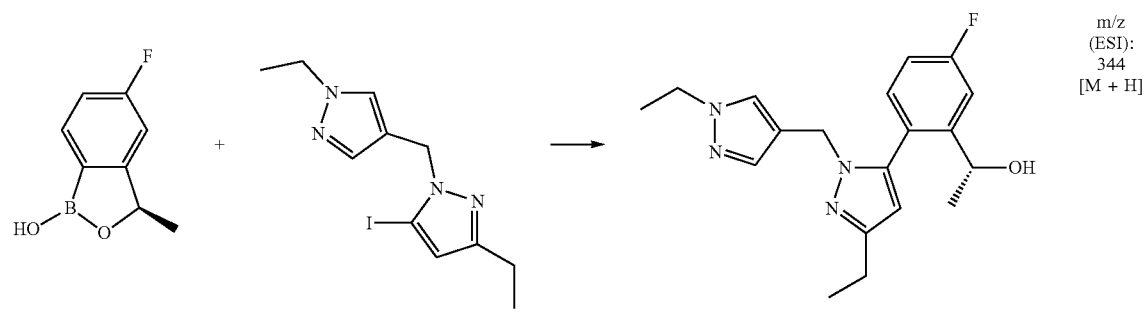
m/z (ESI): 344 [M + H]
(1R)-1-(2-{3-bromo-1-[(1-ethyl-1H-pyrazol-4-yl)methyl]-1H-pyrazol-5-yl}-5-fluorophenyl)ethan-1-ol
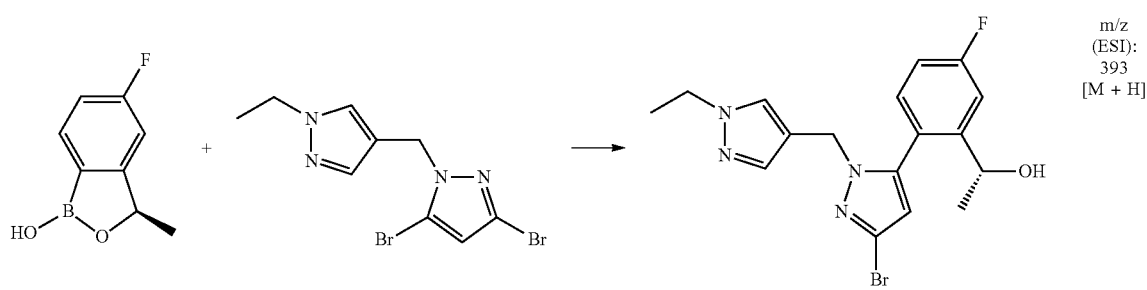
m/z (ESI): 393 [M + H]

(R)-1-(2-(5-((1-(cyclopropylmethyl)-1H-pyrazol-4-yl)methyl)-2-(difluoromethyl)-2H-1,2,3-triazol-4-yl)-5-fluorophenyl)ethan-1-ol

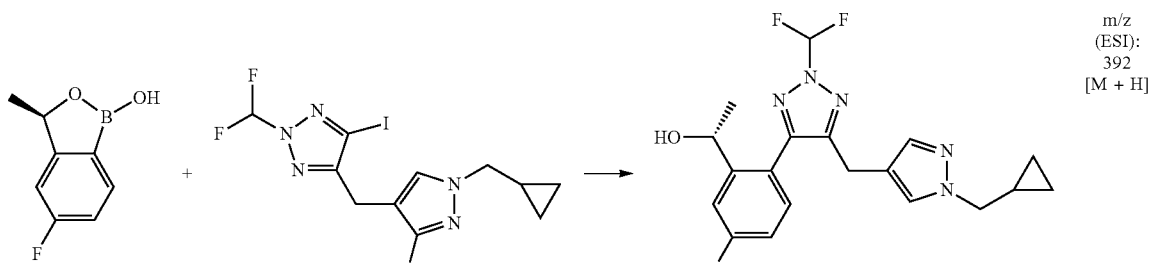

m/z (ESI): 392 [M + H]

(R)-1-(5-fluoro-2-(1-((1-(2-fluoroethyl)-1H-pyrazol-4-yl)methyl)-3-methyl-1H-pyrazol-5-yl)phenyl)ethan-1-ol

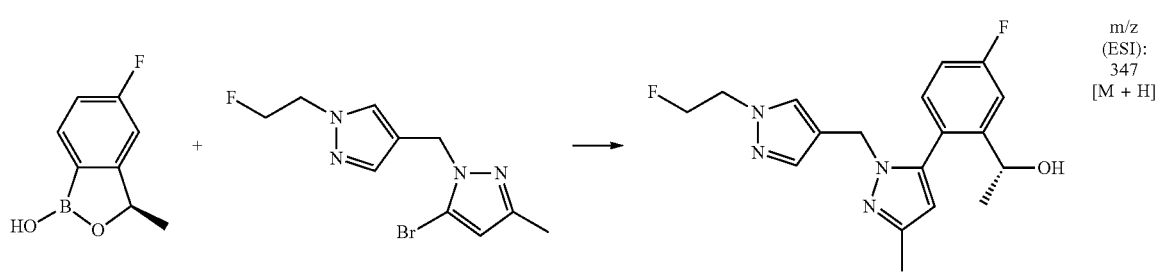

m/z (ESI): 347 [M + H]

(R)-1-((3-(4-fluoro-2-(1-hydroxyethyl)phenyl)pyrazin-2-yl)methyl)-1H-imidazole-4-carbonitrile

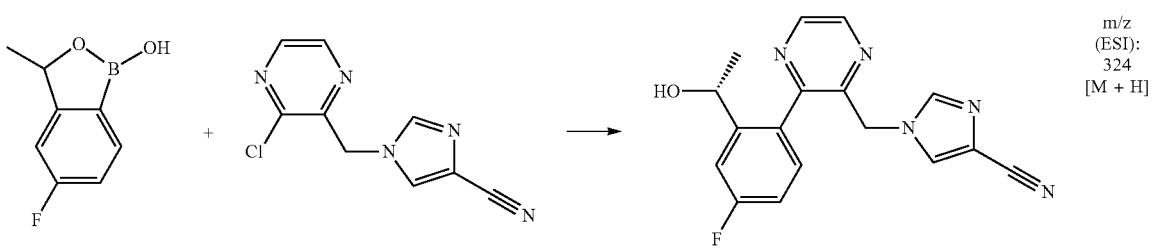

m/z (ESI): 324 [M + H]

1-({5-[4-fluoro-2-(1-hydroxyethyl)phenyl]-1,3-thiazol-4-yl}methyl)-1H-pyrazole-4-carbonitrile

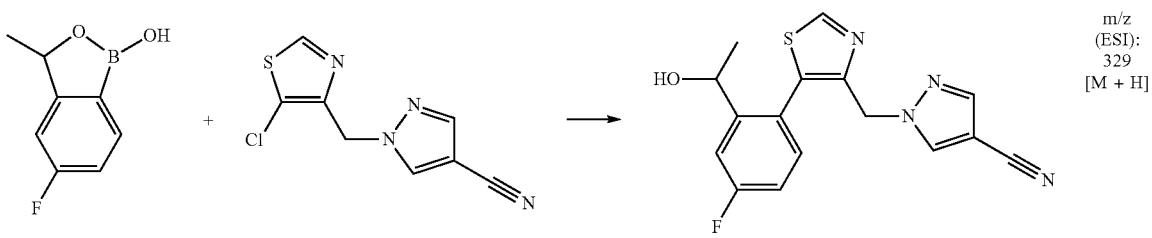

m/z (ESI): 329 [M + H]

1-((3-(4-fluoro-2-(1-hydroxyethyl)phenyl)pyrazin-2-yl)methyl)-1H-pyrazole-4-carbonitrile

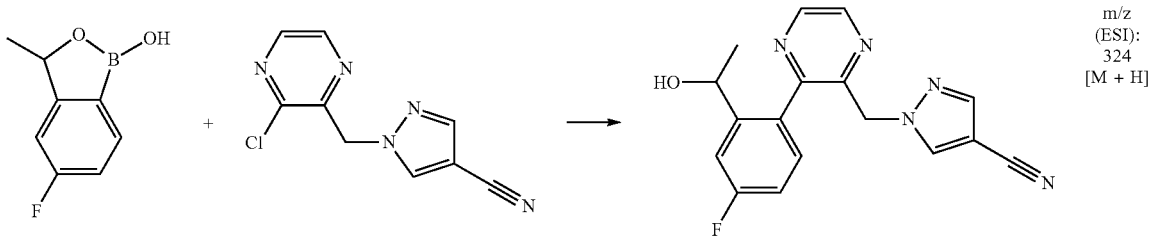

m/z (ESI): 324 [M + H]

1-((5-fluoro-3-(4-fluoro-2-(1-hydroxyethyl)phenyl)pyridin-2-yl)methyl)-1H-imidazole-4-carbonitrile

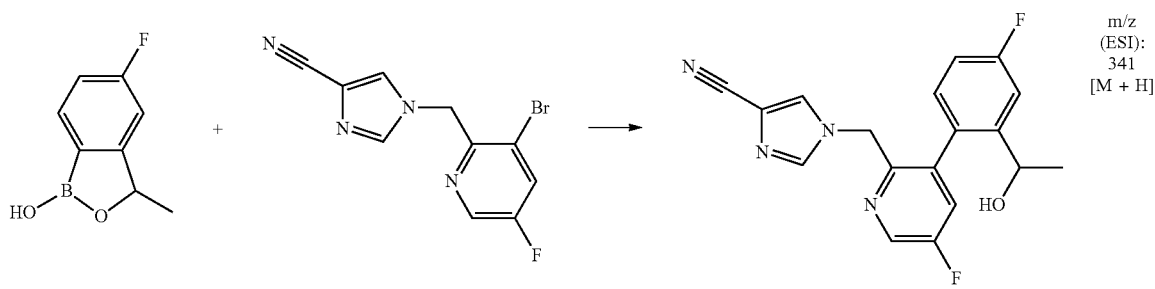

m/z (ESI): 341 [M + H]

(2-(5-(((1-(cyclopropylmethyl)-3-methyl-1H-pyrazol-4-yl)methyl)-2-methyl-2H-1,2,3-triazol-4-yl)-5-fluorophenyl)methanol

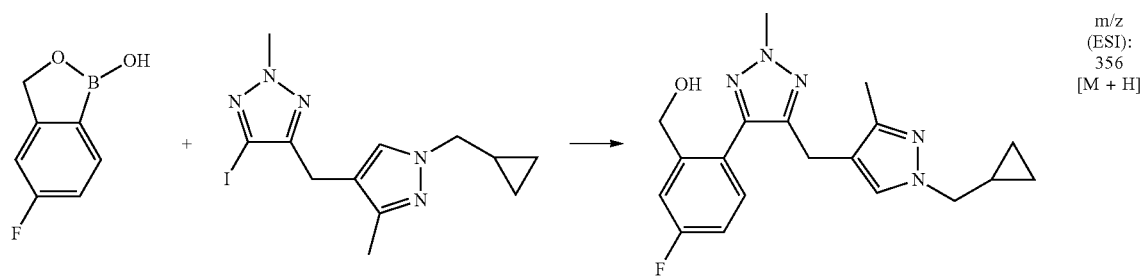

m/z (ESI): 356 [M + H]

1-(2-(5-(((1-(cyclopropylmethyl)-3-methyl-1H-pyrazol-4-yl)methyl)-2-methyl-2H-1,2,3-triazol-4-yl)-3,5-difluorophenyl)ethan-1-ol

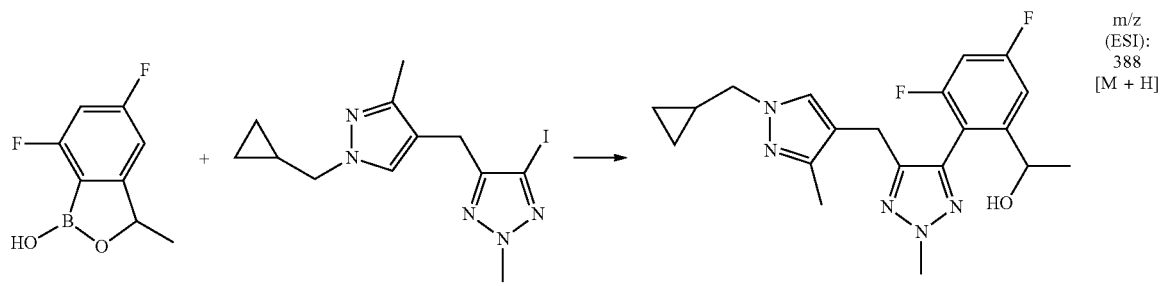

m/z (ESI): 388 [M + H]

2-((tert-butyldimethylsilyl)oxy)-1-(2-(5-(((1-(cyclopropylmethyl)-3-methyl-1H-pyrazol-4-yl)methyl)-2-methyl-2H-1,2,3-triazol-4-yl)-5-fluorophenyl)ethan-1-ol

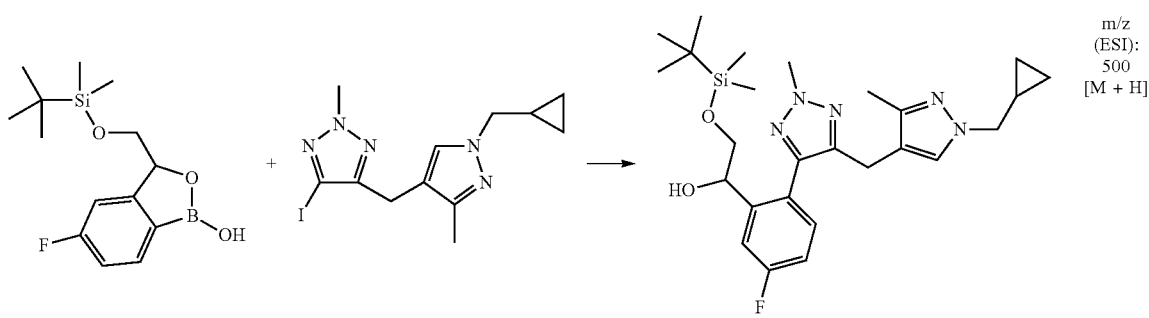

m/z (ESI): 500 [M + H]

(R)-1-(2-(3-chloro-1-((3-ethyl-1-(4-methoxybenzyl)-1H-pyrazol-5-yl)methyl)-1H-pyrazol-5-yl)-5-fluorophenyl)ethan-1-ol

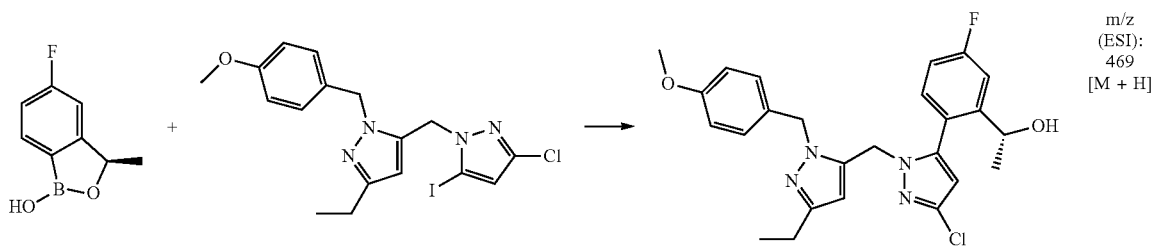

m/z (ESI): 469 [M + H]

(R)-1-(2-(5-((3-ethyl-1-methyl-1H-pyrazol-5-yl)methyl)-2-methyl-2H-1,2,3-triazol-4-yl)-5-fluorophenyl)ethan-1-ol

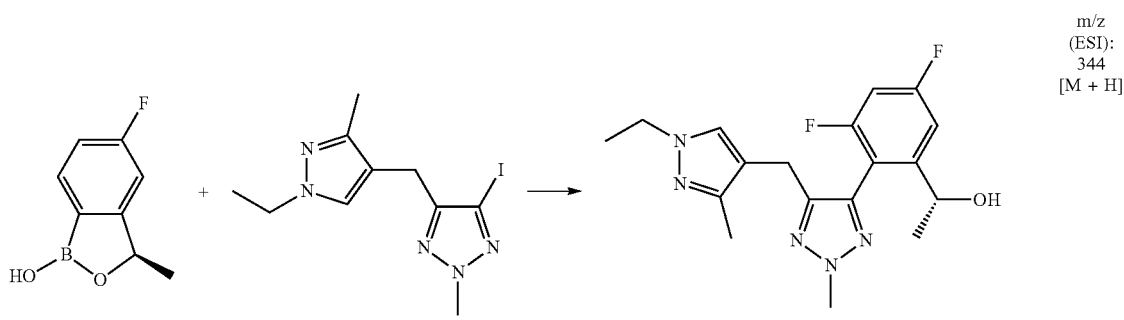

m/z (ESI): 344 [M + H]

(R)-1-(2-(1-((3-(cyclopropylmethyl)-1-methyl-1H-pyrazol-5-yl)methyl)-1H-1,2,4-triazol-5-yl)-5-fluorophenyl)ethan-1-ol

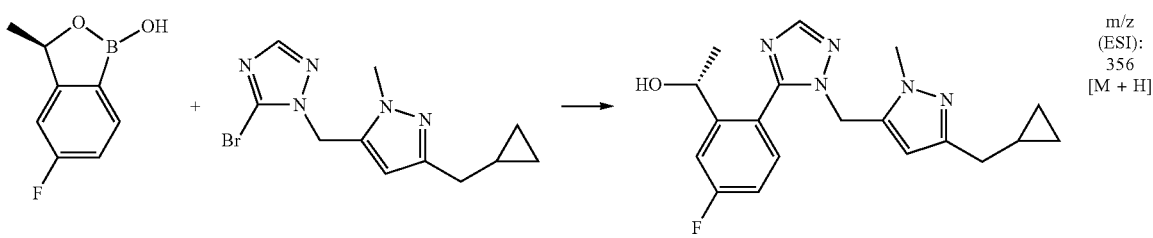

m/z (ESI): 356 [M + H]

(1R)-1-[2-(5-{[3-(cyclopropylmethyl)-1-methyl-1H-pyrazol-5-yl]methyl}-2-methyl-2H-1,2,3-triazol-4-yl)-5-fluorophenyl]ethan-1-ol

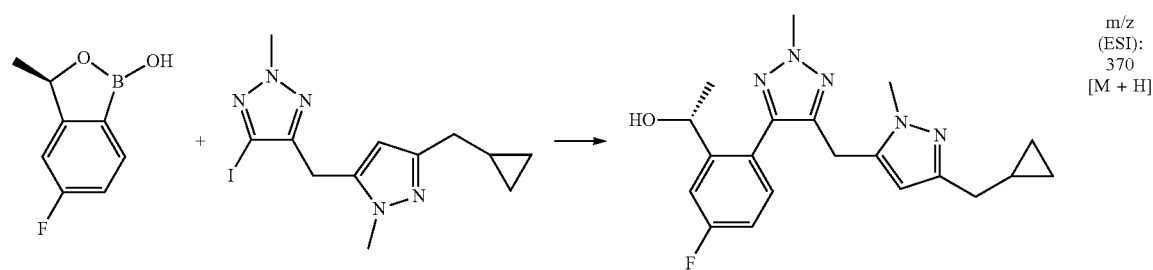

m/z (ESI): 370 [M + H]

(R)-(1-ethyl-1H-pyrrol-3-yl)(5-(4-fluoro-2-(1-hydroxyethyl)phenyl)-2-methyl-2H-1,2,3-triazol-4-yl)methanone

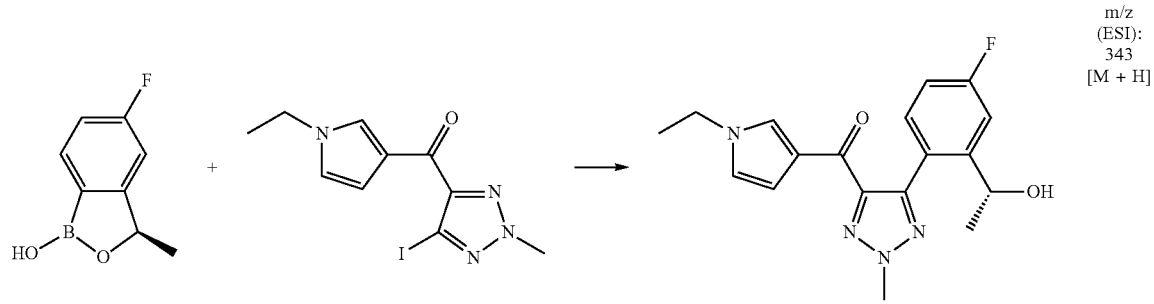

m/z (ESI): 343 [M + H]

Synthesis of 1-(2-(1-((3-ethylisoxazol-5-yl)methyl)-1H-tetrazol-5-yl)-5-fluorophenyl)ethan-1-one

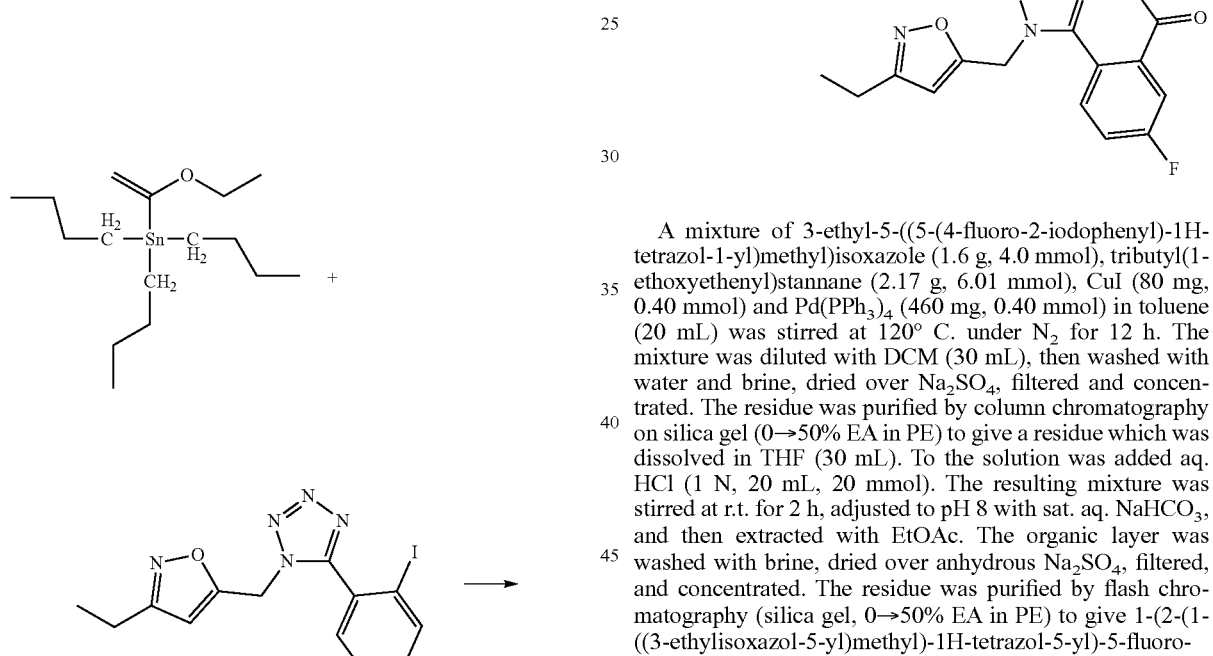

A mixture of 3-ethyl-5-((5-(4-fluoro-2-iodophenyl)-1H-tetrazol-1-yl)methyl)isoxazole (1.6 g, 4.0 mmol), tributyl(1-ethoxyethenyl)stannane (2.17 g, 6.01 mmol), CuI (80 mg, 0.40 mmol) and Pd(PPh$_3$)$_4$ (460 mg, 0.40 mmol) in toluene (20 mL) was stirred at 120° C. under N$_2$ for 12 h. The mixture was diluted with DCM (30 mL), then washed with water and brine, dried over Na$_2$SO$_4$, filtered and concentrated. The residue was purified by column chromatography on silica gel (0→50% EA in PE) to give a residue which was dissolved in THF (30 mL). To the solution was added aq. HCl (1 N, 20 mL, 20 mmol). The resulting mixture was stirred at r.t. for 2 h, adjusted to pH 8 with sat. aq. NaHCO$_3$, and then extracted with EtOAc. The organic layer was washed with brine, dried over anhydrous Na$_2$SO$_4$, filtered, and concentrated. The residue was purified by flash chromatography (silica gel, 0→50% EA in PE) to give 1-(2-(1-((3-ethylisoxazol-5-yl)methyl)-1H-tetrazol-5-yl)-5-fluorophenyl)ethan-1-one (1.0 g, 79% yield) as a yellow oil. LC/MS (ESI) m/z: 316 [M+H]$^+$.

The following intermediates were synthesized using a similar experimental protocol:

1-(2-{5-[(5-bromo-1-ethyl-1H-pyrazol-4-yl)methyl]-1H-1,2,4-triazol-1-yl}-5-fluorophenyl)ethan-1-one

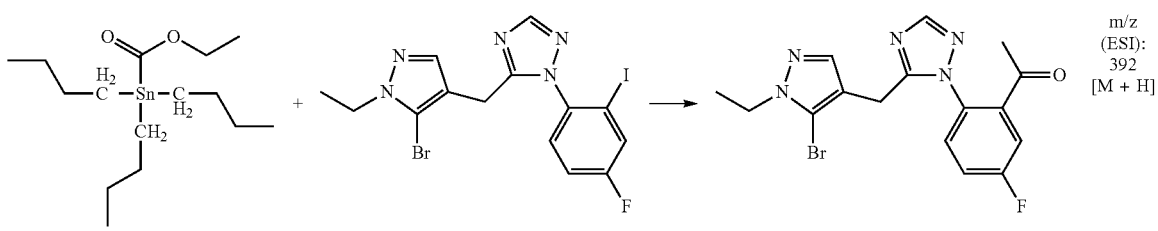

m/z (ESI): 392 [M + H]

1-(2-(4-((1-ethyl-1H-pyrazol-4-yl)methyl)-2-methyloxazol-5-yl)-5-fluorophenyl)ethan-1-one

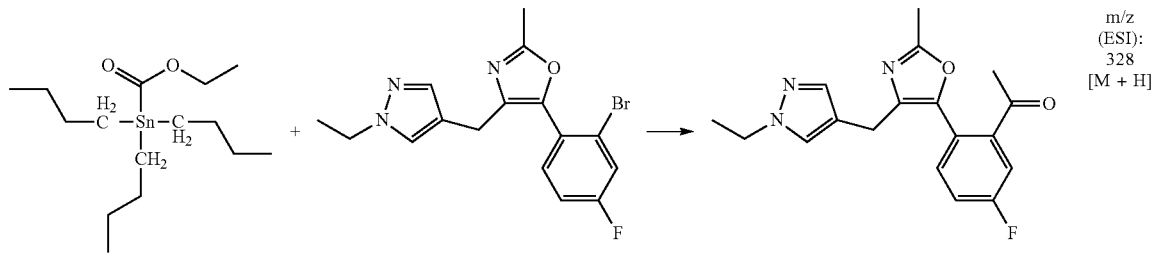

m/z (ESI): 328 [M + H]

1-(2-(1-((1-(cyclopropylmethyl)-1H-pyrazol-4-yl)methyl)-3-methyl-1H-1,2,4-triazol-5-yl)-5-fluorophenyl)ethan-1-one

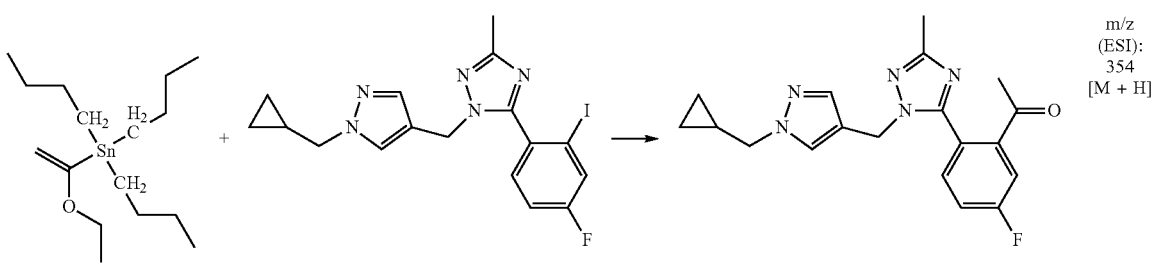

m/z (ESI): 354 [M + H]

Synthesis of (R)-5-bromo-3-(1-(5-fluoro-2-(trimethylstannyl)phenyl)ethoxy)pyridin-2-amine

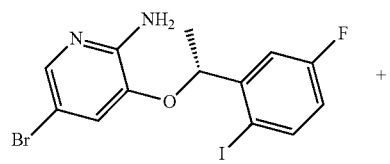

+

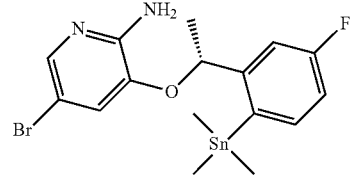

-continued

To a solution of 5-bromo-3-[(1R)-1-(5-fluoro-2-iodophenyl)ethoxy]pyridin-2-amine (4.60 g, 10.5 mmol) in toluene (200 mL) was added tetrakis(triphenylphosphine) palladium (1.36 g, 1.18 mmol) and hexamethyldistannane (2.40 mL, 11.6 mmol). The mixture was stirred at 110° C. for 12 h under an $N_2$ atmosphere. After cooling to r.t., the mixture was treated with aq. KF and EtOAc and separated. The organic layer was washed with brine, dried over anhydrous $Na_2SO_4$, filtered and concentrated. The residue was purified by column chromatography on silica gel (PE:EA=10:1, V/V) to give the target product (1.95 g, yield: 39%) as a white solid. LC/MS ESI (m/z): 475 [M+H]⁺.

The following intermediates were synthesized using a similar experimental protocol:

5-bromo-3-(1-(5-fluoro-2-(trimethylstannyl)phenyl)ethoxy)pyridin-2-amine

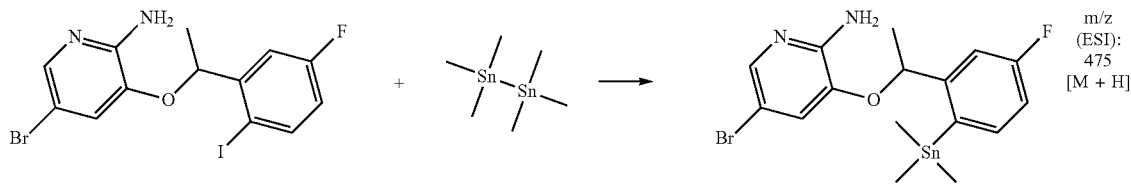

m/z (ESI): 475 [M + H]

305
Synthesis of 1-((5-bromo-1-ethyl-1H-pyrazol-4-yl)methyl)-5-(4-fluoro-2-iodophenyl)-3-methyl-1H-1,2,4-triazole

306
Synthesis of 5-((5-bromo-1-ethyl-1H-pyrazol-4-yl)methyl)-1-(4-fluoro-2-iodophenyl)-3-methyl-1H-1,2,4-triazole

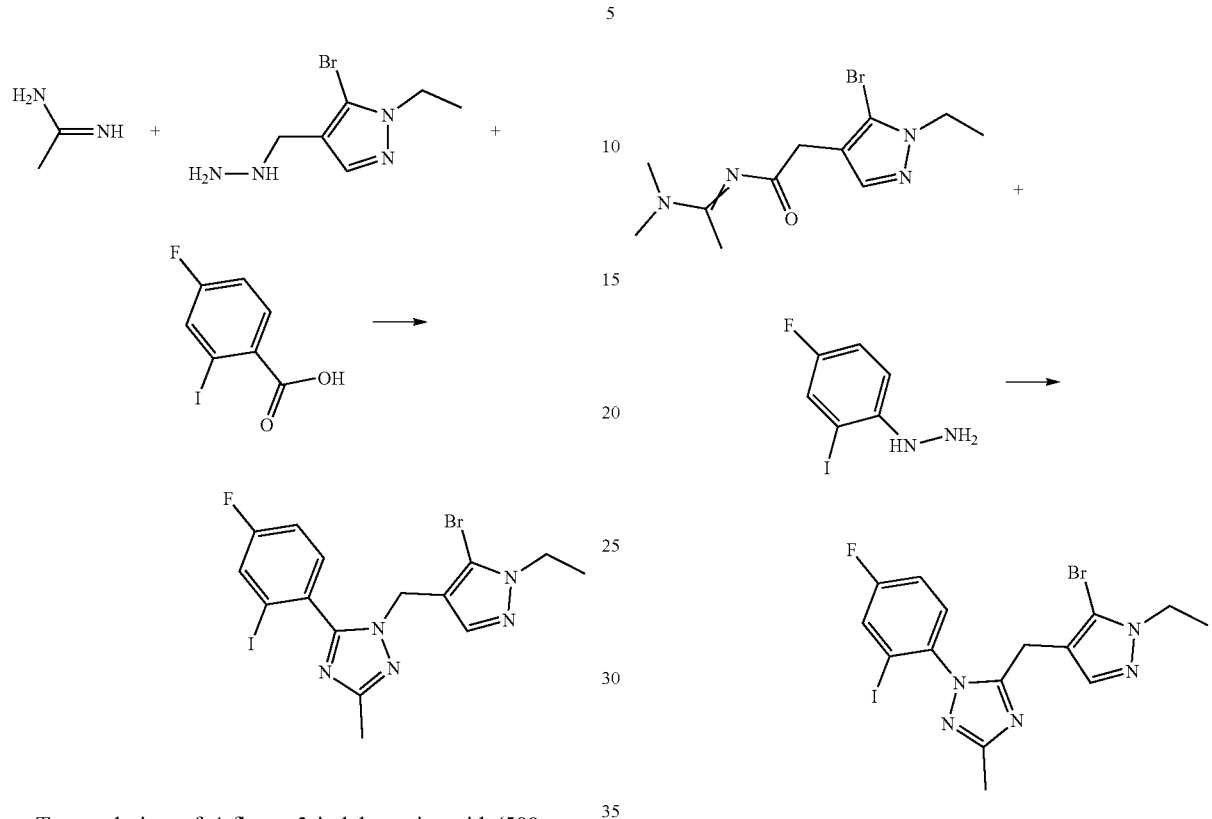

To a solution of 4-fluoro-2-iodobenzoic acid (500 mg, 1.88 mmol), ethanimidamide hydrochloride (0.25 mL, 2.8 mmol) and HATU (786 mg, 2.07 mmol) in DMF (10 mL) was added DIPEA (729 mg, 5.64 mmol). The mixture was stirred at r.t. for 3 h and then. 5-bromo-1-ethyl-4-(hydrazinylmethyl)-1H-pyrazole hydrochloride (722 mg, 2.82 mmol) and HOAc (1.13 g, 18.8 mmol) were added. Stirring continued at 80° C. for 3 h. The mixture was diluted with DCM (60 mL), then washed with sat. aq. NaHCO$_3$ solution and brine, dried over anhydrous Na$_2$SO$_4$, filtered and concentrated. The residue was purified by column chromatography on silica gel (PE:EA=1:1, V/V) to give 1-((5-bromo-1-ethyl-1H-pyrazol-4-yl)methyl)-5-(4-fluoro-2-iodophenyl)-3-methyl-1H-1,2,4-triazole (360 mg, yield: 39%) as a yellow solid. LC-MS (ESI): m/z 490 [M+H]$^+$.

The following intermediates were synthesized using a similar experimental protocol:

To a solution of 2-(5-bromo-1-ethyl-1H-pyrazol-4-yl)-N-(1-(dimethylamino)ethylidene)acetamide (760 mg, 2.02 mmol) in acetic acid (5 mL) at r.t. was added (4-fluoro-2-iodophenyl)hydrazine hydrochloride (801 mg, 2.78 mmol). The mixture was stirred at 60 C for 3 h. Then the reaction mixture was concentrated in vacuo to remove AcOH, the residue was basified to pH 8 with sat. aq. NaHCO$_3$ solution, extracted with EtOAc (3×10 mL), washed with brine (10 mL), dried over anhydrous Na$_2$SO$_4$, filtered and concentrated. The residue was purified by flash chromatography (silica gel, 0→35% EtOAc in PE) to give 5-((5-bromo-1-ethyl-1H-pyrazol-4-yl)methyl)-1-(4-fluoro-2-iodophenyl)-3-methyl-1H-1,2,4-triazole as an orange red solid (580 mg, yield: 59%). LC/MS ESI (m/z): 490 [M+H]$^+$.

1-((1-(cyclopropylmethyl)-1H-pyrazol-4-yl)methyl)-5-(4-fluoro-2-iodophenyl)-3-methyl-1H-1,2,4-triazole

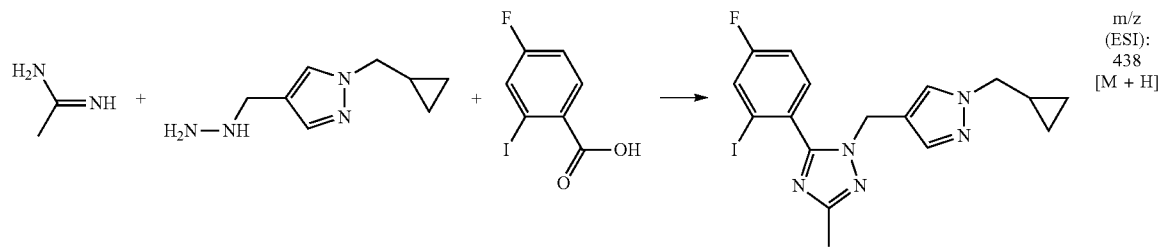

m/z (ESI): 438 [M + H]

Synthesis of 1-[(5-bromo-3-chloro-1-ethyl-1H-pyrazol-4-yl)methyl]-5-(4-fluoro-2-iodophenyl)-1H-1,2,4-triazole

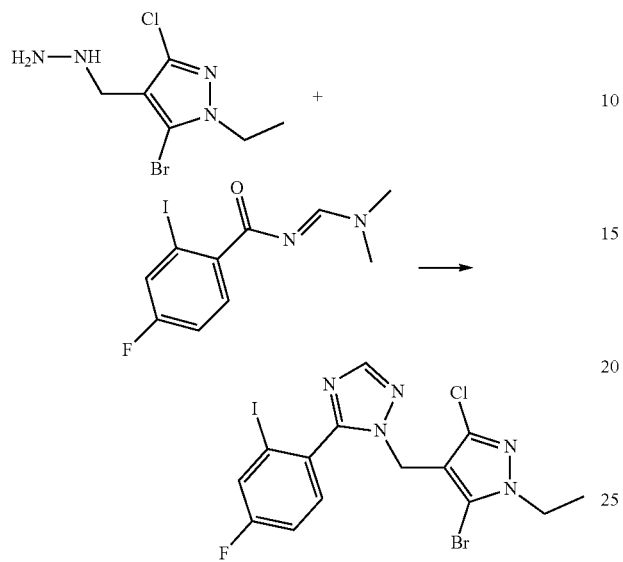

A mixture of 5-bromo-3-chloro-1-ethyl-4-(hydrazinylmethyl)-1H-pyrazole (2.70 g, 10.7 mmol), N-[(1E)-(dimethylamino)methylidene]-4-fluoro-2-iodobenzamide (3.40 g, 10.7 mmol) and NaOAc (3.50 g, 42.6 mmol) in AcOH (50 mL) was stirred at 90° C. for 16 h. The mixture was concentrated under reduced pressure. The residue was dissolved in EA (50 mL). The organic layer was washed with aq. NaHCO$_3$, dried over Na$_2$SO$_4$, and concentrated under reduced pressure. The residue was purified by flash chromatography (0→50% EtOAc in PE) to give 1-[(5-bromo-3-chloro-1-ethyl-1H-pyrazol-4-yl)methyl]-5-(4-fluoro-2-iodophenyl)-1H-1,2,4-triazole (1.5 g, 28%) as pale-yellow solid. LC/MS (ESI): m/z=510 [M+H]$^+$.

Synthesis of (R)-(1-ethyl-1H-pyrazol-4-yl)(4-(4-fluoro-2-(1-hydroxyethyl)phenyl)-1,2,5-thiadiazol-3-yl)methanone

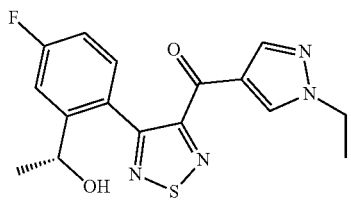 [SMILES: CCn1cc(C(=O)c2nsnc2-c2ccc(F)cc2[C@@H](C)O)cn1]

To a solution of methyl 4-bromo-1,2,5-thiadiazole-3-carboxylate (900 mg, 4.04 mmol), (R)-5-fluoro-3-methylbenzo[c][1,2]oxaborol-1(3H)-ol (700 mg, 4.04 mmol), Pd(dppf)Cl$_2$ (16 mg, 0.022 mmol) in 1,4-dioxane (20 mL) and water (4 mL), was added potassium carbonate (1.12 g, 8.07 mmol). The mixture was degassed with N$_2$ three times, then stirred at 80° C. overnight. After overnight, the reaction mixture was cooled to r.t. and filtered. The filtrate was diluted with water (20 mL), acidified with 1 N HCl aq. to pH 3, and extracted with EA (2×20 mL). The combined organic phases were washed with brine (20 mL), dried over anhydrous Na$_2$SO$_4$, filtered, and concentrated in vacuo. The residue was purified by flash chromatography (0→40% EtOAc in PE) to give (R)-8-fluoro-6-methyl-4H,6H-benzo[5,6]oxepino[3,4-c][1,2,5]thiadiazol-4-one (550 mg, 49%) as a white solid. LC/MS ESI (m/z): 251 [M+H]$^+$.

To a solution of 1-ethyl-4-iodo-1H-pyrazole (352 mg, 1.58 mmol) in THF (7 mL) was added isopropylmagnesium chloride-lithium chloride complex (1.27 mL, 1.65 mmol, 1.3 M in THF) dropwise at r.t., and stirred at r.t. for 2 h. After 2 h, (R)-8-fluoro-6-methyl-4H,6H-benzo[5,6]oxepino[3,4-c][1,2,5]thiadiazol-4-one (285 mg, 1.14 mmol) was added and the resulting mixture was stirred at r.t. for additional 1 h. After 1 h, the reaction mixture was quenched by adding sat. aq. NH$_4$Cl solution (5 mL), extracted with EA (3×5 mL), combined all organic phases, washed with sat. aq. NH$_4$Cl solution (5 mL) and brine (5 mL), dried over anhydrous Na$_2$SO$_4$, filtered, and concentrated in vacuo. The crude product was purified by flash chromatography (0→50% EtOAc in PE) to give (R)-(1-ethyl-1H-pyrazol-4-yl)(4-(4-fluoro-2-(1-hydroxyethyl)phenyl)-1,2,5-thiadiazol-3-yl)methanone (220 mg, 50%) as a yellow solid. LC/MS ESI (m/z): 347 [M+H]$^+$.

Synthesis of 1-(2-(1-((5-bromo-1-ethyl-1H-pyrazol-4-yl)methyl)-1H-pyrazol-5-yl)-5-fluoropyridin-3-yl)ethan-1-one

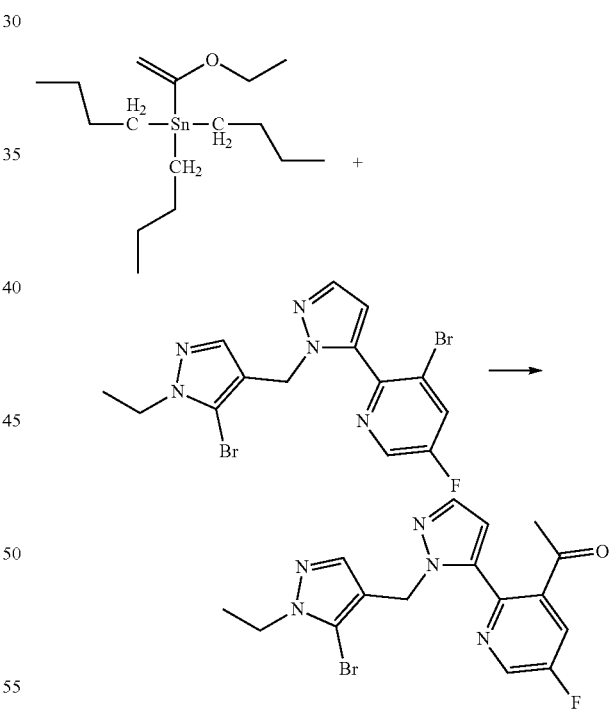

To a solution of 3-bromo-2-(1-((5-bromo-1-ethyl-1H-pyrazol-4-yl)methyl)-1H-pyrazol-5-yl)-5-fluoropyridine (800 mg, 1.86 mmol) and tributyl(1-ethoxyvinyl)stannane (1.1 g, 2.8 mmol) in toluene (50 mL) was added Pd(PPh$_3$)$_4$ (430 mg, 0.370 mmol) under N$_2$. The resulting mixture was stirred under N$_2$ at 100° C. for 8 h. The mixture was cooled to r.t. and 1 N aq. HCl (20 mL) was added. The resulting mixture was stirred at r.t. for 1 h and then neutralized with sat. Na$_2$CO$_3$ to pH 8. The resulting mixture was extracted with EA, dried over anhydrous Na$_2$SO$_4$, concentrated under reduced pressure and purified by flash chromatography on silica gel (0→40% EtOAc in PE) to give 1-(2-(1-((5-bromo-1-ethyl-1H-pyrazol-4-yl)methyl)-1H-pyrazol-5-yl)-5-fluoropyridin-3-yl)ethan-1-one (200 mg, 27% yield) as a yellow solid. LC/MS ESI (m/z): 392 [M+H]⁺.

The following intermediates were synthesized using a similar experimental protocol:

1-(2-{1-[(5-bromo-1-ethyl-1H-pyrazol-4-yl)methyl]-1H-1,2,4-triazol-5-yl}-5-fluorophenyl)ethan-1-one

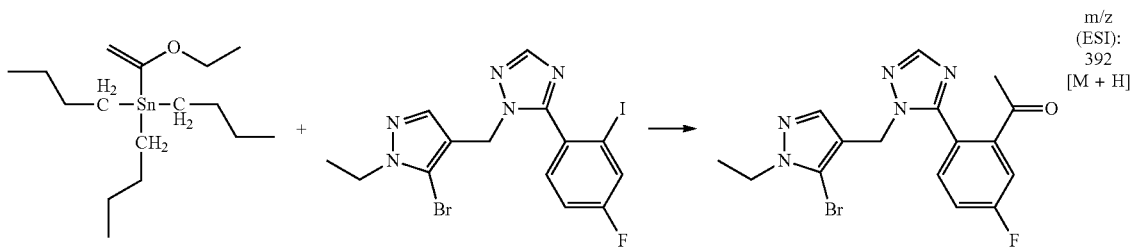

1-(2-{1-[(5-bromo-3-chloro-1-ethyl-1H-pyrazol-4-yl)methyl]-1H-1,2,4-triazol-5-yl}-5-fluorophenyl)ethan-1-one

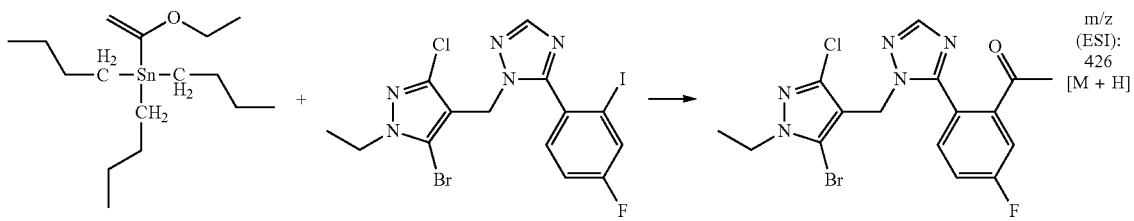

1-(2-(4-((1-(cyclopropylmethyl)-3-methyl-1H-pyrazol-4-yl)methyl)-2-methyloxazol-5-yl)-5-fluorophenyl)ethan-1-one

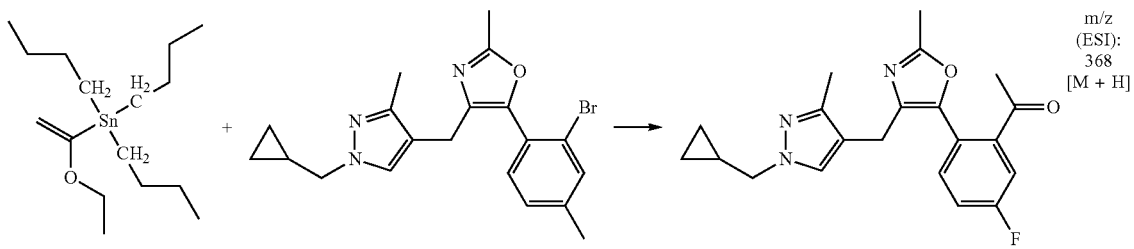

Synthesis of 3-chloro-1-((3-ethyl-1-(4-methoxybenzyl)-1H-pyrazol-5-yl)methyl)-5-iodo-1H-pyrazole

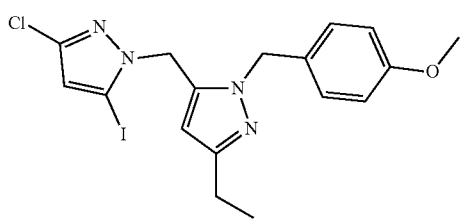 [SMILES: CCc1cc(Cn2nc(Cl)cc2I)n(Cc2ccc(OC)cc2)n1]

To a solution of {3-ethyl-1-[(4-methoxyphenyl)methyl]-1H-pyrazol-5-yl}methanol (2.57 g, 10.4 mmol) in DCM (30 mL) was dropwise added SOCl₂ (1.89 mL, 26.044 mmol) at 0° C. Then the reaction mixture was stirred at r.t. for 2 h. This reaction was quenched with water (10 mL), neutralized with NaHCO₃ (10 mL) to PH=7 and extracted with DCM (3×15 mL). This combined organic layers were concentrated in vacuo to give 5-(chloromethyl)-3-ethyl-1-[(4-methoxyphenyl)methyl]-1H-pyrazole (2.56 g, 93%) as a brown yellow oily substance.

To a solution of 5-(chloromethyl)-3-ethyl-1-[(4-methoxyphenyl)methyl]-1H-pyrazole (2.50 g, 9.44 mmol) in DMF (30 mL) was added 3-chloro-5-iodo-1H-pyrazole (2.26 g, 9.92 mmol) and Cs₂CO₃ (6.15 g, 18.9 mmol). The resulting mixture was stirred at r.t. overnight. The reaction mixture was filtered, and the filtrate was diluted with sat. aq. NH₄Cl solution (100 mL) and EA (100 mL), The organic phase was dried over anhydrous Na₂SO₄, filtered and concentrated in vacuo. The residue was purified by column chromatography on silica gel (0→40% EtOAC in PE) to 3-chloro-1-({3-ethyl-1-[(4-methoxyphenyl)methyl]-1H-pyrazol-5-yl}methyl)-5-iodo-1H-pyrazole (4.2 g, 97%) as a light-yellow solid. LC/MS ESI (m/z): 457 [M+H]+

Synthesis of 5-((5-bromo-1-cyclobutyl-1H-pyrazol-4-yl)methyl)-1-(4-fluoro-2-iodophenyl)-1H-1,2,4-triazole

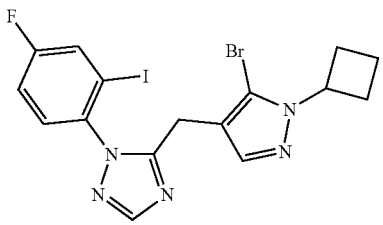 [SMILES: Fc1ccc(-n2ncnc2Cc2cnn(C3CCC3)c2Br)c(I)c1]

A solution of 2-(5-bromo-1-cyclobutyl-1H-pyrazol-4-yl)acetamide (1.70 g, 6.58 mmol) in DMF-DMA (8.82 mL, 65.9 mmol) was stirred at r.t. for 4 h. The mixture was concentrated to give crude 2-(5-bromo-1-cyclobutyl-1H-pyrazol-4-yl)-N-((dimethylamino)methylene)acetamide. LC/MS ESI (m/z): 313 [M+H]$^+$.

To a solution of 2-(5-bromo-1-cyclobutyl-1H-pyrazol-4-yl)-N-((dimethylamino)methylene)acetamide (2.00 g, 6.38 mmol) in AcOH (10 mL) was added (4-fluoro-2-iodophenyl)hydrazine hydrochloride (1.51 g, 6.38 mmol) at rt. The mixture was stirred at 70° C. for 2 h. The mixture was concentrated in vacuo. The residue was purified by flash chromatography (silica gel, 0→30% EtOAc in PE) to afford 5-((5-bromo-1-cyclobutyl-1H-pyrazol-4-yl)methyl)-1-(4-fluoro-2-iodophenyl)-1H-1,2,4-triazole (1.8 g, 56% yield) as a yellow oil. LC/MS ESI (m/z): 502 [M+H]$^+$.

Synthesis of 1-(2-(4-((3-chloro-1-ethyl-1H-pyrazol-4-yl)methyl)-2-methyloxazol-5-yl)-5-fluorophenyl)ethan-1-one

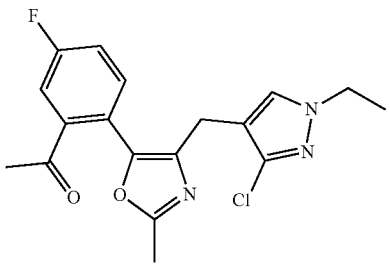 [SMILES: CCn1cc(Cc2nc(C)oc2-c2ccc(F)cc2C(C)=O)c(Cl)n1]

To a stirred solution of (diacetoxyiodo)benzene (2.2 g, 6.7 mmol) and acetonitrile (20 mL) was added TfOH (3.8 g, 25 mmol) at r.t. After stirring at r.t. for 20 min, a solution of 1-(2-bromo-4-fluorophenyl)-3-(3-chloro-1-ethyl-1H-pyrazol-4-yl)propan-1-one (2.0 g, 5.6 mmol) in MeCN (10 mL) was added and the reaction was refluxed for 2.5 h. The reaction was concentrated to dryness. The residue was purified by flash chromatography (0→50% EtOAc in PE) to give 5-(2-bromo-4-fluorophenyl)-4-[(3-chloro-1-ethyl-1H-pyrazol-4-yl)methyl]-2-methyl-1, 3-oxazole (0.21 g, 9.5% yield) as a yellow solid. LC/MS ESI (m/z): 398 [M+H]$^+$.

A mixture of 5-(2-bromo-4-fluorophenyl)-4-((3-chloro-1-ethyl-1H-pyrazol-4-yl)methyl)-2-methyloxazole (200 mg, 0.50 mmol), 1-(ethenyloxy)butane (0.40 mL, 3.1 mmol), DPPP (10 mg, 0.03 mmol), triethylamine (0.08 mL, 0.60 mmol) and Pd(OAc)$_2$ (3 mg, 0.01 mmol) in [bmim][BF$_4$](2 mL) was stirred at 115° C. for 24 h under N$_2$. The reaction was cooled to r.t., HCl (1 mL, 1.5 mmol, 1.5 M in water) and THF (1 mL) were added. Stirring was continued at r.t. for 1 h and then the mixture was extracted with EtOAc (5 mL×2). The combined organic layers were concentrated in vacuo. The residue was purified by flash column chromatography (0→40% EA in PE) to give 1-(2-(4-((3-chloro-1-ethyl-1H-pyrazol-4-yl)methyl)-2-methyloxazol-5-yl)-5-fluorophenyl)ethan-1-one (100 mg, 59% yield) as a yellow oil. LC/MS ESI (m/z): 362 [M+H]$^+$.

Synthesis of 1-(2-(2-((5-bromo-1-ethyl-1H-pyrazol-4-yl)methyl)-1H-imidazol-1-yl)-5-fluorophenyl)ethanone

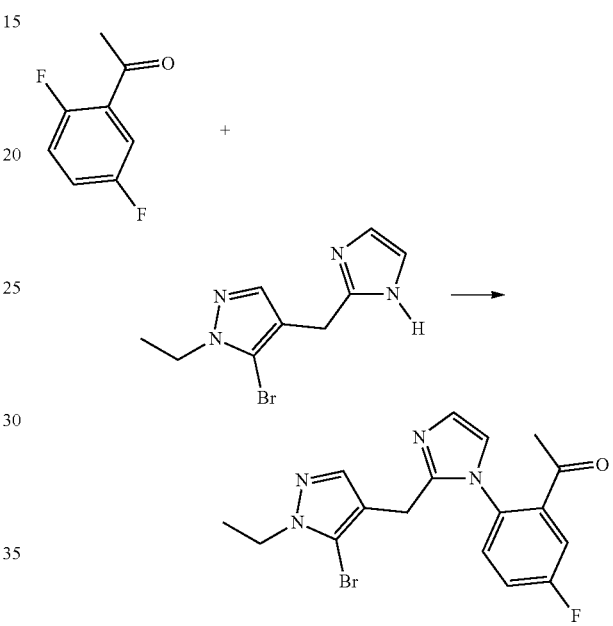

A mixture of 4-((1H-imidazol-2-yl)methyl)-5-bromo-1-ethyl-1H-pyrazole (5.00 g, 19.6 mmol), K$_3$PO$_4$ (8.30 g, 39.2 mmol), 1-(2,5-difluorophenyl)ethanone (6.20 g, 40.0 mmol) in anhydrous DMSO (35 mL) was stirred at 90° C. for 12 h. The mixture was quenched with ice-water, and then extracted with DCM (50 mL). The organic layer was separated, washed with brine, dried over anhydrous Na$_2$SO$_4$, filtered and concentrated. The residue was purified by column chromatography on silica gel (DCM:MeOH=25:1, V/V) to give crude 1-(2-(2-((5-bromo-1-ethyl-1H-pyrazol-4-yl)methyl)-1H-imidazol-1-yl)-5-fluorophenyl)ethanone as a white solid (2.2 g, yield: 29%). LC/MS ESI (m/z): 391 [M+H]$^+$.

Synthesis of 1-(2-{5-[(5-bromo-1-ethyl-1H-pyrazol-4-yl)methyl]-1H-1,2,4-triazol-1-yl}-5-fluorophenyl)ethan-1-ol

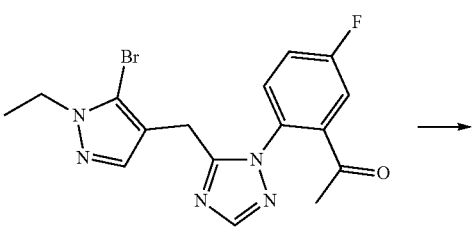

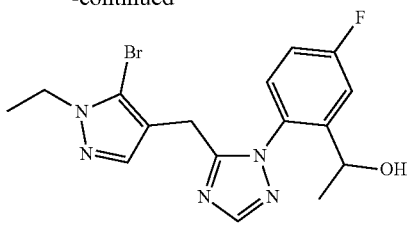

To a solution of 1-(2-{5-[(5-bromo-1-ethyl-1H-pyrazol-4-yl)methyl]-1H-1,2,4-triazol-1-yl}-5-fluorophenyl)ethan-1-one (480 mg, 1.22 mmol) in MeOH (10 mL) was added NaBH₄ (23 mg, 0.61 mmol) at 0° C., and the mixture was stirred at 0° C. for 1 h. The reaction mixture was quenched with ice water, concentrated to remove MeOH, and diluted with DCM. The resulting mixture was washed with sat. aq. NH₄Cl solution and brine, dried over anhydrous Na₂SO₄, filtered, and concentrated to dryness. The residue was purified by flash chromatography (silica gel, 0→20% MeOH in DCM) to give 1-(2-{5-[(5-bromo-1-ethyl-1H-pyrazol-4-yl)methyl]-1H-1,2,4-triazol-1-yl}-5-fluorophenyl)ethan-1-ol (330 mg, 68%) as a yellow oil. LC/MS (ESI) m/z: 394 [M+H]⁺.

The following intermediates were synthesized using a similar experimental protocol:

1-(2-(2-((5-bromo-1-ethyl-1H-pyrazol-4-yl)methyl)-1H-imidazol-1-yl)-5-fluorophenyl)ethanol

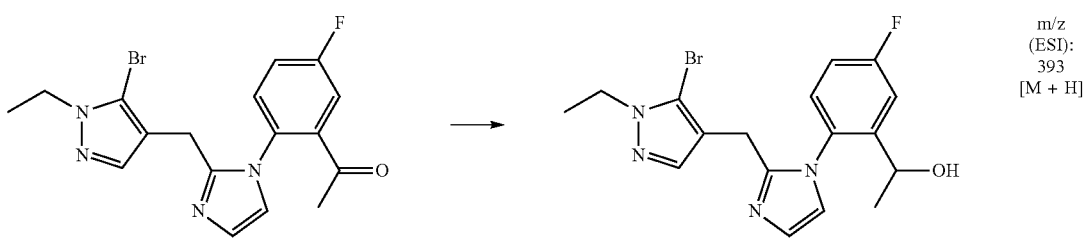

m/z (ESI): 393 [M + H]

1-(2-(5-((5-bromo-1-cyclobutyl-1H-pyrazol-4-yl)methyl)-1H-1,2,4-triazol-1-yl)-5-fluorophenyl)ethan-1-ol

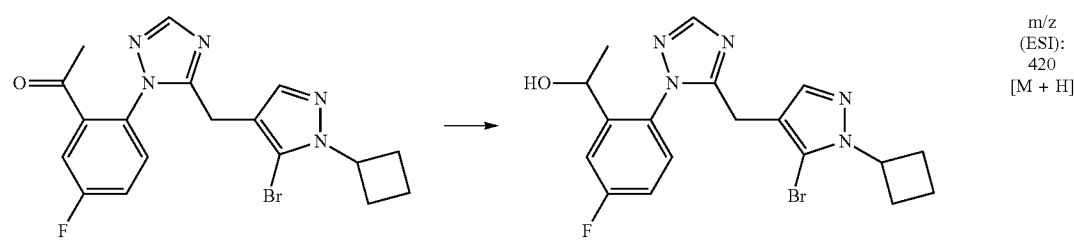

m/z (ESI): 420 [M + H]

1-(2-(4-((1-(cyclopropylmethyl)-3-methyl-1H-pyrazol-4-yl)methyl)-2-methyloxazol-5-yl)-5-fluorophenyl)ethan-1-ol

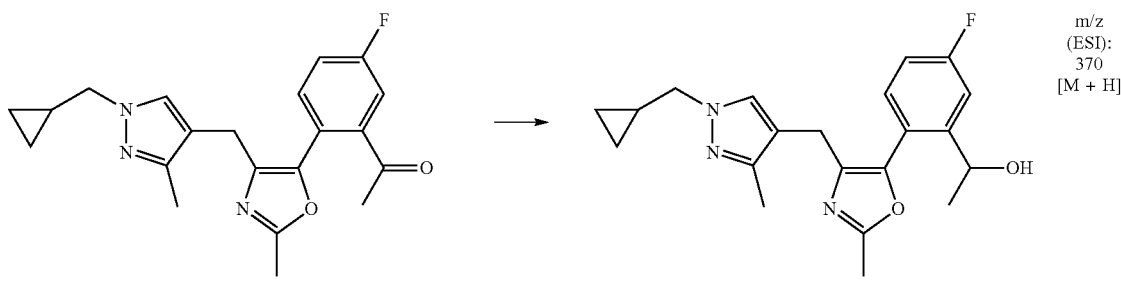

m/z (ESI): 370 [M + H]

1-(2-(4-((1-(cyclopropylmethyl)-1H-pyrazol-4-yl)methyl)-2-methyloxazol-5-yl)-5-fluorophenyl)ethan-1-ol

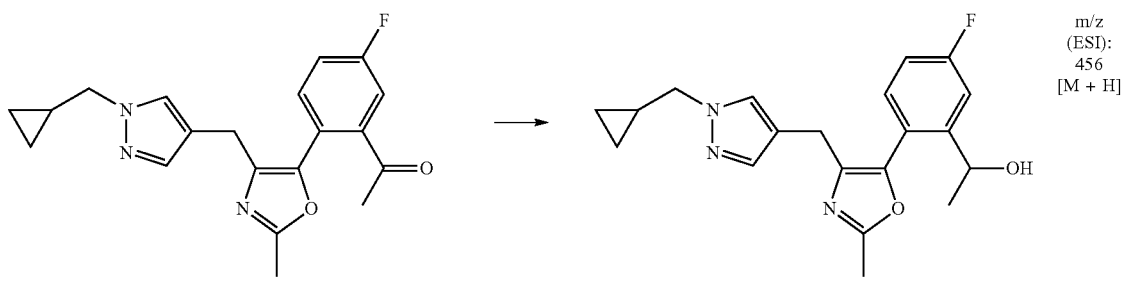

m/z (ESI): 456 [M + H]

Synthesis of 1-(2-(1-((5-bromo-1-ethyl-1H-pyrazol-4-yl)methyl)-3-methyl-1H-1,2,4-triazol-5-yl)-5-fluorophenyl)ethanone

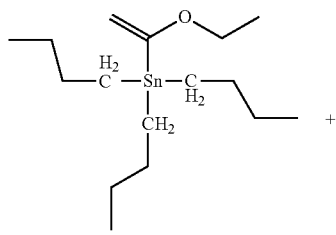

+

To a solution of 1-[(5-bromo-1-ethyl-1H-pyrazol-4-yl)methyl]-5-(4-fluoro-2-iodophenyl)-3-methyl-1H-1,2,4-triazole (600 mg, 1.22 mmol) and tributyl(i-ethoxyethenyl)stannane (486 mg, 1.35 mmol) in toluene (18 mL) was added Pd(PPhs)$_a$(142 mg, 0.120 mmol) and CuI (23 mg, 0.12 mmol). The mixture was charged with N$_2$ twice, then stirred at 100° C. for 12 h. After cooling to r.t., the mixture was poured into sat. aq. KF (50 mL), then stirred for 1 h. The resulting layers were separated, the organic phase was washed with brine, dried over anhydrous Na$_2$SO$_4$, filtered and concentrated. The residue was dissolved in THF (20 mL), and then iN aq. HCl (6.2 mL) was added. The mixture was stirred at r.t. for 2 h. The mixture was concentrated under reduced pressure, and the residue was purified by column chromatography on silica gel (PE:EA=1:1, V/V) to give 1-(2-(1-((5-bromo-1-ethyl-1H-pyrazol-4-yl)methyl)-3-methyl-1H-1,2,4-triazol-5-yl)-5-fluorophenyl)ethanone as a yellow oil (180 mg, yield: 36%). LC-MS (ESI): m/z 406 [M+H]$^+$.

The following intermediates were synthesized using a similar experimental protocol:

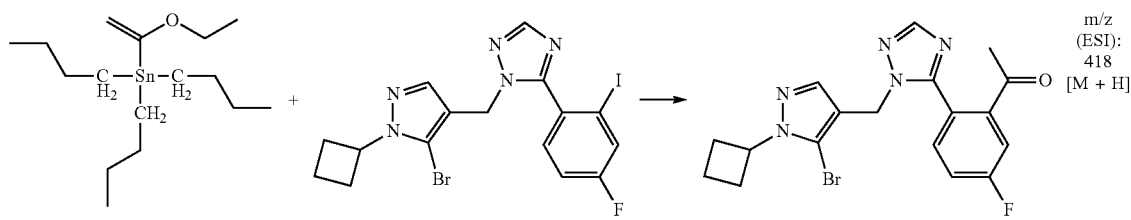

1-(2-(1-((5-bromo-1-cyclobutyl-1H-pyrazol-4-yl)methyl)-1H-1,2,4-triazol-5-yl)-5-fluorophenyl)ethanone m/z (ESI): 418 [M + H]

Synthesis of 1-(2-(4-((1-(cyclopropylmethyl)-1H-pyrazol-4-yl)methyl)-2-methyloxazol-5-yl)-5-fluorophenyl)ethan-1-one

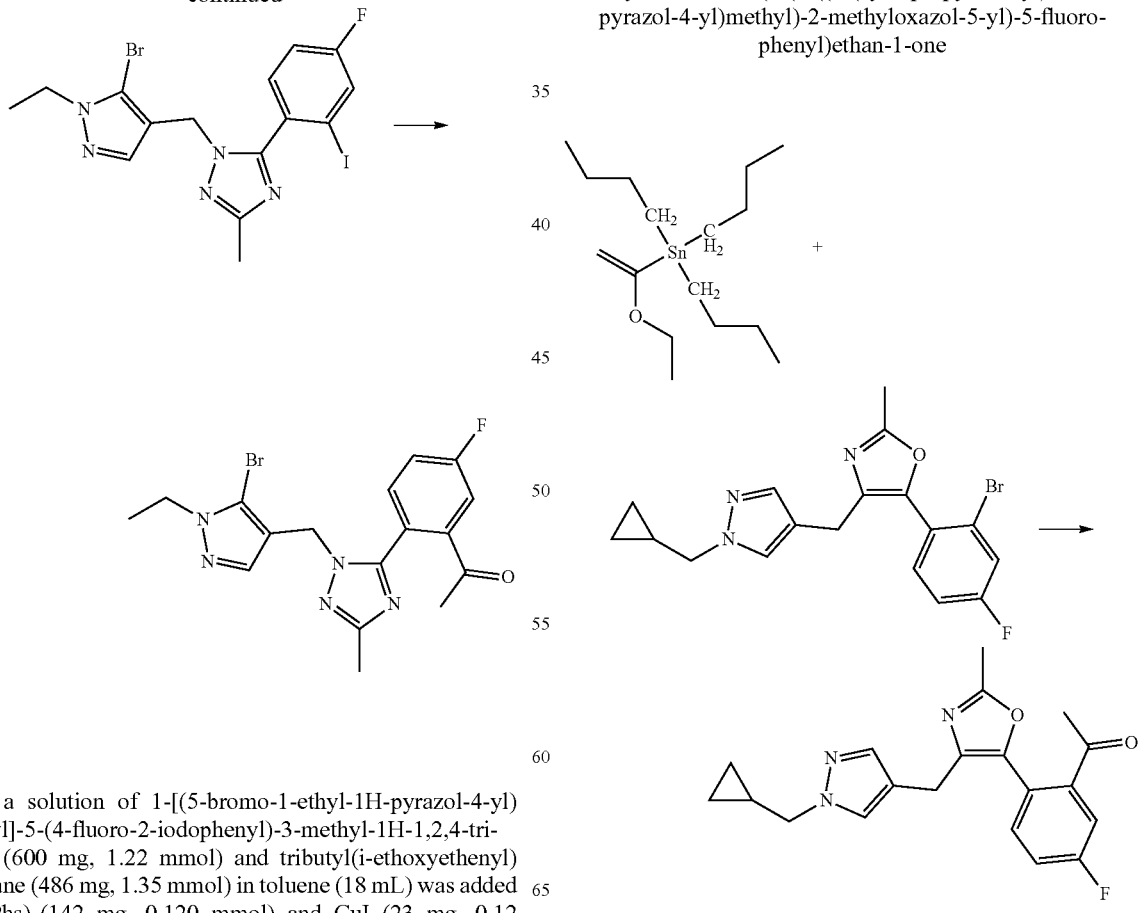

A mixture of 5-(2-bromo-4-fluorophenyl)-4-{[1-(cyclopropylmethyl)-1H-pyrazol-4-yl]methyl}-2-methyl-1,3-oxazole (450 mg, 1.15 mmol), tributyl(1-ethoxyethenyl)stannane (625 mg, 1.73 mmol), CuI (20 mg, 0.12 mmol) and Pd(PPh$_3$)$_4$ (133 mg, 0.115 mmol) in toluene (10 mL) was stirred at 120° C. under N$_2$ for 12 h. The mixture was concentrated and then diluted with THF (10 mL) and aq. HCl (10 mL, 1 N). This mixture was stirred at r.t. for 1 h. This solution was diluted with EtOAc (30 mL), washed with water (20 mL) and brine (30 mL), dried over anhydrous Na$_2$SO$_4$ and concentrated to dryness. The residue was purified by flash column chromatography on silica gel (PE: EtOAc=1:1) to afford 1-(2-(4-((1-(cyclopropylmethyl)-1H-pyrazol-4-yl)methyl)-2-methyloxazol-5-yl)-5-fluorophenyl)ethan-1-one (250 mg, 61% yield) as a yellow oil. LC/MS (ESI) m/z: 354 [M+H]$^+$.

The following intermediates were synthesized using a similar experimental protocol:

aq. HCl and extracted with EA (100 mL×3). The combined organic layers were dried over anhydrous Na$_2$SO$_4$, filtered, and concentrated in vacuo to give crude 5-bromo-2-methyl-1,3-oxazole-4-carboxylic acid (3.8 g, yield: 81%) as a white solid. LC/MS ESI (m/z): 206 [M+H]$^+$.

To a mixture of 5-bromo-2-methyl-1,3-oxazole-4-carboxylic acid (3.8 g, 18 mmol), methoxy(methyl)amine (2.30 g, 24.0 mmol), HOBt (3.70 g, 27.7 mmol) and TEA (10.3 mL, 73.8 mmol) in DMF (50 mL), EDCI (5.30 g, 27.7 mmol) was added at 0° C. The ice bath was removed, and the mixture was stirred for 12 h as it warmed to r.t. The mixture was filtered, and the filtrate extracted with EA (100 mL×3). The combined organic layers were washed with brine (50 mL×3). This solution was dried over anhydrous Na$_2$SO$_4$, filtered, and concentrated in vacuo. The residue was purified by column chromatography on silica gel (25% EtOAc in PE) to give 5-bromo-N-methoxy-N,2-dimethyl-1,3-oxazole-4-

| 1-[2-(4-{[3-chloro-1-(cyclopropylmethyl)-1H-pyrazol-4-yl]methyl}-2-methyl-1,3-oxazol-5-yl)-5-fluorophenyl]ethan-1-one |
|---|

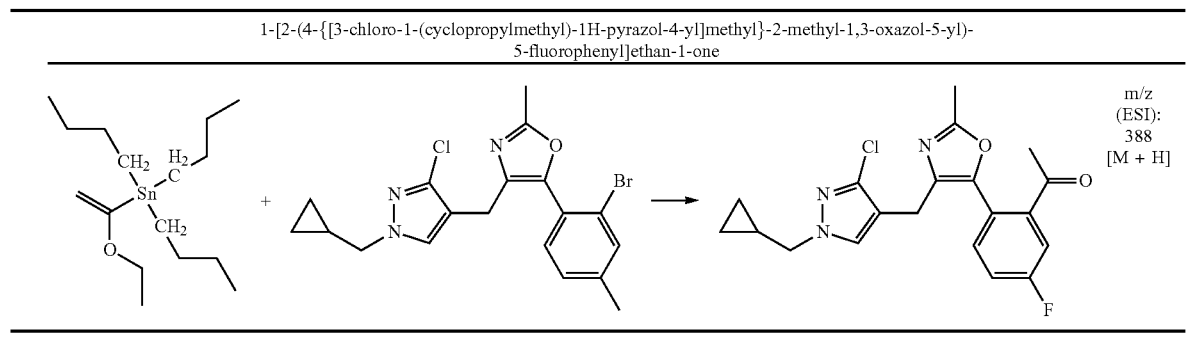

m/z (ESI): 388 [M + H]

Synthesis of 5-(2-bromo-4-fluorophenyl)-4-[3-chloro-1-(cyclopropylmethyl)-1H-pyrazole-4-carbonyl]-2-methyl-1,3-oxazole

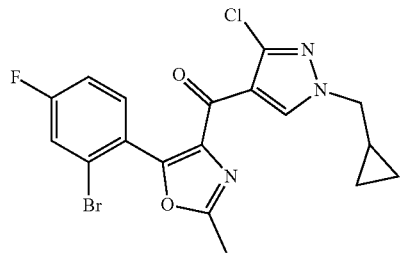 [SMILES: Cc1nc(C(=O)c2cn(CC3CC3)nc2Cl)c(-c2ccc(F)cc2Br)o1]

A mixture of methyl 2-methyl-1,3-oxazole-4-carboxylate (10.0 g, 70.9 mmol), TFA (6.1 mL, 82 mmol) and NBS (15.1 g, 85.0 mmol) in CH$_3$CN (200 mL) was stirred at r.t. for 12 h. The mixture was quenched with sat. aq. Na$_2$S$_2$O$_3$ at 0° C. and adjusted to pH 7 with sat. aq. NaHCO$_3$. The mixture was extracted with EA (200 mL×3). The combined organic phases were dried over anhydrous Na$_2$SO$_4$, filtered and concentrated in vacuo. The residue was purified by column chromatography on silica gel (20% EtOAc in PE) to give methyl 5-bromo-2-methyl-1,3-oxazole-4-carboxylate (5.0 g, yield: 32%) as a light-yellow solid. LC/MS ESI (m/z): 220 [M+H]$^+$.

A mixture of methyl 5-bromo-2-methyl-1,3-oxazole-4-carboxylate (5.0 g, 28 mmol) and lithium hydroxide (2.40 g, 56.8 mmol) in THF (20 mL) and H$_2$O (20 mL) was stirred at r.t. for 12 h. The mixture was adjusted to pH 3 with 1 M carboxamide (2.0 g, yield: 44%) as a light-yellow solid. LC/MS ESI (m/z): 249 [M+H]$^+$.

To a mixture of 3-chloro-1-(cyclopropylmethyl)-4-iodo-1H-pyrazole (2.7 g, 9.6 mmol) in THF (50 mL) was added isopropylmagnesium chloride-lithium chloride complex solution (1.3 M in THF, 9.6 mL). The reaction was thrice degassed with N$_2$ and then stirred at 0° C. for 1 h. To this mixture was added 5-bromo-N-methoxy-N,2-dimethyl-1,3-oxazole-4-carboxamide (2.00 g, 8.03 mmol) and stirring was continued at 0° C. for 2 h. The mixture was quenched with sat. aq. NH$_4$Cl solution (100 mL) at 0° C. and extracted with EA (100 mL×3). The organic layers were combined, dried over anhydrous Na$_2$SO$_4$, filtered and concentrated in vacuo. The residue was purified by column chromatography on silica gel (30% EtOAc in PE) to give 5-bromo-4-[3-chloro-1-(cyclopropylmethyl)-1H-pyrazole-4-carbonyl]-2-methyl-1,3-oxazole (1.07 g, yield: 39%) as a light-yellow oil. LC/MS ESI (m/z): 344 [M+H]$^+$.

A mixture of 5-bromo-4-[3-chloro-1-(cyclopropylmethyl)-1H-pyrazole-4-carbonyl]-2-methyl-1,3-oxazole (250 mg, 0.730 mmol), (2-bromo-4-fluorophenyl)boronic acid (190 mg, 0.870 mmol), Pd(PPh$_3$)$_4$ (84 mg, 0.07 mmol) and Na$_2$CO$_3$ (154 mg, 1.45 mmol) in toluene (6 mL) and EtOH (3 mL) was thrice degassed with N$_2$ and stirred at 80° C. for 12 h. The mixture was concentrated in vacuo to give a residue, which was purified by flash chromatography (PE: EA=1:1, V/V) to give 5-(2-bromo-4-fluorophenyl)-4-[3-chloro-1-(cyclopropylmethyl)-1H-pyrazole-4-carbonyl]-2-methyl-1,3-oxazole (230 mg, yield: 72%) as a light-yellow solid. LC/MS ESI (m/z): 438 [M+H]$^+$.

Synthesis of 5-((5-bromo-1-ethyl-1H-pyrazol-4-yl)methyl)-1-(2-(1-ethoxyvinyl)-4-fluorophenyl)-3-methyl-1H-1,2,4-triazole

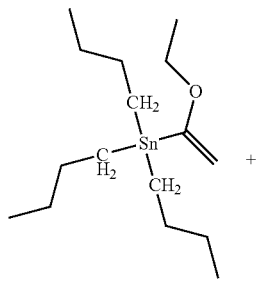

To a solution of 5-((5-bromo-1-ethyl-1H-pyrazol-4-yl)methyl)-1-(4-fluoro-2-iodophenyl)-3-methyl-1H-1,2,4-triazole (580 mg, 1.12 mmol) in toluene (10 mL) was added Pd(PPh$_3$)$_4$ (273 mg, 0.240 mmol), CuI (45 mg, 0.24 mmol) and tributyl(1-ethoxyethenyl)stannane (855 mg, 2.37 mmol). The mixture was thrice degassed under N$_2$ and stirred at 120° C. for 6 h. After cooling to r.t., the reaction mixture was quenched with sat. aq. KF (10 mL) and extracted with EtOAc (3×10 mL). The combined organic phases were washed with brine (10 mL), dried over anhydrous Na$_2$SO$_4$, filtered, and concentrated to give crude 5-((5-bromo-1-ethyl-1H-pyrazol-4-yl)methyl)-1-(2-(1-ethoxyvinyl)-4-fluorophenyl)-3-methyl-1H-1,2,4-triazole as a brown gum (494 mg, yield: 96%). LC/MS ESI (m/z): 434 [M+H]$^+$.

The following intermediates were synthesized using a similar experimental protocol:

| 5-((5-bromo-1-cyclobutyl-1H-pyrazol-4-yl)methyl)-1-(2-(1-ethoxyvinyl)-4-fluorophenyl)-1H-1,2,4-triazole | |
|---|---|
| 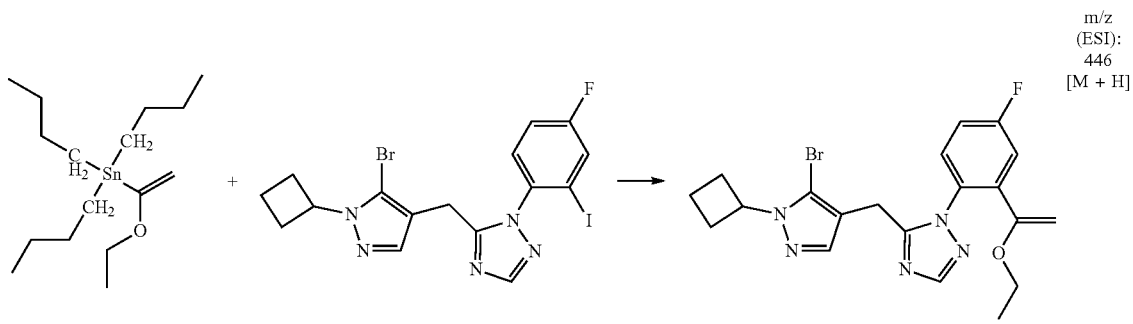 | m/z (ESI): 446 [M + H] |

Synthesis of 1-(2-(5-((5-bromo-1-ethyl-1H-pyrazol-4-yl)methyl)-3-methyl-1H-1,2,4-triazol-1-yl)-5-fluorophenyl)ethan-1-one

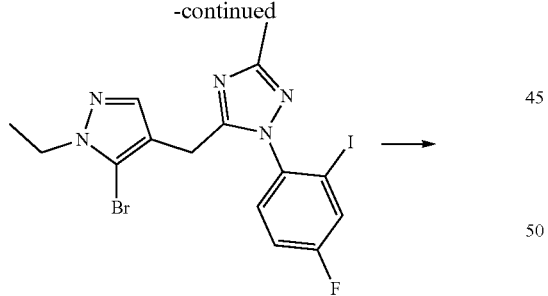

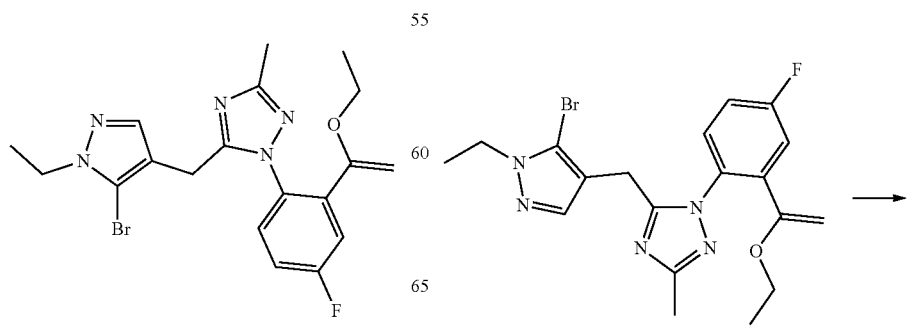

321

-continued

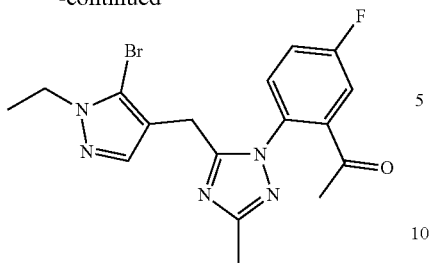

To a solution of 5-((5-bromo-1-ethyl-1H-pyrazol-4-yl)methyl)-1-(2-(1-ethoxyvinyl)-4-fluorophenyl)-3-methyl-1H-1,2,4-triazole (494 mg, 1.14 mmol) in THF (10 mL) at r.t. was added conc. HCl (1.0 mL, 12 mmol). The reaction was stirred at r.t. for 20 min. The reaction mixture was basified to pH 8 with sat. aq. NaHCO$_3$, and extracted with EtOAc (3×10 mL). The combined organic layers were washed with brine (10 mL), dried over anhydrous Na$_2$SO$_4$, filtered, and concentrated. The residue was purified by flash chromatography (silica gel, 0→5% MeOH in DCM) to give 1-(2-(5-((5-bromo-1-ethyl-1H-pyrazol-4-yl)methyl)-3-methyl-1H-1,2,4-triazol-1-yl)-5-fluorophenyl)ethan-1-one as a white solid (250 mg, yield: 54%). LC/MS (ESI) m/z: 406 [M+H]$^+$.

The following intermediates were synthesized using a similar experimental protocol:

| 1-(2-(5-((5-bromo-1-cyclobutyl-1H-pyrazol-4-yl)methyl)-1H-1,2,4-triazol-1-yl)-5-fluorophenyl)ethan-1-one |
|---|

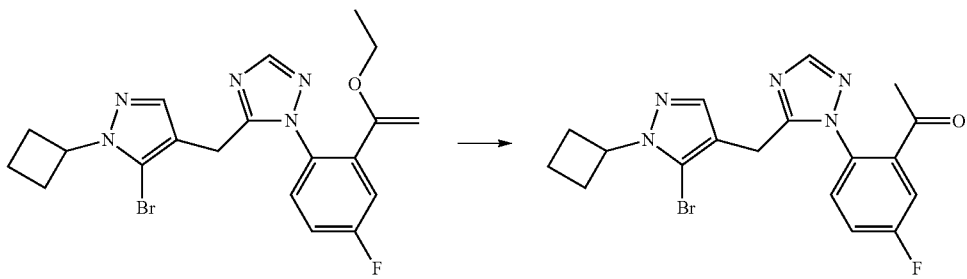 [SMILES: C=C(OCC)c1cc(F)ccc1-n1ncnc1Cc1cnn(C2CCC2)c1Br ; CC(=O)c1cc(F)ccc1-n1ncnc1Cc1cnn(C2CCC2)c1Br]

m/z (ESI): 418 [M + H]

Synthesis of 5-((5-(2-(1-((5-bromo-2-nitropyridin-3-yl)oxy)ethyl)-4-fluorophenyl)-1H-1,2,4-triazol-1-yl)methyl)-3-ethylisoxazole

322

-continued

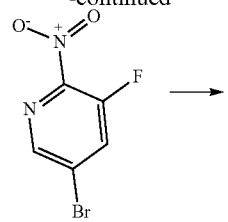

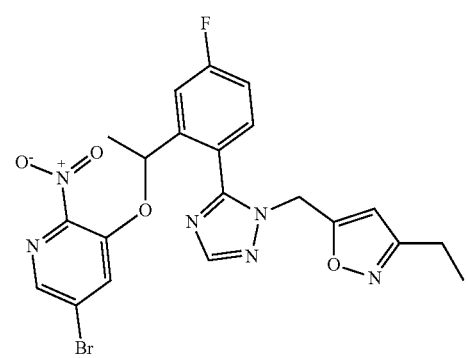

The solution of 1-(2-{1-[(3-ethyl-1,2-oxazol-5-yl)methyl]-1H-1,2,4-triazol-5-yl}-5-fluorophenyl)ethan-1-ol (250 mg, 0.40 mmol) and NaH (24 mg, 0.59 mmol) in THF (5 mL) was stirred at 25° C. for 1 h. To this mixture was added 5-bromo-3-fluoro-2-nitropyridine (131 mg, 0.590 mmol). Stirring was continued at 25° C. for 2 h. The reaction was quenched with ice-water and partitioned between EA and water. The layers were separated, and the aq. layer was extracted with EA. The organic layer was washed with sat. NH$_4$C and brine, dried over anhydrous Na$_2$SO$_4$, filtered, and concentrated in vacuo. The residue was purified by flash chromatography (0→10% MeOH in DCM) to give 5-((5-(2-(1-((5-bromo-2-nitropyridin-3-yl)oxy)ethyl)-4-fluorophenyl)-1H-1,2,4-triazol-1-yl)methyl)-3-ethylisoxazole (198 mg, yield: 97%) as a yellow solid. LC/MS ESI (m/z): 517 [M+H]$^+$.

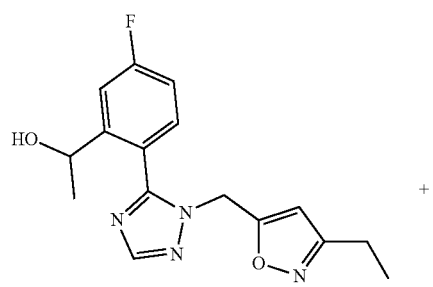

+

The following intermediates were synthesized using a similar experimental protocol:

5-bromo-3-[1-(2-{1-[(5-bromo-1-ethyl-1H-pyrazol-4-yl)methyl]-1H-1,2,4-triazol-5-yl}-5-fluorophenyl)ethoxy]-2-nitropyridine

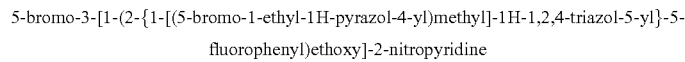

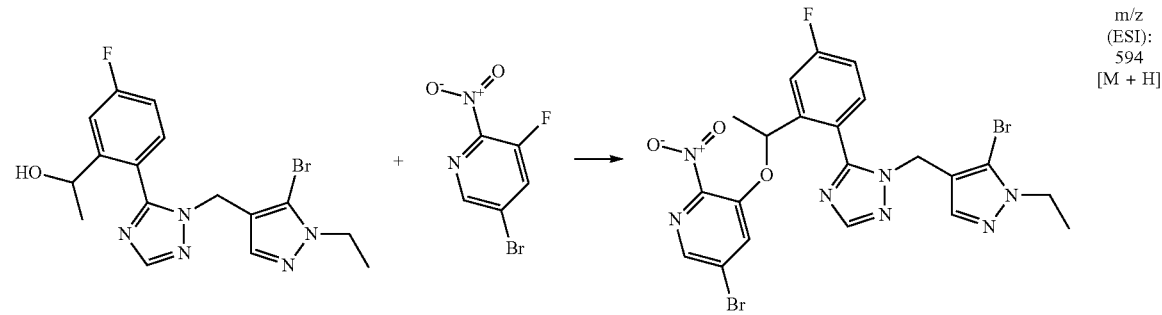

m/z (ESI): 594 [M + H]

5-bromo-3-(1-(2-(5-((5-bromo-1-cyclobutyl-1H-pyrazol-4-yl)methyl)-1H-1,2,4-triazol-1-yl)-5-fluorophenyl)ethoxy)-2-nitropyridine

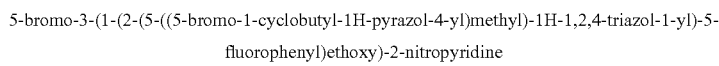

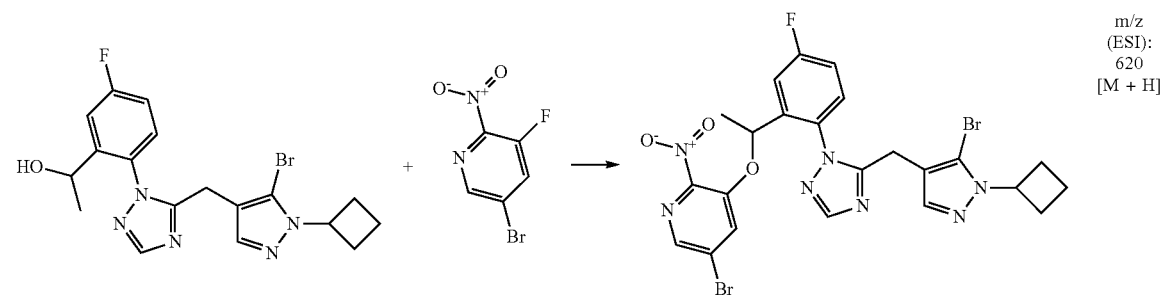

m/z (ESI): 620 [M + H]

5-bromo-3-[1-(2-{1-[(5-bromo-3-chloro-1-ethyl-1H-pyrazol-4-yl)methyl]-1H-1,2,4-triazol-5-yl}-5-fluorophenyl)ethoxy]-2-nitropyridine

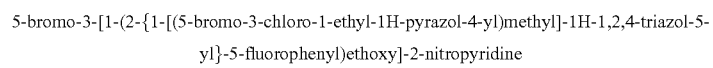

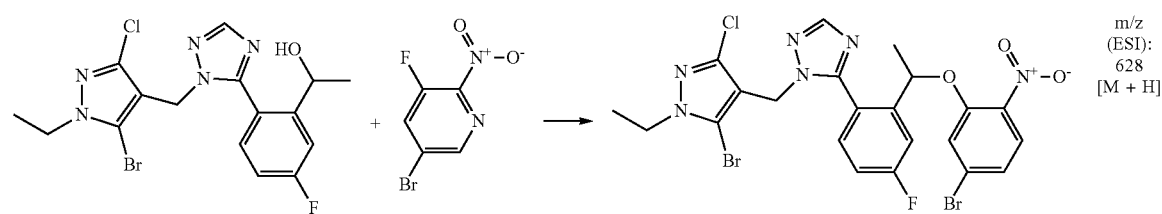

m/z (ESI): 628 [M + H]

5-bromo-3-(1-(2-(2-((5-bromo-1-ethyl-1H-pyrazol-4-yl)methyl)pyridin-3-yl)-5-fluorophenyl)ethoxy)-2-nitropyridine

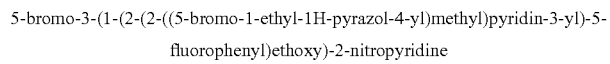

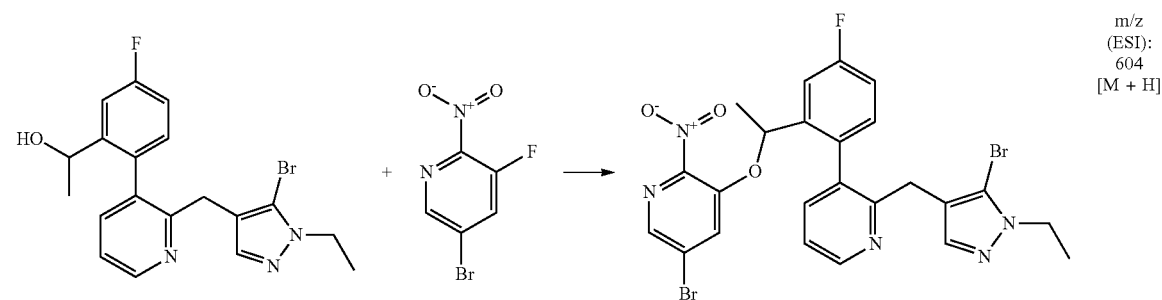

m/z (ESI): 604 [M + H]

(R)-5-((5-(2-(1-((5-bromo-2-nitropyridin-3-yl)oxy)ethyl)-4-fluorophenyl)-1H-1,2,4-triazol-1-yl)methyl)-3-cyclobutylisoxazole

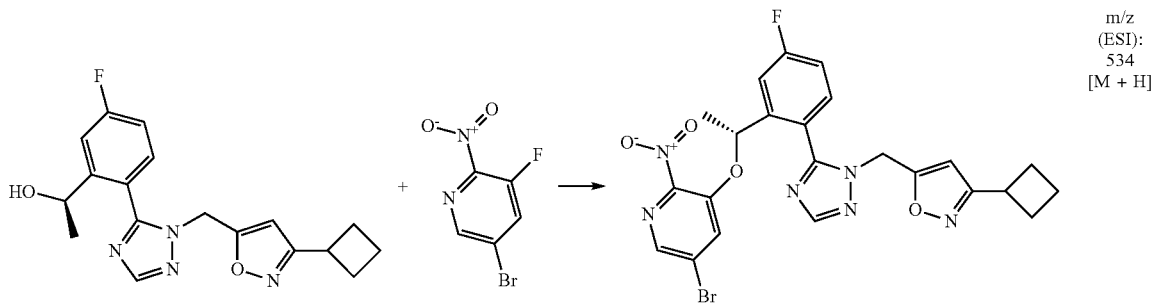

m/z (ESI): 534 [M + H]

5-bromo-3-[(1R)-1-(2-{4-[(1-ethyl-1H-1,2,3-triazol-4-yl)methyl]-1,3-thiazol-5-yl}-5-fluorophenyl)ethoxy]-2-nitropyridine

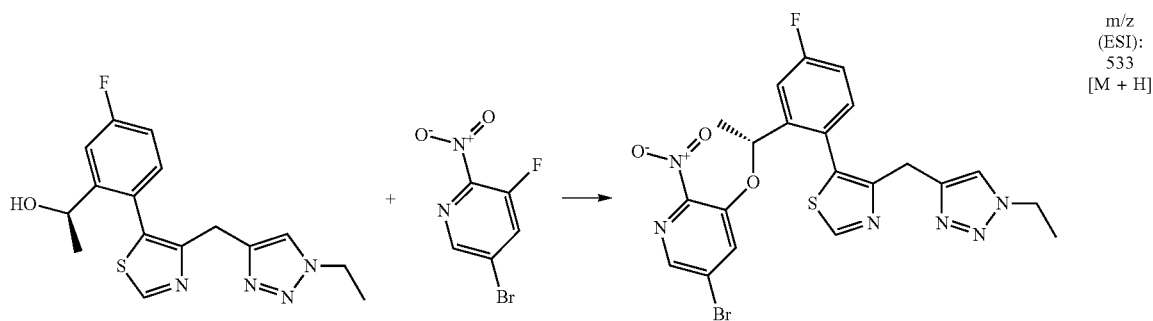

m/z (ESI): 533 [M + H]

(R)-5-bromo-3-(1-(2-(5-((1-(cyclopropylmethyl)-1H-1,2,3-triazol-4-yl)methyl)-2-methyl-2H-1,2,3-triazol-4-yl)-5-fluorophenyl)ethoxy)-2-nitropyridine

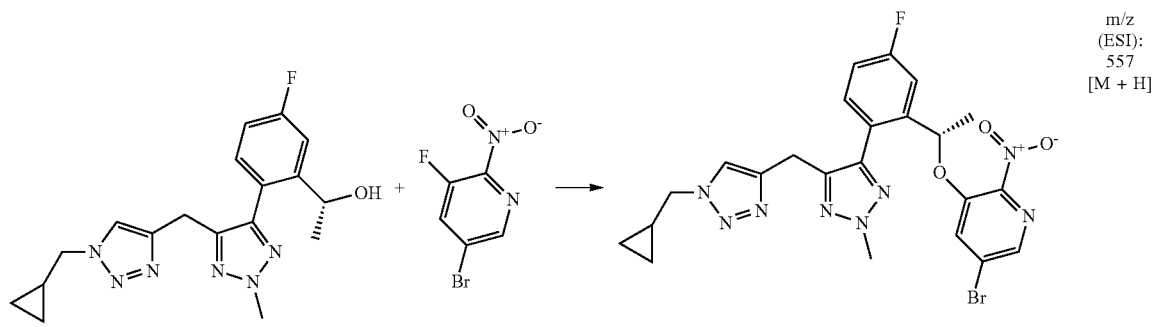

m/z (ESI): 557 [M + H]

(R)-5-((5-(2-(1-((5-bromo-2-nitropyridin-3-yl)oxy)ethyl)-4-fluorophenyl)-1H-1,2,4-triazol-1-yl)methyl)-3-(cyclopropylmethyl)isoxazole

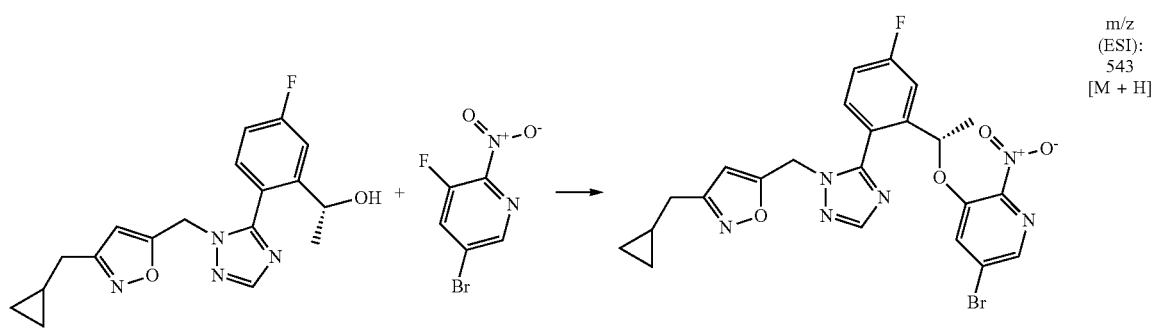

m/z (ESI): 543 [M + H]

(R)-5-bromo-3-(1-(2-(5-((3-chloro-1-(2,2-difluoroethyl)-1H-pyrazol-4-yl)methyl)-2-methyl-2H-1,2,3-triazol-4-yl)-5-fluorophenyl)ethoxy)-2-nitropyridine

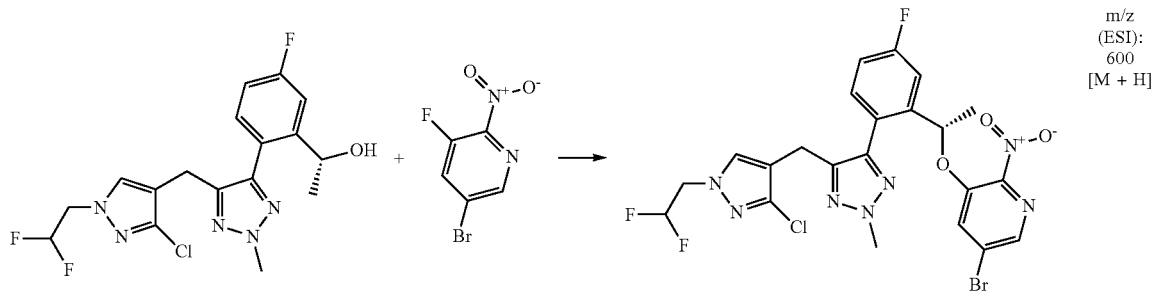

m/z (ESI): 600 [M + H]

(R)-5-bromo-3-(1-(2-(3-((1-(cyclopropylmethyl)-1H-pyrazol-4-yl)methyl)-1-methyl-1H-pyrazol-4-yl)-5-fluorophenyl)ethoxy)-2-nitropyridine

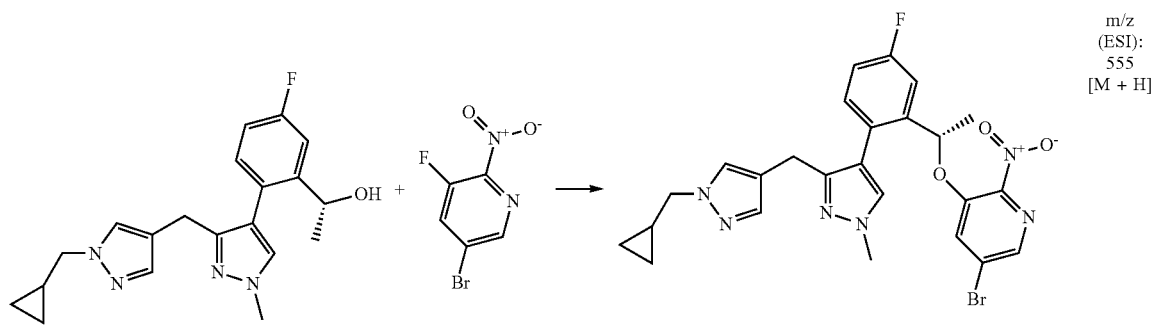

m/z (ESI): 555 [M + H]

5-bromo-3-[(1R)-1-[2-(5-{[1-(cyclopropylmethyl)-3-methyl-1H-pyrazol-4-yl]methyl}-2-methyl-2H-1,2,3-triazol-4-yl)-5-fluorophenyl]ethoxy]-2-nitropyridine

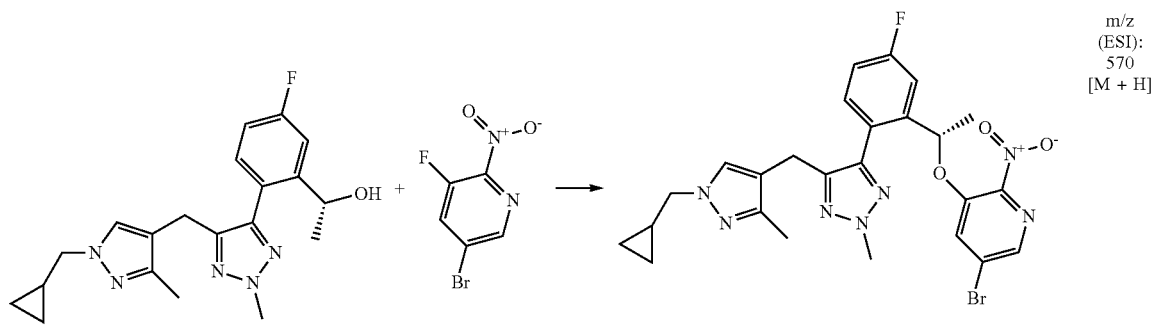

m/z (ESI): 570 [M + H]

(R)-5-bromo-3-(1-(2-(2-((1-(cyclopropylmethyl)-1H-pyrazol-4-yl)methyl)-5-fluoropyridin-3-yl)-5-fluorophenyl)ethoxy)-2-nitropyridine

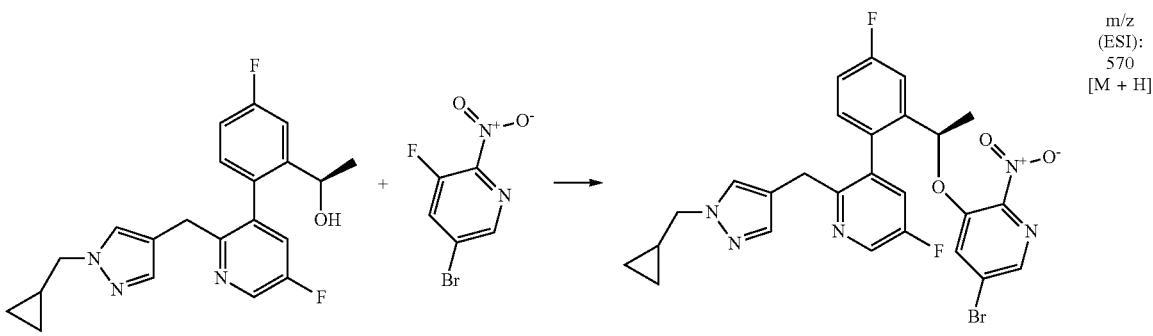

m/z (ESI): 570 [M + H]

(R)-5-bromo-3-(1-(2-(2-((1-(2,2-difluoroethyl)-1H-pyrazol-4-yl)methyl)-5-fluoropyridin-3-yl)-5-fluorophenyl)ethoxy)-2-nitropyridine

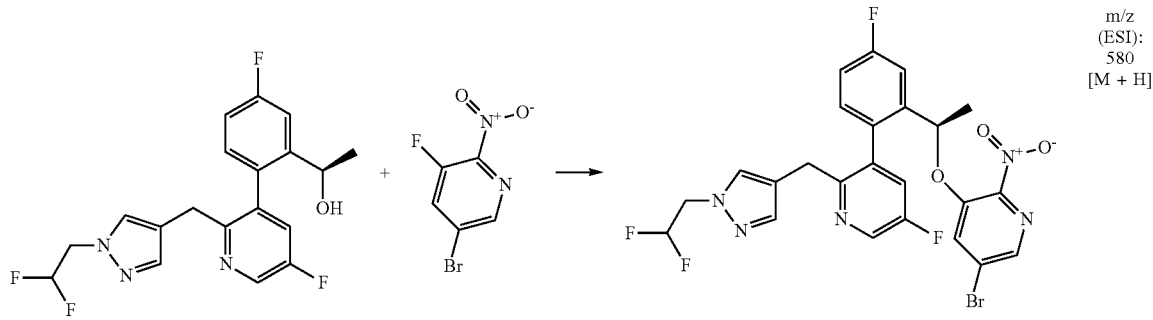

m/z (ESI): 580 [M + H]

(R)-5-bromo-3-(1-(5-fluoro-2-(2-methyl-5-((1-(oxetan-3-yl)-1H-pyrazol-4-yl)methyl)-2H-1,2,3-triazol-4-yl)phenyl)ethoxy)-2-nitropyridine

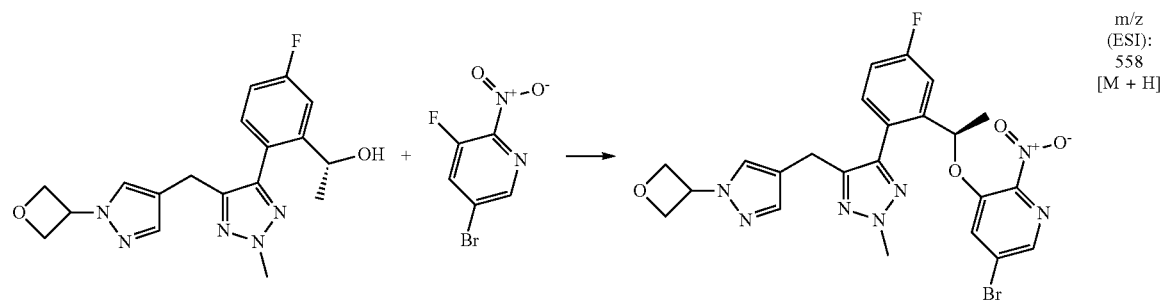

m/z (ESI): 558 [M + H]

5-bromo-3-[(1R)-1-[2-(5-{[3-chloro-1-(cyclopropylmethyl)-1H-pyrazol-4-yl]methyl}-2-methyl-2H-1,2,3-triazol-4-yl)-5-fluorophenyl]ethoxy]-2-nitropyridine

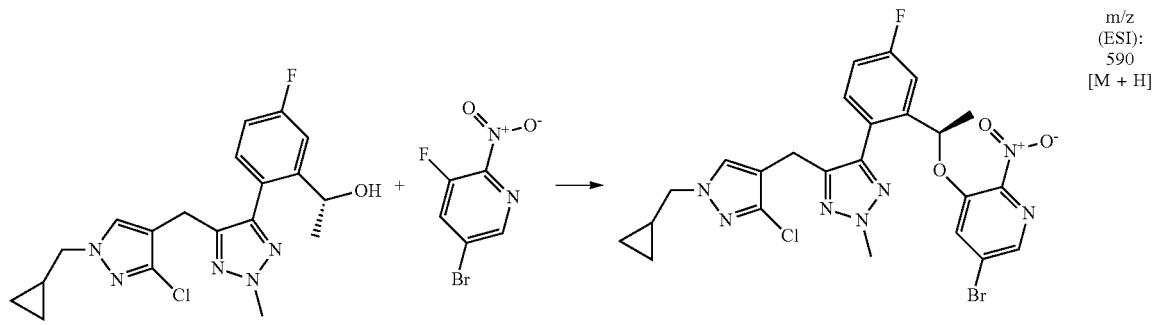

m/z (ESI): 590 [M + H]

1-[[4-(2-[1-[(5-bromo-2-nitropyridin-3-yl)oxy]ethyl]-4-fluorophenyl)-1,3-thiazol-5-yl]methyl]pyrazole-4-carbonitrile

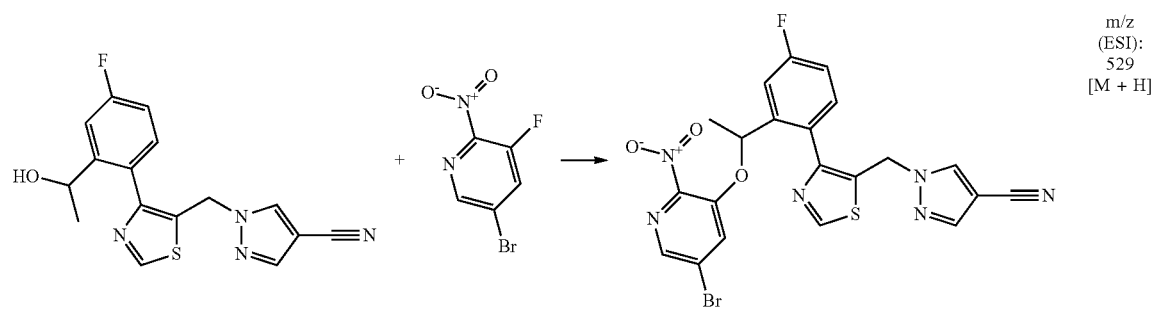

m/z (ESI): 529 [M + H]

-continued 5-(2-(1-((5-bromo-2-nitropyridin-3-yl)oxy)ethyl)-4-fluorophenyl)-4-((1-ethyl-1H-pyrazol-4-yl)methyl)-2-methyloxazole

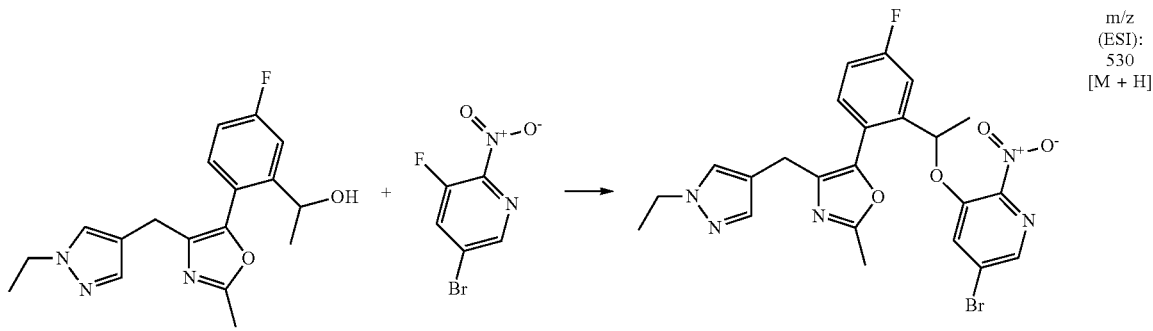

m/z (ESI): 530 [M + H]

5-bromo-3-(2-((tert-butyldimethylsilyl)oxy)-1-(2-(5-((1-(cyclopropylmethyl)-3-methyl-1H-pyrazol-4-yl)methyl)-2-methyl-2H-1,2,3-triazol-4-yl)-5-fluorophenyl)ethoxy)-2-nitropyridine

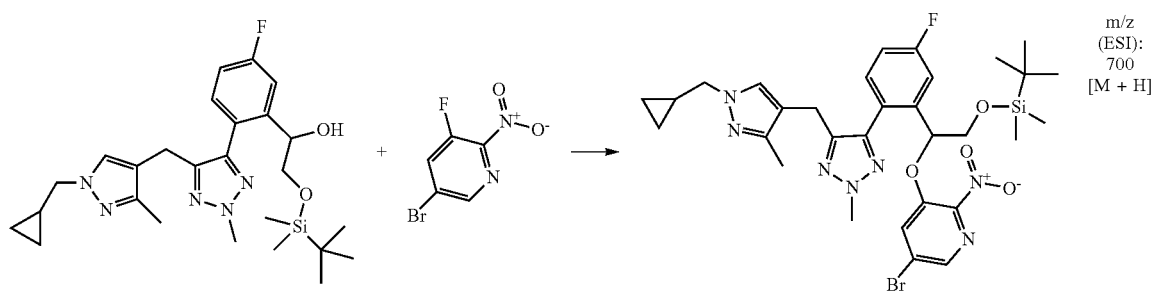

m/z (ESI): 700 [M + H]

(R)-5-bromo-3-(1-(2-(5-((3-ethyl-1-methyl-1H-pyrazol-5-yl)methyl)-2-methyl-2H-1,2,3-triazol-4-yl)-5-fluorophenyl)ethoxy)-2-nitropyridine

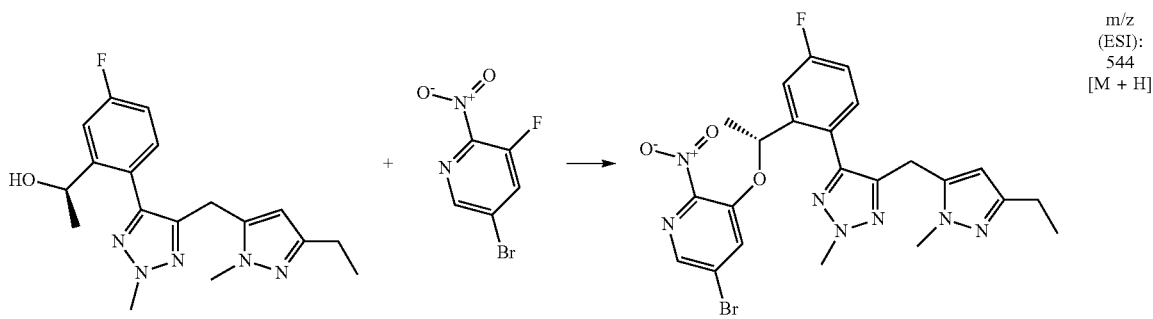

m/z (ESI): 544 [M + H]

5-bromo-3-[(1R)-1-[2-(5-{[3-(cyclopropylmethyl)-1-methyl-1H-pyrazol-5-yl]methyl}-2-methyl-2H-1,2,3-triazol-4-yl)-5-fluorophenyl]ethoxy]-2-nitropyridine

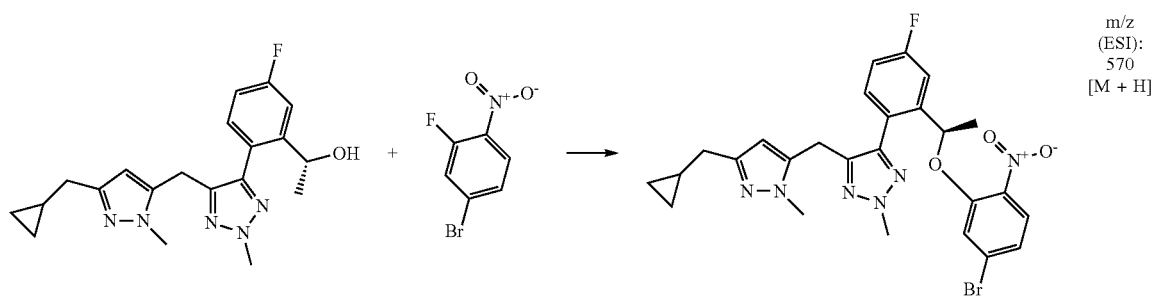

m/z (ESI): 570 [M + H]

333

Synthesis of (R)-1-((3-(2-(1-((5-bromo-2-nitropyridin-3-yl)oxy)ethyl)-4-fluorophenyl)pyrazin-2-yl)methyl)-1H-imidazole-4-carbonitrile

334

Synthesis of 4-bromo-5-((5-(2-(1-((5-bromo-2-nitropyridin-3-yl)oxy)ethyl)-4-fluorophenyl)-1H-1,2,4-triazol-1-yl)methyl)-3-ethylisothiazole

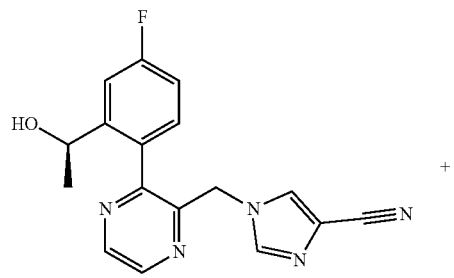 +

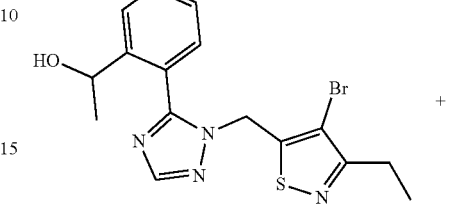 +

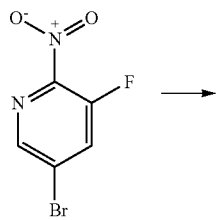 →

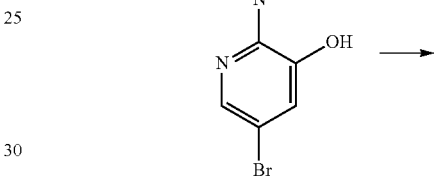 →

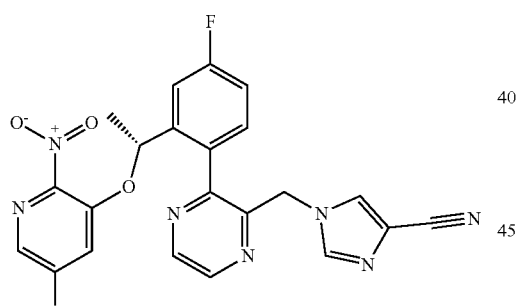

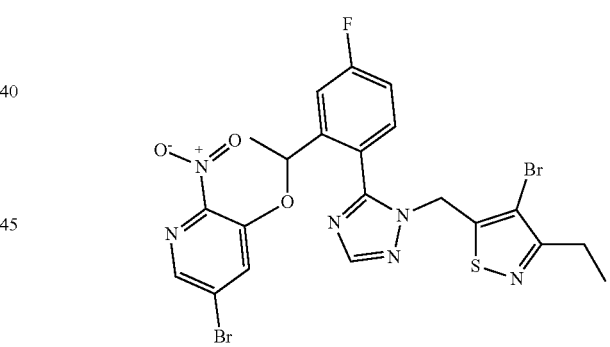

A mixture of (R)-1-((3-(4-fluoro-2-(1-hydroxyethyl)phenyl)pyrazin-2-yl)methyl)-1H-imidazole-4-carbonitrile (200 mg, 0.62 mmol), 5-bromo-3-fluoro-2-nitropyridine (205 mg, 0.930 mmol) and $Cs_2CO_3$ (403 mg, 1.24 mmol) in anhydrous THF (5 mL) was stirred at 80° C. in a sealed tube for 3 h. After cooling to r.t., the reaction mixture was filtered through celite, and the filtrate was partitioned between EA and water. The organic layer was separated, dried over anhydrous $Na_2SO_4$, filtered, and concentrated in vacuo. The residue was purified by flash chromatography (silica gel, 0→3% MeOH in DCM) to give (R)-1-((3-(2-(1-((5-bromo-2-nitropyridin-3-yl)oxy)ethyl)-4-fluorophenyl)pyrazin-2-yl)methyl)-1H-imidazole-4-carbonitrile (60 mg, 19% yield) as a white solid. LC/MS ESI (m/z): 524 [M+H]$^+$.

A solution of 1-(2-(1-(((4-bromo-3-ethylisothiazol-5-yl)methyl)-1H-1,2,4-triazol-5-yl)-5-fluorophenyl)ethan-1-ol (800 mg, 1.95 mmol), 5-bromo-2-nitropyridin-3-ol (1.70 g, 7.80 mmol) and $PPh_3$ (1.02 g, 3.90 mmol) in toluene (80 mL) was added DIAD (1.80 g, 5.85 mmol) dropwise at 0° C. under $N_2$ atmosphere. The resulting solution was stirred at 80° C. for 16 h and then filtered. The filtrate was concentrated under vacuum and the residue was purified by flash phase chromatography on silica gel (0→80% EtOAc in PE) to afford 4-bromo-5-((5-(2-(1-((5-bromo-2-nitropyridin-3-yl)oxy)ethyl)-4-fluorophenyl)-1H-1,2,4-triazol-1-yl)methyl)-3-ethylisothiazole (400 mg) as a white solid. LC-MS (ESI) m/z: 611 [M+H]$^+$.

Compounds

Example 1 (Method A)

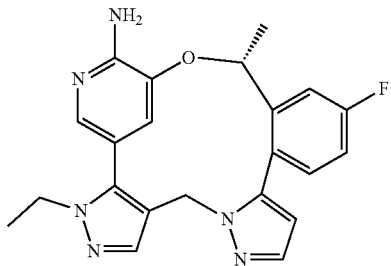 [SMILES: CCn1ncc2c1-c1cnc(N)c(c1)O[C@H](C)c1cc(F)ccc1-c1ccnn1C2]

Name: (19R)-3-ethyl-16-fluoro-19-methyl-20-oxa-3,4,8,9,23-pentaazapentacyclo[19.3.1.0$^{2,6}$.0$^{8,12}$.0$^{13,18}$]pentacosa-1(24),2(6),4,9,11,13,15,17,21(25),22-decaen-22-amine
NMR: 1H NMR (400 MHz, DMSO) δ 7.77-7.73 (m, 1H), 7.73 (s, 1H), 7.60 (d, J = 1.8 Hz, 1H), 7.50 (d, J = 1.8 Hz, 1H), 7.36 (dd, J = 8.6, 5.8 Hz, 1H), 7.23 (td, J = 8.4, 2.8 Hz, 1H), 6.42 (d, J = 1.8 Hz, 1H), 6.19 (s, 2H), 5.89 (d, J = 1.7 Hz, 1H), 5.53-5.40 (m, 1H), 5.05 (d, J = 14.6 Hz, 1H), 4.33 (d, J = 14.5 Hz, 1H), 4.14-3.98 (m, 2H), 1.76 (d, J = 6.3 Hz, 3H), 1.28 (t, J = 7.2 Hz, 3H).
LCMS: Method C; t$_g$: 1.18 min; m/z: 405 [M + H]

A mixture of 5-bromo-1-ethyl-4-((5-iodo-1H-pyrazol-1-yl)methyl)-1H-pyrazole (500 mg, 1.31 mmol), (R)-5-bromo-3-(1-(5-fluoro-2-(trimethylstannyl)phenyl)ethoxy)pyridin-2-amine (1.24 g, 2.62 mmol), Pd$_2$(dba)$_3$ (240 mg, 0.262 mmol), AsPh$_3$ (409 mg, 1.31 mmol) and CuI (24.9 mg, 0.131 mmol) in DMF (50 mL) was heated at 100° C. for 12 h. The mixture was cooled to r.t., treated with aq. KF, and extracted three times with ethyl acetate. The combined organic layers were washed with brine, dried over anhydrous Na$_2$SO$_4$, filtered, and concentrated. The residue was purified by column chromatography on silica gel (0→50% EtOAc in PE) to give (R)-5-bromo-3-(1-(2-(1-((5-bromo-1-ethyl-1H-pyrazol-4-yl)methyl)-1H-pyrazol-5-yl)-5-fluorophenyl)ethoxy)pyridin-2-amine as a yellow oil (238 mg, yield: 32%). LC/MS ESI (m/z): 563 [M+H]$^+$.

A mixture of (R)-5-bromo-3-(1-(2-(1-((5-bromo-1-ethyl-1H-pyrazol-4-yl)methyl)-1H-pyrazol-5-yl)-5-fluorophenyl)ethoxy)pyridin-2-amine (238 mg, 0.420 mmol), B$_2$Pin$_2$ (321 mg, 1.27 mmol), Pd(OAc)$_2$ (19 mg, 0.084 mmol), cataCXium A (30 mg, 0.084 mmol) and NaOH (2 M in H$_2$O, 0.42 mL, 0.84 mmol) in MeOH (20 mL) was heated at 80° C. for 4 h. The reaction mixture was filtered, and the filtrate was extracted with DCM (50 mL×2). The combined organic layers were washed with brine, dried over anhydrous Na$_2$SO$_4$, filtered, and concentrated. The residue was purified by column chromatography on silica gel (0→100% EtOAc in PE) followed by prep-HPLC (Column: Gemini 5 um C18 250*21.2 mm; MeCN in H$_2$O+0.1% FA) to give the target product (5.6 mg, 3.3% yield) as a white solid. LC/MS ESI (m/z): 405 [M+H]$^+$.

The following compounds were prepared in a similar manner:

| Example 2 | 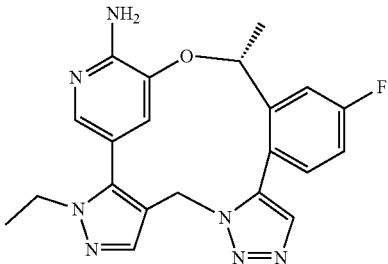 [SMILES: CCn1ncc2c1-c1cnc(N)c(c1)O[C@H](C)c1cc(F)ccc1-c1cnnn1C2] | (19R)-3-ethyl-16-fluoro-19-methyl-20-oxa-3,4,8,9,10,23-hexaazapentacyclo[19.3.1.0$^{2,6}$.0$^{8,12}$.0$^{13,18}$]pentacosa-1(24),2(6),4,9,11,13,15,17,21(25),22-decaen-22-amine<br>1H NMR (400 MHz, DMSO) δ 7.96 (s, 1H), 7.85-7.80 (m, 2H), 7.51 (d, J = 1.4 Hz, 1H), 7.43-7.39 (m, 1H), 7.32-7.27 (m, 1H), 6.24 (s, 2H), 5.78 (s, 1H), 5.41-5.32 (m, 2H), 4.38 (d, J = 14.9 Hz, 1H), 4.06 (dd, J = 13.8, 6.9 Hz, 2H), 1.77 (d, J = 6.2 Hz, 3H), 1.28 (t, J = 7.2 Hz, 3H).<br>LCMS Method C; t$_R$: 0.86 min; m/z: 406 [M + H] |
|---|---|---|
| Example 3 | 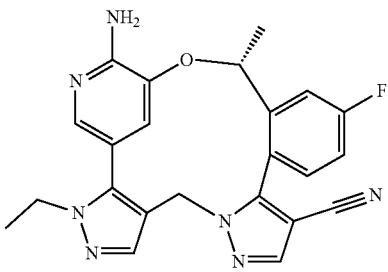 [SMILES: CCn1ncc2c1-c1cnc(N)c(c1)O[C@H](C)c1cc(F)ccc1-c1c(C#N)cnn1C2] | (19R)-22-amino-3-ethyl-16-fluoro-19-methyl-20-oxa-3,4,8,9,23-pentaazapentacyclo[19.3.1.0$^{2,6}$.0$^{8,12}$.0$^{13,18}$]pentacosa-1(24),2(6),4,9,11,13,15,17,21(25),22-decaene-11-carbonitrile<br>1H NMR (400 MHz, DMSO) δ 8.24 (s, 1H), 7.89 (d, J = 10.0 Hz, 1H), 7.75 (s, 1H), 7.51 (t, J = 7.1 Hz, 2H), 7.38-7.32 (m, 1H), 6.27 (s, 2H), 5.99 (s, 1H), 5.47-5.40 (m, 1H), 5.13 (d, J = 14.7 Hz, 1H), 4.30 (d, J = 14.6 Hz, 1H), 4.10-4.03 (m, 2H), 1.85 (d, J = 6.0 Hz, 3H), 1.29 (t, J = 7.2 Hz, 3H).<br>LCMS Method F; t$_R$: 1.30 min; m/z: 430 [M + H] |

| | | |
|---|---|---|
| Example 4 | 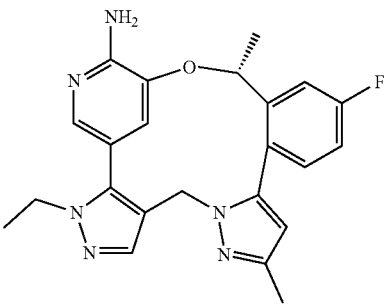 [SMILES: CCn1ncc2c1-c1cnc(N)c(c1)O[C@H](C)c1cc(F)ccc1-c1cc(C)nn1C2] | (19R)-3-ethyl-16-fluoro-10,19-dimethyl-20-oxa-3,4,8,9,23-pentaazapentacyclo[19.3.1.0²,⁶.0⁸,¹².0¹³,¹⁸]pentacosa-1(24),2(6),4,9,11,13,15,17,21(25),22-decaen-22-amine<br>1H NMR (400 MHz, DMSO-d6) δ 7.76-7.69 (m, 2H), 7.49 (d, J = 1.72 Hz, 1H), 7.34-7.29 (m, 1H), 7.24-7.17 (m, 1H), 6.18 (s, 2H), 5.99 (s, 1H), 5.50 (d, J = 4.88 Hz, 1H), 4.96 (d, J = 14.6 Hz, 1H), 4.25 (d, J = 14.52 Hz, 1H), 4.11-3.99 (m, 2H), 3.30 (d, 1H), 2.20 (s, 3H), 1.75 (d, J = 6.24 Hz, 3H), 1.30 (t, J = 7.12 Hz, 3H)<br>LCMS Method A; $t_R$: 1.26 min; m/z: 419 [M + H] |
| Example 5 | 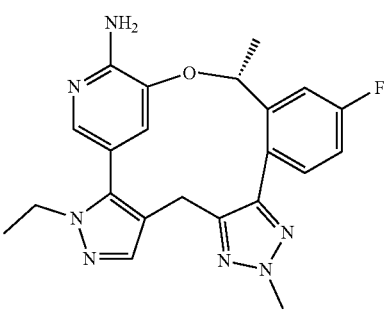 [SMILES: CCn1ncc2c1-c1cnc(N)c(c1)O[C@H](C)c1cc(F)ccc1-c1nn(C)nc1C2] | (19R)-3-ethyl-16-fluoro-10,19-dimethyl-20-oxa-3,4,9,10,11,23-hexaazapentacyclo[19.3.1.0²,⁶.0⁸,¹².0¹³,¹⁸]pentacosa-1(24),2(6),4,8,11,13,15,17,21(25),22-decaen-22-amine<br>1H NMR (400 MHz, DMSO-d6) δ 7.78 (dd, J = 10.3, 2.0 Hz, 1H), 7.57 (s, 1H), 7.42 (d, J = 1.5 Hz, 1H), 7.19 (dd, J = 7.7, 4.1 Hz, 2H), 6.12 (s, 2H), 6.07 (s, 1H), 5.26 (m, 1H), 4.15 (s, 3H), 3.99 (dd, J = 7.1, 4.2 Hz, 2H), 3.77 (d, J = 15.6 Hz, 1H), 2.98 (d, J = 15.6 Hz, 1H), 1.70 (d, J = 6.2 Hz, 3H), 1.26 (t, J = 7.2 Hz, 3H)<br>LCMS Method F; $t_R$: 0.86 min; m/z: 420 [M + H] |
| Example 6 | 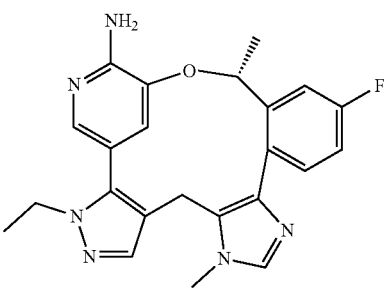 [SMILES: CCn1ncc2c1-c1cnc(N)c(c1)O[C@H](C)c1cc(F)ccc1-c1ncn(C)c1C2] | (19R)-3-ethyl-16-fluoro-9,19-dimethyl-20-oxa-3,4,9,11,23-pentaazapentacyclo[19.3.1.0²,⁶.0⁸,¹².0¹³,¹⁸]pentacosa-1(24),2(6),4,8(12),10,13,15,17,21(25),22-decaen-22-amine<br>1H NMR (400 MHz, DMSO-d6) δ 7.70 (s, 1H), 7.69-7.61 (m, 1H), 7.62 (s, 1H), 7.37 (d, J = 1.6 Hz, 1H), 7.06 (d, J = 2.8 Hz, 1H), 7.04 (d, J = 1.9 Hz, 1H), 6.32 (d, J = 1.5 Hz, 1H), 6.04 (s, 2H), 5.53-5.42 (m, 1H), 4.03-3.96 (m, 2H), 3.90 (d, J = 16.1 Hz, 1H), 3.65 (s, 3H), 1.73 (d, J = 6.2 Hz, 3H), 1.25 (t, J = 7.1 Hz, 3H).<br>LCMS Method D; $t_R$: 1.67 min; m/z: 419 [M + H] |
| Example 7 | 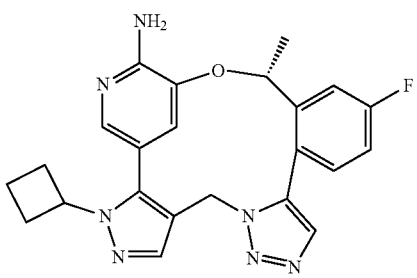 [SMILES: C[C@H]1Oc2cc(cnc2N)-c2c(cnn2C2CCC2)Cn2nncc2-c2ccc(F)cc21] | (19R)-3-cyclobutyl-16-fluoro-19-methyl-20-oxa-3,4,8,9,10,23-hexaazapentacyclo[19.3.1.0²,⁶.0⁸,¹².0¹³,¹⁸]pentacosa-1(24),2(6),4,9,11,13,15,17,21(25),22-decaen-22-amine<br>1H NMR (400 MHz, DMSO) δ 7.96 (s, 1H), 7.89 (s, 1H), 7.82 (dd, J = 10.3, 2.7 Hz, 1H), 7.44-7.36 (m, 2H), 7.32-7.25 (m, 1H), 6.25 (s, 2H), 5.77 (d, J = 1.5 Hz, 1H), 5.35 (dd, J = 20.1, 11.7 Hz, 2H), 4.78 (p, J = 8.1 Hz, 1H), 4.37 (d, J = 14.9 Hz, 1H), 2.69-2.55 (m, 1H), 2.42 (s, 1H), 2.14-2.02 (m, 1H), 1.78 (s, 3H), 1.76-1.65 (m, 3H).<br>LCMS Method F; $t_R$: 0.83 min; m/z: 432 [M + H] |
| Example 8 | 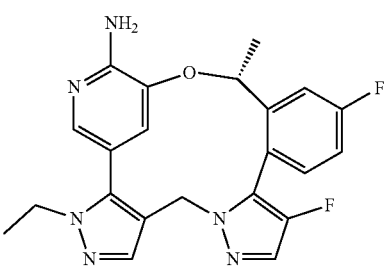 [SMILES: CCn1ncc2c1-c1cnc(N)c(c1)O[C@H](C)c1cc(F)ccc1-c1c(F)cnn1C2] | (19R)-3-ethyl-11,16-difluoro-19-methyl-20-oxa-3,4,8,9,23-pentaazapentacyclo[19.3.1.0²,⁶.0⁸,¹².0¹³,¹⁸]pentacosa-1(24),2(6),4,9,11,13,15,17,21(25),22-decaen-22-amine<br>1H NMR (400 MHz, DMSO) δ 7.82 (dd, J = 10.2, 2.7 Hz, 1H), 7.71 (s, 1H), 7.69 (d, J = 4.8 Hz, 1H), 7.49 (d, J = 1.8 Hz, 1H), 7.43 (dd, J = 8.6, 5.8 Hz, 1H), 7.29 (td, J = 8.4, 2.7 Hz, 1H), 6.23 (s, 2H), 5.97 (d, J = 1.7 Hz, 1H), 5.40 (d, J = 6.3 Hz, 1H), 5.03 (d, J = 14.7 Hz, 1H), 4.25 (d, J = 14.7 Hz, 1H), 4.05 (td, J = 12.6, 6.9 Hz, 2H), 1.73 (d, J = 6.2 Hz, 3H), 1.28 (t, J = 7.2 Hz, 3H).<br>LCMS Method F; $t_R$: 0.89 min; m/z: 423 [M + H] |

| Example 9 | 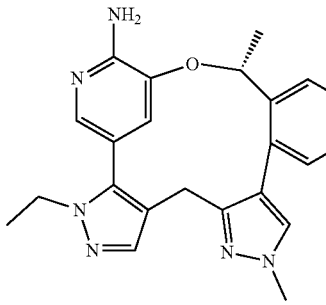 | (19R)-3-ethyl-16-fluoro-10,19-dimethyl-20-oxa-3,4,9,10,23-pentaazapentacyclo[19.3.1.0$^{2,6}$.0$^{8,12}$.0$^{13,18}$]pentacosa-1(24),2(6),4,8,11,13,15,17,21(25),22-decaen-22-amine<br>1H NMR (400 MHz, DMSO) δ 7.74 (s, 1H), 7.65 (dd, J = 10.3, 2.5 Hz, 1H), 7.52 (s, 1H), 7.43 (d, J = 1.7 Hz, 1H), 7.13-7.06 (m, 2H), 6.26 (d, J = 1.5 Hz, 1H), 6.07 (s, 2H), 5.37-5.28 (m, 1H), 4.05-3.96 (m, 2H), 3.84 (s, 3H), 3.63 (d, J = 15.4 Hz, 1H), 2.97-2.89 (m, 1H), 1.73 (d, J = 6.3 Hz, 3H), 1.30-1.25 (m, 3H).<br>LCMS Method E; $t_R$: 0.80 min; m/z: 419 [M + H] |
|---|---|---|
| Example 10 | 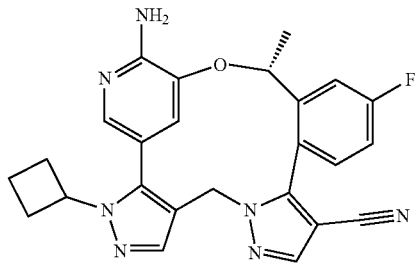 [SMILES: C[C@H]1Oc2cc(cnc2N)-c2c(cnn2C2CCC2)Cn2ncc(C#N)c2-c2ccc(F)cc21] | (19R)-22-amino-3-cyclobutyl-16-fluoro-19-methyl-20-oxa-3,4,8,9,23-pentaazapentacyclo[19.3.1.0$^{2,6}$.0$^{8,12}$.0$^{13,18}$]pentacosa-1(24),2(6),4,9,11,13,15,17,21(25),22-decaene-11-carbonitrile<br>1H NMR (400 MHz, DMSO) δ 8.24 (s, 1H), 7.89 (d, J = 10.3 Hz, 1H), 7.81 (s, 1H), 7.56-7.48 (m, 1H), 7.39 (s, 1H), 7.36 (d, J = 7.9 Hz, 1H), 6.27 (s, 2H), 6.00 (s, 1H), 5.48-5.40 (m, 1H), 5.13 (d, J = 15.1 Hz, 1H), 4.85-4.75 (m, 1H), 4.30 (d, J = 14.6 Hz, 1H), 2.64 (dd, J = 19.7, 8.9 Hz, 2H), 2.46-2.38 (m, 1H), 2.14-2.05 (m, 1H), 1.85 (d, J = 6.2 Hz, 3H), 1.80-1.67 (m, 2H).<br>LCMS Method F; $t_R$: 1.06 min; m/z: 456 [M + H] |
| Example 11 | 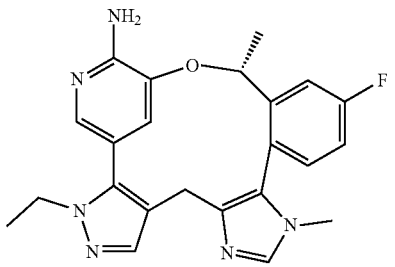 [SMILES: CCn1ncc2c1-c1cnc(N)c(c1)O[C@H](C)c1cc(F)ccc1-c1c(ncn1C)C2] | (19R)-3-ethyl-16-fluoro-11,19-dimethyl-20-oxa-3,4,9,11,23-pentaazapentacyclo[19.3.1.0$^{2,6}$.0$^{8,12}$.0$^{13,18}$]pentacosa-1(24),2(6),4,8(12),9,13,15,17,21(25),22-decaen-22-amine<br>1H NMR (400 MHz, DMSO-d6) δ 7.80 (dd, J = 10.3, 2.8 Hz, 1H), 7.66 (s, 1H), 7.51 (s, 1H), 7.47 (d, J = 1.9 Hz, 1H), 7.22 (td, J = 8.4, 2.7 Hz, 1H), 7.15 (dd, J = 8.6, 5.9 Hz, 1H), 6.54 (d, J = 1.9 Hz, 1H), 6.10 (s, 2H), 5.14-5.04 (m, 1H), 4.09-3.98 (m, 2H), 3.53 (d, J = 15.2 Hz, 1H), 3.37 (s, 3H), 2.81 (d, J = 15.1 Hz, 1H), 1.78 (d, J = 6.1 Hz, 3H), 1.26 (t, J = 7.1 Hz, 3H).<br>LCMS Method G; $t_R$: 2.19 min; m/z: 419 [M + H] |
| Example 12 | 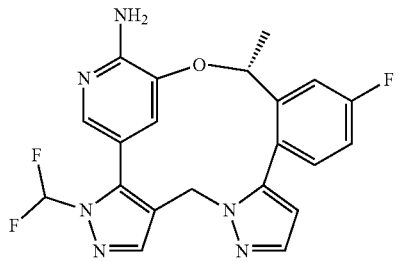 [SMILES: C[C@H]1Oc2cc(cnc2N)-c2c(cnn2C(F)F)Cn2nccc2-c2ccc(F)cc21] | (19R)-3-(difluoromethyl)-16-fluoro-19-methyl-20-oxa-3,4,8,9,23-pentaazapentacyclo[19.3.1.0$^{2,6}$.0$^{8,12}$.0$^{13,18}$]pentacosa-1(24),2(6),4,9,11,13,15,17,21(25),22-decaen-22-amine<br>1H NMR (400 MHz, DMSO) δ 8.06 (s, 1H), 7.76 (dd, J = 10.3, 2.8 Hz, 1H), 7.68 (t, J = 57.6 Hz, 1H), 7.63 (d, J = 1.8 Hz, 1H), 7.46 (s, 1H), 7.39 (dd, J = 8.5, 5.7 Hz, 1H), 7.29-7.22 (m, 1H), 6.46 (d, J = 1.8 Hz, 1H), 6.38 (s, 2H), 5.89 (s, 1H), 5.48 (d, J = 4.4 Hz, 1H), 5.13 (d, J = 14.7 Hz, 1H), 4.34 (d, J = 14.5 Hz, 1H), 1.76 (d, J = 6.3 Hz, 3H).<br>LCMS Method F; $t_R$: 1.10 min; m/z: 427 [M + H] |
| Example 13 | 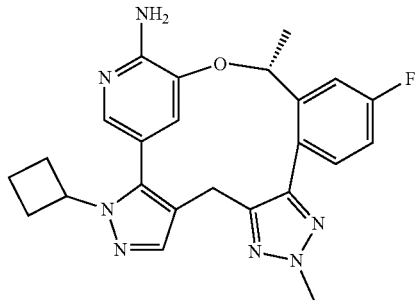 [SMILES: C[C@H]1Oc2cc(cnc2N)-c2c(cnn2C2CCC2)Cc2nn(C)nc2-c2ccc(F)cc21] | (19R)-3-cyclobutyl-16-fluoro-10,19-dimethyl-20-oxa-3,4,9,10,11,23-hexaazapentacyclo[19.3.1.0$^{2,6}$.0$^{8,12}$.0$^{13,18}$]pentacosa-1(24),2(6),4,8,11,13,15,17,21(25),22-decaen-22-amine<br>1H NMR (400 MHz, DMSO) δ 7.78 (dd, J = 10.3, 2.2 Hz, 1H), 7.64 (s, 1H), 7.31 (d, J = 1.7 Hz, 1H), 7.23-7.15 (m, 2H), 6.13 (s, 2H), 6.07 (d, J = 1.7 Hz, 1H), 5.33-5.18 (m, 1H), 4.76-4.61 (m, 1H), 4.16 (s, 3H), 3.78 (d, J = 15.6 Hz, 1H), 2.97 (d, J = 15.5 Hz, 1H), 2.66-2.59 (m, 1H), 2.48-2.36 (m, 2H), 2.10-2.00 (m, 1H), 1.78-1.73 (m, 1H), 1.71 (d, J = 6.3 Hz, 3H), 1.69-1.64 (m, 1H).<br>LCMS Method F; $t_R$: 0.82 min; m/z: 446 [M + H] |

| | | |
|---|---|---|
| Example 14 | 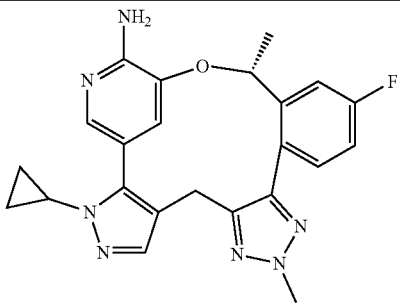 | (19R)-3-cyclopropyl-16-fluoro-10,19-dimethyl-20-oxa-3,4,9,10,11,23-hexaazapentacyclo[19.3.1.0²,⁶.0⁸,¹².0¹³,¹⁸]pentacosa-1(24),2(6),4,8,11,13,15,17,21(25),22-decaen-22-amine<br>1H NMR (400 MHz, DMSO) δ 7.77 (dd, J = 10.3, 2.1 Hz, 1H), 7.67 (d, J = 1.8 Hz, 1H), 7.50 (s, 1H), 7.21 (m, 2H), 6.20 (br s, 2H), 6.10 (s, 1H), 5.24 (d, J = 6.2 Hz, 1H), 4.15 (s, 3H), 3.78 (d, J = 15.7 Hz, 1H), 3.57 (dt, J = 11.0, 3.6 Hz, 1H), 3.00 (d, J = 15.6 Hz, 1H), 1.71 (d, J = 6.3 Hz, 3H), 1.00-0.90 (m, 2H), 0.83-0.72 (m, 2H).<br>LCMS Method F; $t_R$: 0.91 min; m/z: 432 [M + H] |
| Example 15 | 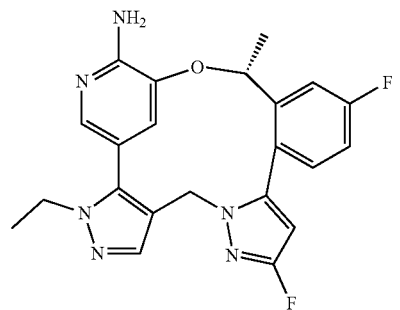 | (19R)-3-ethyl-10,16-difluoro-19-methyl-20-oxa-3,4,8,9,23-pentaazapentacyclo[19.3.1.0²,⁶.0⁸,¹².0¹³,¹⁸]pentacosa-1(24),2(6),4,9,11,13,15,17,21(25),22-decaen-22-amine<br>1H NMR (400 MHz, DMSO) δ 7.77 (dd, J = 10.3, 2.7 Hz, 1H), 7.69 (s, 1H), 7.50 (d, J = 1.8 Hz, 1H), 7.43 (dd, J = 8.5, 5.7 Hz, 1H), 7.25 (td, J = 8.4, 2.7 Hz, 1H), 6.23 (d, J = 6.1 Hz, 1H), 6.21 (s, 2H), 6.09 (d, J = 1.7 Hz, 1H), 5.59-5.43 (m, 1H), 4.93 (d, J = 14.6 Hz, 1H), 4.25 (d, J = 14.7 Hz, 1H), 4.15-4.01 (m, 2H), 1.75 (d, J = 6.3 Hz, 3H), 1.30 (t, J = 7.2 Hz, 3H).<br>LCMS Method F; $t_R$: 1.07 min; m/z: 423 [M + H] |
| Example 16 | 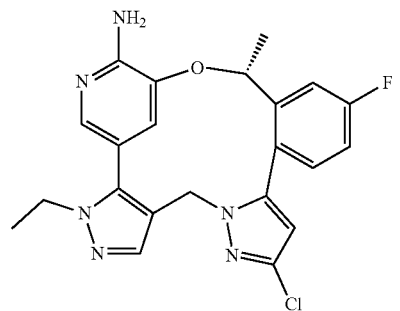 | (19R)-10-chloro-3-ethyl-16-fluoro-19-methyl-20-oxa-3,4,8,9,23-pentaazapentacyclo[19.3.1.0²,⁶.0⁸,¹².0¹³,¹⁸]pentacosa-1(24),2(6),4,9,11,13,15,17,21(25),22-decaen-22-amine<br>1H NMR (400 MHz, MeOD) δ 7.83 (s, 1H), 7.60 (dd, J = 9.9, 2.7 Hz, 1H), 7.48 (d, J = 1.6 Hz, 1H), 7.34 (dd, J = 8.6, 5.6 Hz, 1H), 7.20-7.10 (m, 1H), 6.38 (s, 1H), 6.22 (d, J = 1.7 Hz, 1H), 5.64 (q, J = 6.4 Hz, 1H), 5.01 (d, J = 14.7 Hz, 1H), 4.56-4.48 (m, 1H), 4.29-4.05 (m, 2H), 1.82 (d, J = 6.3 Hz, 3H), 1.37 (dd, J = 9.1, 5.3 Hz, 3H).<br>LCMS Method G; $t_R$: 0.94 min; m/z: 439 [M + H] |
| Example 17 | 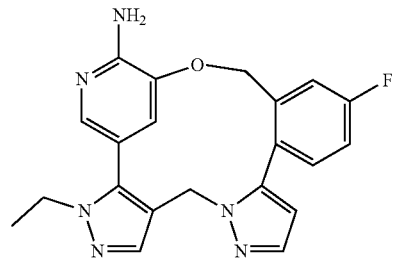 [SMILES: CCn1ncc2c1-c1cnc(N)c(c1)OCc1cc(F)ccc1-c1ccnn1C2] | 3-ethyl-16-fluoro-20-oxa-3,4,8,9,23-pentaazapentacyclo[19.3.1.0²,⁶.0⁸,¹².0¹³,¹⁸]pentacosa-1(24),2(6),4,9,11,13,15,17,21(25),22-decaen-22-amine<br>1H NMR (400 MHz, DMSO) δ 7.81 (s, 1H), 7.72-7.55 (m, 3H), 7.41 (ddd, J = 11.2, 8.5, 4.3 Hz, 2H), 6.40 (d, J = 1.7 Hz, 1H), 6.13 (s, 1H), 5.31 (d, J = 3.2 Hz, 2H), 5.14 (d, J = 14.7 Hz, 1H), 4.44 (d, J = 14.7 Hz, 1H), 4.10 (q, J = 7.2 Hz, 2H), 1.30 (t, J = 7.2 Hz, 3H).<br>LCMS Method H; $t_R$: 1.05 min; m/z: 391 [M + H] |

Example 18 (Method B)

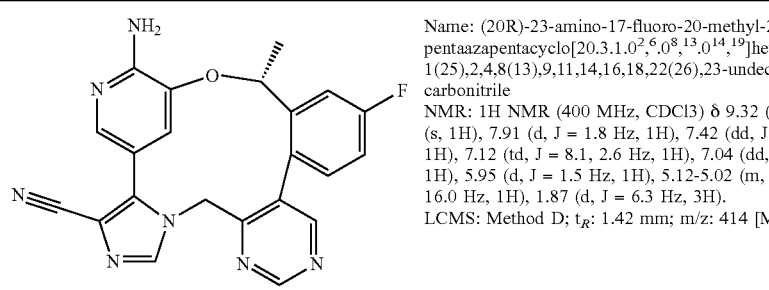

Name: (20R)-23-amino-17-fluoro-20-methyl-21-oxa-4,6,9,11,24-pentaazapentacyclo[20.3.1.0²,⁶.0⁸,¹³.0¹⁴,¹⁹]hexacosa-1(25),2,4,8(13),9,11,14,16,18,22(26),23-undecaene-3-carbonitrile
NMR: 1H NMR (400 MHz, CDCl3) δ 9.32 (s, 1H), 8.64 (s, 1H), 7.98 (s, 1H), 7.91 (d, J = 1.8 Hz, 1H), 7.42 (dd, J = 9.4, 2.6 Hz, 1H), 7.12 (td, J = 8.1, 2.6 Hz, 1H), 7.04 (dd, J = 8.5, 5.4 Hz, 1H), 5.95 (d, J = 1.5 Hz, 1H), 5.12-5.02 (m, 4H), 4.72 (d, J = 16.0 Hz, 1H), 1.87 (d, J = 6.3 Hz, 3H).
LCMS: Method D; $t_R$: 1.42 mm; m/z: 414 [M + H]

To a solution of 1-[(5-bromopyrimidin-4-yl)methyl]-1H-imidazole-4-carbonitrile (400 mg, 1.52 mmol) and 5-bromo-3-[(1R)-1-[5-fluoro-2-(trimethylstannyl)phenyl]ethoxy]pyridin-2-amine (1.44 g, 3.03 mmol) in DMF (5 mL) was added AsPh₃ (464 mg, 1.52 mmol), CuI (2.8 mg, 0.015 mmol) and Pd₂(dba)₃ (138 mg, 0.151 mmol). The mixture was stirred under N₂ at 100° C. overnight. After concentration in vacuo to remove DMF, the residue was purified by column chromatography on silica gel (0→100% EtOAc in PE) to give 1-[(5-{2-[(1R)-1-[(2-amino-5-bromopyridin-3-yl)oxy]ethyl]-4-fluorophenyl}pyrimidin-4-yl)methyl]-1H-imidazole-4-carbonitrile (320 mg, 43% yield) as a yellow solid. LC/MS ESI (m/z): 494 [M+H]⁺

To a solution of 1-[(5-{2-[(1R)-1-[(2-amino-5-bromopyridin-3-yl)oxy]ethyl]-4-fluorophenyl}pyrimidin-4-yl)methyl]-1H-imidazole-4-carbonitrile (270 mg, 0.540 mmol) in 2-methyl-2-butanol (10 mL) was added KOAc (169 mg, 1.64 mmol), cataCXium A (78 mg, 0.22 mmol) and Pd(OAc)₂ (110 mg, 0.11 mmol). The resulting mixture was degassed with N₂ three times and then stirred at 120° C. in a sealed tube overnight. After concentration in vacuo, the residue was purified by prep-HPLC (Gemini 5 um C18 250*21.2 mm, MeCN in H₂O+0.1% FA) to give the target product (40 mg, 18% yield) as a white solid. LC/MS ESI (m/z): 414 [M+H]⁺.

The following compounds were prepared in a similar manner:

Example 19
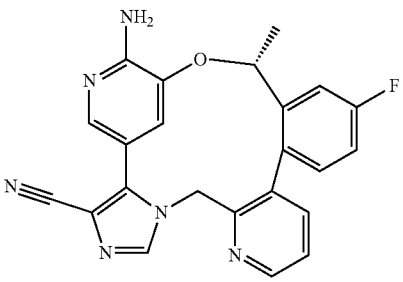 [SMILES: C[C@H]1Oc2cc(cnc2N)-c2c(C#N)ncn2Cc2ncccc2-c2ccc(F)cc21]
(20R)-23-amino-17-fluoro-20-methyl-21-oxa-4,6,9,24-tetraazapentacyclo[20.3.1.0²,⁶.0⁸,¹³.0¹⁴,¹⁹]hexacosa-1(25),2,4,8(13),9,11,14,16,18,22(26),23-undecaene-3-carbonitrile
1H NMR (400 MHz, DMSO) δ 8.73 (dd, J = 4.7, 1.7 Hz, 1H), 8.16 (s, 1H), 7.80 (dd, J = 7.7, 1.7 Hz, 1H), 7.71 (dd, J = 10.3, 2.7 Hz, 1H), 7.61 (d, J = 1.9 Hz, 1H), 7.53 (dd, J = 7.7, 4.8 Hz, 1H), 7.29 (dd, J = 8.6, 5.8 Hz, 1H), 7.23 (td, J = 8.4, 2.7 Hz, 1H), 6.42 (s, 2H), 6.02 (d, J = 1.8 Hz, 1H), 5.44 (d, J = 15.9 Hz, 1H), 5.14-5.06 (m, 1H), 4.46 (d, J = 15.8 Hz, 1H), 1.80 (d, J = 6.3 Hz, 3H).
LCMS Method C; $t_R$: 1.19 min; m/z: 413 [M + H]

Example 20
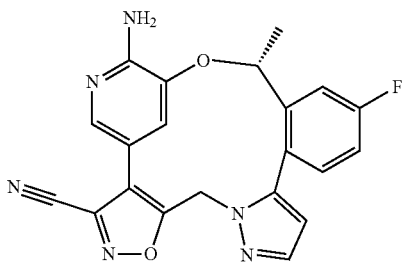 [SMILES: C[C@H]1Oc2cc(cnc2N)-c2c(C#N)noc2Cn2nccc2-c2ccc(F)cc21]
(19R)-22-amino-16-fluoro-19-methyl-5,20-dioxa-4,8,9,23-tetraazapentacyclo[19.3.1.0²,⁶.0⁸,¹².0¹³,¹⁸]pentacosa-1(24),2(6),3,9,11,13(18),14,16,21(25),22-decaene-3-carbonitrile
1H NMR (400 MHz, DMSO) δ 7.73 (d, J = 1.7 Hz, 1H), 7.70 (dd, J = 10.3, 2.7 Hz, 1H), 7.65 (d, J = 1.8 Hz, 1H), 7.50 (dd, J = 8.6, 5.8 Hz, 1H), 7.33 (td, J = 8.4, 2.7 Hz, 1H), 6.61 (d, J = 1.8 Hz, 1H), 6.33 (s, 2H), 5.75 (s, 1H), 5.65 (d, J = 15.7 Hz, 1H), 5.45-5.36 (m, 1H), 4.88 (d, J = 15.7 Hz, 1H), 1.78 (d, J = 6.3 Hz, 3H).
LCMS Method F; $t_R$: 1.19 min; m/z: 403 [M + H]

Example 21
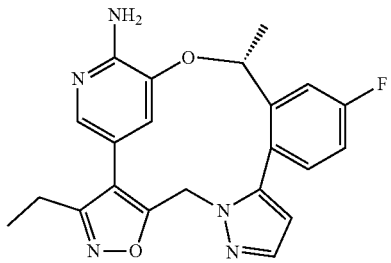 [SMILES: CCc1noc2c1-c1cnc(N)c(c1)O[C@H](C)c1cc(F)ccc1-c1ccnn1C2]
(19R)-3-ethyl-16-fluoro-19-methyl-5,20-dioxa-4,8,9,23-tetraazapentacyclo[19.3.1.0²,⁶.0⁸,¹².0¹³,¹⁸]pentacosa-1(24),2(6),3,9,11,13,15,17,21(25),22-decaen-22-amine
1H NMR (400 MHz, DMSO-d6) δ 7.73 (dd, J = 10.2, 2.8 Hz, 1H), 7.69 (d, J = 1.8 Hz, 1H), 7.50 (d, J = 1.8 Hz, 1H), 7.45 (dd, J = 8.6, 5.7 Hz, 1H), 7.29 (td, J = 8.5, 2.8 Hz, 1H), 6.54 (d, J = 1.9 Hz, 1H), 6.04 (d, J = 3.8 Hz, 2H), 5.75 (d, J = 1.9 Hz, 1H), 5.45-5.41 (m, 1H), 5.39 (d, J = 15.4 Hz, 1H), 4.68 (d, J = 15.3 Hz, 1H), 2.81-2.74 (m, 1H), 2.68 (q, J = 7.7 Hz, 1H), 1.76 (d, J = 6.3 Hz, 3H), 1.13 (t, J = 7.5 Hz, 3H).
LCMS Method B; $t_R$: 2.01 min; m/z: 406 [M + H]

Example 22
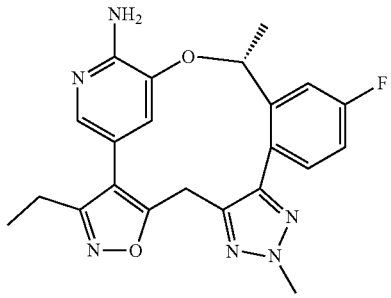 [SMILES: CCc1noc2c1-c1cnc(N)c(c1)O[C@H](C)c1cc(F)ccc1-c1nn(C)nc1C2]
(19R)-3-ethyl-16-fluoro-10,19-dimethyl-5,20-dioxa-4,9,10,11,23-pentaazapentacyclo[19.3.1.0²,⁶.0⁸,¹².0¹³,¹⁸]pentacosa-1(24),2(6),3,8,11,13,15,17,21(25),22-decaen-22-amine
1H NMR (400 MHz, DMSO) δ 7.76 (dd, J = 10.3, 2.6 Hz, 1H), 7.44 (s, 1H), 7.32-7.19 (m, 2H), 6.00 (d, J = 6.9 Hz, 3H), 5.29-5.18 (m, 1H), 4.25-4.14 (m, 4H), 3.43 (s, 1H), 2.78-2.54 (m, 2H), 1.71 (d, J = 6.2 Hz, 3H), 1.10 (t, J = 7.5 Hz, 3H).
LCMS Method F; $t_R$: 0.98 min; m/z: 421 [M + H]

| Example 23 | 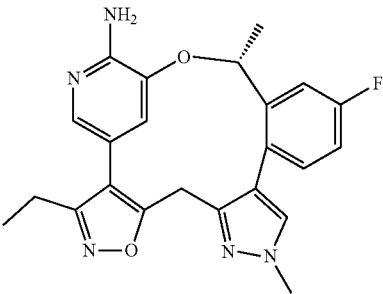 [SMILES: CCc1noc2c1-c1cnc(N)c(c1)O[C@H](C)c1cc(F)ccc1-c1cn(C)nc1C2] | (19R)-3-ethyl-16-fluoro-10,19-dimethyl-5,20-dioxa-4,9,10,23-tetraazapentacyclo[19.3.1.0$^{2,6}$.0$^{8,12}$.0$^{13,18}$]pentacosa-1(24),2(6),3,8,11,13,15,17,21(25),22-decaen-22-amine<br>1H NMR (400 MHz, DMSO) δ 7.86 (s, 1H), 7.66-7.60 (m, 1H), 7.45 (d, J = 1.8 Hz, 1H), 7.18-7.13 (m, 2H), 6.20 (d, J = 1.6 Hz, 1H), 5.93 (s, 2H), 5.31-5.22 (m, 1H), 4.04 (d, J = 15.6 Hz, 1H), 3.88 (s, 3H), 3.37 (s, 1H), 2.79-2.57 (m, 2H), 1.73 (d, J = 6.3 Hz, 3H), 1.12 (t, J = 7.5 Hz, 3H).<br>LCMS Method F; $t_R$: 0.90 min; m/z: 420 [M + H] |
| --- | --- | --- |
| Example 24 | 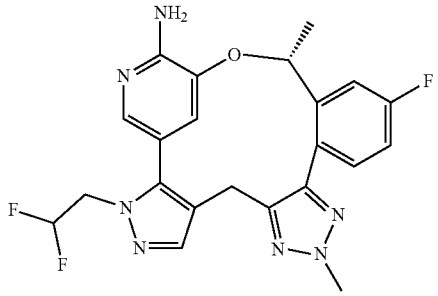 [SMILES: C[C@H]1Oc2cc(cnc2N)-c2c(cnn2CC(F)F)Cc2nn(C)nc2-c2ccc(F)cc21] | (19R)-3-(2,2-difluoroethyl)-16-fluoro-10,19-dimethyl-20-oxa-3,4,9,10,11,23-hexaazapentacyclo[19.3.1.0$^{2,6}$.0$^{8,12}$.0$^{13,18}$]pentacosa-1(24),2(6),4,8,11,13,15,17,21(25),22-decaen-22-amine<br>1H NMR (400 MHz, DMSO) δ 7.79 (dd, J = 10.4, 2.3 Hz, 1H), 7.70 (s, 1H), 7.45 (d, J = 1.8 Hz, 1H), 7.23-7.15 (m, 2H), 6.35 (tt, J = 4, 56 Hz, 1H), 6.20 (d, J = 9.9 Hz, 2H), 6.05 (d, J = 1.7 Hz, 1H), 5.26 (d, J = 4.6 Hz, 1H), 4.42 (ddd, J = 31.3, 14.8, 3.9 Hz, 2H), 4.16 (s, 3H), 3.81 (d, J = 15.6 Hz, 1H), 2.99 (d, J = 15.6 Hz, 1H), 1.71 (d, J = 6.2 Hz, 3H).<br>LCMS Method F; $t_R$: 0.95 min; m/z: 456 [M + H] |
| Example 25 | 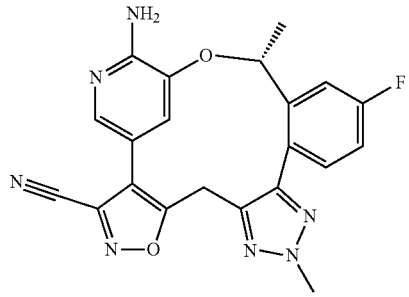 [SMILES: C[C@H]1Oc2cc(cnc2N)-c2c(C#N)noc2Cc2nn(C)nc2-c2ccc(F)cc21] | (19R)-22-amino-16-fluoro-10,19-dimethyl-5,20-dioxa-4,9,10,11,23-pentaazapentacyclo[19.3.1.0$^{2,6}$.0$^{8,12}$.0$^{13,18}$]pentacosa-1(24),2(6),3,8,11,13,15,17,21(25),22-decaene-3-carbonitrile<br>1H NMR (400 MHz, DMSO) δ 7.73 (d, J = 12.9 Hz, 1H), 7.61 (s, 1H), 7.37-7.17 (m, 2H), 6.27 (s, 2H), 6.04 (s, 1H), 5.20 (d, J = 6.1 Hz, 1H), 4.49 (d, J = 16.1 Hz, 1H), 4.21 (s, 3H), 3.61 (d, J = 16.1 Hz, 1H), 1.73 (d, J = 6.2 Hz, 3H).<br>LCMS Method I; $t_R$: 1.33 min; m/z: 418 [M + H] |
| Example 26 | 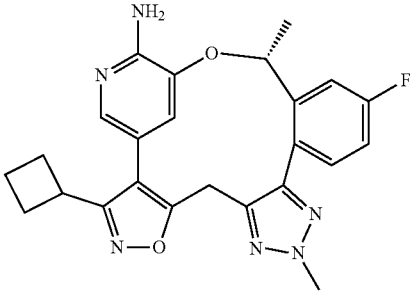 [SMILES: C[C@H]1Oc2cc(cnc2N)-c2c(C3CCC3)noc2Cc2nn(C)nc2-c2ccc(F)cc21] | (19R)-3-cyclobutyl-16-fluoro-10,19-dimethyl-5,20-dioxa-4,9,10,11,23-pentaazapentacyclo[19.3.1.0$^{2,6}$.0$^{8,12}$.0$^{13,18}$]pentacosa-1(24),2(6),3,8,11,13,15,17,21(25),22-decaen-22-amine<br>1H NMR (400 MHz, DMSO) δ 7.75 (dd, J = 10.2, 2.5 Hz, 1H), 7.30 (d, J = 1.8 Hz, 1H), 7.29-7.18 (m, 2H), 5.98 (d, J = 5.7 Hz, 3H), 5.21 (d, J = 8.4 Hz, 1H), 4.18 (d, J = 12.8 Hz, 15 Relaxa 1.0000tion 4H), 3.56-3.49 (m, 1H), 3.42 (s, 1H), 2.36-2.24 (m, 2H), 2.08 (dd, J = 10.1, 6.9 Hz, 2H), 1.96 (d, J = 8.6 Hz, 1H), 1.84 (s, 1H), 1.70 (d, J = 6.3 Hz, 3H).<br>LCMS Method F; $t_R$: 0.97 min; m/z: 447 [M + H] |
| Example 27 | 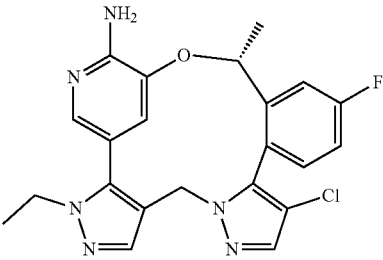 [SMILES: CCn1ncc2c1-c1cnc(N)c(c1)O[C@H](C)c1cc(F)ccc1-c1c(Cl)cnn1C2] | (19R)-11-chloro-3-ethyl-16-fluoro-19-methyl-20-oxa-3,4,8,9,23-pentaazapentacyclo[19.3.1.0$^{2,6}$.0$^{8,12}$.0$^{13,18}$]pentacosa-1(24),2(6),4,9,11,13,15,17,21(25),22-decaen-22-amine<br>1H NMR (400 MHz, MeOD-d4) δ 7.83 (s, 1H), 7.66 (s, 1H), 7.64 (dd, J = 10.0, 2.7 Hz, 1H), 7.48 (s, 1H), 7.30 (dd, J = 8.6, 5.6 Hz, 1H), 7.20 (td, J = 8.3, 2.7 Hz, 1H), 6.21 (d, J = 1.6 Hz, 1H), 5.49-5.34 (m, 1H), 5.05 (d, J = 14.7 Hz, 1H), 4.48 (d, J = 14.7 Hz, 1H), 4.24-4.09 (m, 2H), 1.91 (d, J = 6.2 Hz, 3H), 1.36 (t, J = 7.2 Hz, 3H).<br>LCMS Method F; $t_R$: 1.07 min; m/z: 439 [M + H] |

-continued

| | | |
|---|---|---|
| Example 28 | 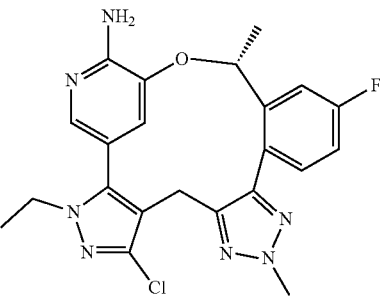 [SMILES: CCn1nc(Cl)c2c1-c1cnc(N)c(c1)O[C@H](C)c1cc(F)ccc1-c1nn(C)nc1C2] | (19R)-5-chloro-3-ethyl-16-fluoro-10,19-dimethyl-20-oxa-3,4,9,10,11,23-hexaazapentacyclo[19.3.1.0$^{2,6}$.0$^{8,12}$.0$^{13,18}$]pentacosa-1(24),2(6),4,8,11,13,15,17,21(25),22-decaen-22-amine<br>1H NMR (400 MHz, DMSO) δ 7.79 (dd, J = 10.4, 2.7 Hz, 1H), 7.47 (d, J = 1.8 Hz, 1H), 7.31-7.15 (m, 2H), 6.24 (s, 2H), 6.08 (d, J = 1.7 Hz, 1H), 5.27 (dd, J = 6.3, 1.8 Hz, 1H), 4.18 (s, 3H), 4.05-3.93 (m, 2H), 3.74 (d, J = 15.8 Hz, 1H), 2.96 (d, J = 15.7 Hz, 1H), 1.71 (d, J = 6.2 Hz, 3H), 1.27 (t, J = 7.2 Hz, 3H).<br>LCMS Method F; $t_R$: 0.95 min; m/z: 454 [M + H] |
| Example 29 | 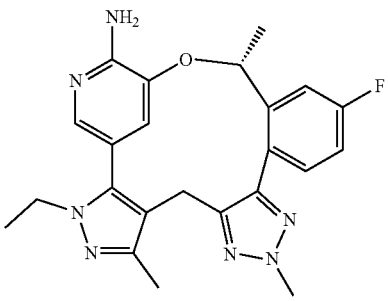 [SMILES: CCn1nc(C)c2c1-c1cnc(N)c(c1)O[C@H](C)c1cc(F)ccc1-c1nn(C)nc1C2] | (19R)-3-ethyl-16-fluoro-5,10,19-trimethyl-20-oxa-3,4,9,10,11,23-hexaazapentacyclo[19.3.1.0$^{2,6}$.0$^{8,12}$.0$^{13,18}$]pentacosa-1(24),2(6),4,8,11,13,15,17,21(25),22-decaen-22-amine<br>1H NMR (400 MHz, MeOD-d4) δ 7.58 (dd, J = 10.1, 2.7 Hz, 1H), 7.39 (d, J = 1.7 Hz, 1H), 7.20 (dd, J = 8.5, 5.7 Hz, 1H), 7.10 (td, J = 8.3, 2.7 Hz, 1H), 6.24 (d, J = 1.7 Hz, 1H), 5.35 (dd, J = 6.3, 2.0 Hz, 1H), 4.20 (s, 3H), 4.12-3.94 (m, 2H), 3.74 (d, J = 15.8 Hz, 1H), 3.11 (d, J = 15.8 Hz, 1H), 2.44 (s, 3H), 1.80 (d, J = 6.3 Hz, 3H), 1.27 (t, J = 7.2 Hz, 3H).<br>LCMS Method F; $t_R$: 0.90 min; m/z: 434 [M + H] |
| Example 30 | 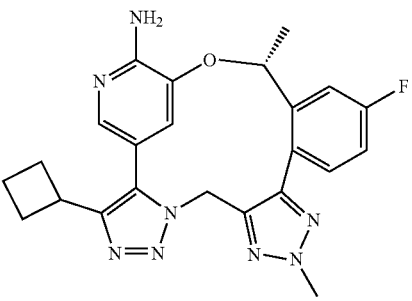 [SMILES: C[C@H]1Oc2cc(cnc2N)-c2c(C3CCC3)nnn2Cc2nn(C)nc2-c2ccc(F)cc21] | (19R)-3-cyclobutyl-16-fluoro-10,19-dimethyl-20-oxa-4,5,6,9,10,11,23-heptaazapentacyclo[19.3.1.0$^{2,6}$.0$^{8,12}$.0$^{13,18}$]pentacosa-1(24),2,4,8,11,13,15,17,21(25),22-decaen-22-amine<br>1H NMR (400 MHz, DMSO-d6) δ 7.81 (d, J = 9.9 Hz, 1H), 7.31-7.15 (m, 3H), 6.23 (s, 2H), 6.16 (s, 1H), 5.79 (d, J = 16.4 Hz, 1H), 5.32 (s, 1H), 4.49 (d, J = 16.7 Hz, 1H), 4.21 (s, 3H), 3.25-3.17 (m, 1H), 2.35-2.21 (m, 3H), 2.03 (s, 1H), 1.97-1.87 (m, 1H), 1.82 (s, 1H), 1.72 (d, J = 4.9 Hz, 3H).<br>LCMS Method F; $t_R$: 0.81 min; m/z: 447 [M + H] |
| Example 31 | 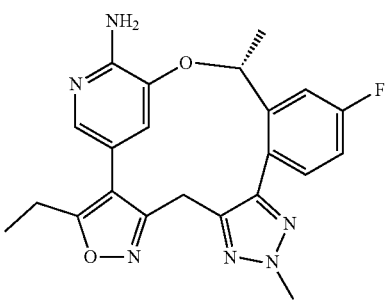 [SMILES: CCc1onc2c1-c1cnc(N)c(c1)O[C@H](C)c1cc(F)ccc1-c1nn(C)nc1C2] | (19R)-3-ethyl-16-fluoro-10,19-dimethyl-4,20-dioxa-5,9,10,11,23-pentaazapentacyclo[19.3.1.0$^{2,6}$.0$^{8,12}$.0$^{13,18}$]pentacosa-1(24),2,5,8,11,13,15,17,21(25),22-decaen-22-amine<br>1H NMR (400 MHz, CD3OD) δ 7.58 (dd, J = 10.0, 2.7 Hz, 1H), 7.31-7.24 (m, 2H), 7.13 (td, J = 8.3, 2.7 Hz, 1H), 6.13 (d, J = 1.7 Hz, 1H), 5.36 (dd, J = 6.3, 1.9 Hz, 1H), 4.23 (s, 3H), 4.14 (d, J = 15.2 Hz, 1H), 3.40 (d, J = 15.2 Hz, 1H), 2.78 (ddd, J = 15.2, 7.6, 3.8 Hz, 2H), 1.81 (d, J = 6.3 Hz, 3H), 1.24 (t, J = 7.6 Hz, 3H).<br>LCMS Method F; $t_R$: 1.16 min; m/z: 421 [M + H] |
| Example 32 | 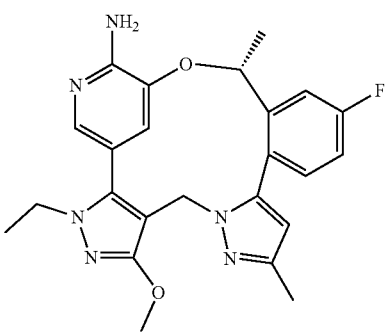 [SMILES: CCn1nc(OC)c2c1-c1cnc(N)c(c1)O[C@H](C)c1cc(F)ccc1-c1cc(C)nn1C2] | (19R)-3-ethyl-16-fluoro-5-methoxy-10,19-dimethyl-20-oxa-3,4,8,9,23-pentaazapentacyclo[19.3.1.0$^{2,6}$.0$^{8,12}$.0$^{13,18}$]pentacosa-1(24),2(6),4,9,11,13,15,17,21(25),22-decaen-22-amine<br>1H NMR (400 MHz, DMSO) δ 7.71 (dd, J = 10.3, 2.7 Hz, 1H), 7.45 (d, J = 1.8 Hz, 1H), 7.35 (dd, J = 8.5, 5.8 Hz, 1H), 7.21 (td, J = 8.4, 2.8 Hz, 1H), 6.20 (br, 2H), 6.17 (s, 1H), 5.97 (d, J = 1.6 Hz, 1H), 5.55-5.42 (m, 1H), 4.84 (d, J = 14.6 Hz, 1H), 4.12 (d, J = 14.6 Hz, 1H), 4.00-3.83 (m, 5H), 2.21 (s, 3H), 1.75 (d, J = 6.3 Hz, 3H), 1.28 (t, J = 7.1 Hz, 3H).<br>LCMS Method F; $t_R$: 0.91 min; m/z: 449 [M + H] |

Example 33 (Method C)

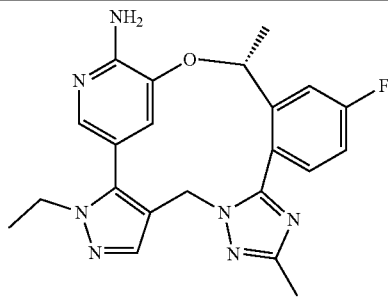

Name: (19R)-3-ethyl-16-fluoro-10,19-dimethyl-20-oxa-3,4,8,9,11,23-hexaazapentacyclo[19.3.1.0$^{2,6}$.0$^{8,12}$.0$^{13,18}$]pentacosa-1(24),2(6),4,9,11,13,15,17,21(25),22-decaen-22-amine
NMR: 1H NMR (400 MHz, DMSO) δ 7.83 (dd, J = 10.3, 2.6 Hz, 1H), 7.73 (s, 1H), 7.49-7.44 (m, 2H), 7.26 (td, J = 8.4, 2.7 Hz, 1H), 6.22 (s, 2H), 5.82 (d, J = 1.7 Hz, 1H), 5.53-5.42 (m, 1H), 5.08 (d, J = 14.7 Hz, 1H), 4.33 (d, J = 14.7 Hz, 1H), 4.11-3.97 (m, 2H), 2.31 (s, 3H), 1.74 (d, J = 6.2 Hz, 3H), 1.30 (t, J = 7.2 Hz, 3H).
LCMS: Method C; $t_R$: 0.45 min; m/z: 420 [M + H]

A mixture of 5-bromo-3-(1-(2-(1-((5-bromo-1-ethyl-1H-pyrazol-4-yl)methyl)-3-methyl-1H-1,2,4-triazol-5-yl)-5-fluorophenyl)ethoxy)-2-nitropyridine (180 mg, 0.30 mmol), iron powder (165 mg, 2.95 mmol) and NH$_4$Cl (157 mg, 2.95 mmol) in EtOH (10 mL) and H$_2$O (2 mL) was stirred at 80° C. for 1 h. After cooling to r.t., the mixture was filtered, and the filtrate was concentrated under reduced pressure. The residue was diluted with DCM (40 mL), washed with water and brine, dried over anhydrous Na$_2$SO$_4$, filtered and concentrated. The residue was purified by column chromatography on silica gel (50% EtOAc in PE) to give 5-bromo-3-(1-(2-(1-((5-bromo-1-ethyl-1H-pyrazol-4-yl)methyl)-3-methyl-1H-1,2,4-triazol-5-yl)-5-fluorophenyl)ethoxy)pyridin-2-amine as a white solid (125 mg, 72% yield). LC-MS (ESI): m/z 578 [M+H]$^+$.

To a solution of 5-bromo-3-(1-(2-(1-((5-bromo-1-ethyl-1H-pyrazol-4-yl)methyl)-3-methyl-1H-1,2,4-triazol-5-yl)-5-fluorophenyl)ethoxy)pyridin-2-amine (120 mg, 0.21 mmol), bis(pinacolato)diboron (158 mg, 0.62 mmol), Pd(OAc)$_2$ (9.3 mg, 0.04 mmol) and cataCXium A (15 mg, 0.04 mmol) in MeOH (10 mL) was added a solution of NaOH (17 mg, 0.42 mmol) in H$_2$O (1 mL). The mixture was charged with N$_2$ twice, and then stirred at 70° C. for 12 h. After cooling to r.t., the mixture was filtered, and the filtrate was concentrated under reduced pressure. The residue was diluted with DCM (50 mL), washed with water and brine, dried over anhydrous Na$_2$SO$_4$, filtered, and concentrated. The residue was purified by column chromatography on silica gel (5% MeOH in DCM) to give a yellow oil, which was further purified by chiral SFC (ChiralCel OJ-H 4.6×250 mm, 5 μm, 5→40% MeOH+0.05% DEA in CO$_2$) to obtain the eutomer ($t_R$ 5.8 m, 5.6 mg, yield: 6.3%) and distomer ($t_R$ 6.3 ml, 5.4 mg, yield: 6.1%2) as white solids. LMS ESI (m/z): 420 [M+H]C.

The following compounds were prepared in a similar manner:

| Example | | |
|---|---|---|
| Example 34 | 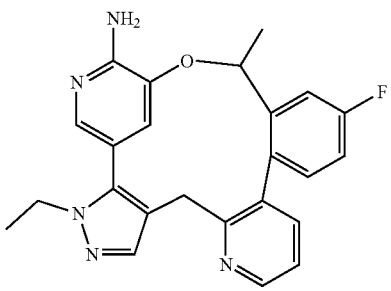 [SMILES: CCn1ncc2c1-c1cnc(N)c(c1)OC(C)c1cc(F)ccc1-c1cccnc1C2] | 3-ethyl-17-fluoro-20-methyl-21-oxa-3,4,9,24-tetraazapentacyclo[20.3.1.0$^{2,6}$.0$^{8,13}$.0$^{14,19}$]hexacosa-1(25),2(6),4,8(13),9,11,14,16,18,22(26),23-undecaen-23-amine<br>1H NMR (400 MHz, DMSO) δ 8.62 (dd, J = 4.7, 1.6 Hz, 1H), 7.70 (dd, J = 10.4, 2.6 Hz, 1H), 7.61 (dd, J = 6.8, 2.4 Hz, 2H), 7.47 (d, J = 1.4 Hz, 1H), 7.33 (dd, J = 7.6, 4.8 Hz, 1H), 7.23-7.15 (m, 2H), 6.12 (s, 2H), 6.01 (s, 1H), 5.14 (d, J = 4.9 Hz, 1H), 4.10-3.98 (m, 2H), 3.81 (d, J = 15.3 Hz, 1H), 3.31-3.30 (m, 1H), 1.78 (d, J = 6.2 Hz, 3H), 1.27 (t, J = 7.2 Hz, 3H).<br>LCMS Method C; $t_R$: 1.10 min; m/z: 416 [M + H] |
| Example 35 | 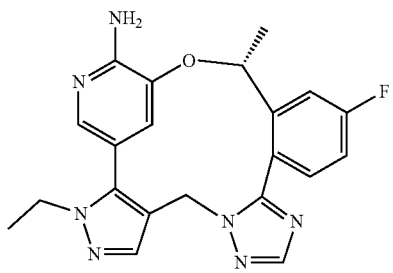 [SMILES: CCn1ncc2c1-c1cnc(N)c(c1)O[C@H](C)c1cc(F)ccc1-c1ncnn1C2] | (19R)-3-ethyl-16-fluoro-19-methyl-20-oxa-3,4,8,9,11,23-hexaazapentacyclo[19.3.1.0$^{2,6}$.0$^{8,12}$.0$^{13,18}$]pentacosa-1(24),2(6),4,9,11,13,15,17,21(25),22-decaen-22-amine<br>1HNMR(400 MHz, DMSO) δ 8.12 (s, 1H), 7.85 (dd, J = 10.3, 2.7 Hz, 1H), 7.76 (s, 1H), 7.55-7.44 (m, 2H), 7.33-7.22 (m, 1H), 6.24 (s, 2H), 5.70 (d, J = 1.7 Hz, 1H), 5.42 (d, J = 4.5 Hz, 1H), 5.17 (d, J = 14.8 Hz, 1H), 4.42 (d, J = 14.8 Hz, 1H), 4.10-3.98 (m, 2H), 1.74 (d, J = 6.2 Hz, 3H), 1.28 (t, J = 7.2 Hz, 3H)<br>LCMS Method A; $t_R$: 0.91 min; m/z: 406 [M + H] |

-continued

| Example 36 | 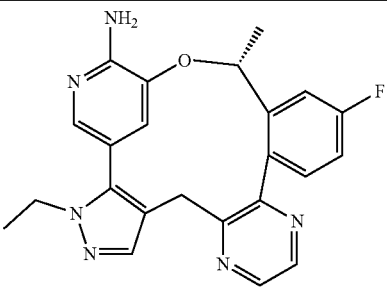 | (20R)-3-ethyl-17-fluoro-20-methyl-21-oxa-3,4,9,12,24-pentaazapentacyclo[20.3.1.0$^2$,$^6$.0$^8$,$^{13}$.0$^{14,19}$]hexacosa-1(25),2(6),4,8(13),9,11,14,16,18,22(26),23-undecaen-23-amine<br>1H NMR (400 MHz, DMSO) δ 8.69 (d, J = 2.4 Hz, 1H), 8.59 (d, J = 2.3 Hz, 1H), 7.75 (dd, J = 10.4, 2.7 Hz, 1H), 7.61 (s, 1H), 7.47 (d, J = 1.8 Hz, 1H), 7.33 (dd, J = 8.6, 5.8 Hz, 1H), 7.19 (td, J = 8.5, 2.7 Hz, 1H), 6.15 (s, 2H), 5.94 (d, J = 1.6 Hz, 1H), 5.22 (m, 1H), 4.06-3.99 (m, 2H), 3.95 (d, J = 15.3 Hz, 1H), 3.30 (d, J = 4.4 Hz, 1H), 1.74 (d, J = 6.2 Hz, 3H), 1.27 (t, J = 7.2 Hz, 3H).<br>LCMS Method C; t$_R$: 1.04 min; m/z: 417 [M + H] |
| --- | --- | --- |
| Example 37 | 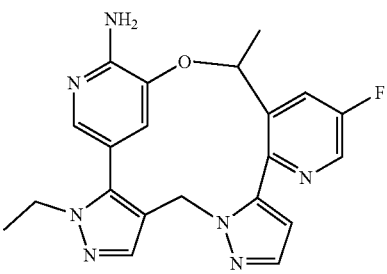 [SMILES: CCn1ncc2c1-c1cnc(N)c(c1)OC(C)c1cc(F)cnc1-c1ccnn1C2] | 3-ethyl-16-fluoro-19-methyl-20-oxa-3,4,8,9,14,23-hexaazapentacyclo[19.3.1.0$^2$,$^6$.0$^8$,$^{12}$.0$^{13,18}$]pentacosa-1(24),2(6),4,9,11,13,15,17,21(25),22-decaen-22-amine<br>1H NMR (400 MHz, DMSO-d6) δ 8.64 (d, J = 2.8 Hz, 1H), 8.31 (dd, J = 9.7, 2.9 Hz, 1H), 7.73 (s, 1H), 7.61 (d, J = 1.8 Hz, 1H), 7.49 (d, J = 1.8 Hz, 1H), 6.51 (d, J = 1.8 Hz, 1H), 6.18 (s, 2H), 5.90 (d, J = 1.8 Hz, 1H), 5.53 (q, J = 6.0, 4.9 Hz, 1H), 5.04 (d, J = 14.9 Hz, 1H), 4.40 (d, J = 14.8 Hz, 1H), 4.09-3.98 (m, 2H), 1.82 (d, J = 6.3 Hz, 3H), 1.27 (t, J = 7.2 Hz, 3H).<br>LCMS Method D; t$_R$: 2.75 min; m/z: 406 [M + H] |
| Example 38 | 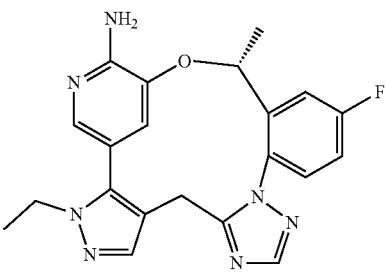 [SMILES: CCn1ncc2c1-c1cnc(N)c(c1)O[C@H](C)c1cc(F)ccc1-n1ncnc1C2] | (19R)-3-ethyl-16-fluoro-19-methyl-20-oxa-3,4,9,11,12,23-hexaazapentacyclo[19.3.1.0$^2$,$^6$.0$^8$,$^{12}$.0$^{13,18}$]pentacosa-1(24),2(6),4,8,10,13,15,17,21(25),22-decaen-22-amine<br>1H NMR (400 MHz, DMSO) δ 8.21 (s, 1H), 7.97 (dd, J = 9.8, 2.9 Hz, 1H), 7.69 (s, 1H), 7.59-7.55 (m, 2H), 7.39 (d, J = 2.9 Hz, 1H), 6.29 (s, 2H), 5.97 (s, 1H), 5.27 (d, J = 5.8 Hz, 1H), 4.11 (dd, J = 13.7, 6.7 Hz, 2H), 4.05 (d, J = 16.1 Hz, 1H), 3.17 (d, J = 15.9 Hz, 1H), 1.77 (d, J = 6.2 Hz, 3H), 1.35 (t, J = 7.2 Hz, 3H).<br>LCMS Method C; t$_R$: 0.81 min; m/z: 406 [M + H] |
| Example 39 | 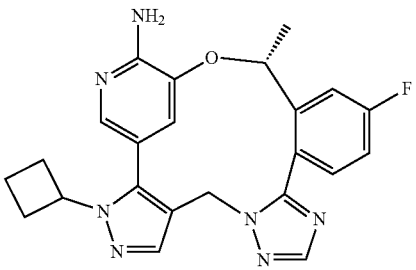 [SMILES: C[C@H]1Oc2cc(cnc2N)-c2c(cnn2C2CCC2)Cn2ncnc2-c2ccc(F)cc21] | (19R)-3-cyclobutyl-16-fluoro-19-methyl-20-oxa-3,4,8,9,11,23-hexaazapentacyclo[19.3.1.0$^2$,$^6$.0$^8$,$^{12}$.0$^{13,18}$]pentacosa-1(24),2(6),4,9,11,13,15,17,21(25),22-decaen-22-amine<br>1H NMR (400 MHz, DMSO) δ 8.12 (s, 1H), 7.84 (dd, J = 10.3, 2.7 Hz, 1H), 7.81 (s, 1H), 7.52 (dd, J = 8.5, 5.7 Hz, 1H), 7.37 (d, J = 1.7 Hz, 1H), 7.32-7.25 (m, 1H), 6.24 (s, 2H), 5.69 (s, 1H), 5.43 (d, J = 4.6 Hz, 1H), 5.17 (d, J = 14.8 Hz, 1H), 4.75 (dd, J = 16.2, 8.4 Hz, 1H), 4.41 (d, J = 14.8 Hz, 1H), 2.61 (dd, J = 19.4, 9.8 Hz, 1H), 2.43-2.37 (m, 1H), 2.12-2.03 (m, 1H), 1.78-1.75 (m, 1H), 1.74 (d, J = 6.1 Hz, 3H), 1.73-1.67 (m, 2H).<br>LCMS Method C; t$_R$: 0.56 min; m/z: 432 [M + H] |
| Example 40 | 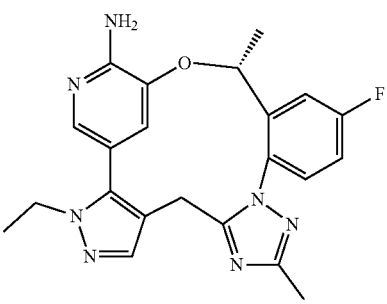 [SMILES: CCn1ncc2c1-c1cnc(N)c(c1)O[C@H](C)c1cc(F)ccc1-n1nc(C)nc1C2] | (19R)-3-ethyl-16-fluoro-10,19-dimethyl-20-oxa-3,4,9,11,12,23-hexaazapentacyclo[19.3.1.0$^2$,$^6$.0$^8$,$^{12}$.0$^{13,18}$]pentacosa-1(24),2(6),4,8,10,13,15,17,21(25),22-decaen-22-amine<br>1H NMR (400 MHz, DMSO-d6) δ 7.88 (dd, J = 9.8, 3.0 Hz, 1H), 7.60 (s, 1H), 7.49 (d, J = 1.9 Hz, 1H), 7.45 (dd, J = 8.7, 5.2 Hz, 1H), 7.30 (td, J = 8.6, 3.1 Hz, 1H), 6.21 (s, 2H), 6.00 (d, J = 1.9 Hz, 1H), 5.27 (q, J = 5.5 Hz, 1H), 4.10-4.01 (m, 2H), 3.92 (d, J = 16.0 Hz, 1H), 3.03 (d, J = 16.0 Hz, 1H), 2.30 (s, 3H), 1.71 (d, J = 6.1 Hz, 3H), 1.28 (d, J = 7.2 Hz, 3H).<br>LCMS Method D; t$_R$: 3.05 min; m/z: 420 [M + H] |
| Example 41 | 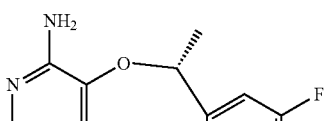 | (19R)-3-cyclobutyl-16-fluoro-19-methyl-20-oxa-3,4,9,11,12,23-hexaazapentacyclo[19.3.1.0$^2$,$^6$.0$^8$,$^{12}$.0$^{13,18}$]pentacosa-1(24),2(6),4,8,10,13,15,17,21(25),22-decaen-22-amine<br>1H NMR (400 MHz, DMSO) δ 8.14 (s, 1H), 7.90 (d, J = |

Example 46 (Method D)

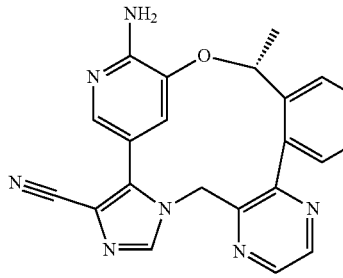

Name: (20R)-23-amino-17-fluoro-20-methyl-21-oxa-4,6,9,12,24-pentaazapentacyclo[20.3.1.0$^{2,6}$.0$^{8,13}$.0$^{14,19}$]hexacosa-1(25),2,4,8(13),9,11,14,16,18,22(26),23-undecaene-3-carbonitrile
NMR: 1H NMR (400 MHz, DMSO-d6) δ 8.82-8.76 (m, 2H), 8.19 (s, 1H), 7.77 (dd, J = 10.3, 2.8 Hz, 1H), 7.58 (d, J = 1.9 Hz, 1H), 7.38 (dd, J = 8.5, 5.7 Hz, 1H), 7.24 (td, J = 8.4, 2.6 Hz, 1H), 6.42 (s, 2H), 6.03 (d, J = 2.0 Hz, 1H), 5.56 (d, J = 16.0 Hz, 1H), 5.21 (d, J = 6.9 Hz, 1H), 4.48 (d, J = 15.9 Hz, 1H), 1.74 (d, J = 6.1 Hz, 3H).
LCMS: Method D; t$_R$: 1.52 min; m/z: 414 [M + H]

A mixture of (R)-1-((3-(2-(1-((5-bromo-2-nitropyridin-3-yl)oxy)ethyl)-4-fluorophenyl)pyrazin-2-yl)methyl)-1H-imidazole-4-carbonitrile (55 mg, 0.11 mmol), iron powder (30 mg, 0.53 mmol) and NH$_4$Cl (45 mg, 0.84 mmol) in EtOH (5 mL) and H$_2$O (1 mL) was stirred at 75° C. for 1 h. After cooling to r.t., the mixture was filtered through celite, and the filtrate was concentrated under reduced pressure. The residue was diluted with EA, washed with water and brine, dried over anhydrous Na$_2$SO$_4$, filtered, and concentrated. The residue was purified by column chromatography (silica gel, 0→3% MeOH in DCM) to give (R)-1-((3-(2-(1-((2-amino-5-bromopyridin-3-yl)oxy)ethyl)-4-fluorophenyl)pyrazin-2-yl)methyl)-1H-imidazole-4-carbonitrile as a white solid (35 mg, 58% yield). LC/MS ESI (m/z): 494 [M+H]$^+$.

A mixture of (R)-1-((3-(2-(1-((2-amino-5-bromopyridin-3-yl)oxy)ethyl)-4-fluorophenyl)pyrazin-2-yl)methyl)-1H-imidazole-4-carbonitrile (35 mg, 0.070 mmol), Pd(OAc)$_2$ (3.0 mg, 0.014 mmol), cataCXium A (10 mg, 0.030 mmol) and KOAc (35 mg, 0.35 mmol) in 2-methyl-2-butanol (3 mL) was charged with N$_2$ twice and stirred at 120° C. in a sealed tube for 12 h. After cooling to rt, the mixture was diluted with dichloromethane, and then washed with water and brine. The combined organic layers were dried over Na$_2$SO$_4$, filtered, and concentrated. The residue was purified by column chromatography on silica gel (100% EtOAc) and then by prep-HPLC (Gemini C18 250×21.2 mm 5 μm, CH$_3$CN in H$_2$O+0.1% FA) to give the target product as a white solid (12 mg, 40% yield). LC-MS (ESI): (m/z): 414 [M+H]$^+$.

The following compounds were prepared in a similar manner:

| Example 47 | 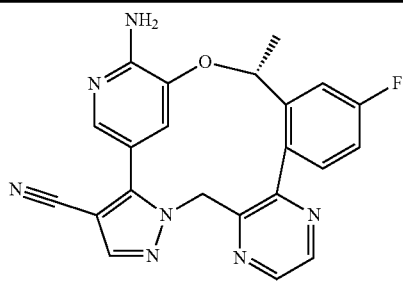 | (20R)-23-amino-17-fluoro-20-methyl-21-oxa-5,6,9,12,24-pentaazapentacyclo[20.3.1.0$^{2,6}$.0$^{8,13}$.0$^{14,19}$]hexacosa-1(25),2,4,8,10,12,14(19),15,17,22(26),23-undecaene-3-carbonitrile<br>1H NMR (400 MHz, DMSO) δ 8.78 (s, 2H), 8.15 (s, 1H), 7.76 (d, J = 10.2 Hz, 1H), 7.63 (s, 1H), 7.46 (dd, J = 8.2, 5.9 Hz, 1H), 7.29-7.18 (m, 1H), 6.50 (s, 2H), 6.12 (s, 1H), 5.70 (d, J = 16.0 Hz, 1H), 5.29-5.07 (m, 1H), 4.74 (d, J = 16.0 Hz, 1H), 1.75 (d, J = 6.0 Hz, 3H).<br>LCMS Method C; t$_R$: 0.89 min; m/z: 414 [M + H] |
|---|---|---|
| Example 48 | 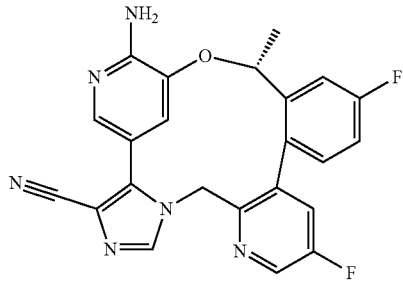 [SMILES: C[C@H]1Oc2cc(cnc2N)-c2c(C#N)ncn2Cc2ncc(F)cc2-c2ccc(F)cc21] | (20R)-23-amino-11,17-difluoro-20-methyl-21-oxa-4,6,9,24-tetraazapentacyclo[20.3.1.0$^{2,6}$.0$^{8,13}$.0$^{14,19}$]hexacosa-1(25),2,4,8(13),9,11,14,16,18,22(26),23-undecaene-3-carbonitrile<br>1H NMR (400 MHz, DMSO) δ 8.75 (d, J = 2.8 Hz, 1H), 8.15 (s, 1H), 7.86 (dd, J = 9.0, 2.8 Hz, 1H), 7.72 (dd, J = 10.3, 2.6 Hz, 1H), 7.60 (d, J = 1.9 Hz, 1H), 7.30 (dd, J = 8.5, 5.9 Hz, 1H), 7.24 (td, J = 8.4, 2.7 Hz, 1H), 6.43 (s, 2H), 6.11 (d, J = 1.6 Hz, 1H), 5.38 (d, J = 15.8 Hz, 1H), 5.24 (d, J = 4.4 Hz, 1H), 4.41 (d, J = 15.8 Hz, 1H), 1.81 (d, J = 6.2 Hz, 3H).<br>LCMS Method F; t$_R$: 1.03 min; m/z: 431 [M + H] |
| Example 49 | 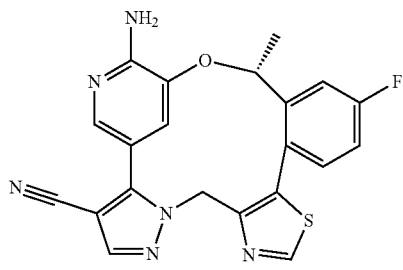 [SMILES: C[C@H]1Oc2cc(cnc2N)-c2c(C#N)cnn2Cc2ncsc2-c2ccc(F)cc21] | (19R)-22-amino-16-fluoro-19-methyl-20-oxa-11-thia-5,6,9,23-tetraazapentacyclo[19.3.1.0$^{2,6}$.0$^{8,12}$.0$^{13,18}$]pentacosa-1(24),2,4,8(12),9,13,15,17,21(25),22-decaene-3-carbonitrile<br>1HNMR (300 MHz, DMSO-d6) δ 9.29 (s, 1H), 8.15 (s, 1H), 7.77 (dd, J = 10.2, 2.8 Hz, 1H), 7.65 (d, J = 1.9 Hz, 1H), 7.38 (dd, J = 8.6, 5.8 Hz, 1H), 7.26 (td, J = 8.4, 2.7 Hz, 1H), 6.58 (d, J = 2.0 Hz, 1H), 6.52 (s, 2H), 5.54 (d, J = 15.9 Hz, 1H), 5.47-5.30 (m, 1H), 4.58 (d, J = 15.8 Hz, 1H), 1.74 (d, J = 6.2 Hz, 3H).<br>LCMS Method C; t$_R$: 1.28 min; m/z: 419 [M + H] |

| Example 50 | 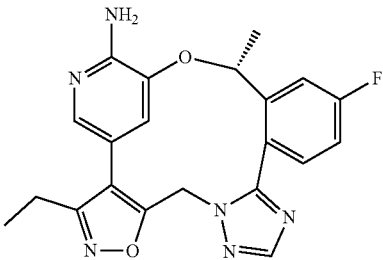 [SMILES: CCc1noc2c1-c1cnc(N)c(c1)O[C@H](C)c1cc(F)ccc1-c1ncnn1C2] | (19R)-3-ethyl-16-fluoro-19-methyl-5,20-dioxa-4,8,9,11,23-pentaazapentacyclo[19.3.1.0²,⁶.0⁸,¹².0¹³,¹⁸]pentacosa-1(24),2(6),3,9,11,13,15,17,21(25),22-decaen-22-amine<br>1H NMR (400 MHz, DMSO-d6) δ 8.23 (s, 1H), 7.82 (dd, J = 10.2, 2.7 Hz, 1H), 7.60 (dd, J = 8.6, 5.7 Hz, 1H), 7.50 (d, J = 1.9 Hz, 1H), 7.34 (td, J = 8.4, 2.7 Hz, 1H), 6.10 (s, 2H), 5.55 (d, J = 1.9 Hz, 1H), 5.50 (d, J = 15.4 Hz, 1H), 5.43-5.36 (m, 1H), 4.82 (d, J = 15.4 Hz, 1H), 2.77 (dd, J = 15.7, 7.6 Hz, 1H), 2.68-2.63 (m, 1H), 1.74 (d, J = 6.2 Hz, 3H), 1.13 (t, J = 7.5 Hz, 3H).<br>LCMS Method B; $t_R$: 1.54 min; m/z: 407 [M + H] |
| --- | --- | --- |
| Example 51 | 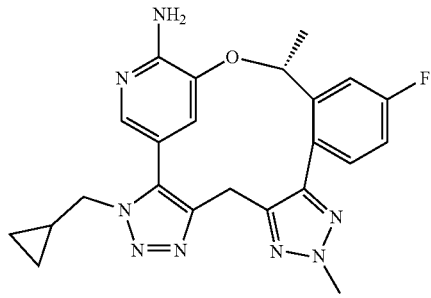 | (19R)-3-(cyclopropylmethyl)-16-fluoro-10,19-dimethyl-20-oxa-3,4,5,9,10,11,23-heptaazapentacyclo[19.3.1.0²,⁶.0⁸,¹².0¹³,¹⁸]pentacosa-1(24),2(6),4,8,11,13,15,17,21(25),22-decaen-22-amine<br>1H NMR (400 MHz, DMSO) δ 7.61 (dd, J = 10.4, 2.5 Hz, 1H), 7.38 (d, J = 1.6 Hz, 1H), 7.16-6.98 (m, 2H), 6.10 (s, 2H), 5.89 (s, 1H), 5.18-5.04 (m, 1H), 4.07-3.87 (m, 6H), 3.07 (d, J = 15.5 Hz, 1H), 1.55 (d, J = 6.2 Hz, 3H), 0.99-0.89 (m, 1H), 0.34-0.22 (m, 2H), 0.19-0.08 (m, 1H), 0.03--0.05 (m, 1H).<br>LCMS Method F; $t_R$: 0.92 min; m/z: 447 [M + H] |
| Example 52 | 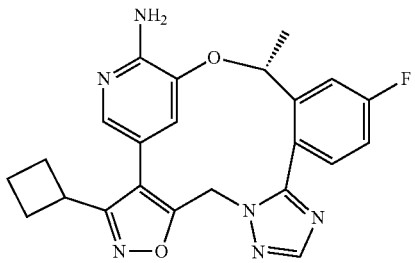 [SMILES: C[C@H]1Oc2cc(cnc2N)-c2c(C3CCC3)noc2Cn2ncnc2-c2ccc(F)cc21] | (19R)-3-cyclobutyl-16-fluoro-19-methyl-5,20-dioxa-4,8,9,11,23-pentaazapentacyclo[19.3.1.0²,⁶.0⁸,¹².0¹³,¹⁸]pentacosa-1(24),2(6),3,9,11,13,15,17,21(25),22-decaen-22-amine<br>1H NMR (400 MHz, DMSO-d6) δ 8.24 (s, 1H), 7.82 (dd, J = 10.2, 2.7 Hz, 1H), 7.60 (dd, J = 8.6, 5.7 Hz, 1H), 7.37-7.32 (m, 2H), 6.09 (s, 2H), 5.54 (d, J = 1.9 Hz, 1H), 5.51 (d, J = 15.5 Hz, 1H), 5.42-5.35 (m, 1H), 4.82 (d, J = 15.5 Hz, 1H), 3.61 (t, J = 8.4 Hz, 1H), 2.36-2.26 (m, 2H), 2.14-2.07 (m, 2H), 2.03-1.95 (m, 1H), 1.85 (s, 1H), 1.74 (d, J = 6.2 Hz, 3H).<br>LCMS Method H; $t_R$: 0.89 min; m/z: 433 [M + H] |
| Example 53 | 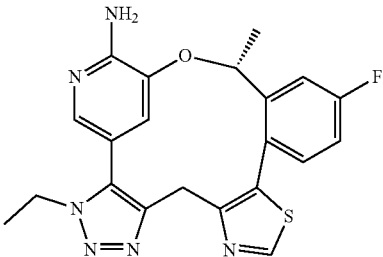 [SMILES: CCn1nnc2c1-c1cnc(N)c(c1)O[C@H](C)c1cc(F)ccc1-c1scnc1C2] | (19R)-3-ethyl-16-fluoro-19-methyl-20-oxa-11-thia-3,4,5,9,23-pentaazapentacyclo[19.3.1.0²,⁶.0⁸,¹².0¹³,¹⁸]pentacosa-1(24),2(6),4,8(12),9,13,15,17,21(25),22-decaen-22-amine<br>1H NMR (400 MHz, DMSO) δ 9.19 (s, 1H), 7.74 (dd, J = 10.2, 2.7 Hz, 1H), 7.59 (d, J = 1.7 Hz, 1H), 7.37 (dd, J = 8.6, 5.8 Hz, 1H), 7.25 (td, J = 8.4, 2.8 Hz, 1H), 6.38 (d, J = 1.5 Hz, 1H), 6.27 (s, 2H), 5.36 (d, J = 4.9 Hz, 1H), 4.42-4.23 (m, 2H), 4.15 (d, J = 15.2 Hz, 1H), 3.35 (d, J = 6 Hz, 1H), 1.72 (d, J = 6.3 Hz, 3H), 1.35 (t, J = 7.3 Hz, 3H).<br>LCMS Method H; $t_R$: 0.69 min; m/z: 423 [M + H] |
| Example 54 | 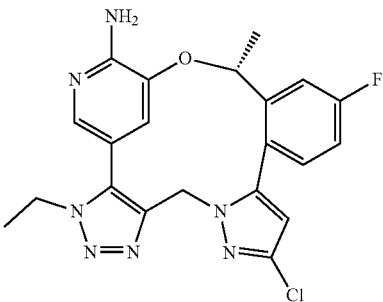 [SMILES: CCn1nnc2c1-c1cnc(N)c(c1)O[C@H](C)c1cc(F)ccc1-c1cc(Cl)nn1C2] | (19R)-10-chloro-3-ethyl-16-fluoro-19-methyl-20-oxa-3,4,5,8,9,23-hexaazapentacyclo[19.3.1.0²,⁶.0⁸,¹².0¹³,¹⁸]pentacosa-1(24),2(6),4,9,11,13,15,17,21(25),22-decaen-22-amine<br>1H NMR (400 MHz, DMSO) δ 7.76 (d, J = 12.6 Hz, 1H), 7.60 (s, 1H), 7.52 (dd, J = 8.5, 5.8 Hz, 1H), 7.29 (t, J = 8.4 Hz, 1H), 6.65 (s, 1H), 6.35 (s, 2H), 5.99 (s, 1H), 5.49 (d, J = 5.6 Hz, 1H), 5.31 (d, J = 14.9 Hz, 1H), 4.56 (d, J = 14.9 Hz, 1H), 4.36 (t, J = 11.1 Hz, 2H), 1.77 (s, 3H), 1.40 (d, J = 7.2 Hz, 3H).<br>LCMS Method F; $t_R$: 0.94 min; m/z: 440 [M + H] |

| | | |
|---|---|---|
| Example 55 | 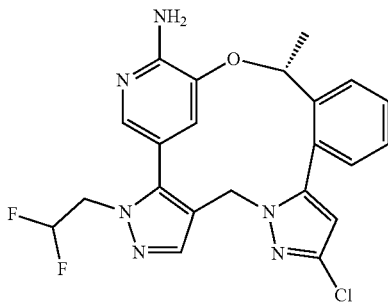 | (19R)-10-chloro-3-(2,2-difluoroethyl)-16-fluoro-19-methyl-20-oxa-3,4,8,9,23-pentaazapentacyclo[19.3.1.0$^{2,6}$.0$^{8,12}$.0$^{13,18}$]pentacosa-1(24),2(6),4,9,11,13,15,17,21(25),22-decaen-22-amine<br>1H NMR (400 MHz, DMSO) δ 7.85 (s, 1H), 7.78 (dd, J = 10.3, 2.7 Hz, 1H), 7.53 (d, J = 1.7 Hz, 1H), 7.42 (dd, J = 8.6, 5.7 Hz, 1H), 7.26 (td, J = 8.4, 2.7 Hz, 1H), 6.59 (s, 1H), 6.39 (tt, J~4, 56 Hz, 1H), 6.29 (br s, 2H), 6.01 (d, J = 1.5 Hz, 1H), 5.48 (d, J = 4.6 Hz, 1H), 5.05 (d, J = 14.7 Hz, 1H), 4.51 (ddd, J = 32.2, 14.7, 3.9 Hz, 2H), 4.29 (d, J = 14.6 Hz, 1H), 1.76 (d, J = 6.2 Hz, 3H).<br>LCMS Method A; t$_R$: 1.49 min; m/z: 475 [M + H] |
| Example 56 | 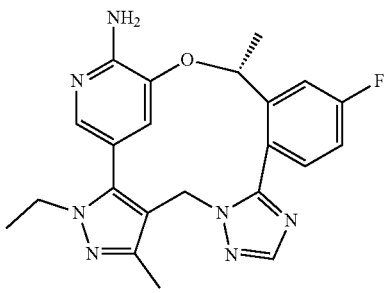 [SMILES: CCn1nc(C)c2c1-c1cnc(N)c(c1)O[C@H](C)c1cc(F)ccc1-c1ncnn1C2] | (19R)-3-ethyl-16-fluoro-5,19-dimethyl-20-oxa-3,4,8,9,11,23-hexaazapentacyclo[19.3.1.0$^{2,6}$.0$^{8,12}$.0$^{13,18}$]pentacosa-1(24),2(6),4,9,11,13,15,17,21(25),22-decaen-22-amine<br>1H NMR (400 MHz, DMSO) δ 8.13 (s, 1H), 7.85 (dd, J = 10.3, 2.7 Hz, 1H), 7.52 (dd, J = 8.6, 5.7 Hz, 1H), 7.47 (d, J = 1.8 Hz, 1H), 7.29 (td, J = 8.4, 2.7 Hz, 1H), 6.22 (s, 2H), 5.71 (d, J = 1.6 Hz, 1H), 5.40 (d, J = 4.4 Hz, 1H), 5.12 (d, J = 14.9 Hz, 1H), 4.33 (d, J = 14.9 Hz, 1H), 4.05-3.88 (m, 2H), 2.40 (s, 3H), 1.74 (d, J = 6.2 Hz, 3H), 1.26 (t, J = 7.2 Hz, 3H).<br>LCMS Method F; t$_R$: 0.71 min; m/z: 420 [M + H] |
| Example 57 | 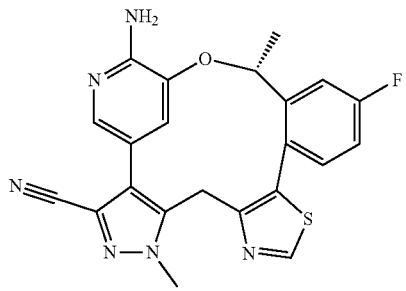 [SMILES: C[C@H]1Oc2cc(cnc2N)-c2c(C#N)nn(C)c2Cc2ncsc2-c2ccc(F)cc21] | (19R)-22-amino-16-fluoro-5,19-dimethyl-20-oxa-11-thia-4,5,9,23-tetraazapentacyclo[19.3.1.0$^{2,6}$.0$^{8,12}$.0$^{13,18}$]pentacosa-1(24),2(6),3,8(12),9,13,15,17,21(25),22-decaene-3-carbonitrile<br>1H NMR (400 MHz, DMSO) δ 9.28 (s, 1H), 7.73 (dd, J = 10.2, 2.7 Hz, 1H), 7.55 (d, J = 1.8 Hz, 1H), 7.41-7.35 (m, 1H), 7.33-7.25 (m, 1H), 6.35 (s, 1H), 6.10 (s, 2H), 5.32-5.24 (m, 1H), 4.32 (d, J = 15.9 Hz, 1H), 4.23 (s, 3H), 3.53-3.50 (m, 1H), 1.71 (d, J = 6.3 Hz, 3H).<br>LCMS Method F; t$_R$: 1.09 min; m/z: 433 [M + H] |
| Example 58 | 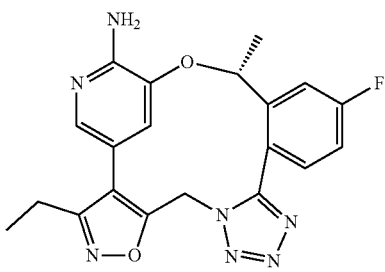 [SMILES: CCc1noc2c1-c1cnc(N)c(c1)O[C@H](C)c1cc(F)ccc1-c1nnnn1C2] | (19R)-3-ethyl-16-fluoro-19-methyl-5,20-dioxa-4,8,9,10,11,23-hexaazapentacyclo[19.3.1.0$^{2,6}$.0$^{8,12}$.0$^{13,18}$]pentacosa-1(24),2(6),3,9,11,13,15,17,21(25),22-decaen-22-amine<br>1H NMR (400 MHz, DMSO) δ 7.98 (dd, J = 10.2, 2.6 Hz, 1H), 7.72 (dd, J = 8.7, 5.6 Hz, 1H), 7.57 (d, J = 1.8 Hz, 1H), 7.49 (td, J = 8.4, 2.7 Hz, 1H), 6.21 (s, 2H), 5.84 (d, J = 15.8 Hz, 1H), 5.59 (d, J = 1.7 Hz, 1H), 5.35 (d, J = 4.4 Hz, 1H), 5.03 (d, J = 15.8 Hz, 1H), 2.91-2.64 (m, 2H), 1.82 (d, J = 6.2 Hz, 3H), 1.19 (t, J = 7.5 Hz, 3H).<br>LCMS Method F; t$_R$: 0.83 min; m/z: 408 [M + H] |
| Example 59 | 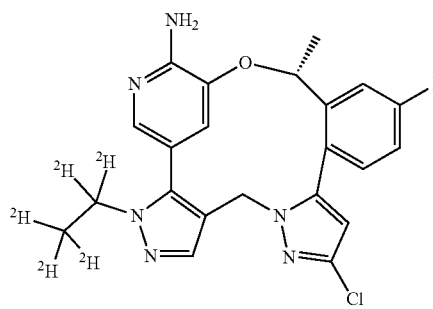 | (19R)-10-chloro-3-[(1,1,2,2,2-$^2$H$_5$)ethyl]-16-fluoro-19-methyl-20-oxa-3,4,8,9,23-pentaazapentacyclo[19.3.1.0$^{2,6}$.0$^{8,12}$.0$^{13,18}$]pentacosa-1(24),2(6),4,9,11,13,15,17,21(25),22-decaen-22-amine<br>1H NMR (400 MHz, DMSO) δ 7.77 (dd, J = 10.3, 2.7 Hz, 1H), 7.73 (s, 1H), 7.50 (d, J = 1.8 Hz, 1H), 7.42 (dd, J = 8.6, 5.8 Hz, 1H), 7.25 (td, J = 8.4, 2.7 Hz, 1H), 6.58 (s, 1H), 6.22 (s, 2H), 6.02 (d, J = 1.6 Hz, 1H), 5.47 (t, J = 5.4 Hz, 1H), 5.01 (d, J = 14.7 Hz, 1H), 4.28 (d, J = 14.6 Hz, 1H), 1.76 (d, J = 6.3 Hz, 3H).<br>LCMS Method F; t$_R$: 1.15 min; m/z: 444 [M + H] |

| | | |
|---|---|---|
| Example 60 | 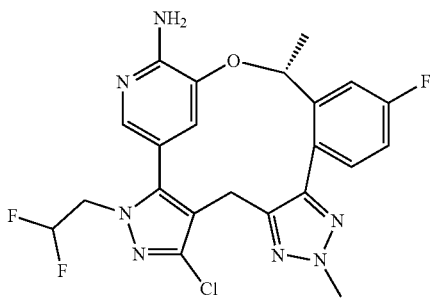 [SMILES: C[C@H]1Oc2cc(cnc2N)-c2c(c(Cl)nn2CC(F)F)Cc2nn(C)nc2-c2ccc(F)cc21] | (19R)-5-chloro-3-(2,2-difluoroethyl)-16-fluoro-10,19-dimethyl-20-oxa-3,4,9,10,11,23-hexaazapentacyclo[19.3.1.0$^{2,6}$.0$^{8,12}$.0$^{13,18}$]pentacosa-1(24),2(6),4,8,11,13,15,17,21(25),22-decaen-22-amine<br>1H NMR (400 MHz, DMSO) δ 7.80 (dd, J = 10.3, 2.7 Hz, 1H), 7.48 (d, J = 1.8 Hz, 1H), 7.27 (dd, J = 8.5, 5.9 Hz, 1H), 7.20 (td, J = 8.4, 2.7 Hz, 1H), 6.37 (tt, J = 4, 56 Hz, 1H), 6.31 (br s, 2H), 6.06 (d, J = 1.6 Hz, 1H), 5.26 (d, J = 4.5 Hz, 1H), 4.53-4.35 (m, 2H), 4.18 (s, 3H), 3.76 (d, J = 15.8 Hz, 1H), 2.97 (d, J = 15.8 Hz, 1H), 1.72 (d, J = 6.2 Hz, 3H).<br>LCMS Method F; t$_R$: 1.29 min; m/z: 490 [M + H] |
| Example 61 | 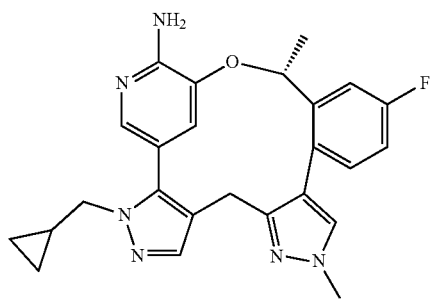 [SMILES: C[C@H]1Oc2cc(cnc2N)-c2c(cnn2CC2CC2)Cc2nn(C)cc2-c2ccc(F)cc21] | (19R)-3-(cyclopropylmethyl)-16-fluoro-10,19-dimethyl-20-oxa-3,4,9,10,23-pentaazapentacyclo[19.3.1.0$^{2,6}$.0$^{8,12}$.0$^{13,18}$]pentacosa-1(24),2(6),4,8,11,13,15,17,21(25),22-decaen-22-amine<br>1H NMR (400 MHz, DMSO) δ 7.66 (s, 1H), 7.57 (dd, J = 10.3, 2.6 Hz, 1H), 7.43 (s, 1H), 7.38 (d, J = 1.7 Hz, 1H), 7.08-6.95 (m, 2H), 6.17 (d, J = 1.5 Hz, 1H), 6.00 (s, 2H), 5.30-5.17 (m, 1H), 3.94-3.66 (m, 5H), 3.55 (d, J = 15.4 Hz, 1H), 2.86 (d, J = 15.3 Hz, 1H), 1.64 (d, J = 6.3 Hz, 3H), 1.04-0.93 (m, 1H), 0.40-0.23 (m, 2H), 0.21-0.10 (m, 1H), 0.05--0.08 (m, 1H).<br>LCMS Method I; t$_R$: 0.74 min; m/z: 445 [M + H] |
| Example 62 | 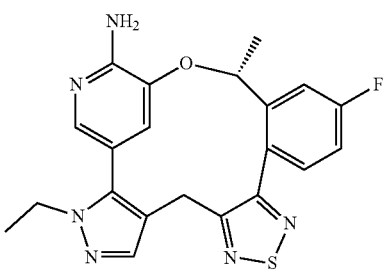 [SMILES: CCn1ncc2c1-c1cnc(N)c(c1)O[C@H](C)c1cc(F)ccc1-c1nsnc1C2] | (19R)-3-ethyl-16-fluoro-19-methyl-20-oxa-10-thia-3,4,9,11,23-pentaazapentacyclo[19.3.1.0$^{2,6}$.0$^{8,12}$.0$^{13,18}$]pentacosa-1(24),2(6),4,8,11,13,15,17,21(25),22-decaen-22-amine<br>1H NMR (400 MHz, DMSO-d6) δ 7.82 (dd, J = 10.4, 2.7 Hz, 1H), 7.66 (s, 1H), 7.45 (d, J = 1.8 Hz, 1H), 7.40 (dd, J = 8.6, 5.7 Hz, 1H), 7.25 (td, J = 8.4, 2.8 Hz, 1H), 6.18 (s, 2H), 5.77 (d, J = 1.9 Hz, 1H), 5.18-5.08 (m, 1H), 4.01 (qd, J = 7.0, 2.7 Hz, 2H), 3.95 (d, J = 15.6 Hz, 1H), 3.35 (d, 1H), 1.72 (d, J = 6.2 Hz, 3H), 1.26 (t, J = 7.2 Hz, 3H).<br>LCMS Method F; t$_R$: 1.09 min; m/z: 423 [M + H] |
| Example 63 | 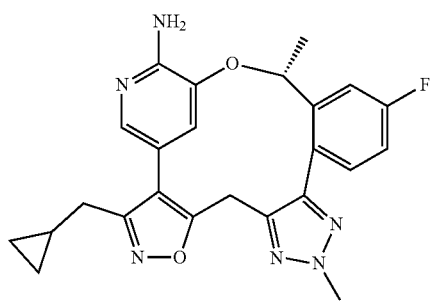 [SMILES: C[C@H]1Oc2cc(cnc2N)-c2c(CC3CC3)noc2Cc2nn(C)nc2-c2ccc(F)cc21] | (19R)-3-(cyclopropylmethyl)-16-fluoro-10,19-dimethyl-5,20-dioxa-4,9,10,11,23-pentaazapentacyclo[19.3.1.0$^{2,6}$.0$^{8,12}$.0$^{13,18}$]pentacosa-1(24),2(6),3,8,11,13,15,17,21(25),22-decaen-22-amine<br>1H NMR (400 MHz, DMSO) δ 7.76 (dd, J = 10.3, 2.6 Hz, 1H), 7.45 (d, J = 1.7 Hz, 1H), 7.31-7.18 (m, 2H), 6.01 (s, 3H), 5.30-5.14 (m, 1H), 4.23-4.15 (m, 4H), 3.43 (s, 1H), 2.55 (dd, J = 6.6, 5.6 Hz, 2H), 1.70 (d, J = 6.2 Hz, 3H), 0.98-0.80 (m, 1H), 0.42-0.32 (m, 2H), 0.15--0.03 (m, 2H).<br>LCMS Method H; t$_R$: 1.14 min; m/z: 447 [M + H] |
| Example 64 | 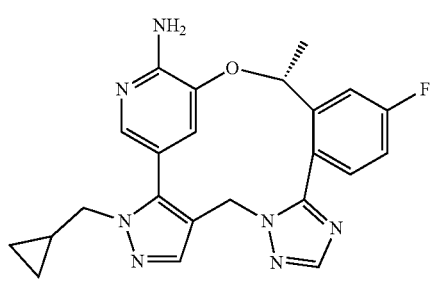 | (19R)-3-(cyclopropylmethyl)-16-fluoro-5,19-dimethyl-20-oxa-3,4,8,9,11,23-hexaazapentacyclo[19.3.1.0$^{2,6}$.0$^{8,12}$.0$^{13,18}$]pentacosa-1(24),2(6),4,9,11,13,15,17,21(25),22-decaen-22-amine<br>1H NMR (400 MHz, DMSO) δ 8.14 (s, 1H), 7.85 (dd, J = 10.3, 2.7 Hz, 1H), 7.55-7.46 (m, 2H), 7.29 (td, J = 8.4, 2.7 Hz, 1H), 6.22 (s, 2H), 5.72 (d, J = 1.7 Hz, 1H), 5.40 (d, J = 4.6 Hz, 1H), 5.12 (d, J = 14.9 Hz, 1H), 4.33 (d, J = 14.9 Hz, 1H), 3.91 (dd, J = 14.4, 6.1 Hz, 1H), 3.75 (dd, J = 14.4, 7.5 Hz, 1H), 2.40 (s, 3H), 1.74 (d, J = 6.2 Hz, 3H), 1.14-1.03 (m, 1H), 0.46-0.33 (m, 2H), 0.23 (dd, J = 9.1, 4.3 Hz, 1H), 0.06 (dd, J = 9.2, 4.3 Hz, 1H).<br>LCMS Method F; t$_R$: 0.78 min; m/z: 446 [M + H] |

| Example 65 | 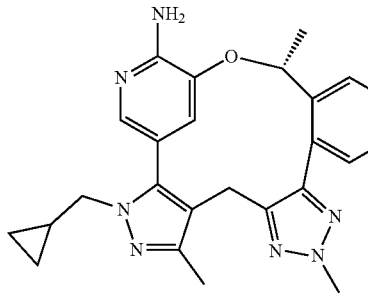 | (19R)-3-(cyclopropylmethyl)-16-fluoro-5,10,19-trimethyl-20-oxa-3,4,9,10,11,23-hexaazapentacyclo[19.3.1.0²,⁶.0⁸,¹².0¹³,¹⁸]pentacosa-1(24),2(6),4,8,11,13,15,17,21(25),22-decaen-22-amine<br>1H NMR (400 MHz, CDCl3) δ 7.31 (dd, J = 9.4, 2.2 Hz, 1H), 7.28 (d, J = 1.4 Hz, 1H), 7.18-7.11 (m, 2H), 6.45 (s, 1H), 5.34 (d, J = 5.2 Hz, 1H), 5.13-4.41 (m, 2H), 4.22 (s, 3H), 4.02 (dd, J = 14.5, 5.9 Hz, 1H), 3.76 (d, J = 15.7 Hz, 2H), 3.13 (d, J = 15.9 Hz, 1H), 2.52 (s, 3H), 1.87 (d, J = 6.3 Hz, 3H), 1.08 (s, 1H), 0.63-0.41 (m, 2H), 0.32 (M, 1H), 0.16 (M, 1H).<br>LCMS Method F; $t_R$: 0.94 min; m/z: 460 [M + H] |
| --- | --- | --- |
| Example 66 | 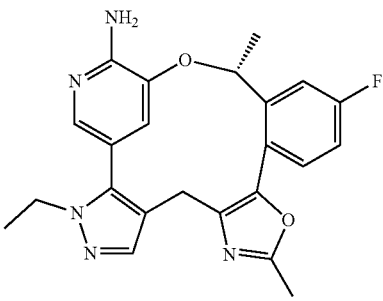 [SMILES: CCn1ncc2c1-c1cnc(N)c(c1)O[C@H](C)c1cc(F)ccc1-c1oc(C)nc1C2] | (19R)-3-ethyl-16-fluoro-10,19-dimethyl-11,20-dioxa-3,4,9,23-tetraazapentacyclo[19.3.1.0²,⁶.0⁸,¹².0¹³,¹⁸]pentacosa-1(24),2(6),4,8(12),9,13,15,17,21(25),22-decaen-22-amine<br>1H NMR (400 MHz, DMSO) δ 7.83 (dd, J = 10.3, 2.6 Hz, 1H), 7.52 (s, 1H), 7.43 (d, J = 1.8 Hz, 1H), 7.29-7.16 (m, 2H), 6.55 (d, J = 1.6 Hz, 1H), 6.10 (br, 2H), 5.39-5.25 (m, 1H), 4.11-3.91 (m, 2H), 3.55 (d, J = 15.3 Hz, 1H), 2.89 (d, J = 15.2 Hz, 1H), 2.42 (s, 3H), 1.71 (d, J = 6.2 Hz, 3H), 1.25 (t, J = 7.2 Hz, 3H).<br>LCMS Method F; $t_R$: 0.92 min; m/z: 420 [M + H] |
| Example 67 | 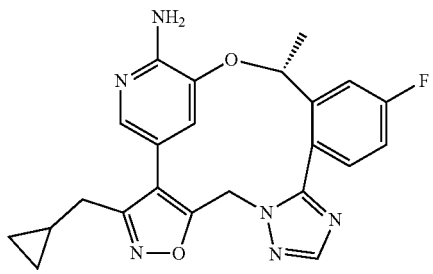 [SMILES: C[C@H]1Oc2cc(cnc2N)-c2c(CC3CC3)noc2Cn2ncnc2-c2ccc(F)cc21] | (19R)-3-(cyclopropylmethyl)-16-fluoro-19-methyl-5,20-dioxa-4,8,9,11,23-pentaazapentacyclo[19.3.1.0²,⁶.0⁸,¹².0¹³,¹⁸]pentacosa-1(24),2(6),3,9,11,13,15,17,21(25),22-decaen-22-amine<br>1H NMR (400 MHz, DMSO) δ 8.24 (s, 1H), 7.82 (dd, J = 10.2, 2.7 Hz, 1H), 7.59 (dd, J = 8.6, 5.7 Hz, 1H), 7.50 (d, J = 1.8 Hz, 1H), 7.34 (td, J = 8.4, 2.7 Hz, 1H), 6.11 (s, 2H), 5.56 (d, J = 1.5 Hz, 1H), 5.50 (d, J = 15.5 Hz, 1H), 5.39 (d, J = 4.8 Hz, 1H), 4.82 (d, J = 15.4 Hz, 1H), 2.62 (t, J = 7.1 Hz, 2H), 1.73 (d, J = 6.2 Hz, 3H), 0.93-0.85 (m, 1H), 0.44-0.35 (m, 2H), 0.14-0.00 (m, 2H).<br>LCMS Method H; $t_R$: 1.03 min; m/z: 433 [M + H] |
| Example 68 | 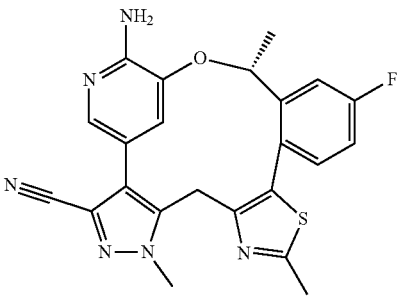 [SMILES: Cc1nc2c(s1)-c1ccc(F)cc1[C@@H](C)Oc1cc(cnc1N)-c1c(C#N)nn(C)c1C2] | (19R)-22-amino-16-fluoro-5,10,19-trimethyl-20-oxa-11-thia-4,5,9,23-tetraazapentacyclo[19.3.1.0²,⁶.0⁸,¹².0¹³,¹⁸]pentacosa-1(24),2(6),3,8(12),9,13,15,17,21(25),22-decaene-3-carbonitrile<br>1H NMR (400 MHz, DMSO-d6) δ 7.70 (dd, J = 10.2, 2.8 Hz, 1H), 7.55 (d, J = 1.9 Hz, 1H), 7.35 (dd, J = 8.6, 5.8 Hz, 1H), 7.27 (td, J = 8.3, 2.6 Hz, 1H), 6.47 (d, J = 1.9 Hz, 1H), 6.10 (s, 2H), 5.38-5.28 (m, 1H), 4.22 (d, J = 15.6 Hz, 1H), 4.21 (s, 3H), 3.28 (d, J = 13.3 Hz, 1H), 2.69 (s, 3H), 1.70 (d, J = 6.2 Hz, 3H).<br>LCMS Method F; $t_R$: 1.02 min; m/z: 447 [M + H] |
| Example 69 | 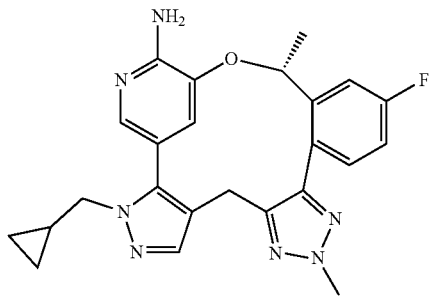 [SMILES: C[C@H]1Oc2cc(cnc2N)-c2c(cnn2CC2CC2)Cc2nn(C)nc2-c2ccc(F)cc21] | (19R)-3-(cyclopropylmethyl)-16-fluoro-10,19-dimethyl-20-oxa-3,4,9,10,11,23-hexaazapentacyclo[19.3.1.0²,⁶.0⁸,¹².0¹³,¹⁸]pentacosa-1(24),2(6),4,8,11,13,15,17,21(25),22-decaen-22-amine<br>1H NMR (400 MHz, DMSO) δ 7.76 (dd, J = 10.2, 1.9 Hz, 1H), 7.64 (s, 1H), 7.54 (d, J = 1.6 Hz, 1H), 7.28-7.21 (m, 2H), 6.39 (s, 1H), 5.44 (d, J = 6.2 Hz, 1H), 4.17 (s, 3H), 3.94 (s, 1H), 3.84 (d, J = 7.6 Hz, 2H), 3.02 (d, J = 15.6 Hz, 1H), 1.75 (d, J = 6.2 Hz, 3H), 1.09 (s, 1H), 0.41 (ddd, J = 13.5, 8.4, 4.1 Hz, 2H), 0.27 (dd, J = 9.1, 4.2 Hz, 1H), 0.11 (dd, J = 9.0, 4.1 Hz, 1H).<br>LCMS Method H; $t_R$: 1.01 min; m/z: 446 [M + H] |

| Example 70 | 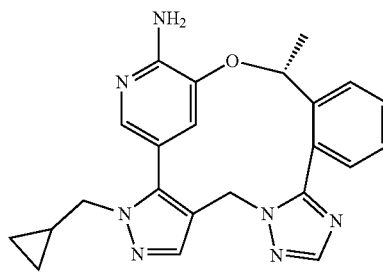 | (19R)-3-(cyclopropylmethyl)-16-fluoro-19-methyl-20-oxa-3,4,8,9,11,23-hexaazapentacyclo[19.3.1.0$^{2,6}$.0$^{8,12}$.0$^{13,18}$]pentacosa-1(24),2(6),4,9,11,13,15,17,21(25),22-decaen-22-amine<br>1H NMR (400 MHz, DMSO) δ 8.15 (s, 1H), 7.84-7.80 (m, 2H), 7.60-7.54 (m, 2H), 7.34 (td, J = 8.4, 2.7 Hz, 1H), 5.98 (s, 1H), 5.54 (d, J = 6.3 Hz, 1H), 5.21 (d, J = 14.9 Hz, 1H), 4.49 (d, J = 14.8 Hz, 1H), 4.04-4.00 (m, 1H), 3.91-3.86 (m, 1H), 1.77 (d, J = 6.2 Hz, 3H), 1.18-1.05 (m, 1H), 0.46-0.35 (m, 2H), 0.27 (dd, J = 9.1, 4.2 Hz, 1H), 0.10 (dd, J = 9.0, 4.2 Hz, 1H).<br>LCMS Method H; t$_R$: 0.86 min; m/z: 432 [M + H] |
| --- | --- | --- |
| Example 71 | 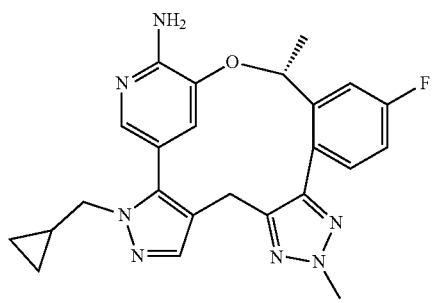 | 3-(cyclopropylmethyl)-16-fluoro-5,10-dimethyl-20-oxa-3,4,9,10,11,23-hexaazapentacyclo[19.3.1.0$^{2,6}$.0$^{8,12}$.0$^{13,18}$]pentacosa-1(24),2(6),4,8,11,13,15,17,21(25),22-decaen-22-amine<br>1H NMR (400 MHz, DMSO) δ 7.73 (dd, J = 10.1, 2.0 Hz, 1H), 7.45 (d, J = 1.8 Hz, 1H), 7.27-7.20 (m, 2H), 6.15-6.07 (m, 3H), 5.12 (d, J = 13.3 Hz, 1H), 4.95 (d, J = 14.2 Hz, 1H), 4.16 (s, 3H), 3.85 (dd, J = 14.3, 6.0 Hz, 1H), 3.73 (d, J = 5.4 Hz, 1H), 3.69 (d, J = 6.9 Hz, 1H), 2.94 (d, J = 15.7 Hz, 1H), 2.35 (s, 3H), 1.14-1.05 (m, 1H), 0.47-0.34 (m, 2H), 0.28-0.20 (m, 1H), 0.13-0.06 (m, 1H).<br>LCMS Method F; t$_R$: 0.90 min; m/z: 446 [M + H] |
| Example 72 | 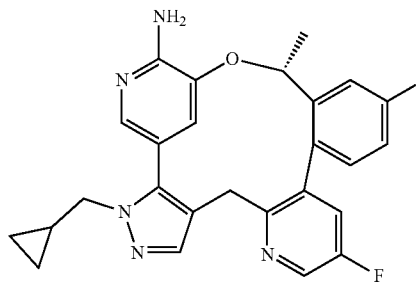 | (20R)-3-(cyclopropylmethyl)-11,17-difluoro-20-methyl-21-oxa-3,4,9,24-tetraazapentacyclo[20.3.1.0$^{2,6}$.0$^{8,13}$.0$^{14,19}$]hexacosa-1(25),2(6),4,8(13),9,11,14,16,18,22(26),23-undecaen-23-amine<br>1H NMR (400 MHz, DMSO) δ 8.67 (d, J = 2.8 Hz, 1H), 8.18 (s, 2H), 7.66 (ddd, J = 17.0, 10.2, 2.6 Hz, 4H), 7.35-7.19 (m, 2H), 6.43 (s, 1H), 5.49 (q, J = 5.1 Hz, 1H), 4.02 (dd, J = 14.5, 6.3 Hz, 1H), 3.93-3.77 (m, 2H), 3.26 (d, J = 15.4 Hz, 1H), 1.84 (d, J = 6.2 Hz, 3H), 1.15-1.03 (m, 1H), 0.48-0.33 (m, 2H), 0.33-0.20 (m, 1H), 0.11 (dq, J = 9.4, 4.9 Hz, 1H).<br>LCMS Method F; t$_R$: 1.07 min; m/z: 460 [M + H] |
| Example 73 | 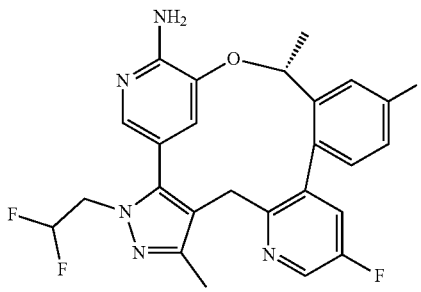 | (20R)-3-(2,2-difluoroethyl)-11,17-difluoro-20-methyl-21-oxa-3,4,9,24-tetraazapentacyclo[20.3.1.0$^{2,6}$.0$^{8,13}$.0$^{14,19}$]hexacosa-1(25),2(6),4,8(13),9,11,14,16,18,22(26),23-undecaen-23-amine<br>1H NMR (400 MHz, DMSO) δ 8.66 (d, J = 2.8 Hz, 1H), 7.78 (s, 1H), 7.71-7.63 (m, 2H), 7.56 (d, J = 1.5 Hz, 1H), 7.30 (dd, J = 8.6, 5.9 Hz, 1H), 7.25 (td, J = 8.4, 2.7 Hz, 1H), 6.35 (tt, J = 4, 56 Hz, 1H), 6.33 (s, 1H), 5.44 (q, J = 4.7 Hz, 1H), 4.54 (tt, J = 14.9, 4.2 Hz, 2H), 3.86 (d, J = 14.9 Hz, 1H), 3.27 (d, J = 15.4 Hz, 1H), 1.83 (d, J = 6.2 Hz, 3H).<br>LCMS Method F; t$_R$: 1.06 min; m/z: 470 [M + H] |
| Example 74 | 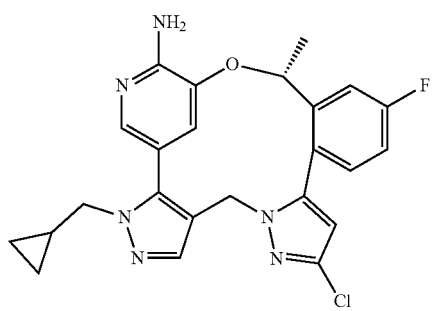 [SMILES: C[C@H]1Oc2cc(cnc2N)-c2c(cnn2CC2CC2)Cn2nc(Cl)cc2-c2ccc(F)cc21] | (19R)-10-chloro-3-(cyclopropylmethyl)-16-fluoro-19-methyl-20-oxa-3,4,8,9,23-pentaazapentacyclo[19.3.1.0$^{2,6}$.0$^{8,12}$.0$^{13,18}$]pentacosa-1(24),2(6),4,9,11,13,15,17,21(25),22-decaen-22-amine<br>1H NMR (400 MHz, DMSO) δ 7.75 (dd, J = 10.2, 2.5 Hz, 1H), 7.72 (s, 1H), 7.52 (d, J = 1.7 Hz, 1H), 7.39 (dd, J = 8.6, 5.8 Hz, 1H), 7.24 (td, J = 8.4, 2.7 Hz, 1H), 6.56 (s, 1H), 6.20 (s, 2H), 6.02 (s, 1H), 5.48 (d, J = 7.8 Hz, 1H), 5.01 (d, J = 14.6 Hz, 1H), 4.28 (d, J = 14.6 Hz, 1H), 4.03-3.97 (m, 1H), 3.86 (d, J = 9.0 Hz, 1H), 1.75 (d, J = 6.2 Hz, 3H), 1.10 (s, 1H), 0.41 (d, J = 33.5 Hz, 2H), 0.27 (d, J = 13.9 Hz, 1H), 0.15-0.03 (m, 1H).<br>LCMS Method F; t$_R$: 1.29 min; m/z: 465 [M + H] |

| Example 75 | 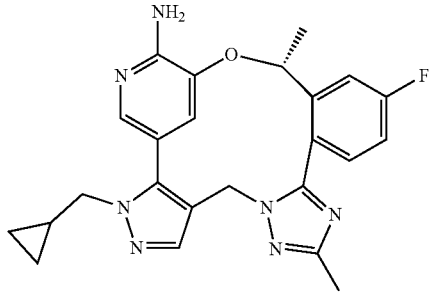 [SMILES: Cc1nc2n(n1)Cc1cnn(CC3CC3)c1-c1cnc(N)c(c1)O[C@H](C)c1cc(F)ccc1-2] | (19R)-3-(cyclopropylmethyl)-16-fluoro-10,19-dimethyl-20-oxa-3,4,8,9,11,23-hexaazapentacyclo[19.3.1.0$^{2,6}$.0$^{8,12}$.0$^{13,18}$]pentacosa-1(24),2(6),4,9,11,13,15,17,21(25),22-decaen-22-amine<br>1H NMR (400 MHz, DMSO) δ 7.83 (dd, J = 10.3, 2.7 Hz, 1H), 7.73 (s, 1H), 7.52-7.44 (m, 2H), 7.26 (dt, J = 8.4, 4.2 Hz, 1H), 6.22 (s, 2H), 5.83 (d, J = 1.7 Hz, 1H), 5.47 (d, J = 4.4 Hz, 1H), 5.08 (d, J = 14.7 Hz, 1H), 4.33 (d, J = 14.7 Hz, 1H), 3.99 (dd, J = 14.4, 6.2 Hz, 1H), 3.84 (dd, J = 14.4, 7.5 Hz, 1H), 2.31 (s, 3H), 1.74 (d, J = 6.2 Hz, 3H), 1.15-1.09 (m, 1H), 0.47-0.36 (m, 2H), 0.30-0.24 (m, 1H), 0.14-0.08 (m, 1H).<br>LCMS Method F; t$_R$: 0.85 min; m/z: 446 [M + H] |
| Example 76 | 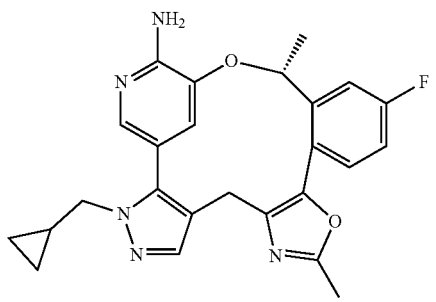 [SMILES: Cc1nc2c(o1)-c1ccc(F)cc1[C@@H](C)Oc1cc(cnc1N)-c1c(cnn1CC1CC1)C2] | (19R)-3-(cyclopropylmethyl)-16-fluoro-10,19-dimethyl-11,20-dioxa-3,4,9,23-tetraazapentacyclo[19.3.1.0$^{2,6}$.0$^{8,12}$.0$^{13,18}$]pentacosa-1(24),2(6),4,8(12),9,13,15,17,21(25),22-decaen-22-amine<br>1H NMR (400 MHz, DMSO) δ 7.84 (dd, J = 10.3, 2.6 Hz, 1H), 7.51 (s, 1H), 7.45 (d, J = 1.8 Hz, 1H), 7.28-7.16 (m, 2H), 6.55 (s, 1H), 6.11 (s, 2H), 5.32 (d, J = 4.4 Hz, 1H), 3.86 (ddd, J = 21.7, 14.4, 6.9 Hz, 2H), 3.55 (d, J = 15.3 Hz, 1H), 2.89 (d, J = 15.2 Hz, 1H), 2.42 (s, 3H), 1.71 (d, J = 6.2 Hz, 3H), 1.08 (s, 1H), 0.40 (d, J = 14.9, 8.3, 4.1 Hz, 2H), 0.25 (dt, J = 8.7, 4.4 Hz, 2H), 0.08 (dt, J = 9.0, 4.6 Hz, 1H).<br>LCMS Method F; t$_R$: 0.69 min; m/z: 446 [M + H] |
| Example 77 | 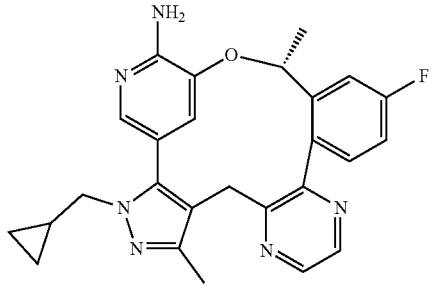 [SMILES: Cc1nn(CC2CC2)c2c1Cc1nccnc1-c1ccc(F)cc1[C@@H](C)Oc1cc-2cnc1N] | (20R)-3-(cyclopropylmethyl)-17-fluoro-5,20-dimethyl-21-oxa-3,4,9,12,24-pentaazapentacyclo[20.3.1.0$^{2,6}$.0$^{8,13}$.0$^{14,19}$]hexacosa-1(25),2(6),4,8(13),9,11,14,16,18,22(26),23-undecaen-23-amine<br>1H NMR (400 MHz, DMSO) δ 8.67 (d, J = 2.4 Hz, 1H), 8.57 (d, J = 2.3 Hz, 1H), 7.72 (dd, J = 10.4, 2.7 Hz, 1H), 7.43 (d, J = 1.7 Hz, 1H), 7.34 (dd, J = 8.5, 5.8 Hz, 1H), 7.21-7.13 (m, 1H), 6.10 (s, 2H), 5.93 (s, 1H), 5.22-5.12 (m, 1H), 3.94-3.85 (m, 1H), 3.76-3.69 (m, 1H), 3.65-3.62 (m, 1H), 3.22-3.19 (m, 1H), 2.40 (s, 3H), 1.72 (d, J = 6.2 Hz, 3H), 1.10-1.01 (m, 1H), 0.45-0.28 (m, 2H), 0.26-0.15 (m, 1H), 0.08--0.01 (m, 1H).<br>LCMS Method F; t$_R$: 0.85 min; m/z: 457 [M + H] |
| Example 78 | 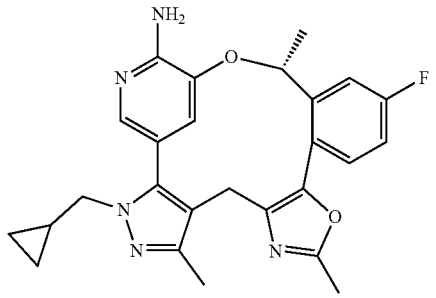 [SMILES: Cc1nc2c(o1)-c1ccc(F)cc1[C@@H](C)Oc1cc(cnc1N)-c1c(c(C)nn1CC1CC1)C2] | (19R)-3-(cyclopropylmethyl)-16-fluoro-5,10,19-trimethyl-11,20-dioxa-3,4,9,23-tetraazapentacyclo[19.3.1.0$^{2,6}$.0$^{8,12}$.0$^{13,18}$]pentacosa-1(24),2(6),4,8(12),9,13,15,17,21(25),22-decaen-22-amine<br>1H NMR (400 MHz, DMSO) δ 7.84 (dd, J = 10.2, 2.6 Hz, 1H), 7.43 (d, J = 1.8 Hz, 1H), 7.29-7.13 (m, 2H), 6.54 (d, J = 1.7 Hz, 1H), 6.08 (s, 2H), 5.30 (d, J = 4.5 Hz, 1H), 3.83 (dd, J = 14.3, 6.2 Hz, 1H), 3.71 (dd, J = 14.4, 7.4 Hz, 1H), 3.47 (d, J = 15.4 Hz, 1H), 2.80 (d, J = 15.4 Hz, 1H), 2.42 (s, 3H), 2.32 (s, 3H), 1.71 (d, J = 6.2 Hz, 3H), 1.12-1.03 (m, 1H), 0.46-0.32 (m, 2H), 0.26-0.19 (m, 1H), 0.10-0.01 (m, 1H).<br>LCMS Method F; t$_R$: 1.16 min; m/z: 460 [M + H] |
| Example 79 | 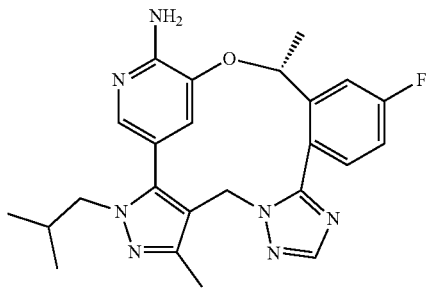 [SMILES: Cc1nn(CC(C)C)c2c1Cn1ncnc1-c1ccc(F)cc1[C@@H](C)Oc1cc-2cnc1N] | (19R)-16-fluoro-5,19-dimethyl-3-(2-methylpropyl)-20-oxa-3,4,8,9,11,23-hexaazapentacyclo[19.3.1.0$^{2,6}$.0$^{8,12}$.0$^{13,18}$]pentacosa-1(24),2(6),4,9,11,13,15,17,21(25),22-decaen-22-amine<br>1H NMR (400 MHz, DMSO) δ 8.14 (s, 1H), 7.85 (dd, J = 10.3, 2.7 Hz, 1H), 7.52 (dd, J = 8.6, 5.7 Hz, 1H), 7.45 (d, J = 1.8 Hz, 1H), 7.29 (td, J = 8.4, 2.7 Hz, 1H), 6.21 (s, 2H), 5.66 (d, J = 1.6 Hz, 1H), 5.40 (d, J = 4.6 Hz, 1H), 5.12 (d, J = 14.9 Hz, 1H), 4.33 (d, J = 14.8 Hz, 1H), 3.76 (dd, J = 7.3, 4.2 Hz, 2H), 2.40 (s, 3H), 2.02 (dt, J = 13.6, 6.7 Hz, 1H), 1.74 (d, J = 6.2 Hz, 3H), 0.75 (d, J = 6.7 Hz, 3H), 0.59 (d, J = 6.6 Hz, 3H).<br>LCMS Method F; t$_R$: 1.00 min; m/z: 448 [M + H] |

| | | |
|---|---|---|
| Example 80 | 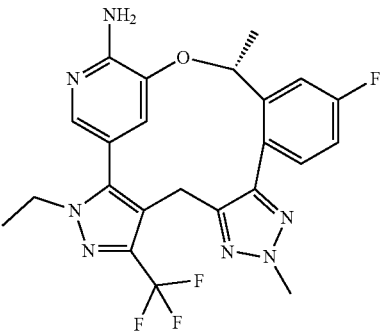 [SMILES: CCn1nc(C(F)(F)F)c2c1-c1cnc(N)c(c1)O[C@H](C)c1cc(F)ccc1-c1nn(C)nc1C2] | (19R)-3-ethyl-16-fluoro-10,19-dimethyl-5-(trifluoromethyl)-20-oxa-3,4,9,10,11,23-hexaazapentacyclo[19.3.1.0$^{2,6}$.0$^{8,12}$.0$^{13,18}$]pentacosa-1(24),2(6),4,8,11,13,15,17,21(25),22-decaen-22-amine<br>1H NMR (400 MHz, DMSO) δ 7.80 (dd, J = 10.4, 2.7 Hz, 1H), 7.50 (d, J = 1.8 Hz, 1H), 7.28 (dd, J = 8.5, 5.8 Hz, 1H), 7.18 (td, J = 8.4, 2.7 Hz, 1H), 6.26 (s, 2H), 6.09 (d, J = 1.8 Hz, 1H), 5.28 (d, J = 6.2 Hz, 1H), 4.15 (s, 3H), 4.12-4.05 (m, 2H), 3.90 (d, J = 16.2 Hz, 1H), 3.01 (d, J = 16.3 Hz, 1H), 1.71 (d, J = 6.2 Hz, 3H), 1.29 (t, J = 7.2 Hz, 3H).<br>LCMS Method F; t$_R$: 1.18 min; m/z: 488 [M + H] |
| Example 81 | 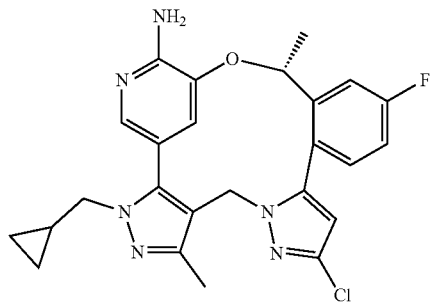 [SMILES: Cc1nn(CC2CC2)c2c1Cn1nc(Cl)cc1-c1ccc(F)cc1[C@@H](C)Oc1cc-2cnc1N] | (19R)-10-chloro-3-(cyclopropylmethyl)-16-fluoro-5,19-dimethyl-20-oxa-3,4,8,9,23-pentaazapentacyclo[19.3.1.0$^{2,6}$.0$^{8,12}$.0$^{13,18}$]pentacosa-1(24),2(6),4,9,11,13,15,17,21(25),22-decaen-22-amine<br>1H NMR (400 MHz, MeOD) δ 7.59 (dd, J = 9.8, 2.8 Hz, 1H), 7.48 (d, J = 1.8 Hz, 1H), 7.34 (dd, J = 8.6, 5.6 Hz, 1H), 7.15 (td, J = 8.2, 2.7 Hz, 1H), 6.34 (s, 1H), 6.22 (d, J = 5.5 Hz, 1H), 5.63 (d, J = 7.2 Hz, 1H), 5.34 (s, 1H), 4.42 (d, J = 14.8 Hz, 1H), 4.06-3.99 (m, 1H), 3.93-3.83 (m, 1H), 2.50 (s, 3H), 1.81 (d, J = 6.4 Hz, 3H), 0.89 (d, J = 6.9 Hz, 1H), 0.52-0.38 (m, 2H), 0.32-0.24 (m, 1H), 0.11-0.03 (m, 1H).<br>LCMS Method K; t$_R$: 1.63 min; m/z: 479 [M + H] |
| Example 82 | 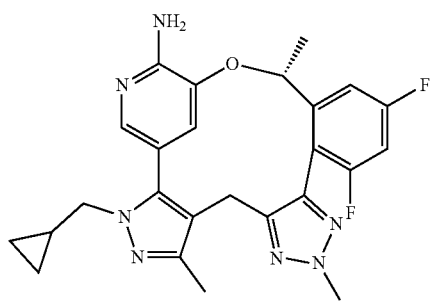 [SMILES: Cc1nn(CC2CC2)c2c1Cc1nn(C)nc1-c1c(F)cc(F)cc1[C@@H](C)Oc1cc-2cnc1N] | (19R)-3-(cyclopropylmethyl)-14,16-difluoro-5,10,19-trimethyl-20-oxa-3,4,9,10,11,23-hexaazapentacyclo[19.3.1.0$^{2,6}$.0$^{8,12}$.0$^{13,18}$]pentacosa-1(24),2(6),4,8,11,13,15,17,21(25),22-decaen-22-amine<br>1H NMR (400 MHz, DMSO) δ 7.66 (d, J = 8.3 Hz, 1H), 7.39 (d, J = 1.7 Hz, 1H), 7.25 (td, J = 9.3, 2.4 Hz, 1H), 6.07 (s, 2H), 6.06 (d, J = 4.0 Hz, 1H), 5.18 (d, J = 4.7 Hz, 1H), 4.12 (s, 3H), 3.78 (dd, J = 14.3, 6.2 Hz, 1H), 3.65 (dd, J = 14.4, 7.4 Hz, 1H), 3.56 (d, J = 15.7 Hz, 1H), 2.77 (d, J = 14.7 Hz, 1H), 2.28 (s, 3H), 1.61 (d, J = 6.2 Hz, 3H), 1.08-0.95 (m, 1H), 0.40-0.25 (m, 2H), 0.16 (td, J = 9.1, 4.9 Hz, 1H), −0.01 (td, J = 9.1, 4.8 Hz, 1H).<br>LCMS Method F; t$_R$: 1.14 min; m/z: 478 [M + H] |
| Example 83 | 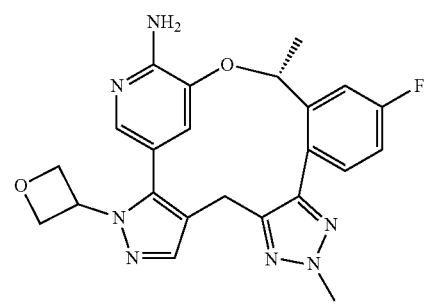 [SMILES: C[C@H]1Oc2cc(cnc2N)-c2c(cnn2C2COC2)Cc2nn(C)nc2-c2ccc(F)cc21] | (19R)-16-fluoro-10,19-dimethyl-3-(oxetan-3-yl)-20-oxa-3,4,9,10,11,23-hexaazapentacyclo[19.3.1.0$^{2,6}$.0$^{8,12}$.0$^{13,18}$]pentacosa-1(24),2(6),4,8,11,13,15,17,21(25),22-decaen-22-amine<br>1H NMR (400 MHz, DMSO) δ 7.81-7.73 (m, 2H), 7.25 (s, 1H), 7.23-7.16 (m, 2H), 6.16 (s, 2H), 6.06 (s, 1H), 5.50-5.38 (m, 1H), 5.25 (d, J = 6.4 Hz, 1H), 4.90 (dt, J = 12.7, 6.3 Hz, 3H), 4.63 (t, J = 6.9 Hz, 1H), 4.16 (s, 3H), 3.81 (d, J = 15.5 Hz, 1H), 2.98 (d, J = 15.7 Hz, 1H), 1.70 (d, J = 5.8 Hz, 3H).<br>LCMS Method K; t$_R$: 0.60 min; m/z: 448 [M + H] |
| Example 84 | 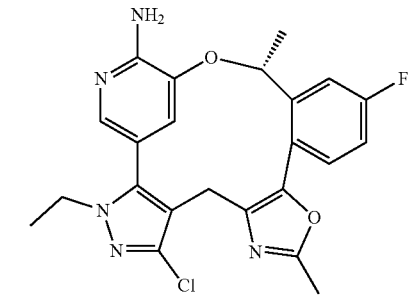 [SMILES: CCn1nc(Cl)c2c1-c1cnc(N)c(c1)O[C@H](C)c1cc(F)ccc1-c1oc(C)nc1C2] | (19R)-5-chloro-3-ethyl-16-fluoro-10,19-dimethyl-11,20-dioxa-3,4,9,23-tetraazapentacyclo[19.3.1.0$^{2,6}$.0$^{8,12}$.0$^{13,18}$]pentacosa-1(24),2(6),4,8(12),9,13,15,17,21(25),22-decaen-22-amine<br>1H NMR (400 MHz, DMSO) δ 7.84 (dd, J = 10.3, 2.7 Hz, 1H), 7.46 (d, J = 1.6 Hz, 1H), 7.30 (dd, J = 8.5, 5.9 Hz, 1H), 7.25-7.12 (m, 1H), 6.55 (d, J = 1.7 Hz, 1H), 6.21 (s, 2H), 5.37-5.23 (m, 1H), 4.05-3.90 (m, 2H), 3.53 (d, J = 15.5 Hz, 1H), 2.85 (d, J = 15.4 Hz, 1H), 2.43 (s, 3H), 1.71 (d, J = 6.2 Hz, 3H), 1.26 (t, J = 7.2 Hz, 3H).<br>LCMS Method F; t$_R$: 1.23 min; m/z: 454 [M + H] |

| Example 85 | 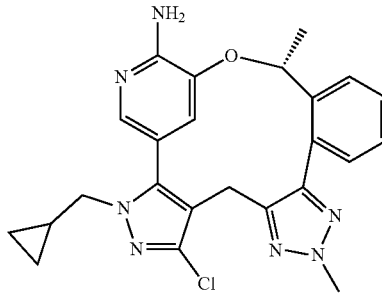 | (19R)-5-chloro-3-(cyclopropylmethyl)-16-fluoro-10,19-dimethyl-20-oxa-3,4,9,10,11,23-hexaazapentacyclo[19.3.1.0$^{2,6}$.0$^{8,12}$.0$^{13,18}$]pentacosa-1(24),2(6),4,8,11,13,15,17,21(25),22-decaen-22-amine<br>1H NMR (400 MHz, DMSO) δ 7.79 (dd, J = 10.3, 2.6 Hz, 1H), 7.48 (d, J = 1.8 Hz, 1H), 7.26 (dd, J = 8.5, 5.9 Hz, 1H), 7.23-7.11 (m, 1H), 6.24 (s, 2H), 6.07 (d, J = 1.6 Hz, 1H), 5.27 (d, J = 4.5 Hz, 1H), 4.18 (s, 3H), 3.92 (dd, J = 14.4, 6.2 Hz, 1H), 3.81-3.75 (m, 1H), 3.73 (d, J = 10.5 Hz, 1H), 2.96 (d, J = 15.7 Hz, 1H), 1.71 (d, J = 6.2 Hz, 3H), 1.10 (s, 1H), 0.43 (ddd, J = 14.3, 8.4, 5.0 Hz, 2H), 0.26 (dd, J = 9.1, 4.3 Hz, 1H), 0.09 (dd, J = 9.2, 4.3 Hz, 1H).<br>LCMS Method K; t$_R$: 1.17 min; m/z: 480 [M + H] |
|---|---|---|
| Example 86 | 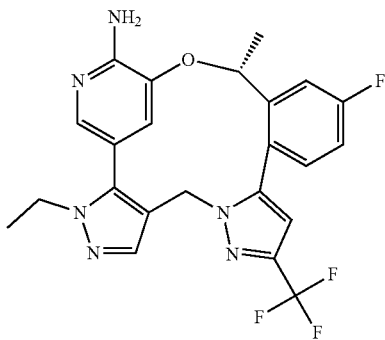 [SMILES: CCn1ncc2c1-c1cnc(N)c(c1)O[C@H](C)c1cc(F)ccc1-c1cc(C(F)(F)F)nn1C2] | (19R)-3-ethyl-16-fluoro-19-methyl-10-(trifluoromethyl)-20-oxa-3,4,8,9,23-pentaazapentacyclo[19.3.1.0$^{2,6}$.0$^{8,12}$.0$^{13,18}$]pentacosa-1(24),2(6),4,9,11,13,15,17,21(25),22-decaen-22-amine<br>1H NMR (400 MHz, DMSO) δ 7.82-7.77 (m, 2H), 7.51 (d, J = 1.8 Hz, 1H), 7.46 (dd, J = 8.6, 5.7 Hz, 1H), 7.27 (td, J = 8.4, 2.7 Hz, 1H), 6.99 (s, 1H), 6.24 (s, 2H), 5.94 (d, J = 1.6 Hz, 1H), 5.42 (d, J = 4.8 Hz, 1H), 5.15 (d, J = 14.7 Hz, 1H), 4.39 (d, J = 14.7 Hz, 1H), 4.07 (ddd, J = 14.1, 6.9, 2.2 Hz, 2H), 1.78 (d, J = 6.3 Hz, 3H), 1.32 (t, J = 7.2 Hz, 3H).<br>LCMS Method F; t$_R$: 1.31 min; m/z: 473 [M + H] |
| Example 87 | 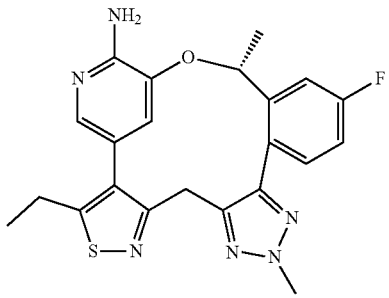 [SMILES: CCc1snc2c1-c1cnc(N)c(c1)O[C@H](C)c1cc(F)ccc1-c1nn(C)nc1C2] | (19R)-3-ethyl-16-fluoro-10,19-dimethyl-20-oxa-4-thia-5,9,10,11,23-pentaazapentacyclo[19.3.1.0$^{2,6}$.0$^{8,12}$.0$^{13,18}$]pentacosa-1(24),2,5,8,11,13,15,17,21(25),22-decaen-22-amine<br>1H NMR (400 MHz, DMSO-d6) δ 7.83 (dd, J = 10.5, 2.7 Hz, 1H), 7.31 (d, J = 1.9 Hz, 1H), 7.28-7.13 (m, 2H), 6.08 (d, J = 2.0 Hz, 1H), 5.99 (s, 2H), 5.34-5.24 (m, 1H), 4.16 (s, 3H), 4.07 (d, J = 14.8 Hz, 1H), 3.25(d, J = 14.8 Hz, 1H), 2.79 (ddt, J = 39.2, 15.7, 7.7 Hz, 2H), 1.71 (d, J = 6.3 Hz, 3H), 1.17 (t, J = 7.5 Hz, 3H).<br>LCMS Method K; t$_R$: 1.07 min; m/z: 437 [M + H] |
| Example 88 | 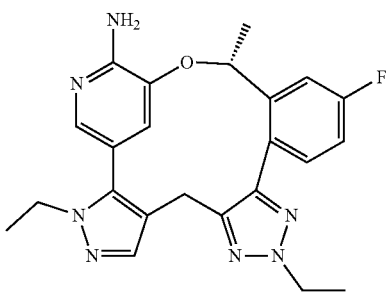 [SMILES: CCn1nc2c(n1)-c1ccc(F)cc1[C@@H](C)Oc1cc(cnc1N)-c1c(cnn1CC)C2] | (19R)-3,10-diethyl-16-fluoro-19-methyl-20-oxa-3,4,9,10,11,23-hexaazapentacyclo[19.3.1.0$^{2,6}$.0$^{8,12}$.0$^{13,18}$]pentacosa-1(24),2(6),4,8,11,13,15,17,21(25),22-decaen-22-amine<br>1H NMR (400 MHz, DMSO) δ 7.78 (dd, J = 10.4, 2.6 Hz, 1H), 7.58 (s, 1H), 7.43 (d, J = 1.8 Hz, 1H), 7.26-7.15 (m, 2H), 6.12 (s, 2H), 6.03 (d, J = 1.7 Hz, 1H), 5.22 (d, J = 4.4 Hz, 1H), 4.45 (m, 2H), 3.99 (m, 2H), 3.79 (d, J = 15.6 Hz, 1H), 3.00 (d, J = 15.6 Hz, 1H), 1.71 (d, J = 6.3 Hz, 3H), 1.46 (t, J = 7.3 Hz, 3H), 1.26 (t, J = 7.2 Hz, 3H).<br>LCMS Method H; t$_R$: 1.03 min; m/z: 434 [M + H] |
| Example 89 | 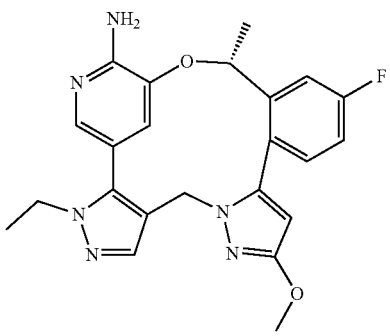 [SMILES: CCn1ncc2c1-c1cnc(N)c(c1)O[C@H](C)c1cc(F)ccc1-c1cc(OC)nn1C2] | (19R)-3-ethyl-16-fluoro-10-methoxy-19-methyl-20-oxa-3,4,8,9,23-pentaazapentacyclo[19.3.1.0$^{2,6}$.0$^{8,12}$.0$^{13,18}$]pentacosa-1(24),2(6),4,9,11,13,15,17,21(25),22-decaen-22-amine<br>1H NMR (400 MHz, DMSO) δ 7.74 (dd, J = 10.3, 2.7 Hz, 1H), 7.68 (s, 1H), 7.49 (d, J = 1.8 Hz, 1H), 7.35 (dd, J = 8.6, 5.8 Hz, 1H), 7.26-7.16 (m, 1H), 6.19 (s, 2H), 6.10 (d, J = 1.6 Hz, 1H), 5.90 (s, 1H), 5.65-5.48 (m, 1H), 4.88 (d, J = 14.6 Hz, 1H), 4.22 (d, J = 14.5 Hz, 1H), 4.14-3.95 (m, 2H), 3.78 (s, 3H), 1.75 (d, J = 6.3 Hz, 3H), 1.30 (t, J = 7.2 Hz, 3H).<br>LCMS Method F; t$_R$: 0.81 min; m/z: 435 [M + H] |

| | | |
|---|---|---|
| Example 90 | 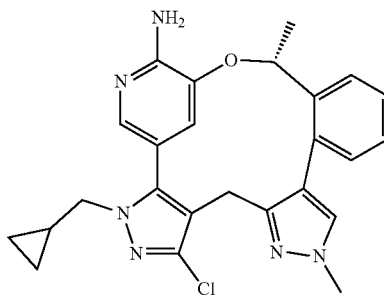 | (19R)-5-chloro-3-(cyclopropylmethyl)-16-fluoro-10,19-dimethyl-20-oxa-3,4,9,10,23-pentaazapentacyclo[19.3.1.0$^{2,6}$.0$^{8,12}$.0$^{13,18}$]pentacosa-1(24),2(6),4,8,11,13,15,17,21(25),22-decaen-22-amine<br>1H NMR (400 MHz, DMSO) δ 7.79 (s, 1H), 7.63 (d, J = 9.7 Hz, 1H), 7.55 (s, 1H), 7.17 (d, J = 7.4 Hz, 2H), 6.45 (s, 1H), 5.45 (d, J = 5.1 Hz, 1H), 3.97 (dd, J = 14.4, 6.3 Hz, 1H), 3.85 (s, 3H), 3.83-3.78 (m, 1H), 3.66 (d, J = 15.7 Hz, 1H), 2.94 (d, J = 15.6 Hz, 1H), 1.77 (d, J = 6.3 Hz, 3H), 1.17-1.07 (m, 1H), 0.52-0.37 (m, 2H), 0.33-0.25 (m, 1H), 0.15-0.09 (m, 1H).<br>LCMS Method K; $t_R$: 1.18 min; m/z: 479 [M + H] |
| Example 91 | 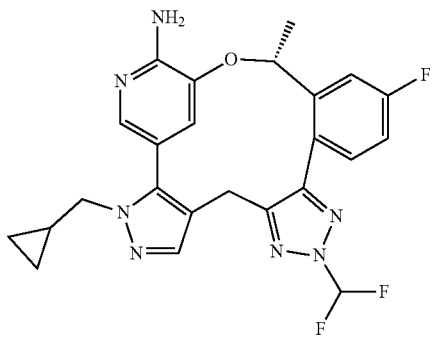 [SMILES: C[C@H]1Oc2cc(cnc2N)-c2c(cnn2CC2CC2)Cc2nn(C(F)F)nc2-c2ccc(F)cc21] | (19R)-3-(cyclopropylmethyl)-10-(difluoromethyl)-16-fluoro-19-methyl-20-oxa-3,4,9,10,11,23-hexaazapentacyclo[19.3.1.0$^{2,6}$.0$^{8,12}$.0$^{13,18}$]pentacosa-1(24),2(6),4,8,11,13,15,17,21(25),22-decaen-22-amine<br>1H NMR (400 MHz, DMSO) δ 7.91 (t, J = 57.6 Hz, 1H), 7.62 (dd, J = 10.4, 2.7 Hz, 1H), 7.40 (s, 1H), 7.23 (d, J = 1.8 Hz, 1H), 7.13 (dd, J = 8.5, 5.8 Hz, 1H), 7.01 (td, J = 8.4, 2.7 Hz, 1H), 5.94 (s, 2H), 5.75 (d, J = 1.7 Hz, 1H), 5.08-4.92 (m, 1H), 3.76-3.62 (m, 2H), 3.57 (dd, J = 14.4, 7.4 Hz, 1H), 2.81 (d, J = 15.7 Hz, 1H), 1.49 (d, J = 6.2 Hz, 3H), 0.85 (qd, J = 7.8, 4.0 Hz, 1H), 0.25-0.07 (m, 2H), 0.01 (td, J = 9.1, 4.8 Hz, 1H), –0.16 (td, J = 9.2, 4.9 Hz, 1H).<br>LCMS Method F; $t_R$: 1.05 min; m/z: 482 [M + H] |
| Example 92 | 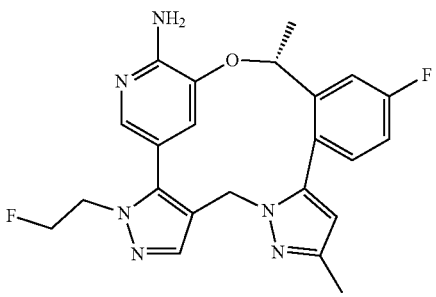 [SMILES: Cc1cc2n(n1)Cc1cnn(CCF)c1-c1cnc(N)c(c1)O[C@H](C)c1cc(F)ccc1-2] | (19R)-16-fluoro-3-(2-fluoroethyl)-10,19-dimethyl-20-oxa-3,4,8,9,23-pentaazapentacyclo[19.3.1.0$^{2,6}$.0$^{8,12}$.0$^{13,18}$]pentacosa-1(24),2(6),4,9,11,13,15,17,21(25),22-decaen-22-amine<br>1H NMR (400 MHz, DMSO) δ 7.79 (s, 1H), 7.74 (dd, J = 10.3, 2.7 Hz, 1H), 7.51 (d, J = 1.5 Hz, 1H), 7.33 (dd, J = 8.6, 5.8 Hz, 1H), 7.22 (td, J = 8.4, 2.7 Hz, 1H), 6.20 (d, J = 8.5 Hz, 3H), 5.99 (d, J = 1.5 Hz, 1H), 5.50 (d, J = 4.8 Hz, 1H), 4.98 (d, J = 14.6 Hz, 1H), 4.92-4.68 (m, 2H), 4.45-4.29 (m, 2H), 4.26 (d, J = 14.5 Hz, 1H), 2.21 (s, 3H), 1.75 (d, J = 6.3 Hz, 3H).<br>LCMS Method F; $t_R$: 0.93 min; m/z: 437 [M + H] |
| Example 93 | 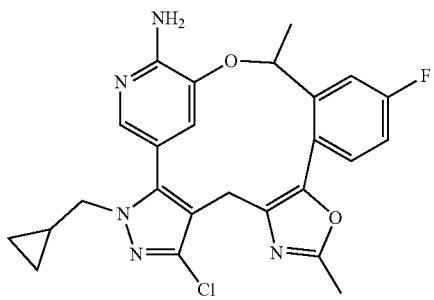 [SMILES: Cc1nc2c(o1)-c1ccc(F)cc1C(C)Oc1cc(cnc1N)-c1c(c(Cl)nn1CC1CC1)C2] | 5-chloro-3-(cyclopropylmethyl)-16-fluoro-10,19-dimethyl-11,20-dioxa-3,4,9,23-tetraazapentacyclo[19.3.1.0$^{2,6}$.0$^{8,12}$.0$^{13,18}$]pentacosa-1(24),2(6),4,8(12),9,13,15,17,21(25),22-decaen-22-amine<br>1H NMR (400 MHz, MeOD) δ 7.64 (dd, J = 10.0, 2.7 Hz, 1H), 7.44 (d, J = 1.6 Hz, 1H), 7.27 (dd, J = 8.5, 5.6 Hz, 1H), 7.11 (td, J = 8.3, 2.7 Hz, 1H), 6.69 (d, J = 1.7 Hz, 1H), 5.43-5.35 (m, 1H), 3.92 (ddd, J = 22.0, 14.5, 6.9 Hz, 2H), 3.68 (d, J = 15.5 Hz, 1H), 3.07 (d, J = 15.5 Hz, 1H), 2.50 (s, 3H), 1.81 (d, J = 6.3 Hz, 3H), 1.13-1.04 (m, 1H), 0.53-0.37 (m, 2H), 0.26 (td, J = 9.6, 4.9 Hz, 1H), 0.05 (td, J = 9.8, 4.8 Hz, 1H).<br>LCMS Method K; $t_R$: 1.38 min; m/z: 480 [M + H] |
| Example 94 | 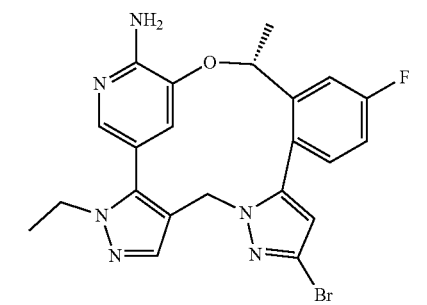 [SMILES: CCn1ncc2c1-c1cnc(N)c(c1)O[C@H](C)c1cc(F)ccc1-c1cc(Br)nn1C2] | (19R)-10-bromo-3-ethyl-16-fluoro-19-methyl-20-oxa-3,4,8,9,23-pentaazapentacyclo[19.3.1.0$^{2,6}$.0$^{8,12}$.0$^{13,18}$]pentacosa-1(24),2(6),4,9,11,13,15,17,21(25),22-decaen-22-amine<br>1H NMR (400 MHz, DMSO) δ 7.77 (dd, J = 10.2, 2.6 Hz, 1H), 7.75 (d, J = 4.2 Hz, 1H), 7.50 (d, J = 1.8 Hz, 1H), 7.41 (dd, J = 8.6, 5.7 Hz, 1H), 7.25 (td, J = 8.4, 2.7 Hz, 1H), 6.65 (s, 1H), 6.22 (s, 2H), 6.01 (d, J = 1.4 Hz, 1H), 5.47 (d, J = 6.4 Hz, 1H), 5.04 (d, J = 15 Hz, 1H), 4.30 (d, J = 14.8 Hz, 1H), 4.08 (qt, J = 14.0, 7.2 Hz, 2H), 1.76 (d, J = 6.2 Hz,3H), 1.31 (t, J = 7.2 Hz, 3H).<br>LCMS Method F; $t_R$: 1.16 min; m/z: 483 [M + H] |

Example 95 (Method F)

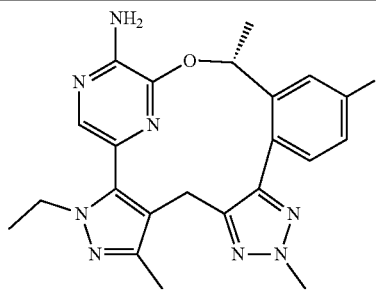

Name: (19R)-3-(cyclopropylmethyl)-16-fluoro-5,10,19-trimethyl-20-oxa-3,4,9,10,11,23,25-heptaazapentacyclo[19.3.1.0$^{2,6}$.0$^{8,12}$.0$^{13,18}$]pentacosa-1(24),2(6),4,8,11,13,15,17,21(25),22-decaen-22-amine
NMR: 1H NMR (400 MHz, DMSO) δ 7.72 (dd, J = 10.2, 2.5 Hz, 1H), 7.56 (s, 1H), 7.26-7.10 (m, 2H), 6.69 (s, 2H), 5.81-5.47 (m, 1H), 4.12 (s, 3H), 3.91 (dd, J = 14.4, 6.0 Hz, 1H), 3.75 (dd, J = 14.4, 7.4 Hz, 1H), 3.53 (d, J = 15.3 Hz, 1H), 2.99 (d, J = 15.3 Hz, 1H), 2.35 (s, 3H), 1.61 (d, J = 6.6 Hz, 3H), 1.09 (dd, J = 12.3, 6.1 Hz, 1H), 0.50-0.35 (m, 2H), 0.30-0.22 (m, 1H), 0.15-0.06 (m, 1H).
LCMS: Method H; t$_R$: 1.49 min; m/z: 461 [M + H]

To a solution of (R)-1-(2-(5-((1-(cyclopropylmethyl)-3-methyl-1H-pyrazol-4-yl)methyl)-2-methyl-2H-1,2,3-triazol-4-yl)-5-fluorophenyl)ethan-1-ol (320 mg, 0.870 mmol) in THF (5 mL) was added NaH (42 mg, 1.0 mmol, 60% in mineral oil) at 0° C. After stirring at 0° C. for 30 min, 5-bromo-3-chloropyrazin-2-amine (180 mg, 0.870 mmol) was added and stirring was continued at r.t. for 3 h. The reaction was quenched with sat. aq. NH$_4$Cl (20 mL) and extracted with EtOAc (50 mL). The organic layer was dried over anhydrous Na$_2$SO$_4$, filtered, and concentrated to give crude (R)-5-bromo-3-(1-(2-(5-((1-(cyclopropylmethyl)-3-methyl-1H-pyrazol-4-yl)methyl)-2-methyl-2H-1,2,3-triazol-4-yl)-5-fluorophenyl)ethoxy)pyrazin-2-amine (200 mg, 43%) as a yellow oil. LC/MS (ESI) (m/z): 541 [M+H]$^+$.

To a solution of (R)-5-bromo-3-(1-(2-(5-((1-(cyclopropylmethyl)-3-methyl-1H-pyrazol-4-yl)methyl)-2-methyl-2H-1,2,3-triazol-4-yl)-5-fluorophenyl)ethoxy)pyrazin-2-amine (150 mg, 0.280 mmol) in 2-methyl-2-butanol (5 mL) were added potassium acetate (136 mg, 1.40 mmol), cataCXium A (60 mg, 0.17 mmol), and Pd(OAc)$_2$ (13 mg, 0.06 mmol) under N$_2$. The vessel was sealed, thrice degassed with N$_2$, and then stirred at 120° C. overnight. The reaction mixture was cooled to r.t. and concentrated under reduced pressure. The residue was purified by prep-TLC (5% MeOH in DCM) followed by prep-HPLC (YMC-Actus Triart C18 250*21 mm, MeCN in H$_2$O+0.1% FA) to give the target product (11 mg, 8.2%) as a white solid. LC/MS (ESI) (m/z): 461 [M+H]$^+$.

Example 96 (Method H)

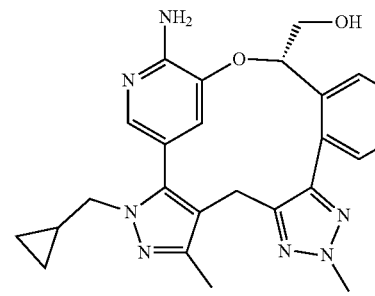

Name: [(19S)-22-amino-3-(cyclopropylmethyl)-16-fluoro-5,10-dimethyl-20-oxa-3,4,9,10,11,23-hexaazapentacyclo[19.3.1.0$^{2,6}$.0$^{8,12}$.0$^{13,18}$]pentacosa-1(24),2(6),4,8,11,13,15,17,21(25),22-decaen-19-yl]methanol
NMR: 1H NMR (400 MHz, MeOD) δ 7.55 (dd, J = 10.0, 2.7 Hz, 1H), 7.46 (d, J = 1.6 Hz, 1H), 7.26 (dd, J = 8.5, 5.7 Hz, 1H), 7.15 (td, J = 8.3, 2.7 Hz, 1H), 6.27 (d, J = 1.7 Hz, 1H), 5.28-5.21 (m, 1H), 4.25-4.19 (m, 4H), 4.01 (dd, J = 12.3, 3.2 Hz, 1H), 3.96 (dd, 1H), 3.84 (dd, J = 14.6, 7.4 Hz, 1H), 3.76 (d, J = 15.9 Hz, 1H), 3.11 (d, J = 15.9 Hz, 1H), 2.46 (s, 3H), 1.11-1.01 (m, 1H), 0.51-0.41 (m, 1H), 0.41-0.32 (m, 1H), 0.28-0.21 (m, 1H), 0.01--0.02 (m, 1H).
LCMS: Method F; t$_R$: 0.82 min; m/z: 476 [M + H]

To a solution of 5-bromo-3-{2-[(tert-butyldimethylsilyl)oxy]-1-[2-(5-{[1-(cyclopropylmethyl)-3-methyl-1H-pyrazol-4-yl]methyl}-2-methyl-2H-1,2,3-triazol-4-yl)-5-fluorophenyl]ethoxy}-2-nitropyridine (620 mg, 0.90 mmol) in EtOH (6.0 mL) and H$_2$O (1.5 mL) was added iron powder (247 mg, 4.40 mmol) and NH$_4$Cl (379 mg, 7.10 mmol) at 75° C. The reaction was stirred at 75° C. for 2 h. The mixture was filtered through celite, and the filtrate was concentrated. The residue was purified by flash chromatography (0 to 100% EA in PE) to give 5-bromo-3-{2-[(tertbutyldimethylsilyl)oxy]-1-[2-(5-{[1-(cyclopropylmethyl)-3-methyl-1H-pyrazol-4-yl]methyl}-2-methyl-2H-1,2,3-triazol-4-yl)-5-fluorophenyl]ethoxy}pyridin-2-amine (300 mg, yield: 51%) as a brown solid. LC/MS ESI (m/z): 670 [M+H]$^+$ A mixture of 5-bromo-3-{2-[(tert-butyldimethylsilyl)oxy]-1-[2-(5-{[1-(cyclopropylmethyl)-3-methyl-1H-pyrazol-4-yl]methyl}-2-methyl-2H-1,2,3-triazol-4-yl)-5-fluorophenyl]ethoxy}pyridin-2-amine (100 mg, 0.150 mmol), KOAc (73 mg, 0.74 mmol), Pd(OAc)$_2$ (7 mg, 0.03 mmol) and cataCXium A (21 mg, 0.06 mmol) in 2-methyl-2-butanol (5.0 mL) was sealed in a reaction tube tube. The mixture was twice degassed with N$_2$ and then stirred at 120° C. overnight. The mixture was diluted with EA (5 mL), washed with water (3 mL) and brine, dried over anhydrous Na$_2$SO$_4$, filtered, and concentrated. The residue was purified by prep-TLC (6% MeOH in DCM) to give 19-{[(tert-butyldimethylsilyl)oxy]methyl}-3-(cyclopropylmethyl)-16-fluoro-5,10-dimethyl-20-oxa-3,4,9,10,11,23-hexaazapentacyclo[19.3.1.0$^{2,6}$.0$^{8,12}$.0$^{13,18}$]pentacosa-1 (24),2 (6),4,8,11, 13,15,17,21 (25),22-decaen-22-amine (20 mg, yield: 23%) as a yellow solid. LC/MS ESI (m/z): 590 [M+H]$^+$.

To a solution of 19-{[(tert-butyldimethylsilyl)oxy]methyl}-3-(cyclopropylmethyl)-16-fluoro-5,10-dimethyl-20-oxa-3,4,9,10,11,23-hexaazapentacyclo[19.3.1.0$^{2,6}$.0$^{8,}$ 12.0$^{13,18}$]pentacosa-1 (24),2 (6),4,8,11,13,15,17,21 (25),22-decaen-22-amine (40 mg, 0.07 mmol) in THF (2.0 mL) was added TBAF (0.4 mL, 0.4 mmol, 1 M in THF). The mixture was stirred at r.t. for 2 h. The mixture was diluted with EA (5 mL), washed with water (3 mL) and brine (3 mL×3), dried over anhydrous Na$_2$SO$_4$, filtered, and concentrated. The residue was purified by prep-TLC, followed by chiral SFC (ChiralPak IG, 250×21.2 mm 5 μm, 40% EtOH+0.1% aq. NH$_3$ in CO$_2$) to give the eutomer ($t_R$: 3.15 min) and distomer ($t_R$: 6.41 min). The eutomer was further purified by prep-HPLC (YMC-Actus Triart C18 250*2 1 mm, MeCN in H$_2$O+0.1% FA) to give the target product (2.2 mg, yield: 6.2%) as a white solid. LC-MS ESI (m/z): 476 [M+H]$^+$.

Example 97 (Method J)

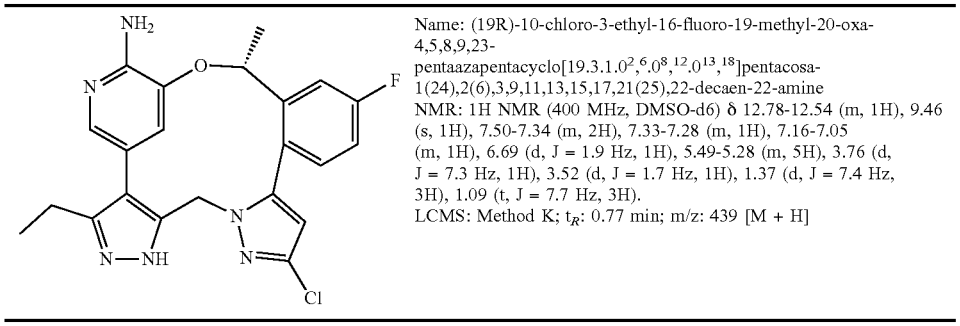

Name: (19R)-10-chloro-3-ethyl-16-fluoro-19-methyl-20-oxa-4,5,8,9,23-pentaazapentacyclo[19.3.1.0$^{2,6}$.0$^{8,12}$.0$^{13,18}$]pentacosa-1(24),2(6),3,9,11,13,15,17,21(25),22-decaen-22-amine
NMR: 1H NMR (400 MHz, DMSO-d6) δ 12.78-12.54 (m, 1H), 9.46 (s, 1H), 7.50-7.34 (m, 2H), 7.33-7.28 (m, 1H), 7.16-7.05 (m, 1H), 6.69 (d, J = 1.9 Hz, 1H), 5.49-5.28 (m, 5H), 3.76 (d, J = 7.3 Hz, 1H), 3.52 (d, J = 1.7 Hz, 1H), 1.37 (d, J = 7.4 Hz, 3H), 1.09 (t, J = 7.7 Hz, 3H).
LCMS: Method K; $t_R$: 0.77 min; m/z: 439 [M + H]

To a solution of (19R)-10-chloro-3-ethyl-16-fluoro-5-[(4-methoxyphenyl)methyl]-19-methyl-20-oxa-4,5,8,9,23-pentaazapentacyclo[19.3.1.0$^{2,6}$.0$^{8,12}$.0$^{13,18}$]pentacosa-1 (24),2 (6),3,9,11,13,15,17,21 (25),22-decaen-22-amine (210 mg, 0.376 mmol) in DCE (5 mL), was added trifluoroacetic acid (5.0 mL, 68 mmol) and trifluoromethanesulfonic acid (2.0 mL, 23 mmol). The reaction was stirred at 75° C. for 1.5 h. The mixture was neutralized with sat. aq. NaHCO$_3$ and then extracted with DCM (3×10 mL). The combined organic phases were washed with sat. NaHCO$_3$ (10 mL) and brine (10 mL), dried over anhydrous Na$_2$SO$_4$, filtered, and concentrated in vacuo. The residue was purified by prep-TLC (0→7% MeOH in DCM) followed by prep-HPLC (YMC-Actus Triart C18 250*21 mm, MeCN in H$_2$O+0.1% FA) to give the target product (1.5 mg, 0.93%) as a white residue. LC/MS (ESI) (m/z): 439 [M+H]$^+$.

Example 98 (Method L)

the mixture was cooled to r.t. and filtered. The filtrate was concentrated, and the residue was purified by flash chromatography (silica gel, 50% EtOAc in PE) to give (R)-5-bromo-3-(1-(2-(5-((3-ethyl-1-methyl-1H-pyrazol-5-yl)methyl)-2-methyl-2H-1,2,3-triazol-4-yl)-5-fluorophenyl) ethoxy)pyridin-2-amine (80 mg, 94% yield) as a white solid. LC/MS ESI (m/z): 514 [M+H]$^+$.

To a mixture of (R)-5-bromo-3-(1-(2-(5-((3-ethyl-1-methyl-1H-pyrazol-5-yl)methyl)-2-methyl-2H-1,2,3-triazol-4-yl)-5-fluorophenyl)ethoxy)pyridin-2-amine (90 mg, 0.17 mmol) in DMF (5 mL) was added NBS (37 mg, 0.21 mmol) at r.t. The mixture was stirred at r.t. for 1 h. The mixture was slowly poured into water (10 mL) and extracted with ethyl acetate (10 mL×3). The combined organic layers were washed with brine (10 mL×2), dried over anhydrous Na$_2$SO$_4$, filtered, and concentrated. The residue was purified by flash chromatography (silica gel, 0→50% EtOAc in PE) to give (R)-5-bromo-3-(1-(2-(5-((4-bromo-3-ethyl-1-methyl-1H-pyrazol-5-yl)methyl)-2-methyl-2H-1,2,3-triazol-4-yl)-5-fluorophenyl)ethoxy)pyridin-2-amine (70 mg, 67% yield) as a colorless oil. LC/MS ESI (m/z): 592 [M+H]$^+$.

To a solution of (R)-5-bromo-3-(1-(2-(5-((4-bromo-3-ethyl-1-methyl-1H-pyrazol-5-yl)methyl)-2-methyl-2H-1,2, 3-triazol-4-yl)-5-fluorophenyl)ethoxy)pyridin-2-amine (70 mg, 0.12 mmol) in MeOH (30 mL) was added 4,4,4',4',5,5, 5',5'-octamethyl-2,2'-bi(1,3,2-dioxaborolane) (90 mg, 0.35 mmol). The mixture was thrice degassed with N$_2$ and then Pd(OAc)$_2$ (5 mg, 0.02 mmol), cataCXium A (9 mg, 0.02 mmol) and aq. CsF (0.12 mL, 0.24 mmol, 2 N in water) were added. The mixture was again degassed with N$_2$ and stirred

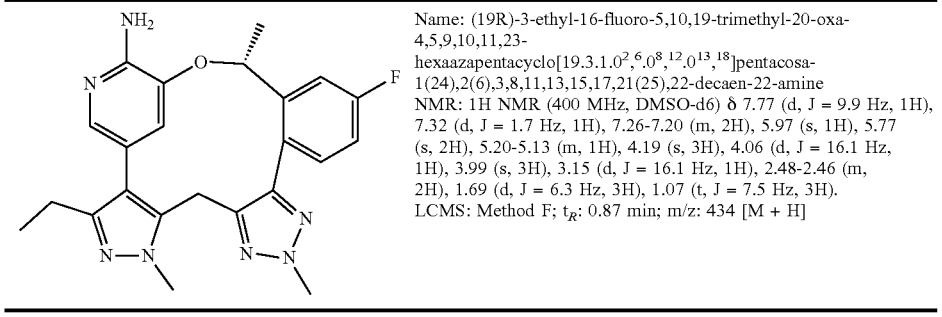

Name: (19R)-3-ethyl-16-fluoro-5,10,19-trimethyl-20-oxa-4,5,9,10,11,23-hexaazapentacyclo[19.3.1.0$^{2,6}$.0$^{8,12}$.0$^{13,18}$]pentacosa-1(24),2(6),3,8,11,13,15,17,21(25),22-decaen-22-amine
NMR: 1H NMR (400 MHz, DMSO-d6) δ 7.77 (d, J = 9.9 Hz, 1H), 7.32 (d, J = 1.7 Hz, 1H), 7.26-7.20 (m, 2H), 5.97 (s, 1H), 5.77 (s, 2H), 5.20-5.13 (m, 1H), 4.19 (s, 3H), 4.06 (d, J = 16.1 Hz, 1H), 3.99 (s, 3H), 3.15 (d, J = 16.1 Hz, 1H), 2.48-2.46 (m, 2H), 1.69 (d, J = 6.3 Hz, 3H), 1.07 (t, J = 7.5 Hz, 3H).
LCMS: Method F; $t_R$: 0.87 min; m/z: 434 [M + H]

To a solution of (R)-5-bromo-3-(1-(2-(5-((3-ethyl-1-methyl-1H-pyrazol-5-yl)methyl)-2-methyl-2H-1,2,3-triazol-4-yl)-5-fluorophenyl)ethoxy)-2-nitropyridine (90 mg, 0.17 mmol) in EtOH (5 mL) and H$_2$O (1 mL) was added iron powder (92 mg, 1.7 mmol) and NH$_4$Cl (176 mg, 3.30 mmol). The mixture was stirred at 80° C. for 1 h, and then at 80° C. for 5 h. After cooling to r.t., the mixture was concentrated in vacuo, and the residue was purified by flash chromatography (silica gel, 0-5% MeOH in DCM) followed by prep-HPLC (Waters C18 150*19 mm; MeCN in H$_2$O+ 1% FA) to give the target product (4.9 mg, 9.6%) as a white solid. LC/MS ESI (m/z): 434 [M+H]$^+$.

The following compounds were prepared in a similar manner:

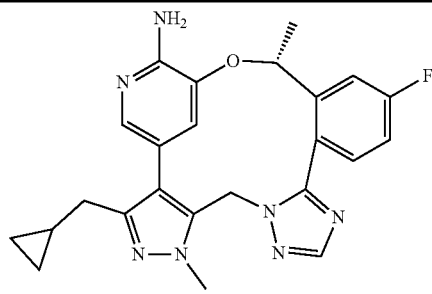

Example 99

(19R)-3-(cyclopropylmethyl)-16-fluoro-5,19-dimethyl-20-oxa-4,5,8,9,11,23-hexaazapentacyclo[19.3.1.0$^{2,6}$.0$^{8,12}$.0$^{13,18}$]pentacosa-1(24),2(6),3,9,11,13,15,17,21(25),22-decaen-22-amine
1H NMR (400 MHz, DMSO) δ 8.21 (s, 1H), 7.84 (dd, J = 10.2, 2.7 Hz, 1H), 7.54 (dd, J = 8.6, 5.7 Hz, 1H), 7.37 (d, J = 1.8 Hz, 1H), 7.32 (td, J = 8.4, 2.7 Hz, 1H), 5.87 (s, 2H), 5.59 (d, J = 1.6 Hz, 1H), 5.49 (d, J = 15.4 Hz, 1H), 5.35 (dt, J = 11.9, 5.9 Hz, 1H), 4.51 (d, J = 15.4 Hz, 1H), 4.07 (s, 3H), 2.44 (d, J = 6.6 Hz, 2H), 1.73 (d, J = 6.2 Hz, 3H), 0.95-0.84 (m, 1H), 0.39-0.27 (m, 2H), 0.07 (ddd, J = 7.8, 6.7, 4.0 Hz, 1H), 0.00--0.07 (m, 1H).
LCMS Method K; t$_R$: 0.60 min; m/z: 446 [M + H]

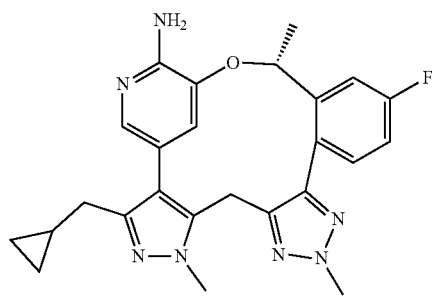 [SMILES: C[C@H]1Oc2cc(cnc2N)-c2c(CC3CC3)nn(C)c2Cc2nn(C)nc2-c2ccc(F)cc21]

Example 100

(19R)-3-(cyclopropylmethyl)-16-fluoro-5,10,19-trimethyl-20-oxa-4,5,9,10,11,23-hexaazapentacyclo[19.3.1.0$^{2,6}$.0$^{8,12}$.0$^{13,18}$]pentacosa-1(24),2(6),3,8,11,13,15,17,21(25),22-decaen-22-amine
1H NMR (400 MHz, DMSO) δ 7.86-7.73 (m, 1H), 7.37 (d, J = 1.6 Hz, 1H), 7.32-7.19 (m, 2H), 6.02 (s, 1H), 5.81 (s, 2H), 5.22 (d, J = 4.9 Hz, 1H), 4.24 (s, 3H), 4.11 (d, J = 16.2 Hz, 1H), 4.04 (s, 3H), 3.19 (d, J = 16.1 Hz, 1H), 2.43 (d, J = 6.5 Hz, 2H), 1.73 (d, J = 6.2 Hz, 3H), 0.91 (d, J = 4.8 Hz, 1H), 0.46-0.27 (m, 2H), 0.11 (dt, J = 7.7, 4.6 Hz, 1H), −0.01 (dt, J = 14.2, 4.8 Hz, 1H).
LCMS Method F; t$_R$: 0.99 min; m/z: 460 [M + H]

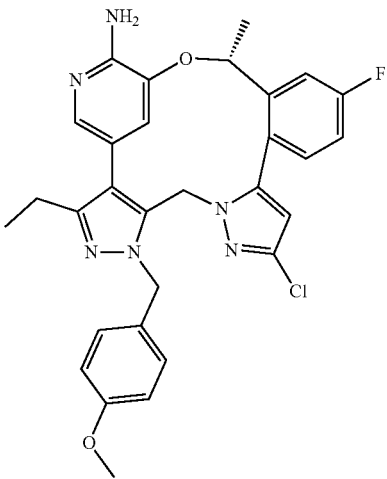 [SMILES: CCc1nn(Cc2ccc(OC)cc2)c2c1-c1cnc(N)c(c1)O[C@H](C)c1cc(F)ccc1-c1cc(Cl)nn1C2]

Example 101

(19R)-10-chloro-3-ethyl-16-fluoro-5-[(4-methoxyphenyl)methyl]-19-methyl-20-oxa-4,5,8,9,23-pentaazapentacyclo[19.3.1.0$^{2,6}$.0$^{8,12}$.0$^{13,18}$]pentacosa-1(24),2(6),3,9,11,13,15,17,21(25),22-decaen-22-amine
LCMS Method F; t$_R$: 1.45 min; m/z: 559 [M + H]

Example 102 (Method N)

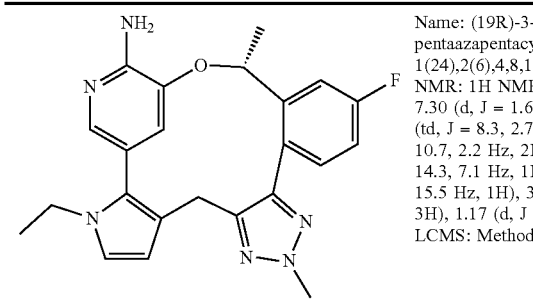

Name: (19R)-3-ethyl-16-fluoro-10,19-dimethyl-20-oxa-3,9,10,11,23-pentaazapentacyclo[19.3.1.0$^{2,6}$.0$^{8,12}$.0$^{13,18}$]pentacosa-1(24),2(6),4,8,11,13,15,17,21(25),22-decaen-22-amine
NMR: 1H NMR (400 MHz, MeOD) δ 7.58 (dd, J = 10.1, 2.7 Hz, 1H), 7.30 (d, J = 1.6 Hz, 1H), 7.15 (dd, J = 8.5, 5.7 Hz, 1H), 7.08 (td, J = 8.3, 2.7 Hz, 1H), 6.70 (d, J = 2.8 Hz, 1H), 6.27 (dd, J = 10.7, 2.2 Hz, 2H), 5.43-5.27 (m, 1H), 4.19 (s, 3H), 3.91 (dt, J = 14.3, 7.1 Hz, 1H), 3.80 (dd, J = 14.1, 7.1 Hz, 1H), 3.69 (d, J = 15.5 Hz, 1H), 3.20 (d, J =15.5 Hz, 1H), 1.79 (d, J = 6.3 Hz, 3H), 1.17 (d, J = 7.2 Hz, 3H).
LCMS: Method F; t$_R$: 1.06 min; m/z: 419 [M + H]

To a solution of (R)-(5-(2-(1-((5-bromo-2-nitropyridin-3-yl)oxy)ethyl)-4-fluorophenyl)-2-methyl-2H-1,2,3-triazol-4-yl)(1-ethyl-1H-pyrrol-3-yl)methanone (166 mg, 0.306 mmol) in MeOH (3 mL) and NH$_4$Cl (3 mL) was added iron powder (85.3 mg, 1.53 mmol). Then the mixture was stirred at 85° C. under N$_2$ for 4 h. The reaction was filtered and the filtrate was concentrated under reduced pressure. The residue was purified by column chromatography on silica gel (0→50% of EtOAc in PE) to give (R)-(5-(2-(1-((2-amino-5-bromopyridin-3-yl)oxy)ethyl)-4-fluorophenyl)-2-methyl- 2H-1,2,3-triazol-4-yl)(1-ethyl-1H-pyrrol-3-yl)methanone (95 mg, 61% yield) as a yellow solid. LC/MS (ESI) m/z: 513.0 [M+H]⁺.

To a solution of (R)-(5-(2-(1-((2-amino-5-bromopyridin-3-yl)oxy)ethyl)-4-fluorophenyl)-2-methyl-2H-1,2,3-triazol-4-yl)(1-ethyl-1H-pyrrol-3-yl)methanone (95 mg, 0.19 mmol) in 2-methyl-2-butanol (5 mL) were added cataCXium A (32 mg, 0.089 mmol), Pd(OAc)₂ (10 mg, 0.044 mmol) and KOAc (36 mg, 0.37 mmol). The mixture was thrice degassed under N₂ atmosphere and stirred at 120° C. for 12 h. The mixture was cooled to r.t. and partitioned between EtOAc (10 mL) and water (10 mL). The organic phase was dried over anhydrous Na₂SO₄, filtered, and concentrated to dryness. The residue was purified by prep-TLC (50% EtOAc in PE) followed by prep-HPLC (Gemini 5 um C18 250*21.2 mm, MeCN in H₂O+0.1% FA) to give (19R)-22-amino-3-ethyl-16-fluoro-10,19-dimethyl-20-oxa-3,9,10,11,23-pentaazapentacyclo[19.3.1.0$^{2,6}$.0$^{8,12}$.0$^{13,18}$]pentacosa-1 (24),2 (6),4,8,11,13,15,17,21 (25),22-decaen-7-one (12 mg, 15% yield) as a white solid. LC/MS (ESI) m/z: 433.0 [M+H]⁺.

NaBH₄ (1.0 mg, 0.028 mmol) was added to solution of (19R)-22-amino-3-ethyl-16-fluoro-10,19-dimethyl-20-oxa-3,9,10,11,23-pentaazapentacyclo[19.3.1.0$^{2,6}$.0$^{8,12}$.0$^{13,18}$]pentacosa-1 (24),2 (6),4,8,11,13,15,17,21 (25),22-decaen-7-one (8.0 mg, 0.018 mmol) in EtOH (2 mL) at 0° C. and the reaction mixture was stirred at r.t. for 16 h. The reaction mixture was diluted with ethyl acetate (20 mL) and washed with water (3×20 mL). The organic layer was washed with brine (20 mL), dried over Na₂SO₄, filtered, and concentrated. The residue was purified by prep-TLC (50% EtOAc in PE, R$_f$=0.3) to give (19R)-22-amino-3-ethyl-16-fluoro-10,19-dimethyl-20-oxa-3,9,10,11,23-pentaazapentacyclo[19.3.1.0$^{2,6}$.0$^{8,12}$.0$^{13,18}$]pentacosa-1 (24),2 (6),4,8,11,13,15,17,21 (25),22-decaen-7-ol (8 mg, 99% yield) as a yellow solid. LC/MS (ESI) m/z: 435.2 [M+H]⁺.

To a solution of (19R)-22-amino-3-ethyl-16-fluoro-10,19-dimethyl-20-oxa-3,9,10,11,23-pentaazapentacyclo[19.3.1.0$^{2,6}$.0$^{8,12}$.0$^{13,18}$]pentacosa-1 (24),2 (6),4,8,11,13,15,17,21 (25),22-decaen-7-ol (3 mg, 0.007 mmol) in DCM (3 mL) was added TES (1 mL) and TFA (1 mL) at r.t. The mixture was stirred at r.t. for 16 h, and then diluted with EtOAc (10 mL). This solution was washed with H₂O (10 mL), dried over anhydrous Na₂SO₄, filtered, and concentrated. The residue was purified with prep-TLC (50% EtOAc in PE, R$_f$=0.4) and prep-HPLC (YMC-Actus Triart C18 250*21 mm, MeCN in H₂O+0.1% FA) to afford the target product (1.3 mg, yield: 19%) as a white solid. LC/MS (ESI) m/z: 419 [M+H]⁺.

Inhibition Assays

Example 103

Biochemical Kinase Assay

First, 250 nL of compound dissolved in DMSO (100-fold of the desired concentration) was dispensed into a 384-well plate. A 12.5 µL substrate solution containing ATP (2 mM) and fluorogenic phosphorylation substrate AQT0101 (26 µM for ALK and ROS1, AssayQuant) or AQT0104 (26 µM for TRKA, AssayQuant) in buffer (50 mM HEPES pH 7.5, 0.01% Brij-35, 0.5 mM EGTA, 10 mM MgCl₂) was added and mixed thoroughly. Then, a 12.5 µL kinase solution containing ALK-wt (1.5 nM, Carna, 08-518), ALK ALK L1196M/G1202R (3 nM, SignalChem, A19-12NG), ROS1-wt (0.6 nM, Carna, 08-163), ROS1-G2032R (0.5 nM, SignalChem, R14-12BG), or TRKA-wt (1 nM, BPS Bio, 40280) kinase domains in buffer (50 nM HEPES pH 7.5, 0.01% Brij-35, 2% glycerol, 0.4 mg/mL BSA, 0.5 mM EGTA, and 10 mM MgCl₂) was added and mixed thoroughly. The plate was sealed and read by SpectraMax Paradigm at λ=485 nm every 2 minutes for 120 minutes at 30° C. Exemplary data is given in Table 3. Initial rates of reaction (v) were calculated from the change in fluorescence intensity over time during the initial, linear portion of the reaction. Finally, apparent inhibitory constants (K$_i^{app}$) were determined from regression of v and I (inhibitor concentration) to Morrison Equation (E=enzyme concentration):

$$v = 1 - \frac{(E + I + K_i^{app}) - \sqrt{(E + I + K_i^{app})^2 - 4EI}}{2E}$$

Exemplary data is given in Table 3 (nd=not determined).

TABLE 3

Biochemical Assay Activity Summary.

| Example | ALK-L1196M-G1202R | ALK-wt | ROS1-G2032R | ROS1-wt | TRKA-wt |
|---|---|---|---|---|---|
| 1 | A | A | A | A | B |
| 2 | B | A | B | A | C |
| 3 | A | A | A | A | B |
| 4 | A | A | A | A | B |
| 5 | A | A | A | A | B |
| 7 | A | A | B | A | C |
| 8 | A | A | A | A | C |
| 9 | A | A | A | A | B |
| 10 | A | A | A | A | C |
| 12 | B | A | B | A | C |
| 13 | A | A | A | A | C |
| 14 | A | A | A | A | B |
| 15 | A | A | A | A | B |
| 16 | A | A | A | A | A |
| 18 | B | A | B | A | C |
| 19 | A | A | A | A | C |
| 20 | B | A | B | A | C |
| 21 | A | A | A | A | B |
| 22 | A | A | A | A | B |
| 23 | A | A | A | A | B |
| 24 | A | A | A | A | C |
| 25 | B | A | B | A | C |
| 26 | A | A | A | A | C |
| 28 | A | A | A | A | C |
| 29 | A | A | A | A | B |
| 30 | A | A | A | A | C |
| 33 | A | A | A | A | B |
| 34 | A | A | A | A | B |
| 35 | A | A | A | A | B |
| 36 | A | A | A | A | B |
| 37 | B | A | A | A | C |
| 38 | A | A | A | A | B |
| 39 | A | A | A | A | C |
| 40 | A | A | A | A | B |
| 41 | A | A | A | A | C |
| 42 | A | A | A | A | B |
| 44 | B | A | B | A | C |
| 45 | A | A | A | A | C |
| 46 | B | A | B | A | C |
| 47 | B | A | C | A | C |
| 48 | A | A | A | A | B |
| 49 | B | A | B | A | C |
| 50 | A | A | B | A | B |
| 51 | A | A | A | A | B |
| 52 | A | A | A | A | C |
| 53 | A | A | A | A | C |
| 54 | B | A | A | A | B |
| 55 | B | A | A | A | C |
| 56 | A | A | A | A | B |

TABLE 3-continued

Biochemical Assay Activity Summary.

| Example | ALK-L1196M-G1202R | ALK-wt | ROS1-G2032R | ROS1-wt | TRKA-wt |
|---|---|---|---|---|---|
| 58 | B | A | B | A | B |
| 60 | B | B | B | A | C |
| 61 | A | A | A | A | C |
| 62 | A | A | A | A | B |
| 63 | A | A | A | A | C |
| 64 | A | A | A | A | C |
| 65 | A | A | A | A | C |
| 66 | A | A | A | A | B |
| 69 | A | A | A | A | C |
| 70 | A | A | A | A | C |
| 71 | A | A | B | A | C |
| 72 | A | A | A | A | B |
| 73 | A | A | A | A | B |
| 74 | A | A | A | A | B |
| 75 | A | A | A | A | B |
| 76 | A | A | A | A | C |
| 79 | B | A | C | A | C |
| 80 | B | A | B | A | C |
| 82 | A | A | A | A | C |
| 83 | A | A | A | A | C |
| 84 | A | A | A | A | C |
| 85 | A | A | A | A | C |
| 86 | A | A | A | A | A |
| 87 | B | A | B | A | C |
| 88 | A | A | A | A | B |
| 89 | A | A | A | nd | B |
| 90 | A | A | A | A | C |
| 92 | A | A | A | A | C |
| 95 | A | A | A | A | C |
| 96 | A | A | A | A | C |
| 98 | A | A | A | A | B |
| 99 | A | A | A | A | C |
| 100 | A | A | A | A | C |

Compound potency can be interpreted by binning $K_i^{app}$ values against the targets: bin A for high potency, $K_i^{app} < 50$ nM; bin B for medium potency, 50 nM $\leq K_i^{app} \leq$ 500 nM; and bin C for low potency, $K_i^{app} > 500$ nM. Compounds are more desirable if they exhibit smaller $K_i^{app}$ values against the on-target kinases (ROS1 or ALK) and larger $K_i^{app}$ values against the off-target kinase (TRKA). Compounds that potently inhibit the on-target kinases (ROS1 or ALK) are also expected to inhibit ROS1 or ALK oncoproteins that are expressed in human cancers, providing support for the potential clinical efficacy of such compounds. Similarly, compounds that do not potently inhibit the off-target kinase (TRKA) are expected to poorly inhibit TRK-family kinases in humans and hence avoid potential clinical toxicity arising from TRKA, TRKB, or TRKC inhibition.

Example 104

Generation of Ba/F3 Stable Cell Lines

Genes encoding CD74-ROS1 wild-type (wt), CD74-ROS1 G2032R, CD74-ROS1 S1986F, CD74-ROS1 L2026M, CD74-ROS1 D2033N, EML4-ALKwt (variant 1), EML4-ALK G1202R (variant 1), EML4-ALK L1196M/G1202R (variant 1), EML4-ALK G1202R/G1269A (variant 1), EML4-ALK G1202R/L1198F (variant 1), and TPM3-TRKA were synthesized at GeneRay, cloned into the retroviral construct pMSCV-puro (Biovector), and packaged into retroviral particles. The virus was used to infect Ba/F3 cells (RIKEN) at multiplicity of infection=1 for 1 day. Infected cells were rescued in media (RPMI-1640 with 10% fetal bovine serum and 1% streptomycin and penicillin) supplemented with mouse IL-3 (10 ng/mL) for 2 days, and stable cell lines were selected by IL-3 withdrawal and puromycin (0.8 μg/mL) for 7 days. Monoclones were selected by single-cell dilution in IL-3-free medium containing puromycin (0.8 μg/mL). Transformation of desired genes was confirmed by Sanger sequencing and western blot using the following antibodies: ROS1 (CST #3287), ALK (CST #3633), and pan-TRK (Abcam #76291).

Cell Proliferation Assay

Stable cells were plated at 1,000 cells/well (40 μL) in a 384-well plate for 1 day. Test compounds (40 nL) were then added in a 3-fold dilution series using the TECAN EV0200 liquid handler and incubated for 72 hours. Plates were equilibrated at room temperature for 15 minutes followed by addition of 40 μL CellTiter-Glo reagent (Promega). Luminescence was measured on a plate reader. Half-maximal inhibitory concentration ($IC_{50}$) was calculated from percent inhibition and inhibitor concentration using four-parameter logistic regression. Compound potency can be interpreted by binning $IC_{50}$ values: bin A for high potency, 0.1 nM $\leq IC_{50} <$ 50 nM; bin B for medium potency, 50 nM $\leq IC_{50} \leq$ 500 nM; and bin C for low potency, $IC_{50} >$ 500 nM. Compounds are more desirable if they exhibit smaller $IC_{50}$ values against the on-target Ba/F3 cells (ROS1- or ALK-fusion) and larger $IC_{50}$ values against the off-target Ba/F3 cells (TRKA-fusion). Exemplary data is given in Table 4. (nd=not determined).

TABLE 4

Cell Assay Activity Summary.

| Example | CD74-ROS1-G2032R | CD74-ROS1-wt | EML4-ALK-L1196M-G1202R | EML4-ALK-wt | TPM3-NTRK1-wt |
|---|---|---|---|---|---|
| 1 | A | A | B | A | C |
| 2 | A | nd | C | nd | C |
| 3 | A | A | B | A | C |
| 4 | A | A | B | A | B |
| 5 | A | A | A | A | B |
| 6 | A | nd | A | A | B |
| 7 | A | A | B | A | C |
| 8 | A | nd | B | nd | C |
| 9 | A | A | A | A | C |
| 10 | A | A | B | A | C |
| 11 | A | nd | B | nd | C |
| 12 | A | A | C | B | C |
| 13 | A | A | A | A | C |
| 14 | A | A | B | A | B |
| 15 | A | A | A | A | B |
| 16 | A | A | A | A | B |
| 17 | B | A | C | B | C |
| 18 | B | A | C | B | C |
| 19 | A | A | A | A | C |
| 20 | B | A | C | B | C |
| 21 | A | A | B | A | B |
| 22 | A | A | B | A | B |
| 23 | A | A | B | A | B |
| 24 | A | A | B | A | C |
| 25 | A | A | C | B | C |
| 26 | A | A | A | A | B |
| 27 | A | nd | B | A | C |
| 28 | A | A | B | A | B |
| 29 | A | A | A | A | B |
| 30 | A | A | B | A | C |
| 31 | A | nd | B | nd | B |
| 32 | A | A | B | A | B |
| 33 | A | A | B | A | B |
| 34 | A | A | A | A | B |
| 35 | A | A | B | A | C |
| 36 | A | nd | A | nd | B |

TABLE 4-continued

Cell Assay Activity Summary.

| Example | CD74-ROS1-G2032R | CD74-ROS1-wt | EML4-ALK-L1196M-G1202R | EML4-ALK-wt | TPM3-NTRK1-wt |
|---|---|---|---|---|---|
| 37 | A | A | B | A | C |
| 38 | A | A | B | A | C |
| 39 | A | A | B | A | C |
| 40 | A | A | B | A | B |
| 41 | A | A | A | A | C |
| 42 | A | A | B | A | B |
| 43 | A | A | B | B | C |
| 44 | A | A | B | A | C |
| 45 | A | A | B | A | C |
| 46 | A | A | B | A | C |
| 47 | B | A | C | A | C |
| 48 | A | A | A | A | C |
| 49 | B | A | C | A | C |
| 50 | A | A | B | A | C |
| 51 | A | A | A | A | C |
| 52 | A | A | B | A | C |
| 53 | A | A | B | A | C |
| 54 | A | A | B | A | B |
| 55 | A | A | B | A | C |
| 56 | A | A | B | A | B |
| 57 | A | nd | B | nd | C |
| 58 | B | A | C | B | B |
| 60 | A | A | C | B | C |
| 61 | A | A | A | A | C |
| 62 | A | A | A | A | B |
| 63 | A | A | A | A | B |
| 64 | A | A | B | A | C |
| 65 | A | A | A | A | C |
| 66 | A | A | A | A | B |
| 67 | A | A | B | A | C |
| 68 | A | nd | B | nd | C |
| 69 | A | A | A | A | C |
| 70 | A | A | B | A | C |
| 71 | A | A | B | B | C |
| 72 | A | A | A | A | B |
| 73 | A | A | B | A | B |
| 74 | A | A | A | A | B |
| 75 | A | A | A | A | B |
| 76 | A | A | A | A | C |
| 77 | A | nd | A | A | C |
| 78 | A | A | B | A | C |
| 79 | C | A | C | A | C |
| 80 | A | A | C | B | C |
| 81 | A | A | C | B | C |
| 82 | A | A | B | A | C |
| 83 | A | A | B | A | B |
| 84 | A | A | B | B | C |
| 85 | A | A | A | A | C |
| 86 | A | A | B | A | B |
| 87 | A | A | C | A | B |
| 88 | A | A | B | A | B |
| 89 | A | A | B | A | B |
| 90 | A | A | B | A | C |
| 91 | A | A | A | A | B |
| 92 | A | A | B | A | B |
| 93 | A | A | B | B | C |
| 94 | A | A | B | A | B |
| 95 | A | A | A | A | C |
| 96 | nd | nd | B | nd | C |
| 98 | A | A | A | A | B |
| 99 | A | A | B | A | C |
| 100 | A | A | A | A | C |
| 102 | B | A | C | B | C |

Potencies of the compounds provided herein were compared to commercially available ROS1 inhibitors (tested in the same assays) to assess relative potencies across ROS1 mutations. Exemplary data of one compound of Formula (I) and several ROS1 inhibitors are given in Table 5.

TABLE 5

Cell Potency Compared to Reference Compounds:

| Cell with ROS1 fusion | A compound of Formula (I) | Crizotinib | Entrectinib | Lorlatinib | Repotrectinib |
|---|---|---|---|---|---|
| Wild-type | A | B | B | A | A |
| G2032R | A | D | D | C | B |
| S1986F | A | B | B | A | A |
| L2026M | A | C | B | A | A |
| D2033N | A | B | B | A | A |

A: ≤10 nM
B: >10 nM and ≤100 nM
C: >100 nM and ≤500 nM
D: >500 nM and <1000 nM

Ba/F3 proliferation is driven by the transduced oncogenes in the same way that cancer cell proliferation in humans is driven by the expression of equivalent oncogenes. Hence, compounds that potently inhibit the proliferation of the on-target Ba/F3 cells (ROS1- or ALK-fusion) are also expected to inhibit human cancers that express equivalent oncogenes, providing support for the potential clinical efficacy of such compounds. Similarly, compounds that do not potently inhibit the off-target Ba/F3 cells (TRKA fusion) are expected to poorly inhibit TRK-family kinases in humans and hence avoid the clinical toxicity arising from TRKA, TRKB, or TRKC inhibition.

TRKA selectivity was calculated by dividing a compound's TRKA potency by its primary target potency (e.g. TPM3-NTRK1-wt $IC_{50}$/CD74-ROS1-wt $IC_{50}$). Compound selectivity can be interpreted by binning ratio values: bin A for very high selectivity, ratio >30-fold; bin B for high selectivity, ratio >10-fold; bin C for moderate selectivity, ratio ≥1; and bin D for low selectivity, ratio <1. Compounds are more desirable if they exhibit higher selectivity ratios. Exemplary data are given in Table 6. (nd=not determined).

TABLE 6

Cell Assay Selectivity Summary.

| Example | TPM3-NTRK1-wt/CD74-ROS1-G2032R | TPM3-NTRK1-wt/CD74-ROS1-wt | TPM3-NTRK1-wt/EML4-ALK-L1196M-G1202R | TPM3-NTRK1-wt/EML4-ALK-wt |
|---|---|---|---|---|
| 1 | A | A | B | A |
| 2 | A | nd | C | nd |
| 3 | A | A | C | A |
| 4 | A | A | C | B |
| 5 | A | A | C | A |
| 6 | A | nd | C | A |
| 7 | A | A | B | A |
| 8 | A | nd | C | nd |
| 9 | A | A | B | A |
| 10 | A | A | B | A |
| 11 | A | nd | B | nd |
| 12 | A | A | C | A |
| 13 | A | A | A | A |
| 14 | A | A | C | A |
| 15 | A | A | C | A |
| 16 | A | A | C | B |
| 17 | A | A | C | B |
| 18 | A | A | C | A |
| 19 | A | A | A | A |
| 20 | A | A | C | A |
| 21 | B | A | C | A |
| 22 | A | A | C | B |
| 23 | A | A | C | B |
| 24 | A | A | B | A |
| 25 | A | A | C | A |

TABLE 6-continued

Cell Assay Selectivity Summary.

| Example | TPM3-NTRK1-wt/CD74-ROS1-G2032R | TPM3-NTRK1-wt/CD74-ROS1-wt | TPM3-NTRK1-wt/EML4-ALK-L1196M-G1202R | TPM3-NTRK1-wt/EML4-ALK-wt |
|---|---|---|---|---|
| 26 | A | A | C | A |
| 27 | A | nd | C | B |
| 28 | A | A | C | B |
| 29 | A | A | C | A |
| 30 | A | A | C | A |
| 31 | A | nd | C | nd |
| 32 | A | A | C | B |
| 33 | A | A | C | A |
| 34 | A | A | B | A |
| 35 | A | A | C | A |
| 36 | A | nd | B | nd |
| 37 | A | A | B | A |
| 38 | A | A | C | A |
| 39 | A | A | B | A |
| 40 | A | A | C | B |
| 41 | A | A | B | A |
| 42 | A | A | C | B |
| 43 | A | A | C | B |
| 44 | A | A | C | A |
| 45 | A | A | A | A |
| 46 | A | A | A | A |
| 47 | B | A | C | A |
| 48 | A | A | B | A |
| 49 | B | A | C | A |
| 50 | B | A | C | A |
| 51 | A | A | A | A |
| 52 | A | A | C | A |
| 53 | A | A | C | B |
| 54 | A | A | D | C |
| 55 | A | A | C | A |
| 56 | A | A | C | B |
| 57 | A | nd | C | nd |
| 58 | C | A | D | C |
| 60 | A | A | B | A |
| 61 | A | A | A | A |
| 62 | A | A | C | A |
| 63 | A | A | B | A |
| 64 | A | A | A | A |
| 65 | A | A | A | A |
| 66 | A | A | C | B |
| 67 | A | A | C | A |
| 68 | A | nd | C | nd |
| 69 | A | A | A | A |
| 70 | A | A | A | A |
| 71 | A | A | B | A |
| 72 | A | A | A | A |
| 73 | A | A | C | A |
| 74 | A | A | B | A |
| 75 | A | A | B | A |
| 76 | A | A | A | A |
| 77 | A | nd | A | A |
| 78 | A | A | A | A |
| 79 | B | A | C | A |
| 80 | A | A | C | B |
| 81 | A | A | C | A |
| 82 | A | A | A | A |
| 83 | A | A | C | A |
| 84 | A | A | C | B |
| 85 | A | A | A | A |
| 86 | A | A | D | C |
| 87 | B | A | D | A |
| 88 | A | A | C | B |
| 89 | A | A | D | B |
| 90 | A | A | A | A |
| 91 | A | A | B | A |
| 92 | A | A | C | B |
| 93 | A | A | B | A |
| 94 | A | A | C | B |
| 95 | A | A | A | A |
| 96 | nd | nd | A | nd |
| 98 | A | A | C | A |
| 99 | A | A | B | A |
| 100 | A | A | A | A |
| 102 | B | A | C | B |

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject disclosure have been discussed, the above specification is illustrative and not restrictive. Many variations of the disclosure will become apparent to those skilled in the art upon review of this specification and the claims below. The full scope of the disclosure should be determined by reference to the claims, along with their full scope of equivalents, and the specification, along with such variations.

What is claimed is:

1. A compound of Formula (I):

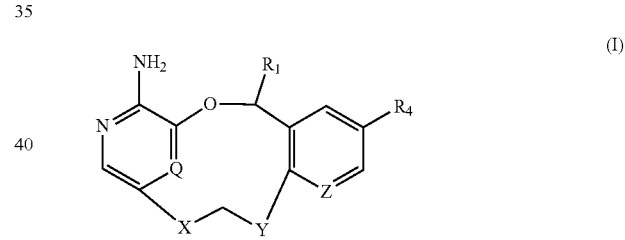

or a pharmaceutically acceptable salt, enantiomer, or tautomer thereof, wherein:
Q is CH;
Z is $CR_5$;
X is:

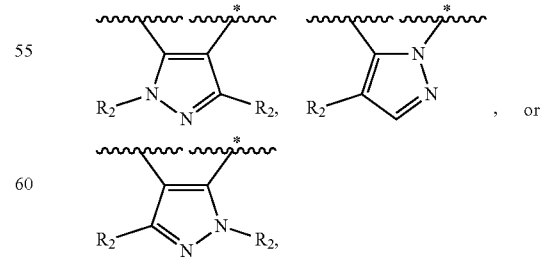

wherein:
* indicates the point of attachment of X to the —$CH_2$— group bonded to Y;

Y is:

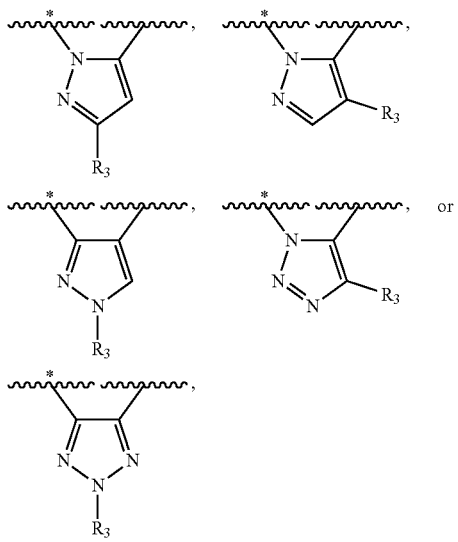

wherein:
* indicates the point of attachment of Y to the —CH$_2$— group bonded to X;
R$_1$ is H, CH$_3$, or CH$_2$OH;
each R$_2$ is independently H, halo, C$_{1-4}$ alkyl, C$_{1-4}$ haloalkyl, CH$_2$—C$_{3-4}$ cycloalkyl, OC$_{1-4}$ alkyl, C$_{3-6}$ cycloalkyl, or C$_{3-6}$ heterocycloalkyl;
R$_3$ is H, halo, CN, C$_{1-4}$ alkyl, C$_{1-4}$ haloalkyl, or OC$_{1-4}$ alkyl;
R$_4$ is H or F; and
R$_5$ is H or F.

2. A compound of Formula (I-B):

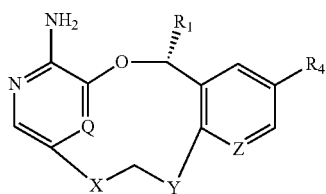

(I-B)

or a pharmaceutically acceptable salt thereof, wherein:
Q is CH;
Z is CR$_5$;
X is:

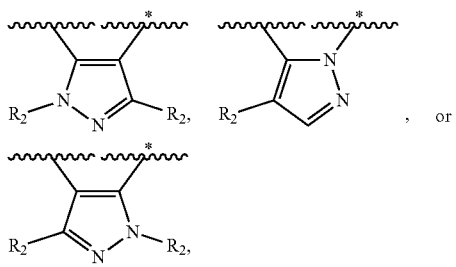

wherein:
* indicates the point of attachment of X to the —CH$_2$— group bonded to Y;
Y is:

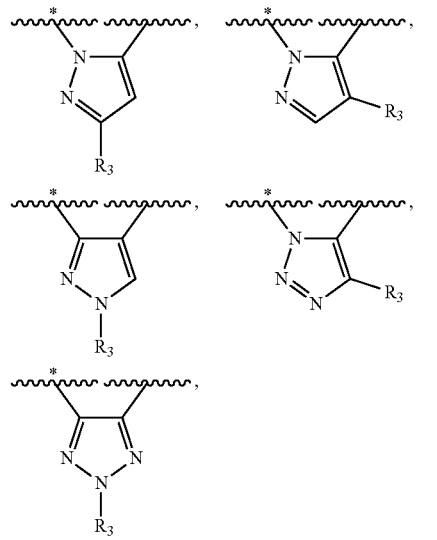

wherein:
* indicates the point of attachment of Y to the —CH$_2$— group bonded to X;
R$_1$ is H, CH$_3$, or CH$_2$OH;
each R$_2$ is independently H, halo, C$_{1-4}$ alkyl, C$_{1-4}$ haloalkyl, CH$_2$—C$_{3-4}$ cycloalkyl, OC$_{1-4}$ alkyl, C$_{3-6}$ cycloalkyl, or C$_{3-6}$ heterocycloalkyl;
R$_3$ is H, halo, CN, C$_{1-4}$ alkyl, C$_{1-4}$ haloalkyl, or OC$_{1-4}$ alkyl;
R$_4$ is H or F; and
R$_5$ is H or F.

3. The compound of claim 2, or a pharmaceutically acceptable salt thereof, wherein each R$_2$ is independently H, Cl, CH$_3$, CH$_2$CH$_3$, CH$_2$CH(CH$_3$)$_2$, CHF$_2$, CF$_3$, CH$_2$CH$_2$F, CH$_2$CHF$_2$, CH$_2$-cyclopropyl, OCH$_3$, cyclopropyl, cyclobutyl, or oxetanyl.

4. The compound of claim 2, or a pharmaceutically acceptable salt thereof, wherein R$_3$ is H, F, Cl, CN, CH$_3$, or H$_2$CH$_3$.

5. The compound of claim 4, or a pharmaceutically acceptable salt thereof, wherein R$_4$ is F.

6. The compound of claim 5, or a pharmaceutically acceptable salt thereof, wherein R$_5$ is H.

7. The compound of claim 2, wherein the compound is:

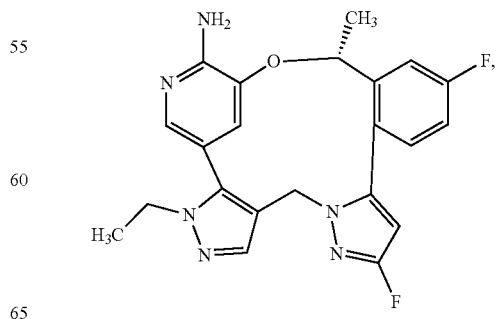

or a pharmaceutically acceptable salt thereof.

8. The compound of claim 2, wherein the compound is:

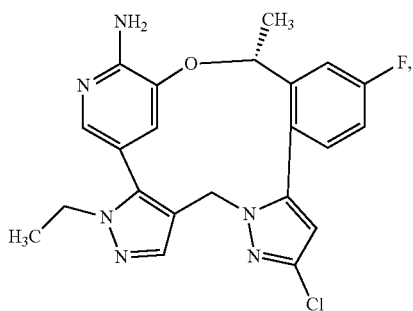 [SMILES: CCn1ncc2c1-c1cnc(N)c(c1)O[C@H](C)c1cc(F)ccc1-c1cc(F)nn1C2]

or a pharmaceutically acceptable salt thereof.

9. The compound of claim 2, wherein the compound is:

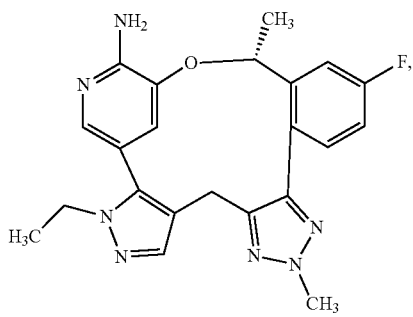 [SMILES: CCn1ncc2c1-c1cnc(N)c(c1)O[C@H](C)c1cc(F)ccc1-c1nn(C)nc1C2]

or a pharmaceutically acceptable salt thereof.

10. The compound of claim 2, wherein the compound is:

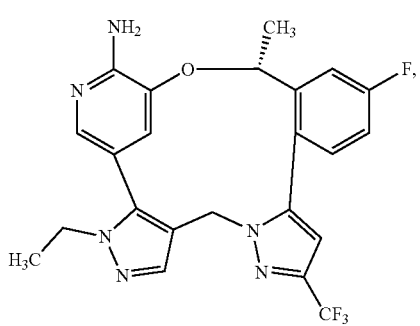 [SMILES: CCn1ncc2c1-c1cnc(N)c(c1)O[C@H](C)c1cc(F)ccc1-c1cc(C(F)(F)F)nn1C2]

or a pharmaceutically acceptable salt thereof.

11. The compound of claim 2, wherein the compound is:

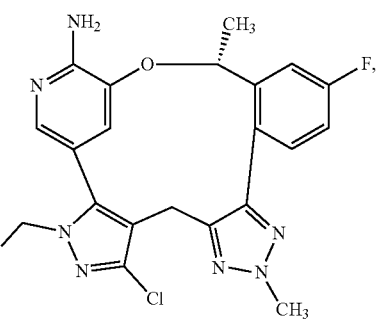

or a pharmaceutically acceptable salt thereof.

12. The compound of claim 2, wherein the compound is:

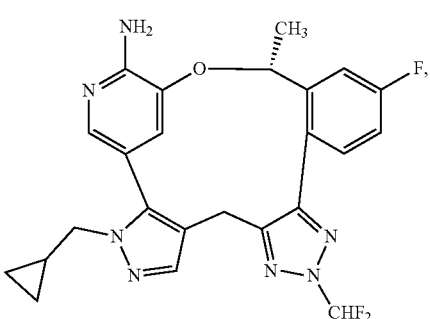

or a pharmaceutically acceptable salt thereof.

13. The compound of claim 2, wherein the compound is:

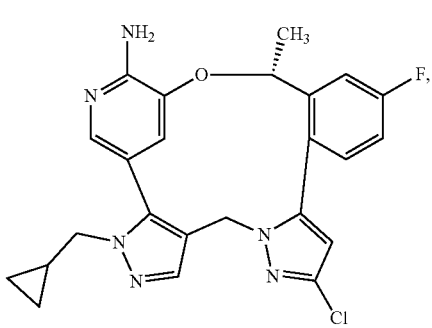 [SMILES: C[C@H]1Oc2cc(cnc2N)-c2c(cnn2CC2CC2)Cn2nc(Cl)cc2-c2ccc(F)cc21]

or a pharmaceutically acceptable salt thereof.

14. The compound of claim 2, wherein the compound is:

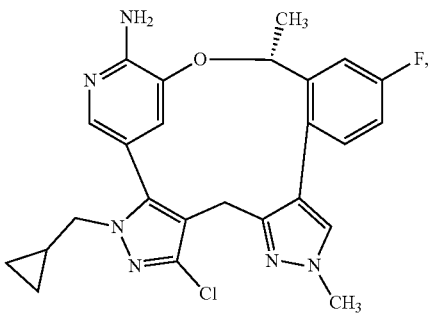 [SMILES: C[C@H]1Oc2cc(cnc2N)-c2c(c(Cl)nn2CC2CC2)Cc2nn(C)cc2-c2ccc(F)cc21]

or a pharmaceutically acceptable salt thereof.

15. The compound of claim 2, wherein the compound is:

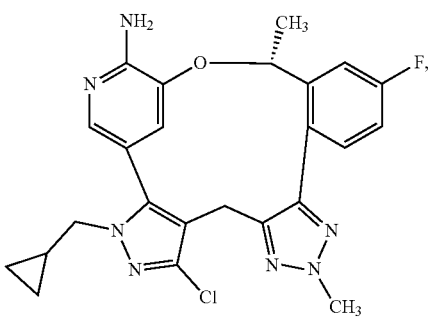 [SMILES: C[C@H]1Oc2cc(cnc2N)-c2c(c(Cl)nn2CC2CC2)Cc2nn(C)nc2-c2ccc(F)cc21]

or a pharmaceutically acceptable salt thereof.

16. The compound of claim 2, wherein the compound is:

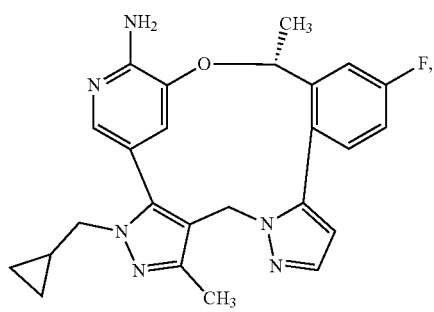 [SMILES: Cc1nn(CC2CC2)c2c1Cn1nccc1-c1ccc(F)cc1[C@@H](C)Oc1cc-2cnc1N]

or a pharmaceutically acceptable salt thereof.

17. The compound of claim 2, wherein the compound is:

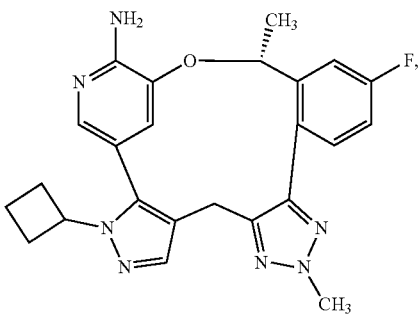 [SMILES: C[C@H]1Oc2cc(cnc2N)-c2c(cnn2C2CCC2)Cc2nn(C)nc2-c2ccc(F)cc21]

or a pharmaceutically acceptable salt thereof.

18. The compound of claim 2, wherein the compound is:

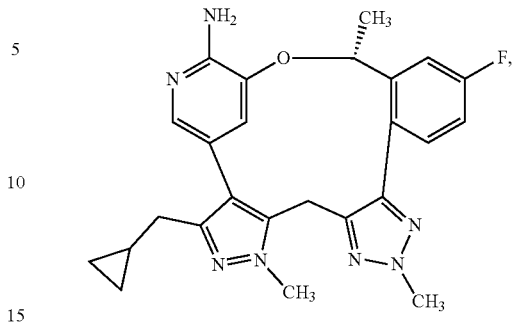

or a pharmaceutically acceptable salt thereof.

19. A pharmaceutical composition comprising (i) a pharmaceutically acceptable carrier or excipient, and (ii) the compound of claim 7, or a pharmaceutically acceptable salt thereof.

20. A pharmaceutical composition comprising (i) a pharmaceutically acceptable carrier or excipient, and (ii) the compound of claim 8, or a pharmaceutically acceptable salt thereof.

21. A pharmaceutical composition comprising (i) a pharmaceutically acceptable carrier or excipient, and (ii) the compound of claim 9, or a pharmaceutically acceptable salt thereof.

22. A pharmaceutical composition comprising (i) a pharmaceutically acceptable carrier or excipient, and (ii) the compound of claim 10, or a pharmaceutically acceptable salt thereof.

23. A pharmaceutical composition comprising (i) a pharmaceutically acceptable carrier or excipient, and (ii) the compound of claim 11, or a pharmaceutically acceptable salt thereof.

24. A pharmaceutical composition comprising (i) a pharmaceutically acceptable carrier or excipient, and (ii) the compound of claim 12, or a pharmaceutically acceptable salt thereof.

25. A pharmaceutical composition comprising (i) a pharmaceutically acceptable carrier or excipient, and (ii) the compound of claim 13, or a pharmaceutically acceptable salt thereof.

26. A pharmaceutical composition comprising (i) a pharmaceutically acceptable carrier or excipient, and (ii) the compound of claim 14, or a pharmaceutically acceptable salt thereof.

27. A pharmaceutical composition comprising (i) a pharmaceutically acceptable carrier or excipient, and (ii) the compound of claim 15, or a pharmaceutically acceptable salt thereof.

28. A pharmaceutical composition comprising (i) a pharmaceutically acceptable carrier or excipient, and (ii) the compound of claim 16, or a pharmaceutically acceptable salt thereof.

29. A pharmaceutical composition comprising (i) a pharmaceutically acceptable carrier or excipient, and (ii) the compound of claim 17, or a pharmaceutically acceptable salt thereof.

30. A pharmaceutical composition comprising (i) a pharmaceutically acceptable carrier or excipient, and (ii) the compound of claim 18, or a pharmaceutically acceptable salt thereof.

* * * * *